(12) United States Patent
Patel et al.

(10) Patent No.: US 9,187,432 B2
(45) Date of Patent: Nov. 17, 2015

(54) INTERMEDIATES TO PREPARE HERBICIDAL PYRIMIDONE DERIVATIVES

(71) Applicant: E I DU PONT DE NEMOURS AND COMPANY, Wilmington, DE (US)

(72) Inventors: Kanu Maganbhai Patel, Wilmington, DE (US); Thomas Paul Selby, Hockessin, DE (US); Brenton Todd Smith, Ladera Ranch, CA (US); Andrew Edmund Taggi, Newark, DE (US); Patrick Ryan Kovacs, New Castle, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/573,370

(22) Filed: Dec. 17, 2014

(65) Prior Publication Data

US 2015/0105549 A1 Apr. 16, 2015

Related U.S. Application Data

(62) Division of application No. 13/391,647, filed as application No. PCT/US2010/047944 on Sep. 7, 2010, now Pat. No. 8,952,024.

(60) Provisional application No. 61/240,792, filed on Sep. 9, 2009.

(51) Int. Cl.
*C07D 239/36* (2006.01)
*A01N 43/54* (2006.01)
(Continued)

(52) U.S. Cl.
CPC .............. *C07D 239/36* (2013.01); *A01N 43/54* (2013.01); *A01N 43/56* (2013.01); *A01N 43/78* (2013.01);
(Continued)

(58) Field of Classification Search
CPC .. C07D 419/12; C07D 417/12; C07D 413/12; C07D 411/12; C07D 409/12; C07D 407/12; C07D 405/12; C07D 403/12
See application file for complete search history.

(56) References Cited

U.S. PATENT DOCUMENTS 3,696,197 A * 10/1972 Meszaros et al. .......... 514/259.4
3,823,135 A    7/1974 Pilgram et al.
(Continued)

FOREIGN PATENT DOCUMENTS

EP    0 568 041 A1    11/1993
EP    1 055 683 A1    11/2000
(Continued)

OTHER PUBLICATIONS

Juby P. F et al, "1,6-Dihydro-6-OXO-2-Phenylpyrimidine-5-Carboxylic Acids and Esters", Journal of Medicinal Chemical, American Chemistry Society, Washington, US, vol. 22, No. 3, Jan. 1, 1979, pp. 263-269, Compounds 88, 89, 90.
(Continued)

*Primary Examiner* — Alexander R Pagano

(57) ABSTRACT

Disclosed are compounds of Formula 1, including all stereoisomers, N-oxides, and salts thereof,

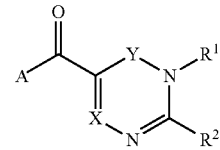

1

X is CH or N;
Y is C(O) or S(O)$_2$; provided that when Y is S(O)$_2$, then X is CH;
A is a radical selected from the group consisting of

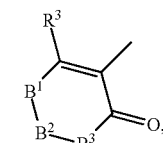

A-1

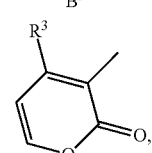

A-2

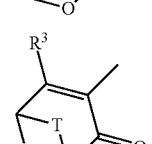

A-3

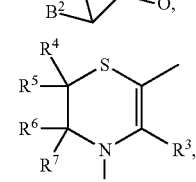

A-4

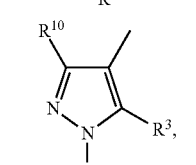

A-5

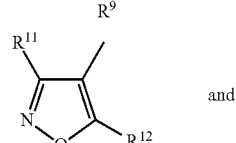

A-6 and

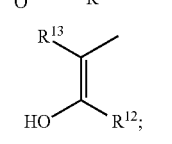

A-7 and $B^1$, $B^2$, $B^3$, T, $R^1$, $R^2$ $R^3$, $R^4$, $R^5$, $R^6$, $R^7$, $R^8$, $R^9$, $R^{10}$, $R^{11}$, $R^{12}$ and $R^{13}$ are as defined in the disclosure. Also disclosed are compositions containing the compounds of Formula 1 and methods for controlling undesired vegetation comprising contacting the undesired vegetation or its environment with an effective amount of a compound or a composition of the invention.

10 Claims, No Drawings

(51) Int. Cl.

| | | |
|---|---|---|
| A01N 43/56 | (2006.01) | |
| A01N 43/80 | (2006.01) | |
| C07D 401/04 | (2006.01) | |
| C07D 401/14 | (2006.01) | |
| C07D 403/06 | (2006.01) | |
| C07D 403/12 | (2006.01) | |
| C07D 403/14 | (2006.01) | |
| C07D 405/04 | (2006.01) | |
| C07D 405/06 | (2006.01) | |
| C07D 405/12 | (2006.01) | |
| C07D 405/14 | (2006.01) | |
| C07D 409/04 | (2006.01) | |
| C07D 409/06 | (2006.01) | |
| C07D 409/14 | (2006.01) | |
| C07D 413/04 | (2006.01) | |
| C07D 413/06 | (2006.01) | |
| C07D 413/14 | (2006.01) | |
| C07D 417/04 | (2006.01) | |
| C07D 417/14 | (2006.01) | |
| C07D 471/04 | (2006.01) | |
| C07D 487/04 | (2006.01) | |
| C07D 498/04 | (2006.01) | |
| A01N 43/78 | (2006.01) | |
| A01N 43/90 | (2006.01) | |
| C07D 493/08 | (2006.01) | |
| C07D 407/12 | (2006.01) | |
| C07D 409/12 | (2006.01) | |
| C07D 411/12 | (2006.01) | |
| C07D 413/12 | (2006.01) | |
| C07D 417/12 | (2006.01) | |
| C07D 419/12 | (2006.01) | |

(52) U.S. Cl.
CPC .............. *A01N 43/80* (2013.01); *A01N 43/90* (2013.01); *C07D 401/04* (2013.01); *C07D 401/14* (2013.01); *C07D 403/06* (2013.01); *C07D 403/12* (2013.01); *C07D 403/14* (2013.01); *C07D 405/04* (2013.01); *C07D 405/06* (2013.01); *C07D 405/12* (2013.01); *C07D 405/14* (2013.01); *C07D 409/04* (2013.01); *C07D 409/06* (2013.01); *C07D 409/14* (2013.01); *C07D 413/04* (2013.01); *C07D 413/06* (2013.01); *C07D 413/14* (2013.01); *C07D 417/04* (2013.01); *C07D 417/14* (2013.01); *C07D 471/04* (2013.01); *C07D 487/04* (2013.01); *C07D 493/08* (2013.01); *C07D 498/04* (2013.01); *C07D 407/12* (2013.01); *C07D 409/12* (2013.01); *C07D 411/12* (2013.01); *C07D 413/12* (2013.01); *C07D 417/12* (2013.01); *C07D 419/12* (2013.01)

(56) References Cited

U.S. PATENT DOCUMENTS

| | | | | |
|---|---|---|---|---|
| 4,008,220 | A | * | 2/1977 | Tobiki et al. .................. 540/315 |
| 4,267,180 | A | * | 5/1981 | Haskell et al. ................ 514/196 |
| 4,315,933 | A | * | 2/1982 | Mich et al. .................... 514/196 |
| 4,840,953 | A | * | 6/1989 | Matsutani et al. ........ 514/259.41 |
| 5,366,955 | A | | 11/1994 | Nagano et al. |
| 8,952,024 | B2 | * | 2/2015 | Patel et al. .................... 514/269 |
| 2010/0323887 | A1 | * | 12/2010 | Holyoke et al. .............. 504/100 |
| 2012/0149573 | A1 | * | 6/2012 | Patel et al. .................... 504/131 |

FOREIGN PATENT DOCUMENTS

| | | |
|---|---|---|
| EP | 1 982 978 A1 | 10/2008 |
| WO | 97/46207 A2 | 12/1997 |
| WO | 00/67746 A1 | 11/2000 |
| WO | 2006/133242 A2 | 12/2006 |
| WO | 2007/088876 A1 | 1/2007 |
| WO | 2009016841 A1 | 2/2009 |
| WO | 2010089993 A1 | 8/2010 |
| WO | 2012002096 A1 | 1/2012 |
| WO | 2012039141 A1 | 3/2012 |
| WO | 2012045721 A2 | 4/2012 |

OTHER PUBLICATIONS

Takayasu Kitagawa et al, "Equilibrium Studies of 5-Substituted 4-Hydroxy-2-Methlpyrimidines", Chemical & Pharmaceutical Bulletin, vol. 22, No. 6, 1974, pp. 1239-1255, p. 1253; Compound 28.
Gupta et al, "Synthesis & Pharmacological Evaluation of Ethyl 3-Substituted-Phenyl-2-Methylmercapto/Phenyl/Methyl-4(3H)-Pyrimidone-5-Carboxylates", Indian Journal of Chemistry, vol. 21B, Mar. 1982, pp. 228-233, p. 230, Table 4, Compounds 86-97, 113.
Kraamer, W. & Shirmer, U., Editors, Modern Crop Proection Compound, vol. 1; Chapters 4.1, 4.2 and 4.3, 2007; Wiley-VCH Verlag GMBH & Co. KGAA, Weinheim.
Tice, C. M. & Bryman, L. M., "Regiocontrolled Synthesis of 3-Substituted-6-Trifluoromethyl-4(3h)-Pyrimidinones", Tetrahedron 57 (2001) 2689-2700.

\* cited by examiner

INTERMEDIATES TO PREPARE HERBICIDAL PYRIMIDONE DERIVATIVES

FIELD OF THE INVENTION

This invention relates to certain bis-nitrogen heterocycles, their salts and compositions, and methods of their use for controlling undesirable vegetation. This invention also relates to certain intermediates and a method useful for preparing these bis-nitrogen heterocycles and their salts. This invention als relates to certain bis-nitrogen oxo or sulfono heterocycles, their salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

International patent application publication WO 2007/088876 discloses pyridone compounds of Formula i

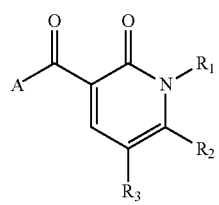

i wherein inter alia $R_1$ is $C_1$-$C_6$ alkyl; $R_2$ and $R_3$ are each independently hydrogen, cyano, or nitro; and A is a A-1 through A-5 as defined therein as herbicides.

The bis-nitrogen containing oxo and sulfono heterocycles of the present invention are not disclosed in this publication.

SUMMARY OF THE INVENTION

This invention is directed to compounds of Formula 1 (including all stereoisomers), N-oxides, and salts thereof, agricultural compositions containing them and their use as herbicides:

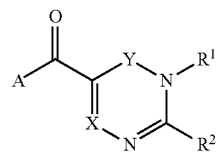

1 wherein
X is CH;
Y is C(O);

A is a radical selected from the group consisting of

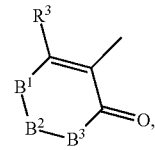

A-1

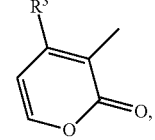

A-2

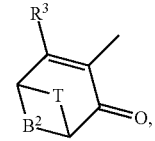

A-3

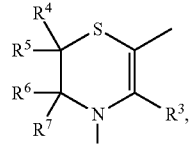

A-4

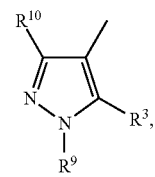

A-5

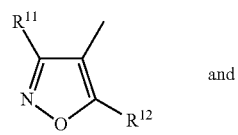

A-6 and

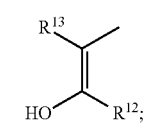

A-7

$B^1$ and $B^3$ are each independently a radical selected from the group consisting of

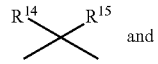

C-1 and

C-2

$B^2$ is a radical selected from the group consisting of

C-3

-continued

C-4

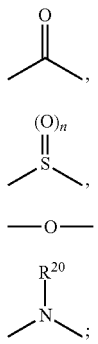

C-5

C-6

—O— and

C-7

$R^{20}$
\N\

$R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2NHCN$, —$SO_2NHOH$, —NHCHO, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{12}$ haloalkynyl, $C_3$-$C_{12}$ cycloalkyl, $C_3$-$C_{12}$ halocycloalkyl, $C_4$-$C_{14}$ alkylcycloalkyl, $C_4$-$C_{14}$ cycloalkylalkyl, $C_6$-$C_{18}$ cycloalkylcycloalkyl, $C_4$-$C_{14}$ halocycloalkylalkyl, $C_5$-$C_{16}$ alkylcycloalkylalkyl, $C_3$-$C_{12}$ cycloalkenyl, $C_3$-$C_{12}$ halocycloalkenyl, $C_2$-$C_{12}$ alkoxyalkyl, $C_3$-$C_{12}$ alkoxyalkenyl, $C_4$-$C_{14}$ alkylcycloalkyl, $C_4$-$C_{14}$ alkoxycycloalkyl, $C_4$-$C_{14}$ cycloalkoxyalkyl, $C_5$-$C_{14}$ cycloalkoxyalkoxyalkyl, $C_3$-$C_{14}$ alkoxyalkoxyalkyl, $C_2$-$C_{12}$ alkylthioalkyl, $C_2$-$C_{12}$ alkylsulfinylalkyl, $C_2$-$C_{12}$ alkylsulfonylalkyl, $C_2$-$C_{12}$ alkylaminoalkyl, $C_3$-$C_{14}$ dialkylaminoalkyl, $C_2$-$C_{12}$ haloalkylaminoalkyl, $C_4$-$C_{14}$ cycloalkylaminoalkyl, $C_2$-$C_{12}$ alkylcarbonyl, $C_2$-$C_{12}$ haloalkylcarbonyl, $C_4$-$C_{14}$ cycloalkylcarbonyl, $C_2$-$C_{12}$ alkoxycarbonyl, $C_4$-$C_{16}$ cycloalkoxycarbonyl, $C_5$-$C_{14}$ cycloalkylalkoxycarbonyl, $C_2$-$C_{12}$ alkylaminocarbonyl, $C_3$-$C_{14}$ dialkylaminocarbonyl, $C_4$-$C_{14}$ cycloalkylaminocarbonyl, $C_2$-$C_9$ cyanoalkyl, $C_1$-$C_{10}$ hydroxyalkyl, $C_4$-$C_{14}$ cycloalkenylalkyl, $C_2$-$C_{12}$ haloalkoxyalkyl, $C_2$-$C_{12}$ alkoxyhaloalkyl, $C_2$-$C_{12}$ haloalkoxyhaloalkyl, $C_4$-$C_{14}$ halocycloalkoxyalkyl, $C_4$-$C_{14}$ cycloalkenyloxyalkyl, $C_4$-$C_{14}$ halocycloalkenyloxyalkyl, $C_3$-$C_{14}$ dialkoxyalkyl, $C_3$-$C_{14}$ alkoxyalkylcarbonyl, $C_3$-$C_{14}$ alkoxycarbonylalkyl, $C_2$-$C_{12}$ haloalkoxycarbonyl, $C_1$-$C_{10}$ alkoxy, $C_1$-$C_{10}$ haloalkoxy, $C_3$-$C_{12}$ cycloalkoxy, $C_3$-$C_{12}$ halocycloalkoxy, $C_4$-$C_{14}$ cycloalkylalkoxy, $C_2$-$C_{10}$ alkenyloxy, $C_2$-$C_{10}$ haloalkenyloxy, $C_2$-$C_{10}$ alkynyloxy, $C_3$-$C_{10}$ haloalkynyloxy, $C_2$-$C_{12}$ alkoxyalkoxy, $C_2$-$C_{12}$ alkylcarbonyloxy, $C_2$-$C_{12}$ haloalkylcarbonyloxy, $C_4$-$C_{14}$ cycloalkylcarbonyloxy, $C_3$-$C_{14}$ alkylcarbonylalkoxy, $C_1$-$C_{10}$ alkylthio, $C_1$-$C_{10}$ haloalkylthio, $C_3$-$C_{12}$ cycloalkylthio, $C_1$-$C_{10}$ alkylsulfinyl, $C_1$-$C_{10}$ haloalkylsulfinyl, $C_1$-$C_{10}$ alkylsulfonyl, $C_1$-$C_{10}$ haloalkylsulfonyl, $C_3$-$C_{12}$ cycloalkylsulfonyl, $C_2$-$C_{12}$ alkylcarbonylthio, $C_2$-$C_{12}$ alkyl(thiocarbonyl)thio, $C_3$-$C_{12}$ cycloalkylsulfinyl, $C_1$-$C_{10}$ alkylaminosulfonyl, $C_2$-$C_{12}$ dialkylaminosulfonyl, $C_1$-$C_{10}$ alkylamino, $C_2$-$C_{12}$ dialkylamino, $C_1$-$C_{10}$ haloalkylamino, $C_2$-$C_{12}$ halodialkylamino, $C_3$-$C_{12}$ cycloalkylamino, $C_2$-$C_{12}$ alkylcarbonylamino, $C_2$-$C_{12}$ haloalkylcarbonylamino, $C_1$-$C_{10}$ alkylsulfonylamino, $C_1$-$C_{10}$ haloalkylsulfonylamino or $C_4$-$C_{14}$ cycloalkyl(alkyl)amino;

$W^1$ is $C_1$-$C_6$ alkylene, $C_2$-$C_6$ alkenylene or $C_2$-$C_6$ alkynylene;
$W^2$ is $C_1$-$C_6$ alkylene;
$R^2$ is phenyl or —$W^3$(phenyl), each optionally substituted on ring members with up to five substituents selected from $R^{21}$; or -G or —$W^4$G; or H, cyano, hydroxy, amino, nitro, —CHO, —C(=O)OH, —C(=O)$NH_2$, —C(=S)$NH_2$, —C(=O)NHCN, —C(=O)NHOH, —SH, —$SO_2NH_2$, —$SO_2NHCN$, —$SO_2NHOH$, —$SF_5$, —NHCHO, —$NHNH_2$, —NHOH, —NHCN, —NHC(=O)$NH_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl, $C_2$-$C_8$ haloalkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_2$-$C_8$ alkylcarbonylthio, $C_2$-$C_8$ alkyl(thiocarbonyl)thio, $C_3$-$C_8$ cycloalkylsulfinyl, $C_1$-$C_6$ alkylaminosulfonyl, $C_2$-$C_8$ dialkylaminosulfonyl, $C_3$-$C_{10}$ halotrialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino or $C_4$-$C_{10}$ cycloalkyl(alkyl)amino; or $R^1$ and $R^2$ are taken together along with the atoms to which they are attached to make a 5-, 6- or 7-membered unsaturated, partially unsaturated or fully unsaturated ring along with members consisting of up to 2 oxygen atoms, 2 nitrogen atoms or 2 sulfur atoms or up to two —S(O)—, —S(O)$_2$—, —C(O)— groups optionally substituted on carbon atom ring members selected from halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_2$-$C_8$ alkoxyalkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy; and optionally substituted on nitrogen ring members selected from H and $C_1$-$C_6$ alkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy;

$W^3$ is $C_1$-$C_6$ alkylene, $C_2$-$C_6$ alkenylene or $C_2$-$C_6$ alkynylene;

$W^4$ is $C_1$-$C_6$ alkylene;

$R^3$ is H, halogen, cyano, hydroxy, —O$^-$M$^+$, amino, nitro, —CHO, —C(=O)OH, —C(=O)NH$_2$, —C(=S)NH$_2$, —SH, —SO$_2$NH$_2$, —SO$_2$NHCN, —SO$_2$NHOH, —OCN, —SCN, —SF$_5$, —NHNH$_2$, —NHOH, —N=C=O, —N=C=S, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylsulfonyloxy, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino or $C_1$-$C_6$ haloalkylsulfonylamino; or benzyloxy, phenyloxy, benzylcarbonyloxy, phenylcarbonyloxy, phenylsulfonyloxy, benzylsulfonyloxy, phenylthio, benzylthio, phenylsulfinyl, benzylsulfinyl, phenylsulfonyl or benzylsulfonyl, each optionally substituted on ring members with up to five substituents selected from $R^{21}$;

M$^+$ is an alkali metal cation or an ammonium cation;

$R^4$, $R^5$, $R^6$ and $R^7$ are each independently H, halogen, hydroxy, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy or $C_3$-$C_8$ halocycloalkoxy; or phenyl or benzyl, each optionally substituted on ring members with up to five substituents selected from $R^{21}$;

$R^8$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl or $C_3$-$C_8$ halocycloalkyl; or benzyl optionally substituted on ring members with up to five substituents selected from $R^{21}$;

$R^9$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

$R^{10}$ is H, halogen, cyano, hydroxy, amino, nitro, SH, —SO$_2$NH$_2$, —SO$_2$NHCN, —SO$_2$NHOH, —OCN, —SCN, —SF$_5$, —NHCHO, —NHNH$_2$, —N$_3$, —NHOH, —NHCN, —NHC(=O)NH$_2$, —N=C=O, —N=C=S, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

$R^{11}$ is H, halogen, cyano, hydroxy, amino, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl or $C_2$-$C_8$ alkylsulfonylalkyl; or phenyl optionally substituted with up to five substituents selected from $R^{21}$;

$R^{12}$ is H, halogen, cyano, hydroxy, amino, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl or $C_2$-$C_8$ alkoxycarbonylamino;

$R^{13}$ is H, halogen, cyano, hydroxy, amino, nitro or $C_2$-$C_8$ alkoxycarbonyl;

n is 0, 1, or 2;

each $R^{14}$, $R^{15}$, $R^{18}$ and $R^{19}$ is independently H, halogen, cyano, hydroxy or $C_1$-$C_6$ alkyl; or a pair of $R^{14}$ and $R^{18}$ is taken together as $C_2$-$C_6$ alkylene or $C_2$-$C_6$ alkenylene;

$R^{20}$ is H, $C_1$-$C_6$ haloalkyl, $C_2$-$C_6$ haloalkenyl, $C_1$-$C_6$ alkoxy, $C_1$-$C_6$ haloalkoxy, $C_3$-$C_8$ cycloalkoxy, $C_1$-$C_6$ alkyl, $C_2$-$C_6$ alkenyl, $C_2$-$C_6$ alkynyl or $C_3$-$C_8$ cycloalkyl;

T is $C_1$-$C_6$ alkylene or $C_2$-$C_6$ alkenylene;

each G is independently a 5- or 6-membered heterocyclic ring or an 8-, 9- or 10-membered fused bicyclic ring system, each ring or ring system optionally substituted with up to five substituents selected from $R^{21}$ on carbon ring members and $R^{22}$ on nitrogen ring members;

each $R^{21}$ is independently halogen, cyano, hydroxy, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —OCN, —SCN, —SF$_5$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylamino, $C_2$-$C_8$ dialkylamino, $C_1$-$C_6$ haloalkylamino, $C_2$-$C_8$ halodialkylamino or $C_3$-$C_8$ cycloalkylamino; and each $R^{22}$ is independently $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl.

More particularly, this invention pertains to a compound of Formula 1 (including all stereoisomers), an N-oxide, or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein)

This invention also relates to a herbicidal mixture of (a) a compound of Formula 1 and (b) at least one additional active ingredient.

This invention is also directed to an intermediate compound of Formula 1Q (including all stereoisomers), N-oxides, and salts thereof:

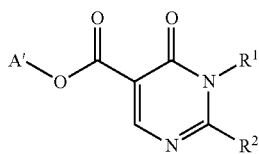

1Q wherein A' is a radical selected from the group consisting of

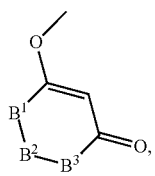

A'-1

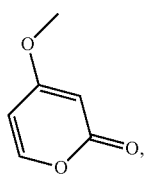

A'-2

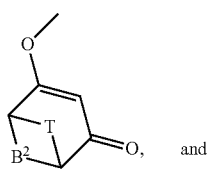

A'-3

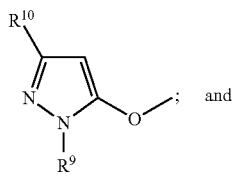

A'-5

$R^1$, $R^2$, $B^1$, $B^2$, $B^3$, T, $R^9$ and $R^{10}$ are as defined above for a compound of Formula 1 which is useful for preparing a compound of Formula 1.

This invention is also directed to a compound of Formula 1R (including all stereoisomers), N-oxides, and salts thereof:

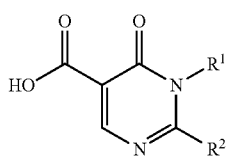

1R wherein
$R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkoxyalkyl, $C_2$-$C_8$ alkylthioalkyl, $C_2$-$C_8$ alkylsulfinylalkyl or $C_2$-$C_8$ alkylsulfonylalkyl;

$W^1$ is $C_1$-$C_6$ alkylene, $C_2$-$C_6$ alkenylene or $C_2$-$C_6$ alkynylene;

$W^2$ is $C_1$-$C_6$ alkylene;

$R^2$ is phenyl or —$W^3$(phenyl), each substituted on ring members with up to two substituents selected from $R^{21}$; or -G; or $C_1$-$C_6$ alkyl or $C_3$-$C_8$ cycloalkyl;

$W^3$ is $C_1$-$C_6$ alkylene, $C_2$-$C_6$ alkenylene or $C_2$-$C_6$ alkynylene;

each G is independently a 5- or 6-membered heterocyclic ring or an 8-, 9- or 10-membered fused bicyclic ring system, each ring or ring system optionally substituted with up to five substituents selected from $R^{21}$ on carbon ring members and $R^{22}$ on nitrogen ring members;

each $R^{21}$ is independently halogen, cyano, hydroxy, amino, nitro, —CHO, —C(=O)OH, —C(=O)$NH_2$, —C(=S)$NH_2$, —C(=O)NHCN, —C(=O)NHOH, —SH, —$SO_2NH_2$, —$SO_2$NHCN, —$SO_2$NHOH, —OCN, —SCN, —$SF_5$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylamino, $C_2$-$C_8$ dialkylamino, $C_1$-$C_6$ haloalkylamino, $C_2$-$C_8$ halodialkylamino or $C_3$-$C_8$ cycloalkylamino; and each $R^{22}$ is independently $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl which is useful for preparing a compound of Formula 1.

This invention is also directed to a compound of Formula 1S (including all stereoisomers), N-oxides, and salts thereof:

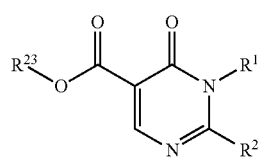

1S wherein
$R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_8$ alkylsulfinylalkyl or $C_2$-$C_8$ alkylsulfonylalkyl;

$W^1$ is $C_1$-$C_6$ alkylene, $C_2$-$C_6$ alkenylene or $C_2$-$C_6$ alkynylene;

$W^2$ is $C_1$-$C_6$ alkylene;

$R^2$ is phenyl or —$W^3$(phenyl), each substituted on ring members with up to two substituents selected from $R^{21}$; or -G; or $C_1$-$C_6$ alkyl or $C_3$-$C_8$ cycloalkyl;

$W^3$ is $C_1$-$C_6$ alkylene, $C_2$-$C_6$ alkenylene or $C_2$-$C_6$ alkynylene;

each G is independently a 5- or 6-membered heterocyclic ring or an 8-, 9- or 10-membered fused bicyclic ring system, each ring or ring system optionally substituted with up to five substituents selected from $R^{21}$ on carbon ring members and $R^{22}$ on nitrogen ring members;

each $R^{21}$ is independently halogen, cyano, hydroxy, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —OCN, —SCN, —SF$_5$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylamino, $C_2$-$C_8$ dialkylamino, $C_1$-$C_6$ haloalkylamino, $C_2$-$C_8$ halodialkylamino or $C_3$-$C_8$ cycloalkylamino;

each $R^{22}$ is independently $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl; and $R^{23}$ is an optionally substituted carbon moiety which is useful for preparing a compound of Formula 1.

This invention is also directed to a process for preparing a compound of Formula 1 from a compound of formula 1Q in the presence of cesium fluoride:

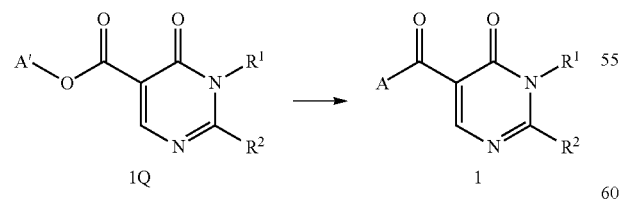

1Q → 1 wherein A' is a radical selected from A'-1, A'-2, A'-3 and A'-5 as defined above for a compound of Formula 1Q; and A is radical selected from A-1, A-2, A-3 and A-5 as defined above for a compound of Formula 1; and $R^1$ and $R^2$ are as defined above for a compound of Formula 1 which is useful for preparing a compound of Formula 1.

This invention is also directed to compounds of Formula 1P (including all stereoisomers), N-oxides, and salts thereof, agricultural compositions containing them and their use as herbicides:

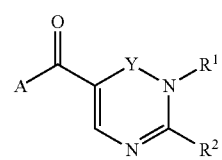

1P wherein
X is CH or N;
Y is C(O) or S(O)$_2$; provided that when Y is S(O)$_2$, then X is CH;
A is a radical selected from the group consisting of

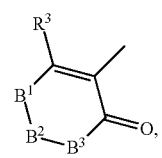

A-1

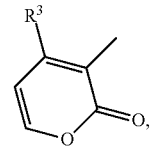

A-2

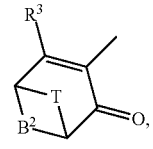

A-3

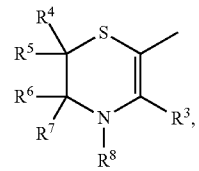

A-4

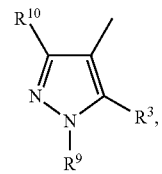

A-5

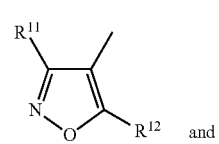

A-6 and

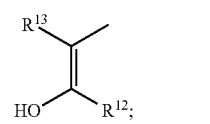

A-7

$B^1$ and $B^3$ are each independently a radical selected from the group consisting of

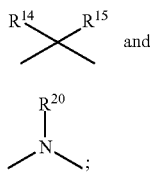

B² is a radical selected from the group consisting of

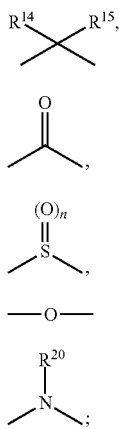

R¹ is phenyl, phenylsulfonyl, —W¹(phenyl), —W¹(S-phenyl), —W¹(SO₂-phenyl), —W²(SO₂CH₂-phenyl) or —W²(SCH₂-phenyl), each optionally substituted on ring members with up to five substituents selected from $R^{21}$; or -G or —W²G; or cyano, hydroxy, amino, —C(=O)OH, —C(=O)NHCN, —C(=O)NHOH, —SO₂NH₂, —SO₂NHCN, —SO₂NHOH, —NHCHO, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_5$-$C_{10}$ cycloalkoxyalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl, $C_2$-$C_8$ haloalkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_2$-$C_8$ alkylcarbonylthio, $C_2$-$C_8$ alkyl(thiocarbonyl)thio, $C_3$-$C_8$ cycloalkylsulfinyl, $C_1$-$C_6$ alkylaminosulfonyl, $C_2$-$C_8$ dialkylaminosulfonyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino or $C_4$-$C_{10}$ cycloalkyl(alkyl)amino;

W¹ is $C_1$-$C_6$ alkylene, $C_2$-$C_6$ alkenylene or $C_2$-$C_6$ alkynylene;

W² is $C_1$-$C_6$ alkylene;

R² is phenyl or —W³(phenyl), each optionally substituted on ring members with up to five substituents selected from $R^{21}$; or -G or —W⁴G; or H, cyano, hydroxy, amino, nitro, —CHO, —C(=O)OH, —C(=O)NH₂, —C(=S)NH₂, —C(=O)NHCN, —C(=O)NHOH, —SH, —SO₂NH₂, —SO₂NHCN, —SO₂NHOH, —SF₅, —NHCHO, —NHNH₂, —NHOH, —NHCN, —NHC(=O)NH₂, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl, $C_2$-$C_8$ haloalkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_2$-$C_8$ alkylcarbonylthio, $C_2$-$C_8$ alkyl(thiocarbonyl)thio, $C_3$-$C_8$ cycloalkylsulfinyl, $C_1$-$C_6$ alkylaminosulfonyl, $C_2$-$C_8$ dialkylaminosulfonyl, $C_3$-$C_{10}$ halotrialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino or $C_4$-$C_{10}$ cycloalkyl(alkyl)amino;

$W^3$ is $C_1$-$C_6$ alkylene, $C_2$-$C_6$ alkenylene or $C_2$-$C_6$ alkynylene;

$W^4$ is $C_1$-$C_6$ alkylene;

$R^3$ is H, halogen, cyano, hydroxy, —O⁻M⁺, amino, nitro, —CHO, —C(=O)OH, —C(=O)NH$_2$, —C(=S)NH$_2$, —SH, —SO$_2$NH$_2$, —SO$_2$NHCN, —SO$_2$NHOH, —OCN, —SCN, —SF$_5$, —NHNH$_2$, —NHOH, —N=C=O, —N=C=S, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylsulfonyloxy, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino or $C_1$-$C_6$ haloalkylsulfonylamino; or benzyloxy, phenyloxy, benzylcarbonyloxy, phenylcarbonyloxy, phenylsulfonyloxy, benzylsulfonyloxy, phenylthio, benzylthio, phenylsulfinyl, benzylsulfinyl, phenylsulfonyl or benzylsulfonyl, each optionally substituted on ring members with up to five substituents selected from $R^{21}$;

M⁺ is an alkali metal cation or an ammonium cation;

$R^4$, $R^5$, $R^6$ and $R^7$ are each independently H, halogen, hydroxy, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy or $C_3$-$C_8$ halocycloalkoxy; or phenyl or benzyl, each optionally substituted on ring members with up to five substituents selected from $R^{21}$;

$R^8$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl or $C_3$-$C_8$ halocycloalkyl; or benzyl optionally substituted on ring members with up to five substituents selected from $R^{21}$;

$R^9$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

$R^{10}$ is H, halogen, cyano, hydroxy, amino, nitro, SH, —SO$_2$NH$_2$, —SO$_2$NHCN, —SO$_2$NHOH, —OCN, —SCN, —SF$_5$, —NHCHO, —NHNH$_2$, —N$_3$, —NHOH, —NHCN, —NHC(=O)NH$_2$, —N=C=O, —N=C=S, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

$R^{11}$ is H, halogen, cyano, hydroxy, amino, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl or $C_2$-$C_8$ alkylsulfonylalkyl; or phenyl optionally substituted with up to five substituents selected from $R^{21}$;

$R^{12}$ is H, halogen, cyano, hydroxy, amino, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl or $C_2$-$C_8$ alkoxycarbonylamino;

$R^{13}$ is H, halogen, cyano, hydroxy, amino, nitro or $C_2$-$C_8$ alkoxycarbonyl;

n is 0, 1, or 2;

each $R^{14}$, $R^{15}$, $R^{18}$ and $R^{19}$ is independently H, halogen, cyano, hydroxy or $C_1$-$C_6$ alkyl; or a pair of $R^{14}$ and $R^{18}$ is taken together as $C_2$-$C_6$ alkylene or $C_2$-$C_6$ alkenylene;

$R^{20}$ is H, $C_1$-$C_6$ haloalkyl, $C_2$-$C_6$ haloalkenyl, $C_1$-$C_6$ alkoxy, $C_1$-$C_6$ haloalkoxy, $C_3$-$C_8$ cycloalkoxy, $C_1$-$C_6$ alkyl, $C_2$-$C_6$ alkenyl, $C_2$-$C_6$ alkynyl or $C_3$-$C_8$ cycloalkyl;

T is $C_1$-$C_6$ alkylene or $C_2$-$C_6$ alkenylene;

each G is independently a 5- or 6-membered heterocyclic ring or an 8-, 9- or 10-membered fused bicyclic ring system, each ring or ring system optionally substituted with up to five substituents selected from $R^{21}$ on carbon ring members and $R^{22}$ on nitrogen ring members;

each $R^{21}$ is independently halogen, cyano, hydroxy, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —OCN, —SCN, —SF$_5$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylamino, $C_2$-$C_8$ dialkylamino, $C_1$-$C_6$ haloalkylamino, $C_2$-$C_8$ halodialkylamino or $C_3$-$C_8$ cycloalkylamino; and each $R^{22}$ is independently $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl.

More particularly, this invention pertains to a compound of Formula 1P (including all stereoisomers), an N-oxide, or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture of (a) a compound of Formula 1P and (b) an active ingredient selected from a photosystem II inhibitor.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$, $R^2$ and $R^3$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkoxyalkenyl" includes straight-chain or branched alkenyl substituted by an alkoxy group. Examples of "alkoxyalkenyl" include $CH_3OCH=CH$, $CH_3C(OCH_3)=CH$ and $CH_3CH_2OCH=CHCH_2$. "Alkoxyalkoxyalkyl" denotes alkoxyalkoxy substitution on alkyl. Examples of "alkoxyalkoxyalkyl" include $CH_3OCH_2OCH_2$, $CH_3OCH_2OCH_2CH_2$, $CH_3CH_2OCH_2OCH_2$ and $CH_3OCH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)-$, $CH_3CH_2S(O)-$, $CH_3CH_2CH_2S(O)-$, $(CH_3)_2CHS(O)-$ and the different butylsulfonyl, pentylsulfinyl and hexylsulfinyl isomers. Examples of "alkylsulfonyl" include $CH_3S(O)_2-$, $CH_3CH_2S(O)_2-$, $CH_3CH_2CH_2S(O)_2-$, $(CH_3)_2CHS(O)_2-$, and the different butylsulfonyl, pentylsulfonyl and hexylsulfonyl isomers. The terms "cycloalkylsulfinyl" and "cycloalkylsulfonyl are defined analogously to the terms "alkylsulfinyl" and "alkylsulfonyl" above.

"Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonylalkyl" include the corresponding sulfoxides and sulfones, respectively. "Alkylamino" includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkylaminoalkyl" denotes alkylamino substitution on alkyl.

Examples of "alkylaminoalkyl" include $CH_3NHCH_2$, $CH_3NHCH_2CH_2$, $CH_3CH_2NHCH_2$, $CH_3CH_2CH_2CH_2NHCH_2$ and $CH_3CH_2NHCH_2CH_2$. Examples of "dialkylaminoalkyl" include $((CH_3)_2CH)_2NCH_2$, $(CH_3CH_2CH_2)_2NCH_2$ and $CH_3CH_2(CH_3)NCH_2CH_2$. The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$.

"Alkylcarbonylthio" denotes a straight-chain or branched alkylcarbonyl attached to and linked through a sulfur atom. Examples of "alkylcarbonylthio" include $CH_3C(=O)S$, $CH_3CH_2CH_2C(=O)S$ and $(CH_3)_2CHC(=O)S$. The term "alkyl(thiocarbonyl)oxy" refers to an alkylsulfinyl moiety group bonded to an oxygen atom. Examples of "alkyl(thiocarbonyl)oxy", include $CH_3CH_2OS(O)$ and $CH_3CH_2CH_2OS(O)$. The term "alkyl(thiocarbonyl)thio" refers to an alkylsulfinyl moiety bonded to a sulfur atom. Examples "alkyl(thiocarbonyl)thio" include $CH_3CH_2S(O)S$.

"Trialkylsilyl" includes 3 branched and/or straight-chain alkyl radicals attached to and linked through a silicon atom, such as trimethylsilyl, triethylsilyl and tert-butyldimethylsilyl. Examples of "halotrialkylsilyl" include $CF_3(CH_3)_2Si$—, $(CF_3)_3Si$—, and $CH_2Cl(CH_3)_2Si$—. "Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2CH_2$. "Cyanoalkyl" denotes an alkyl group substituted with one cyano group. Examples of "cyanoalkyl" include $NCCH_2$, $NCCH_2CH_2$ and $CH_3CH(CN)CH_2$.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. The term "alkylcycloalkyl" denotes alkyl substitution on a cycloalkyl moiety. Examples of "alkylcycloalkyl" include methylcyclopropyl, ethylcyclopentyl, and other straight-chain or branched alkyl groups bonded to cycloalkyl moiety. The term "alkoxycycloalkyl" denotes alkoxy substitution on a cycloalkyl moiety. Examples of "alkoxycycloalkyl" include methoxycyclopropyl, ethoxycyclopentyl, and other straight-chain or branched alkoxy groups bonded to a cycloalkyl moiety. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. Examples of "cyanocycloalkyl" include 4-cyanocyclohexyl and 3-cyanocyclopentyl. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "halocycloalkyl", "haloalkoxy", "haloalkylthio", haloalkylsulfinyl, haloalkylsulfonyl, "haloalkenyloxy", "haloalkynyloxy" "haloalkenyl", "haloalkynyl", "haloalkoxyalkyl", "haloalkoxyalkoxy" "haloalkoxyhaloalkoxy", "haloalkoxyhaloalkyl", "halo alkylamino", "haloalkylaminoalkyl" "halocycloalkoxy", "halocycloalkoxyalkyl", "halocycloalkylalkyl", "halocycloalkenyl", "halocycloalkenyloxy", "halocycloalkenyloxy", "halocycloalkenyloxyalkyl", "alkoxyhaloalkoxy", alkoxyhaloalkyl, haloalkylcarbonyloxy, and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. Examples of "haloalkenyl" include $(Cl)_2C=CHCH_2$— and $CF_3CH_2CH=CHCH_2$—. Examples of "haloalkynyl" include $HC≡CCHCl$—, $CF_3C≡C$—, $CCl_3C≡C$— and $FCH_2C≡CCH_2$—. Examples of "haloalkoxyalkoxy" include $CF_3OCH_2O$—, $ClCH_2CH_2OCH_2CH_2O$—, $Cl_3CCH_2OCH_2O$— as well as branched alkyl derivatives. Examples of "haloalkylamino" include $CF_3(CH_3)CHNH$, $(CF_3)_2CHNH$ and $CH_2ClCH_2NH$. The term "halodialkyl", either alone or in compound words such as "halodialkylamino", means at least one of the two alkyl groups is substituted with at least one halogen atom, and independently each halogenated alkyl group may be partially or fully substituted with halogen atoms which may be the same or different. Examples of "halodialkylamino" include $(BrCH_2CH_2)_2N$ and $BrCH_2CH_2(ClCH_2CH_2)N$.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3OC(=O)$—, $CH_3CH_2OC(=O)$—, $CH_3CH_2CH_2OC(=O)$—, $(CH_3)_2CHOC(=O)$— and the different butoxy- or pentoxycarbonyl isomers. The terms "haloalkylcarbonyl" "haloalkoxycarbonyl", "alkoxyalkylcarbonyl", "cycloalkoxycarbonyl", "cycloalkylalkoxycarbonyl", "cycloalkylaminocarbonyl" are defined analogously.

The term "alkoxycarbonylamino" denotes a straight-chain or branched alkoxy moieties bonded to a $C(=O)$ moiety of carbonylamino group. Examples of "alkoxycarbonylamino" include $CH_3OC(=O)NH$— and $CH_3CH_2OC(=O)NH$—. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$. The term "alkylcarbonyloxy" denotes straight-chain or branched alkyl bonded to a $C(=O)O$ moiety. Examples of "alkylcarbonyloxy" include $CH_3CH_2C(=O)O$ and $(CH_3)_2CHC(=O)O$. The term "alkylcarbonylalkoxy" denotes alkylcarbonyl bonded to an alkoxy moiety. Examples of "alkylcarbonylalkoxy" include $CH_3C(=O)CH_2CH_2O$ and $CH_3CH_2C(=O)CH_2O$. Examples of "alkoxycarbonyloxy" include $CH_3CH_2CH_2OC(=O)O$ and $(CH_3)_2CHOC(=O)O$. The term "cycloalkylcarbonyloxy" denotes a cycloalkylcarbonyl group bonded to oxygen. Examples of "cycloalkylcarbonyloxy" include c-Pr—$C(O)O$— and c-hexyl-$C(O)O$—.

"Alkylsulfonylamino" denotes an NH radical substituted with alkylsulfonyl. Examples of "alkylsulfonylamino" include $CH_3CH_2S(=O)_2NH-$ and $(CH_3)_2CHS(=O)_2NH-$. The term "alkylsulfonyloxy" denotes an alkylsulfonyl group bonded to an oxygen atom. Examples of "alkylsulfonyloxy" include $CH_3S(=O)_2O-$, $CH_3CH_2S(=O)_2O-$, $CH_3CH_2CH_2S(=O)_2O-$, $(CH_3)_2CHS(=O)_2O-$, and the different butylsulfonyloxy, pentylsulfonyloxy and hexylsulfonyloxy isomers.

The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy moieties bonded to straight-chain or branched alkyl groups. The term "cycloalkylthio" denotes cycloalkyl attached to and linked through a sulfur atom such as cyclopropylthio and cyclopentylthio; "cycloalkylsulfonyl" includes the corresponding sulfones. "Alkylcycloalkylalkyl" denotes an alkyl group substituted with alkylcycloalkyl. Examples of "alkylcycloalkylalkyl" include 1-, 2-, 3- or 4-methyl or -ethyl cyclohexylmethyl. The term "cycloalkoxyalkoxyalkyl" denotes a cycloalkoxy moiety attached to an alkoxyalkyl group. Examples of the "cycloalkoxyalkoxyalkyl" include (tetrahydrofuran-2-yl)$CH_2OCH_2-$, (tetrahydrofuran-3-yl)$CH_2CH_2OCH_2-$ or (oxiran-2-yl)$CH_2OCH_2CH_2-$. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

"Dialkoxyalkyl" denotes two independent alkoxy groups substituted on same carbon of the alkyl group. Examples of "dialkoxyalkyl" include $(CH_3O)_2CH-$ and $CH_3CH_2O(CH_3O)CH-$. "Cycloalkylamino" denotes an NH radical substituted with cycloalkyl. Examples of "cycloalkylamino" include cyclopropylamino and cyclohexylamino. "Cycloalkyl(alkyl)amino" means a cycloalkylamino group where the hydrogen atom is replaced by an alkyl radical. Examples of "cycloalkyl(alkyl)amino" include groups such as cyclopropyl(methyl)amino, cyclobutyl(butyl)amino, cyclopentyl(propyl)amino, cyclohexyl(methyl)amino and the like. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups.

"Cycloalkylcarbonyl" denotes cycloalkyl bonded to a $C(=O)$ group including, for example, cyclopropylcarbonyl and cyclopentylcarbonyl. The term "cycloalkoxycarbonyl" means cycloalkoxy bonded to a $C(=O)$ group, for example, cyclopropyloxycarbonyl and cyclopentyloxycarbonyl. "Cycloalkylaminocarbonyl" denotes cycloalkylamino bonded to a $C(=O)$ group, for example, cyclopentylaminocarbonyl and cyclohexylaminocarbonyl. "Cycloalkylalkoxycarbonyl" denotes cycloalkylalkoxy bonded to a $C(=O)$ group. Examples of "cycloalkylalkoxycarbonyl" include cyclopropylethoxycarbonyl and cyclopentylmethoxycarbonyl. "Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy.

The term "cycloalkenylalkyl" denotes cycloalkenyl substitution on an alkyl moiety. Examples of "cycloalkenylalkyl" include cyclobutenylmethyl, cyclopentenylethyl, and other cycloalkenyl moieties bonded to straight-chain or branched alkyl groups. The term "cycloalkenyloxy" denotes cycloalkenyl linked through an oxygen atom such as cyclopentenyloxy and cyclohexenyloxy. The term "cycloalkenyloxyalkyl" denotes cycloalkenyloxy substitution on an alkyl moiety. Examples of "cycloalkenyloxyalkyl" include cyclobutenyloxymethyl, cyclopentenyloxyethyl, and other cycloalkenyloxy moieties bonded to straight-chain or branched alkyl groups.

The term "alkylaminosulfonyl" denotes a straight-chain or branched alkylamino moiety bonded to a sulfonyl group. Examples of an "alkylaminosulfonyl" group include $CH_3NHS(O)_2-$ or $CH_3CH_2CH_2NHS(O)_2-$. The term "dialkylaminosulfonyl" denotes a straight-chain or branched dialkylamino moiety bonded to a sulfonyl group. Examples of a "dialkylaminosulfonyl" group include $(CH_3)_2NS(O)_2-$ or $(CH_3CH_2CH_2)_2NS(O)_2-$.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates $CH_3OCH_2-$; $C_3$ alkoxyalkyl designates, for example, $CH_3CH(OCH_3)-$, $CH_3OCH_2CH_2-$ or $CH_3CH_2OCH_2-$; and $C_4$ alkoxyalkyl designates the various isomers of an alkyl group substituted with an alkoxy group containing a total of four carbon atoms, examples including $CH_3CH_2CH_2OCH_2-$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents, e.g., $(R^v)_r$, r is 1, 2, 3, 4 or 5 in U-1 of Exhibit 2. When a group contains a substituent which can be hydrogen, for example $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{18}$, $R^{19}$ or $R^{20}$, then when this substituent is taken as hydrogen, it is recognized that this is equivalent to said group being unsubstituted. When a variable group is shown to be optionally attached to a position, for example $(R^v)_r$ in Q-29 of Exhibit 1 then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent G) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "ring member" refers to an atom or other moiety (e.g., $C(=O)$, $C(=S)$, $S(O)$ or $S(O)_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" denotes a carbocylcic ring system in which no ring in the ring system is aromatic. The term "nonaromatic heterocyclic ring system" denotes a heterocyclic ring system in which no ring in the ring system is aromatic.

As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When G is a 5- or 6-membered nitrogen-containing heterocyclic ring, it may be attached to the remainder of Formula 1 through any available carbon or nitrogen ring atom, unless otherwise described. When G is (among others) a 5- or 6-membered heterocyclic ring it may be saturated or unsaturated, optionally substituted with one or more substituents selected from a group of substituents as defined in the Summary of the Invention. Examples of a 5- or 6-membered unsaturated aromatic heterocyclic ring optionally substituted with from one or more substituents include the rings Q-1 through Q-60 illustrated in Exhibit 1 wherein $R^V$ is any substituent as defined in the Summary of the Invention for $R^{21}$ on carbon ring members or $R^{22}$ on nitrogen ring members, and r is an integer from 0 to 4, limited by the number of available positions on each Q group. As Q-29, Q-30, Q-36, Q-37, Q-38, Q-39, Q-40, Q-41, Q-42 and Q-43 have only one available position, for these Q groups r is limited to the integers 0 or 1, and r being 0 means that the Q group is unsubstituted and a hydrogen is present at the position indicated by $(R^V)_r$.

Exhibit 1

Q-1
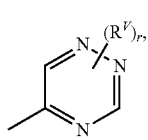

Q-2
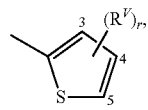

Q-3
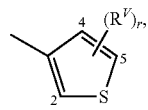

Q-4
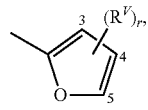

Q-5
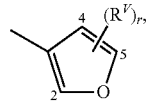

Q-6
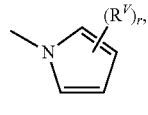

Q-7
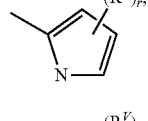

Q-8
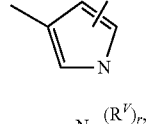

Q-9
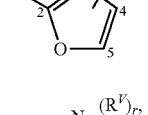

Q-10
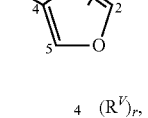

Q-11
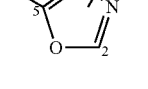

Q-12
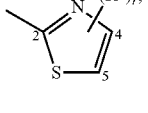

Q-13
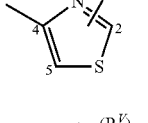

Q-14
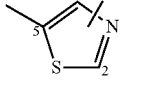

-continued
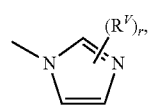 Q-15
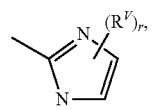 Q-16
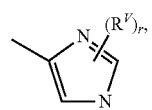 Q-17
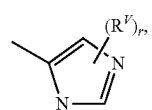 Q-18
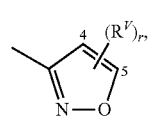 Q-19
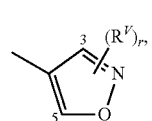 Q-20
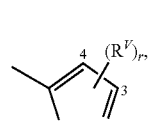 Q-21
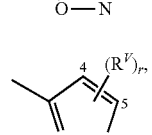 Q-22
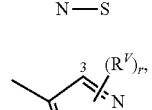 Q-23
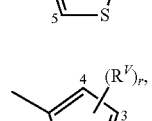 Q-24
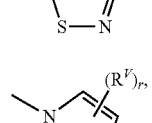 Q-25
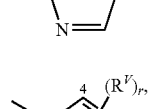 Q-26
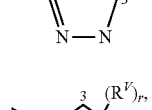 Q-27
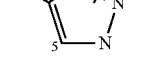
-continued
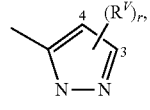 Q-28
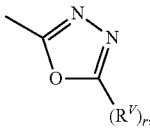 Q-29
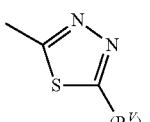 Q-30
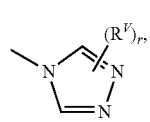 Q-31
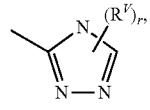 Q-32
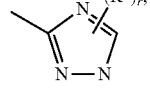 Q-33
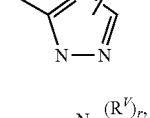 Q-34
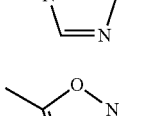 Q-35
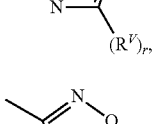 Q-36
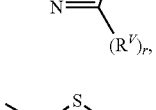 Q-37
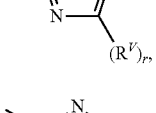 Q-38
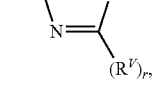 Q-39

-continued

Q-40 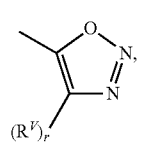

Q-41 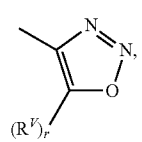

Q-42 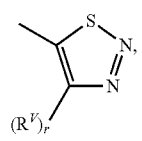

Q-43 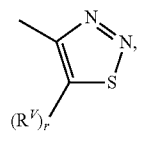

Q-44 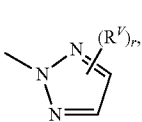

Q-45 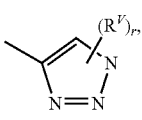

Q-46 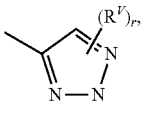

Q-47 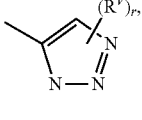

Q-48 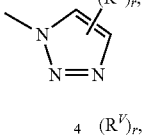

Q-49 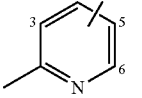

Q-50 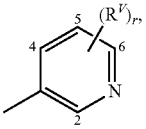

Q-51 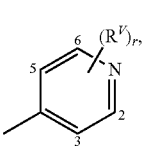

-continued

Q-52 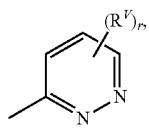

Q-53 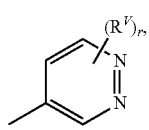

Q-54 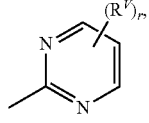

Q-55 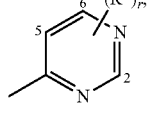

Q-56 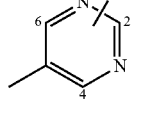

Q-57 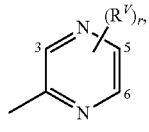

Q-58 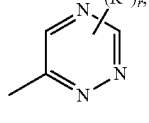

Q-59 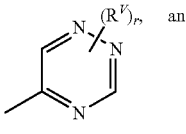 and

Q-60 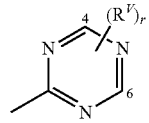

Note that when G is a 5- or 6-membered saturated or unsaturated non-aromatic heterocyclic ring optionally substituted with one or more substituents selected from the group of substituents as defined in the Summary of the Invention for $R^{21}$ one or two carbon ring members of the heterocycle can optionally be in the oxidized form of a carbonyl moiety.

Examples of a 5- or 6-membered saturated or non-aromatic unsaturated heterocyclic ring include the rings U-1 through U-36 as illustrated in Exhibit 2. Note that when the attachment point on the U group is illustrated as floating, the U group can be attached to the remainder of Formula 1 through any available carbon or nitrogen of the U group by replacement of a hydrogen atom. The optional substituents corresponding to $R^v$ can be attached to any available carbon or nitrogen by replacing a hydrogen atom. For these U rings, r is typically an integer from 0 to 4, limited by the number of available positions on each U group.

Note that when G comprises a ring selected from U-29 through U-36, $U^2$ is selected from O, S or N. Note that when $U^2$ is N, the nitrogen atom can complete its valence by substitution with either H or the substituents corresponding to $R^v$ as defined in the Summary of the Invention for U (i.e. $R^{22}$).

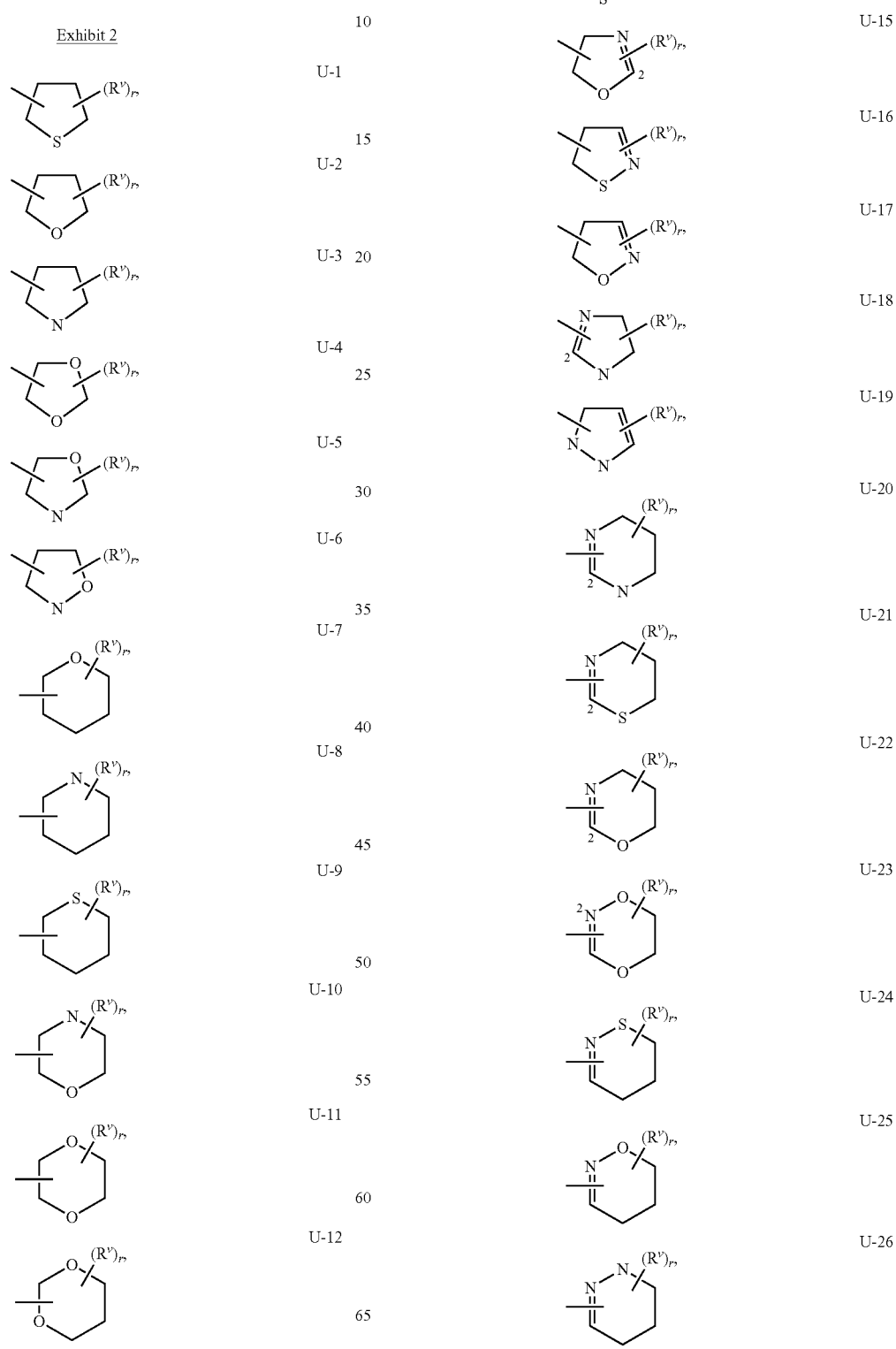

Exhibit 2

-continued

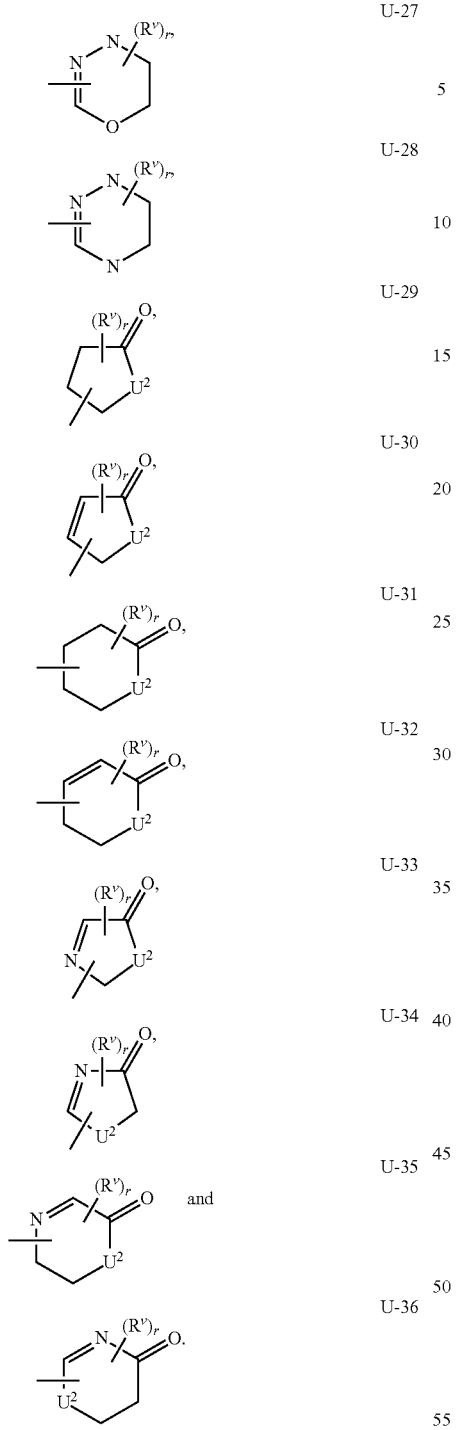

U-27

U-28

U-29

U-30

U-31

U-32

U-33

U-34

U-35 and

U-36

As noted above, G can be (among others) an 8-, 9- or 10-membered fused bicyclic ring system optionally substituted with one or more substituents selected from a group of substituents as defined in the Summary of the Invention (i.e. $R^{21}$). Examples of 8-, 9- or 10-membered fused bicyclic ring system optionally substituted with from one or more substituents include the rings Q-81 through Q-123 illustrated in Exhibit 3 wherein $R^v$ is any substituent as defined in the Summary of the Invention for G (i.e. $R^{21}$ or $R^{22}$), and r is typically an integer from 0 to 4.

Exhibit 3

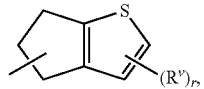

U-81

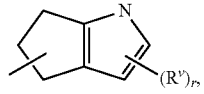

U-82

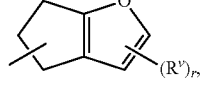

U-83

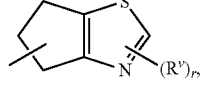

U-84

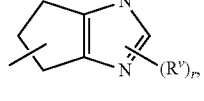

U-85

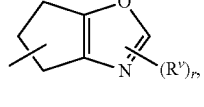

U-86

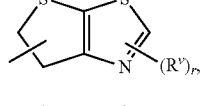

U-87

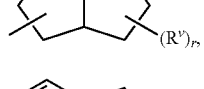

U-88

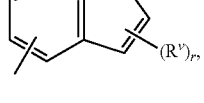

U-89

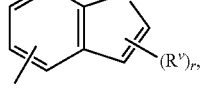

U-90

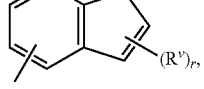

U-91

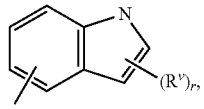

U-92

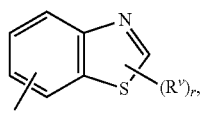

Q-93

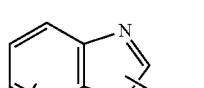

Q-94

| | | | |
|---|---|---|---|
| 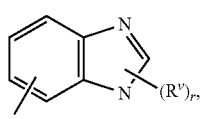 | Q-95 | 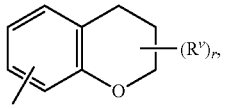 | Q-108 |
| 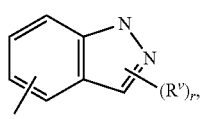 | Q-96 | 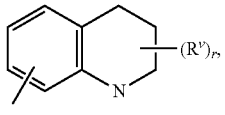 | Q-109 |
| 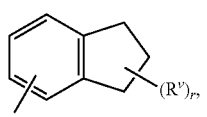 | Q-97 | 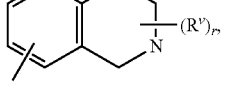 | Q-110 |
| 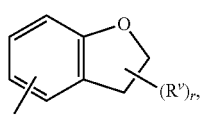 | Q-98 | 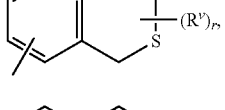 | Q-111 |
| 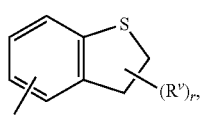 | Q-99 | 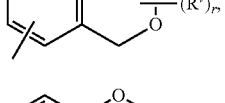 | Q-112 |
| 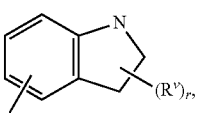 | Q-100 | 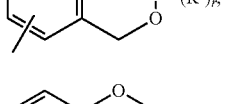 | Q-113 |
| 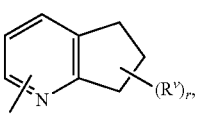 | Q-101 | 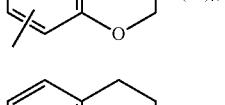 | Q-114 |
| 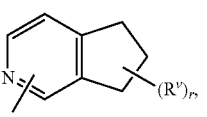 | Q-102 | 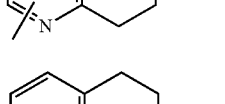 | Q-115 |
| 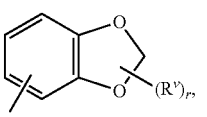 | Q-103 | 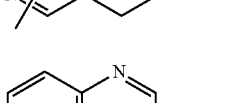 | Q-116 |
| 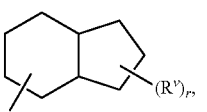 | Q-104 | 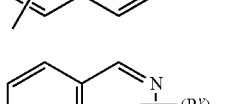 | Q-117 |
| 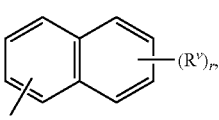 | Q-105 | 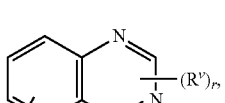 | Q-118 |
| 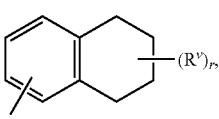 | Q-106 | 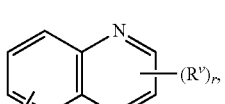 | Q-119 |
| 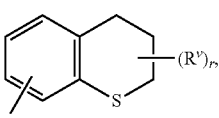 | Q-107 | | Q-120 |

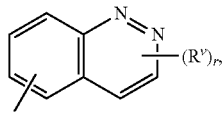

Q-121

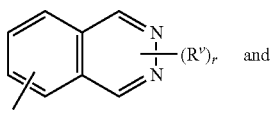 and

Q-122

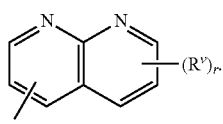

Q-123

Although $R^v$ groups are shown in the structures Q-1 through Q-60 and Q-81 through Q-123, it is noted that they do not need to be present since they are optional substituents. The nitrogen atoms that require substitution to fill their valence are substituted with H or $R^v$. Note that when the attachment point between $(R^v)_r$ and the Q group is illustrated as floating, $(R^v)_r$ can be attached to any available carbon atom or nitrogen atom of the Q group. Note that when the attachment point on the Q group is illustrated as floating, the Q group can be attached to the remainder of Formula 1 through any available carbon or nitrogen of the Q group by replacement of a hydrogen atom. Note that some Q groups can only be substituted with less than 4 $R^v$ groups (e.g., Q-1 through Q-5, Q-7 through Q-48, and Q-52 through Q-60).

As noted in the Summary of the Invention, $R^1$ and $R^2$ are taken together along with the atoms to which they are attached to make a 5-, 6- or 7-membered unsaturated, partially unsaturated or fully unsaturated ring along with members consisting of up to 2 oxygen atoms, 2 nitrogen atoms or 2 sulfur atoms or up to two —S(O)—, —S(O)$_2$—, —C(O)— groups. Besides the possibility of $R^1$ and $R^2$ being separate substituents, they may also be connected to form a ring fused to the ring to which they are attached. The fused ring can be a 5-, 6- or 7-membered ring including as ring members the two atoms shared with the ring to which the substituents are attached. The other 3, 4 or 5 ring members of the fused ring are provided by $R^1$ and $R^2$ substituents taken together. These other ring members can include up to 5 carbon atoms (as allowed by the ring size) and optionally up to 3 heteroatoms selected from up to 2 O, up to 2 S and up to 3 N. The fused ring is optionally substituted with up to 3 substituents as noted in the Summary of the Invention. Exhibit 4 provides, as illustrative examples, rings formed by $R^1$ and $R^2$ taken together. As these rings are fused with a ring of Formula 1, a portion of the Formula 1 ring is shown and the truncated lines represent the ring bonds of the Formula 1 ring. The rings depicted are fused to the two adjacent atoms of a ring as shown in Formula 1. The optional substituents $(R^v)_r$ are independently selected from the group consisting of halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_2$-$C_8$ alkoxyalkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy; on carbon atom ring members. The optional substituents $(R^v)_r$ are independently selected from the group consisting of H and $C_1$-$C_6$ alkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy; on nitrogen ring members. Substituents are limited by the number of available positions on each T-ring. When the attachment point between $(R^v)_r$ and the T-ring is illustrated as floating, $R^v$ may be bonded to any available T-ring carbon or nitrogen atom (as applicable). One skilled in the art recognizes that while r is nominally an integer from 0 to 3, some of the rings shown in Exhibit 4 have less than 3 available positions, and for these groups r is limited to the number of available positions. When "r" is 0 this means the ring is unsubstituted and hydrogen atoms are present at all available positions. If r is 0 and $(R^v)_r$ is shown attached to a particular atom, then hydrogen is attached to that atom. The nitrogen atoms that require substitution to fill their valence are substituted with H or $R^v$. Furthermore, one skilled in the art recognizes that some of the rings shown in Exhibit 4 can form tautomers, and the particular tautomer depicted is representative of all the possible tautomers.

Exhibit 4

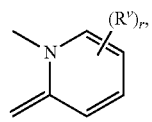

T-1

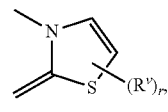

T-2

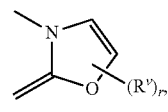

T-3

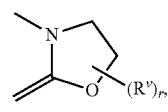

T-4

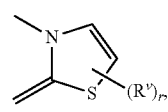

T-5

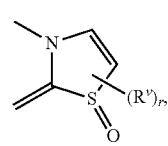

T-6

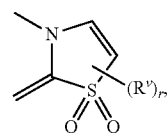

T-7

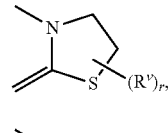

T-8

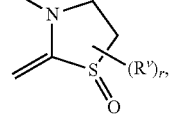

T-9

| | | | |
|---|---|---|---|
| 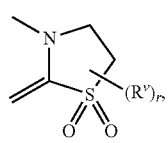 | T-10 | 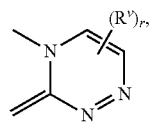 | T-21 |
| 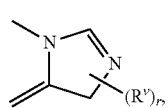 | T-11 | 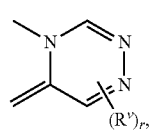 | T-22 |
| 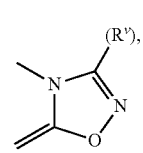 | T-12 | 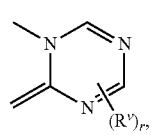 | T-23 |
| 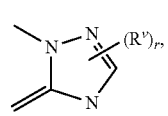 | T-13 | 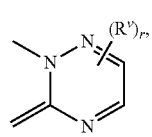 | T-24 |
| 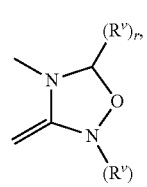 | T-14 | 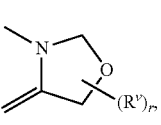 | T-25 |
| | | 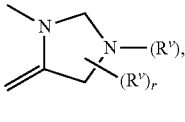 | T-26 |
| 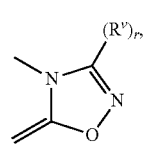 | T-15 | 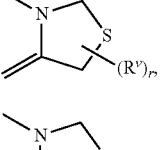 | T-27 |
| 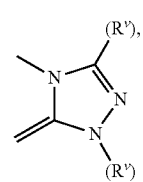 | T-16 | 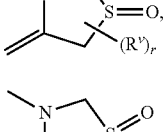 | T-28 |
| | | 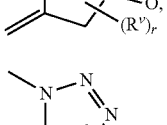 | T-29 |
| 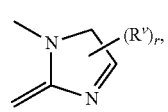 | T-17 | 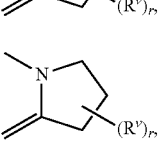 | T-30 |
| 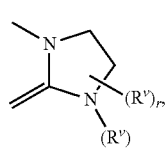 | T-18 | | |
| | | | T-31 |
| 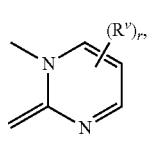 | T-19 | 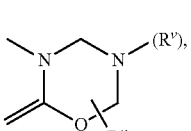 | T-32 |
| 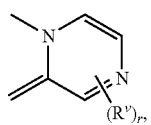 | T-20 | 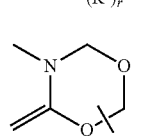 | T-33 |

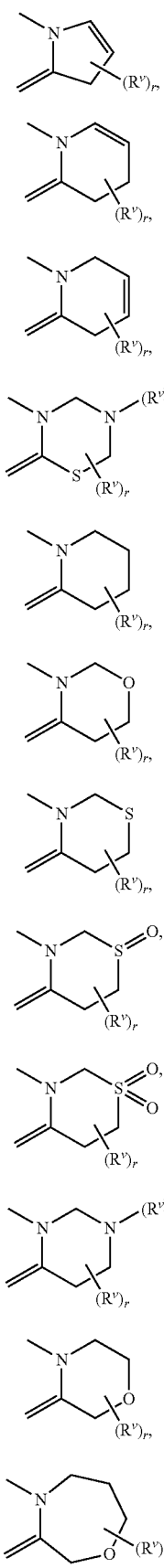
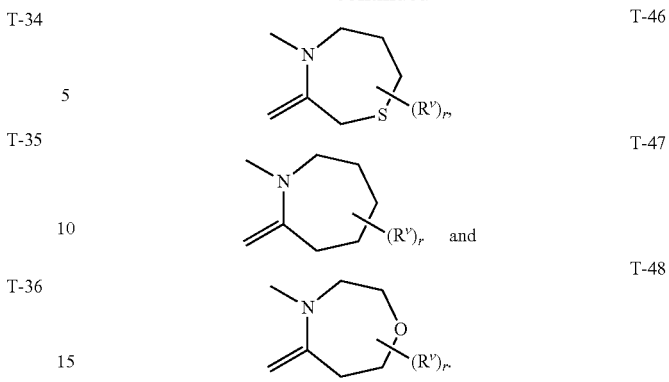

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will recognize that when A is A-1, A-2 or A-3, and the $R^3$ variable is hydroxy or $O^-M^+$, then the resulting compound of Formula 1 can exist in either the "triketone" tautomer or the "di-keto enol" tautomer. Likewise, when A is A-1, A-2 or A-3, and the $R^3$ variable is —SH, the resulting compound of Formula 1 can exist in either the the "di-keto thioketo" tautomer or the "di-keto thioenol" tautomer. In any of these cases and for the purposes of this invention both tautomeric combinations represent fully functional species of the present invention. For example, named species using the phrase "2-(1,3-cyclohexanedione)" is synonomous with the term "3-oxo-1-cyclohexen-1-yl".

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention also include (where Formula 1 as used in the following Embodiments includes N-oxides and salts thereof):

Embodiment 1

A compound of Formula 1 wherein A is A-1, A-3, A-4, A-5 or A-6.

Embodiment 2

A compound of Embodiment 1 wherein A is A-1, A-3, A-5 or A-6.

Embodiment 3

A compound of Embodiment 2 wherein A is A-1, A-3 or A-5.

Embodiment 4

A compound of Embodiment 3 wherein A is A-1 or A-3.

Embodiment 5

A compound of Embodiment 4 wherein A is A-1.

Embodiment 6

A compound of Embodiment 4 wherein A is A-3.

Embodiment 7

A compound of Formula 1 or any one of Embodiments 1 through 5 wherein A is other than A-1.

Embodiment 8

A compound of Formula 1 or any one of Embodiments 1 through 7 wherein $B^1$ is C-1.

Embodiment 9

A compound of Formula 1 or any one of Embodiments 1 through 7 wherein $B^1$ is C-2.

Embodiment 10

A compound of Formula 1 or any one of Embodiments 1 through 9 wherein $B^2$ is C-3.

Embodiment 11

A compound of Formula 1 or any one of Embodiments 1 through 9 wherein $B^2$ is C-4.

Embodiment 12

A compound of Formula 1 or any one of Embodiments 1 through 11 wherein $B^3$ is C-1.

Embodiment 13

A compound of Formula 1 or any one of Embodiments 1 through 11 wherein $B^3$ is C-2.

Embodiment 14

A compound of Formula 1 or any one of Embodiments 1 through 13 wherein $R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2NHCN$, —$SO_2NHOH$, —NHCHO, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{12}$ haloalkynyl, $C_3$-$C_{12}$ cycloalkyl, $C_3$-$C_{12}$ halocycloalkyl, $C_4$-$C_{14}$ alkylcycloalkyl, $C_4$-$C_{14}$ cycloalkylalkyl, $C_6$-$C_{18}$ cycloalkylcycloalkyl, $C_4$-$C_{14}$ halocycloalkylalkyl, $C_5$-$C_{16}$ alkylcycloalkylalkyl, $C_3$-$C_{12}$ cycloalkenyl, $C_3$-$C_{12}$ halocycloalkenyl, $C_2$-$C_{12}$ alkoxyalkyl, $C_3$-$C_{12}$ alkoxyalkenyl, $C_4$-$C_{14}$ alkylcycloalkyl, $C_4$-$C_{14}$ alkoxycycloalkyl, $C_4$-$C_{14}$ cycloalkoxyalkyl, $C_5$-$C_{14}$ cycloalkoxyalkoxyalkyl, $C_3$-$C_{14}$ alkoxyalkoxyalkyl, $C_2$-$C_{12}$ alkylthioalkyl, $C_2$-$C_{12}$ alkylsulfinylalkyl, $C_2$-$C_{12}$ alkylsulfonylalkyl, $C_2$-$C_{12}$ alkylaminoalkyl, $C_3$-$C_{14}$ dialkylaminoalkyl, $C_2$-$C_{12}$ haloalkylaminoalkyl, $C_4$-$C_{14}$ cycloalkylaminoalkyl, $C_2$-$C_{12}$ alkylcarbonyl, $C_2$-$C_{12}$ haloalkylcarbonyl, $C_4$-$C_{14}$ cycloalkylcarbonyl, $C_2$-$C_{12}$ alkoxycarbonyl, $C_4$-$C_{16}$ cycloalkoxycarbonyl, $C_5$-$C_{14}$ cycloalkylalkoxycarbonyl, $C_2$-$C_{12}$ alkylaminocarbonyl, $C_3$-$C_{14}$ dialkylaminocarbonyl, $C_4$-$C_{14}$ cycloalkylaminocarbonyl, $C_2$-$C_9$ cyanoalkyl, $C_1$-$C_{10}$ hydroxyalkyl, $C_4$-$C_{14}$ cycloalkenylalkyl, $C_2$-$C_{12}$ haloalkoxyalkyl, $C_2$-$C_{12}$ alkoxyhaloalkyl, $C_2$-$C_{12}$ haloalkoxyhaloalkyl, $C_4$-$C_{14}$ halocycloalkoxyalkyl, $C_4$-$C_{14}$ cycloalkenyloxyalkyl, $C_4$-$C_{14}$ halocycloalkenyloxyalkyl, $C_3$-$C_{14}$ dialkoxyalkyl, $C_3$-$C_{14}$ alkoxyalkylcarbonyl, $C_3$-$C_{14}$ alkoxycarbonylalkyl or $C_2$-$C_{12}$ haloalkoxycarbonyl.

Embodiment 15

A compound of Formula 1 or any one of Embodiments 1 through 14 wherein $R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2$NHCN, —$SO_2$NHOH, —NHCHO, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl or $C_2$-$C_8$ haloalkoxycarbonyl.

Embodiment 16

A compound of Embodiment 15 wherein $R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{12}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl or $C_2$-$C_8$ alkylsulfonylalkyl.

Embodiment 17

A compound of Embodiment 16 wherein $R^1$ is phenyl or —$W^1$(phenyl), each optionally substituted on ring members with up to two substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl $C_3$-$C_{10}$ alkoxyalkenyl, $C_4$-$C_{10}$ alkylcycloalkyl or $C_4$-$C_{10}$ alkoxycycloalkyl.

Embodiment 18

A compound of Embodiment 17 wherein $R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl.

Embodiment 19

A compound of Embodiment 18 wherein $R^1$ is phenyl, 4-ethylphenyl, 4-methoxyphenyl, 3,5-dimethylphenyl, 3,4-dimethoxyphenyl, 3-fluoro-2-methylphenyl, 4-fluoro-3-methylphenyl or 5-chloro-2-methylphenyl.

Embodiment 20

A compound of Embodiment 19 wherein $R^1$ is phenyl, 3,4-dimethoxyphenyl or 5-chloro-2-methylphenyl.

Embodiment 21

A compound of Embodiment 20 wherein $R^1$ is phenyl.

Embodiment 22

A compound of Embodiment 19 wherein $R^1$ is 3,4-dimethoxyphenyl.

Embodiment 23

A compound of Embodiment 19 wherein $R^1$ is 5-chloro-2-methylphenyl.

Embodiment 24

A compound of Formula 1 or any one of Embodiments 1 through 21 wherein $R^1$ is other than phenyl.

Embodiment 25

A compound of Embodiment 17 wherein $R^1$ is -G or —$W^2$G; $C_1$-$C_6$ alkyl, $C_3$-$C_8$ cycloalkyl, or $C_2$-$C_8$ alkoxyalkyl.

Embodiment 26

A compound of Embodiment 25 wherein $R^1$ is -G or —$W^2$G.

Embodiment 27

A compound of Embodiment 26 wherein $R^1$ is $C_1$-$C_6$ alkyl, $C_3$-$C_8$ cycloalkyl, or $C_2$-$C_8$ alkoxyalkyl.

Embodiment 28

A compound of Embodiment 27 wherein $R^1$ is n-Pr, i-Pr, n-Bu, c-hexyl, c-heptyl, —$CH_2CH_2OCH_3$, —$CH_2CH_2CH_2OCH_3$ or —$CH_2CH_2OCH_2CH_3$.

Embodiment 29

A compound of Embodiment 28 wherein $R^1$ is n-Pr, c-hexyl, —$CH_2CH_2OCH_3$ or —$CH_2CH_2CH_2OCH_3$.

Embodiment 29a

A compound of Embodiment 29 wherein $R^1$ is n-Pr or —$CH_2CH_2OCH_3$.

Embodiment 29b

A compound of Embodiment 29 wherein $R^1$ is c-hexyl.

Embodiment 30

A compound of Formula 1 or any one of Embodiments 1 through 17 wherein $W^1$ is $C_1$-$C_6$ alkylene.

Embodiment 31

A compound of Embodiment 30 wherein $W^1$ is —$CH_2$—.

Embodiment 32

A compound of Formula 1 or any one of Embodiments 1 through 17, 25 or 26 wherein $W^2$ is —$CH_2$—.

Embodiment 33

A compound of Formula 1 or any one of Embodiments 1 through 32 wherein $R^2$ is phenyl or —$W^3$(phenyl), each optionally substituted on ring members with up to five substituents selected from $R^{21}$; or -G; $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ cycloalkoxyalkyl, $C_4$-$C_{10}$ cycloalkoxylalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkoxycarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_3$-$C_8$ cycloalkylsulfinyl or $C_3$-$C_{10}$ halotrialkylsilyl.

Embodiment 34

A compound of Embodiment 33 wherein $R^2$ is phenyl or —$W^3$(phenyl), each optionally substituted on ring members with up to two substituents selected from $R^{21}$; or -G or; or $C_1$-$C_6$ alkyl or $C_3$-$C_8$ cycloalkyl.

Embodiment 35

A compound of Embodiment 34 wherein $R^2$ is phenyl optionally substituted on ring members with up to two substituents selected from $R^{21}$; or -G; or $C_1$-$C_6$ alkyl, $C_3$-$C_8$ cycloalkyl.

Embodiment 36

A compound of Embodiment 35 wherein $R^2$ is phenyl, 2-methylphenyl, 3-methylphenyl, 4-chlorophenyl, 3-fluorophenyl or 3,5-difluorophenyl.

Embodiment 36a

A compound of Embodiment 35 wherein $R^2$ is phenyl, 3-bromophenyl, 3-chlorophenyl, or 2-methylphenyl.

Embodiment 37

A compound of Embodiment 35 wherein $R^2$ is phenyl.

Embodiment 38

A compound of Formula 1 or any one of Embodiments 1 through 36 wherein $R^2$ is other than phenyl.

Embodiment 39

A compound of Embodiment 35 wherein $R^2$ is 3-thienyl or 2-thienyl.

Embodiment 40

A compound of Embodiment 35 wherein $R^2$ is n-propyl, n-butyl, or cyclopropyl.

Embodiment 41

A compound of Formula 1 or any one of Embodiments 1 through 13 wherein $R^1$ and $R^2$ are taken together along with the atoms to which they are attached to make a 6- or 7-membered unsaturated, partially unsaturated or fully unsaturated ring along with members consisting of up to 2 oxygen atoms, 2 nitrogen atoms or 2 sulfur atoms or up to two —S(O)—, —S(O)$_2$—, —C(O)— groups optionally substituted on carbon atom ring members selected from halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_2$-$C_8$ alkoxyalkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy; and optionally substituted on nitrogen ring members selected from H and $C_1$-$C_6$ alkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy.

Embodiment 42

A compound of Embodiment 41 wherein $R^1$ and $R^2$ are taken together along with the atoms to which they are attached to make a 6- or 7-membered unsaturated, partially unsaturated or fully unsaturated ring along with members consisting of up to 1 oxygen atoms, 1 nitrogen atoms or 1 sulfur atoms or up to one —S(O)—, —S(O)$_2$—, —C(O)— groups optionally substituted on carbon atom ring members selected from halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_2$-$C_8$ alkoxyalkyl; and optionally substituted on nitrogen ring members selected from H and $C_1$-$C_6$ alkyl.

Embodiment 43

A compound of Embodiment 42 wherein $R^1$ and $R^2$ are taken together along with the atoms to which they are attached to make a 7-membered partially unsaturated ring optionally substituted with halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl on carbon atom ring members.

Embodiment 44

A compound of Embodiment 43 wherein $R^1$ and $R^2$ are taken together along with the atoms to which they are attached to make an unsubstituted 7-membered partially unsaturated ring.

Embodiment 45

A compound of Formula 1 or any one of Embodiments 1 through 34 wherein $W^3$ is —CH$_2$—.

Embodiment 46

A compound of Formula 1 or any one of Embodiments 1 through 32 wherein $W^4$ is —CH$_2$—.

Embodiment 47

A compound of Formula 1 or any one of Embodiments 1 through 46 wherein $R^3$ is hydroxy, —O$^-$M$^+$, $C_2$-$C_8$ alkylcarbonyloxy, $C_2$-$C_8$ haloalkylcarbonyloxy, $C_4$-$C_{10}$ cycloalkylcarbonyloxy or $C_3$-$C_{10}$ alkylcarbonylalkoxy; or benzyloxy, phenyloxy, benzylcarbonyloxy, phenylcarbonyloxy, phenylsulfonyloxy or benzylsulfonyloxy, each optionally substituted on ring members with up to two substituents selected from $R^{21}$.

Embodiment 48

A compound of Embodiment 47 wherein $R^3$ is hydroxy, —O$^-$M$^+$ or $C_2$-$C_8$ alkylcarbonyloxy; or phenylsulfonyloxy optionally substituted with up to two substituents selected from $R^{21}$.

Embodiment 49

A compound of Embodiment 48 wherein M$^+$ is a sodium or potassium metal cation.

Embodiment 50

A compound of Embodiment 49 wherein $R^3$ is hydroxy or $C_2$-$C_8$ alkylcarbonyloxy.

Embodiment 51

A compound of Embodiment 50 wherein $R^3$ is hydroxy or —OC(=O)CH$_2$CH(CH$_3$)$_2$.

Embodiment 52

A compound of Formula 1 or any one of Embodiments 1, 7 and 14 through 51 wherein $R^4$, $R^5$, $R^6$ and $R^7$ are each independently H, or $C_1$-$C_6$ alkyl.

Embodiment 53

A compound of Formula 1 or any one of Embodiments 1, 7 and 14 through 52 wherein $R^8$ is $C_1$-$C_6$ alkyl or $C_3$-$C_8$ cycloalkyl.

Embodiment 54

A compound of Embodiment 53 wherein $R^8$ is CH$_3$, CH$_2$CH$_3$ or cyclopropyl.

Embodiment 55

A compound of Formula 1 or any one of Embodiments 1 through 3, 7 and 14 through 51 wherein $R^9$ is $C_1$-$C_6$ alkyl.

Embodiment 56

A compound of Embodiment 55 wherein $R^9$ is CH$_2$CH$_3$.

Embodiment 57

A compound of Formula 1 or any one of Embodiments 1 through 3, 7 and 14 through 51 wherein $R^{10}$ is H, halogen or $C_1$-$C_6$ alkyl.

Embodiment 58

A compound of Embodiment 57 wherein $R^{10}$ is H or CH$_3$.

Embodiment 59

A compound of Formula 1 or any one of Embodiments 1, 2, 8, 10 and 12 through 51 wherein $R^{11}$ is H or $C_1$-$C_6$ alkyl.

Embodiment 60

A compound of Embodiment 59 wherein $R^{11}$ is H.

Embodiment 61

A compound of Formula 1 or any one of Embodiments 1, 2, 8, 10 and 12 through 51 wherein $R^{12}$ is H, halogen, cyano, hydroxy, amino or $C_1$-$C_6$ alkyl.

Embodiment 62

A compound of Embodiment 61 wherein $R^{12}$ is H, halogen, cyano, $C_1$-$C_6$ alkyl or $C_3$-$C_8$ cycloalkyl.

Embodiment 63

A compound of Embodiment 62 wherein $R^{12}$ is $CH_3$, $CH_2CH_3$ or cyclopropyl.

Embodiment 64

A compound of Formula 1 or any one of Embodiments 7 and 15 through 51 wherein $R^{13}$ is H, halogen, cyano or nitro.

Embodiment 65

A compound of Embodiment 64 wherein $R^{13}$ is cyano or nitro.

Embodiment 66

A compound of Formula 1 or any one of Embodiments 1 through 65 wherein when instances of $R^{14}$ and $R^{18}$ are taken alone (i.e. $R^{14}$ and $R^{18}$ are not taken together as alkylene or alkenylene), then independently said instances of $R^{14}$ and $R^{18}$ are H or $C_1$-$C_6$ alkyl.

Embodiment 67

A compound of Embodiment 66 wherein when instances of $R^{14}$ and $R^{18}$ are taken alone, then independently said instances of $R^{14}$ and $R^{18}$ are H or $CH_3$.

Embodiment 68

A compound of Embodiment 68 wherein when instances of $R^{14}$ and $R^{18}$ are taken alone, then independently said instances of $R^{14}$ and $R^{18}$ are H.

Embodiment 69

A compound of Formula 1 or any one of Embodiments 1 through 68 wherein when instances of $R^{14}$ and $R^{18}$ are taken together, then said instances of $R^{14}$ and $R^{18}$ are taken together as —$CH_2CH_2CH_2$— or —CH=CHCH$_2$—.

Embodiment 70

A compound of Formula 1 or any one of Embodiments 1 through 68 wherein all instances of $R^{14}$ and $R^{18}$ are taken alone.

Embodiment 71

A compound of Formula 1 or any one of Embodiments 1 through 70 wherein independently each $R^{15}$ and $R^{19}$ is H or $C_1$-$C_6$ alkyl.

Embodiment 72

A compound of Embodiment 71 wherein independently each $R^{15}$ and $R^{19}$ is H or $CH_3$.

Embodiment 73

A compound of Embodiment 72 wherein independently each $R^{15}$ and $R^{19}$ is H.

Embodiment 73a

A compound of Embodiments 67 and 72 wherein each $R^{14}$, $R^{15}$, $R^{18}$ and $R^{19}$ is H or $CH_3$.

Embodiment 73b

A compound of Embodiment 73 wherein each $R^{14}$, $R^{15}$, $R^{18}$ and $R^{19}$ is H.

Embodiment 74

A compound of Formula 1 or any one of Embodiments 1 through 73 wherein $R^{20}$ is H, $C_1$-$C_6$ alkyl, $C_2$-$C_6$ alkenyl or $C_3$-$C_8$ cycloalkyl.

Embodiment 75

A compound of Embodiment 74 wherein $R^{20}$ is H or $CH_3$.

Embodiment 76

A compound of Formula 1 or any one of Embodiments 1 through 4, 6, 10, 11 and 14 through 51 wherein T is —$CH_2CH_2$— or —CH=CH—.

Embodiment 77

A compound of Embodiment 76 wherein T is —$CH_2CH_2$—.

Embodiment 78

A compound of Formula 1 or any one of Embodiments 1 through 17 wherein each G is independently a 5- or 6-membered heterocyclic ring optionally substituted with up to five substituents selected from $R^{21}$ on carbon ring members and $R^{22}$ on nitrogen ring members.

Embodiment 79

A compound of Embodiment 78 wherein G is

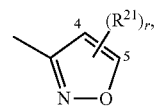

G-1

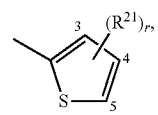

G-2

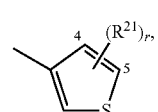

G-3

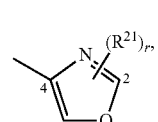

G-4

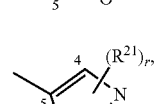

G-5 r is 0, 1, 2 or 3.

Embodiment 80

A compound of Embodiment 79 wherein G is G-2, G-3, G-9, G-15, G-18, G-19 or G-20.

Embodiment 81

A compound of Embodiment 79 wherein when $R^1$ is G, then G is G-18, G-19 or G-20.

Embodiment 82

A compound of Embodiment 81 wherein when $R^1$ is G, then G is G-19 or G-20.

Embodiment 83

A compound of Embodiment 82 wherein when $R^1$ is G, then G is G-20.

Embodiment 84

A compound of Embodiment 82 wherein when $R^1$ is G, then G is G-19.

Embodiment 85

A compound of Embodiment 79 wherein when $R^2$ is G, then G is G-2, G-3 or G-15.

Embodiment 86

A compound of Embodiment 84 wherein when $R^2$ is G, then G is G-2 or G-3.

Embodiment 87

A compound of Embodiment 84 wherein when $R^2$ is G, then G is G-2.

Embodiment 88

A compound of Embodiment 84 wherein when $R^2$ is G, then G is G-3.

Embodiment 89

A compound of Formula 1 or any one of Embodiments 1 through 88 wherein each $R^{21}$ is independently halogen, cyano, hydroxy, nitro, —CHO, —SH, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or $C_3$-$C_8$ cycloalkylsulfonyl.

Embodiment 90

A compound of Embodiment 91 wherein each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment 91

A compound of Embodiment 92 wherein each $R^{21}$ is independently fluorine, chlorine, bromine, $CH_3$, $CF_3$, $OCH_3$, $OCF_3$ or $SCH_3$.

Embodiment 92

A compound of Formula 1 or any one of Embodiments 1 through 91 wherein each $R^{22}$ is independently $C_1$-$C_6$ alkyl or $C_1$-$C_6$ haloalkyl.

Embodiment 93

A compound of Embodiment 92 wherein each $R^{22}$ is independently $CH_3$ or $CH_2CF_3$.

This invention also includes a herbicidal mixture comprising (a) a compound of Formula 1 and (b) at least one additional active ingredient selected from (b1) photosystem II inhibitors, (b2) AHAS inhibitors, (b3) ACCase inhibitors, (b4) auxin mimics and (b5) EPSP inhibitors.

Embodiment 94

A herbicidal mixture comprising (a) a compound of Formula 1 and (b) at least one additional active ingredient selected from (b1), (b2) and (b3).

Embodiment 95

A herbicidal mixture comprising (a) a compound of Formula 1 and (b) at least one additional active ingredient selected from (b1).

Embodiment 96

A herbicidal mixture of Embodiment 95 comprising (a) a compound of Formula 1 and (b) one additional active ingredient selected from the group consisting of ametryn, amicarbazone, atrazine, bentazon, bromacil, bromoxynil, chlorotoluron, dimethametryn, diuron, hexazinone, isoproturon, metribuzin, pyridate, simazine and terbutryn.

Embodiment 97

A herbicidal mixture of Embodiment 95 comprising (a) a compound of Formula 1; and (b) bromoxynil.

Embodiment 98

A herbicidal mixture of Embodiment 95 comprising (a) a compound of Formula 1; and (b) dimethametryn.

Embodiment 99

A herbicidal mixture comprising (a) a compound of Formula 1 and (b) diuron and hexazinone.

Combinations of Embodiments 1-93 are illustrated by:

Embodiment A

A compound of Formula 1 wherein
A is A-1, A-3, A-4, A-5 or A-6;
$R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2$NHCN, —$SO_2$NHOH, —NHCHO, $C_1$-$C_{10}$ alkyl, $C_2$-$C_{10}$ alkenyl, $C_2$-$C_{10}$ alkynyl, haloalkyl, $C_2$-$C_{10}$ haloalkenyl, $C_2$-$C_{12}$ haloalkynyl, $C_3$-$C_{12}$ cycloalkyl, $C_3$-$C_{12}$ halocycloalkyl, $C_4$-$C_{14}$ alkylcycloalkyl, $C_4$-$C_{14}$ cycloalkylalkyl, $C_6$-$C_{18}$ cycloalkylcycloalkyl, $C_4$-$C_{14}$ halocycloalkylalkyl, $C_5$-$C_{16}$ alkylcycloalkylalkyl, $C_3$-$C_{12}$ cycloalkenyl, $C_3$-$C_{12}$ halocycloalkenyl, $C_2$-$C_{12}$ alkoxyalkyl, $C_3$-$C_{12}$ alkoxyalkenyl, $C_4$-$C_{14}$ alkylcycloalkyl, $C_4$-$C_{14}$ alkoxycycloalkyl, $C_4$-$C_{14}$ cycloalkoxyalkyl, $C_5$-$C_{14}$ cycloalkoxyalkoxyalkyl, $C_3$-$C_{14}$ alkoxyalkoxyalkyl, $C_2$-$C_{12}$ alkylthioalkyl, $C_2$-$C_{12}$ alkylsulfinylalkyl, $C_2$-$C_{12}$ alkylsulfonylalkyl, $C_2$-$C_{12}$ alkylaminoalkyl, $C_3$-$C_{14}$ dialkylaminoalkyl, $C_2$-$C_{12}$ haloalkylaminoalkyl, $C_4$-$C_{14}$ cycloalkylaminoalkyl, $C_2$-$C_{12}$ alkylcarbonyl, $C_2$-$C_{12}$ haloalkylcarbonyl, $C_4$-$C_{14}$ cycloalkylcarbonyl, $C_2$-$C_{12}$ alkoxycarbonyl, $C_4$-$C_{16}$ cycloalkoxycarbonyl, $C_5$-$C_{14}$ cycloalkylalkoxycarbonyl, $C_2$-$C_{12}$ alkylaminocarbonyl, $C_3$-$C_{14}$ dialkylaminocarbonyl, $C_4$-$C_{14}$ cycloalkylaminocarbonyl, $C_2$-$C_9$ cyanoalkyl, $C_1$-$C_{10}$ hydroxyalkyl, $C_4$-$C_{14}$ cycloalkenylalkyl, $C_2$-$C_{12}$ haloalkoxyalkyl, $C_2$-$C_{12}$ alkoxyhaloalkyl, $C_2$-$C_{12}$ haloalkoxyhaloalkyl, $C_4$-$C_{14}$ halocycloalkoxyalkyl, $C_4$-$C_{14}$ cycloalkenyloxyalkyl, $C_4$-$C_{14}$ halocycloalkenyloxyalkyl, $C_3$-$C_{14}$ dialkoxyalkyl, $C_3$-$C_{14}$ alkoxyalkylcarbonyl, $C_3$-$C_{14}$ alkoxycarbonylalkyl or $C_2$-$C_{12}$ haloalkoxycarbonyl;
$W^1$ is $C_1$-$C_6$ alkylene;
$W^2$ is —$CH_2$—;
$R^2$ is phenyl or —$W^3$(phenyl), each optionally substituted on ring members with up to five substituents selected from $R^{21}$; or -G; $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ cycloalkoxyalkyl, $C_4$-$C_{10}$ cycloalkoxylalkoxyalkyl, $C_3$-$C_{10}$ alkoxyalkoxyalkyl, $C_2$-$C_8$ alkylthioalkyl, $C_2$-$C_8$ alkylsulfonylalkyl, $C_2$-$C_8$ alkylsulfonylalkyl, $C_2$-$C_8$ alkylcarbonyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_3$-$C_8$ cycloalkylsulfinyl or $C_3$-$C_{10}$ halotrialkylsilyl;

$W^3$ is —$CH_2$—;
$W^4$ is —$CH_2$—;
$R^1$ and $R^2$ are taken together along with the atoms to which they are attached to make a 6- or 7-membered unsaturated, partially unsaturated or fully unsaturated ring along with members consisting of up to 2 oxygen atoms, 2 nitrogen atoms or 2 sulfur atoms or up to two —S(O)—, —S(O)$_2$—, —C(O)— groups optionally substituted on carbon atom ring members selected from halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl and $C_2$-$C_8$ alkoxyalkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy; and optionally substituted on nitrogen ring members selected from H and $C_1$-$C_6$ alkyl; and phenyl optionally substituted with up to 5 substituents selected from cyano, nitro, halogen, $C_1$-$C_6$ alkyl, $C_1$-$C_6$ alkoxy and $C_1$-$C_6$ haloalkoxy;
$R^3$ is hydroxy, $C_2$-$C_8$ alkylcarbonyloxy, $C_2$-$C_8$ haloalkylcarbonyloxy, $C_4$-$C_{10}$ cycloalkylcarbonyloxy or $C_3$-$C_{10}$ alkylcarbonylalkoxy; or benzyloxy, phenyloxy, benzylcarbonyloxy, phenylcarbonyloxy, phenylsulfonyloxy or benzylsulfonyloxy, each optionally substituted on ring members with up to two substituents selected from $R^{21}$;
$M^+$ is a sodium or potassium metal cation;
$R^9$ is $C_1$-$C_6$ alkyl;
$R^{10}$ is H, halogen or $C_1$-$C_6$ alkyl;
$R^{11}$ is H or $C_1$-$C_6$ alkyl;
$R^{12}$ is H, halogen, cyano, hydroxy, amino or $C_1$-$C_6$ alkyl;
$R^{13}$ is cyano or nitro;
each $R^{14}$, $R^{15}$, $R^{18}$ and $R^{19}$ is H or $CH_3$;
$R^{14}$ and $R^{18}$ are taken together as —$CH_2CH_2CH_2$— or —CH=CHCH$_2$—;
$R^{20}$ is H or $CH_3$;
T is —$CH_2CH_2$— or —CH=CH—;
each G is G-1 through G-20 (as depicted in Embodiment 79);
r is 0, 1, 2 or 3;
each $R^{21}$ is independently halogen, cyano, hydroxy, nitro, —CHO, —SH, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or $C_3$-$C_8$ cycloalkylsulfonyl; and each $R^{22}$ is independently $C_1$-$C_6$ alkyl or $C_1$-$C_6$ haloalkyl.

Embodiment B

A compound of Embodiment A wherein
X is CH;
A is A-3 or A-5;
$B^2$ is C-3;
$R^1$ is phenyl, —$W^1$(phenyl), —$W^1$(S-phenyl), —$W^1$(SO$_2$-phenyl), —$W^2$(SO$_2$CH$_2$-phenyl) or —$W^2$(SCH$_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkoxyalkyl, $C_2$-$C_8$ alkylthioalkyl or $C_2$-$C_8$ alkylsulfonylalkyl;
$R^2$ is phenyl or —$W^3$(phenyl), each optionally substituted on ring members with up to two substituents selected from $R^{21}$; or $C_1$-$C_6$ alkyl, $C_1$-$C_6$ haloalkyl, $C_3$-$C_8$ cycloalkyl, $C_1$-$C_6$ alkoxy, $C_1$-$C_6$ alkylthio or $C_1$-$C_6$ alkylsulfonyl;
$R^3$ is hydroxy or —O$^-$M$^+$; or phenylsulfonyloxy optionally substituted on ring members with up to two substituents selected from $R^{21}$;
$R^9$ is $CH_2CH_3$;
$R^{10}$ is H or $CH_3$;
$W^1$ is —$CH_2$—;
$W^3$ is —$CH_2$—;
G is G-13, G-14, G-15, G-16 or G-17; and
each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment C

A compound of Embodiment A wherein
A is A-1, A-3 or A-5;
$B^1$ is C-1;
$B^2$ is C-3;
$B^3$ is C-1;
$R^1$ is phenyl, —$W^1$(phenyl), —$W^1$(S-phenyl), —$W^1$(SO$_2$-phenyl), —$W^2$(SO$_2$CH$_2$-phenyl) or —$W^2$(SCH$_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_{12}$ alkylsulfonylalkyl or $C_2$-$C_8$ alkylsulfonylalkyl;

$W^1$ is —$CH_2$—;
$R^2$ is phenyl or —$W^3$(phenyl), each optionally substituted on ring members with up to two substituents selected from $R^{21}$; or -G or; or $C_1$-$C_6$ alkyl or $C_3$-$C_8$ cycloalkyl;
$R^1$ and $R^2$ are taken together along with the atoms to which they are attached to make an unsubstituted 7-membered partially unsaturated ring;
$R^3$ is hydroxy or $C_2$-$C_8$ alkylcarbonyloxy;
$R^9$ is $CH_2CH_3$;
$R^{10}$ is H or $CH_3$;
G is G-2, G-3, G-9, G-15, G-18, G-19 or G-20; and
$R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment D

A compound of Embodiment C wherein
A is A-1 or A-3;
$R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl;
$R^2$ is phenyl, 2-methylphenyl, 3-methylphenyl, 3-bromophenyl, 3-chlorophenyl, 4-chlorophenyl, 3-fluorophenyl or 3,5-difluorophenyl;
$R^3$ is hydroxy or —$OC(=O)CH_2CH(CH_3)_2$;
each $R^{14}$, $R^{15}$, $R^{18}$ and $R^{19}$ is H or $CH_3$; and T is —$CH_2CH_2$—.

Embodiment E

A compound of Embodiment D wherein
A is A-1;
$R^1$ is phenyl, 4-ethylphenyl, 4-methoxyphenyl, 3,5-dimethylphenyl, 3,4-dimethoxyphenyl, 3-fluoro-2-methylphenyl, 4-fluoro-3-methylphenyl or 5-chloro-2-methylphenyl;
$R^2$ is phenyl, 3-chlorophenyl, or 2-methylphenyl;
$R^3$ is hydroxy or —$OC(=O)CH_2CH(CH_3)_2$; and each $R^{14}$, $R^{15}$, $R^{18}$ and $R^{19}$ is H.

Embodiment F

A compound of Embodiment C wherein
A is A-3;
$R^1$ is n-Pr or —$CH_2CH_2OCH_3$;
$R^2$ is phenyl, 2-methylphenyl, 3-methylphenyl, 4-chlorophenyl, 3-fluorophenyl or 3,5-difluorophenyl;
$R^3$ is hydroxy; and
each $R^{14}$, $R^{15}$, $R^{18}$ and $R^{19}$ is H.

Embodiment G

A compound of Embodiment C wherein
A is A-1;
$R^1$ is -G or —$W^2G$; $C_1$-$C_6$ alkyl, $C_3$-$C_8$ cycloalkyl, or $C_2$-$C_8$ alkoxyalkyl;
G is G-19 or G-20;
$R^2$ is phenyl, 2-methylphenyl, 3-methylphenyl, 4-chlorophenyl, 3-fluorophenyl or 3,5-difluorophenyl;
$R^3$ is hydroxy; and
each $R^{14}$, $R^{15}$, $R^{18}$ and $R^{19}$ is H.

Embodiment H

A compound of Embodiment C wherein
A is A-1;
$R^1$ is n-Pr, c-hexyl, —$CH_2CH_2OCH_3$ or —$CH_2CH_2CH_2OCH_3$;
$R^2$ is 3-thienyl or 2-thienyl;
$R^3$ is hydroxy; and
each $R^{14}$, $R^{15}$, $R^{18}$ and $R^{19}$ is H.

Specific embodiments include a compound of Formula 1 selected from:
5-[(2-hydroxy-6-oxo-1-cyclohexen-1-yl)carbonyl]-2,3-diphenyl-4(3H)-pyrimidinone (Compound 2),
5-[(2-hydroxy-6-oxo-1-cyclohexane-1-yl)carbonyl]-3-(3-methoxypropyl)-2-(3-methylphenyl)-4(3H)-pyrimidinone (Compound 118),
5-[(2-hydroxy-6-oxo-cyclohexen-1-yl)carbonyl]-3-(2-methoxyethyl)-2-(3-thienyl)-4(3H)-pyrimidinone (Compound 97),
5-[(2-hydroxy-6-oxo-cyclohexen-1-yl)carbonyl]-3-(4-methoxyphenyl)-2-phenyl-4(3H)-pyrimidinone (Compound 4),
5-[(2-hydroxy-6-oxo-cyclohexen-1-yl)carbonyl]-3-(3-methoxypropyl)-2-phenyl-4(3H)-pyrimidinone (Compound 81) and
3-cyclohexyl-5-[(2-hydroxy-6-oxo-cyclohexen-1-yl)carbonyl]-2-phenyl-4(3H)-pyrimidinone (Compound 128).

Embodiments of the present invention as described in the Summary of the Invention also include (where Formula 1Q from the Summary of the Invention as used in the following Embodiments includes N-oxides and salts thereof):

Embodiment 1Q

A compound of Formula 1Q wherein A' is A'-1, A'-3 or A'-5.

Embodiment 2Q

A compound of Embodiment 2Q wherein A' is A'-1 or A'-3.

Embodiment 3Q

A compound of Embodiment 3Q wherein A' is A'-1.

Embodiment 4Q

A compound of Embodiment 4Q wherein A' is A'-3.

Embodiment 5Q

A compound of Formula 1Q or any one of Embodiments 1Q through 4Q wherein $B^1$ is C-1.

Embodiment 6Q

A compound of Formula 1Q or any one of Embodiments 1Q through 4Q wherein $B^1$ is C-2.

Embodiment 7Q

A compound of Formula 1Q or any one of Embodiments 1Q through 6Q wherein $B^2$ is C-3.

Embodiment 8Q

A compound of Formula 1Q or any one of Embodiments 1Q through 9Q wherein $B^2$ is C-4.

Embodiment 9Q

A compound of Formula 1Q or any one of Embodiments 1Q through 8Q wherein $B^3$ is C-1.

Embodiment 10Q

A compound of Formula 1Q or any one of Embodiments 1Q through 8Q wherein $B^3$ is C-2.

Embodiment 11Q

A compound of Formula 1Q or any one of Embodiments 1Q through 10Q wherein $R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_{12}$ alkylsulfinylalkyl or $C_2$-$C_8$ alkylsulfonylalkyl.

Embodiment 12Q

A compound of Embodiment 11Q wherein $R^1$ is phenyl or —$W^1$(phenyl), each optionally substituted on ring members with up to two substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl $C_3$-$C_{10}$ alkoxyalkenyl, $C_4$-$C_{10}$ alkylcycloalkyl or $C_4$-$C_{10}$ alkoxycycloalkyl.

Embodiment 13Q

A compound of Embodiment 12Q wherein $R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl.

Embodiment 14Q

A compound of Embodiment 13Q wherein $R^1$ is phenyl, 4-ethylphenyl, 4-methoxyphenyl, 3,5-dimethylphenyl, 3,4-dimethoxyphenyl, 3-fluoro-2-methylphenyl, 4-fluoro-3-methylphenyl or 5-chloro-2-methylphenyl. Embodiment 15Q. A compound of Embodiment 14Q wherein $R^1$ is phenyl, 3,4-dimethoxyphenyl or 5-chloro-2-methylphenyl.

Embodiment 16Q

A compound of Embodiment 15Q wherein $R^1$ is phenyl.

Embodiment 17Q

A compound of Embodiment 14Q wherein $R^1$ is 3,4-dimethoxyphenyl.

Embodiment 18Q

A compound of Embodiment 14Q wherein $R^1$ is 5-chloro-2-methylphenyl.

Embodiment 19Q

A compound of Formula 1Q or any one of Embodiments 1 through 16Q wherein $R^1$ is other than phenyl.

Embodiment 20Q

A compound of Embodiment 11Q wherein $R^1$ is -G or —$W^2$G; $C_1$-$C_6$ alkyl, $C_3$-$C_8$ cycloalkyl, or $C_2$-$C_8$ alkoxyalkyl.

Embodiment 21Q

A compound of Embodiment 20Q wherein $R^1$ is -G or —$W^2$G.

Embodiment 22Q

A compound of Embodiment 20Q wherein $R^1$ is $C_1$-$C_6$ alkyl, $C_3$-$C_8$ cycloalkyl or $C_2$-$C_8$ alkoxyalkyl.

Embodiment 23Q

A compound of Embodiment 22Q wherein $R^1$ is n-Pr, i-Pr, n-Bu, c-hexyl, —$CH_2CH_2OCH_3$, —$CH_2CH_2CH_2OCH_3$ or —$CH_2CH_2OCH_2CH_3$.

Embodiment 24Q

A compound of Embodiment 23Q wherein $R^1$ is n-Pr, c-hexyl, —$CH_2CH_2OCH_3$ or —$CH_2CH_2CH_2OCH_3$.

Embodiment 25Q

A compound of Formula 1Q or any one of Embodiments 1Q through 12Q wherein $W^1$ is $C_1$-$C_6$ alkylene.

Embodiment 26Q

A compound of Embodiment 25Q wherein $W^1$ is —$CH_2$—.

Embodiment 27Q

A compound of Formula 1Q or any one of Embodiments 1Q through 12Q, 20Q or 21Q wherein $W^2$ is —$CH_2$—.

Embodiment 28Q

A compound of Formula 1Q or any one of Embodiments Embodiment 1Q through 27Q wherein $R^2$ is phenyl or —$W^3$ (phenyl), each optionally substituted on ring members with up to two substituents selected from $R^{21}$; or -G or; or $C_1$-$C_6$ alkyl or $C_3$-$C_8$ cycloalkyl.

Embodiment 29Q

A compound of Embodiment 28Q wherein $R^2$ is phenyl optionally substituted on ring members with up to two substituents selected from $R^{21}$; or -G; or $C_1$-$C_6$ alkyl, $C_3$-$C_8$ cycloalkyl.

Embodiment 30Q

A compound of Embodiment 29Q wherein $R^2$ is phenyl, 2-methylphenyl, 3-methylphenyl, 3-bromophenyl, 3-chlorophenyl, 4-chlorophenyl, 3-fluorophenyl or 3,5-difluorophenyl.

Embodiment 31Q

A compound of Embodiment 30Q wherein $R^2$ is phenyl.

Embodiment 32Q

A compound of Formula 1Q or any one of Embodiments 1Q through 30Q wherein $R^2$ is other than phenyl.

Embodiment 33Q

A compound of Embodiment 32Q wherein $R^2$ is 3-thienyl or 2-thienyl.

Embodiment 34Q

A compound of Embodiment 33Q wherein $R^2$ is n-propyl, n-butyl, or cyclopropyl.

Embodiment 35Q

A compound of Formula 1Q or any one of Embodiments 1Q through 28Q wherein $W^3$ is —$CH_2$—.

Embodiment 36Q

A compound of Formula 1Q or any one of Embodiments 1Q through 3Q, 7Q and 14Q through 51Q wherein $R^9$ is $C_1$-$C_6$ alkyl.

Embodiment 37Q

A compound of Formula 1Q or any one of Embodiments 1Q or 11Q through 36Q wherein $R^9$ is $CH_2CH_3$.

Embodiment 38Q

A compound of Formula 1Q or any one of Embodiments 1Q or 11Q through 36Q wherein $R^{10}$ is H, halogen or $C_1$-$C_6$ alkyl.

Embodiment 39Q

A compound of Embodiment 38Q wherein $R^{10}$ is H or $CH_3$.

Embodiment 40Q

A compound of Formula 1Q or any one of Embodiments 1Q through 39Q wherein when instances of $R^{14}$ and $R^{18}$ are taken alone (i.e. $R^{14}$ and $R^{18}$ are not taken together as alkylene or alkenylene), then independently said instances of $R^{14}$ and $R^{18}$ are H or $C_1$-$C_6$ alkyl.

Embodiment 41Q

A compound of Embodiment 40Q wherein when instances of $R^{14}$ and $R^{18}$ are taken alone, then independently said instances of $R^{14}$ and $R^{18}$ are H or $CH_3$.

Embodiment 42Q

A compound of Embodiment 41Q wherein when instances of $R^{14}$ and $R^{18}$ are taken alone, then independently said instances of $R^{14}$ and $R^{18}$ are H.

Embodiment 43Q

A compound of Formula 1Q or any one of Embodiments 1Q through 42Q wherein independently each $R^{15}$ and $R^{19}$ is is H or $CH_3$.

Embodiment 44Q

A compound of Embodiment 43Q wherein independently each $R^{15}$ and $R^{19}$ is H.

Embodiment 45Q

A compound of Formula 1Q or any one of Embodiments 1Q through 44Q wherein $R^{20}$ is H, $C_1$-$C_6$ alkyl, $C_2$-$C_6$ alkenyl or $C_3$-$C_8$ cycloalkyl.

Embodiment 46Q

A compound of Embodiment 45Q wherein $R^{20}$ is H or $CH_3$.

Embodiment 47Q

A compound of Formula 1Q or any one of Embodiments 1Q, 2Q, 4Q, 7Q, 8Q and 11Q through 46Q wherein T is —$CH_2CH_2$— or —CH=CH—.

Embodiment 48Q

A compound of Embodiment 47Q wherein T is —$CH_2CH_2$—.

Embodiment 49Q

A compound of Formula 1Q or any one of Embodiments 1Q through 48Q wherein G is G-2, G-3, G-9, G-15, G-18, G-19 or G-20 (as depicted in Embodiment 79).

Embodiment 50Q

A compound of Embodiment 49Q wherein when $R^1$ is G, then G is G-19 or G-20.

Embodiment 51Q

A compound of Embodiment 50Q wherein when $R^1$ is G, then G is G-19.

Embodiment 52Q

A compound of Embodiment 50Q wherein when $R^1$ is G, then G is G-20.

Embodiment 53Q

A compound of Embodiment 49Q wherein when $R^2$ is G, then G is G-2, G-3 or G-15.

Embodiment 54Q

A compound of Embodiment 53Q wherein when $R^2$ is G, then G is G-2.

Embodiment 55Q

A compound of Embodiment 53Q wherein when $R^2$ is G, then G is G-3.

Embodiment 56Q

A compound of Formula 1Q or any one of Embodiments 1Q through 55Q wherein each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment 57Q

A compound of Embodiment 56Q wherein each $R^{21}$ is independently fluorine, chlorine, bromine, $CH_3$, $CF_3$, $OCH_3$, $OCF_3$ or $SCH_3$.

Embodiment 58Q

A compound of Formula 1Q or any one of Embodiments 1Q through 57Q wherein each $R^{22}$ is independently $C_1$-$C_6$ alkyl or $C_1$-$C_6$ haloalkyl.

Embodiment 59Q

A compound of Embodiment 58Q wherein each $R^{22}$ is independently $CH_3$ or $CH_2CF_3$.

Embodiments of the present invention as described in the Summary of the Invention also include (where Formula 1R from the Summary of the Invention as used in the following Embodiments include N-oxides and salts thereof):

Embodiment 1R

A compound of Formula 1R wherein $R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_{12}$ alkylsulfinylalkyl or $C_2$-$C_8$ alkylsulfonylalkyl.

Embodiment 2R

A compound of Embodiment 1R wherein $R^1$ is phenyl or —$W^1$(phenyl), each optionally substituted on ring members with up to two substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl or $C_4$-$C_{10}$ alkoxycycloalkyl.

Embodiment 3R

A compound of Embodiment 2R wherein $R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl.

Embodiment 4R

A compound of Embodiment 3R wherein $R^1$ is phenyl, 4-ethylphenyl, 4-methoxyphenyl, 3,5-dimethylphenyl, 3,4-dimethoxyphenyl, 3-fluoro-2-methylphenyl, 4-fluoro-3-methylphenyl or 5-chloro-2-methylphenyl.

Embodiment 5R

A compound of Embodiment 4R wherein $R^1$ is phenyl, 3,4-dimethoxyphenyl or 5-chloro-2-methylphenyl.

Embodiment 6R

A compound of Embodiment 5R wherein $R^1$ is phenyl.

Embodiment 7R

A compound of Embodiment 4R wherein $R^1$ is 3,4-dimethoxyphenyl.

Embodiment 8R

A compound of Embodiment 4R wherein $R^1$ is 5-chloro-2-methylphenyl.

Embodiment 9R

A compound of Formula 1R or any one of Embodiments 1R through 8R wherein $R^1$ is other than phenyl.

Embodiment 10R

A compound of Formula 1R or any one of Embodiments 1R and 2R R wherein $R^1$ is -G or —$W^2$G; $C_1$-$C_6$ alkyl, $C_3$-$C_8$ cycloalkyl, or $C_2$-$C_8$ alkoxyalkyl.

Embodiment 11R

A compound of Embodiment 10R wherein $R^1$ is -G or —$W^2$G.

Embodiment 12R

A compound of Embodiment 10R wherein $R^1$ is $C_1$-$C_6$ alkyl, $C_3$-$C_8$ cycloalkyl, or $C_2$-$C_8$ alkoxyalkyl.

Embodiment 13R

A compound of Embodiment 12R wherein $R^1$ is n-Pr, i-Pr, n-Bu, c-hexyl, —$CH_2CH_2OCH_3$, —$CH_2CH_2CH_2OCH_3$ or —$CH_2CH_2OCH_2CH_3$.

Embodiment 14R

A compound of Embodiment 13R wherein $R^1$ is n-Pr, c-hexyl, —$CH_2CH_2OCH_3$ or —$CH_2CH_2CH_2OCH_3$.

Embodiment 15R

A compound of Formula 1R or any one of Embodiments 1R and 2R wherein $W^1$ is $C_1$-$C_6$ alkylene.

Embodiment 16R

A compound of Embodiment 15R wherein $W^1$ is —$CH_2$—.

Embodiment 17R

A compound of Formula 1R or any one of Embodiments 1R, 2R 10R and 11R wherein $W^2$ is —$CH_2$—.

Embodiment 18R

A compound of Formula 1R or any one of Embodiments Embodiment 1R through 17R wherein $R^2$ is phenyl or —$W^3$ (phenyl), each optionally substituted on ring members with up to two substituents selected from $R^{21}$; or -G or; or $C_1$-$C_6$ alkyl or $C_3$-$C_8$ cycloalkyl.

Embodiment 19R

A compound of Embodiment 18R wherein $R^2$ is phenyl optionally substituted on ring members with up to two substituents selected from $R^{21}$; or -G; or $C_1$-$C_6$ alkyl or $C_3$-$C_8$ cycloalkyl.

Embodiment 20R

A compound of Embodiment 19R wherein $R^2$ is phenyl, 2-methylphenyl, 3-methylphenyl, 3-bromophenyl, 3-chlorophenyl, 4-chlorophenyl, 3-fluorophenyl or 3,5-difluorophenyl.

Embodiment 21R

A compound of Embodiment 20R wherein $R^2$ is phenyl.

Embodiment 22R

A compound of Formula 1R or any one of Embodiments 1R through 21R wherein $R^2$ is other than phenyl.

Embodiment 23R

A compound of Embodiment 22R wherein $R^2$ is 3-thienyl or 2-thienyl.

Embodiment 24R

A compound of Embodiment 23R wherein $R^2$ is n-propyl, n-butyl, or cyclopropyl.

Embodiment 25R

A compound of Formula 1R or any one of Embodiments 1R through 18R wherein $W^3$ is —$CH_2$—.

Embodiment 26R

A compound of Formula 1R or any one of Embodiments 1R through 25R wherein G is G-2, G-3, G-9, G-15, G-18, G-19 or G-20 (as depicted in Embodiment 79).

Embodiment 27R

A compound of Embodiment 26R wherein when $R^1$ is G, then G is G-19 or G-20.

Embodiment 28R

A compound of Embodiment 27R wherein when $R^1$ is G, then G is G-19.

Embodiment 29R

A compound of Embodiment 28R wherein when $R^1$ is G, then G is G-20.

Embodiment 30R

A compound of Embodiment 26R wherein when $R^2$ is G, then G is G-2, G-3 or G-15.

Embodiment 31R

A compound of Embodiment 30R wherein when $R^2$ is G, then G is G-2.

Embodiment 32R

A compound of Embodiment 31R wherein when $R^2$ is G, then G is G-3.

Embodiment 33R

A compound of Formula 1R or any one of Embodiments 1R through 32R wherein each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment 34R

A compound of Embodiment 33R wherein each $R^{21}$ is independently fluorine, chlorine, bromine, $CH_3$, $CF_3$, $OCH_3$, $OCF_3$ or $SCH_3$.

Embodiment 35R

A compound of Formula 1R or any one of Embodiments 1R through 32R wherein each $R^{22}$ is independently $C_1$-$C_6$ alkyl or $C_1$-$C_6$ haloalkyl.

Embodiment 36R

A compound of Embodiment 35R wherein each $R^{22}$ is independently $CH_3$ or $CH_2CF_3$.

Embodiments of the present invention as described in the Summary of the Invention also include (where Formula 1S from the Summary of the Invention as used in the following Embodiments includes N-oxides and salts thereof):

Embodiment 1S

A compound of Formula 1S wherein $R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_{12}$ alkylsulfinylalkyl or $C_2$-$C_8$ alkylsulfonylalkyl.

Embodiment 2S

A compound of Embodiment 1S wherein $R^1$ is phenyl or —$W^1$(phenyl), each optionally substituted on ring members with up to two substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl.

Embodiment 3S

A compound of Embodiment 2S wherein $R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl.

Embodiment 4S

A compound of Embodiment 3S wherein $R^1$ is phenyl, 4-ethylphenyl, 4-methoxyphenyl, 3,5-dimethylphenyl, 3,4-dimethoxyphenyl, 3-fluoro-2-methylphenyl, 4-fluoro-3-methylphenyl or 5-chloro-2-methylphenyl.

Embodiment 5S

A compound of Embodiment 4S wherein $R^1$ is phenyl, 3,4-dimethoxyphenyl or 5-chloro-2-methylphenyl.

Embodiment 6S

A compound of Embodiment 5S wherein $R^1$ is phenyl.

Embodiment 7S

A compound of Embodiment 4S wherein $R^1$ is 3,4-dimethoxyphenyl.

Embodiment 8S

A compound of Embodiment 4S wherein $R^1$ is 5-chloro-2-methylphenyl.

Embodiment 9S

A compound of Formula 1S or any one of Embodiments 1S through 8S wherein $R^1$ is other than phenyl.

Embodiment 10S

A compound of Formula 1S or any one of Embodiments 1S and 2S wherein $R^1$ is -G or —$W^2$G; $C_1$-$C_6$ alkyl, $C_3$-$C_8$ cycloalkyl, or $C_2$-$C_8$ alkoxyalkyl.

Embodiment 11S

A compound of Embodiment 10S wherein $R^1$ is -G or —$W^2$G.

Embodiment 12S

A compound of Embodiment 10S wherein $R^1$ is $C_1$-$C_6$ alkyl, $C_3$-$C_8$ cycloalkyl, or $C_2$-$C_8$ alkoxyalkyl.

Embodiment 13S

A compound of Embodiment 12S wherein $R^1$ is n-Pr, i-Pr, n-Bu, c-hexyl, —$CH_2CH_2OCH_3$, —$CH_2CH_2CH_2OCH_3$ or —$CH_2CH_2OCH_2CH_3$.

Embodiment 14S

A compound of Embodiment 13S wherein $R^1$ is n-Pr, c-hexyl, —$CH_2CH_2OCH_3$ or —$CH_2CH_2CH_2OCH_3$.

Embodiment 15S

A compound of Formula 1S or any one of Embodiments 1S and 2S wherein $W^1$ is $C_1$-$C_6$ alkylene.

Embodiment 16S

A compound of Embodiment 15S wherein $W^1$ is —$CH_2$—.

Embodiment 17S

A compound of Formula 1S or any one of Embodiments 1S, 2S 10S and 11S wherein $W^2$ is —$CH_2$—.

Embodiment 18S

A compound of Formula 1S or any one of Embodiments Embodiment 1S through 17S wherein $R^2$ is phenyl or —$W^3$(phenyl), each optionally substituted on ring members with up to two substituents selected from $R^{21}$; or -G or; or $C_1$-$C_6$ alkyl or $C_3$-$C_8$ cycloalkyl.

Embodiment 19S

A compound of Embodiment 18S wherein $R^2$ is phenyl optionally substituted on ring members with up to two substituents selected from $R^{21}$; or -G; or $C_1$-$C_6$ alkyl, $C_3$-$C_8$ cycloalkyl.

Embodiment 20S

A compound of Embodiment 19S wherein $R^2$ is phenyl, 2-methylphenyl, 3-methylphenyl, 3-bromophenyl, 3-chlorophenyl, 4-chlorophenyl, 3-fluorophenyl or 3,5-difluorophenyl.

Embodiment 21S

A compound of Embodiment 20S wherein $R^2$ is phenyl.

Embodiment 22S

A compound of Formula 1S or any one of Embodiments 1S through 21S wherein $R^2$ is other than phenyl.

Embodiment 23S

A compound of Embodiment 22S wherein $R^2$ is 3-thienyl or 2-thienyl.

Embodiment 24S

A compound of Embodiment 23S wherein $R^2$ is n-propyl, n-butyl, or cyclopropyl.

Embodiment 25S

A compound of Formula 1S or any one of Embodiments 1S through 18S wherein $W^3$ is —$CH_2$—.

Embodiment 26S

A compound of Formula 1S or any one of Embodiments 1S through 25S wherein G is G-2, G-3, G-9, G-15, G-18, G-19 or G-20 (as depicted in Embodiment 79).

Embodiment 27S

A compound of Embodiment 26S wherein when $R^1$ is G, then G is G-19 or G-20.

Embodiment 28S

A compound of Embodiment 27S wherein when $R^1$ is G, then G is G-19.

Embodiment 29S

A compound of Embodiment 28S wherein when $R^1$ is G, then G is G-20.

Embodiment 30S

A compound of Embodiment 26S wherein when $R^2$ is G, then G is G-2, G-3 or G-15.

Embodiment 31S

A compound of Embodiment 30R wherein when $R^2$ is G, then G is G-2.

Embodiment 32S

A compound of Embodiment 31R wherein when $R^2$ is G, then G is G-3.

Embodiment 33S

A compound of Formula 1R or any one of Embodiments 1R through 32R wherein each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment 34S

A compound of Embodiment 33R wherein each $R^{21}$ is independently fluorine, chlorine, bromine, $CH_3$, $CF_3$, $OCH_3$, $OCF_3$ or $SCH_3$.

Embodiment 35S

A compound of Formula 1R or any one of Embodiments 1R through 32R wherein each $R^{22}$ is independently $C_1$-$C_6$ alkyl or $C_1$-$C_6$ haloalkyl.

Embodiment 36S

A compound of Embodiment 58Q wherein each $R^{22}$ is independently $CH_3$ or $CH_2CF_3$.

Embodiment 37S

A compound of Formula 1S or any on of Embodiments 1S through 36S wherein when $R^{23}$ is an optionally substituted carbon moiety, $R^{23}$ is $C_1$-$C_{16}$ alkyl; or phenyl or benzyl optionally substituted with halogen, nitro, cyano or hydroxy on ring members.

Embodiment 38S

A compound of Embodiment 37S wherein when $R^{23}$ is an optionally substituted carbon moiety, $R^{23}$ is $C_1$-$C_{10}$ alkyl; or phenyl or benzyl optionally substituted with halogen or nitro on ring members.

Embodiment 39S

A compound of Embodiment 38S wherein when $R^{23}$ is an optionally substituted carbon moiety, $R^{23}$ is $C_1$-$C_6$ alkyl; or benzyl optionally substituted with halogen or nitro on ring members.

Embodiment 40S

A compound of Embodiment 39S wherein when $R^{23}$ is an optionally substituted carbon moiety, $R^{23}$ is $C_1$-$C_6$ alkyl; or unsubstituted benzyl.

Embodiment 41S

A compound of Embodiment 40S wherein when $R^{23}$ is an optionally substituted carbon moiety, $R^{23}$ is $C_1$-$C_6$ alkyl.

Embodiment 42S

A compound of Embodiment 41S wherein when $R^{23}$ is an optionally substituted carbon moiety, $R^{23}$ is unsubstituted benzyl.

Embodiment 43S

A compound of Embodiment 42S wherein when $R^{23}$ is an optionally substituted carbon moiety, $R^{23}$ is ethyl, n-propyl, n-butyl or i-propyl.

Embodiment 44S

A compound of Embodiment 43S wherein when $R^{23}$ is an optionally substituted carbon moiety, $R^{23}$ is ethyl, n-propyl or i-propyl.

Embodiment 45S

A compound of Embodiment 44S wherein when $R^{23}$ is an optionally substituted carbon moiety, $R^{23}$ is ethyl.

Embodiments of the present invention as described in the Summary of the Invention also include (where Formula 1P as used in the following Embodiments includes N-oxides and salts thereof):

Embodiment P1

A compound of Formula 1P wherein X is N.

Embodiment P2

A compound of Formula 1P wherein X is CH.

Embodiment P3

A compound of Formula 1P or any one of Embodiments P1 through P2 wherein Y is C(O).

Embodiment P4

A compound of Formula 1P or Embodiment P2 wherein Y is $S(O)_2$.

Embodiment P5

A compound of Formula 1P or any one of Embodiments P1 through P4 wherein A is A-1, A-3, A-4, A-5 or A-6.

Embodiment P6

A compound of Embodiment P5 wherein A is A-1, A-3, A-5 or A-6.

Embodiment P7

A compound of Embodiment P6 wherein A is A-3 or A-5.

Embodiment P8

A compound of Embodiment P7 wherein A is A-3.

Embodiment P9

A compound of Embodiment P6 wherein A is A-1 or A-6.

Embodiment P10

A compound of Embodiment P9 wherein A is A-1.

Embodiment P11

A compound of Formula 1P or any one of Embodiments P1 through P9 wherein A is other than A-1.

Embodiment P12

A compound of Formula 1P or any one of Embodiments P1 through P11 wherein $B^1$ is C-1.

Embodiment P13

A compound of Formula 1P or any one of Embodiments P1 through P11 wherein $B^1$ is C-2.

Embodiment P14

A compound of Formula 1P or any one of Embodiments P1 through P13 wherein $B^2$ is C-3.

Embodiment P15

A compound of Formula 1P or any one of Embodiments P1 through P13 wherein $B^2$ is C-4.

Embodiment P16

A compound of Formula 1P or any one of Embodiments P1 through P13 wherein $B^2$ is C-6

Embodiment P17

A compound of Formula 1P or any one of Embodiments P1 through P13 wherein $B^2$ is C-7.

Embodiment P18

A compound of Formula 1P or any one of Embodiments P1 through P17 wherein $B^3$ is C-1.

Embodiment P19

A compound of Formula 1P or any one of Embodiments P1 through P17 wherein $B^3$ is C-2.

Embodiment P20

A compound of Formula 1P or any one of Embodiments P1 through P19 wherein $R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2NHCN$, —$SO_2NHOH$, —NHCHO, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl or $C_2$-$C_8$ haloalkoxycarbonyl.

Embodiment P21

A compound of Embodiment P20 wherein $R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkoxyalkyl, $C_2$-$C_8$ alkylthioalkyl or $C_2$-$C_8$ alkylsulfonylalkyl.

Embodiment P22

A compound of Embodiment P21 wherein $R^1$ is phenyl or —$W^1$(phenyl), each optionally substituted on ring members with up to two substituents selected from $R^{21}$; or $C_1$-$C_6$ alkyl or $C_2$-$C_6$ alkenyl.

Embodiment P23

A compound of Embodiment P22 wherein $R^1$ is phenyl, 2-fluorophenyl, 3-fluorophenyl, 4-fluorophenyl, 2-chlorophenyl, 3-chlorophenyl, 4-chlorophenyl, 4-methylphenyl, 2-methylphenyl, 4-methoxyphenyl, 2,3-dimethylphenyl, $CH_2$(phenyl), $CH_3$ or $CH_2CH_3$.

Embodiment P24

A compound of Embodiment P23 wherein $R^1$ is phenyl.

Embodiment P25

A compound of Formula 1P or any one of Embodiments P1 through P22 wherein $W^1$ is $C_1$-$C_6$ alkylene.

Embodiment P26

A compound of Embodiment P25 wherein $W^1$ is —$CH_2$—.

Embodiment P27

A compound of Formula 1P or any one of Embodiments P1 through P21 or P25 or P26 wherein $W^2$ is —$CH_2$—.

Embodiment P28

A compound of Formula 1P or any one of Embodiments P1 through P27 wherein $R^2$ is phenyl or —$W^3$(phenyl), each optionally substituted on ring members with up to five substituents selected from $R^{21}$; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_4$-$C_{10}$ cycloalkoxyalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_3$-$C_8$ cycloalkylsulfinyl or $C_3$-$C_{10}$ halotrialkylsilyl.

Embodiment P29

A compound of Embodiment P28 wherein $R^2$ is phenyl or —$W^3$(phenyl), each optionally substituted on ring members with up to two substituents selected from $R^{21}$; or $C_1$-$C_6$ alkyl, $C_1$-$C_6$ haloalkyl, $C_3$-$C_8$ cycloalkyl, $C_1$-$C_6$ alkoxy, $C_1$-$C_6$ alkylthio or $C_1$-$C_6$ alkylsulfonyl.

Embodiment P30

A compound of Embodiment P29 wherein $R^2$ is phenyl or $CH_2$(phenyl), each optionally substituted on ring members with up to two substituents selected from $R^{21}$; or $C_1$-$C_6$ alkyl, $C_3$-$C_8$ cycloalkyl or $C_1$-$C_6$ alkylthio.

Embodiment P31

A compound of Embodiment P30 wherein $R^2$ is phenyl, 2-chlorophenyl, 3-chlorophenyl, 4-chlorophenyl, $CH_2CH_3$, cyclopropyl or $SCH_3$.

Embodiment P32

A compound of Formula 1P or any one of Embodiments P1 through P29 wherein $W^3$ is $C_1$-$C_6$ alkylene.

Embodiment P33

A compound of Embodiment P32 wherein $W^3$ is —$CH_2$—.

Embodiment P34

A compound of Formula 1P or any one of Embodiments P1 through P27 or P32 or P33 wherein $W^4$ is —$CH_2$—.

Embodiment P35

A compound of Formula 1P or any one of Embodiments P1 through P34 wherein $R^3$ is hydroxy, $C_2$-$C_8$ alkylcarbonyloxy, $C_2$-$C_8$ haloalkylcarbonyloxy, $C_4$-$C_{10}$ cycloalkylcarbonyloxy or $C_3$-$C_{10}$ alkylcarbonylalkoxy; or benzyloxy, phenyloxy, benzylcarbonyloxy, phenylcarbonyloxy, phenylsulfonyloxy or benzylsulfonyloxy, each optionally substituted on ring members with up to two substituents selected from $R^{21}$.

Embodiment P36

A compound of Embodiment P35 wherein $R^3$ is hydroxy or —$O^-M^+$; or phenylsulfonyloxy optionally substituted with up to two substituents selected from $R^{21}$.

Embodiment P37

A compound of Embodiment P36 wherein $R^3$ is hydroxy; or phenylsulfonyloxy substituted with $CH_3$ at the 4-position.

Embodiment P38

A compound of Formula 1P or any one of Embodiments P1 through P36 wherein $M^+$ is a sodium or potassium metal cation.

Embodiment P39

A compound of Formula 1P or any of Embodiments P1 through P7 and P12 through P38 wherein $R^4$, $R^5$, $R^6$ and $R^7$ are each independently H, or $C_1$-$C_6$ alkyl.

Embodiment P40

A compound of Formula 1P or any one of Embodiments P1 through P7 and 12 through 39 wherein $R^8$ is $C_1$-$C_6$ alkyl or $C_3$-$C_8$ cycloalkyl.

Embodiment P41

A compound of Embodiment P40 wherein $R^8$ is $CH_3$, $CH_2CH_3$ or cyclopropyl.

Embodiment P42

A compound of Formula 1P or any one of Embodiments P1 through P9 and 12 through 41 wherein $R^9$ is $C_1$-$C_6$ alkyl.

Embodiment P43

A compound of Embodiment P42 wherein $R^9$ is $CH_2CH_3$.

Embodiment P44

A compound of Formula 1P or any one of Embodiments P1 through P9 and 12 through 41 wherein $R^{10}$ is H, halogen or $C_1$-$C_6$ alkyl.

Embodiment P45

A compound of Embodiment P44 wherein $R^{10}$ is H or $CH_3$.

Embodiment P46

A compound of Formula 1P or any one of Embodiments P1 through P8, P10, and P12 through P45 wherein $R^{11}$ is H or $C_1$-$C_6$ alkyl.

Embodiment P47

A compound of Embodiment P46 wherein $R^{11}$ is H.

Embodiment P48

A compound of Formula 1P or any one of Embodiments P1 through P8, P10, and P12 through P47 wherein $R^{12}$ is H, halogen, cyano, hydroxy, amino or $C_1$-$C_6$ alkyl.

Embodiment P49

A compound of Embodiment P48 wherein $R^{12}$ is H, halogen, cyano, $C_1$-$C_6$ alkyl or $C_3$-$C_8$ cycloalkyl.

Embodiment P50

A compound of Embodiment P49 wherein $R^{12}$ is $CH_3$, $CH_2CH_3$ or cyclopropyl.

Embodiment P51

A compound of Formula 1P or any one of Embodiments P1 through P6 and P12 through P50 wherein $R^{13}$ is H, halogen, cyano or nitro.

Embodiment P52

A compound of Embodiment P51 wherein $R^{13}$ is cyano or nitro.

Embodiment P53

A compound of Formula 1P or any one of Embodiments P1 through P52 wherein when instances of $R^{14}$ and $R^{18}$ are taken alone (i.e. $R^{14}$ and $R^{18}$ are not taken together as alkylene or alkenylene), then independently said instances of $R^{14}$ and $R^{18}$ are H or $C_1$-$C_6$ alkyl.

Embodiment P53a

A compound of Embodiment P53 wherein when instances of $R^{14}$ and $R^{18}$ are taken alone, then independently said instances of $R^{14}$ and $R^{18}$ are H or $CH_3$.

Embodiment P53b

A compound of Embodiment P53a wherein when instances of $R^{14}$ and $R^{18}$ are taken alone, then independently said instances of $R^{14}$ and $R^{18}$ are H.

Embodiment P53c

A compound of Formula 1P or any one of Embodiments P1 through P53b wherein when instances of $R^{14}$ and $R^{18}$ are taken together, then said instances of $R^{14}$ and $R^{18}$ are taken together as —$CH_2CH_2CH_2$— or —CH=CH—$CH_2$—.

Embodiment P53d

A compound of Formula 1P or any one of Embodiments P1 through P53b wherein all instances of $R^{14}$ and $R^{18}$ are taken alone.

Embodiment P54

A compound of Formula 1P or any one of Embodiments P1 through P53d wherein independently each $R^{15}$ and $R^{19}$ is H or $C_1$-$C_6$ alkyl.

Embodiment P54a

A compound of Embodiment P54 wherein independently each $R^{15}$ and $R^{19}$ is H or $CH_3$.

Embodiment P55

A compound of Embodiment P54a wherein independently each $R^{15}$ and $R^{19}$ is H.

Embodiment P56

A compound of Formula 1P or any one of Embodiments P1 through P55 wherein $R^{20}$ is H, $C_1$-$C_6$ alkyl, $C_2$-$C_6$ alkenyl or $C_3$-$C_8$ cycloalkyl.

Embodiment P57

A compound of Embodiment P56 wherein $R^{20}$ is H or $CH_3$.

Embodiment P58

A compound of Formula 1P or any one of Embodiments P1 through P57 wherein T is —$CH_2CH_2$— or —CH=CH—.

Embodiment P59

A compound of Formula 1P or any one of Embodiments P1 through P58 wherein each G is independently a 5- or 6-membered heterocyclic ring optionally substituted with up to five substituents selected from $R^{21}$ on carbon ring members and $R^{22}$ on nitrogen ring members.

Embodiment P60

A compound of Embodiment P59 wherein G is selected from

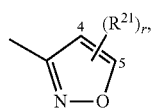
G-1

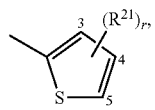
G-2

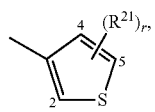
G-3

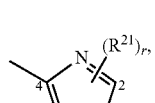
G-4

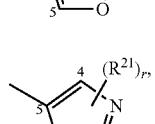
G-5

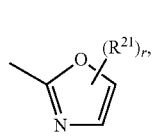
G-6

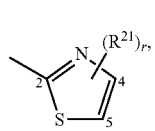
G-7

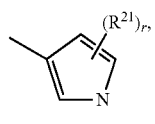
G-8

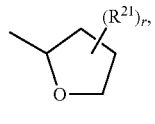
G-9

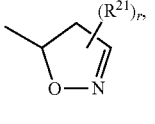
G-10

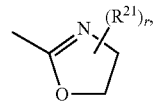
G-11

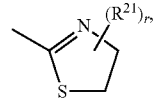
G-12

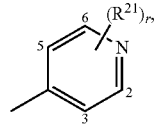
G-13

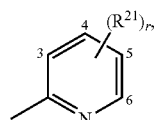
G-14

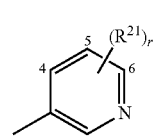
G-15

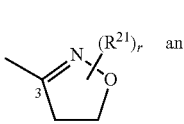
G-16

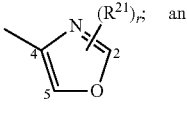
G-17 r is 0, 1, 2 or 3.

Embodiment P61

A compound of Embodiment P60 wherein G is G-13, G-14, G-15, G-16 or G-17.

Embodiment P62

A compound of Formula 1P or any one of Embodiments P1 through P61 wherein each $R^{21}$ is independently halogen, cyano, hydroxy, nitro, —CHO, —SH, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or $C_3$-$C_8$ cycloalkylsulfonyl.

Embodiment P63

A compound of Embodiment P62 wherein each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment P64

A compound of Embodiment P61 wherein each $R^{21}$ is independently fluorine, chlorine, $CH_3$, $CF_3$, $OCH_3$, $OCF_3$ or $SCH_3$.

Embodiment P65

A compound of Formula 1P or any one of Embodiments P1 through P64 wherein each $R^{22}$ is independently $C_1$-$C_6$ alkyl or $C_1$-$C_6$ haloalkyl.

Embodiment P66

A compound of Embodiment P1 through 65 wherein each $R^{22}$ is independently $CH_3$ or $CH_2CF_3$.

This invention also includes a herbicidal mixture of (a) a compound of Formula 1P and (b) an active ingredient selected from photosystem II inhibitors.

Embodiment P67

A herbicidal mixture comprising (a) a compound of Formula 1P and (b) an additional herbicidal ingredient selected from photosystem II inhibitors.

Embodiment P68

A herbicidal mixture of Embodiment P67 comprising (a) a compound of Formula 1P and (b) an additional herbicidal compound selected from the group consisting of ametryn, amicarbazone, atrazine, bentazon, bromacil, bromoxynil, chlorotoluron, diuron, hexazinone, isoproturon, metribuzin, pyridate, simazine and terbutryn.

Embodiment P69

A herbicidal mixture of Embodiment P68 comprising (a) a compound of Formula 1P; and (b) bromoxynil.

Embodiments of this invention, including Embodiments P1-P69 above as well as any other embodiments described herein, can be combined in any manner, and the descriptions of variables in the embodiments pertain not only to the compounds of Formula 1P but also to the starting compounds and intermediate compounds useful for preparing the compounds of Formula 1P. In addition, embodiments of this invention, including Embodiments 1-66 above as well as any other embodiments described herein, and any combination thereof, pertain to the compositions and methods of the present invention.

Combinations of Embodiments 1-66 are illustrated by:

Embodiment PA

A compound of Formula 1P wherein
Y is C(O);
A is A-1, A-3, A-5 or A-6;
$R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2NHCN$, —$SO_2NHOH$, —NHCHO, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl or $C_2$-$C_8$ haloalkoxycarbonyl;

$W^1$ is $C_1$-$C_6$ alkylene
$W^2$ is —$CH_2$—;
$R^2$ is phenyl or —$W^3$(phenyl), each optionally substituted on ring members with up to five substituents selected from $R^{21}$; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_4$-$C_{10}$ cycloalkoxylalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_3$-$C_8$ cycloalkylsulfinyl or $C_3$-$C_{10}$ halotrialkylsilyl;

$W^3$ is $C_1$-$C_6$ alkylene;
$W^4$ is —$CH_2$—;
$R^3$ is hydroxy, $C_2$-$C_8$ alkylcarbonyloxy, $C_2$-$C_8$ haloalkylcarbonyloxy, $C_4$-$C_{10}$ cycloalkylcarbonyloxy or $C_3$-$C_{10}$ alkylcarbonylalkoxy; or benzyloxy, phenyloxy, benzylcarbonyloxy, phenylcarbonyloxy, phenylsulfonyloxy or benzylsulfonyloxy, each optionally substituted on ring members with up to two substituents selected from $R^{21}$;

$M^+$ is a sodium or potassium metal cation;

$R^9$ is $C_1$-$C_6$ alkyl;

$R^{10}$ is H, halogen or $C_1$-$C_6$ alkyl;

$R^{11}$ is H or $C_1$-$C_6$ alkyl;

$R^{12}$ is H, halogen, cyano, hydroxy, amino or $C_1$-$C_6$ alkyl;

$R^{13}$ is cyano or nitro;

each $R^{14}$, $R^{15}$, $R^{18}$ and $R^{19}$ is independently H or $CH_3$; or a pair of $R^{14}$ and $R^{18}$ is taken together as —$CH_2CH_2CH_2$— or —CH=CH—$CH_2$—;

$R^{20}$ is H, $C_1$-$C_6$ alkyl, $C_2$-$C_6$ alkenyl or $C_3$-$C_8$ cycloalkyl;

T is —$CH_2CH_2$— or —CH=CH—;

each G is selected from G-1 through G-23 (as depicted in Embodiment 79);

r is 0, 1, 2 or 3;

each $R^{21}$ is independently halogen, cyano, hydroxy, nitro, —CHO, —SH, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl or $C_3$-$C_8$ cycloalkylsulfonyl; and $R^{22}$ is independently $C_1$-$C_6$ alkyl or $C_1$-$C_6$ haloalkyl.

Embodiment PB

A compound of Embodiment PA wherein

X is CH;

A is A-3 or A-5;

$B^2$ is C-3;

$R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkoxyalkyl, $C_2$-$C_8$ alkylthioalkyl or $C_2$-$C_8$ alkylsulfonylalkyl;

$R^2$ is phenyl or —$W^3$(phenyl), each optionally substituted on ring members with up to two substituents selected from $R^{21}$; or $C_1$-$C_6$ alkyl, $C_1$-$C_6$ haloalkyl, $C_3$-$C_8$ cycloalkyl, $C_1$-$C_6$ alkoxy, $C_1$-$C_6$ alkylthio or $C_1$-$C_6$ alkylsulfonyl;

$R^3$ is hydroxy or —$O^-M^+$; or phenylsulfonyloxy optionally substituted on ring members with up to two substituents selected from $R^{21}$;

$R^9$ is $CH_2CH_3$;

$R^{10}$ is H or $CH_3$;

$W^1$ is —$CH_2$—;

$W^3$ is —$CH_2$—;

G is G-13, G-14, G-15, G-16 or G-17; and each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment PC

A compound of Embodiment PA wherein:

X is CH;

A is A-1 or A-6;

$B^1$ is C-1, $B^2$ is C-3 and $B^3$ is C-1;

$R^1$ is phenyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkoxyalkyl, $C_2$-$C_8$ alkylthioalkyl or $C_2$-$C_8$ alkylsulfonylalkyl;

$R^2$ is phenyl or —$W^3$(phenyl), each optionally substituted on ring members with up to two substituents selected from $R^{21}$; or $C_1$-$C_6$ alkyl, $C_1$-$C_6$ haloalkyl, $C_3$-$C_8$ cycloalkyl, $C_1$-$C_6$ alkoxy, $C_1$-$C_6$ alkylthio or $C_1$-$C_6$ alkylsulfonyl;

$R^3$ is hydroxy or —$O^-M^+$; or phenylsulfonyloxy optionally substituted on ring members with up to two substituents selected from $R^{21}$;

$R^{11}$ is H;

each $R^{14}$, $R^{15}$, $R^{18}$ and $R^{19}$ is independently H or $CH_3$;

$R^{12}$ is H, halogen, cyano, $C_1$-$C_6$ alkyl or $C_3$-$C_8$ cycloalkyl;

$W^1$ is —$CH_2$—;

$W^3$ is —$CH_2$—;

G is G-13, G-14, G-15, G-16 or G-17; and each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

Embodiment PD

A compound of Embodiment PC wherein:

A is A-1;

$R^1$ is phenyl or —$W^1$(phenyl) each optionally substituted on ring members with up to two substituents selected from $R^{21}$; or $C_1$-$C_6$ alkyl or $C_2$-$C_6$ alkenyl; $R^2$ is phenyl or $CH_2$(phenyl), each optionally substituted on ring members with up to two substituents selected from $R^{21}$; or $C_1$-$C_6$ alkyl, $C_3$-$C_8$ cycloalkyl or $C_1$-$C_6$ alkylthio;

$R^3$ is hydroxy; or phenylsulfonyloxy substituted with $CH_3$ at the 4-position; and each $R^{21}$ is independently fluorine, chlorine, $CH_3$, $CF_3$, $OCH_3$, $OCF_3$ or $SCH_3$.

Embodiment PE

A compound of Embodiment PD wherein:

$R^1$ is phenyl, 2-fluorophenyl, 3-fluorophenyl, 4-fluorophenyl, 2-chlorophenyl, 3-chlorophenyl, 4-chlorophenyl, 4-methylphenyl, 2-methylphenyl, 4-methoxyphenyl, 2,3-dimethylphenyl, $CH_2$(phenyl), $CH_3$ or $CH_2CH_3$;

$R^2$ is phenyl, 2-chlorophenyl, 3-chlorophenyl, 4-chlorophenyl, $CH_2CH_3$, c-Pr or $SCH_3$.

Specific embodiments include the compound of Formula 1P which is:

5-[(2-hydroxy-6-oxo-1-cyclohexen-1-yl)carbonyl]-2,3-diphenyl-4(3H)-pyrimidinone.

This invention also relates to a method for controlling undesired vegetation comprising applying to the locus of the vegetation a herbicidally effective amount of a compound of the invention (e.g., as a composition described herein). Of note as embodiments relating to methods of use are those involving the compounds of embodiments described above.

This invention also includes herbicidal mixture comprising (a) a compound of Formula 1P and (b) an additional herbicidal ingredient selected from a photosystem II inhibitor. Also noteworthy as embodiments are herbicidal compositions of the present invention comprising the compounds of embodiments described above.

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include, but are not limited to ametryn, atrazine, cyanazine, desmetryne, dimethametryn, prometon, prometryne, propazine, simazine, simetryn, terbumeton, terbuthylazine, terbutryne, trietazine, hexazinone, metamitron, metribuzin, amicarbazone, bromacil, lenacil, terbacil, chloridazon, desmedipham, phenmedipham, chlorobromuron, chlorotoluron, chloroxuron, dimefuron, diuron, ethidimuron, fenuron, fluometuron, isoproturon, isouron, linuron, methabenzthiazuron, metobromuron, metoxuron, monolinuron, neburon, siduron, tebuthiuron, propanil, pentanochlor, bromofenoxim, bromoxynil, ioxynil, bentazon, pyridate and pyridafol.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for DNA synthesis and cell growth. Examples of AHAS inhibitors include but are not limited to amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl (including sodium salt), foramsulfuron, halosulfuron-methyl, imazosulfuron, iodosulfuron-methyl (including sodium salt), mesosulfuron-methyl, metazosulfuron, metsulfuron-methyl, nicosulfuron, oxasulfuron, primisulfuron-methyl, propyrisulfuron, prosulfuron, pyrazosulfuron-ethyl, rimsulfuron, sulfometuron-methyl, sulfosulfuron, thifensulfuron-methyl, triasulfuron, tribenuron-methyl, trifloxysulfuron (including sodium salt), triflusulfuron-methyl, tritosulfuron, imazapic, imazamethabenz-methyl, imazamox, imazapyr, imazaquin, imazethapyr, cloransulam-methyl, diclosulam, florasulam, flumetsulam, metosulam, penoxsulam, bispyribac-sodium, pyribenzoxim, pyriftalid, pyrithiobac-sodium, pyriminobac-methyl, thiencarbazone, flucarbazone-sodium and propoxycarbazone-sodium.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include but are not limited to clodinafop, cyhalofop, diclofop, fenoxaprop, fluazifop, haloxyfop, propaquizafop, quizalofop, alloxydim, butroxydim, clethodim, cycloxydim, pinoxaden, profoxydim, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include but are not limited to aminocyclopyrachlor, aminopyralid benazolin-ethyl, chloramben, clomeprop, clopyralid, dicamba, 2,4-D, 2,4-DB, dichlorprop, fluroxypyr, mecoprop, MCPA, MCPB, 2,3,6-TBA, picloram, triclopyr, quinclorac, quinmerac.

"EPSP (5-enol-pyruvylshikimate-3-phosphate) synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

One or more of the following methods and variations as described in Schemes 1-18 can be used to prepare the compounds of Formula 1. The definitions of A, $B^1$, $B^2$, $B^3$, $R^1$, $R^2$, $R^3$, $R^4$, $R^5$, $R^6$, $R^7$, $R^8$, $R^9$, $R^{10}$, $R^{12}$ and $R^{13}$ in the compounds of Formulae 1-34 below are as defined above in the Summary of the Invention unless otherwise noted. Compounds of Formulae 1a-1h are various subsets of the compounds of Formula 1, and all substituents for Formulae 1a-1h are as defined above for Formula 1.

Compounds of Formula 1a, 1b or 1c (where $R^3$ is hydroxy) can be prepared via the two-step process shown in Schemes 1a, 1b and 1c respectively. Intermediate 4a, 4b or 4c can be prepared by reacting dione 2 with intermediate 3 where G is a nucleophilic reaction leaving group (e.g., $G^1$ is a halogen, alkoxycarbonyl, haloalkylcarbonyloxy, haloalkoxycarbonyloxy, pyridinyl or imidazoyl group). Reaction of intermediate 4a, 4b or 4c with the appropriate cyano compound (e.g., acetone cyanohydrin, potassium cyanide, sodium cyanide) in the presence of a base such as triethylamine or pyridine leads to a compound of Formula 1a, 1b or 1c. Alternatively a fluoride anion source such as potassium fluoride or cesium fluoride and optionally in the presence of a phase transfer catalyst (e.g. tetrabutyl ammonium bromide, etc.) can be used in this transformation. A solvent such as dimethylsulfoxide, N,N-dimethylformamide, acetonitrile or dichloromethane at ambient temperature to the reflux temperature of the solvent can lead to a compound of Formula 1a, 1b or 1c. (Formula 1a is Formula 1 wherein A is A-1; Formula 1b is Formula 1 wherein A is A-2; Formula 1c is Formula 1 wherein A is A-3.) Alternatively, compounds of Formula 1a, 1b or 1c can be prepared by Process 2 (in Schemes 1a, 1b and 1c respectively) by reacting dione 2a, 2b or 2c with intermediate 3 in the presence of a cyano compound or a fluoride anion source along with a base. For additional reaction conditions for this general coupling methodology, see Edmunds, A. in *Modern Crop Protection Compounds*; Kramer, W. and Schirmer, U., Eds.; Wiley, Weinheim, 2007; Chapter 4.3 and references cited therein.

Scheme 1a
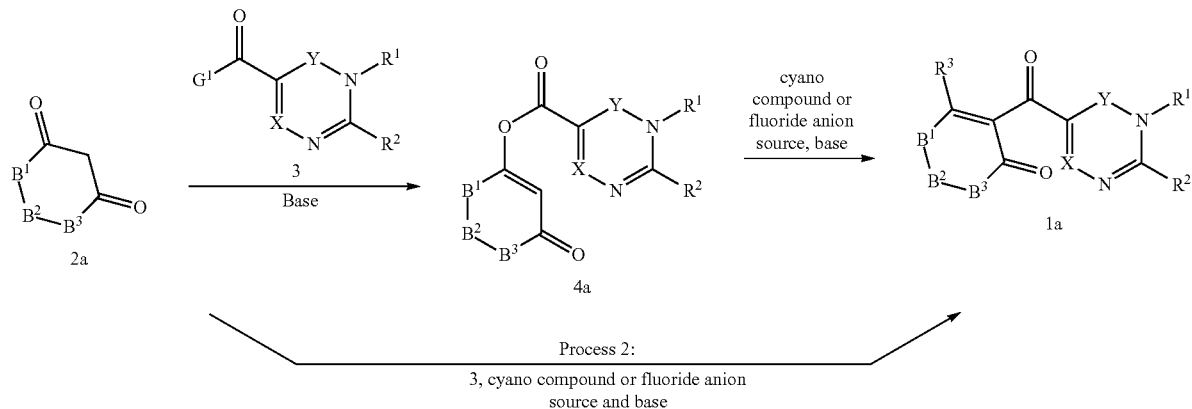
Scheme 1b
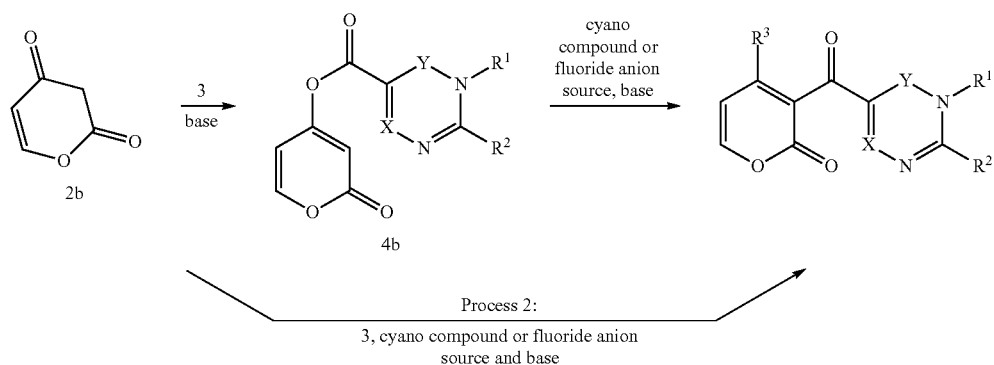
Scheme 1c
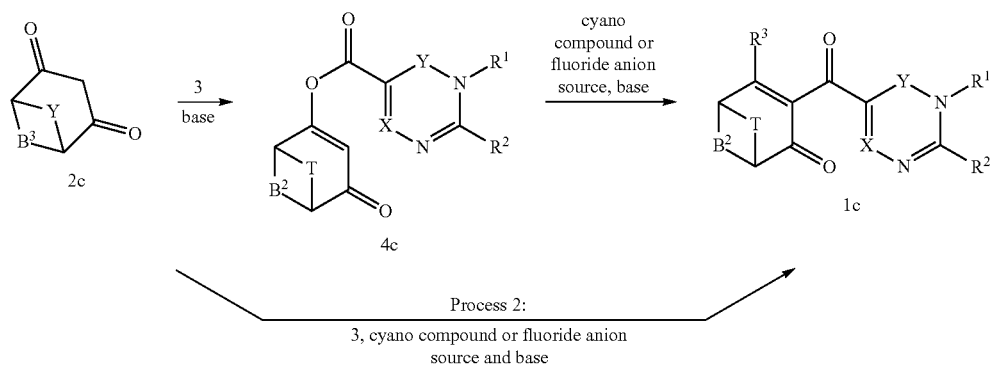
Compounds of Formula 1a, 1b or 1c can also be prepared as shown in Scheme 2, by reacting dione 2a, 2b or 2c with intermediate 3a in the presence of a base or Lewis acid. For reaction conditions for this general coupling methodology, see Edmunds, A. in *Modern Crop Protection Compounds*; Kramer, W. and Schirmer, U., Eds.; Wiley, Weinheim, 2007; Chapter 4.3 and references cited therein.

Scheme 2

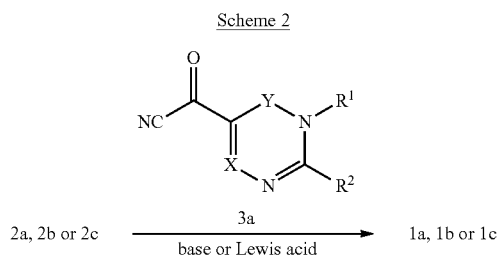

As shown in Scheme 3, intermediate 4a, 4b or 4c can also be prepared by allowing dione 2a, 2b or 2c to react with acid 6 in the presence of a dehydrating condensation agent such as 2-chloro-1-pyridinium iodide (known as the Mukaiyama coupling agent), dicyclohexyl carbodiimide (DCC) or the like and optionally in the presence of a base. For additional reaction conditions for this general enol ester coupling methodology, see Edmunds, A. in *Modern Crop Protection Compounds*; Kramer, W. and Schirmer, U., Eds.; Wiley, Weinheim, 2007; Chapter 4.3 and references cited therein.

Scheme 3

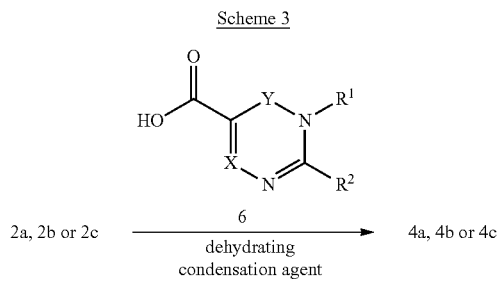

Intermediate 4a, 4b or 4c can also be made by the palladium-catalyzed carbonylation reaction of a compound of Formula 7 in the presence of dione 2a, 2b or 2c (Scheme 4). For reaction conditions for this general enol ester forming methodology, see Edmunds, A. in *Modern Crop Protection Compounds*; Kramer, W. and Schirmer, U., Eds.; Wiley, Weinheim, 2007; Chapter 4.3 and references cited therein.

Scheme 4

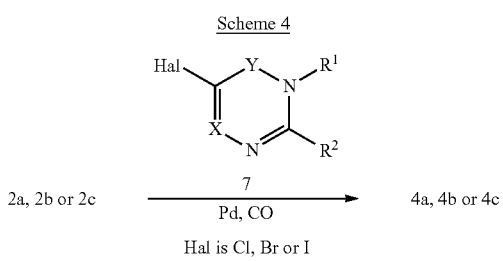

Compounds of Formula 1a, 1b or 1c (where $R^3$ is bonded through oxygen) are prepared by reacting compounds of Formula 1a, 1b or 1c with intermediate 8 where X is a nucleophilic reaction leaving group, also known as a nucleofuge in the presence of a base as shown in Scheme 5. Alternatively, compounds of Formula 1a, 1b and 1c (where $R^3$ is bonded through nitrogen, sulfur or carbon) can be prepared using the appropriate halogenating agent followed by nucleophilic addition. For reaction conditions for this general functionalization method, see Edmunds, A. or Almisick A. V. in *Modern Crop Protection Compounds*; Kramer, W. and Schirmer, U., Eds.; Wiley, Weinheim, 2007; Chapter 4.3 or Chapter 4.4, and references cited therein.

Scheme 5

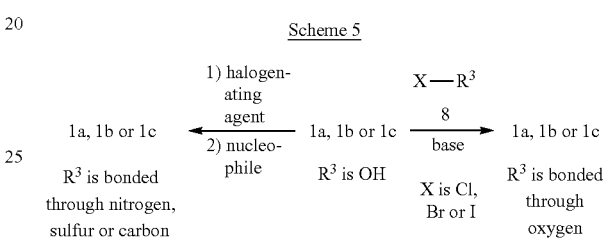

As shown in Scheme 6, compounds of Formula 1d (i.e. Formula 1 wherein A is A-4 and $R^3$ is OH) can be prepared by the reaction of intermediate 9 with intermediate 3 in the presence of a Lewis base, for example n-butyllithium or lithium diisopropylamide in an appropriate solvent such as tetrahydrofuran or diethyl ether. For reaction conditions for this type of transformation, see JP 2003327580.

Scheme 6

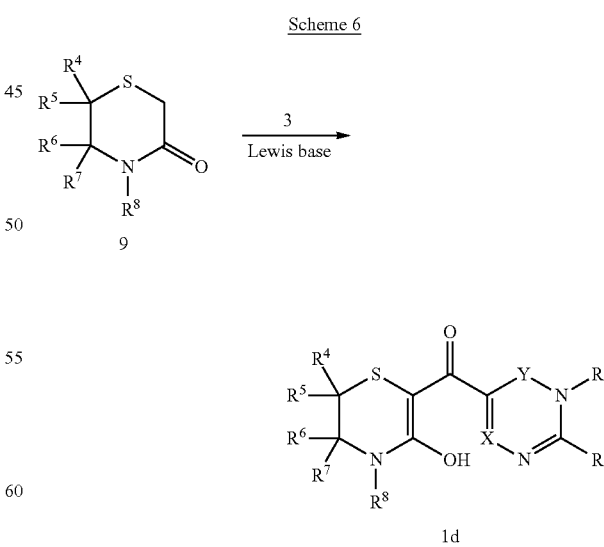

Compounds of Formula 1e (i.e. Formula 1 wherein A is A-5 and $R^3$ is OH) can be prepared via a two-step process as shown in Scheme 7. Intermediate 12 can be prepared by reacting pyrazole 11 with intermediate 3 where $G^1$ is a nucleophilic reaction leaving group (i.e. $G^1$ is a halogen atom, alkoxycarbonyl, haloalkylcarbonyloxy, benzoyloxy, pyridinyl or imidazoyl group). Reaction of intermediate 12 with the appropriate cyano compound in the presence of a base leads to a compound of Formula 1e. Alternatively, a compound of Formula 1e can be prepared directly by reacting intermediate 11 with intermediate 3 (Process 2, Scheme 7) in the presence of a cyano compound or a fluoride anion source with a base. For reaction conditions for this general coupling methodology, see Almisick A. V. in *Modern Crop Protection Compounds*; Kramer, W. and Schirmer, U., Eds.; Wiley, Weinheim, 2007; Chapter 4.4, and references cited therein.

Compounds of Formula 17 can be prepared by reacting intermediate 3 with a compound Formula 16 in an appropriate solvent in the presence of a base. Thereafter intermediate 17 can be rearranged into the compound of Formula 1g (i.e. Formula 1 wherein A is A-7) in the presence of a cyano compound and a base as shown in Scheme 9. For reaction conditions for this general coupling methodology, see Almisick A. V. in *Modern Crop Protection Compounds*; Kramer, W. and Schirmer, U., Eds.; Wiley, Weinheim, 2007; Chapter 4.4, and references cited therein.

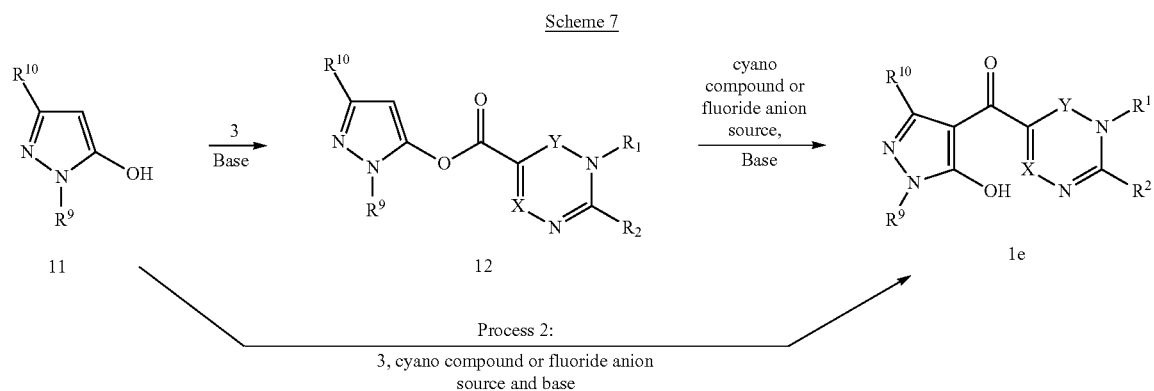

Compounds of Formula 1f (i.e. Formula 1 wherein A is A-5) wherein $R^3$ is bonded through oxygen can be prepared by reacting a compound of Formula 1e with intermediate 8 (where X is a nucleophilic reaction leaving group, also known as a nucleofuge) in the presence of a base as shown in Scheme 8. Alternatively compounds of Formula 1f wherein $R^3$ is bonded through nitrogen, sulfur or carbon can be prepared using the appropriate halogenating agent followed by nucleophilic displacement. For reaction conditions for these general functionalization methods, see Almisick A. V. in *Modern Crop Protection Compounds*; Kramer, W. and Schirmer, U., Eds.; Wiley, Weinheim, 2007; Chapter 4.4, and references cited therein.

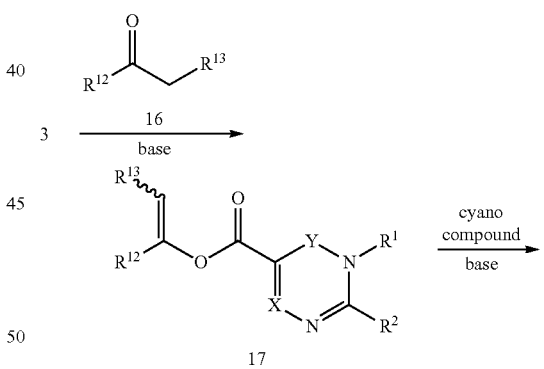

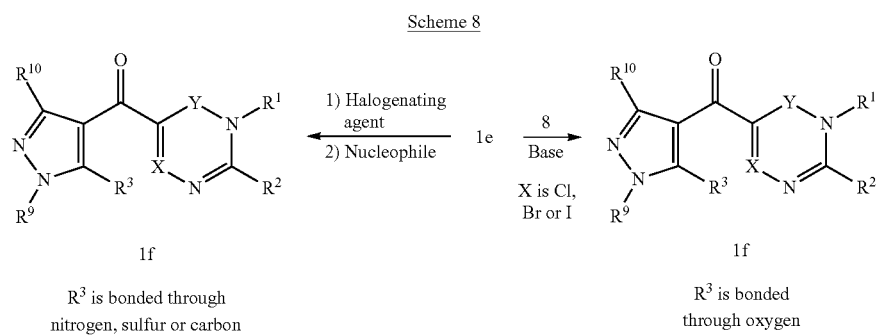

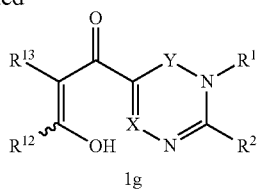

1g

Compounds of Formula 19 can be prepared from corresponding compounds of Formula 1g wherein R¹³ is an alkoxycarbonyl in the presence of an acid such as hydrogen chloride, sulfuric or acetic acid and optionally in the presence of a solvent such as tetrahydrofuran, diethyl ether or dichloromethane as shown in Scheme 10. Intermediate 19 is then reacted with an orthoformate ester or N,N-dimethylformamide dimethylacetal (DMF-DMA) in the presence of an acid to obtain intermediate 20. Reaction of intermediate 20 with hydroxylamine hydrochloride salt in a solvent such as ethanol, acetonitrile, water or acetic acid provides isoxazole compounds of Formula 1h (i.e. Formula 1 wherein A is A-6 and R¹¹ is H). For reaction conditions for this general cyclization methodology, see Almisick A. V. in *Modern Crop Protection Compounds*; Kramer, W. and Schirmer, U., Eds.; Wiley, Weinheim, 2007; Chapter 4.4, and references cited therein.

Scheme 10

As illustrated in Scheme 11, sulfoxides and sulfones of Formula 1 wherein R² is a substituent bonded through a sulfoxide or sulfone radical can be prepared by oxidation of the compounds of Formula 1 wherein R² is a substituent bonded through a sulfide radical. In a typical procedure, an oxidizing agent in an amount from 1 to 4 equivalents depending on the oxidation state of the product desired is added to a solution of the compound of Formula 1 in a solvent. Useful oxidizing agents include Oxone® (potassium peroxymonosulfate), hydrogen peroxide, sodium periodate, peracetic acid and 3-chloroperbenzoic acid. The solvent is selected with regard to the oxidizing agent employed. Aqueous ethanol or aqueous acetone is preferably used with potassium peroxymonosulfate, and dichloromethane is generally preferable with 3-chloroperbenzoic acid. Useful reaction temperatures typically range from 0 to 90° C. Particular procedures useful for oxidizing sulfides to sulfoxides and sulfones are described by Brand et al., *J. Agric. Food Chem.* 1984, 32, 221-226 and references cited therein.

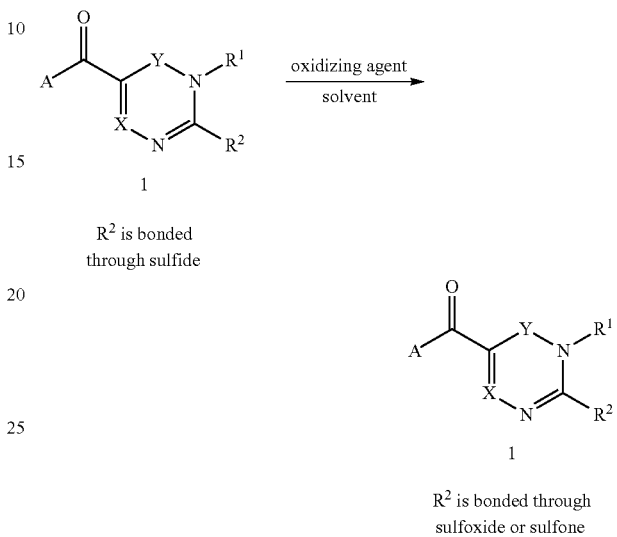

Scheme 11

One skilled in the art will realize that acid chlorides of Formula 3d (i.e. Formula 3 wherein G¹ is Cl) are easily prepared from the acid of Formula 6 (Scheme 12) by numerous well-known methods. For example reacting the acid with a chlorinating reagent such as oxalyl chloride or thionyl chloride in a solvent such as dichloromethane or toluene and optionally in the presence of a catalytic amount of N,N-dimethylformamide can provide the corresponding acid chloride of Formula 3d.

Scheme 12

Compounds of Formula 6 can be prepared from esters of Formula 23 by numerous well-known methods, for example standard saponification procedures using aqueous bases such as LiOH, NaOH or KOH in a solvent such methanol or ethanol as described in Scheme 13. Alternatively, a dealkylating agent such as lithium iodide or trimethylsilyl iodide can be used in the presence of a base in a solvent such as pyridine or ethyl acetate. Additional reaction procedures for deesterification can be found in PCT Patent Publication WO 2006/133242. Boron tribromide (BBr$_3$) can alternatively be used to to prepare a compound of Formula 6 from a compound of Formula 23 in a solvent such as dichloromethane. Procedures using boron tribromide can be found in *Bioorg. & Med. Chem. Lett.* 2009, 19(16), 4733-4739.

Scheme 13

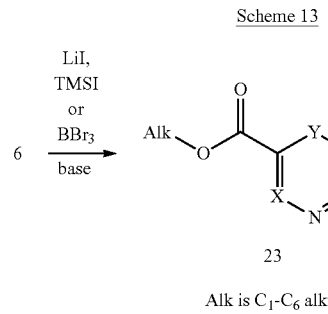

Alk is C$_1$-C$_6$ alkyl

Pyrimidinone esters of Formula 23a (i.e. Formula 23 wherein Alk is ethyl, X is CH and Y is C(O)) are prepared as illustrated in Scheme 14 by N-alkylation of pyridones of Formula 26 with agents such as alkyl halides in the presence of a base such as sodium hydride or potassium carbonate in a solvent such as N,N-dimethylformamide, tetrahydrofuran or diethyl ether.

Scheme 14

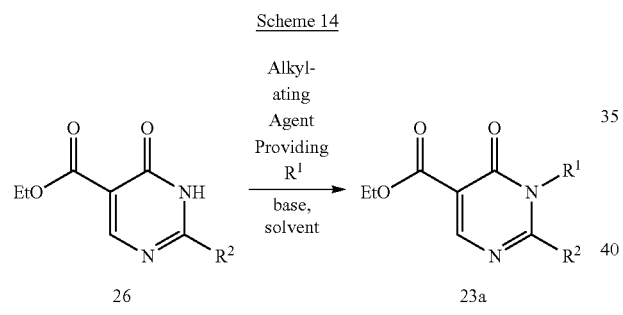

Pyrimidinone esters of Formula 23a can be made by the method of Scheme 15. In this method an methylene malonate of Formula 28 is cyclized with an amidine salt of Formula 29 wherein X is a halogen or sulfonate counter ion in the presence of excess base such as sodium alkoxide or potassium carbonate in an appropriate solvent such as ethanol (generally at the reflux temperature of the solvent) to give the corresponding pyrimidinone of Formula 3f. Examples of this synthetic method are reported in PCT Patent Publication WO 2006/133242 or *Tetrahedron* 2001, 57, 2689.

Scheme 15

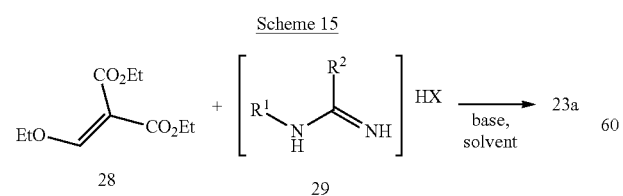

Pyrimidinone esters of Formula 26 can be prepared by the method of Scheme 16. In this method, an ethylene malonate of Formula 28 is cyclized with an amidine salt Formula 29a wherein X is a halogen or sulfonate counter ion in the presence of excess base such as sodium alkoxide or potassium carbonate in an appropriate solvent such as methanol (generally at the reflux temperature of the solvent) to give the corresponding pyrimidinone of Formula 26. Examples of this synthetic procedure are reported in PCT Patent Publication WO 2006/133242, *Tetrahedron* 2001, 57, 2689.

Scheme 16

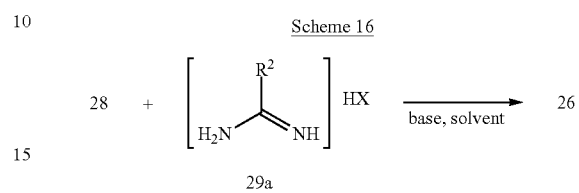

Thiones of Formula 23b (i.e. Formula 23 wherein Alk is ethyl, X is CH and Y is S(O)$_2$) can be made by the method of Scheme 17. In this method amidines of Formula 29 is reacted with acetal 30 in the presence of a base such as triethylamine, pyridine or potassium carbonate to give the corresponding azabutadiene 31. Reacting this compound with the sulfonic acid chloride 32 as shown in Scheme 17 in the presence of a base such as triethylamine, pyridine or potassium carbonate in an appropriate solvent results in the corresponding compound of Formula 33. The corresponding thiones of formula 23b can be obtained by reacting the compound of Formula 33 with iodomethane and subsequent treatment with a base such as triethylamine. Examples of this synthetic methodology are reported in *Synthesis* 2000, 5, 695.

Scheme 17

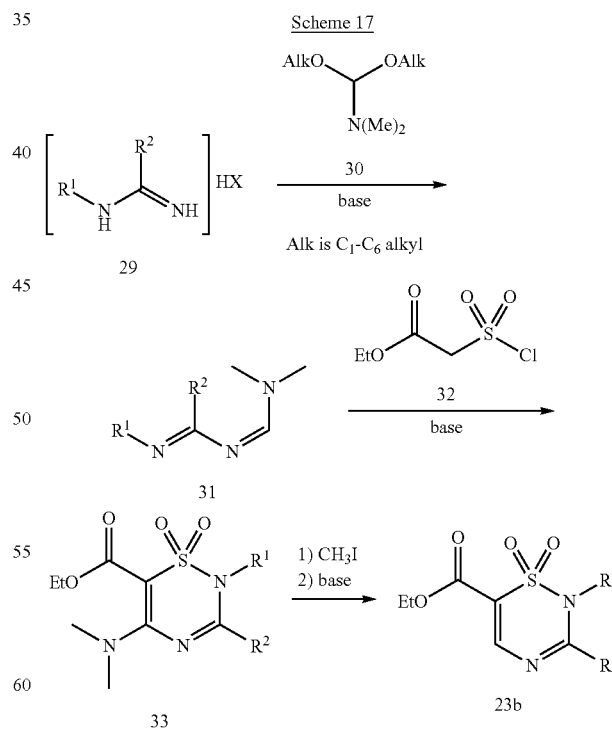

Triazines of Formula 23c (i.e. Formula 23 wherein Alk is ethyl, X is N and Y is C(O)) can be made by the method of Scheme 18. In this method a ketomalonate of Formula 34 is cyclized with a semicarbazide of Formula 29c wherein X is a halogen or sulfonate counter ion with or without the presence of excess base such as sodium alkoxide or potassium carbonate in an appropriate solvent such as ethanol or t-butanol (generally at the reflux temperature of the solvent) to the corresponding triazine of Formula 23c. Examples of this synthetic methodology are found in *Eur. J. Med. Chem.* 2008, 43(5), 1085, *Bull. Soc. Chim. Fr.* 1976, (11-12, Pt. 2), 1825 and *J. Org. Chem.* 1962, 27, 976.

Scheme 18

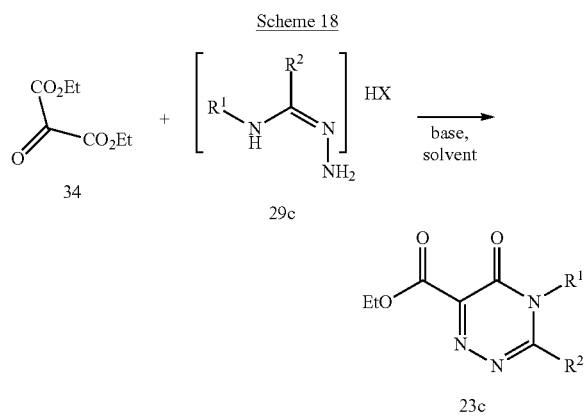

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane at 400 MHz unless otherwise noted; "s" means singlet, "m" means multiplet, "br s" means broad singlet, "d" means doublet, "t" means triplet, "dt" means doublet of triplets, "q" means quartet and "sep" means septet.

Example 1

Preparation of 5-[(2-hydroxy-6-oxo-1-cyclohexen-1-yl)carbonyl]-2,3-diphenyl-4(3H)-pyrimidinone (Compound 2)

Step A: Preparation of N-phenylbenzenecarboximidamide sodium salt

To a stirred solution of sodium bis(trimethylsilyl)amide (1.0 M in tetrahydrofuran, 21.5 mL, 21.5 mmol) in tetrahydrofuran (10 mL) was added aniline (2.0 g, 21.5 mmol) and allowed to stir for 10 min at room temperature. Benzonitrile (2.21 g, 21.5 mmol) was added, and the reaction mixture was stirred for 1 h at room temperature. The solid that precipitated was filtered, washed with diethyl ether and dried under reduced pressure to afford the title product as an off-white solid (4.0 g), which was used without further purification in the next step.

Step B: Preparation of (A) 1,6-dihydro-6-oxo-1,2-diphenyl-5-pyrimidinecarboxylic acid ethyl ester and (B) 1,6-dihydro-6-oxo-1,2-diphenyl-5-pyrimidinecarboxylic acid To a stirred solution of N-phenylbenzenecarboximidamide sodium salt (i.e. the product from Step A) (6.0 g, 27.5 mmol) in acetonitrile (30 mL) was added ammonium chloride (1.47 g, 27.5 mmol) followed by diethyl ethoxymethylenemalonate (5.94 g, 27.5 mmol). The reaction mixture was heated and stirred at reflux for 2 h. The reaction mixture was concentrated under reduced pressure to give a residue. Water (30 mL) was added to the residue, followed by a saturated solution of sodium bicarbonate (30 mL), and the mixture was extracted with ethyl acetate. The aqueous layer was separated and retained. The organic layer was dried (MgSO$_4$) and concentrated under reduced pressure. The resulting residue was purified by column chromatography eluting with 30% ethyl acetate in hexanes to afford the title product (A) as a white solid (2.80 g).

$^1$H NMR (CDCl$_3$) δ 8.81 (s, 1H), 7.11-7.33 (m, 10H), 4.41 (m, 2H), 1.39 (m, 3H).

The above retained aqueous layer was acidified with 1 N hydrochloric acid until the pH was 1-2, and the mixture was extracted with dichloromethane. The organic layer was dried (MgSO$_4$) and concentrated under reduced pressure to provide a solid, which was washed with diethyl ether and dried under reduced pressure to afford the title product (B) as a white solid (680 mg).

$^1$H NMR (DMSO-d$_6$) δ 13.03 (s, 1H), 8.79 (s, 1H), 7.22-7.36 (m, 10H).

Step B1: Preparation of 1,6-dihydro-6-oxo-1,2-diphenyl-5-pyrimidinecarboxylic acid (alternate preparation to Step B, product (B))

To a stirred solution of 1,6-dihydro-6-oxo-1,2-diphenyl-5-pyrimidinecarboxylic acid ethyl ester (i.e. Step B product (A)) (2.30 g, 7.18 mmol) in pyridine (15 mL) was added lithium iodide (2.46 g, 18.0 mmol). The reaction mixture was heated to reflux with stirring for 24 h. The reaction mixture was concentrated under reduced pressure. To the resulting residue was added water (10 mL) followed by 1 N hydrochloric acid until the pH was 7. The solution was filtered though Celite® diatomaceous filter aid. The filtrate was acidified with 1 N hydrochloric acid until the pH was 1, and the mixture was extracted with dichloromethane. The organic layer was dried (MgSO$_4$) and concentrated under reduced pressure to afford a solid, which was washed with diethyl ether and dried under reduced pressure to afford the title product as a white solid (1.40 g).

$^1$H NMR (DMSO-d$_6$) δ 13.03 (s, 1H), 8.79 (s, 1H), 7.22-7.36 (m, 10H).

Step C: Preparation of 3-oxo-1-cyclohexen-1-yl 1,6-dihydro-6-oxo-1,2-diphenyl-5-pyrimidinecarboxylate To a stirred solution of 1,6-dihydro-6-oxo-1,2-diphenyl-5-pyrimidinecarboxylic acid (i.e. Step B product (B) or the product from Step B1) (1.40 g, 4.8 mmol) in dichloromethane (30 mL) was added oxalyl chloride (1.21 g, 9.61 mmol) at 0° C. followed by catalytic amount (2 drops) of N,N-dimethylformamide. The reaction mixture was allowed to warm to room temperature and stir for 1 h. Then the reaction mixture was concentrated under reduced pressure. To the resulting residue was added dichloromethane (30 mL), 1,3-cyclohexanedione (646 mg, 5.76 mmol), followed by triethylamine (976 mg, 9.60 mmol), and the reaction mixture was stirred at room temperature for 30 min. Saturated aqueous ammonium chloride solution was added, and the mixture was extracted with dichloromethane. The organic layer was dried (MgSO$_4$) and concentrated under reduced pressure. The residue was purified by column chromatography eluting with 50% ethyl acetate in hexanes to afford the title product as a white solid (1.1 g).

$^1$H NMR (CDCl$_3$) δ 8.89 (s, 1H), 7.31-7.36 (m, 5H), 7.24-7.26 (m, 3H), 7.12-7.15 (m, 2H), 6.04 (m, 1H), 2.68 (m, 2H), 2.45 (m, 2H), 2.11 (m, 2H).

Step D: Preparation of 5-[(2-hydroxy-6-oxo-1-cyclohexen-1-yl)carbonyl]-2,3-diphenyl-4(3H)-pyrimidinone (Compound 2)

To a stirred solution of 3-oxo-1-cyclohexen-1-yl 1,6-dihydro-6-oxo-1,2-diphenyl-5-pyrimidinecarboxylate (i.e. the product from Step C) (640 mg, 1.65 mmol) in acetonitrile (20 mL) was added triethylamine (401 mg, 3.97 mmol), followed by a catalytic amount of acetone cyanohydrin (3 drops). The reaction mixture was stirred for 24 h at room temperature and then concentrated under reduced pressure. To the resulting residue was added dichloromethane and 1 N hydrochloric acid. The organic layer was separated, and the aqueous layer was extracted with dichloromethane. The combined organic layers were dried (MgSO$_4$) and concentrated under reduced pressure. The residue was purified by column chromatography eluting with 100% ethyl acetate to afford the title product, a compound of the present invention, as a white solid (150 mg).

$^1$H NMR (CDCl$_3$) δ 8.24 (s, 1H), 7.12-7.34 (m, 10H), 2.70 (m, 2H), 2.48 (m, 2H), 2.03 (m, 2H).

Example 2

Preparation of 5-[(2-hydroxy-6-oxo-1-cyclohexen-1-yl)carbonyl]-2-phenyl-3-(phenylmethyl)-4(3H)-pyrimidinone (Compound 17)

Step A: Preparation of N-(phenylmethyl)-benzenecarboximidamide

To a stirred solution of ethylbenzimidate hydrochloride (3.0 g, 16.2 mmol) in N,N-dimethylformamide (10 mL) was added triethylamine (1.60 g, 16.2 mmol). The reaction mixture was allowed to stir at room temperature for 1 h and then filtered to remove triethylamine salts, which were rinsed with N,N-dimethylformamide (5 mL). Benzylamine (1.23 g, 11.5 mmol) was added to the filtrate, and the mixture was heated to 65° C. for 24 h. To the cooled mixture was added water (80 mL) and ethyl acetate. The organic layer was washed with water and brine, then dried (MgSO$_4$) and concentrated under reduced pressure to afford the title product as a clear oil (2.80 g).

$^1$H NMR (CDCl$_3$) δ 7.61 (m, 2H), 7.26-4.43 (m, 8H), 4.57 (m, 2H), 4.37 (m, 1H), 1.42 (m, 1H).

Step B: Preparation of ethyl 1,6-dihydro-6-oxo-2-phenyl-1-(phenylmethyl)-5-pyrimidinecarboxylate To a stirred solution of N-(phenylmethyl)-benzenecarboximidamide (i.e. the product from Step A) (2.54 g, 12.1 mmol) in ethanol (15 mL) was added diethyl ethoxymethylenemalonate (2.61 g, 12.1 mmol), and the reaction mixture was heated to reflux for 24 h. The reaction mixture was then allowed to cool to room temperature and concentrated under reduced pressure. The residue was purified by column chromatography eluting with 30% ethyl acetate in hexanes to afford the title product as a white solid (2.9 g).

$^1$H NMR (CDCl$_3$) δ 8.71 (s, 1H), 7.51 (m, 1H), 7.42 (m, 2H), 7.33 (m, 2H), 7.23 (m, 3H), 6.93 (m, 2H), 5.28 (s, 2H), 4.42 (m, 2H), 1.40 (m, 3H).

Step C: Preparation of 1,6-dihydro-6-oxo-2-phenyl-1-(phenylmethyl)-5-pyrimidinecarboxylic acid To a stirred solution of ethyl 1,6-dihydro-6-oxo-2-phenyl-1-(phenylmethyl)-5-pyrimidinecarboxylate (i.e. the product from Step B) (2.9 g, 8.6 mmol) in pyridine (15 mL) was added lithium iodide (3.01 g, 21.7 mmol). The reaction mixture was heated to reflux for 4 h, cooled, and then stirred at room temperature for 72 h. The reaction mixture was concentrated under reduced pressure. To the resulting residue was added water (10 mL), followed by 1 N hydrochloric acid until the pH was 7. The solution was filtered through Celite® diatomaceous filter aid, and the filtrate was acidified with 1 N hydrochloric acid until the pH was 1. The mixture was extracted with dichloromethane, and the organic layer was dried (MgSO$_4$) and concentrated under reduced pressure to afford a solid, which was washed with diethyl ether and dried under reduced pressure to afford the title product as a white solid (2.2 g).

Step D: Preparation of 3-oxo-1-cyclohexen-1-yl 1,6-dihydro-6-oxo-2-phenyl-1-(phenylmethyl)-5-pyrimidinecarboxylate To a stirred solution of 1,6-dihydro-6-oxo-2-phenyl-1-(phenylmethyl)-5-pyrimidinecarboxylic acid (i.e. the product from Step C) (1.00 g, 3.26 mmol) in dichloromethane (30 mL) at 0° C., was added oxalyl chloride (823 mg, 6.53 mmol) followed by a catalytic amount of N,N-dimethylformamide (2 drops). The reaction mixture was allowed to warm to room temperature and stir for 1 h. Then the reaction mixture was concentrated under reduced pressure. To the resulting residue was added dichloromethane (30 mL) and 1,3-cyclohexanedione (440 mg, 3.90 mmol), followed by triethylamine (990 mg, 9.80 mmol), and the reaction mixture was stirred at room temperature for 30 min Saturated aqueous ammonium chloride solution was added to the reaction mixture, which was then extracted with dichloromethane. The organic layer was dried (MgSO$_4$) and concentrated under reduced pressure. The residue was purified by column chromatography eluting with 50% ethyl acetate in hexanes to afford the title product as a white solid (500 mg).

$^1$H NMR (CDCl$_3$) δ 8.81 (s, 1H), 7.55 (m, 1H), 7.45 (m, 2H), 7.37 (m, 2H), 7.25 (m, 3H), 6.95 (m, 2H), 6.03 (s, 1H), 5.30 (s, 2H), 2.69 (m, 2H), 2.46 (m, 2H), 2.12 (m, 2H).

Step E: Preparation of 5-[(2-hydroxy-6-oxo-1-cyclohexen-1-yl)carbonyl]-2-phenyl-3-(phenylmethyl)-4(3H)-pyrimidinone (Compound 17)

To a stirred solution of 3-oxo-1-cyclohexen-1-yl 1,6-dihydro-6-oxo-2-phenyl-1-(phenylmethyl)-5-pyrimidinecarboxylate (i.e. the product from Step D) (450 mg, 1.12 mmol) in acetonitrile (15 mL) was added triethylamine (272 mg, 2.69 mmol), followed by a catalytic amount (3 drops) of acetone cyanohydrin. The reaction mixture was stirred for 24 h at room temperature and then concentrated under reduced pressure. To the resulting residue were added dichloromethane and 1 N hydrochloric acid, and the aqueous layer was extracted with dichloromethane. The organic layer was dried (MgSO$_4$) and concentrated under reduced pressure. The residue was purified by column chromatography eluting with ethyl acetate to afford the title product, a compound of the present invention, as a white solid (160 mg).

$^1$H NMR (CDCl$_3$) δ 16.44 (br s, 1H), 8.17 (s, 1H), 7.47 (m, 1H), 7.37 (m, 2H), 7.21-7.30 (m, 5H), 6.95 (m, 2H), 5.20 (s, 2H), 2.72 (m, 2H), 2.51 (m, 2H), 2.06 (m, 2H).

Example 3

Preparation of 5-[(1-ethyl-5-hydroxy-1H-pyrazol-4-yl)carbonyl]-2-phenyl-3-(phenylmethyl)-4(3H)-pyrimidinone (Compound 20)

Step A: Preparation of 1-ethyl-1H-pyrazol-5-yl 1,6-dihydro-6-oxo-2-phenyl-1-(phenylmethyl)-5-pyrimidinecarboxylate To a stirred solution of 1,6-dihydro-6-oxo-2-phenyl-1-(phenylmethyl)-5-pyrimidinecarboxylic acid (i.e. the product from Example 2, Step C) (1.20 g, 3.92 mmol) in dichloromethane (30 mL) was added oxalyl chloride (998 mg, 7.84 mmol) at 0° C. followed by a catalytic amount (4-drops) of N,N-dimethylformamide. The reaction mixture was allowed to warm to room temperature and stir for 1 h. The reaction mixture was then concentrated under reduced pressure. To the resulting residue was added dichloromethane (30 mL) and 5-hydroxy-1-ethyl-1H-pyrazole, (572 mg, 4.7 mmol), followed by triethylamine (1.18 g, 11.8 mmol), and the reaction mixture was stirred at room temperature for 30 min. Saturated aqueous ammonium chloride solution was added to the reaction mixture, which was then extracted with dichloromethane. The organic layer was dried (MgSO$_4$) and concentrated under reduced pressure. The residue was purified by column chromatography eluting with 70% ethyl acetate in hexanes to afford the title product as a white solid (700 mg).

$^1$H NMR (CDCl$_3$) δ 8.90 (s, 1H), 7.56 (m, 1H), 7.46 (m, 3H), 7.38 (m, 2H), 7.26 (m, 3H), 6.95 (m, 2H), 6.29 (m, 1H), 5.34 (s, 2H), 4.19 (m, 2H), 1.45 (m, 3H).

Step B: Preparation of 5-[(1-ethyl-5-hydroxy-1H-pyrazol-4-yl)carbonyl]-2-phenyl-3-(phenylmethyl)-4(3H)-pyrimidinone (Compound 20)

To a stirred solution of 1-ethyl-1H-pyrazol-5-yl 1,6-dihydro-6-oxo-2-phenyl-1-(phenylmethyl)-5-pyrimidinecarboxylate (i.e. the product from Step A) (650 mg, 1.62 mmol) in acetonitrile (15 mL) was added triethylamine (393 mg, 3.70 mmol), followed by a catalytic amount (5 drops) of acetone cyanohydrin. The reaction mixture was stirred for 24 h at room temperature and then concentrated under reduced pressure. To the residue were added dichloromethane and 1 N hydrochloric acid, and the aqueous layer was extracted with dichloromethane. The organic layer was dried (MgSO$_4$) and concentrated under reduced pressure. The residue was purified by column chromatography eluting with 10% methanol in ethyl acetate to afford the title product, a compound of the present invention, as a white solid (150 mg).

$^1$H NMR (CDCl$_3$) δ 8.56 (s, 1H), 7.86 (s, 1H), 7.53 (m, 1H), 7.39-7.46 (m, 4H), 7.24 (m, 3H), 6.97 (m, 2H), 5.33 (s, 2H), 4.04 (m, 2H), 1.42 (m, 3H).

Example 4

Step A: Preparation of 5-[[1-ethyl-5-[[(4-methylphenyl)sulfonyl]oxy]-1H-pyrazol-4-yl]carbonyl]-2-phenyl-3-(phenylmethyl)-4(3H)-pyrimidinone (Compound 21)

To a stirred solution of 5-[(1-ethyl-5-hydroxy-1H-pyrazol-4-yl)carbonyl]-2-phenyl-3-(phenylmethyl)-4(3H)-pyrimidinone (i.e. the product from Example 3, Step B) (300 mg, 0.75 mmol) in acetonitrile (10 mL) was added triethylamine (116 mg, 1.12 mmol), followed by p-toluenesulfonyl chloride (171 mg, 0.90 mmol), and the reaction mixture was stirred at room temperature for 72 h. Saturated aqueous ammonium chloride solution was added to the mixture, and the aqueous layer was extracted with dichloromethane. The organic layer was dried (MgSO$_4$) and concentrated under reduced pressure. The residue was purified by column chromatography eluting with 50% ethyl acetate in hexanes to afford the title product, a compound of the present invention, as a white solid (160 mg).

$^1$H NMR (CDCl$_3$) δ 8.07 (s, 1H), 7.84 (s, 1H), 7.74 (m, 2H), 7.44 (m, 2H), 7.25-7.35 (m, 8H), 6.95 (m, 2H), 5.23 (s, 2H), 4.00 (m, 2H), 2.41 (s, 3H), 1.42 (m, 3H).

Example 5

Preparation of 3-(3-fluoro-2-methylphenyl)-5-[(2-hydroxy-6-oxo-1-cyclohexen-1-yl)carbonyl]-2-phenyl-4(3H)-pyrimidinone (Compound 47)

Step A: Preparation of N-(3-fluoro-2-methylphenyl)benzenecarboximidamide sodium salt (1:1)

To a stirred solution of sodium bis(trimethylsilyl)amide (1.0 M in tetrahydrofuran, 200.0 mL, 200.0 mmol) was added 3-fluoro-2-methylaniline (25.0 g, 200.0 mmol) and allowed to stir for 10 min at room temperature. Benzonitrile (20.6 g, 200.0 mmol) was added, and the reaction mixture was stirred for 1 h at room temperature. The reaction mixture was concentrated and the solid that formed was filtered, washed with diethyl ether and dried under reduced pressure to afford the title product as a grey solid (51.0 g), which was used without further purification in the next step.

Step B: Preparation of 1-(3-fluoro-2-methylphenyl)-1,6-dihydro-6-oxo-2-phenyl-5-pyrimidinecarboxylic acid To a stirred solution of N-(3-fluoro-2-methylphenyl)benzenecarboximidamide sodium salt (1:1) (i.e. the product from Example 5, Step A) (51.0 g, 200 mmol) in acetonitrile (300 mL) was added diethyl ethoxymethylenemalonate (44.04 g, 200 mmol). The reaction was stirred at room temperature for 30 min followed by the addition of water (3.6 mL, 200 mmol). The reaction was then stirred for another 30 min Water (100 mL) was added to the residue, followed by a saturated solution of sodium bicarbonate (300 mL), and the mixture was extracted with ethyl acetate. The aqueous layer was acidified with concentrated hydrochloric acid until the pH was 1-2, and the mixture was extracted with dichloromethane. The organic layer was dried (MgSO$_4$) and concentrated under reduced pressure to provide a solid, which was washed with diethyl ether and dried under reduced pressure to afford the title product as a off-white solid (18 g).

$^1$H NMR (CDCl$_3$) δ 12.68 (s, 1H), 9.15 (s, 1H), 7.43 (m, 1H), 7.19-7.38 (m, 5H), 7.12 (m, 1H), 6.88 (m, 1H), 2.03 (s, 3H).

Step C: Preparation of 3-oxo-1-cyclohexen-1-yl 1-(3-fluoro-2-methylphenyl)-1,6-dihydro-6-oxo-2-phenyl-5-pyrimidinecarboxylate To a stirred solution of 1-(3-fluoro-2-methylphenyl)-1,6-dihydro-6-oxo-2-phenyl-5-pyrimidinecarboxylic acid (i.e. the product from Example 5, Step B) (41.0 g, 126 mmol) in dichloromethane (400 mL) was added oxalyl chloride (31.05 g, 252.0 mmol) at 0° C. followed by a catalytic amount (7 drops) of N,N-dimethylformamide. The reaction mixture was allowed to warm to room temperature and stir for 1 h. The reaction mixture was then concentrated under reduced pressure. To the resulting residue was added dichloromethane (400 mL), 1,3-cyclohexanedione (17.03 g, 152 mmol), followed by triethylamine (38.30 g, 379 mmol) and the reaction mixture was stirred at room temperature for 30 min. Saturated aqueous ammonium chloride solution was added, and the mixture was extracted with dichloromethane. The organic layer was washed once with water. Then the organic layer was dried (MgSO$_4$) and concentrated under reduced pressure. The resulting solid was washed with chlorobutane to afford the title product pure as an off-white solid (37.6 g).

$^1$H NMR (CDCl$_3$) δ 8.92 (s, 1H), 7.24-7.40 (m, 5H), 7.18 (m, 1H), 7.05 (m, 1H), 6.87 (m, 1H), 6.05 (s, 1H), 2.68 (m, 2H), 2.45 (m, 2H), 2.11 (m, 2H), 2.03 (s, 3H).

Step D: Preparation of 3-(3-fluoro-2-methylphenyl)-5-[(2-hydroxy-6-oxo-1-cyclohexen-1-yl)-carbonyl]-2-phenyl-4(3H)-pyrimidinone To a stirred solution of 3-oxo-1-cyclohexen-1-yl 1-(3-fluoro-2-methylphenyl)-1,6-dihydro-6-oxo-2-phenyl-5-pyrimidinecarboxylate (i.e. the product from Example 5, Step C) (42 g, 100.4 mmol) in acetonitrile (200 mL) was added cesium fluoride (30.5 g, 200.8 mmol). The reaction mixture was stirred for 24 h at room temperature. Water and ethyl acetate was added to the reaction mixture and the water layer was extracted several times with ethyl acetate. The combined organic layers were dried (MgSO$_4$) and concentrated under reduced pressure. The resulting solid was washed several times with ether and filtered, followed by the addition 60 mL of ethyl acetate and let stir for 2 h. The resulting solid was then washed again with ether and dried under reduced pressure to afford the title product, a compound of the present invention, as a yellow solid (26 g).

$^1$H NMR (CDCl$_3$) δ 16.38 (s, 1H), 8.28 (s, 1H), 7.21-7.34 (m, 5H), 7.11 (m, 1H), 7.00 (m, 1H), 6.86 (m, 1H), 2.70 (m, 2H), 2.47 (m, 2H), 2.10 (m, 3H), 2.03 (m, 2H).

Example 6

Preparation of 5-[(5-cyclopropyl-4-isoxazolyl)carbonyl]-2,3-diphenyl-4(3H)-pyrimidinone (Compound 223)

Step A: Preparation of 1-cyclopropyl-3-(1,6-dihydro-6-oxo-1,2-diphenyl-5-pyrimidinyl)-1,3-propanedione To a mixture of 1,6-dihydro-6-oxo-1,2-diphenyl-5-pyrimidinecarboxylic acid (i.e. the product from Example 1, step B) (1.84 g, 6.3 mmol) and toluene (6.3 mL) was added phosphorus pentachloride (1.31 g, 6.3 mmol) at ambient temperature. The resulting mixture was heated at reflux under a nitrogen atmosphere for 6 h. The resulting yellow solution was concentrated to give 1.53 g of the acid chloride as a yellow solid.

n-Butyllithium (2.5M solution in hexanes, 2.2 mL, 5.6 mmol) was added dropwise to a solution of N,N-diisopropylamine (0.82 mL, 5.8 mmol) and anhydrous tetrahydrofuran (8 mL) at –78° C. under a nitrogen atmosphere. The resulting solution was warmed to 0° C., stirred for 30 min, and then cooled to –78° C. Cyclopropyl methyl ketone (0.55 mL, 5.6 mmol) was added dropwise at below –65° C. The resulting solution was stirred at –78° C. for 30 min and was then treated with a slurry of the acid chloride as prepared above (823 mg, 2.7 mmol) in anhydrous tetrahydrofuran (5 mL) added dropwise via syringe at below 60° C. Additional anhydrous tetrahydrofuran (5 mL) was used to complete the transfer of the acid chloride. The resulting mixture was stirred at –78° C. for 1 h and was then treated with saturated aqueous ammonium chloride (7 mL) at below –50° C. The resulting mixture was stirred at ambient temperature for 15 min and was partitioned between ethyl acetate (100 mL) and saturated aqueous ammonium chloride (50 mL). The organic layer was dried over MgSO$_4$, filtered, and concentrated onto silica gel (2.5 g). The residue was purified by medium pressure liquid chromatography using a 24 g silica column and eluting with a gradient of 0 to 100% ethyl acetate in hexanes to provide the title compound as a pale yellow glassy solid (250 mg).

$^1$HNMR (400 MHz, CDCl$_3$) δ 15.88 (s, 1H), 8.93 (s, 1H), 7.40-7.33 (m, 3H), 7.33-7.26 (m, 3H), 7.24-7.19 (m, 3H), 7.14 (apparent d, 2H), 1.81 (sep, 1H), 1.20-1.15 (m, 2H), 0.99-0.92 (m, 2H).

Step B: Preparation of 1-cyclopropyl-3-(1,6-dihydro-6-oxo-1,2-diphenyl-5-pyrimidinyl)-2-(ethoxymethylene)-1,3-propanedione A suspension of 1-cyclopropyl-3-(1,6-dihydro-6-oxo-1,2-diphenyl-5-pyrimidinyl)-1,3-propanedione (i.e. the product from Example 6, Step A) (165 mg, 0.46 mmol), triethyl orthoformate (0.23 mL, 1.4 mmol), and acetic anhydride (0.92 mL) was heated at 110° C. under a nitrogen atmosphere for 4 h. The residue was dissolved in toluene (5 mL) and the resulting solution was concentrated under reduced pressure at 50° C. The residue was re-dissolved in toluene (5 mL) and the resulting solution was concentrated at 50° C. to give 181 mg of the title compound as a brown oil that was used in the next step without further purification. $^1$H NMR analysis showed the product to contain a mixture of Z- and E-olefin isomers.

$^1$HNMR (400 MHz, CDCl$_3$) 8.63 and 8.47 (2s, 1H total), 7.68 and 7.62 (2s, 1H total), 7.33-7.16 (m, 8H), 7.10-7.02 (m, 2H), 4.27 and 4.16 (2q, 2H total), 2.64-2.57 (m, <1H), 1.42 and 1.33 (3t, 3H total), 1.11-1.06 and 1.04-0.98 (2m, 2H total), 0.91-0.82 (m, 2H).

Step C: Preparation of 5-[(5-cyclopropyl-4-isoxazolyl)carbonyl]-2,3-diphenyl-4(3H)-pyrimidinone Anhydrous sodium acetate (68 mg, 0.83 mmol) was added to a solution of 1-cyclopropyl-3-(1,6-dihydro-6-oxo-1,2-diphenyl-5-pyrimidinyl)-2-(ethoxymethylene)-1,3-propanedione (i.e. the product from Example 6, Step B) (171 mg, 0.41 mmol) in ethanol (4 mL) at 0° C. Hydroxylamine hydrochloride (29 mg, 0.42 mmol) was added and the resulting suspension was stirred at 0° C. for 30 min and then at ambient temperature for 2 h. The resulting mixture was diluted with ethyl acetate (20 mL) and ethanol (20 mL), concentrated onto 0.8 g silica gel, and the residue purified by medium pressure liquid chromatography using a 12 g silica gel column and eluting with 0 to 100% ethyl acetate in hexanes to obtain 14 mg of the title compound, a compound of the present invention as a yellow glassy solid.

$^1$HNMR (400 MHz, CDCl$_3$) 8.56 (s, 1H), 8.45 (s, 1H), 7.40-7.30 (m, 6H), 7.25-7.20 (m, 2H), 7.16-7.12 (m, 2H), 3.02-2.93 (m, 1H), 1.37-1.32 (m, 2H), 1.27-1.22 (m, 2H).

Example 7

Preparation of 5-[(2-hydroxy-6-oxo-1-cyclohexen-1-yl)carbonyl]-3-phenyl-2-(3-pyridinyl)-4(3H)-pyrimidone (Compound 113)

Step A: Preparation of N-phenyl-3-pyridinecarboximidamide

Sodium hydride (60% in mineral oil, 11.52 g, 288 mmol) was added portion-wise over 30 min to a stirred solution of 3-pyridinecarbonitrile (30 g, 288 mmol) and aniline (26 g, 290 mmol) in dimethylsulfoxide (150 mL) at 10° C. The reaction mixture was allowed to warm to ambient temperature with stirring for 18 h. The reaction mixture was slowly and cautiously poured into water containing crushed ice. The solid that precipitated was filtered, washed with petroleum ether, dissolved in dichloromethane and dried over anhydrous Na$_2$SO$_4$. The volatiles were removed under reduced pressure (high vacuum) and the residue was dried to afford 36.5 g of the title compound as a yellow solid.

$^1$H NMR (CDCl$_3$, 500 MHz) δ 9.06 (s, 1H), 8.68 (d, 1H), 8.22 (d, 1H), 7.38-7.35 (m, 3H), 7.08 (t, 1H), 6.97 (d, 2H), 5.00 (s, 2H).

Step B: Preparation of ethyl 1,6-dihydro-6-oxo-1-phenyl-2-(3-pyridinyl)-5-pyrimidinecarboxylate A suspension of the N-phenyl-3-pyridinecarboximidamide (i.e. the product from Example 7, Step A) (36.5 g, 185 mmol) in diethyl ethoxymethylenemalonate (60 g, 280 mmol) was heated to 160° C. for 8 h. Ethanol formed in the reaction was collected using a distillation head attached to the flask containing the heated reaction mixture. The reaction mixture was then cooled to ambient temperature when the formation of a solid was observed. A mixture of diethyl ether/petroleum ether (8:2) was added to the reaction mixture was filtered. The collected solid was washed with additional ether/petroleum ether (4:1) followed by n-chlorobutane/petroleum ether (1:1) to obtain 51 g of the title compound as a light brown powder.

$^1$H NMR (CDCl$_3$, 500 MHz) δ 8.79 (s, 1H), 8.57 (dd, 1H), 8.52 (dd, 1H), 7.58 (dt, 1H), 7.38-7.35 (m, 3H), 7.16-7.13 (m, 3H), 4.41 (q, 2H), 1.39 (t, 3H).

Step C: Preparation of 1,6-dihydro-6-oxo-1-phenyl-2-(3-pyridinyl)-5-pyrimidinecarboxylic acid A suspension of ethyl 1,6-dihydro-6-oxo-1-phenyl-2-(3-pyridinyl)-5-pyrimidinecarboxylate (i.e. the product from Example 7, Step B) (5.0 g, 15.5 mmol) and lithium iodide (powder, 5.2 g, 38.8 mmol) in pyridine (15 mL) was heated to 125-130° C. for 12 h. After cooling to ambient temperature, excess solvent was removed under reduced pressure. The resulting residue was dissolved in water (100 mL) and acidified with hydrochloric acid (6 N) to pH 7. The resulting dark brown solution was extracted with ethyl acetate (1×100 mL) to remove the non polar impurities. The aqueous layer was again extracted with dichloromethane/methanol (95:5) (2×50 mL). After initial extractions, the aqueous layer was slowly acidified to pH 4 and further extracted with dichloromethane/methanol (95:5) (3×50 mL). The combined neutral and acidic extracts were washed with brine and dried over anhydrous Na$_2$SO$_4$. The residue obtained after removal of the solvent was dried under high-vacuum to obtain 3.4 g of the title compound as a light brown solid.

$^1$H NMR (CDCl$_3$, 500 MHz) δ 12.67 (br s, 1H), 9.12 (s, 1H), 8.60-8.57 (m, 2H), 7.65 (dt, 1H), 7.47-7.46 (m, 3H), 7.22-7.19 (m, 3H).

Step D: Preparation of 3-oxo-1-cyclohexen-1-yl 1,6-dihydro-6-oxo-1-phenyl-2-(3-pyridinyl)-5-pyrimidinecarboxylate To a stirred suspension of 1,6-dihydro-6-oxo-1-phenyl-2-(3-pyridinyl)-5-pyrimidinecarboxylic acid (i.e. the product from Example 7, Step C) (10.7 g, 36.3 mmol) in dichloromethane (150 mL) at ambient temperature was added 2-chloro-N-methyl pyridinium iodide (also known as the Mukaiyama reagent) (14.8 g, 57.9 mmol) followed by cyclohexanedione (6.5 g, 58 mmol) and triethylamine (9.2 g, 91 mmol). The reaction mixture was left stirring at ambient temperature overnight, then diluted with dichloromethane, washed with water, brine and dried over anhydrous Na$_2$SO$_4$. The residue obtained after removal of the solvent under vacuum was purified by tituration with n-chlorobutane/petroleum ether mixtures to obtain 9.8 g of the title compound as a light brown solid.

$^1$H NMR (CDCl$_3$, 500 MHz) δ 8.89 (s, 1H), 8.60 (d, 1H) 8.54 (dd, 1H), 7.61 (dt, 1H), 7.42-7.37 (m, 3H), 7.19-7.14 (m, 3H), 6.04 (s, 1H), 2.69-2.66 (m, 2H), 2.45-2.42 (m, 2H), 2.10 (q, 2H).

Step E: Preparation of 5-[(2-hydroxy-6-oxo-1-cyclohexen-1-yl)carbonyl]-3-phenyl-2-(3-pyridinyl)-4(3H)-pyrimidone To a stirred solution of 3-oxo-1-cyclohexen-1-yl 1,6-dihydro-6-oxo-1-phenyl-2-(3-pyridinyl)-5-pyrimidinecarboxylate (i.e. the product from Example 7, Step D) (11.1 g, 28.6 mmol) in acetonitrile (166 mL) was added cesium fluoride (8.71 g, 57.3 mmol) followed by catalytic amount (~50 mg) of tetrabutylammonium bromide at ambient temperature. After stirring for 3 h at ambient temperature, the reaction mixture was diluted with ethyl acetate, washed with water, brine and dried over anhydrous Na$_2$SO$_4$. The volatile components were removed under reduced pressure and the residue was subjected to silica gel column chromatography eluting with ethyl acetate/petroleum ether (1:1) to ethyl acetate to dichloromethane/methanol (95:5). The product obtained was washed with minimum amount of methanol to afford 1.4 g of the title compound, a compound of the present invention as a light yellow solid.

$^1$H NMR (CDCl$_3$, 500 MHz) mixture of tautomers δ 16.45 (s, 0.8H), 8.57-8.50 (m, 2H), 8.21 (s, 1H), 7.57 (d, 1H), 7.35 (d, 3H), 7.16-7.13 (m, 3H), 5.29 (s, 0.2H,), 2.71 (br s, 2H), 2.47 (br s, 2H), 2.04-2.02 (m, 2H).

Example 8

Preparation of 5-[(2-hydroxy-6-oxo-1-cyclohexen-1-yl)carbonyl]-2-phenyl-3-(cis/trans-tetrahydro-1-oxido-2H-thiopyran-4-yl)-4(3H)-pyrimidinone (Compound 168) and 5-[(2-hydroxy-6-oxo-1-cyclohexen-1-yl)carbonyl]-2-phenyl-3-(trans/cis-tetrahydro-1-oxido-2H-thiopyran-4-yl)-4(3H)-pyrimidinone (Compound 169)

Step A: Preparation of 5-[(2-hydroxy-6-oxo-1-cyclohexen-1-yl)carbonyl]-2-phenyl-3-(cis/trans-tetrahydro-1-oxido-2H-thiopyran-4-yl)-4(3H)-pyrimidinone and 5-[(2-hydroxy-6-oxo-1-cyclohexen-1-yl)carbonyl]-2-phenyl-3-(trans/cis-tetrahydro-1-oxido-2H-thiopyran-4-yl)-4(3H)-pyrimidinone To 5-[(2-hydroxy-6-oxo-1-cyclohexen-1-yl)carbonyl]-2-phenyl-3-(tetrahydro-2H-thiopyran-4-yl)-4(3H)-pyrimidinone (the tautomer known as 2-[[1,6-dihydro-6-oxo-2-phenyl-1-(tetrahydro-2H-thiopyran-4-yl)-5-pyrimidinyl]carbonyl]-1,3-cyclohexanedione) (0.15 g, 0.37 mmol) in a mixture of 5.0 mL water and 5.0 mL methanol at room temperature was added NaIO$_4$ (0.074 g, 0.35 mmol). After approximately 45 min, additional NaIO$_4$ (0.011 g, 0.05 mmol) was added and stirring was continued for an additional 2 h. The reaction mixture was extracted with dichloromethane and the combined organics were dried over MgSO$_4$ concentrated under reduced pressure and purified by medium pressure liquid chromatography on silica gel eluting with 0 to 10% methanol in chloroform to provide 0.07 g of Compound 168 (alternatively known as 2-[[1,6-dihydro-6-oxo-2-phenyl-1-(cis/trans-tetrahydro-1-oxido-2H-thiopyran-4-yl)-5-pyrimidinyl]carbonyl]-1,3-cyclohexanedione) and and 0.03 g of Compound 169 (alternatively known as 2-[[1,6-dihydro-6-oxo-2-phenyl-1-(trans/cis-tetrahydro-1-oxido-2H-thiopyran-4-yl)-5-pyrimidinyl]carbonyl]-1,3-cyclohexanedione) both as solids.

$^1$H NMR of Compound 168 (CDCl$_3$) δ16.58 (br s, 1H), 7.99 (s, 1H), 7.58 (m, 3H), 7.47 (m, 2H), 4.14 (m, 1H), 3.39 (m, 2H), 3.12 (m, 2H), 2.74 (t, 2H), 2.49 (t, 2H), 2.37 (t, 2H), 2.05 (m, 4H).

$^1$H NMR Compound 169 (CDCl$_3$) δ16.42 (br s, 1H), 8.00 (s, 1H), 7.54 (m, 5H), 4.06 (m, 1H), 3.65 (m, 2H), 3.07 (m, 2H), 2.60 (br s, 4H), 2.17 (m, 2H), 2.07 (m, 2H), 1.80 (d, 2H).

Example 9

Preparation of 2-(3,5-difluorophenyl)-5-[(2-hydroxy-4-oxobicyclo[3.2.1]oct-2-en-3-yl)carbonyl]-3-(2-methoxyethyl)-4(3H)-pyrimidinone (Compound 243)

Step A: Preparation of 3,5-difluorobenzenecarboxamidic acid ethyl ester hydrochloride (1:1)

To a stirred solution of 3,5-difluorobenzonitirile (25 g, 180 mmol) in ethanol (336 mL) and dichloromethane (180 mL) at 0° C., was added acetyl chloride (128 mL, 1800 mmol) drop wise via addition funnel. The reaction mixture was allowed to warm to room temperature and stir for 24 h. The reaction mixture was then concentrated under reduced pressure to afford a solid, which was washed with diethyl ether and dried under reduced pressure to afford the title product as a white solid (21.5 g) which was carried forward to the next step without further purification.

Step B: Preparation of 3,5-difluoro-N-(2-methoxyethyl)benzenecarboximidamide hydrochloride (1:1)

To a stirred solution of 3,5-difluorobenzenecarboxamidic acid ethyl ester hydrochloride (5.39 g, 24.3 mmol) (i.e. the product from Example 9, Step A) in methanol (25 mL) at 0° C., was added 2-methoxy-1-ethylamine (2.2 mL, 25.5 mmol). The reaction mixture was allowed to warm to room temperature and stir for 24 h. The reaction mixture was concentrated under reduced pressure to afford the title product as a gummy oil, which was used without further purification in the next step.

Step C: Preparation of ethyl 2-(3,5-difluorophenyl)-1,6-dihydro-1-(2-methoxyethyl)-6-oxo-5-pyrimidinecarboxyate To a stirred solution of 3,5-difluoro-N-(2-methoxyethyl) benzenecarboximidamide hydrochloride (1:1 (i.e. the product from Example 9, Step B) (24.3 mmol) in ethanol (25 mL) was added diethyl ethoxymethylenemalonate (5.25 g, 24.3 mmol) followed by sodium ethoxide (21% soln) (9.1 mL, 24.3 mmol). The reaction mixture was heated and stirred at reflux for 24 h. The reaction mixture was cooled to room temperature concentrated under reduced pressure. The residue was purified by column chromatography eluting with 50% ethyl acetate in hexanes to afford the title product as a white solid (6.1 g).

$^1$H NMR (CDCl$_3$) δ 8.65 (s, 1H), 7.14 (m, 2H), 6.98 (m, 1H), 4.41 (m, 2H), 4.21 (m, 2H), 3.67 (m, 2H), 3.22 (s, 3H), 1.40 (m, 3H).

Step D: Preparation of 2-(3,5-difluorophenyl)-1,6-dihydro-1-(2-methoxyethyl)-6-oxo-5-pyrimidinecarboxylic acid To a stirred solution of ethyl ethyl 2-(3,5-difluorophenyl)-1,6-dihydro-1-(2-methoxyethyl)-6-oxo-5-pyrimidinecarboxyate (i.e. the product from Example 9, Step C) (1.14 g, 3.37 mmol) in ethyl acetate (10 mL) was added lithium iodide powder (1.35 g, 10.0 mmol). The reaction mixture was heated to reflux for 24 h, cooled, and then stirred at room temperature for 72 h. The reaction mixture was concentrated under reduced pressure. To the resulting residue was added water (10 mL), followed by 6 N hydrochloric acid until the pH was 2. The mixture was extracted with dichloromethane, and the organic layer was dried (MgSO$_4$) and concentrated under reduced pressure to afford a solid, which was washed with diethyl ether and dried under reduced pressure to afford the title product as a white solid (700 mg).

$^1$H NMR (CDCl$_3$) δ 12.88 (s, 1H), 8.99 (s, 1H), 7.20 (m, 2H), 7.03 (m, 1H), 4.32 (m, 2H), 3.69 (m, 2H), 3.25 (s, 3H).

Step E: Preparation of 2-(3,5-difluorophenyl)-5-[(2-hydroxy-4-oxobicyclo[3.2.1]oct-2-en-3-yl)carbonyl]-3-(2-methoxyethyl)-4(3H)-pyrimidinone To 2-(3,5-difluorophenyl)-1,6-dihydro-1-(2-methoxyethyl)-6-oxo-5-pyrimidinecarboxylic acid (i.e. the product from Example 9, Step D) (0.25 g, 0.81 mmol) in 10 mL of dichloromethane was added oxalyl chloride (0.21 g, 1.6 mmol) and one drop of N,N-dimethylformamide. The reaction mixture was stirred at room temperature for 2 h and then concentrated under reduced pressure. The remaining crude oil was re-dissolved in dichloromethane (10 mL) and then treated with bicycle[3.2.1]octane-2,4-dione (0.12 g, 0.88 mmol) (prepared according to U.S. Pat. No. 6,815,563) and triethylamine (0.16 g, 1.6 mmol). After 30 min at room temperature, a catalytic amount of 2-hydroxy-2-methyl-propanenitrile (0.0075 g, 0.088 mmol) and triethylamine (0.16 g, 1.6 mmol) were added and the reaction mixture was stirred at ambient temperature over night. The reaction mixture was then concentrated under reduced pressure and purified by medium pressure liquid chromatography on silica gel eluting with 0 to 10% methanol in chloroform to provide 0.180 g of the title compound (also known as 3-[[2-(3,5-difluorophenyl)-1,6-dihydro-1-(2-methoxyethyl)-6-oxo-5-pyrimidinyl]carbonyl]biciclo[3.2.1]octane-2,4-dione), a compound of the present invention, as a solid.

$^1$H NMR (CDCl$_3$) δ 16.58 (br s, 1H), 8.05 (s, 1H), 7.17 (m, 2H), 6.96 (m, 1H), 4.18 (br s, 2H), 3.61 (t, 2H), 3.26 (br s, 3H), 3.09 (br s, 1H), 2.96 (br s, 1H), 2.26 (d, 1H), 2.17 (br s, 2H), 2.02 (br s, 1H), 1.88 (br s, 1H), 1.73 (m, 1H).

Example 10

Preparation of 5-[(2-hydroxy-6-oxo-1-cyclohexen-1-yl)carbonyl]-3-(2-methoxyethyl)-2-(3-thienyl)-4(3H)-pyrimidinone (Compound 97)

Step A: Preparation of 3-thiophenecarboximidic acid ethyl ester hydrochloride

To a solution of thiophene-3-carbonitrile (10 g, 9.2 mmol) in dichloromethane (100 mL) and ethanol (170 mL) at 0° C. was added acetyl chloride (114 g, 145 mmol). The reaction was allowed to slowly warm to ambient temperature and stir 16 h. The reaction mixture was then concentrated under reduced pressure to yield a solid which was triturated with diethyl ether resulting in 17.1 g of 3-thiophenecarboximidic acid ethyl ester hydrochloride as a white solid.

$^1$H NMR (DMSO-d$_6$) δ 11.77 (br s, 2H), 8.92 (m, 1H), 7.90 (m, 1H), 7.83 (m, 1H), 4.60 (q, 2H), 1.46 (t, 3H).

Step B: Preparation of ethyl 1,6-dihydro-1-(2-methoxyethyl)-6-oxo-2-(3-thienyl)-5-pyrimidinecarboxylate 2-Methoxy-1-ethylamine (0.86 g, 11.4 mmol) was added to a solution of 3-thiophenecarboximidic acid ethyl ester hydrochloride (2.0 g, 10.4 mmol) in methanol (10 mL), which was then stirred at ambient temperature for 1.5 h. The reaction mixture was then concentrated under reduced pressure and redissolved in ethanol (10 mL). Sodium ethoxide solution (21% w/w in ethanol, 3.4 g, 10 mmol) and diethyl ethoxymethylenemalonate (2.2 g, 10 mmol) were added and the mixture was heated to reflux for 2 h before being concentrated under reduced pressure and purified by medium pressure liquid chromatography on silica gel eluting with 0 to 100% ethyl acetate in hexanes to provide 1.82 g of the title compound as an oil.

$^1$H NMR (CDCl$_3$) δ 8.68 (s, 1H), 8.06 (m, 1H), 7.48 (m, 1H), 7.43 (m, 1H), 4.38 (m, 4H), 3.81 (t, 2H), 3.29 (s, 3H), 1.40 (t, 3H).

Step C: 1,6-dihydro-1-(2-methoxyethyl)-6-oxo-2-(3-thienyl)-5-pyrimidinecarboxylic acid Ethyl 1,6-dihydro-1-(2-methoxyethyl)-6-oxo-2-(3-thienyl)-5-pyrimidinecarboxylate a (1.82 g, 5.90 mmol) (i.e. the product from Example 10, Step B) was dissolved in ethyl acetate and treated with lithium iodide (powder, 2.36 g, 17.6 mmol) and heated to reflux for 16 h. The crude reaction mixture was concentrated under reduced pressure and then aqueous sodium bicarbonate solution was added and the resulting solution was extracted with ethyl acetate which was then discarded. The aqueous layer was made acidic with hydrochloric acid (1 N) and then extracted with dichloromethane (2×40 mL). The combined organics were dried over MgSO$_4$ and concentrated under reduced pressure to provide the title compound as a solid.

$^1$H NMR (CDCl$_3$) δ 12.96 (br s, 1H), 8.99 (s, 1H), 8.17 (m, 1H), 7.53 (m, 1H), 7.48 (m, 1H), 4.47 (t, 2H), 3.83 (t, 2H), 3.32 (s, 3H).

Step D: Preparation of 5-[(2-hydroxy-6-oxo-1-cyclohexen-1-yl)carbonyl]-3-(2-methoxyethyl)-2-(3-thienyl)-4(3H)-pyrimidinone To 1,6-dihydro-1-(2-methoxyethyl)-6-oxo-2-(3-thienyl)-5-pyrimidinecarboxylic acid (i.e. the product from Example 10, Step C) (0.5 g, 1.8 mmol) in 10 mL of dichloromethane was added oxalyl chloride (0.45 g, 3.6 mmol) and one drop of N,N-dimethylformamide. The reaction mixture was stirred at room temperature for 2 h and then concentrated under reduced pressure. The crude oil was redissolved in 10 mL of dichloromethane and treated with 1,3-cyclohexanedione (0.22 g, 2.0 mmol) and triethylamine (0.18 g, 1.8 mmol). The reaction mixture was stirred for 30 min then treated with a catalytic amount of 2-hydroxy-2-methyl-propanenitrile (0.015 g, 0.18 mmol) and triethylamine (0.182 g, 1.8 mmol) and stirred at ambient temperature for 16 h. The reaction mixture was then concentrated under reduced pressure and purified by medium pressure liquid chromatography on silica gel eluting with 0 to 10% methanol in chloroform to provide 0.160 g of the title compound (also known as 2-[[1,6-dihydro-1-(2-methoxyethyl)-6-oxo-2-(3-thienyl)-5-pyrimidinyl]carbonyl]-1,3-cyclohexanedione), a compound of the invention, as a solid.

$^1$H NMR (CDCl$_3$) δ 16.51 (s, 1H), 8.14 (s, 1H), 7.97 (m, 1H), 7.43 (m, 2H), 4.29 (t, 2H), 3.70 (t, 2H), 3.29 (s, 3H), 2.73 (t, 2H), 2.50 (t, 2H), 2.08 (m, 2H).

Example 11

Preparation of 3-cyclohexyl-5-[(2-hydroxy-6-oxo-1-cyclohexen-1-yl)carbonyl]-2-phenyl-4(3H)-pyrimidinone (Compound 128)

Step A: Preparation of ethyl 1-cyclohexyl-1,6-dihydro-6-oxo-2-phenyl-5-pyrimidinecarboxyate Cyclohexylamine (0.58 g, 5.8 mmol) was added to a solution of ethyl benzenecarboximidic acid ethyl ester (1.0 g, 5.4 mmol) in methanol (10 mL), which was then stirred at room temperature for 16 h. The reaction mixture was then concentrated under reduced pressure and then redissolved in ethanol (10 mL). Sodium ethoxide solution (21% w/w in ethanol, 1.8 g, 5.5 mmol) and diethyl ethoxymethylenemalonate (1.2 g, 5.5 mmol) were added and the mixture was heated to reflux for 16 h before being concentrated under reduced pressure and purified by medium pressure liquid chromatography on silica gel eluting with 0 to 100% ethyl acetate in hexanes to provide 1.41 g of the title compound as a yellow oil.

¹H NMR (CDCl₃) δ 8.58 (s, 1H), 7.53 (m, 3H), 7.45 (m, 2H), 4.41 (m, 2H), 3.94 (m, 1H), 2.76 (m, 2H), 1.78 (d, 2H), 1.67 (d, 2H), 1.53 (d, 1H), 1.42 (m, 3H), 1.21 (m, 1H), 0.96 (m, 2H).

Step B: Preparation of 1-cyclohexyl-1,6-dihydro-6-oxo-2-phenyl-5-pyrimidinecarboxylic acid Ethyl 1-cyclohexyl-1,6-dihydro-6-oxo-2-phenyl-5-pyrimidinecarboxyate (1.41 g, 4.32 mmol) (i.e. the product from Example 11, Step A) was dissolved in ethyl acetate and treated with lithium iodide (powder, 1.72 g, 12.8 mmol) and heated to reflux for 16 h. The crude reaction mixture was concentrated under reduced pressure and then aqueous sodium bicarbonate was added and the resulting solution was extracted with ethyl acetate which was then discarded. The aqueous layer was made acidic with hydrochloric acid (1 N) and then extracted with dichloromethane (2×40 mL). The combined organic extracts were dried over MgSO₄ and concentrated under reduced pressure resulting in 0.58 g of the title product as a solid.

¹H NMR (CDCl₃) δ 13.30 (br. s., 1H), 8.94 (s, 1H), 7.59 (m, 3H), 7.48 (m, 2H), 4.12 (m, 1H), 2.68 (m, 2H), 1.84 (d, 2H), 1.74 (d, 2H), 1.60 (d, 1H), 1.22 (m, 1H), 1.03 (m, 2H).

Step C: Preparation of 2-[(1-cyclohexyl-1,6-dihydro-6-oxo-2-phenyl-5-pyrimidinyl)carbonyl]-1,3-cyclohexanedione To 1-cyclohexyl-1,6-dihydro-6-oxo-2-phenyl-5-pyrimidinecarboxylic acid (i.e. the product from Example 11, Step B) (0.58 g, 1.5 mmol) in 10 mL of dichloromethane was added oxalyl chloride (0.490 g, 3.9 mmol) and one drop of N,N-dimethylformamide. The reaction was stirred at ambient temperature for 2 h and then concentrated under reduced pressure. The crude oil was then redissolved in 10 mL of dichloromethane and then treated with 1,3-cyclohexanedione (0.24 g, 2.1 mmol) and triethylamine (0.39 g, 3.8 mmol) stirred for 30 min, then treated with a catalytic amount of 2-hydroxy-2-methyl-propanenitrile (0.015 g, 0.15 mmol) and triethylamine (0.393 g, 3.8 mmol) and stirred at ambient temperature for 16 h. The reaction mixture was then concentrated under reduced pressure and purified by medium pressure liquid chromatography on silica gel eluting with 0 to 10% methanol in chloroform to provide 0.570 g of the title compound, a compound of the invention, as a solid.

¹H NMR (CDCl₃) δ 16.61 (s, 1H), 8.02 (s, 1H), 7.50 (m, 5H), 3.93 (m, 1H), 2.73 (t, 2H), 2.61 (m, 2H), 2.51 (t, 2H), 2.08 (m, 2H), 1.74 (m, 4H), 1.51 (d, 1H), 1.19 (m, 1H), 0.97 (m, 2H).

By the procedures described herein together with methods known in the art, the following compounds of Tables 1 to 32 can be prepared. The following abbreviations are used in the Tables which follow: Me means methyl, Et means ethyl, n-Pr means normal propyl, i-Pr means isopropyl, c-Pr means cyclopropyl, n-Bu means normal butyl, i-Bu means isobutyl, s-Bu means secondary butyl, c-Bu means cyclobutyl, t-Bu means tertiary butyl, n-pent means normal pentyl, c-Pent means cyclopentyl, n-Hex means normal hexyl, hept means heptyl, c-Hex means cyclohexyl, Ph means phenyl, OMe means methoxy, OEt means ethoxy, SMe means methylthio, SEt means ethylthio, thp means tetrahydropyran, thtp means tetrahydrothiopyran, thf means tetrahydrofuran, —CN means cyano, —NO₂ means nitro, S(O)Me means methylsulfinyl, SO₂ means sulfonyl and S(O)₂Me means methylsulfonyl.

TABLE 1

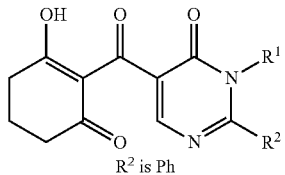

R² is Ph

| R¹ |
|---|
| Me |
| Et |
| n-Pr |
| i-Pr |
| c-Pr |
| n-Bu |
| i-Bu |
| s-Bu |
| c-Bu |
| t-Bu |
| n-pent |
| c-Pent |
| n-Hex |
| c-Hex |
| Ph |
| CH₂-c-Pr |
| CH₂-c-Bu |
| CH₂SPh |
| CH₂SCH₃ |
| CH₂CF₃ |
| CH₂Ph |
| Ph(4-Me) |
| CH₂CHC(CH₃)₂ |
| CH₂CH₂C≡CH |
| CH₂CH=CCl₂ |
| CH₂CH=CF₂ |
| CH₂CF=CF₂ |
| CH₂CCl=CCl₂ |
| CH₂C=CCH₃ |
| CH₂OCH₂CH₃ |
| CH₂CH₂OCH₃ |
| CH₂SO₂CH₃ |
| CH₂SCH₂CH₃ |
| Ph(2,3-di-OMe) |
| CH₂SO₂-n-Pr |
| CH₂CH₂SO₂Et |
| Ph(2,4-di-OMe) |
| Ph(2,5-di-OMe) |
| Ph(2,6-di-OMe) |
| Ph(3,5-di-OMe) |
| CH₂Ph(2-OMe) |
| CH₂Ph(3-OMe) |
| CH₂Ph(4-OMe) |
| CH₂CH₂SMe |
| CH₂SCH₂Ph |
| CH₂SO₂Ph |
| CH₂CH₂SEt |
| Ph(2,4-di-Cl) |
| Ph(2,5-di-Cl) |
| Ph(2,6-di-Cl) |
| Ph(3,5-di-Cl) |
| Ph(2,3-di-Me) |
| Ph(2,4-di-Me) |
| Ph(2,5-di-Me) |
| Ph(2,6-di-Me) |
| Ph(3,5-di-Me) |
| CH₂-c-Hex |
| Ph(2,3-di-F) |
| Ph(2,4-di-F) |
| Ph(2,5-di-F) |
| Ph(2,6-di-F) |
| CH₂CH₂CF₃ |
| CH₂C≡CH |
| Ph(2,3 -di-Cl) |
| Ph(3,5-di-F) |
| isoxazolin-2-yl |
| Ph(2-Cl) |
| Ph(3-Cl) |
| Ph(4-Cl) |

TABLE 1-continued

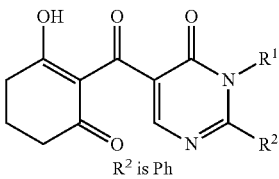

$R^2$ is Ph $R^1$

Ph(2-Me)
Ph(3-Me)
CH$_2$OCH$_3$
CH$_2$CH=CH$_2$
Ph(2-OMe)
Ph(3-OMe)
Ph(4-OMe)
Ph(2-CN)
Ph(3-CN)
Ph(4-CN)
Ph(2-F)
Ph(3-F)
Ph(4-F)
CH$_2$S-n-Pr
CH$_2$-c-Pent
oxazolin-2-yl
2-pyridinyl
3-pyridinyl
4-pyridinyl
Ph(2-NO$_2$)
Ph(3-NO$_2$)
Ph(4-NO$_2$)
Ph(2-CF$_3$)
Ph(3-CF$_3$)
Ph(4-CF$_3$)
Ph(2-Br)
Ph(3-Br)
Ph(4-Br)
CH$_2$Ph(2-Me)
CH$_2$Ph(3-Me)
CH$_2$Ph(4-Me)
CH$_2$Ph(2-Cl)
CH$_2$Ph(3-Cl)
CH$_2$Ph(4-Cl)
thiazol-3-yl
thiazol-2-yl
thiazolin-2-yl
thiazol-2-yl
oxazol-2-yl
CH$_2$CF$_2$CF$_3$
CH=CH$_2$
CH$_2$(thf-2-yl)
CH$_2$(3-methylisoxazolin-5-yl)
isoxazolin-4-yl
CH$_2$(3-methylisoxazol-5-yl)
5-methylisoxazol-3-yl
4-methyloxazol-2-yl
4-methylthiazol-2-yl
CH$_2$CH$_2$CH=CH$_2$
CH$_2$SO$_2$CH$_2$CH$_3$
CH$_2$CH$_2$SO$_2$Me
CH$_2$OCH$_2$OCH$_3$
3-methylthiazol-2-yl
5-chloropyridin-2-yl
5-methylpyridin-2-yl
5-methoxypyridin-2-yl
6-methylpyridin-2-yl
6-methylpyridin-3-yl
3-methoxypyridin-4-yl
3-methylpyridin-4-yl
3-chloropyridin-4-yl
CH$_2$OCH$_2$CH$_2$OCH$_3$
CH$_2$C(CH$_3$)C(CH$_3$)$_2$
n-hept
c-hept
thp-4-yl
thtp-4-yl
Ph(2,3-di-OMe)
Ph(3,4-di-OMe)

TABLE 1-continued

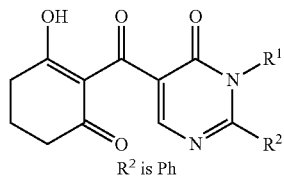

$R^2$ is Ph $R^1$

Ph(3,4-di-Me)
Ph(3,4-di-F)
Ph(3,4,5-tri-OMe)
Ph(2-I)
Ph(3-I)
Ph(4-I)
Ph(2-Et)
Ph(3-Et)
Ph(4-Et)
CH$_2$CH$_2$OCH$_2$CH$_3$
CH(CH$_3$)CH$_2$OCH$_3$
Ph(2-OCF$_3$)
Ph(3-OCF$_3$)
Ph(4-OCF$_3$)
Ph(2-Me-3-F)
Ph(2-Me-4-F)
Ph(2-Me-5-F)
Ph(2-F-3-Me)
Ph(2-F-4-Me)
Ph(2-F-5-Me)
Ph(3-F-4-Me)
Ph(3-F-5-Me)
Ph(3-Me-4-F)
CH$_2$CH$_2$CH$_2$OCH$_3$
CH$_2$CH$_2$CH$_2$OCH$_2$CH$_3$
CH$_2$(thp-2-yl)
CH$_2$(thp-4-yl)
CH$_2$CH$_2$CH=CH$_2$
CH$_2$C≡CH
CH$_2$CH$_2$SCH$_3$
CH$_2$CH$_2$SOCH$_3$
CH$_2$CH$_2$SO$_2$CH$_3$
CH$_2$CH$_2$CH$_2$SCH$_3$
CH$_2$CH$_2$CH$_2$SOCH$_3$
CH$_2$CH$_2$CH$_2$SO$_2$CH$_3$
c-hex(3-OCH$_3$)
c-hex(4-OCH$_3$)
c-hex(3,4-di-OCH$_3$)
c-hex(3,5-di-OCH$_3$)
CH$_2$CH$_2$SCH$_3$ The present disclosure also includes Tables 1A through 57A, each of which is constructed the same as Table 1 above except that the row heading in Table 1 (i.e. "$R^2$ is Ph") is replaced with the respective row headings shown below. For example, in Table 1A the row heading is "$R^2$ is Me", and $R^1$ is as defined in Table 1 above. Thus, the first entry in Table 1A specifically discloses a compound of Formula 1 wherein X is CH; Y is C(O); $R^1$ is Me; $R^2$ is Me; $R^3$ is OH; A is A-1; $B^1$ is C-1; $B^2$ is C-3; $B^3$ is C-1; and each $R^{14}$, $R^{15}$, $R^{18}$ and $R^{19}$ is H. Tables 2A through 57A are constructed similarly.

| Table | Row Heading |
|---|---|
| 1A | $R^2$ is Me |
| 2A | $R^2$ is Et |
| 3A | $R^2$ is n-Pr |
| 4A | $R^2$ is c-Pr |
| 5A | $R^2$ is SMe |
| 6A | $R^2$ is SO$_2$Me |
| 7A | $R^2$ is CF$_3$ |
| 8A | $R^2$ is Ph(2-Cl) |
| 9A | $R^2$ is Ph(3-Cl) |
| 10A | $R^2$ is Ph(4-Cl) |

-continued

| Table | Row Heading |
|---|---|
| 11A | R² is Ph(2-Me) |
| 12A | R² is Ph(3-Me) |
| 13A | R² is Ph(4-Me) |
| 14A | R² is Ph(2-OMe) |
| 15A | R² is Ph(3-OMe) |
| 16A | R² is Ph(4-OMe) |
| 17A | R² is Ph(2-F) |
| 18A | R² is Ph(3-F) |
| 19A | R² is Ph(4-F) |
| 20A | R² is OMe |
| 21A | R² is OEt |
| 22A | R² is CH₂Ph |
| 23A | R² is 2-pyridinyl |
| 24A | R² is 3-pyridinyl |
| 25A | R² is 4-pyridinyl |
| 26A | R² is H |
| 27A | R² is Ph(3,5-di-F) |
| 28A | R² is Ph(3,4-di-F) |
| 29A | R² is Ph(3,4,5-tri-F) |
| 30A | R² is Ph(2,3-di-F) |
| 31A | R² is Ph(3-CF₃) |
| 32A | R² is Ph(4-CF₃) |
| 33A | R² is Ph(3,5-di-CF₃) |
| 34A | R² is n-Bu |
| 35A | R² is CH₂OCH₃, |
| 36A | R² is CH₂CH₂OCH₃ |
| 37A | R² is CH₂CH₂CF₃ |
| 38A | R² is CH₂CF₃ |
| 39A | R² is n-pent |
| 40A | R² is c-pent |
| 41A | R² is c-Hex |
| 42A | R² is n-Hex |
| 43A | R² is thp-4-yl |
| 44A | R² is Ph(2-CN) |
| 45A | R² is Ph(3-CN) |
| 46A | R² is Ph(4-CN) |
| 47A | R² is Ph(2-C≡CH) |
| 48A | R² is Ph(3-C≡CH) |
| 49A | R² is Ph(4-C≡CH) |
| 50A | R² is Ph(3-Me, 2-F) |
| 51A | R² is Ph(3-Me-4-F) |
| 52A | R² is Ph(3-Me, 5-F) |
| 53A | R² is Ph(3-Me, 6-F) |
| 54A | R² is Ph(3-F, 2-Me) |
| 55A | R² is Ph(3-F-4-Me) |
| 56A | R² is Ph(3-F-5-Me) |
| 57A | R² is Ph(3-F, 6-Me) |

TABLE 2

R¹ is Me

| R² | R³ | R¹⁴ᵃ | R¹⁵ᵃ | R¹⁸ | R¹⁹ | R¹⁴ᵇ | R¹⁵ᵇ |
|---|---|---|---|---|---|---|---|
| Et | OH | Me | H | H | H | H | H |
| CF₃ | OH | Me | H | H | H | H | H |
| n-Pr | OH | Me | H | H | H | H | H |
| c-Pr | OH | Me | H | H | H | H | H |
| Ph | OH | Me | H | H | H | H | H |
| Ph(2-Cl) | OH | Me | H | H | H | H | H |
| Ph(3-Cl) | OH | Me | H | H | H | H | H |
| Ph(4-Cl) | OH | Me | H | H | H | H | H |
| SMe | OH | Me | H | H | H | H | H |
| SO₂Me | OH | Me | H | H | H | H | H |
| n-Bu | OH | Me | H | H | H | H | H |
| Ph(2-F) | OH | Me | H | H | H | H | H |
| Ph(3-F) | OH | Me | H | H | H | H | H |
| Ph(4-F) | OH | Me | H | H | H | H | H |
| Ph(3,5-di-F) | OH | Me | H | H | H | H | H |
| Ph(2-Me) | OH | Me | H | H | H | H | H |
| Ph(3-Me) | OH | Me | H | H | H | H | H |
| Ph(4-Me) | OH | Me | H | H | H | H | H |
| Ph(3,5-di-Me) | OH | Me | H | H | H | H | H |
| 2-pyridinyl | OH | Me | H | H | H | H | H |
| 3-pyridinyl | OH | Me | H | H | H | H | H |
| 4-pyridinyl | OH | Me | H | H | H | H | H |
| Et | OH | Me | Me | H | H | H | H |
| CF₃ | OH | Me | Me | H | H | H | H |
| n-Pr | OH | Me | Me | H | H | H | H |
| c-Pr | OH | Me | Me | H | H | H | H |
| Ph | OH | Me | Me | H | H | H | H |
| Ph(2-Cl) | OH | Me | Me | H | H | H | H |
| Ph(3-Cl) | OH | Me | Me | H | H | H | H |
| Ph(4-Cl) | OH | Me | Me | H | H | H | H |
| SMe | OH | Me | Me | H | H | H | H |
| SO₂Me | OH | Me | Me | H | H | H | H |
| Et | OH | H | H | Me | Me | H | H |
| CF₃ | OH | H | H | Me | Me | H | H |
| n-Pr | OH | H | H | Me | Me | H | H |
| c-Pr | OH | H | H | Me | Me | H | H |
| Ph | OH | H | H | Me | Me | H | H |
| Ph(2-Cl) | OH | H | H | Me | Me | H | H |
| Ph(3-Cl) | OH | H | H | Me | Me | H | H |
| Ph(4-Cl) | OH | H | H | Me | Me | H | H |
| SMe | OH | H | H | Me | Me | H | H |
| SO₂Me | OH | H | H | Me | Me | H | H |
| n-Bu | OH | H | H | Me | Me | H | H |
| Ph(2-F) | OH | H | H | Me | Me | H | H |
| Ph(3-F) | OH | H | H | Me | Me | H | H |
| Ph(4-F) | OH | H | H | Me | Me | H | H |
| Ph(3,5-di-F) | OH | H | H | Me | Me | H | H |
| Ph(2-Me) | OH | H | H | Me | Me | H | H |
| Ph(3-Me) | OH | H | H | Me | Me | H | H |
| Ph(4-Me) | OH | H | H | Me | Me | H | H |
| Ph(3,5-di-Me) | OH | H | H | Me | Me | H | H |
| 2-pyridinyl | OH | H | H | Me | Me | H | H |
| 3-pyridinyl | OH | H | H | Me | Me | H | H |
| 4-pyridinyl | OH | H | H | Me | Me | H | H |
| Et | OH | Me | Me | H | H | Me | Me |
| CF₃ | OH | Me | Me | H | H | Me | Me |
| n-Pr | OH | Me | Me | H | H | Me | Me |
| c-Pr | OH | Me | Me | H | H | Me | Me |
| Ph | OH | Me | Me | H | H | Me | Me |
| Ph(2-Cl) | OH | Me | Me | H | H | Me | Me |
| Ph(3-Cl) | OH | Me | Me | H | H | Me | Me |
| Ph(4-Cl) | OH | Me | Me | H | H | Me | Me |
| SMe | OH | Me | Me | H | H | Me | Me |
| SO₂Me | OH | Me | Me | H | H | Me | Me |
| n-Bu | OH | Me | Me | H | H | Me | Me |
| Ph(2-F) | OH | Me | Me | H | H | Me | Me |
| Ph(3-F) | OH | Me | Me | H | H | Me | Me |
| Ph(4-F) | OH | Me | Me | H | H | Me | Me |
| Ph(3,5-di-F) | OH | Me | Me | H | H | Me | Me |
| Ph(2-Me) | OH | Me | Me | H | H | Me | Me |
| Ph(3-Me) | OH | Me | Me | H | H | Me | Me |
| Ph(4-Me) | OH | Me | Me | H | H | Me | Me |
| Ph(3,5-di-Me) | OH | Me | Me | H | H | Me | Me |
| 2-pyridinyl | OH | Me | Me | H | H | Me | Me |
| 3-pyridinyl | OH | Me | Me | H | H | Me | Me |
| 4-pyridinyl | OH | Me | Me | H | H | Me | Me |
| Et | SPh | H | H | H | H | H | H |
| CF₃ | SPh | H | H | H | H | H | H |
| n-Pr | SPh | H | H | H | H | H | H |

TABLE 2-continued

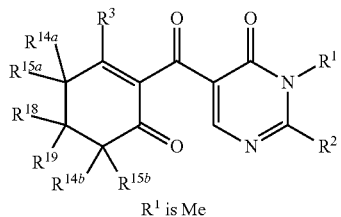

R¹ is Me

| R² | R³ | R¹⁴ᵃ | R¹⁵ᵃ | R¹⁸ | R¹⁹ | R¹⁴ᵇ | R¹⁵ᵇ |
|---|---|---|---|---|---|---|---|
| c-Pr | SPh | H | H | H | H | H | H |
| Ph | SPh | H | H | H | H | H | H |
| Ph(2-Cl) | SPh | H | H | H | H | H | H |
| Ph(3-Cl) | SPh | H | H | H | H | H | H |
| Ph(4-Cl) | SPh | H | H | H | H | H | H |
| SMe | SPh | H | H | H | H | H | H |
| SO₂Me | SPh | H | H | H | H | H | H |
| n-Bu | SPh | H | H | H | H | H | H |
| Ph(2-F) | SPh | H | H | H | H | H | H |
| Ph(3-F) | SPh | H | H | H | H | H | H |
| Ph(4-F) | SPh | H | H | H | H | H | H |
| Ph(3,5-di-F) | SPh | H | H | H | H | H | H |
| Ph(2-Me) | SPh | H | H | H | H | H | H |
| Ph(3-Me) | SPh | H | H | H | H | H | H |
| Ph(4-Me) | SPh | H | H | H | H | H | H |
| Ph(3,5-di-Me) | SPh | H | H | H | H | H | H |
| 2-pyridinyl | SPh | H | H | H | H | H | H |
| 3-pyridinyl | SPh | H | H | H | H | H | H |
| 4-pyridinyl | SPh | H | H | H | H | H | H |
| Et | OMe | H | H | H | H | H | H |
| CF₃ | OMe | H | H | H | H | H | H |
| n-Pr | OMe | H | H | H | H | H | H |
| c-Pr | OMe | H | H | H | H | H | H |
| Ph | OMe | H | H | H | H | H | H |
| Ph(2-Cl) | OMe | H | H | H | H | H | H |
| Ph(3-Cl) | OMe | H | H | H | H | H | H |
| Ph(4-Cl) | OMe | H | H | H | H | H | H |
| SMe | OMe | H | H | H | H | H | H |
| SO₂Me | OMe | H | H | H | H | H | H |
| n-Bu | OMe | H | H | H | H | H | H |
| Ph(2-F) | OMe | H | H | H | H | H | H |
| Ph(3-F) | OMe | H | H | H | H | H | H |
| Ph(4-F) | OMe | H | H | H | H | H | H |
| Ph(3,5-di-F) | OMe | H | H | H | H | H | H |
| Ph(2-Me) | OMe | H | H | H | H | H | H |
| Ph(3-Me) | OMe | H | H | H | H | H | H |
| Ph(4-Me) | OMe | H | H | H | H | H | H |
| Ph(3,5-di-Me) | OMe | H | H | H | H | H | H |
| 2-pyridinyl | OMe | H | H | H | H | H | H |
| 3-pyridinyl | OMe | H | H | H | H | H | H |
| 4-pyridinyl | OMe | H | H | H | H | H | H |
| Et | OSO₂Ph(4-Me) | H | H | H | H | H | H |
| CF₃ | OSO₂Ph(4-Me) | H | H | H | H | H | H |
| n-Pr | OSO₂Ph(4-Me) | H | H | H | H | H | H |
| c-Pr | OSO₂Ph(4-Me) | H | H | H | H | H | H |
| Ph | OSO₂Ph(4-Me) | H | H | H | H | H | H |
| Ph(2-Cl) | OSO₂Ph(4-Me) | H | H | H | H | H | H |
| Ph(3-Cl) | OSO₂Ph(4-Me) | H | H | H | H | H | H |
| Ph(4-Cl) | OSO₂Ph(4-Me) | H | H | H | H | H | H |
| SMe | OSO₂Ph(4-Me) | H | H | H | H | H | H |
| SO₂Me | OSO₂Ph(4-Me) | H | H | H | H | H | H |
| n-Bu | OSO₂Ph(4-Me) | H | H | H | H | H | H |
| Ph(2-F) | OSO₂Ph(4-Me) | H | H | H | H | H | H |
| Ph(3-F) | OSO₂Ph(4-Me) | H | H | H | H | H | H |
| Ph(4-F) | OSO₂Ph(4-Me) | H | H | H | H | H | H |
| Ph(3,5-di-F) | OSO₂Ph(4-Me) | H | H | H | H | H | H |
| Ph(2-Me) | OSO₂Ph(4-Me) | H | H | H | H | H | H |
| Ph(3-Me) | OSO₂Ph(4-Me) | H | H | H | H | H | H |
| Ph(4-Me) | OSO₂Ph(4-Me) | H | H | H | H | H | H |
| Ph(3,5-di-Me) | OSO₂Ph(4-Me) | H | H | H | H | H | H |
| 2-pyridinyl | OSO₂Ph(4-Me) | H | H | H | H | H | H |
| 3-pyridinyl | OSO₂Ph(4-Me) | H | H | H | H | H | H |
| 4-pyridinyl | OSO₂Ph(4-Me) | H | H | H | H | H | H |
| Et | OH | Me | Me | —C(O)— | | Me | Me |
| CF₃ | OH | Me | Me | —C(O)— | | Me | Me |
| n-Pr | OH | Me | Me | —C(O)— | | Me | Me |
| c-Pr | OH | Me | Me | —C(O)— | | Me | Me |

TABLE 2-continued

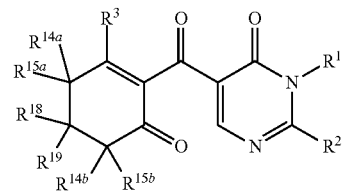

R¹ is Me

| R² | R³ | R¹⁴ᵃ | R¹⁵ᵃ | R¹⁸ | R¹⁹ | R¹⁴ᵇ | R¹⁵ᵇ |
|---|---|---|---|---|---|---|---|
| Ph | OH | Me | Me | —C(O)— | | Me | Me |
| Ph(2-Cl) | OH | Me | Me | —C(O)— | | Me | Me |
| Ph(3-Cl) | OH | Me | Me | —C(O)— | | Me | Me |
| Ph(4-Cl) | OH | Me | Me | —C(O)— | | Me | Me |
| SMe | OH | Me | Me | —C(O)— | | Me | Me |
| SO₂Me | OH | Me | Me | —C(O)— | | Me | Me |
| n-Bu | OH | Me | Me | —C(O)— | | Me | Me |
| Ph(2-F) | OH | Me | Me | —C(O)— | | Me | Me |
| Ph(3-F) | OH | Me | Me | —C(O)— | | Me | Me |
| Ph(4-F) | OH | Me | Me | —C(O)— | | Me | Me |
| Ph(3,5-di-F) | OH | Me | Me | —C(O)— | | Me | Me |
| Ph(2-Me) | OH | Me | Me | —C(O)— | | Me | Me |
| Ph(3-Me) | OH | Me | Me | —C(O)— | | Me | Me |
| Ph(4-Me) | OH | Me | Me | —C(O)— | | Me | Me |
| Ph(3,5-di-Me) | OH | Me | Me | —C(O)— | | Me | Me |
| 2-pyridinyl | OH | Me | Me | —C(O)— | | Me | Me |
| 3-pyridinyl | OH | Me | M | —C(O)— | | Me | Me |
| 4-pyridinyl | OH | Me | Me | —C(O)— | | Me | Me |

The present disclosure also includes Tables 1B through 38B, each of which is constructed the same as Table 2 above except that the row heading in Table 2 (i.e. "R¹ is Me") is replaced with the respective row headings shown below. For example, in Table 1B the row heading is "R¹ is Et", and R², R³, R¹⁴ᵃ, R¹⁵ᵃ, R¹⁸, R¹⁹, R¹⁴ᵇ and R¹⁵ᵇ are as defined in Table 2 above. Thus, the first entry in Table 1B specifically discloses a compound of Formula 1 wherein X is CH; Y is C(O); R¹ is Et; R² is Et, R³ is OH; A is A-1; B¹ is C-1, B² is C-3 and B³ is C-1; R¹⁴ᵃ is Me; R¹⁵ᵃ is H; R¹⁸ is H; is H; R¹⁹ is H; R¹⁴ᵇ is H; and R¹⁵ᵇ is H. Tables 2B through 38B are constructed similarly.

| Table | Row Heading |
|---|---|
| 1B | R¹ is Et |
| 2B | R¹ is CH₂CF₃ |
| 3B | R¹ is CH₂CH=CH₂ |
| 4B | R¹ is CH₂C≡CH |
| 5B | R¹ is Ph |
| 6B | R¹ is Ph(2-Me) |
| 7B | R¹ is Ph(4-Me) |
| 8B | R¹ is Ph(2-Cl) |
| 9B | R¹ is Ph(3-Cl) |
| 10B | R¹ is n-Pr |
| 11B | R¹ is c-Pr |
| 12B | R¹ is n-Bu |
| 13B | R¹ is i-Bu |
| 14B | R¹ is n-pent |
| 15B | R¹ is n-Hex |
| 16B | R¹ is thp-4-yl |
| 17B | R¹ is thtp-4yl |
| 18B | R¹ is c-Hex |
| 19B | R¹ is CH₂CH₂OCH₃ |
| 20B | R¹ is CH₂CH₂OCH₂CH₃ |
| 21B | R¹ is CH₂CH₂CH₂OCH₃ |
| 22B | R¹ is CH₂CH₂CH₂OCH₂CH₃ |
| 23B | R¹ is Ph(3-OMe) |
| 24B | R¹ is Ph(4-OMe) |
| 25B | R¹ is Ph(3,4-di-OMe) |
| 26B | R¹ is Ph(2-F) |
| 27B | R¹ is Ph(3-F) |
| 28B | R¹ is Ph(4-F) |
| 29B | R¹ is Ph(3-Me) |

-continued

| Table | Row Heading |
|---|---|
| 30B | $R^1$ is Ph(2-Me-3-F) |
| 31B | $R^1$ is Ph(2-Me-4-F) |
| 32B | $R^1$ is Ph(2-Me-5-F) |
| 33B | $R^1$ is Ph(2-F-3-Me) |
| 34B | $R^1$ is Ph(2-F-4-Me) |
| 35B | $R^1$ is Ph(2-F-5-Me) |
| 36B | $R^1$ is Ph(3-F-4-Me) |
| 37B | $R^1$ is Ph(3-F-5-Me) |
| 38B | $R^1$ is Ph(3-Me-4-F) |

TABLE 3

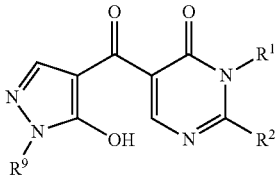

$R^1$ is $CH_3$, $R^9$ $CH_3$

| $R^2$ |
|---|
| Et |
| n-Pr |
| c-Pr |
| $CF_3$ |
| SMe |
| Ph |
| Ph(2-Cl) |
| Ph(3-Cl) |
| Ph(4-Cl) |
| Ph(3-F) |
| Ph(3,5-di-F) |
| Ph(3-Me) |

The present disclosure also includes Tables 1C through 37C, each of which is constructed the same as Table 3 above except that the row heading in Table 3 (i.e. "$R^1$ is $CH_3$, $R^9$ is $CH_3$") is replaced with the respective row headings shown below. For example, in Table 1C the row heading is "$R^1$ is $CH_2CH_3$, $R^9$ is $CH_3$", and $R^2$ is as defined in Table 3 above. Thus, the first entry in Table 1C specifically discloses a compound of Formula 1 wherein X is CH; Y is C(O); $R^1$ is $CH_2CH_3$; $R^2$ is Et; A is A-5; $R^3$ is OH; $R^9$ is $CH_3$; and $R^{10}$ is H. Tables 2C through 27C are constructed similarly.

| Table | Row Heading |
|---|---|
| 1C | $R^1$ is $CH_2CH_3$, $R^9$ is $CH_3$ |
| 2C | $R^1$ is $CH_2CH=CH_2$, $R^9$ is $CH_3$ |
| 3C | $R^1$ is $CH_2C\equiv CH$, $R^9$ is $CH_3$ |
| 4C | $R^1$ is Ph, $R^9$ is $CH_3$ |
| 5C | $R^1$ is Ph(2-Me), $R^9$ is $CH_3$ |
| 6C | $R^1$ is Ph(4-Me), $R^9$ is $CH_3$ |
| 7C | $R^1$ is Ph(2-Me), $R^9$ is $CH_3$ |
| 8C | $R^1$ is Ph(3-Cl), $R^9$ is $CH_3$ |
| 9C | $R^1$ is $CH_3$, $R^9$ is $CH_2CH_3$ |
| 10C | $R^1$ is $CH_2CH_3$, $R^9$ is $CH_2CH_3$ |
| 11C | $R^1$ is $CH_2CH=CH_2$, $R^9$ is $CH_2CH_3$ |
| 12C | $R^1$ is $CH_2C\equiv CH$, $R^9$ is $CH_2CH_3$ |
| 13C | $R^1$ is Ph, $R^9$ is $CH_2CH_3$ |
| 14C | $R^1$ is Ph(2-Me), $R^9$ is $CH_2CH_3$ |
| 15C | $R^1$ is Ph(4-Me), $R^9$ is $CH_2CH_3$ |
| 16C | $R^1$ is Ph(2-Cl), $R^9$ is $CH_2CH_3$ |
| 17C | $R^1$ is Ph(3-Cl), $R^9$ is $CH_2CH_3$ |
| 18C | $R^1$ is n-Bu, $R^9$ is $CH_3$ |
| 19C | $R^1$ is n-pent, $R^9$ is $CH_3$ |
| 20C | $R^1$ is n-Hex, $R^9$ is $CH_3$ |
| 21C | $R^1$ is thp-4-yl, $R^9$ is $CH_3$ |
| 22C | $R^1$ is thtp-4-yl, $R^9$ is $CH_3$ |
| 23C | $R^1$ is c-Hex, $R^9$ is $CH_3$ |
| 24C | $R^1$ is $CH_2CH_2OCH_3$, $R^9$ is $CH_3$ |
| 25C | $R^1$ is $CH_2CH_2OCH_2CH_3$, $R^9$ is $CH_3$ |
| 26C | $R^1$ is $CH_2CH_2CH_2OCH_3$, $R^9$ is $CH_3$ |
| 27C | $R^1$ is $CH_2CH_2CH_2OEt$, $R^9$ is $CH_3$ |
| 28C | $R^1$ is n-Bu, $R^9$ is $CH_2CH_3$ |
| 29C | $R^1$ is n-pent, $R^9$ is $CH_2CH_3$ |
| 30C | $R^1$ is n-Hex, $R^9$ is $CH_2CH_3$ |
| 31C | $R^1$ is thp-4-yl, $R^9$ is $CH_2CH_3$ |
| 32C | $R^1$ is thtp-4-yl, $R^9$ is $CH_2CH_3$ |
| 33C | $R^1$ is c-Hex, $R^9$ is $CH_2CH_3$ |
| 34C | $R^1$ is $CH_2CH_2OCH_3$, $R^9$ is $CH_2CH_3$ |
| 35C | $R^1$ is $CH_2CH_2OCH_2CH_3$, $R^9$ is $CH_2CH_3$ |
| 36C | $R^1$ is $CH_2CH_2CH_2OCH_3$, $R^9$ is $CH_2CH_3$ |
| 37C | $R^1$ is $CH_2CH_2CH_2OEt$, $R^9$ is $CH_2CH_3$ |

TABLE 4

$R^1$ is $CH_3$, $R^9$ is $CH_3$

| $R^2$ |
|---|
| Et |
| n-Pr |
| c-Pr |
| $CF_3$ |
| SMe |
| Ph |
| Ph(2-Cl) |
| Ph(3-Cl) |
| Ph(4-Cl) |
| Ph(3-F) |
| Ph(3,5-di-F) |
| Ph(3-Me) |

The present disclosure also includes Tables 1D through 37D, each of which is constructed the same as Table 4 above except that the row heading in Table 4 (i.e. "$R^1$ is $CH_3$, $R^9$ is $CH_3$") is replaced with the respective row headings shown below. For example, in Table 1D the row heading is "$R^1$ is $CH_2CH_3$, $R^9$ is $CH_3$", and $R^2$ is as defined in Table 4 above. Thus, the first entry in Table 1D specifically discloses a compound of Formula 1 wherein X is CH; Y is C(O); $R^1$ is $CH_2CH_3$; $R^2$ is Et; A is A-5; $R^3$ is OH; $R^9$ is $CH_3$; and $R^{10}$ is $CH_3$. Tables 2D through 37D are constructed similarly.

| Table | Row Heading |
|---|---|
| 1D | $R^1$ is $CH_2CH_3$, $R^9$ is $CH_3$ |
| 2D | $R^1$ is $CH_2CH=CH_2$, $R^9$ is $CH_3$ |
| 3D | $R^1$ is $CH_2C\equiv CH$, $R^9$ is $CH_3$ |
| 4D | $R^1$ is Ph, $R^9$ is $CH_3$ |
| 5D | $R^1$ is Ph(2-Me), $R^9$ is $CH_3$ |
| 6D | $R^1$ is Ph(4-Me), $R^9$ is $CH_3$ |
| 7D | $R^1$ is Ph(2-Me), $R^9$ is $CH_3$ $R^5$ is $CH_3$ |
| 8D | $R^1$ is Ph(3-Cl), $R^9$ is $CH_3$ |
| 9D | $R^1$ is $CH_3$, $R^9$ is $CH_2CH_3$ |
| 10D | $R^1$ is $CH_2CH_3$, $R^9$ is $CH_2CH_3$ |

-continued

| Table | Row Heading |
|---|---|
| 11D | $R^1$ is $CH_2CH=CH_2$, $R^9$ is $CH_2CH_3$ |
| 12D | $R^1$ is $CH_2C\equiv CH$, $R^9$ is $CH_2CH_3$ |
| 13D | $R^1$ is Ph, $R^9$ is $CH_2CH_3$ |
| 14D | $R^1$ is Ph(2-Me), $R^9$ is $CH_2CH_3$ |
| 15D | $R^1$ is Ph(4-Me), $R^9$ is $CH_2CH_3$ |
| 16D | $R^1$ is Ph(2-Cl), $R^9$ is $CH_2CH_3$ |
| 17D | $R^1$ is Ph(3-Cl), $R^9$ is $CH_2CH_3$ |
| 18D | $R^1$ is n-Bu, $R^9$ is $CH_3$ |
| 19D | $R^1$ is n-pent, $R^9$ is $CH_3$ |
| 20D | $R^1$ is n-Hex, $R^9$ is $CH_3$ |
| 21D | $R^1$ is thp-4-yl, $R^9$ is $CH_3$ |
| 22D | $R^1$ is thtp-4-yl, $R^9$ is $CH_3$ |
| 23D | $R^1$ is c-Hex, $R^9$ is $CH_3$ |
| 24D | $R^1$ is $CH_2CH_2OCH_3$, $R^9$ is $CH_3$ |
| 25D | $R^1$ is $CH_2CH_2OCH_2CH_3$, $R^9$ is $CH_3$ |
| 26D | $R^1$ is $CH_2CH_2CH_2OCH_3$, $R^9$ is $CH_3$ |
| 27D | $R^1$ is $CH_2CH_2CH_2OEt$, $R^9$ is $CH_3$ |
| 28D | $R^1$ is n-Bu, $R^9$ is $CH_2CH_3$ |
| 29D | $R^1$ is n-pent, $R^9$ is $CH_2CH_3$ |
| 30D | $R^1$ is n-Hex, $R^9$ is $CH_2CH_3$ |
| 31D | $R^1$ is thp-4-yl, $R^9$ is $CH_2CH_3$ |
| 32D | $R^1$ is thtp-4-yl, $R^9$ is $CH_2CH_3$ |
| 33D | $R^1$ is c-Hex, $R^9$ is $CH_2CH_3$ |
| 34D | $R^1$ is $CH_2CH_2OCH_3$, $R^9$ is $CH_2CH_3$ |
| 35D | $R^1$ is $CH_2CH_2OCH_2CH_3$, $R^9$ is $CH_2CH_3$ |
| 36D | $R^1$ is $CH_2CH_2CH_2OCH_3$, $R^9$ is $CH_2CH_3$ |
| 37D | $R^1$ is $CH_2CH_2CH_2OEt$, $R^9$ is $CH_2CH_3$ |

TABLE 5

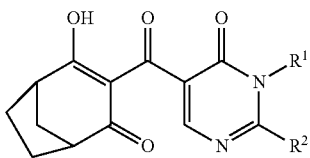

$R^2$ is Ph

| $R^1$ |
|---|
| Me |
| Et |
| n-Pr |
| i-Pr |
| c-Pr |
| n-Bu |
| i-Bu |
| s-Bu |
| c-Bu |
| t-Bu |
| n-pent |
| c-Pent |
| n-Hex |
| c-Hex |
| Ph |
| $CH_2$-c-Pr |
| $CH_2$-c-Bu |
| $CH_2SPh$ |
| $CH_2SCH_3$ |
| $CH_2CF_3$ |
| $CH_2Ph$ |
| Ph(4-Me) |
| $CH_2CHC(CH_3)_2$ |
| $CH_2CH_2C\equiv CH$ |
| $CH_2CH=CCl_2$ |
| $CH_2CH=CF_2$ |
| $CH_2CF=CF_2$ |
| $CH_2CCl=CCl_2$ |
| $CH_2C\equiv CCH_3$ |
| $CH_2OCH_2CH_3$ |
| $CH_2CH_2OCH_3$ |
| $CH_2SO_2CH_3$ |
| $CH_2SCH_2CH_3$ |

TABLE 5-continued

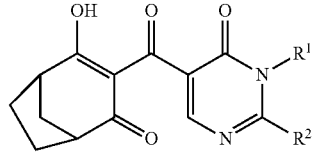

$R^2$ is Ph

| $R^1$ |
|---|
| Ph(2,3-di-OMe) |
| $CH_2SO_2$-n-Pr |
| $CH_2CH_2SO_2Et$ |
| Ph(2,4-di-OMe) |
| Ph(2,5-di-OMe) |
| Ph(2,6-di-OMe) |
| Ph(3,5-di-OMe) |
| $CH_2Ph$(2-OMe) |
| $CH_2Ph$(3-OMe) |
| $CH_2Ph$(4-OMe) |
| $CH_2CH_2SMe$ |
| $CH_2SCH_2Ph$ |
| $CH_2SO_2Ph$ |
| $CH_2CH_2SEt$ |
| Ph(2,4-di-Cl) |
| Ph(2,5-di-Cl) |
| Ph(2,6-di-Cl) |
| Ph(3,5-di-Cl) |
| Ph(2,3-di-Me) |
| Ph(2,4-di-Me) |
| Ph(2,5-di-Me) |
| Ph(2,6-di-Me) |
| Ph(3,5-di-Me) |
| $CH_2$-c-Hex |
| Ph(2,3-di-F) |
| Ph(2,4-di-F) |
| Ph(2,5-di-F) |
| Ph(2,6-di-F) |
| $CH_2CH_2CF_3$ |
| $CH_2C\equiv CH$ |
| Ph(2,3-di-Cl) |
| Ph(3,5-di-F) |
| isoxazolin-2-yl |
| Ph(2-Cl) |
| Ph(3-Cl) |
| Ph(4-Cl) |
| Ph(2-Me) |
| Ph(3-Me) |
| $CH_2OCH_3$ |
| $CH_2CH=CH_2$ |
| Ph(2-OMe) |
| Ph(3-OMe) |
| Ph(4-OMe) |
| Ph(2-CN) |
| Ph(3-CN) |
| Ph(4-CN) |
| Ph(2-F) |
| Ph(3-F) |
| Ph(4-F) |
| $CH_2S$-n-Pr |
| $CH_2$-c-Pent |
| oxazolin-2-yl |
| 2-pyridinyl |
| 3-pyridinyl |
| 4-pyridinyl |
| Ph(2-$NO_2$) |
| Ph(3-$NO_2$) |
| Ph(4-$NO_2$) |
| Ph(2-$CF_3$) |
| Ph(3-$CF_3$) |
| Ph(4-$CF_3$) |
| Ph(2-Br) |
| Ph(3-Br) |
| Ph(4-Br) |
| $CH_2Ph$(2-Me) |
| $CH_2Ph$(3-Me) |
| $CH_2Ph$(4-Me) |

TABLE 5-continued

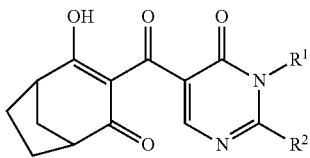

R² is Ph

R¹

CH₂Ph(2-Cl)
CH₂Ph(3-Cl)
CH₂Ph(4-Cl)
thiazol-3-yl
thiazol-2-yl
thiazolin-2-yl
thiazol-2-yl
oxazol-2-yl
CH₂CF₂CF₃
CH=CH₂
CH₂(thf-2-yl)
CH₂(3-methylisoxazolin-5-yl)
isoxazolin-4-yl
CH₂(3-methylisoxazol-5-yl)
5-methylisoxazol-3-yl
4-methyloxazol-2-yl
4-methylthiazol-2-yl
CH₂CH₂CH=CH₂
CH₂SO₂CH₂CH₃
CH₂CH₂SO₂Me
CH₂OCH₂OCH₃
3-methylthiazol-2-yl
5-chloropyridin-2-yl
5-methylpyridin-2-yl
5-methoxypyridin-2-yl
6-methylpyridin-2-yl
6-methylpyridin-3-yl
3-methoxypyridin-4-yl
3-methylpyridin-4-yl
3-chloropyridin-4-yl
CH₂OCH₂CH₂OCH₃
CH₂C(CH₃)C(CH₃)₂
n-hept
c-hept
thp-4-yl
thtp-4-yl
Ph(2,3-di-OMe)
Ph(3,4-di-OMe)
Ph(3,4-di-Me)
Ph(3,4-di-F)
Ph(3,4,5-tri-OMe)
Ph(2-I)
Ph(3-I)
Ph(4-I)
Ph(2-Et)
Ph(3-Et)
Ph(4-Et)
CH₂CH₂OCH₂CH₃
CH(CH₃)CH₂OCH₃
Ph(2-OCF₃)
Ph(3-OCF₃)
Ph(4-OCF₃)
Ph(2-Me-3-F)
Ph(2-Me-4-F)
Ph(2-Me-5-F)
Ph(2-F-3-Me)
Ph(2-F-4-Me)
Ph(2-F-5-Me)
Ph(3-F-4-Me)
Ph(3-F-5-Me)
Ph(3-Me-4-F)
CH₂CH₂CH₂OCH₃
CH₂CH₂CH₂OCH₂CH₃
CH₂(thp-2-yl)
CH₂(thp-4-yl)
CH₂CH₂CH=CH₂
CH₂C≡CH

TABLE 5-continued

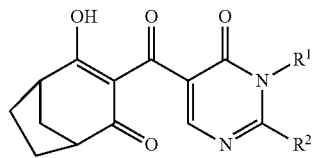

R² is Ph

R¹

CH₂CH₂SCH₃
CH₂CH₂SOCH₃
CH₂CH₂SO₂CH₃
CH₂CH₂CH₂SCH₃
CH₂CH₂CH₂SOCH₃
CH₂CH₂CH₂SO₂CH₃
c-hex(3-OCH₃)
c-hex(4-OCH₃)
c-hex(3,4-di-OCH₃)
c-hex(3,5-di-OCH₃)
CH₂CH₂SCH₃

The present disclosure also includes Tables 1E through 57E, each of which is constructed the same as Table 1 above except that the row heading in Table 1 (i.e. "R² is Ph") is replaced with the respective row headings shown below. For example, in Table 1E the row heading is "R² is Me", and R¹ is as defined in Table 5 above. Thus, the first entry in Table 1E specifically discloses a compound of Formula 1 wherein X is CH; Y is C(O); R¹ is Me; R² is Me; R³ is OH; A is A-1; B¹ is C-1; B² is C-3; B³ is C-1; and each R¹⁴, R¹⁵, R¹⁸ and R¹⁹ is H. Tables 2E through 57E are constructed similarly.

| Table | Row Heading |
|---|---|
| 1E | R² is Me |
| 2E | R² is Et |
| 3E | R² is n-Pr |
| 4E | R² is c-Pr |
| 5E | R² is SMe |
| 6E | R² is SO₂Me |
| 7E | R² is CF₃ |
| 8E | R² is Ph(2-Cl) |
| 9E | R² is Ph(3-Cl) |
| 10E | R² is Ph(4-Cl) |
| 11E | R² is Ph(2-Me) |
| 12E | R² is Ph(3-Me) |
| 13E | R² is Ph(4-Me) |
| 14E | R² is Ph(2-OMe) |
| 15E | R² is Ph(3-OMe) |
| 16E | R² is Ph(4-OMe) |
| 17E | R² is Ph(2-F) |
| 18E | R² is Ph(3-F) |
| 19E | R² is Ph(4-F) |
| 20E | R² is OMe |
| 21E | R² is OEt |
| 22E | R² is CH₂Ph |
| 23E | R² is 2-pyridinyl |
| 24E | R² is 3-pyridinyl |
| 25E | R² is 4-pyridinyl |
| 26E | R² is H |
| 27E | R² is Ph(3,5-di-F) |
| 28E | R² is Ph(3,4-di-F) |
| 29E | R² is Ph(3,4,5-tri-F) |
| 30E | R² is Ph(2,3-di-F) |
| 31E | R² is Ph(3-CF₃) |
| 32E | R² is Ph(4-CF₃) |
| 33E | R² is Ph(3,5-di-CF₃) |
| 34E | R² is n-Bu |
| 35E | R² is CH₂OCH₃ |
| 36E | R² is CH₂CH₂OCH₃ |
| 37E | R² is CH₂CH₂CF₃ |
| 38E | R² is CH₂CF₃ |

| Table | Row Heading |
|---|---|
| 39E | $R^2$ is n-pent |
| 40E | $R^2$ is c-pent |
| 41E | $R^2$ is c-Hex |
| 42E | $R^2$ is n-Hex |
| 43E | $R^2$ is thp-4-yl |
| 44E | $R^2$ is Ph(2-CN) |
| 45E | $R^2$ is Ph(3-CN) |
| 46E | $R^2$ is Ph(4-CN) |
| 47E | $R^2$ is Ph(2-C≡CH) |
| 48E | $R^2$ is Ph(3-C≡CH) |
| 49E | $R^2$ is Ph(4-C≡CH) |
| 50E | $R^2$ is Ph(3-Me, 2-F) |
| 51E | $R^2$ is Ph(3-Me-4-F) |
| 52E | $R^2$ is Ph(3-Me, 5-F) |
| 53E | $R^2$ is Ph(3-Me, 6-F) |
| 54E | $R^2$ is Ph(3-F, 2-Me) |
| 55E | $R^2$ is Ph(3-F-4-Me) |
| 56E | $R^2$ is Ph(3-F-5-Me) |
| 57E | $R^2$ is Ph(3-F, 6-Me) |

TABLE 6

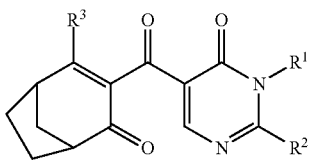

$R^1$ is phenyl

| $R^2$ | $R^3$ |
|---|---|
| Et | OMe |
| n-Pr | OMe |
| c-Pr | OMe |
| $CF_3$ | OMe |
| SMe | OMe |
| Ph | OMe |
| Ph(3-F) | OMe |
| Ph(3,5-di-F) | OMe |
| Ph(3-Me) | OMe |
| Et | SPh |
| n-Pr | SPh |
| c-Pr | SPh |
| $CF_3$ | SPh |
| SMe | SPh |
| Ph | SPh |
| Ph(3-F) | SPh |
| Ph(3,5-di-F) | SPh |
| Ph(3-Me) | SPh |
| Et | $OSO_2Ph$ |
| n-Pr | $OSO_2Ph$ |
| c-Pr | $OSO_2Ph$ |
| $CF_3$ | $OSO_2Ph$ |
| SMe | $OSO_2Ph$ |
| Ph | $OSO_2Ph$ |
| Ph(3-F) | $OSO_2Ph$ |
| Ph(3,5-di-F) | $OSO_2Ph$ |
| Ph(3-Me) | $OSO_2Ph$ |
| Et | OC(O)Ph |
| n-Pr | OC(O)Ph |
| c-Pr | OC(O)Ph |
| $CF_3$ | OC(O)Ph |
| SMe | OC(O)Ph |
| Ph | OC(O)Ph |
| Et | OC(O)Ph |
| Ph(3-F) | OC(O)Ph |
| Ph(3,5-di-F) | OC(O)Ph |
| Ph(3-Me) | OC(O)Ph |
| n-Pr | $OC(O)CH_3$ |
| c-Pr | $OC(O)CH_3$ |
| $CF_3$ | $OC(O)CH_3$ |
| SMe | $OC(O)CH_3$ |

TABLE 6-continued $R^1$ is phenyl

| $R^2$ | $R^3$ |
|---|---|
| Ph | $OC(O)CH_3$ |
| Ph(3-F) | $OC(O)CH_3$ |
| Ph(3,5-di-F) | $OC(O)CH_3$ |
| Ph(3-Me) | $OC(O)CH_3$ |

The present disclosure also includes Tables 1F through 11F, each of which is constructed the same as Table 6 above except that the row heading in Table 6 (i.e. "$R^1$ is Ph") is replaced with the respective row headings shown below. For example, in Table 1F the row heading is "$R^1$ is n-Pr", and $R^2$ is as defined in Table 6 above. Thus, the first entry in Table 1F specifically discloses a compound of Formula 1 wherein X is CH; Y is C(O); $R^1$ is phenyl; $R^2$ n-Pr; $R^3$ is OMe; A is A-3; $B^2$ is C-3; T is —$CH_2CH_2$—; $R^{18}$ and $R^{19}$ are both H. Tables 2F through 11F are constructed similarly.

| Table | Row Heading |
|---|---|
| 1F | $R^1$ is n-Pr |
| 2F | $R^1$ is n-Bu |
| 3F | $R^1$ is n-pent |
| 4F | $R^1$ is n-Hex |
| 5F | $R^1$ is thp-4-yl |
| 6F | $R^1$ is thtp-4-yl |
| 7F | $R^1$ is c-Hex |
| 8F | $R^1$ is $CH_2CH_2OCH_3$ |
| 9F | $R^1$ is $CH_2CH_2OCH_2CH_3$ |
| 10F | $R^1$ is $CH_2CH_2CH_2OCH_3$ |
| 11F | $R^1$ is $CH_2CH_2CH_2OCH_2CH_3$ |

TABLE 7

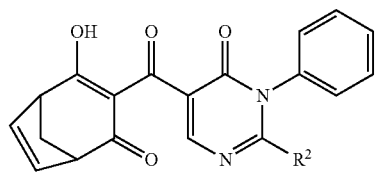

| $R^2$ | $R^2$ | $R^2$ | $R^2$ | $R^2$ | $R^2$ |
|---|---|---|---|---|---|
| Et | n-Pr | c-Pr | $CF_3$ | SMe | Ph |
| Ph(2-Me) | Ph(3-Cl) | Ph(4-Cl) | Ph(2-Me) | Ph(3-Me) | Ph(4-Me) |

TABLE 8

[Structure: isoxazole-C(=O)-pyrimidinone with R¹ on N, R² on C2, R¹² on isoxazole]

R¹² is c-Pr

| R¹ | R² |
|---|---|
| CH₃ | Et |
| CH₃ | n-Pr |
| CH₃ | c-Pr |
| CH₃ | CF₃ |
| CH₃ | SMe |
| CH₃ | Ph |
| CH₃ | Ph(2-Cl) |
| CH₃ | Ph(3-Cl) |
| CH₃ | Ph(4-Cl) |
| CH₃ | Ph(3-F) |
| CH₃ | Ph(3,5-di-F) |
| CH₃ | Ph(3-Me) |
| Et | Et |
| Et | n-Pr |
| Et | c-Pr |
| Et | CF₃ |
| Et | SMe |
| Et | Ph |
| Et | Ph(2-Cl) |
| Et | Ph(3-Cl) |
| Et | Ph(4-Cl) |
| Et | Ph(3-F) |
| Et | Ph(3,5-di-F) |
| Et | Ph(3-Me) |
| CH₂CH=CH₂ | Et |
| CH₂CH=CH₂ | n-Pr |
| CH₂CH=CH₂ | c-Pr |
| CH₂CH=CH₂ | CF₃ |
| CH₂CH=CH₂ | SMe |
| CH₂CH=CH₂ | Ph |
| CH₂CH=CH₂ | Ph(2-Cl) |
| CH₂CH=CH₂ | Ph(3-Cl) |
| CH₂CH=CH₂ | Ph(4-Cl) |
| CH₂CH=CH₂ | Ph(3-F) |
| CH₂CH=CH₂ | Ph(3,5-di-F) |
| CH₂CH=CH₂ | Ph(3-Me) |
| CH₂C≡CH | Et |
| CH₂C≡CH | n-Pr |
| CH₂C≡CH | c-Pr |
| CH₂C≡CH | CF₃ |
| CH₂C≡CH | SMe |
| CH₂C≡CH | Ph |
| CH₂C≡CH | Ph(2-Cl) |
| CH₂C≡CH | Ph(3-Cl) |
| CH₂C≡CH | Ph(4-Cl) |
| CH₂C≡CH | Ph(3-F) |
| CH₂C≡CH | Ph(3,5-di-F) |
| CH₂C≡CH | Ph(3-Me) |
| Ph | Et |
| Ph | n-Pr |
| Ph | c-Pr |
| Ph | CF₃ |
| Ph | SMe |
| Ph | Ph |
| Ph | Ph(2-Cl) |
| Ph | Ph(3-Cl) |
| Ph | Ph(4-Cl) |
| Ph | Ph(3-F) |
| Ph | Ph(3,5-di-F) |
| Ph | Ph(3-Me) |
| Ph(2-Me) | Et |
| Ph(2-Me) | n-Pr |
| Ph(2-Me) | c-Pr |
| Ph(2-Me) | CF₃ |
| Ph(2-Me) | SMe |
| Ph(2-Me) | Ph |
| Ph(2-Me) | Ph(2-Cl) |
| Ph(2-Me) | Ph(3-Cl) |
| Ph(2-Me) | Ph(4-Cl) |
| Ph(2-Me) | Ph(3-F) |
| Ph(2-Me) | Ph(3,5-di-F) |
| Ph(2-Me) | Ph(3-Me) |
| Ph(4-Me) | Et |
| Ph(4-Me) | n-Pr |
| Ph(4-Me) | c-Pr |
| Ph(4-Me) | CF₃ |
| Ph(4-Me) | SMe |
| Ph(4-Me) | Ph |
| Ph(4-Me) | Ph(2-Cl) |
| Ph(4-Me) | Ph(3-Cl) |
| Ph(4-Me) | Ph(4-Cl) |
| Ph(4-Me) | Ph(3-F) |
| Ph(4-Me) | Ph(3,5-di-F) |
| Ph(4-Me) | Ph(3-Me) |
| Ph(2-Cl) | Et |
| Ph(2-Cl) | n-Pr |
| Ph(2-Cl) | c-Pr |
| Ph(2-Cl) | CF₃ |
| Ph(2-Cl) | SMe |
| Ph(2-Cl) | Ph |
| Ph(2-Cl) | Ph(2-Cl) |
| Ph(2-Cl) | Ph(3-Cl) |
| Ph(2-Cl) | Ph(4-Cl) |
| Ph(2-Cl) | Ph(3-F) |
| Ph(2-Cl) | Ph(3,5-di-F) |
| Ph(2-Cl) | Ph(3-Me) |
| Ph(3-Cl) | Et |
| Ph(3-Cl) | n-Pr |
| Ph(3-Cl) | c-Pr |
| Ph(3-Cl) | CF₃ |
| Ph(3-Cl) | SMe |
| Ph(3-Cl) | Ph |
| Ph(3-Cl) | Ph(2-Cl) |
| Ph(3-Cl) | Ph(3-Cl) |
| Ph(3-Cl) | Ph(4-Cl) |
| Ph(3-Cl) | Ph(3-F) |
| Ph(3-Cl) | Ph(3,5-di-F) |
| Ph(3-Cl) | Ph(3-Me) |
| n-Pr | Et |
| n-Pr | n-Pr |
| n-Pr | c-Pr |
| n-Pr | CF₃ |
| n-Pr | SMe |
| n-Pr | Ph |
| n-Pr | Ph(2-Cl) |
| n-Pr | Ph(3-Cl) |
| n-Pr | Ph(4-Cl) |
| n-Pr | Ph(3-F) |
| n-Pr | Ph(3,5-di-F) |
| n-Pr | Ph(3-Me) |
| c-Pr | Et |
| c-Pr | n-Pr |
| c-Pr | c-Pr |
| c-Pr | CF₃ |
| c-Pr | SMe |
| c-Pr | Ph |
| c-Pr | Ph(2-Cl) |
| c-Pr | Ph(3-Cl) |
| c-Pr | Ph(4-Cl) |
| c-Pr | Ph(3-F) |
| c-Pr | Ph(3,5-di-F) |
| c-Pr | Ph(3-Me) |
| n-Bu | Et |
| n-Bu | n-Pr |
| n-Bu | c-Pr |
| n-Bu | CF₃ |

TABLE 8-continued

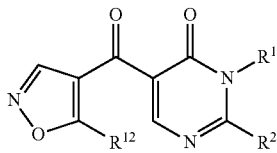

$R^{12}$ is c-Pr

| $R^1$ | $R^2$ |
|---|---|
| n-Bu | SMe |
| n-Bu | Ph |
| n-Bu | Ph(2-Cl) |
| n-Bu | Ph(3-Cl) |
| n-Bu | Ph(4-Cl) |
| n-Bu | Ph(3-F) |
| n-Bu | Ph(3,5-di-F) |
| n-Bu | Ph(3-Me) |
| n-pent | Et |
| n-pent | n-Pr |
| n-pent | c-Pr |
| n-pent | $CF_3$ |
| n-pent | SMe |
| n-pent | Ph |
| n-pent | Ph(2-Cl) |
| n-pent | Ph(3-Cl) |
| n-pent | Ph(4-Cl) |
| n-pent | Ph(3-F) |
| n-pent | Ph(3,5-di-F) |
| n-pent | Ph(3-Me) |
| n-Hex | Et |
| n-Hex | n-Pr |
| n-Hex | c-Pr |
| n-Hex | $CF_3$ |
| n-Hex | SMe |
| n-Hex | Ph |
| n-Hex | Ph(2-Cl) |
| n-Hex | Ph(3-Cl) |
| n-Hex | Ph(4-Cl) |
| n-Hex | Ph(3-F) |
| n-Hex | Ph(3,5-di-F) |
| n-Hex | Ph(3-Me) |
| thp-4-yl | Et |
| thp-4-yl | n-Pr |
| thp-4-yl | c-Pr |
| thp-4-yl | $CF_3$ |
| thp-4-yl | SMe |
| thp-4-yl | Ph |
| thp-4-yl | Ph(2-Cl) |
| thp-4-yl | Ph(3-Cl) |
| thp-4-yl | Ph(4-Cl) |
| thp-4-yl | Ph(3-F) |
| thp-4-yl | Ph(3,5-di-F) |
| thp-4-yl | Ph(3-Me) |
| c-Hex | Et |
| c-Hex | n-Pr |
| c-Hex | c-Pr |
| c-Hex | $CF_3$ |
| c-Hex | SMe |
| c-Hex | Ph |
| c-Hex | Ph(2-Cl) |
| c-Hex | Ph(3-Cl) |
| c-Hex | Ph(4-Cl) |
| c-Hex | Ph(3-F) |
| c-Hex | Ph(3,5-di-F) |
| c-Hex | Ph(3-Me) |
| $CH_2CH_2OCH_3$ | Et |
| $CH_2CH_2OCH_3$ | n-Pr |
| $CH_2CH_2OCH_3$ | c-Pr |
| $CH_2CH_2OCH_3$ | $CF_3$ |
| $CH_2CH_2OCH_3$ | SMe |
| $CH_2CH_2OCH_3$ | Ph |
| $CH_2CH_2OCH_3$ | Ph(2-Cl) |
| $CH_2CH_2OCH_3$ | Ph(3-Cl) |
| $CH_2CH_2OCH_3$ | Ph(4-Cl) |
| $CH_2CH_2OCH_3$ | Ph(3-F) |
| $CH_2CH_2OCH_3$ | Ph(3,5-di-F) |
| $CH_2CH_2OCH_3$ | Ph(3-Me) |

TABLE 8-continued

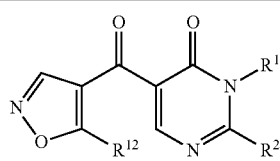

$R^{12}$ is c-Pr

| $R^1$ | $R^2$ |
|---|---|
| $CH_2CH_2OCH_2CH_3$ | Et |
| $CH_2CH_2OCH_2CH_3$ | n-Pr |
| $CH_2CH_2OCH_2CH_3$ | c-Pr |
| $CH_2CH_2OCH_2CH_3$ | $CF_3$ |
| $CH_2CH_2OCH_2CH_3$ | SMe |
| $CH_2CH_2OCH_2CH_3$ | Ph |
| $CH_2CH_2OCH_2CH_3$ | Ph(2-Cl) |
| $CH_2CH_2OCH_2CH_3$ | Ph(3-Cl) |
| $CH_2CH_2OCH_2CH_3$ | Ph(4-Cl) |
| $CH_2CH_2OCH_2CH_3$ | Ph(3-F) |
| $CH_2CH_2OCH_2CH_3$ | Ph(3,5-di-F) |
| $CH_2CH_2OCH_2CH_3$ | Ph(3-Me) |
| $CH_2CH_2CH_2OCH_3$ | Et |
| $CH_2CH_2CH_2OCH_3$ | n-Pr |
| $CH_2CH_2CH_2OCH_3$ | c-Pr |
| $CH_2CH_2CH_2OCH_3$ | $CF_3$ |
| $CH_2CH_2CH_2OCH_3$ | SMe |
| $CH_2CH_2CH_2OCH_3$ | Ph |
| $CH_2CH_2CH_2OCH_3$ | Ph(2-Cl) |
| $CH_2CH_2CH_2OCH_3$ | Ph(3-Cl) |
| $CH_2CH_2CH_2OCH_3$ | Ph(4-Cl) |
| $CH_2CH_2CH_2OCH_3$ | Ph(3-F) |
| $CH_2CH_2CH_2OCH_3$ | Ph(3,5-di-F) |
| $CH_2CH_2CH_2OCH_3$ | Ph(3-Me) |
| $CH_2CH_2CH_2OEt$ | Et |
| $CH_2CH_2CH_2OEt$ | n-Pr |
| $CH_2CH_2CH_2OEt$ | c-Pr |
| $CH_2CH_2CH_2OEt$ | $CF_3$ |
| $CH_2CH_2CH_2OEt$ | SMe |
| $CH_2CH_2CH_2OEt$ | Ph |
| $CH_2CH_2CH_2OEt$ | Ph(2-Cl) |
| $CH_2CH_2CH_2OEt$ | Ph(3-Cl) |
| $CH_2CH_2CH_2OEt$ | Ph(4-Cl) |
| $CH_2CH_2CH_2OEt$ | Ph(3-F) |
| $CH_2CH_2CH_2OEt$ | Ph(3,5-di-F) |
| $CH_2CH_2CH_2OEt$ | Ph(3-Me) |

The present disclosure also includes Tables 1H through 2H, each of which is constructed the same as Table 8 above except that the row heading in Table 8 (i.e. "$R^{12}$ is c-Pr") is replaced with the respective row headings shown below. For example, in Table 1H the row heading is "$R^{12}$ is $CH_3$", and $R^1$ and $R^2$ are as defined in Table 8 above. Thus, the first entry in Table 1H specifically discloses a compound of Formula 1 wherein X is CH; Y is C(O); $R^1$ is $CH_3$; $R^2$ is Et; A is A-6; $R^{11}$ is H; and $R^{12}$ is $CH_3$. Table 2H is constructed similarly.

| Table | Row Heading |
|---|---|
| 1H | $R^{12}$ is $CH_3$ |
| 2H | $R^{12}$ is $CH_2CH_3$ |

TABLE 9

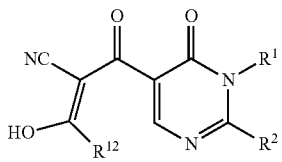

R¹² is c-Pr

| R¹ | R² |
|---|---|
| CH₃ | Et |
| CH₃ | n-Pr |
| CH₃ | c-Pr |
| CH₃ | CF₃ |
| CH₃ | SMe |
| CH₃ | Ph |
| CH₃ | Ph(2-Cl) |
| CH₃ | Ph(3-Cl) |
| CH₃ | Ph(4-Cl) |
| CH₃ | Ph(3-F) |
| CH₃ | Ph(3,5-di-F) |
| CH₃ | Ph(3-Me) |
| Et | Et |
| Et | n-Pr |
| Et | c-Pr |
| Et | CF₃ |
| Et | SMe |
| Et | Ph |
| Et | Ph(2-Cl) |
| Et | Ph(3-Cl) |
| Et | Ph(4-Cl) |
| Et | Ph(3-F) |
| Et | Ph(3,5-di-F) |
| Et | Ph(3-Me) |
| CH₂CH=CH₂ | Et |
| CH₂CH=CH₂ | n-Pr |
| CH₂CH=CH₂ | c-Pr |
| CH₂CH=CH₂ | CF₃ |
| CH₂CH=CH₂ | SMe |
| CH₂CH=CH₂ | Ph |
| CH₂CH=CH₂ | Ph(2-Cl) |
| CH₂CH=CH₂ | Ph(3-Cl) |
| CH₂CH=CH₂ | Ph(4-Cl) |
| CH₂CH=CH₂ | Ph(3-F) |
| CH₂CH=CH₂ | Ph(3,5-di-F) |
| CH₂CH=CH₂ | Ph(3-Me) |
| CH₂C≡CH | Et |
| CH₂C≡CH | n-Pr |
| CH₂C≡CH | c-Pr |
| CH₂C≡CH | CF₃ |
| CH₂C≡CH | SMe |
| CH₂C≡CH | Ph |
| CH₂C≡CH | Ph(2-Cl) |
| CH₂C≡CH | Ph(3-Cl) |
| CH₂C≡CH | Ph(4-Cl) |
| CH₂C≡CH | Ph(3-F) |
| CH₂C≡CH | Ph(3,5-di-F) |
| CH₂C≡CH | Ph(3-Me) |
| Ph | Et |
| Ph | n-Pr |
| Ph | c-Pr |
| Ph | CF₃ |
| Ph | SMe |
| Ph | Ph |
| Ph | Ph(2-Cl) |
| Ph | Ph(3-Cl) |
| Ph | Ph(4-Cl) |
| Ph | Ph(3-F) |
| Ph | Ph(3,5-di-F) |
| Ph | Ph(3-Me) |
| Ph(2-Me) | Et |
| Ph(2-Me) | n-Pr |
| Ph(2-Me) | c-Pr |
| Ph(2-Me) | CF₃ |
| Ph(2-Me) | SMe |
| Ph(2-Me) | Ph |
| Ph(2-Me) | Ph(2-Cl) |

TABLE 9-continued

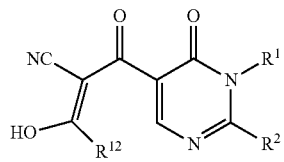

R¹² is c-Pr

| R¹ | R² |
|---|---|
| Ph(2-Me) | Ph(3-Cl) |
| Ph(2-Me) | Ph(4-Cl) |
| Ph(2-Me) | Ph(3-F) |
| Ph(2-Me) | Ph(3,5-di-F) |
| Ph(2-Me) | Ph(3-Me) |
| Ph(4-Me) | Et |
| Ph(4-Me) | n-Pr |
| Ph(4-Me) | c-Pr |
| Ph(4-Me) | CF₃ |
| Ph(4-Me) | SMe |
| Ph(4-Me) | Ph |
| Ph(4-Me) | Ph(2-Cl) |
| Ph(4-Me) | Ph(3-Cl) |
| Ph(4-Me) | Ph(4-Cl) |
| Ph(4-Me) | Ph(3-F) |
| Ph(4-Me) | Ph(3,5-di-F) |
| Ph(4-Me) | Ph(3-Me) |
| Ph(2-Cl) | Et |
| Ph(2-Cl) | n-Pr |
| Ph(2-Cl) | c-Pr |
| Ph(2-Cl) | CF₃ |
| Ph(2-Cl) | SMe |
| Ph(2-Cl) | Ph |
| Ph(2-Cl) | Ph(2-Cl) |
| Ph(2-Cl) | Ph(3-Cl) |
| Ph(2-Cl) | Ph(4-Cl) |
| Ph(2-Cl) | Ph(3-F) |
| Ph(2-Cl) | Ph(3,5-di-F) |
| Ph(2-Cl) | Ph(3-Me) |
| Ph(3-Cl) | Et |
| Ph(3-Cl) | n-Pr |
| Ph(3-Cl) | c-Pr |
| Ph(3-Cl) | CF₃ |
| Ph(3-Cl) | SMe |
| Ph(3-Cl) | Ph |
| Ph(3-Cl) | Ph(2-Cl) |
| Ph(3-Cl) | Ph(3-Cl) |
| Ph(3-Cl) | Ph(4-Cl) |
| Ph(3-Cl) | Ph(3-F) |
| Ph(3-Cl) | Ph(3,5-di-F) |
| Ph(3-Cl) | Ph(3-Me) |
| n-Pr | Et |
| n-Pr | n-Pr |
| n-Pr | c-Pr |
| n-Pr | CF₃ |
| n-Pr | SMe |
| n-Pr | Ph |
| n-Pr | Ph(2-Cl) |
| n-Pr | Ph(3-Cl) |
| n-Pr | Ph(4-Cl) |
| n-Pr | Ph(3-F) |
| n-Pr | Ph(3,5-di-F) |
| n-Pr | Ph(3-Me) |
| n-Bu | Et |
| n-Bu | n-Pr |
| n-Bu | c-Pr |
| n-Bu | CF₃ |
| n-Bu | SMe |
| n-Bu | Ph |
| n-Bu | Ph(2-Cl) |
| n-Bu | Ph(3-Cl) |
| n-Bu | Ph(4-Cl) |
| n-Bu | Ph(3-F) |
| n-Bu | Ph(3,5-di-F) |
| n-Bu | Ph(3-Me) |
| n-pent | Et |
| n-pent | n-Pr |

TABLE 9-continued

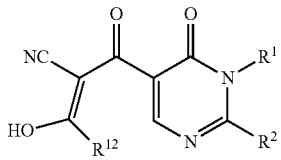

R$^{12}$ is c-Pr

| R$^1$ | R$^2$ |
|---|---|
| n-pent | c-Pr |
| n-pent | CF$_3$ |
| n-pent | SMe |
| n-pent | Ph |
| n-pent | Ph(2-Cl) |
| n-pent | Ph(3-Cl) |
| n-pent | Ph(4-Cl) |
| n-pent | Ph(3-F) |
| n-pent | Ph(3,5-di-F) |
| n-pent | Ph(3-Me) |
| n-Hex | Et |
| n-Hex | n-Pr |
| n-Hex | c-Pr |
| n-Hex | CF$_3$ |
| n-Hex | SMe |
| n-Hex | Ph |
| n-Hex | Ph(2-Cl) |
| n-Hex | Ph(3-Cl) |
| n-Hex | Ph(4-Cl) |
| n-Hex | Ph(3-F) |
| n-Hex | Ph(3,5-di-F) |
| n-Hex | Ph(3-Me) |
| thp-4-yl | Et |
| thp-4-yl | n-Pr |
| thp-4-yl | c-Pr |
| thp-4-yl | CF$_3$ |
| thp-4-yl | SMe |
| thp-4-yl | Ph |
| thp-4-yl | Ph(2-Cl) |
| thp-4-yl | Ph(3-Cl) |
| thp-4-yl | Ph(4-Cl) |
| thp-4-yl | Ph(3-F) |
| thp-4-yl | Ph(3,5-di-F) |
| thp-4-yl | Ph(3-Me) |
| thtp-4-yl | Et |
| thtp-4-yl | n-Pr |
| thtp-4-yl | c-Pr |
| thtp-4-yl | CF$_3$ |
| thtp-4-yl | SMe |
| thtp-4-yl | Ph |
| thtp-4-yl | Ph(2-Cl) |
| thtp-4-yl | Ph(3-Cl) |
| thtp-4-yl | Ph(4-Cl) |
| thtp-4-yl | Ph(3-F) |
| thtp-4-yl | Ph(3,5-di-F) |
| thtp-4-yl | Ph(3-Me) |
| c-Hex | Et |
| c-Hex | n-Pr |
| c-Hex | c-Pr |
| c-Hex | CF$_3$ |
| c-Hex | SMe |
| c-Hex | Ph |
| c-Hex | Ph(2-Cl) |
| c-Hex | Ph(3-Cl) |
| c-Hex | Ph(4-Cl) |
| c-Hex | Ph(3-F) |
| c-Hex | Ph(3,5-di-F) |
| c-Hex | Ph(3-Me) |
| CH$_2$CH$_2$OCH$_3$ | Et |
| CH$_2$CH$_2$OCH$_3$ | n-Pr |
| CH$_2$CH$_2$OCH$_3$ | c-Pr |
| CH$_2$CH$_2$OCH$_3$ | CF$_3$ |
| CH$_2$CH$_2$OCH$_3$ | SMe |
| CH$_2$CH$_2$OCH$_3$ | Ph |
| CH$_2$CH$_2$OCH$_3$ | Ph(2-Cl) |
| CH$_2$CH$_2$OCH$_3$ | Ph(3-Cl) |
| CH$_2$CH$_2$OCH$_3$ | Ph(4-Cl) |

TABLE 9-continued

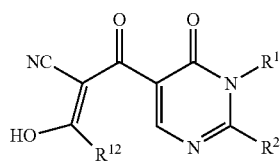

R$^{12}$ is c-Pr

| R$^1$ | R$^2$ |
|---|---|
| CH$_2$CH$_2$OCH$_3$ | Ph(3-F) |
| CH$_2$CH$_2$OCH$_3$ | Ph(3,5-di-F) |
| CH$_2$CH$_2$OCH$_3$ | Ph(3-Me) |
| CH$_2$CH$_2$OCH$_2$CH$_3$ | Et |
| CH$_2$CH$_2$OCH$_2$CH$_3$ | n-Pr |
| CH$_2$CH$_2$OCH$_2$CH$_3$ | c-Pr |
| CH$_2$CH$_2$OCH$_2$CH$_3$ | CF$_3$ |
| CH$_2$CH$_2$OCH$_2$CH$_3$ | SMe |
| CH$_2$CH$_2$OCH$_2$CH$_3$ | Ph |
| CH$_2$CH$_2$OCH$_2$CH$_3$ | Ph(2-Cl) |
| CH$_2$CH$_2$OCH$_2$CH$_3$ | Ph(3-Cl) |
| CH$_2$CH$_2$OCH$_2$CH$_3$ | Ph(4-Cl) |
| CH$_2$CH$_2$OCH$_2$CH$_3$ | Ph(3-F) |
| CH$_2$CH$_2$OCH$_2$CH$_3$ | Ph(3,5-di-F) |
| CH$_2$CH$_2$OCH$_2$CH$_3$ | Ph(3-Me) |
| CH$_2$CH$_2$CH$_2$OCH$_3$ | Et |
| CH$_2$CH$_2$CH$_2$OCH$_3$ | n-Pr |
| CH$_2$CH$_2$CH$_2$OCH$_3$ | c-Pr |
| CH$_2$CH$_2$CH$_2$OCH$_3$ | CF$_3$ |
| CH$_2$CH$_2$CH$_2$OCH$_3$ | SMe |
| CH$_2$CH$_2$CH$_2$OCH$_3$ | Ph |
| CH$_2$CH$_2$CH$_2$OCH$_3$ | Ph(2-Cl) |
| CH$_2$CH$_2$CH$_2$OCH$_3$ | Ph(3-Cl) |
| CH$_2$CH$_2$CH$_2$OCH$_3$ | Ph(4-Cl) |
| CH$_2$CH$_2$CH$_2$OCH$_3$ | Ph(3-F) |
| CH$_2$CH$_2$CH$_2$OCH$_3$ | Ph(3,5-di-F) |
| CH$_2$CH$_2$CH$_2$OCH$_3$ | Ph(3-Me) |
| CH$_2$CH$_2$CH$_2$OEt | Et |
| CH$_2$CH$_2$CH$_2$OEt | n-Pr |
| CH$_2$CH$_2$CH$_2$OEt | c-Pr |
| CH$_2$CH$_2$CH$_2$OEt | CF$_3$ |
| CH$_2$CH$_2$CH$_2$OEt | SMe |
| CH$_2$CH$_2$CH$_2$OEt | Ph |
| CH$_2$CH$_2$CH$_2$OEt | Ph(2-Cl) |
| CH$_2$CH$_2$CH$_2$OEt | Ph(3-Cl) |
| CH$_2$CH$_2$CH$_2$OEt | Ph(4-Cl) |
| CH$_2$CH$_2$CH$_2$OEt | Ph(3-F) |
| CH$_2$CH$_2$CH$_2$OEt | Ph(3,5-di-F) |
| CH$_2$CH$_2$CH$_2$OEt | Ph(3-Me) |

The present disclosure also includes Tables 1J through 2J, each of which is constructed the same as Table 9 above except that the row heading in Table 9 (i.e. "R$^{12}$ is c-Pr") is replaced with the respective row headings shown below. For example, in Table 1J the row heading is "R$^{12}$ is CH$_3$", and R$^1$ and R$^2$ are as defined in Table 9 above. Thus, the first entry in Table 1J specifically discloses a compound of Formula 1 wherein X is CH; Y is C(O); R$^1$ is CH$_3$; R$^2$ is Et; A is A-7; R$^{12}$ is CH$_3$; and R$^{13}$ is cyano. Table 2J is constructed similarly.

| Table | Row Heading |
|---|---|
| 1J | R$^{12}$ is CH$_3$ |
| 2J | R$^{12}$ is CH$_2$CH$_3$ |

TABLE 10

(Structure: cyclopropyl-substituted nitro-enone linked to pyrimidinone with $R^1$, $R^2$, $R^{12}$ substituents)

$R^1$ is phenyl

| $R^2$ |
|---|
| Et |
| Ph(2-Me) |
| n-Pr |
| Ph(3-Cl) |
| c-Pr |
| Ph(4-Cl) |
| CF$_3$ |
| Ph(2-Me) |
| SMe |
| Ph(3-Me) |
| Ph |
| Ph(4-Me) |
| Ph(3-F) |
| Ph(3,5-di-F) |
| Ph(3-Me) |

The present disclosure also includes Tables 1K through 10K, each of which is constructed the same as Table 9 above except that the row heading in Table 10 (i.e. "$R^1$ is Ph") is replaced with the respective row headings shown below. For example, in Table 1K the row heading is "$R^1$ is n-Bu", and $R^2$ is as defined in Table 10 above. Thus, the first entry in Table 1K specifically discloses a compound of Formula 1 wherein X is CH; Y is C(O); $R^1$ is n-Bu; $R^2$ is Ph; A is A-7; $R^{12}$ is hydroxy; and $R^{13}$ is nitro. Table 2K through 10K are constructed similarly.

| Table | Row Heading |
|---|---|
| 1K | $R^1$ is n-Bu |
| 2K | $R^1$ is n-pent |
| 3K | $R^1$ is n-Hex |
| 4K | $R^1$ is thp-4-yl |
| 5K | $R^1$ is thtp-4-yl |
| 6K | $R^1$ is c-Hex |
| 7K | $R^1$ is CH$_2$CH$_2$OCH$_3$ |
| 8K | $R^1$ is CH$_2$CH$_2$OCH$_2$CH$_3$ |
| 9K | $R^1$ is CH$_2$CH$_2$CH$_2$OCH$_3$ |
| 10K | $R^1$ is CH$_2$CH$_2$CH$_2$OCH$_2$CH$_3$ |

TABLE 11

(Structure: hydroxycyclohexenone-carbonyl linked to pyrimidinone-fused ring with Q and $R^{24}$)

| $R^{24}$ | $R^{24}$ | $R^{24}$ | $R^{24}$ | $R^{24}$ |
|---|---|---|---|---|
| Q is CH$_2$ | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |

TABLE 11-continued

| $R^{24}$ | $R^{24}$ | $R^{24}$ | $R^{24}$ | $R^{24}$ |
|---|---|---|---|---|
| Q is —CH$_2$CH$_2$— | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is O | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is NCH$_3$ | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is S | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is S(O) | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is S(O)$_2$ | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |

TABLE 12

Table 12 is constructed the same as Table 11, except the structure is replaced with (bicyclic bridged hydroxyenone-carbonyl pyrimidinone structure with $R^{24}$)

TABLE 13

(Structure: hydroxycyclohexenone-carbonyl linked to pyrimidinone-fused ring with Q and $R^{24}$, variant)

| $R^{24}$ | $R^{24}$ | $R^{24}$ | $R^{24}$ | $R^{24}$ |
|---|---|---|---|---|
| Q is O | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |
| Q is NCH$_3$ | | | | |
| H | Et | n-Pr | OCH$_2$CH$_2$OCH$_3$ | Ph(4-OMe) |
| Ph | Ph(3-Cl) | Ph(3-F) | Ph(3-OMe) | Ph(3,5-di-F) |

TABLE 13-continued

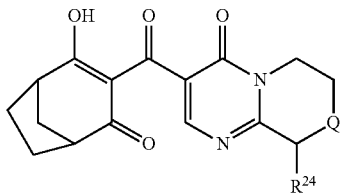

| R²⁴ | R²⁴ | R²⁴ | R²⁴ | R²⁴ |
|---|---|---|---|---|
| Q is S ||||| 
| H | Et | n-Pr | OCH₂CH₂OCH₃ | Ph(4-OMe) |
| Ph | Ph(3-Cl) | Ph(3-F) | Ph(3-OMe) | Ph(3,5-di-F) |
| Q is S(O) |||||
| H | Et | n-Pr | OCH₂CH₂OCH₃ | Ph(4-OMe) |
| Ph | Ph(3-Cl) | Ph(3-F) | Ph(3-OMe) | Ph(3,5-di-F) |
| Q is S(O)₂ |||||
| H | Et | n-Pr | OCH₂CH₂OCH₃ | Ph(4-OMe) |
| Ph | Ph(3-Cl) | Ph(3-F) | Ph(3-OMe) | Ph(3,5-di-F) |

TABLE 14

Table 14 is constructed the same as Table 13, except the structure is replaced with

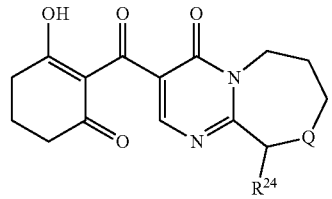

TABLE 15

Table 15 is constructed the same as Table 13, except the structure is replaced with

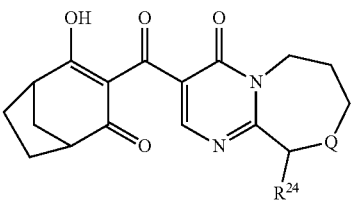

TABLE 16

Table 16 is constructed the same as Table 13, except the structure is replaced with

TABLE 17

Table 17 is constructed the same as Table 13, except the structure is replaced with

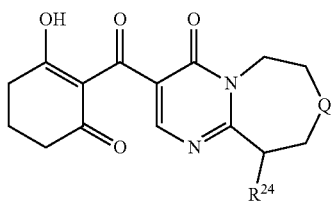

TABLE 18

Table 18 is constructed the same as Table 13, except the structure is replaced with

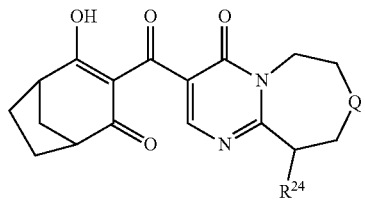

TABLE 19

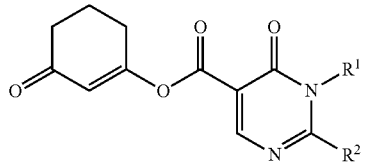

R² is Ph

| R¹ |
|---|
| Me |
| Et |
| n-Pr |
| i-Pr |
| c-Pr |
| n-Bu |
| i-Bu |
| s-Bu |
| c-Bu |
| t-Bu |
| n-pent |
| c-Pent |
| n-Hex |
| c-Hex |
| Ph |
| CH₂-c-Pr |
| CH₂-c-Bu |
| CH₂SPh |
| CH₂SCH₃ |
| CH₂CF₃ |
| CH₂Ph |
| Ph(4-Me) |
| CH₂CHC(CH₃)₂ |
| CH₂CH₂C≡CH |
| CH₂CH=CCl₂ |
| CH₂CH=CF₂ |
| CH₂CF=CF₂ |
| CH₂CCl=CCl₂ |
| CH₂C≡CCH₃ |
| CH₂OCH₂CH₃ |
| CH₂CH₂OCH₃ |
| CH₂SO₂CH₃ |

TABLE 19-continued

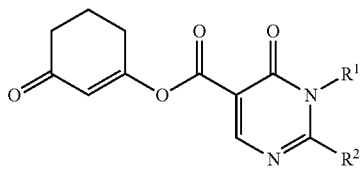

$R^2$ is Ph $R^1$

CH$_2$SCH$_2$CH$_3$
Ph(2,3-di-OMe)
CH$_2$SO$_2$-n-Pr
CH$_2$CH$_2$SO$_2$Et
Ph(2,4-di-OMe)
Ph(2,5-di-OMe)
Ph(2,6-di-OMe)
Ph(3,5-di-OMe)
CH$_2$Ph(2-OMe)
CH$_2$Ph(3-OMe)
CH$_2$Ph(4-OMe)
CH$_2$CH$_2$SMe
CH$_2$SCH$_2$Ph
CH$_2$SO$_2$Ph
CH$_2$CH$_2$SEt
Ph(2,4-di-Cl)
Ph(2,5-di-Cl)
Ph(2,6-di-Cl)
Ph(3,5-di-Cl)
Ph(2,3-di-Me)
Ph(2,4-di-Me)
Ph(2,5-di-Me)
Ph(2,6-di-Me)
Ph(3,5-di-Me)
CH$_2$-c-Hex
Ph(2,3-di-F)
Ph(2,4-di-F)
Ph(2,5-di-F)
Ph(2,6-di-F)
CH$_2$CH$_2$CF$_3$
CH$_2$C≡CH
Ph(2,3-di-Cl)
Ph(3,5-di-F)
isoxazolin-2-yl
Ph(2-Cl)
Ph(3-Cl)
Ph(4-Cl)
Ph(2-Me)
Ph(3-Me)
CH$_2$OCH$_3$
CH$_2$CH═CH$_2$
Ph(2-OMe)
Ph(3-OMe)
Ph(4-OMe)
Ph(2-CN)
Ph(3-CN)
Ph(4-CN)
Ph(2-F)
Ph(3-F)
Ph(4-F)
CH$_2$S-n-Pr
CH$_2$-c-Pent
oxazolin-2-yl
2-pyridinyl
3-pyridinyl
4-pyridinyl
Ph(2-NO$_2$)
Ph(3-NO$_2$)
Ph(4-NO$_2$)
Ph(2-CF$_3$)
Ph(3-CF$_3$)
Ph(4-CF$_3$)
Ph(2-Br)
Ph(3-Br)
Ph(4-Br)
CH$_2$Ph(2-Me)
CH$_2$Ph(3-Me)

TABLE 19-continued

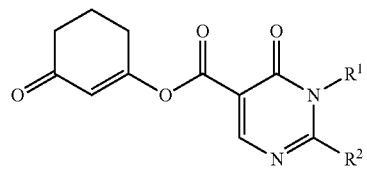

$R^2$ is Ph $R^1$

CH$_2$Ph(4-Me)
CH$_2$Ph(2-Cl)
CH$_2$Ph(3-Cl)
CH$_2$Ph(4-Cl)
thiazol-3-yl
thiazol-2-yl
thiazolin-2-yl
thiazol-2-yl
oxazol-2-yl
CH$_2$CF$_2$CF$_3$
CH═CH$_2$
CH$_2$(thf-2-yl)
CH$_2$(3-methylisoxazolin-5-yl)
isoxazolin-4-yl
CH$_2$(3-methylisoxazol-5-yl)
5-methylisoxazol-3-yl
4-methyloxazol-2-yl
4-methylthiazol-2-yl
CH$_2$CH$_2$CH═CH$_2$
CH$_2$SO$_2$CH$_2$CH$_3$
CH$_2$CH$_2$SO$_2$Me
CH$_2$OCH$_2$OCH$_3$
3-methylthiazol-2-yl
5-chloropyridin-2-yl
5-methylpyridin-2-yl
5-methoxypyridin-2-yl
6-methylpyridin-2-yl
6-methylpyridin-3-yl
3-methoxypyridin-4-yl
3-methylpyridin-4-yl
3-chloropyridin-4-yl
CH$_2$OCH$_2$CH$_2$OCH$_3$
CH$_2$C(CH$_3$)C(CH$_3$)$_2$
n-hept
c-hept
thp-4-yl
thtp-4-yl
Ph(2,3-di-OMe)
Ph(3,4-di-OMe)
Ph(3,4-di-Me)
Ph(3,4-di-F)
Ph(3,4,5-tri-OMe)
Ph(2-I)
Ph(3-I)
Ph(4-I)
Ph(2-Et)
Ph(3-Et)
Ph(4-Et)
CH$_2$CH$_2$OCH$_2$CH$_3$
CH(CH$_3$)CH$_2$OCH$_3$
Ph(2-OCF$_3$)
Ph(3-OCF$_3$)
Ph(4-OCF$_3$)
Ph(2-Me-3-F)
Ph(2-Me-4-F)
Ph(2-Me-5-F)
Ph(2-F-3-Me)
Ph(2-F-4-Me)
Ph(2-F-5-Me)
Ph(3-F-4-Me)
Ph(3-F-5-Me)
Ph(3-Me-4-F)
CH$_2$CH$_2$CH$_2$OCH$_3$
CH$_2$CH$_2$CH$_2$OCH$_2$CH$_3$
CH$_2$(thp-2-yl)
CH$_2$(thp-4-yl)
CH$_2$CH$_2$CH═CH$_2$

TABLE 19-continued

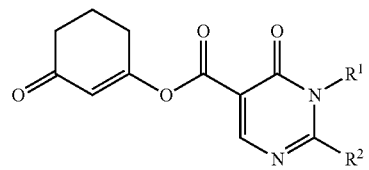

$R^2$ is Ph

| $R^1$ |
|---|
| CH$_2$C≡CH |
| CH$_2$CH$_2$SCH$_3$ |
| CH$_2$CH$_2$SOCH$_3$ |
| CH$_2$CH$_2$SO$_2$CH$_3$ |
| CH$_2$CH$_2$CH$_2$SCH$_3$ |
| CH$_2$CH$_2$CH$_2$SOCH$_3$ |
| CH$_2$CH$_2$CH$_2$SO$_2$CH$_3$ |

The present disclosure also includes Tables 1U through 57U, each of which is constructed the same as Table 19 above except that the row heading in Table 19 (i.e. "$R^2$ is Ph") is replaced with the respective row headings shown below. For example, in Table 1U the row heading is "$R^2$ is Me", and $R^1$ is as defined in Table 19 above. Thus, the first entry in Table 1U specifically discloses a compound of Formula 1 wherein X is CH; Y is C(O); $R^1$ is Me; $R^2$ is Me; $R^3$ is OH; A is A-1; $B^1$ is C-1; $B^2$ is C-3; $B^3$ is C-1; and each $R^{14}$, $R^{15}$, $R^{18}$ and $R^{19}$ is H. Tables 2U through 57U are constructed similarly.

| Table | Row Heading |
|---|---|
| 1U | $R^2$ is Me |
| 2U | $R^2$ is Et |
| 3U | $R^2$ is n-Pr |
| 4U | $R^2$ is c-Pr |
| 5U | $R^2$ is SMe |
| 6U | $R^2$ is SO$_2$Me |
| 7U | $R^2$ is CF$_3$ |
| 8U | $R^2$ is Ph(2-Cl) |
| 9U | $R^2$ is Ph(3-Cl) |
| 10U | $R^2$ is Ph(4-Cl) |
| 11U | $R^2$ is Ph(2-Me) |
| 12U | $R^2$ is Ph(3-Me) |
| 13U | $R^2$ is Ph(4-Me) |
| 14U | $R^2$ is Ph(2-OMe) |
| 15U | $R^2$ is Ph(3-OMe) |
| 16U | $R^2$ is Ph(4-OMe) |
| 17U | $R^2$ is Ph(2-F) |
| 18U | $R^2$ is Ph(3-F) |
| 19U | $R^2$ is Ph(4-F) |
| 20U | $R^2$ is OMe |
| 21U | $R^2$ is OEt |
| 22U | $R^2$ is CH$_2$Ph |
| 23U | $R^2$ is 2-pyridinyl |
| 24U | $R^2$ is 3-pyridinyl |
| 25U | $R^2$ is 4-pyridinyl |
| 26U | $R^2$ is H |
| 27U | $R^2$ is Ph(3,5-di-F) |
| 28U | $R^2$ is Ph(3,4-di-F) |
| 29U | $R^2$ is Ph(3,4,5-tri-F) |
| 30U | $R^2$ is Ph(2,3-di-F) |
| 31U | $R^2$ is Ph(3-CF$_3$) |
| 32U | $R^2$ is Ph(4-CF$_3$) |
| 33U | $R^2$ is Ph(3,5-di-CF$_3$) |
| 34U | $R^2$ is n-Bu |
| 35U | $R^2$ is CH$_2$OCH$_3$ |
| 36U | $R^2$ is CH$_2$CH$_2$OCH$_3$ |
| 37U | $R^2$ is CH$_2$CH$_2$CF$_3$ |
| 38U | $R^2$ is CH$_2$CF$_3$ |
| 39U | $R^2$ is n-pent |
| 40U | $R^2$ is c-pent |
| 41U | $R^2$ is c-Hex |
| 42U | $R^2$ is n-Hex |
| 43U | $R^2$ is thp-4-yl |
| 44U | $R^2$ is Ph(2-CN) |
| 45U | $R^2$ is Ph(3-CN) |
| 46U | $R^2$ is Ph(4-CN) |
| 47U | $R^2$ is Ph(2-C≡CH) |
| 48U | $R^2$ is Ph(3-C≡CH) |
| 49U | $R^2$ is Ph(4-C≡CH) |
| 50U | $R^2$ is Ph(3-Me, 2-F) |
| 51U | $R^2$ is Ph(3-Me-4-F) |
| 52U | $R^2$ is Ph(3-Me, 5-F) |
| 53U | $R^2$ is Ph(3-Me, 6-F) |
| 54U | $R^2$ is Ph(3-F, 2-Me) |
| 55U | $R^2$ is Ph(3-F-4-Me) |
| 56U | $R^2$ is Ph(3-F-5-Me) |
| 57U | $R^2$ is Ph(3-F, 6-Me) |

TABLE 20

Table 20 is constructed the same as Table 19 except the structure is replaced with

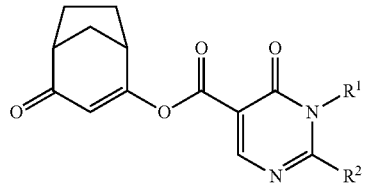

TABLE 21

Table 21 is constructed the same as Table 19 except the structure is replaced with

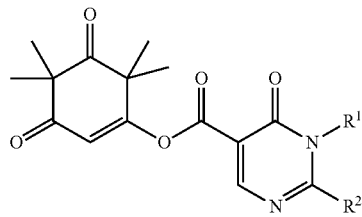

TABLE 22

Table 22 is constructed the same as Table 19 except the structure is replaced with

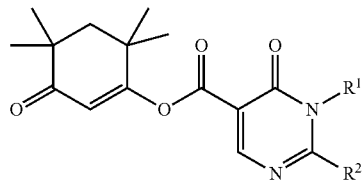

TABLE 23

Table 23 is constructed the same as Table 19 except the structure is replaced with

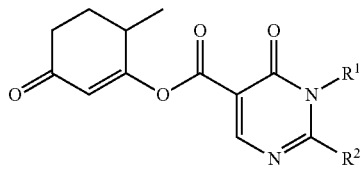

TABLE 24

Table 24 is constructed the same as Table 19 except the structure is replaced with

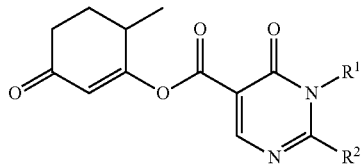

TABLE 25

Table 25 is constructed the same as Table 19 except the structure is replaced with

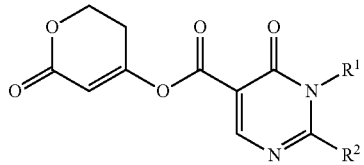

TABLE 26

Table 26 is the same as Table 19 except the structure is replaced with

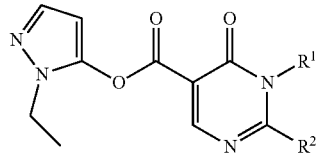

TABLE 27

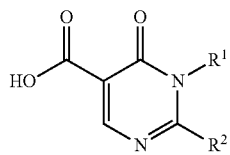

$R^2$ is Ph

| $R^1$ |
|---|
| Me |
| Et |
| n-Pr |
| i-Pr |

TABLE 27-continued

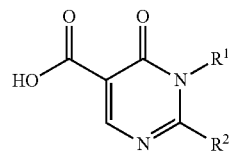

$R^2$ is Ph

| $R^1$ |
|---|
| c-Pr |
| n-Bu |
| i-Bu |
| s-Bu |
| c-Bu |
| t-Bu |
| n-pent |
| c-Pent |
| n-Hex |
| c-Hex |
| Ph |
| $CH_2$-c-Pr |
| $CH_2$-c-Bu |
| $CH_2SPh$ |
| $CH_2SCH_3$ |
| $CH_2CF_3$ |
| $CH_2Ph$ |
| Ph(4-Me) |
| $CH_2CHC(CH_3)_2$ |
| $CH_2CH_2C{\equiv}CH$ |
| $CH_2CH{=}CCl_2$ |
| $CH_2CH{=}CF_2$ |
| $CH_2CF{=}CF_2$ |
| $CH_2CCl{=}CCl_2$ |
| $CH_2C{\equiv}CCH_3$ |
| $CH_2OCH_2CH_3$ |
| $CH_2CH_2OCH_3$ |
| $CH_2SO_2CH_3$ |
| $CH_2SCH_2CH_3$ |
| Ph(2,3-di-OMe) |
| $CH_2SO_2$-n-Pr |
| $CH_2CH_2SO_2Et$ |
| Ph(2,4-di-OMe) |
| Ph(2,5-di-OMe) |
| Ph(2,6-di-OMe) |
| Ph(3,5-di-OMe) |
| $CH_2Ph$(2-OMe) |
| $CH_2Ph$(3-OMe) |
| $CH_2Ph$(4-OMe) |
| $CH_2CH_2SMe$ |
| $CH_2SCH_2Ph$ |
| $CH_2SO_2Ph$ |
| $CH_2CH_2SEt$ |
| Ph(2,4-di-Cl) |
| Ph(2,5-di-Cl) |
| Ph(2,6-di-Cl) |
| Ph(3,5-di-Cl) |
| Ph(2,3-di-Me) |
| Ph(2,4-di-Me) |
| Ph(2,5-di-Me) |
| Ph(2,6-di-Me) |
| Ph(3,5-di-Me) |
| $CH_2$-c-Hex |
| Ph(2,3-di-F) |
| Ph(2,4-di-F) |
| Ph(2,5-di-F) |
| Ph(2,6-di-F) |
| $CH_2CH_2CF_3$ |
| $CH_2C{\equiv}CH$ |
| Ph(2,3-di-Cl) |
| Ph(3,5-di-F) |
| isoxazolin-2-yl |
| Ph(2-Cl) |
| Ph(3-Cl) |
| Ph(4-Cl) |
| Ph(2-Me) |
| Ph(3-Me) |
| $CH_2OCH_3$ |

TABLE 27-continued

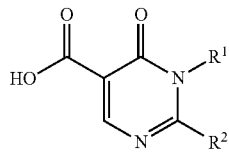

R² is Ph

R¹

CH₂CH=CH₂
Ph(2-OMe)
Ph(3-OMe)
Ph(4-OMe)
Ph(2-CN)
Ph(3-CN)
Ph(4-CN)
Ph(2-F)
Ph(3-F)
Ph(4-F)
CH₂S-n-Pr
CH₂-c-Pent
oxazolin-2-yl
2-pyridinyl
3-pyridinyl
4-pyridinyl
Ph(2-NO₂)
Ph(3-NO₂)
Ph(4-NO₂)
Ph(2-CF₃)
Ph(3-CF₃)
Ph(4-CF₃)
Ph(2-Br)
Ph(3-Br)
Ph(4-Br)
CH₂Ph(2-Me)
CH₂Ph(3-Me)
CH₂Ph(4-Me)
CH₂Ph(2-Cl)
CH₂Ph(3-Cl)
CH₂Ph(4-Cl)
thiazol-3-yl
thiazol-2-yl
thiazolin-2-yl
thiazol-2-yl
oxazol-2-yl
CH₂CF₂CF₃
CH=CH₂
CH₂(thf-2-yl)
CH₂(3-methylisoxazolin-5-yl)
isoxazolin-4-yl
CH₂(3-methylisoxazol-5-yl)
5-methylisoxazol-3-yl
4-methyloxazol-2-yl
4-methylthiazol-2-yl
CH₂CH₂CH=CH₂
CH₂SO₂CH₂CH₃
CH₂CH₂SO₂Me
CH₂OCH₂OCH₃
3-methylthiazol-2-yl
5-chloropyridin-2-yl
5-methylpyridin-2-yl
5-methoxypyridin-2-yl
6-methylpyridin-2-yl
6-methylpyridin-3-yl
3-methoxypyridin-4-yl
3-methylpyridin-4-yl
3-chloropyridin-4-yl
CH₂OCH₂CH₂OCH₃
CH₂C(CH₃)C(CH₃)₂
n-hept
c-hept
thp-4-yl
thtp-4-yl
Ph(2,3-di-OMe)
Ph(3,4-di-OMe)
Ph(3,4-di-Me)
Ph(3,4-di-F)

TABLE 27-continued

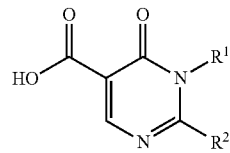

R² is Ph

R¹

Ph(3,4,5-tri-OMe)
Ph(2-I)
Ph(3-I)
Ph(4-I)
Ph(2-Et)
Ph(3-Et)
Ph(4-Et)
CH₂CH₂OCH₂CH₃
CH(CH₃)CH₂OCH₃
Ph(2-OCF₃)
Ph(3-OCF₃)
Ph(4-OCF₃)
Ph(2-Me-3-F)
Ph(2-Me-4-F)
Ph(2-Me-5-F)
Ph(2-F-3-Me)
Ph(2-F-4-Me)
Ph(2-F-5-Me)
Ph(3-F-4-Me)
Ph(3-F-5-Me)
Ph(3-Me-4-F)
CH₂CH₂CH₂OCH₃
CH₂CH₂CH₂OCH₂CH₃
CH₂(thp-2-yl)
CH₂(thp-4-yl)
CH₂CH₂CH=CH₂
CH₂C≡CH
CH₂CH₂SCH₃
CH₂CH₂SOCH₃
CH₂CH₂SO₂CH₃
CH₂CH₂CH₂SCH₃
CH₂CH₂CH₂SOCH₃
CH₂CH₂CH₂SO₂CH₃

The present disclosure also includes Tables 1BB through 57BB, each of which is constructed the same as Table 27 above except that the row heading in Table 27 (i.e. "R² is Ph") is replaced with the respective row headings shown below. For example, in Table 1BB the row heading is "R² is Me", and R¹ is as defined in Table 27 above. Thus, the first entry in Table 1BB specifically discloses a compound of Formula 1 wherein X is CH; Y is C(O); R¹ is Me; R² is Me; R³ is OH; A is A-1; B¹ is C-1; B² is C-3; B³ is C-1; and each R¹⁴, R¹⁵, R¹⁸ and R¹⁹ is H. Tables 2BB through 57BB are constructed similarly.

| Table | Row Heading |
|---|---|
| 1BB | R² is Me |
| 2BB | R² is Et |
| 3BB | R² is n-Pr |
| 4BB | R² is c-Pr |
| 5BB | R² is SMe |
| 6BB | R² is SO₂Me |
| 7BB | R² is CF₃ |
| 8BB | R² is Ph(2-Cl) |
| 9BB | R² is Ph(3-Cl) |
| 10BB | R² is Ph(4-Cl) |
| 11BB | R² is Ph(2-Me) |
| 12BB | R² is Ph(3-Me) |
| 13BB | R² is Ph(4-Me) |
| 14BB | R² is Ph(2-OMe) |
| 15BB | R² is Ph(3-OMe) |
| 16BB | R² is Ph(4-OMe) |

| Table | Row Heading |
|---|---|
| 17BB | $R^2$ is Ph(2-F) |
| 18BB | $R^2$ is Ph(3-F) |
| 19BB | $R^2$ is Ph(4-F) |
| 20BB | $R^2$ is OMe |
| 21BB | $R^2$ is OEt |
| 22BB | $R^2$ is $CH_2Ph$ |
| 23BB | $R^2$ is 2-pyridinyl |
| 24BB | $R^2$ is 3-pyridinyl |
| 25BB | $R^2$ is 4-pyridinyl |
| 26BB | H |
| 27BB | Ph(3,5-di-F) |
| 28BB | Ph(3,4-di-F) |
| 29BB | Ph(3,4,5-tri-F) |
| 30BB | Ph(2,3-di-F) |
| 31BB | Ph(3-$CF_3$) |
| 32BB | Ph(4-$CF_3$) |
| 33BB | Ph(3,5-di-$CF_3$) |
| 34BB | n-Bu |
| 35BB | $CH_2OCH_3$ |
| 36BB | $CH_2CH_2OCH_3$ |
| 37BB | $CH_2CH_2CF_3$ |
| 38BB | $CH_2CF_3$ |
| 39BB | n-pent |
| 40BB | c-pent |
| 41BB | c-Hex |
| 42BB | n-Hex |
| 43BB | thp-4-yl |
| 44BB | Ph(2-CN) |
| 45BB | Ph(3-CN) |
| 46BB | Ph(4-CN) |
| 47BB | Ph(2-C≡CH) |
| 48BB | Ph(3-C≡CH) |
| 49BB | Ph(4-C≡CH) |
| 50BB | Ph(3-Me, 2-F) |
| 51BB | Ph(3-Me-4-F) |
| 52BB | Ph(3-Me, 5-F) |
| 53BB | Ph(3-Me, 6-F) |
| 54BB | Ph(3-F, 2-Me) |
| 55BB | Ph(3-F-4-Me) |
| 56BB | Ph(3-F-5-Me) |
| 57BB | Ph(3-F, 6-Me) |

TABLE 28

Table 28 is constructed the same as Table 27 except the structure is replaced with

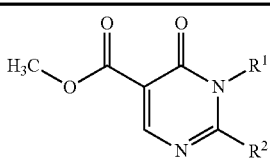

TABLE 29

Table 29 is constructed the same as Table 27 except the structure is replaced with

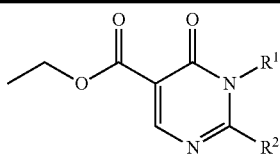

TABLE 30

Table 30 is constructed the same as Table 27 except the structure is replaced with

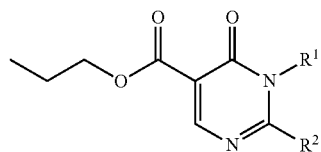

TABLE 31

Table 31 is constructed the same as Table 27 except the structure is replaced with

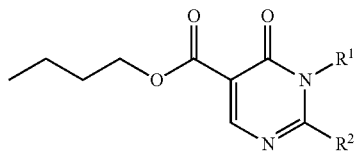

TABLE 32

Table 32 is constructed the same as Table 27 except the structure is replaced with

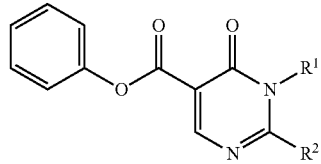

TABLE 33

Table 32 is constructed the same as Table 27 except the structure is replaced with

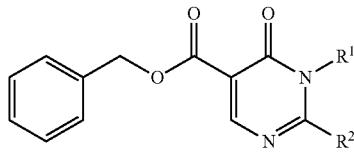

TABLE 34

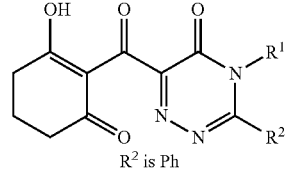

$R^2$ is Ph $R^1$

Me
Et
n-Pr
i-Pr
c-Pr
n-Bu
i-Bu

TABLE 34-continued

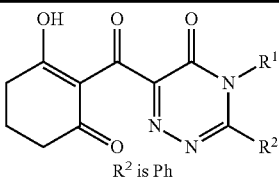

R² is Ph

| R¹ |
|---|
| s-Bu |
| c-Bu |
| t-Bu |
| n-pent |
| CH₂CHC(CH₃)₂ |
| CH₂CH₂C≡CH |
| CH₂CH=CCl₂ |
| CH₂CH=CF₂ |
| CH₂CF=CF₂ |
| CH₂CCl=CCl₂ |
| CH₂C=CCH₃ |
| CH₂OCH₂CH₃ |
| CH₂CH₂OCH₃ |
| CH₂SO₂CH₃ |
| CH₂SCH₂CH₃ |
| CH₂SO₂Ph |
| CH₂SCH₂Ph |
| CH₂CH₂SEt |
| Ph(2,4-di-Cl) |
| Ph(2,5-di-Cl) |
| Ph(2,6-di-Cl) |
| Ph(3,5-di-Cl) |
| Ph(2,3-di-Me) |
| Ph(2,4-di-Me) |
| Ph(2,5-di-Me) |
| Ph(2,6-di-Me) |
| Ph(2-Cl) |
| Ph(3-Cl) |
| Ph(4-Cl) |
| Ph(2-Me) |
| Ph(3-Me) |
| CH₂OCH₃ |
| CH₂CH=CH₂ |
| Ph(2-OMe) |
| Ph(3-OMe) |
| Ph(4-OMe) |
| Ph(2-CN) |
| Ph(4-NO₂) |
| Ph(2-CF₃) |
| Ph(3-CF₃) |
| Ph(4-CF₃) |
| Ph(2-Br) |
| Ph(3-Br) |
| Ph(4-Br) |
| CH₂Ph(2-Me) |
| CH₂Ph(3-Me) |
| CH₂Ph(4-Me) |
| CH₂Ph(2-Cl) |
| c-Pent |
| n-Hex |
| c-Hex |
| Ph |
| CH₂—c-Pr |
| CH₂—c-Bu |
| CH₂SPh |
| CH₂SCH₃ |
| CH₂CF₃ |
| CH₂Ph |
| Ph(2,3-di-OMe) |
| CH₂SO₂—n-Pr |
| CH₂CH₂SO₂Et |
| Ph(2,4-di-OMe) |
| Ph(2,5-di-OMe) |
| Ph(2,6-di-OMe) |
| Ph(3,5-di-OMe) |
| CH₂Ph(2-OMe) |
| CH₂Ph(3-OMe) |
| CH₂Ph(4-OMe) |
| Ph(3,5-di-Me) |

TABLE 34-continued

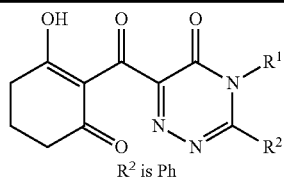

R² is Ph

| R¹ |
|---|
| CH₂—c-Hex |
| Ph(2,3-di-F) |
| Ph(2,4-di-F) |
| Ph(2,5-di-F) |
| Ph(2,6-di-F) |
| CH₂CH₂CF₃ |
| CH₂C≡CH |
| Ph(2,3-di-Cl) |
| Ph(3-NO₂) |
| Ph(3-CN) |
| Ph(4-CN) |
| Ph(2-F) |
| Ph(3-F) |
| Ph(4-F) |
| CH₂S—n-Pr |
| CH₂—c-Pent |
| CH₂CF₂CF₃ |
| CH=CH₂ |
| Ph(2-NO₂) |
| CH₂Ph(3-Cl) |
| CH₂Ph(4-Cl) |
| CH₂CH₂SO₂Me |
| CH₂OCH₂OCH₃ |
| CH₂OCH₂CH₂OCH₃ |
| CH₂C(CH₃)C(CH₃)₂ |
| Ph(4-Me) |
| CH₂CH₂SMe |
| Ph(3,5-di-F) |

The present disclosure also includes Tables 1K through 4K, each of which is constructed the same as Table 11 above except that the row heading in Table 11 (i.e. "R² is Ph") is replaced with the respective row headings shown below. For example, in Table 1K the row heading is "R² is Ph", and R¹ is as defined in Table 11 above. Thus, the first entry in Table 1K specifically discloses a compound of Formula 1P wherein X is N, Y is C(O), R¹ is Me; R² is c-Pr; R³ is OH; A is A-1; B¹ is C-1; B² is C-3; B³ is C-1; and each $R^{14}$, $R^{15}$, $R^{18}$ and $R^{19}$ is H. Tables 2K through 4K are constructed similarly.

| Table | Row Heading |
|---|---|
| 1K | R² is c-Pr |
| 2K | R² is SMe |
| 3K | R² is SO₂Me |
| 4K | R² is CF₃ |

TABLE 35

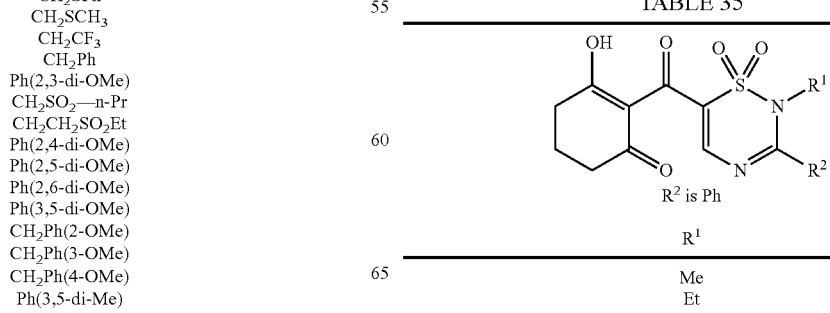

R² is Ph

| R¹ |
|---|
| Me |
| Et |

TABLE 35-continued

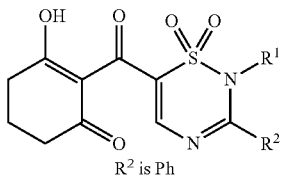

R² is Ph

R¹ n-Pr
i-Pr
c-Pr
n-Bu
CH₂CHC(CH₃)₂
CH₂CH₂C≡CH
CH₂CH=CCl₂
CH₂CH=CF₂
CH₂CF=CF₂
CH₂CCl=CCl₂
CH₂SO₂Ph
CH₂SCH₂Ph
CH₂CH₂SEt
Ph(2,4-di-Cl)
Ph(2,5-di-Cl)
Ph(2,6-di-Cl)
Ph(2-Cl)
Ph(3-Cl)
Ph(4-Cl)
Ph(2-Me)
Ph(3-Me)
CH₂OCH₃
Ph(4-NO₂)
Ph(2-CF₃)
Ph(3-CF₃)
Ph(4-CF₃)
Ph(2-Br)
Ph(3-Br)
i-Bu
s-Bu
c-Bu
t-Bu
n-pent
c-Pent
n-Hex
c-Hex
Ph
CH₂—c-Pr
CH₂—c-Bu
CH₂SPh
CH₂SCH₃
CH₂CF₃
CH₂Ph
CH₂C≡CCH₃
CH₂OCH₂CH₃
CH₂CH₂OCH₃
CH₂SO₂CH₃
CH₂SCH₂CH₃
Ph(2,3-di-OMe)
CH₂SO₂—n-Pr
CH₂CH₂SO₂Et
Ph(2,4-di-OMe)
Ph(2,5-di-OMe)
Ph(2,6-di-OMe)
Ph(3,5-di-OMe)
CH₂Ph(2-OMe)
CH₂Ph(3-OMe)
CH₂Ph(4-OMe)
Ph(3,5-di-Cl)
Ph(2,3-di-Me)
Ph(2,4-di-Me)
Ph(2,5-di-Me)
Ph(2,6-di-Me)
Ph(3,5-di-Me)
CH₂—c-Hex
Ph(2,3-di-F)
Ph(2,4-di-F)
Ph(2,5-di-F)
Ph(2,6-di-F)

TABLE 35-continued

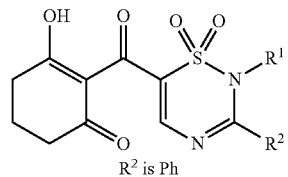

R² is Ph

R¹

CH₂CH₂CF₃
CH₂C≡CH
Ph(2,3-di-Cl)
Ph(3-NO₂)
CH₂CH=CH₂
Ph(2-OMe)
Ph(3-OMe)
Ph(4-OMe)
Ph(2-CN)
Ph(3-CN)
Ph(4-CN)
Ph(2-F)
Ph(3-F)
Ph(4-F)
CH₂S—n-Pr
CH₂—c-Pent
CH₂CF₂CF₃
CH=CH₂
Ph(2-NO₂)
Ph(4-Br)
CH₂Ph(2-Me)
CH₂Ph(3-Me)
CH₂Ph(4-Me)
CH₂Ph(2-Cl)
CH₂Ph(3-Cl)
CH₂Ph(4-Cl)
CH₂CH₂SO₂Me
CH₂OCH₂OCH₃
CH₂OCH₂CH₂OCH₃
CH₂C(CH₃)C(CH₃)₂
Ph(4-Me)
CH₂CH₂SMe
Ph(3,5-di-F)

The present disclosure also includes Tables 1L through 11L, each of which is constructed the same as Table 12 above except that the row heading in Table 12 (i.e. "R² is Ph") is replaced with the respective row headings shown below. For example, in Table 1L the row heading is "R² is Ph", and R¹ is as defined in Table 12 above. Thus, the first entry in Table 1L specifically discloses a compound of Formula 1P wherein X is CH; Y is S(O)₂; R¹ is Me and R² is c-Pr; R³ is OH; A is A-1; B¹ is C-1; B² is C-3; B³ is C-1; and each R¹⁴, R¹⁵, R¹⁸ and R¹⁹ is H. Tables 2L through 11L are constructed similarly.

| Table | Row Heading |
|---|---|
| 1L | R² is c-Pr |
| 2L | R² is n-Pr |
| 3L | R² is SMe |
| 4L | R² is SO₂Me |
| 5L | R² is CF₃ |
| 6L | R² Ph(2-Cl) |
| 7L | R² Ph(3-Cl) |
| 8L | R² is Ph(4-Cl) |
| 9L | R² is Ph(2-Me) |
| 10L | R² is Ph(3-Me) |
| 11L | R² is Ph(4-Me) |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2. Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 4 | 98.5% |
| silica aerogel | 0.5% |
| synthetic amorphous fine silica | 1.0% |

Example B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 12 | 10.0% |
| attapulgite granules (low volatile matter, 0.71/0.30 mm; U.S.S. No. 25-50 sieves) | 90.0% |

Example D

| Extruded Pellet | |
|---|---|
| Compound 8 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 2 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 12 | 5.0% |
| polyvinylpyrrolidone-vinyl acetate copolymer | 30.0% |
| alkylpolyglycoside | 30.0% |
| glyceryl monooleate | 15.0% |
| Water | 20.0% |

These compounds generally show highest activity for early postemergence weed control (i.e. applied when the emerged weed seedlings are still young) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of the invention are particularly useful for selective control of weeds in wheat, barley, and particularly maize, soybean, cotton and perennial plantation crops such as sugarcane and citrus. Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both postemergent and preemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of a compound of this invention is about 0.001 to 20 kg/ha with a typical range of about 0.004 to 1 kg/ha. One skilled in the art can easily determine the herbicidally effective amount necessary for the desired level of weed control.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthaldimethyl, chlorthiamid, cinidon-ethyl, cinmethylin, cinosulfuron, clefoxydim, clethodim, clodinafop-propargyl, clomazone, clomeprop, clopyralid, clopyralid-olamine, cloransulam-methyl, cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halo sulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isox-achlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, BCS (1-bromo-4-[(chloromethyl)sulfonyl]benzene), cloquintocet-mexyl, cyometrinil, cyprosulfonamide, dichlormid, 4-(dichloroacetyl)-1-oxa-4-azospiro[4.5]decane (MON 4660), 2-(dichloromethyl)-2-methyl-1,3-dioxolane (MG 191), dicyclonon, dietholate, fenchlorazole-ethyl, fenclorim, flurazole, fluxofenim, furilazole, isoxadifen-ethyl, mefenpyr-diethyl, mephenate, methoxyphenone ((4-methoxy-3-methylphenyl)(3-methylphenyl)methanone), naphthalic anhydride (1,8-naphthalic anhydride) and oxabetrinil to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of 2,4-D, ametryne, aminocyclopyrachlor, aminopyralid, atrazine, bromacil, bromoxynil, bromoxynil octanoate, carfentrazone-ethyl, chlorimuron-ethyl, chlorsulfuron, clopyralid, clopyralid-olamine, dicamba and its diglycolammonium, dimethylammonium, potassium and sodium salts, diflufenican, dimethenamid, dimethenamid-P, diuron, florasulam, flufenacet, flumetsulam, flumioxazin, flupyrsulfuron-methyl, flupyrsulfuron-methyl-sodium, fluroxypyr, glyphosate (particularly glyphosate-isopropylammonium, glyphosate-sodium, glyphosate-potassium, glyphosate-trimesium), hexazinone, imazamethabenz-methyl, imazaquin, imazethapyr, iodosulfuron-methyl, lactofen, lenacil, linuron, MCPA and its dimethylammonium, potassium and sodium salts, MCPA-isoctyl, MCPA-thioethyl, mesosulfuron-methyl, S-metolachlor, metribuzin, metsulfuron-methyl, nicosulfuron, oxyfluorfen, pendimethalin, pinoxaden, pronamide, prosulfuron, pyroxasulfone, pyroxsulam, quinclorac, rimsulfuron, saflufenacil, sulfentrazone, thifensulfuron-methyl, triasulfuron, tribenuron-methyl, triclopyr, triclopyr-butotyl, and triclopyr-triethylammonium. Specifically preferred mixtures (compound numbers refer to compounds in Index Table A) are selected from the group: compound 2 and 2,4-D; compound 4 and 2,4-D; compound 8 and 2,4-D; compound 12 and 2,4-D; compound 2 and ametryne; compound 4 and ametryne; compound 8 and ametryne; compound 12 and ametryne; compound 2 and aminocyclopyrachlor; compound 4 and aminocyclopyrachlor; compound 8 and aminocyclopyrachlor; compound 12 and aminocyclopyrachlor; compound 2 and aminopyralid; compound 4 and aminopyralid; compound 8 and aminopyralid; compound 12 and aminopyralid; compound 2 and atrazine; compound 4 and atrazine; compound 8 and atrazine; compound 12 and atrazine; compound 2 and bromacil; compound 4 and bromacil; compound 8 and bromacil; compound 12 and bromacil; compound 2 and bromoxynil; compound 4 and bromoxynil; compound 8 and bromoxynil; compound 12 and bromoxynil; compound 2 and bromoxynil octanoate; compound 4 and bromoxynil octanoate; compound 8 and bromoxynil octanoate; compound 12 and bromoxynil octanoate; compound 2 and carfentrazone-ethyl; compound 4 and carfentrazone-ethyl; compound 8 and carfentrazone-ethyl; compound 12 and carfentrazone-ethyl; compound 2 and chlorimuron-ethyl; compound 4 and chlorimuron-ethyl; compound 8 and chlorimuron-ethyl; compound 12 and chlorimuron-ethyl; compound 2 and chlorsulfuron; compound 4 and chlorsulfuron; compound 8 and chlorsulfuron; compound 12 and chlorsulfuron; compound 2 and clopyralid; compound 4 and clopyralid; compound 8 and clopyralid; compound 12 and clopyralid; compound 2 and clopyralid-olamine; compound 4 and clopyralid-olamine; compound 8 and clopyralid-olamine; compound 12 and clopyralid-olamine; compound 2 and dicamba; compound 4 and dicamba; compound 8 and dicamba; compound 12 and dicamba; compound 2 and diflufenican; compound 4 and diflufenican; compound 8 and diflufenican; compound 12 and diflufenican; compound 2 and dimethenamid; compound 4 and dimethenamid; compound 8 and dimethenamid; compound 12 and dimethenamid; compound 2 and dimethenamid-P; compound 4 and dimethenamid-P; compound 8 and dimethenamid-P; compound 12 and dimethenamid-P; compound 2 and diuron; compound 4 and diuron; compound 8 and diuron; compound 12 and diuron; compound 2 and florasulam; compound 4 and florasulam;

compound 8 and florasulam; compound 12 and florasulam; compound 2 and flufenacet; compound 4 and flufenacet; compound 8 and flufenacet; compound 12 and flufenacet; compound 2 and flumetsulam; compound 4 and flumetsulam; compound 8 and flumetsulam; compound 12 and flumetsulam; compound 2 and flumioxazin; compound 4 and flumioxazin; compound 8 and flumioxazin; compound 12 and flumioxazin; compound 2 and flupyrsulfuron-methyl; compound 4 and flupyrsulfuron-methyl; compound 8 and flupyrsulfuron-methyl; compound 12 and flupyrsulfuron-methyl; compound 2 and flupyrsulfuron-methyl-sodium; compound 4 and flupyrsulfuron-methyl-sodium; compound 8 and flupyrsulfuron-methyl-sodium; compound 12 and flupyrsulfuron-methyl-sodium; compound 2 and fluroxypyr; compound 4 and fluroxypyr; compound 8 and fluroxypyr; compound 12 and fluroxypyr; compound 2 and glyphosate; compound 4 and glyphosate; compound 8 and glyphosate; compound 12 and glyphosate; compound 2 and hexazinone; compound 4 and hexazinone; compound 8 and hexazinone; compound 12 and hexazinone; compound 2 and imazamethabenz-methyl; compound 4 and imazamethabenz-methyl; compound 8 and imazamethabenz-methyl; compound 12 and imazamethabenz-methyl; compound 2 and imazaquin; compound 4 and imazaquin; compound 8 and imazaquin; compound 12 and imazaquin; compound 2 and imazethapyr; compound 4 and imazethapyr; compound 8 and imazethapyr; compound 12 and imazethapyr; compound 2 and iodosulfuron-methyl; compound 4 and iodosulfuron-methyl; compound 8 and iodosulfuron-methyl; compound 12 and iodosulfuron-methyl; compound 2 and lactofen; compound 4 and lactofen; compound 8 and lactofen; compound 12 and lactofen; compound 2 and lenacil; compound 4 and lenacil; compound 8 and lenacil; compound 12 and lenacil; compound 2 and linuron; compound 4 and linuron; compound 8 and linuron; compound 12 and linuron; compound 2 and MCPA; compound 4 and MCPA; compound 8 and MCPA; compound 12 and MCPA; compound 2 and MCPA-isoctyl; compound 4 and MCPA-isoctyl; compound 8 and MCPA-isoctyl; compound 12 and MCPA-isoctyl; compound 2 and MCPA-thioethyl; compound 4 and MCPA-thioethyl; compound 8 and MCPA-thioethyl; compound 12 and MCPA-thioethyl; compound 2 and mesosulfuron-methyl; compound 4 and mesosulfuron-methyl; compound 8 and mesosulfuron-methyl; compound 12 and mesosulfuron-methyl; compound 2 and S-metolachlor; compound 4 and S-metolachlor; compound 8 and S-metolachlor; compound 12 and S-metolachlor; compound 2 and metribuzin; compound 4 and metribuzin; compound 8 and metribuzin; compound 12 and metribuzin; compound 2 and metsulfuron-methyl; compound 4 and metsulfuron-methyl; compound 8 and metsulfuron-methyl; compound 12 and metsulfuron-methyl; compound 2 and nicosulfuron; compound 4 and nicosulfuron; compound 8 and nicosulfuron; compound 12 and nicosulfuron; compound 2 and oxyfluorfen; compound 4 and oxyfluorfen; compound 8 and oxyfluorfen; compound 12 and oxyfluorfen; compound 2 and pendimethalin; compound 4 and pendimethalin; compound 8 and pendimethalin; compound 12 and pendimethalin; compound 2 and pinoxaden; compound 4 and pinoxaden; compound 8 and pinoxaden; compound 12 and pinoxaden; compound 2 and pronamide; compound 4 and pronamide; compound 8 and pronamide; compound 12 and pronamide; compound 2 and prosulfuron; compound 4 and prosulfuron; compound 8 and prosulfuron; compound 12 and prosulfuron; compound 2 and pyroxasulfone; compound 4 and pyroxasulfone; compound 8 and pyroxasulfone; compound 12 and pyroxasulfone; compound 2 and pyroxsulam; compound 4 and pyroxsulam; compound 8 and pyroxsulam; compound 12 and pyroxsulam; compound 2 and quinclorac; compound 4 and quinclorac; compound 8 and quinclorac; compound 12 and quinclorac; compound 2 and rimsulfuron; compound 4 and rimsulfuron; compound 8 and rimsulfuron; compound 12 and rimsulfuron; compound 2 and saflufenacil; compound 4 and saflufenacil; compound 8 and saflufenacil; compound 12 and saflufenacil; compound 2 and sulfentrazone; compound 4 and sulfentrazone; compound 8 and sulfentrazone; compound 12 and sulfentrazone; compound 2 and thifensulfuron-methyl; compound 4 and thifensulfuron-methyl; compound 8 and thifensulfuron-methyl; compound 12 and thifensulfuron-methyl; compound 2 and triasulfuron; compound 4 and triasulfuron; compound 8 and triasulfuron; compound 12 and triasulfuron; compound 2 and tribenuron-methyl; compound 4 and tribenuron-methyl; compound 8 and tribenuron-methyl; compound 12 and tribenuron-methyl; compound 2 and triclopyr; compound 4 and triclopyr; compound 8 and triclopyr; compound 12 and triclopyr; compound 2 and triclopyr-butotyl; compound 4 and triclopyr-butotyl; compound 8 and triclopyr-butotyl; compound 12 and triclopyr-butotyl; compound 2 and triclopyr-triethylammonium; compound 4 and triclopyr-triethylammonium; compound 8 and triclopyr-triethylammonium; compound 12 and triclopyr-triethylammonium.

Table A1 lists specific combinations of a compound of Formula 1 (i.e. Component (a)) with an additional active ingredient (i.e. Component (b)) illustrative of the mixtures, compositions and methods of the present invention. The first column of Table A1 lists compound 45 as the illustrative compound of Formula 1. The second column of Table A1 lists the specific Component (b) compound (e.g., "2,4-D" in the first line). The third, fourth and fifth columns of Table A1 lists ranges of weight ratios for rates at which the Component (b) compound is typically applied to a field-grown crop relative to Component (a). Thus, for example, the first line of Table A1 specifically discloses the combination of Component (a) with 2,4-D is typically applied in a weight ratio between 1:192 to 6:1. The remaining lines of Table A1 are to be construed similarly.

TABLE A1

| Component (a) | Component (b) | Typical Weight Ratio | More Typical Weight Ratio | Most Typical Weight Ratio |
|---|---|---|---|---|
| Compound 47 | 2,4-D | 1:192 to 6:1 | 1:64 to 2:1 | 1:24 to 1:3 |
| Compound 47 | acetochlor | 1:768 to 2:1 | 1:256 to 1:2 | 1:96 to 1:11 |
| Compound 47 | acifluorfen | 1:96 to 12:1 | 1:32 to 4:1 | 1:12 to 1:2 |
| Compound 47 | aclonifen | 1:857 to 2:1 | 1:285 to 1:3 | 1:107 to 1:12 |
| Compound 47 | alachlor | 1:768 to 2:1 | 1:256 to 1:2 | 1:96 to 1:11 |
| Compound 47 | ametryn | 1:384 to 3:1 | 1:128 to 1:1 | 1:48 to 1:6 |
| Compound 47 | amicarbazone | 1:192 to 6:1 | 1:64 to 2:1 | 1:24 to 1:3 |
| Compound 47 | amidosulfuron | 1:6 to 168:1 | 1:2 to 56:1 | 1:1 to 11:1 |
| Compound 47 | aminocyclopyrachlor | 1:48 to 24:1 | 1:16 to 8:1 | 1:6 to 2:1 |
| Compound 47 | aminopyralid | 1:20 to 56:1 | 1:6 to 19:1 | 1:2 to 4:1 |

TABLE A1-continued

| Component (a) | Component (b) | Typical Weight Ratio | More Typical Weight Ratio | Most Typical Weight Ratio |
|---|---|---|---|---|
| Compound 47 | amitrole | 1:768 to 2:1 | 1:256 to 1:2 | 1:96 to 1:11 |
| Compound 47 | anilofos | 1:96 to 12:1 | 1:32 to 4:1 | 1:12 to 1:2 |
| Compound 47 | asulam | 1:960 to 2:1 | 1:320 to 1:3 | 1:120 to 1:14 |
| Compound 47 | atrazine | 1:192 to 6:1 | 1:64 to 2:1 | 1:24 to 1:3 |
| Compound 47 | azimsulfuron | 1:6 to 168:1 | 1:2 to 56:1 | 1:1 to 11:1 |
| Compound 47 | beflubutamid | 1:342 to 4:1 | 1:114 to 2:1 | 1:42 to 1:5 |
| Compound 47 | benfuresate | 1:617 to 2:1 | 1:205 to 1:2 | 1:77 to 1:9 |
| Compound 47 | bensulfuron | 1:25 to 45:1 | 1:8 to 15:1 | 1:3 to 3:1 |
| Compound 47 | bentazon | 1:192 to 6:1 | 1:64 to 2:1 | 1:24 to 1:3 |
| Compound 47 | benzobicyclon | 1:85 to 14:1 | 1:28 to 5:1 | 1:10 to 1:2 |
| Compound 47 | benzofenap | 1:257 to 5:1 | 1:85 to 2:1 | 1:32 to 1:4 |
| Compound 47 | bicyclopyrone | 1:42 to 27:1 | 1:14 to 9:1 | 1:5 to 2:1 |
| Compound 47 | bifenox | 1:257 to 5:1 | 1:85 to 2:1 | 1:32 to 1:4 |
| Compound 47 | bispyribac-sodium | 1:10 to 112:1 | 1:3 to 38:1 | 1:1 to 7:1 |
| Compound 47 | bromacil | 1:384 to 3:1 | 1:128 to 1:1 | 1:48 to 1:6 |
| Compound 47 | bromobutide | 1:384 to 3:1 | 1:128 to 1:1 | 1:48 to 1:6 |
| Compound 47 | bromoxynil | 1:96 to 12:1 | 1:32 to 4:1 | 1:12 to 1:2 |
| Compound 47 | butachlor | 1:768 to 2:1 | 1:256 to 1:2 | 1:96 to 1:11 |
| Compound 47 | butafenacil | 1:42 to 27:1 | 1:14 to 9:1 | 1:5 to 2:1 |
| Compound 47 | butylate | 1:1542 to 1:2 | 1:514 to 1:5 | 1:192 to 1:22 |
| Compound 47 | carfenstrole | 1:192 to 6:1 | 1:64 to 2:1 | 1:24 to 1:3 |
| Compound 47 | carfentrazone | 1:128 to 9:1 | 1:42 to 3:1 | 1:16 to 1:2 |
| Compound 47 | chlorimuron | 1:8 to 135:1 | 1:2 to 45:1 | 1:1 to 9:1 |
| Compound 47 | chlorotoluron | 1:768 to 2:1 | 1:256 to 1:2 | 1:96 to 1:11 |
| Compound 47 | chlorsulfuron | 1:6 to 168:1 | 1:2 to 56:1 | 1:1 to 11:1 |
| Compound 47 | cincosulfuron | 1:17 to 68:1 | 1:5 to 23:1 | 1:2 to 5:1 |
| Compound 47 | cinidon-ethyl | 1:384 to 3:1 | 1:128 to 1:1 | 1:48 to 1:6 |
| Compound 47 | cinmethylin | 1:34 to 34:1 | 1:11 to 12:1 | 1:4 to 3:1 |
| Compound 47 | clethodim | 1:48 to 24:1 | 1:16 to 8:1 | 1:6 to 2:1 |
| Compound 47 | clodinafop | 1:20 to 56:1 | 1:6 to 19:1 | 1:2 to 4:1 |
| Compound 47 | clomazone | 1:384 to 3:1 | 1:128 to 1:1 | 1:48 to 1:6 |
| Compound 47 | clomeprop | 1:171 to 7:1 | 1:57 to 3:1 | 1:21 to 1:3 |
| Compound 47 | clopyralid | 1:192 to 6:1 | 1:64 to 2:1 | 1:24 to 1:3 |
| Compound 47 | cloransulam | 1:12 to 96:1 | 1:4 to 32:1 | 1:1 to 6:1 |
| Compound 47 | cumyluron | 1:384 to 3:1 | 1:128 to 1:1 | 1:48 to 1:6 |
| Compound 47 | cyanazine | 1:384 to 3:1 | 1:128 to 1:1 | 1:48 to 1:6 |
| Compound 47 | cyclosulfamuron | 1:17 to 68:1 | 1:5 to 23:1 | 1:2 to 5:1 |
| Compound 47 | cycloxydim | 1:96 to 12:1 | 1:32 to 4:1 | 1:12 to 1:2 |
| Compound 47 | cyhalofop | 1:25 to 45:1 | 1:8 to 15:1 | 1:3 to 3:1 |
| Compound 47 | daimuron | 1:192 to 6:1 | 1:64 to 2:1 | 1:24 to 1:3 |
| Compound 47 | desmedipham | 1:322 to 4:1 | 1:107 to 2:1 | 1:40 to 1:5 |
| Compound 47 | dicamba | 1:192 to 6:1 | 1:64 to 2:1 | 1:24 to 1:3 |
| Compound 47 | dichlobenil | 1:1371 to 1:2 | 1:457 to 1:4 | 1:171 to 1:20 |
| Compound 47 | dichlorprop | 1:925 to 2:1 | 1:308 to 1:3 | 1:115 to 1:13 |
| Compound 47 | diclofop | 1:384 to 3:1 | 1:128 to 1:1 | 1:48 to 1:6 |
| Compound 47 | diclosulam | 1:10 to 112:1 | 1:3 to 38:1 | 1:1 to 7:1 |
| Compound 47 | difenzoquat | 1:288 to 4:1 | 1:96 to 2:1 | 1:36 to 1:4 |
| Compound 47 | diflufenican | 1:857 to 2:1 | 1:285 to 1:3 | 1:107 to 1:12 |
| Compound 47 | diflufenzopyr | 1:12 to 96:1 | 1:4 to 32:1 | 1:1 to 6:1 |
| Compound 47 | dimethachlor | 1:768 to 2:1 | 1:256 to 1:2 | 1:96 to 1:11 |
| Compound 47 | dimethametryn | 1:192 to 6:1 | 1:64 to 2:1 | 1:24 to 1:3 |
| Compound 47 | dimethenamid | 1:384 to 3:1 | 1:128 to 1:1 | 1:48 to 1:6 |
| Compound 47 | dithiopyr | 1:192 to 6:1 | 1:64 to 2:1 | 1:24 to 1:3 |
| Compound 47 | diuron | 1:384 to 3:1 | 1:128 to 1:1 | 1:48 to 1:6 |
| Compound 47 | EPTC | 1:768 to 2:1 | 1:256 to 1:2 | 1:96 to 1:11 |
| Compound 47 | esprocarb | 1:1371 to 1:2 | 1:457 to 1:4 | 1:171 to 1:20 |
| Compound 47 | ethalfluralin | 1:384 to 3:1 | 1:128 to 1:1 | 1:48 to 1:6 |
| Compound 47 | ethametsulfuron | 1:17 to 68:1 | 1:5 to 23:1 | 1:2 to 5:1 |
| Compound 47 | ethoxyfen | 1:8 to 135:1 | 1:2 to 45:1 | 1:1 to 9:1 |
| Compound 47 | ethoxysulfuron | 1:20 to 56:1 | 1:6 to 19:1 | 1:2 to 4:1 |
| Compound 47 | etobenzanid | 1:257 to 5:1 | 1:85 to 2:1 | 1:32 to 1:4 |
| Compound 47 | fenoxaprop | 1:120 to 10:1 | 1:40 to 4:1 | 1:15 to 1:2 |
| Compound 47 | fenoxasulfone | 1:85 to 14:1 | 1:28 to 5:1 | 1:10 to 1:2 |
| Compound 47 | fentrazamide | 1:17 to 68:1 | 1:5 to 23:1 | 1:2 to 5:1 |
| Compound 47 | flazasulfuron | 1:17 to 68:1 | 1:5 to 23:1 | 1:2 to 5:1 |
| Compound 47 | florasulam | 1:2 to 420:1 | 1:1 to 140:1 | 2:1 to 27:1 |
| Compound 47 | fluazifop | 1:192 to 6:1 | 1:64 to 2:1 | 1:24 to 1:3 |
| Compound 47 | flucarbazone | 1:8 to 135:1 | 1:2 to 45:1 | 1:1 to 9:1 |
| Compound 47 | flucetosulfuron | 1:8 to 135:1 | 1:2 to 45:1 | 1:1 to 9:1 |
| Compound 47 | flufenacet | 1:257 to 5:1 | 1:85 to 2:1 | 1:32 to 1:4 |
| Compound 47 | flumetsulam | 1:24 to 48:1 | 1:8 to 16:1 | 1:3 to 3:1 |
| Compound 47 | flumiclorac | 1:10 to 112:1 | 1:3 to 38:1 | 1:1 to 7:1 |
| Compound 47 | flumioxazin | 1:25 to 45:1 | 1:8 to 15:1 | 1:3 to 3:1 |
| Compound 47 | fluometuron | 1:384 to 3:1 | 1:128 to 1:1 | 1:48 to 1:6 |
| Compound 47 | flupyrsulfuron | 1:3 to 336:1 | 1:1 to 112:1 | 2:1 to 21:1 |
| Compound 47 | fluridone | 1:384 to 3:1 | 1:128 to 1:1 | 1:48 to 1:6 |
| Compound 47 | fluroxypyr | 1:96 to 12:1 | 1:32 to 4:1 | 1:12 to 1:2 |

TABLE A1-continued

| Component (a) | Component (b) | Typical Weight Ratio | More Typical Weight Ratio | Most Typical Weight Ratio |
|---|---|---|---|---|
| Compound 47 | flurtamone | 1:857 to 2:1 | 1:285 to 1:3 | 1:107 to 1:12 |
| Compound 47 | fomesafen | 1:96 to 12:1 | 1:32 to 4:1 | 1:12 to 1:2 |
| Compound 47 | foramsulfuron | 1:13 to 84:1 | 1:4 to 28:1 | 1:1 to 6:1 |
| Compound 47 | glufosinate | 1:288 to 4:1 | 1:96 to 2:1 | 1:36 to 1:4 |
| Compound 47 | glyphosate | 1:288 to 4:1 | 1:96 to 2:1 | 1:36 to 1:4 |
| Compound 47 | halosulfuron | 1:17 to 68:1 | 1:5 to 23:1 | 1:2 to 5:1 |
| Compound 47 | haloxyfop | 1:34 to 34:1 | 1:11 to 12:1 | 1:4 to 3:1 |
| Compound 47 | hexazinone | 1:192 to 6:1 | 1:64 to 2:1 | 1:24 to 1:3 |
| Compound 47 | imazamox | 1:13 to 84:1 | 1:4 to 28:1 | 1:1 to 6:1 |
| Compound 47 | imazapic | 1:20 to 56:1 | 1:6 to 19:1 | 1:2 to 4:1 |
| Compound 47 | imazapyr | 1:85 to 14:1 | 1:28 to 5:1 | 1:10 to 1:2 |
| Compound 47 | imazaquin | 1:34 to 34:1 | 1:11 to 12:1 | 1:4 to 3:1 |
| Compound 47 | imazethabenz | 1:171 to 7:1 | 1:57 to 3:1 | 1:21 to 1:3 |
| Compound 47 | imazethapyr | 1:24 to 48:1 | 1:8 to 16:1 | 1:3 to 3:1 |
| Compound 47 | imazosulfuron | 1:27 to 42:1 | 1:9 to 14:1 | 1:3 to 3:1 |
| Compound 47 | indanofan | 1:342 to 4:1 | 1:114 to 2:1 | 1:42 to 1:5 |
| Compound 47 | indaziflam | 1:25 to 45:1 | 1:8 to 15:1 | 1:3 to 3:1 |
| Compound 47 | iodosulfuron | 1:3 to 336:1 | 1:1 to 112:1 | 2:1 to 21:1 |
| Compound 47 | ioxynil | 1:192 to 6:1 | 1:64 to 2:1 | 1:24 to 1:3 |
| Compound 47 | ipfencarbazone | 1:85 to 14:1 | 1:28 to 5:1 | 1:10 to 1:2 |
| Compound 47 | isoproturon | 1:384 to 3:1 | 1:128 to 1:1 | 1:48 to 1:6 |
| Compound 47 | isoxaben | 1:288 to 4:1 | 1:96 to 2:1 | 1:36 to 1:4 |
| Compound 47 | isoxaflutole | 1:60 to 20:1 | 1:20 to 7:1 | 1:7 to 2:1 |
| Compound 47 | lactofen | 1:42 to 27:1 | 1:14 to 9:1 | 1:5 to 2:1 |
| Compound 47 | lenacil | 1:384 to 3:1 | 1:128 to 1:1 | 1:48 to 1:6 |
| Compound 47 | linuron | 1:384 to 3:1 | 1:128 to 1:1 | 1:48 to 1:6 |
| Compound 47 | MCPA | 1:192 to 6:1 | 1:64 to 2:1 | 1:24 to 1:3 |
| Compound 47 | MCPB | 1:288 to 4:1 | 1:96 to 2:1 | 1:36 to 1:4 |
| Compound 47 | mecoprop | 1:768 to 2:1 | 1:256 to 1:2 | 1:96 to 1:11 |
| Compound 47 | mefenacet | 1:384 to 3:1 | 1:128 to 1:1 | 1:48 to 1:6 |
| Compound 47 | mefluidide | 1:192 to 6:1 | 1:64 to 2:1 | 1:24 to 1:3 |
| Compound 47 | mesosulfuron | 1:5 to 224:1 | 1:1 to 75:1 | 1:1 to 14:1 |
| Compound 47 | mesotrione | 1:42 to 27:1 | 1:14 to 9:1 | 1:5 to 2:1 |
| Compound 47 | metamifop | 1:42 to 27:1 | 1:14 to 9:1 | 1:5 to 2:1 |
| Compound 47 | metazachlor | 1:384 to 3:1 | 1:128 to 1:1 | 1:48 to 1:6 |
| Compound 47 | metazosulfuron | 1:25 to 45:1 | 1:8 to 15:1 | 1:3 to 3:1 |
| Compound 47 | methabenzthiazuron | 1:768 to 2:1 | 1:256 to 1:2 | 1:96 to 1:11 |
| Compound 47 | metolachlor | 1:768 to 2:1 | 1:256 to 1:2 | 1:96 to 1:11 |
| Compound 47 | metosulam | 1:8 to 135:1 | 1:2 to 45:1 | 1:1 to 9:1 |
| Compound 47 | metribuzin | 1:192 to 6:1 | 1:64 to 2:1 | 1:24 to 1:3 |
| Compound 47 | metsulfuron | 1:2 to 560:1 | 1:1 to 187:1 | 3:1 to 35:1 |
| Compound 47 | molinate | 1:1028 to 2:1 | 1:342 to 1:3 | 1:128 to 1:15 |
| Compound 47 | napropamide | 1:384 to 3:1 | 1:128 to 1:1 | 1:48 to 1:6 |
| Compound 47 | naptalam | 1:192 to 6:1 | 1:64 to 2:1 | 1:24 to 1:3 |
| Compound 47 | nicosulfuron | 1:12 to 96:1 | 1:4 to 32:1 | 1:1 to 6:1 |
| Compound 47 | norflurazon | 1:1152 to 1:1 | 1:384 to 1:3 | 1:144 to 1:16 |
| Compound 47 | orbencarb | 1:1371 to 1:2 | 1:457 to 1:4 | 1:171 to 1:20 |
| Compound 47 | orthosulfamuron | 1:20 to 56:1 | 1:6 to 19:1 | 1:2 to 4:1 |
| Compound 47 | oryzalin | 1:514 to 3:1 | 1:171 to 1:2 | 1:64 to 1:8 |
| Compound 47 | oxadiargyl | 1:384 to 3:1 | 1:128 to 1:1 | 1:48 to 1:6 |
| Compound 47 | oxadiazon | 1:548 to 3:1 | 1:182 to 1:2 | 1:68 to 1:8 |
| Compound 47 | oxasulfuron | 1:27 to 42:1 | 1:9 to 14:1 | 1:3 to 3:1 |
| Compound 47 | oxaziclomefone | 1:42 to 27:1 | 1:14 to 9:1 | 1:5 to 2:1 |
| Compound 47 | oxyfluorfen | 1:384 to 3:1 | 1:128 to 1:1 | 1:48 to 1:6 |
| Compound 47 | paraquat | 1:192 to 6:1 | 1:64 to 2:1 | 1:24 to 1:3 |
| Compound 47 | pendimethalin | 1:384 to 3:1 | 1:128 to 1:1 | 1:48 to 1:6 |
| Compound 47 | penoxsulam | 1:10 to 112:1 | 1:3 to 38:1 | 1:1 to 7:1 |
| Compound 47 | penthoxamid | 1:384 to 3:1 | 1:128 to 1:1 | 1:48 to 1:6 |
| Compound 47 | pentoxazone | 1:102 to 12:1 | 1:34 to 4:1 | 1:12 to 1:2 |
| Compound 47 | phenmedipham | 1:102 to 12:1 | 1:34 to 4:1 | 1:12 to 1:2 |
| Compound 47 | picloram | 1:96 to 12:1 | 1:32 to 4:1 | 1:12 to 1:2 |
| Compound 47 | picolinafen | 1:34 to 34:1 | 1:11 to 12:1 | 1:4 to 3:1 |
| Compound 47 | pinoxaden | 1:25 to 45:1 | 1:8 to 15:1 | 1:3 to 3:1 |
| Compound 47 | pretilachlor | 1:192 to 6:1 | 1:64 to 2:1 | 1:24 to 1:3 |
| Compound 47 | primisulfuron | 1:8 to 135:1 | 1:2 to 45:1 | 1:1 to 9:1 |
| Compound 47 | prodiamine | 1:384 to 3:1 | 1:128 to 1:1 | 1:48 to 1:6 |
| Compound 47 | profoxydim | 1:42 to 27:1 | 1:14 to 9:1 | 1:5 to 2:1 |
| Compound 47 | prometryn | 1:384 to 3:1 | 1:128 to 1:1 | 1:48 to 1:6 |
| Compound 47 | propachlor | 1:1152 to 1:1 | 1:384 to 1:3 | 1:144 to 1:16 |
| Compound 47 | propanil | 1:384 to 3:1 | 1:128 to 1:1 | 1:48 to 1:6 |
| Compound 47 | propaquizafop | 1:48 to 24:1 | 1:16 to 8:1 | 1:6 to 2:1 |
| Compound 47 | propoxycarbazone | 1:17 to 68:1 | 1:5 to 23:1 | 1:2 to 5:1 |
| Compound 47 | propyrisulfuron | 1:17 to 68:1 | 1:5 to 23:1 | 1:2 to 5:1 |
| Compound 47 | propyzamide | 1:384 to 3:1 | 1:128 to 1:1 | 1:48 to 1:6 |
| Compound 47 | prosulfocarb | 1:1200 to 1:2 | 1:400 to 1:4 | 1:150 to 1:17 |
| Compound 47 | prosulfuron | 1:6 to 168:1 | 1:2 to 56:1 | 1:1 to 11:1 |
| Compound 47 | pyraclonil | 1:42 to 27:1 | 1:14 to 9:1 | 1:5 to 2:1 |

TABLE A1-continued

| Component (a) | Component (b) | Typical Weight Ratio | More Typical Weight Ratio | Most Typical Weight Ratio |
|---|---|---|---|---|
| Compound 47 | pyraflufen | 1:5 to 224:1 | 1:1 to 75:1 | 1:1 to 14:1 |
| Compound 47 | pyrasulfotole | 1:13 to 84:1 | 1:4 to 28:1 | 1:1 to 6:1 |
| Compound 47 | pyrazolynate | 1:857 to 2:1 | 1:285 to 1:3 | 1:107 to 1:12 |
| Compound 47 | pyrazosulfuron | 1:10 to 112:1 | 1:3 to 38:1 | 1:1 to 7:1 |
| Compound 47 | pyrazoxyfen | 1:5 to 224:1 | 1:1 to 75:1 | 1:1 to 14:1 |
| Compound 47 | pyribenzoxim | 1:10 to 112:1 | 1:3 to 38:1 | 1:1 to 7:1 |
| Compound 47 | pyributicarb | 1:384 to 3:1 | 1:128 to 1:1 | 1:48 to 1:6 |
| Compound 47 | pyridate | 1:288 to 4:1 | 1:96 to 2:1 | 1:36 to 1:4 |
| Compound 47 | pyriftalid | 1:10 to 112:1 | 1:3 to 38:1 | 1:1 to 7:1 |
| Compound 47 | pyriminobac | 1:20 to 56:1 | 1:6 to 19:1 | 1:2 to 4:1 |
| Compound 47 | pyrimisulfan | 1:17 to 68:1 | 1:5 to 23:1 | 1:2 to 5:1 |
| Compound 47 | pyrithiobac | 1:24 to 48:1 | 1:8 to 16:1 | 1:3 to 3:1 |
| Compound 47 | pyroxasulfone | 1:85 to 14:1 | 1:28 to 5:1 | 1:10 to 1:2 |
| Compound 47 | pyroxsulam | 1:5 to 224:1 | 1:1 to 75:1 | 1:1 to 14:1 |
| Compound 47 | quinclorac | 1:192 to 6:1 | 1:64 to 2:1 | 1:24 to 1:3 |
| Compound 47 | quizalofop | 1:42 to 27:1 | 1:14 to 9:1 | 1:5 to 2:1 |
| Compound 47 | rimsulfuron | 1:13 to 84:1 | 1:4 to 28:1 | 1:1 to 6:1 |
| Compound 47 | saflufenacil | 1:25 to 45:1 | 1:8 to 15:1 | 1:3 to 3:1 |
| Compound 47 | sethoxydim | 1:96 to 12:1 | 1:32 to 4:1 | 1:12 to 1:2 |
| Compound 47 | simazine | 1:384 to 3:1 | 1:128 to 1:1 | 1:48 to 1:6 |
| Compound 47 | sulcotrione | 1:120 to 10:1 | 1:40 to 4:1 | 1:15 to 1:2 |
| Compound 47 | sulfentrazone | 1:147 to 8:1 | 1:49 to 3:1 | 1:18 to 1:3 |
| Compound 47 | sulfometuron | 1:34 to 34:1 | 1:11 to 12:1 | 1:4 to 3:1 |
| Compound 47 | sulfosulfuron | 1:8 to 135:1 | 1:2 to 45:1 | 1:1 to 9:1 |
| Compound 47 | tebuthiuron | 1:384 to 3:1 | 1:128 to 1:1 | 1:48 to 1:6 |
| Compound 47 | tefuryltrione | 1:42 to 27:1 | 1:14 to 9:1 | 1:5 to 2:1 |
| Compound 47 | tembotrione | 1:31 to 37:1 | 1:10 to 13:1 | 1:3 to 3:1 |
| Compound 47 | tepraloxydim | 1:25 to 45:1 | 1:8 to 15:1 | 1:3 to 3:1 |
| Compound 47 | terbacil | 1:288 to 4:1 | 1:96 to 2:1 | 1:36 to 1:4 |
| Compound 47 | terbuthylatrazine | 1:857 to 2:1 | 1:285 to 1:3 | 1:107 to 1:12 |
| Compound 47 | terbutryn | 1:192 to 6:1 | 1:64 to 2:1 | 1:24 to 1:3 |
| Compound 47 | thenylchlor | 1:85 to 14:1 | 1:28 to 5:1 | 1:10 to 1:2 |
| Compound 47 | thiazopyr | 1:384 to 3:1 | 1:128 to 1:1 | 1:48 to 1:6 |
| Compound 47 | thiencarbazone | 1:3 to 336:1 | 1:1 to 112:1 | 2:1 to 21:1 |
| Compound 47 | thifensulfuron | 1:5 to 224:1 | 1:1 to 75:1 | 1:1 to 14:1 |
| Compound 47 | thiobencarb | 1:768 to 2:1 | 1:256 to 1:2 | 1:96 to 1:11 |
| Compound 47 | topramazone | 1:6 to 168:1 | 1:2 to 56:1 | 1:1 to 11:1 |
| Compound 47 | tralkoxydim | 1:68 to 17:1 | 1:22 to 6:1 | 1:8 to 2:1 |
| Compound 47 | triallate | 1:768 to 2:1 | 1:256 to 1:2 | 1:96 to 1:11 |
| Compound 47 | triasulfuron | 1:5 to 224:1 | 1:1 to 75:1 | 1:1 to 14:1 |
| Compound 47 | triaziflam | 1:171 to 7:1 | 1:57 to 3:1 | 1:21 to 1:3 |
| Compound 47 | tribenuron | 1:3 to 336:1 | 1:1 to 112:1 | 2:1 to 21:1 |
| Compound 47 | triclopyr | 1:192 to 6:1 | 1:64 to 2:1 | 1:24 to 1:3 |
| Compound 47 | trifloxysulfuron | 1:2 to 420:1 | 1:1 to 140:1 | 2:1 to 27:1 |
| Compound 47 | trifluralin | 1:288 to 4:1 | 1:96 to 2:1 | 1:36 to 1:4 |
| Compound 47 | triflusulfuron | 1:17 to 68:1 | 1:5 to 23:1 | 1:2 to 5:1 |
| Compound 47 | tritosulfuron | 1:13 to 84:1 | 1:4 to 28:1 | 1:1 to 6:1 |

The present disclosure also includes Tables A2 through A22 which are each constructed the same as Table A1 above except that entries below the "Component (a)" column heading are replaced with the respective Component (a) Column Entry shown below. Thus, for example, in Table A2 the entries below the "Component (a)" column heading all recite "Compound 50", and the first line below the column headings in Table A2 specifically discloses a mixture of Compound 50 with 2,4-D. Tables A3 through A22 are constructed similarly.

| Table Number | Component (a) Column Entries |
|---|---|
| A2 | Compound 50 |
| A3 | Compound 52 |
| A4 | Compound 59 |
| A5 | Compound 75 |
| A6 | Compound 81 |
| A7 | Compound 82 |
| A8 | Compound 83 |
| A9 | Compound 85 |
| A10 | Compound 87 |
| A11 | Compound 96 |
| A12 | Compound 97 |
| A13 | Compound 107 |
| A14 | Compound 118 |
| A15 | Compound 128 |
| A16 | Compound 133 |
| A17 | Compound 169 |
| A18 | Compound 175 |
| A19 | Compound 186 |
| A20 | Compound 218 |
| A21 | Compound 240 |
| A22 | Compound 243 |

The following Tests demonstrate the herbicidal effect of the compounds of this invention against specific weeds. The weed control afforded by the compounds is not limited, however, to the plant species tested. See Index Tables A-I for compound descriptions. The following abbreviations are used in the Index Tables which follow: "Cmpd" means Compound, Me is methyl, Et is ethyl, c-Pr is cyclopropyl, i-Bu is isobutyl (i.e. —$CH_2CH(CH_3)_2$), Ph is phenyl, OMe is methoxy, c-hex is cyclohexyl, n-hex is normal hexyl Bn in benzyl, acetylene means —C≡CH, and SMe is methylthio. The abbreviation "Ex." stands for "Example" and is followed by a number indicating in which example the compound is prepared. Substitution is noted in parenthases following the listed ring, for example Ph(4-OMe) indicates that the phenyl group is substituted by methoxy at the 4-position (relative to the point of attachment of the phenyl group to the remainder of the Formula 1 compound).

INDEX TABLE A

| Cmpd | R¹ | R² | R³ | m.p. (° C.) |
|---|---|---|---|---|
| 1 | CH₃ | c-Pr | OH | * |
| 2 (Ex. 1) | Ph | Ph | OH | * ** |
| 3 | Et | c-Pr | OH | * |
| 4 | Ph(4-OMe) | Ph | OH | * |
| 7 | Ph | Et | OH | * |
| 8 | Ph(4-Me) | Ph | OH | * |
| 9 | Ph(3-Cl) | Ph | OH | 101-102 |
| 10 | Ph(2-Cl) | Ph | OH | 142-143 |
| 11 | Ph(4-Cl) | Ph | OH | 83-85 |
| 12 | Ph(2-Me) | Ph | OH | 181-182 |
| 13 | Ph(4-Cl) | Ph | O⁻K⁺ | 105-108 |
| 14 | Ph | Ph | O⁻K⁺ | 128-130 |
| 15 | Ph(2-OMe) | Ph | OH | 178-179 |
| 17 (Ex. 2) | —CH₂Ph | Ph | OH | 57-58 ** |
| 18 | Ph(3-Me) | Ph | OH | 77-78 |
| 19 | Ph(3-OMe) | Ph | OH | 87-88 |
| 22 | Ph(3-F) | Ph | OH | 72-74 |
| 23 | —CH₂CH═CH₂ | Ph | OH | 38-40 |
| 24 | Ph(4-F) | Ph | OH | 131-132 |
| 25 | Ph | Ph(4-Cl) | OH | * |
| 26 | Ph(2-F) | Ph | OH | 142-144 |
| 27 | Ph(2,3-di-Me) | Ph | OH | 155-157 |
| 28 | Ph(2,4-di-Me) | Ph | OH | 186-187 |
| 29 | Ph(2,5-di-Me) | Ph | OH | 169-171 |
| 30 | Ph | SMe | OH | 92-94 |
| 31 | Ph(2,6-di-Me) | Ph | OH | 177-178 |
| 32 | Ph(3,4-di-Me) | Ph | OH | 165-166 |
| 33 | Ph(3,5-di-Me) | Ph | OH | 156-157 |
| 34 | Ph | Ph(3-Cl) | OH | 131-135 |
| 35 | Ph | Ph(2-Cl) | OH | 138-142 |
| 36 | Ph(2-Me) | Ph(3-Cl) | OH | 82-83 |
| 37 | Ph(2-Br) | Ph | OH | 170-171 |
| 38 | Ph(3-Br) | Ph | OH | 105-107 |
| 39 | Ph(4-Me) | Ph(3-Cl) | OH | 78-80 |
| 40 | Ph(3-Cl-2-Me) | Ph | OH | 170-171 |
| 41 | Ph(2-Cl-4-Me) | Ph | OH | 183-184 |
| 42 | Ph | n-Bu | OH | 145-147 |
| 43 | Ph(4-Cl-2-Me) | Ph | OH | 172-173 |
| 44 | Ph(5-F-2-Me) | Ph | OH | 169-170 |
| 45 | Ph(3-Me) | Ph(3-Cl) | OH | 69-70 |
| 46 | Ph(2-Cl-6-Me) | Ph | OH | 180-181 |
| 47 (Ex. 5) | Ph(3-F-2-Me) | Ph | OH | 168-169 |
| 48 | Ph(4-F-2-Me) | Ph | OH | 153-155 |
| 49 | Et | Ph | OH | 62-66 |
| 50 | n-Pr | Ph | OH | 106-108 |
| 51 | Ph(2-F-5-Me) | Ph | OH | 159-161 |
| 52 | Ph(5-Cl-2-Me) | Ph | OH | 165-166 |
| 53 | Ph(4-F-3-Me) | Ph | OH | 152-153 |
| 54 | Ph | n-hex | OH | 138-140 |
| 55 | Me | Ph | OH | 152-154 |
| 56 | Ph | 3-thienyl | OH | * |
| 57 | Ph(2,4-di-F) | Ph | OH | 153-154 |
| 58 | Ph(2-F,3-Me) | Ph | OH | 161-162 |
| 59 | —CH₂(tetrahydrofuran-2yl) | Ph | OH | 155-156 |
| 60 | Ph | i-Pr | OH | * |
| 61 | —CH₂C≡CH | Ph | | 151-153 |
| 62 | Ph(2-Me) | n-Bu | OH | 100-101 |
| 63 | Ph(3-Me) | n-Bu | OH | 136-137 |
| 64 | Ph(4-Cl) | Ph(3-Cl) | OH | 140-142 |
| 65 | Ph | 2-thienyl(5-Cl) | OH | * |
| 66 | Ph | 2-thienyl | OH | * |
| 67 | Ph(4-Me) | n-Bu | OH | 143-144 |
| 68 | Ph | i-Bu | OH | * |
| 69 | Ph | Ph(3-Br) | OH | * |

INDEX TABLE A-continued

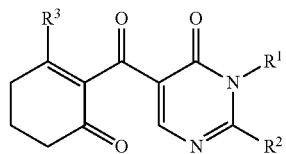

| Cmpd | R¹ | R² | R³ | m.p. (° C.) |
|---|---|---|---|---|
| 70 | Ph | Ph(4-Br) | OH | * |
| 71 | Ph | Ph(2-Br) | OH | * |
| 72 | n-Pr | n-Pr | OH | 95-97 |
| 73 | Ph(2-Me) | n-Pr | OH | 127-128 |
| 74 | —CH₂(tetrahydrofuran-2-yl) | n-Pr | OH | 95-96 |
| 75 | n-Bu | n-Pr | OH | 88-89 |
| 76 | Ph | furan-2-yl | OH | * |
| 77 | n-Pr | 2-thienyl | OH | * |
| 78 | Ph | n-pentyl | OH | * |
| 79 | Ph(3-Me) | n-Pr | OH | 140-142 |
| 80 | Ph | Ph(4-Me) | OH | 164-169 |
| 81 | —CH₂CH₂CH₂OCH₃ | Ph | OH | 121-122 |
| 82 | Ph | Ph(2-Me) | OH | 165-167 |
| 83 | Ph | Ph | OC(=O)—i-Bu | 175-176 |
| 84 | —CH₂(Ph(3,4-di-OMe)) | n-Pr | OH | * |
| 85 | —CH₂CH₂OCH₃ | Ph | OH | 135-137 |
| 86 | n-Bu | Ph | OH | * |
| 87 | Ph | c-Pr | OH | * |
| 88 | Ph | Ph | OC(=O)—c-Pr | 167-168 |
| 89 | n-pentyl | Ph | OH | 100-102 |
| 90 | c-Pr | Ph | OH | 172-174 |
| 91 | —CH₂CH₂OCH₂CH₂OCH₃ | Ph | OH | 138-139 |
| 92 | Ph | c-pentyl | OH | * |
| 93 | n-Pr | 3-thienyl | OH | * |
| 94 | n-hex | Ph | OH | 95-97 |
| 95 | i-Pr | Ph | OH | 163-165 |
| 96 | —CH₂CH₂OCH₂CH₃ | Ph | OH | 129-131 |
| 97 (Ex. 10) | —CH₂CH₂OCH₃ | 3-thienyl | OH | 103-105 |
| 98 | —CH₂(tetrahydrofuran-2-yl) | 3-thienyl | OH | * |
| 99 | c-hex | 3-thienyl | OH | * |
| 100 | n-Pr | Ph(3-OMe) | OH | * |
| 101 | n-Pr | Ph(2-F) | OH | 136-138 |
| 102 | n-Pr | Ph(4-F) | OH | 100-103 |
| 103 | Bn | n-Pr | OH | * |
| 104 | —CH₂(Ph(3-OMe)) | n-Pr | OH | * |
| 105 | —CH₂(Ph(3-OCF₃)) | n-Pr | OH | * |
| 106 | Ph | c-hex | OH | * |
| 107 | —CH(CH₃)CH₂OCH₃ | Ph | OH | 122-123 |
| 108 | —CH₂CH₂OCH₃ | 2-thienyl | OH | * |
| 109 | —CH₂(tetrahydrofuran-2-yl) | 2-thienyl | OH | * |
| 110 | n-Pr | furan-2-yl | OH | * |
| 111 | —CH₂CH₂OCH₃ | furan-2-yl | OH | * |
| 112 | n-Pr | Ph(4-OMe) | OH | * |
| 113 (Ex. 7) | Ph | 3-pyridinyl | OH | ** |
| 114 | Ph | c-Bu | OH | * |
| 115 | Et | Ph(3-Me) | OH | * |
| 116 | n-Bu | Ph(3-Me) | OH | * |
| 117 | —CH₂CH₂OCH₃ | Ph(3-Me) | OH | * |
| 118 | —CH₂CH₂CH₂OCH₃ | Ph(3-Me) | OH | * |
| 119 | —CH₂CH₂OCH₃ | Ph(3,5-di-F) | OH | 154-178 |
| 120 | —CH₂CH₂CH₂OCH₃ | Ph(3,5-di-F) | OH | 139-140 |
| 121 | n-Bu | Ph(3,5-di-F) | OH | 144-145 |
| 122 | Et | Ph(3,5-di-F) | OH | 162-165 |
| 123 | —CH₂CH₂OCH₃ | Ph(3-F) | OH | * |
| 124 | Et | Ph(3-F) | OH | * |
| 125 | n-Bu | Ph(3-F) | OH | * |
| 126 | —CH₂CH₂CH₂OCH₃ | Ph(3-F) | OH | * |
| 127 | n-Pr | Ph(3-F) | OH | * |
| 128 (Ex. 11) | c-hex | Ph | OH | 160-163 ** |
| 129 | tetrahydropyran-4-yl | Ph | OH | * |
| 130 | c-heptyl | Ph | OH | * |
| 131 | c-pentyl | Ph | OH | * |
| 132 | Ph(4-F-3-Me) | Ph(3-Br) | OH | * |
| 133 | Ph(4-F-3-Me) | Ph(3-Cl) | OH | * |
| 134 | n-Pr | Ph(4-Br) | OH | * |
| 135 | n-Pr | 1-Me-pyrazol-3-yl | OH | * |
| 136 | —CH₂CH₂OCH₃ | 1-Me-pyrazol-3-yl | OH | * |
| 137 | Et | Ph(3-Br) | OH | 141-145 |
| 138 | n-Bu | Ph(3-Br) | OH | 112-113 |

INDEX TABLE A-continued

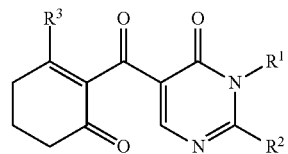

| Cmpd | R¹ | R² | R³ | m.p. (° C.) |
|---|---|---|---|---|
| 139 | —CH₂CH₂OCH₃ | Ph(3-Br) | OH | 115-116 |
| 140 | —CH₂CH₂CH₂OCH₃ | Ph(3-Br) | OH | 118-119 |
| 141 | n-Pr | Ph(3-Br) | OH | 134-137 |
| 142 | —CH₂(tetrahydrofuran-2-yl) | Ph(3-Cl) | OH | * |
| 143 | —CH₂CH₂CH₂OCH₃ | Ph(3-Cl) | OH | * |
| 144 | Ph(5-Cl-2-Me) | Ph(3-Br) | OH | * |
| 145 | Et | Ph(3-Cl) | OH | 114-115 |
| 146 | n-Bu | Ph(3-Cl) | OH | 104-112 |
| 147 | —CH₂CH₂OCH₃ | Ph(3-Cl) | OH | 124-125 |
| 148 | Ph(5-Cl-2-Me) | Ph(3-Cl) | OH | * |
| 149 | n-Pr | 1,4-benzodioxan-6-yl | OH | * |
| 150 | n-Pr | naphthalen-2-yl | OH | * |
| 151 | Ph(4-OMe) | Ph(3-Cl) | OH | 154-156 |
| 152 | n-Pr | Ph(3,5-di-F) | OH | * |
| 153 | n-Pr | c-Pr | OH | 163-165 |
| 154 | Ph(5-F-2-Me) | Ph(3-Br) | OH | * |
| 155 | n-Pr | Ph(3-CF₃) | OH | 129-131 |
| 156 | n-Pr | Ph(3,5-di-Me) | OH | 161-163 |
| 157 | Ph(5-F-2-Me) | Ph(3-Cl) | OH | * |
| 158 | Ph(4-Et) | Ph(3,5-di-F) | OH | 181-182 |
| 159 | Ph(2-Me) | Ph(3,5-di-F) | OH | 166-168 |
| 160 | c-hex | c-Pr | OH | 173-175 |
| 161 | Ph | Ph(3,5-di-F) | OH | 147-148 |
| 162 | Ph(4-Me) | Ph(3,5-di-F) | OH | 191-192 |
| 163 | —CH₂—c-hex | Ph(3,5-di-F) | OH | * |
| 164 | tetrahydrothiopyran-4-yl | Ph | OH | * |
| 165 | c-dodecahexyl | Ph | OH | * |
| 166 | Ph(4-F-2-Me) | Ph(3-Br) | OH | * |
| 167 | Ph(4-F-2-Me) | Ph(3-Cl) | OH | * |
| 168 (Ex. 8) | (cis/trans)-tetrahydro-1-oxido-2H-thiopyran-4-yl | Ph | OH | ** |
| 169 (Ex. 8) | (trans/cis)-tetrahydro-1-oxido-2H-thiopyran-4-yl | Ph | OH | ** |
| 170 | —CH₂C≡CH | Ph(3,5-di-F) | OH | * |
| 171 | —CH₂CH₂OCH₂CH₂OCH₃ | Ph(3,5-di-F) | OH | * |
| 172 | n-Pr | Ph(3-Me) | OH | 116-117 |
| 173 | n-Pr | Ph(3,5-di-Cl) | OH | 97-100 |
| 174 | Ph(4-Et) | Ph(3-Cl) | OH | 146-148 |
| 175 | Ph(4-Et) | Ph(3-Br) | OH | 126-129 |
| 176 | Ph(4-OMe) | Ph(3-Br) | OH | 120-124 |
| 177 | Ph(4-Et) | Ph(3-Br) | OH | 139-142 |
| 178 | Ph(5-F-2-Me) | Ph(3-Me) | OH | * |
| 179 | Ph(5-Cl-2-Me) | Ph(3,5-di-F) | OH | * |
| 180 | —CH₂(tetrahydrofuran-2-yl) | Ph(3,5-di-F) | OH | * |
| 181 | c-hex | Ph(3,5-di-F) | OH | * |
| 182 | —CH₂CH₂OCH₂CH₃ | Ph(3,5-di-F) | OH | * |
| 183 | Ph(5-F-2-Me) | Ph(3,5-di-F) | OH | * |
| 184 | Ph(5-Cl-2-Me) | Ph(3-F) | OH | * |
| 185 | c-hex | Ph(3-Me) | OH | * |
| 186 | tetrahydropyran-4-yl | 3-thienyl | OH | * |
| 187 | c-hex | Ph(3-F) | OH | * |
| 188 | c-hex | furan-2-yl | OH | * |
| 189 | c-hex | 2-thienyl | OH | * |
| 190 | n-Pr | Ph(3-Cl) | OH | 123-125 |
| 191 | Ph(4-F-3-Me) | Ph(3-F) | OH | * |
| 192 | Ph(4-F-2-Me) | Ph(3-Me) | OH | * |
| 193 | n-Bu | c-Pr | OH | 140-142 |
| 194 | c-hex | Ph(3-Et) | OH | * |
| 195 | c-hex | Ph(3-CF₃) | OH | * |
| 196 | c-hex | Ph(3-OMe) | OH | * |
| 197 | c-hex | Ph(4-F) | OH | * |
| 198 | c-hex | Ph(3,4-di-F) | OH | * |
| 199 | Ph | Ph(3-F) | OH | * |
| 200 | Et | Bn | OH | * |
| 201 | Ph(2-Me) | Ph(3-F) | OH | * |
| 202 | Ph(4-Me) | Ph(3-F) | OH | * |
| 203 | Ph(4-OMe) | Ph(3-F) | OH | * |
| 204 | Ph(4-Et) | Ph(3-F) | OH | * |
| 205 | c-hex | Ph(3,4,5-tri-F) | OH | * |

INDEX TABLE A-continued

| Cmpd | R¹ | R² | R³ | m.p. (° C.) |
|---|---|---|---|---|
| 206 | c-hex | Ph(3-Br) | OH | * |
| 207 | —CH₂CH₂CF₃ | Ph | OH | * |
| 208 | —CH₂CH₂CF₃ | Ph(3-F) | OH | 69-70 |
| 209 | Ph(2-Me) | Ph(3-Br) | OH | 144-146 |
| 210 | Ph(2-Me) | Ph(3-Me) | OH | 152-154 |
| 211 | Ph(4-Me) | Ph(3-Me) | OH | 146-148 |
| 212 | Ph(4-OMe) | Ph(3-Me) | OH | 156-158 |
| 213 | Ph(4-Et) | Ph(3-Me) | OH | 147-148 |
| 214 | —CH₂CH₂CHCH₂ | Ph | OH | 124-127 |
| 215 | c-octyl | Ph | OH | |
| 216 | c-hex | Ph(4-acetylene) | OH | * |
| 217 | Ph | n-Pr | OH | 145-147 |
| 218 | Ph(3,4-di-OMe) | Ph | OH | 164-165 |
| 219 | Ph(4-Et) | Ph | OH | 160-162 |
| 220 | Ph(3-Et) | Ph | OH | 126-127 |
| 255 | Ph(2-Et) | Ph | OH | 171-172 |
| 256 | Ph(2,4-diOMe) | Ph | OH | 182-183 |
| 257 | —CH₂CH₂CH₂CH₂CH₂— | | OH | * |

\* See Index Table J for M.S. or ¹H NMR data.
\*\* See synthesis examples for ¹H NMR data.

INDEX TABLE B

| Cmpd | R¹ | R² | R³ | m.p. (° C.) |
|---|---|---|---|---|
| 16 | Ph | Ph | OS(O)₂Ph(4-Me) | 63-65 |
| 20 (Ex. 3) | —CH₂Ph | Ph | OH | 56-57 ** |
| 21 (Ex. 4) | —CH₂Ph | Ph | OS(O)₂Ph(4-Me) | 52-53 ** |
| 221 | n-Pr | 2-thienyl | OH | * |

\* See Index Table J for M.S. or ¹H NMR data.
\*\* See synthesis example for ¹H NMR data.

INDEX TABLE C

| Cmpd | R¹ | R² | m.p. (° C.) |
|---|---|---|---|
| 222 | Ph(2,5-di-Me) | Ph | * |
| 223 (Ex. 6) | Ph | Ph | ** |

\* See Index Table J for M.S. or ¹H NMR data.
\*\* See synthesis examples for ¹H NMR data.

INDEX TABLE D

| Cmpd | R¹ | R² | R³ | m.p. (° C.) |
|---|---|---|---|---|
| 224 | n-Pr | Ph(3,5-di-F) | OH | * |
| 225 | Ph | Ph | OH | 125-127 |

\* See Index Table J for M.S. or ¹H NMR data.

INDEX TABLE E

| Cmpd | R¹ | R² | R³ | m.p. (° C.) |
|---|---|---|---|---|
| 226 | n-Pr | Ph | OH | * |
| 227 | n-Pr | 3-thienyl | OH | * |
| 228 | —CH₂CH₂OCH₃ | 3-thienyl | OH | * |
| 229 | —CH₂(tetrahydrofuran-2-yl) | 3-thienyl | OH | * |
| 230 | n-Pr | furan-2-yl | OH | * |
| 231 | Et | Ph(3-Me) | OH | * |
| 232 | n-Bu | Ph(3-Me) | OH | * |
| 233 | —CH₂CH₂OCH₃ | Ph(3-Me) | OH | * |
| 234 | Ph(3-F-2-Me) | Ph | OH | * |
| 235 | —CH₂CH₂OCH₃ | Ph(3-F) | OH | * |
| 236 | Et | Ph(3-F) | OH | * |
| 237 | n-Bu | Ph(3-F) | OH | * |
| 238 | —CH₂CH₂CH₂OCH₃ | Ph(3-F) | OH | * |
| 239 | Et | Ph | OH | * |

INDEX TABLE E-continued

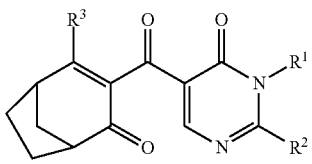

| Cmpd | R¹ | R² | R³ | m.p. (° C.) |
|---|---|---|---|---|
| 240 | n-Bu | Ph | OH | * |
| 241 | n-Pr | 1,4-benzodioxan-6-yl | OH | * |
| 242 | n-Pr | naphthalen-2-yl | OH | * |
| 243 (Ex. 9) | —CH₂CH₂OCH₃ | Ph(3,5-di-F) | OH | ** |
| 244 | —CH₂CH₂CH₂OCH₃ | Ph(3,5-di-F) | OH | * |
| 245 | n-Bu | Ph(3,5-di-F) | OH | * |
| 246 | Ph | Ph(3,5-di-F) | OH | 158-159 |
| 247 | c-dodecahexyl | Ph | OH | * |
| 248 | c-hex | Ph | OH | * |
| 249 | tetrahydropyran-4-yl | Ph | OH | * |
| 250 | —CH₂(tetrahydrofuran-2-yl) | Ph | OH | * |
| 251 | c-hex | Ph(3,4,5-tri-F) | OH | * |
| 252 | c-hex | Ph(3-Br) | OH | * |
| 253 | c-heptyl | Ph | OH | * |
| 254 | c-hex | Ph(4-acetylene) | OH | * |

\* See index table J for ¹H NMR.
\*\* See synthesis example for ¹H NMR data.

INDEX TABLE F

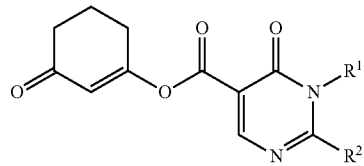

| Cmpd | R¹ | R² | m.p. (° C.) |
|---|---|---|---|
| 2Q (Ex. 1) | Ph | Ph | ** |
| 17Q (Ex. 2) | —CH₂Ph | Ph | ** |
| 23Q | —CH₂CH=CH₂ | Ph | * |
| 47Q (Ex. 5) | Ph(3-F-2-Me) | Ph | ** |
| 59Q | —CH₂(tetrahydrofuran-2yl) | Ph | * |
| 61Q | —CH₂C≡CH | Ph | * |
| 76Q | Ph | 2-furanyl | * |
| 84Q | —CH₂(Ph(3,4-di-OMe)) | n-Pr | * |
| 105Q | —CH₂(Ph(3-OCF₃)) | n-Pr | * |
| 113Q (Ex. 7) | Ph | 3-pyridinyl | ** |
| 153Q | n-Pr | c-Pr | * |
| 163Q | —CH₂—c-hex | Ph(3,5-di-F) | * |
| 212Q | Ph(4-OMe) | Ph(3-Me) | * |
| 257Q | —CH₂CH₂CH₂CH₂CH₂— | | * |

\* See Index Table J for MS or ¹H NMR data.
\*\* See synthesis examples for ¹H NMR data.

INDEX TABLE G

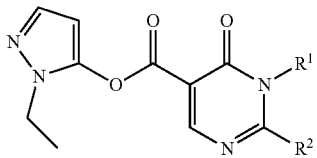

| Cmpd | R¹ | R² | m.p. (° C.) |
|---|---|---|---|
| 20Q (Ex. 3) | —CH₂Ph | Ph | ** |

\*\* See synthesis example for ¹H NMR data.

INDEX TABLE H

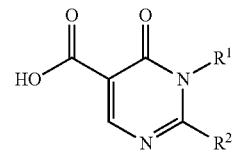

| Cmpd | R¹ | R² | m.p. (° C.) |
|---|---|---|---|
| 2R (Ex. 1) | Ph | Ph | ** |
| 17R (Ex. 2) | —CH₂Ph | Ph | ** |
| 23R | —CH₂CH=CH₂ | Ph | * |
| 47R (Ex. 5) | Ph(3-F-2-Me) | Ph | ** |
| 59R | —CH₂(tetrahydrofuran-2-yl) | Ph | * |
| 61R | —CH₂C≡CH | Ph | * |
| 76R | Ph | 2-furanyl | * |
| 84R | —CH₂(Ph(3,4-di-OMe)) | n-Pr | * |
| 105R | —CH₂(Ph(3-OCF₃)) | n-Pr | * |
| 97R (Ex. 10) | —CH₂CH₂OCH₃ | 3-thienyl | ** |
| 118R | —CH₂CH₂CH₂OCH₃ | Ph(3-Me) | * |
| 113R (Ex. 7) | Ph | 3-pyridinyl | ** |
| 135R | n-Pr | 1-Me-pyrazol-3-yl | * |
| 128R (Ex. 11) | c-hex | Ph | ** |
| 153R | n-Pr | c-Pr | * |
| 163R | —CH₂—c-hex | Ph(3,5-di-F) | * |
| 164R | tetrahydrothiopyran-4-yl | Ph | * |
| 186R | tetrahydropyran-4-yl | 3-thienyl | * |
| 212R | Ph(4-OMe) | Ph(3-Me) | * |
| 216R | c-hex | Ph(4-acetylene) | * |
| 242R | n-Pr | naphthalene-2-yl | * |
| 247R | c-dodecahexyl | Ph | * |
| 243R (Ex. 9) | —CH₂CH₂OCH₃ | Ph(3,5-di-F) | ** |
| 257R | —CH₂CH₂CH₂CH₂CH₂— | | * |

\* See Index Table J for MS or ¹H NMR data.
\*\* See synthesis examples for ¹H NMR data.

INDEX TABLE I

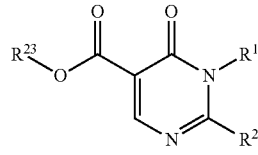

| Cmpd | R¹ | R² | R²³ | m.p. (° C.) |
|---|---|---|---|---|
| 2S (Ex. 1) | Ph | Ph | Et | ** |
| 17S (Ex. 2) | —CH₂Ph | Ph | Et | ** |
| 23S | —CH₂CH=CH₂ | Ph | Et | * |
| 59S | —CH₂(tetrahydrofuran-2-yl) | Ph | Et | * |
| 61S | —CH₂C≡CH | Ph | Et | * |
| 84S | —CH₂(Ph(3,4-di-OMe)) | n-Pr | Et | * |
| 105S | —CH₂(Ph(3-OCF₃)) | n-Pr | Et | * |
| 97S (Ex. 10) | —CH₂CH₂OCH₃ | 3-thienyl | Et | ** |
| 118S | —CH₂CH₂OCH₃ | Ph(3-Me) | Et | * |
| 113S (Ex. 7) | Ph | 3-pyridinyl | Et | ** |
| 135S | n-Pr | 1-Me-pyrazol-3-yl | Et | * |
| 128S (Ex. 11) | c-hex | Ph | Et | ** |
| 153S | n-Pr | c-Pr | Me | * |
| 163S | —CH₂—c-hex | Ph(3,5-di-F) | Et | * |
| 164S | tetrahydrothiopyran-4-yl | Ph | Et | * |
| 186S | tetrahydropyran-4-yl | 3-thienyl | Et | * |
| 212S | Ph(4-OMe) | Ph(3-Me) | Et | * |
| 216S | c-hex | Ph(4-acetylene) | Et | * |
| 242S | n-Pr | naphthalene-2-yl | Et | * |
| 247S | c-dodecahexyl | Ph | Et | * |
| 243S (Ex. 9) | —CH₂CH₂OCH₃ | Ph(3,5-di-F) | Et | ** |
| 257S | —CH₂CH₂CH₂CH₂CH₂— | | Et | * |

\* See Index Table J for MS or ¹H NMR data.
\*\* See synthesis examples for ¹H NMR data.

INDEX TABLE J

| Cmpd | Mass spectra data[a] or $^1$H NMR data[b] |
|---|---|
| 1 | 289 |
| 3 | 303 |
| 4 | 417 |
| 7 | 339 |
| 8 | 401 |
| 25 | 421 |
| 56 | 393 |
| 60 | 353 (ESI, M + 1) |
| 65 | 427 |
| 66 | 393 |
| 68 | 367 (ESI, M + 1) |
| 69 | (500 MHz) δ 16.38 (s, 1H), 8.14 (s, 1H), 7.45 (t, 1H), 7.34 (dd, 1H), 7.32-7.23 (m, 3H), 7.10-7.05 (m, 3H), 7.01-6.95 (m, 1H), 2.64 (t, 2H), 2.40 (t, 2H), 1.96 (dd, 2H). |
| 70 | 465 |
| 71 | 463 (AP, M − H) |
| 76 | 377 |
| 77 | 359 |
| 78 | 381 (ESI, M + H) |
| 84 | 425 (AP, M − H) |
| 86 | 367 |
| 87 | 351 (ESI, M + H) |
| 92 | 379 (ESI, M + H) |
| 93 | 359 |
| 98 | 401 |
| 99 | 399 |
| 100 | 381 (EST, M − H) |
| 103 | δ 16.41 (s, 1H), 8.09 (s, 1H), 7.42 (m, 3H), 7.21 (m, 2H), 5.29 (s, 2H), 2.79 (m, 2H), 2.77 (m, 2H), 2.65 (m, 2H), 2.15 (m, 2H), 1.75 (m, 2H), 0.94 (t, 3H). |
| 104 | δ 16.22 (s, 1H), 8.07 (s, 1H), 7.25 (m, 1H), 6.77 (m, 3H), 5.29 (s, 2H), 3.81 (s, 3H), 2.79 (m, 2H), 2.64 (m, 2H), 2.55 (m, 2H), 2.15 (m, 2H), 1.65 (m, 2H), 0.95 (t, 3H). |
| 105 | δ 16.41 (s, 1H), 8.06 (s, 1H), 7.41 (m, 1H), 7.14 (m, 3H), 5.32 (s, 2H), 2.81 (m, 2H), 2.62 (m, 2H), 2.52 (m, 2H), 2.15 (m, 2H), 1.81 (m, 2H), 0.95 (t, 3H). |
| 106 | 393 (ESI, M + H) |
| 108 | 375 |
| 109 | 401 |
| 110 | 343 |
| 111 | 359 |
| 112 | 382 |
| 114 | 365 (ESI, M + H) |
| 115 | 353 |
| 116 | 381 |
| 117 | 383 |
| 118 | 397 |
| 123 | 387 |
| 124 | 357 |
| 125 | 385 |
| 126 | 401 |
| 127 | δ 8.09 (s, 1H), 7.55-7.46 (m, 1H), 7.33-7.20 (m, 3H), 3.94-3.83 (m, 2H), 2.74 (t, 2H), 2.51 (t, 2H), 2.08 (quin, 2H), 1.63 (sxt, 2H), 0.78 (t, 3H). |
| 129 | 395 |
| 130 | 407 |
| 131 | 379 |
| 132 | 495 (AP, M − H) |
| 133 | 453 |
| 134 | 431 (ESI, M + H) |
| 135 | 357 |
| 136 | 373 |
| 142 | 429 |
| 143 | 417 |
| 144 | (500 MHz) δ 16.32 (br s, 1H), 8.22 (s, 1H), 7.55 (s, 1H), 7.46 (d, 1H), 7.25-7.06 (m, 5H), 2.70 (br s, 2H), 2.46 (d, 2H), 2.14 (s, 3H), 2.08-2.00 (m, 2H) |
| 148 | 469 |
| 149 | 411 |
| 150 | 403 |
| 152 | 389 |
| 154 | 497 |
| 157 | 453 |
| 163 | 443 |
| 164 | 411 |
| 165 | 477 |
| 166 | 495 (AP, M − H) |
| 167 | 453 |
| 170 | 385 |
| 171 | 449 |
| 178 | 433 |
| 179 | 471 |
| 180 | 431 |
| 181 | 429 |
| 182 | 419 |
| 183 | 455 |
| 184 | 453 |
| 185 | δ 16.65 (br s, 1H), 8.00 (s, 1H), 7.20-7.40 (m, 4H), 3.90-4.00 (m, 1H), 0.90-2.80 (m, 19H). |
| 186 | 401 |
| 187 | 411 |
| 188 | 383 |
| 189 | 399 |
| 191 | 437 |
| 192 | 433 |
| 194 | 421 |
| 195 | 461 |
| 196 | 423 |
| 197 | 411 |
| 198 | 429 |
| 199 | 403 (AP, M − H) |
| 200 | 353 |
| 201 | 417 (AP, M − H) |
| 202 | 417 (AP, M − H) |
| 203 | 433 (AP, M − H) |
| 204 | 431 (AP, M − H) |
| 205 | 447 |
| 206 | 471 |
| 207 | 405 (AP, M − H) |
| 215 | 421 |
| 216 | 417 |
| 221 | 359 |
| 222 | 412 |
| 224 | 417 |
| 226 | 379 |
| 227 | 385 |
| 228 | 401 |
| 229 | 427 |
| 230 | 369 |
| 231 | 379 |
| 232 | 407 |
| 233 | 409 |
| 234 | 445 |
| 235 | 413 |
| 236 | 383 |
| 237 | 411 |
| 238 | 427 |
| 239 | 365 |
| 240 | 393 |
| 241 | 437 |
| 242 | 429 |
| 244 | 445 |
| 245 | 429 |
| 247 | 503 |
| 248 | 419 |
| 249 | 421 |
| 250 | δ 16.75 (d, 1H), 8.09 (s, 1H), 7.53 (m, 2H), 7.49 (m, 3H), 4.35 (m, 3H), 3.85 (m, 1H), 3.61 (m, 1H), 3.31 (m, 1H), 3.15 (m, 1H), 2.95 (m, 1H), 2.20-1.20 (m, 9H). |
| 251 | 473 |
| 252 | 497 |
| 253 | 433 |
| 254 | 443 |
| 257 | δ 16.60 (s, 1H), 7.94 (s, 1H), 4.32 (m, 2H), 3.02 (m, 2H), 2.74 (m, 2H), 2.45 (m, 2H), 2.06 (m, 2H), 1.85 (m, 4H), 1.8 (m, 2H). |
| 23Q | δ 8.80 (s, 1H), 7.46-7.66 (m, 5H), 6.04 (m, 1H), 5.86-5.98 (m, 1H), 5.26 (m, 1H), 5.02 (m, 1H), 4.62 (m, 2H), 2.69 (m, 2H), 2.42 (m, 2H), 2.12 (m, 2H). |
| 59Q | δ 8.78 (s, 1H), 7.49-7.57 (m, 5H), 6.03 (s, 1H), 4.28-4.39 (m, 2H), 3.94 (m, 1H), 3.59 (m, 1H), 3.33 (m, 1H), 2.68 (m, 2H), 2.45 (m, 2H), 2.12 (m, 2H), 1.99 (m, 1H), 1.76 (m, 1H), 1.57-1.66 (m, 1H), 1.39 (m, 1H). |

INDEX TABLE J

| Cmpd | Mass spectra data[a] or ¹H NMR data[b] |
|---|---|
| 61Q | δ 8.81 (s, 1H), 7.77 (m, 2H), 7.57 (m, 3H), 6.04 (s, 1H), 4.69 (m, 2H), 2.69 (m, 2H), 2.46 (m, 3H), 2.12 (m, 2H). |
| 76Q | δ 8.91 (s, 1H), 7.60 (m, 3H), 7.56 (m, 1H), 7.28 (dd, 2H), 6.35 (dd, 1H), 6.03 (s, 1H), 5.75 (d, 1H), 2.66 (t, 2H), 2.44 (m, 2H), 2.09 (m, 2H). |
| 84Q | δ 8.71 (s, 1H), 6.80 (m, 2H), 6.78 (d, 1H), 6.01 (s, 1H), 5.34 (s, 2H), 3.86 (d, 6H), 2.8 (m, 2H), 2.75 (m, 2H), 2.45 (m, 2H), 2.20 (m, 2H), 1.80 (m, 2H), 1.00 (t, 3H). |
| 105Q | δ 8.74 (s, 1H), 7.40 (m, 1H), 7.20 (m, 1H), 7.15 (m. 1H), 7.00 (s, 1H), 6.00 (s, 1H), 5.40 (s, 2H), 2.78 (m, 2H), 2.72 (m, 2H), 2.40 (m, 2H), 2.15 (m, 2H), 1.80 (m, 2H), 0.94 (m, 3H). |
| 153Q | (300 MHz) δ 8.57 (s, 1H), 5.98 (s, 1H), 4.25-4.19 (m, 2H), 2.67-2.63 (m, 2H), 2.45-2.41 (m, 2H), 2.13-1.92 (m, 3H), 1.86-1.78 (m, 2H), 1.42-1.37 (m, 2H), 1.26-1.20 (m, 2H), 1.07-1.02 (m, 3H). |
| 163Q | (500 MHz) δ 8.72 (s, 1H), 7.13-6.95 (m, 3H), 6.03 (s, 1H), 3.98 (d, 2H), 2.69 (td, 2H), 2.53-2.39 (m, 2H), 2.12 (quin, 2H), 1.75 (ddt, 1H), 1.66-1.57 (m, 3H), 1.50-1.43 (m, 2H), 1.19-0.99 (m, 3H), 0.77-0.66 (m, 2H). |
| 212Q | δ 8.86 (s., 1H), 7.07-7.32 (m, 4H), 6.80-7.06 (m, 4H), 6.04 (s., 1H), 3.78 (s, 3H), 2.67 (m, 2H), 2.44 (m, 2H), 2.27 (s, 3H), 2.11 (m, 2H). |
| 257Q | δ 8.60 (s, 1H), 6.00 (s, 1H), 4.40 (m, 2H), 3.15 (m, 2H), 2.66 (m, 2H), 2.44 (m, 2H), 2.15 (m, 2H), 1.85 (m, 6H). |
| 23R | δ 9.03 (s, 1H), 7.42-7.76 (m, 5H), 5.82-6.04 (m, 1H), 5.42 (m, 1H), 5.04 (m, 1H), 4.72 (m, 2H). |
| 59R | δ 9.00 (s, 1H), 7.48-7.60 (m, 5H), 4.35 (m, 1H), 4.24-4.32 (m, 1H), 4.06 (m, 1H), 3.53-3.65 (m, 1H), 3.29-3.41 (m, 1H), 2.02 (m, 1H), 1.79 (m, 1H), 1.57-1.69 (m, 1H), 1.41 (m, 1H). |
| 61R | δ 13.02 (br s, 1H), 8.65 (s, 1H), 7.73 (m, 2H), 7.62 (m, 3H), 4.58 (m, 2H), 3.44 (m, 1H). |
| 76R | δ 12.64 (br s, 1H), 9.11 (s, 1H), 7.66 (m, 3H), 7.56 (d, 1H), 7.33 (m, 2H), 6.39 (dd, 1H), 5.93 (d, 1H). |
| 84R | δ 13.00 (br s, 1H), 8.92 (s, 1H), 6.80 (d, 1H), 6.79 (s, 1H), 6.85 (d, 1H), 5.34 (s, 2H), 3.87 (d, 6H), 2.80 (m, 2H), 1.80 (m, 2H), 1.01 (t, 3H). |
| 105R | δ 12.8 (br s, 1H), 8.94 (s, 1H), 7.45 (m, 1H), 7.25 (m, 1H), 7.15 (m, 1H), 7.05 (s, 1H), 5.41 (s, 2H), 2.77 (m, 2H), 1.88 (m, 2H), 0.99 (t, 3H). |
| 118R | δ 8.98 (s, 1H), 7.42 (m, 2H), 7.33 (m, 2H), 4.26 (m, 2H), 3.31 (t, 3H), 3.16 (s, 3H), 2.45 (s, 3H), 1.95 (m, 3H). |
| 135R | δ 13.33 (s, 1H), 8.95 (s, 1H), 7.50 (d, 1H), 7.11 (d, 1H), 4.69 (m, 2H), 4.04 (s, 3H), 1.86 (m, 2H), 1.01 (t, 3H). |
| 153R | (300 MHz) δ 13.15 (br s, 1H), 8.76 (s, 1H), 4.31-4.25 (m, 2H), 2.04-1.99 (m, 1H), 1.90-1.80 (m, 2H), 1.45-1.41 (m, 2H), 1.31-1.25 (m, 2H), 1.09 (t, 3H). |
| 163R | (500 MHz) δ 12.77 (br s, 1H), 7.19-6.94 (m, 3H), 4.08 (d, 2H), 1.86-1.52 9m, 4H), 1.44 (d, 2H), 1.22-0.95 (m, 3H), 0.82-0.63 (m, 2H). |
| 164R | δ 13.12 (br s, 1H), 8.95 (s, 1H), 7.59 (m, 3H), 7.46 (m, 2H), 4.09 (s, 1H), 3.08 (d, 2H), 2.69 (d, 2H), 2.46 (m, 2H), 2.05 (m, 2H). |
| 186R | δ 13.12 (br s, 1H), 8.93 (s, 1H), 7.83 (m, 1H), 7.58 (m, 1H), 7.29 (m, 1H), 4.56 (m, 1H), 4.09 (m, 2H), 3.26 (m, 2H), 3.12 (m, 2H), 1.67 (m, 2H). |
| 212R | δ 9.09 (s, 1H), 6.98-7.21 (m, 6H), 6.90 (d, 2H), 3.81 (s, 3H), 2.28 (s, 3H). |
| 216R | δ 13.25 (br s, 1H), 8.93 (s, 1H), 7.67 (m, 2H), 7.48 (m, 2H), 4.06 (m, 1H), 3.28 (s, 1H), 2.68 (dd, 2H), 1.85 (d, 2H), 1.73 (d, 2H), 1.63 (m, 1H), 1.24 (m, 1H), 1.05 (m, 2H). |
| 242R | δ 13.14 (br s, 1H), 9.03 (s, 1H), 8.05 (m, 2H), 7.96 (d, 2H), 7.65 (ddd, 2H), 7.56 (dd, 1H), 4.14 (m, 2H), 1.75 (m, 2H), 0.80 (t, 3H). |
| 247R | δ 13.26 (br s, 1H), 8.96 (s, 1H), 7.57 (m, 3H), 7.46 (m, 2H), 4.45 (m, 1H), 2.32 (m, 2H), 1.99 (m, 2H), 1.18 (m, 15H), 0.69 (m, 3H). |
| 257R | δ 13.00 (br s, 1H), 8.75 (m, 1H), 4.42 (m, 2H), 3.10 (m, 2H), 1.82 (m, 6H) |
| 23S | δ 8.70 (s, 1H), 7.49-7.53 (m, 5H), 5.85-5.97 (m, 1H), 5.25 (m, 1H), 4.95 (m, 1H), 4.59 (m, 2H), 4.41 (m, 2H), 1.40 (m, 3H). |
| 59S | δ 8.68 (s, 1H), 7.46-7.55 (m, 5H), 4.40 (m, 2H), 4.28-4.35 (m, 2H), 3.88 (m, 1H), 3.58 (m, 1H), 3.31 (m, 1H), 1.91-2.02 (m, 1H), 1.52-1.81 (m, 4H), 1.39 (m, 3H). |
| 61S | δ 8.72 (s, 1H), 7.76 (m, 2H), 7.55 (m, 3H), 4.66 (m, 2H), 4.42 (m, 2H), 2.41 (s, 1H), 1.42 (m, 3H). |
| 84S | δ 8.62 (s, 1H), 6.81 (m, 2H), 6.70 (m, 1H), 5.29 (s, 2H), 4.39 (q, 2H), 3.86 (d, 6H), 2.76 (t, 2H), 1.73 (m, 2H), 1.40 (t, 3H), 0.98 (t, 3H). |
| 105S | δ 8.64 (s, 1H), 7.42 (m, 1H), 7.20 (m, 1H), 7.18 (m, 1H), 7.00 (s, 1H), 5.34 (s, 2H), 4.39 (m, 2H), 2.65 (m, 2H), 1.75 (m, 2H), 1.40 (m, 3H), 0.95 (t, 3H). |
| 118S | δ 8.66 (s, 1H), 7.38 (m, 2H), 7.29 (m, 2H), 4.40 (m, 2H), 4.11 (m, 2H), 3.30 (t, 2H), 3.15 (s, 3H), 2.43 (s, 3H), 1.93 (m, 2H), 1.40 (t, 3H). |
| 135S | δ 8.68 (s, 1H), 7.47 (d, 1H), 6.98 (d, 1H), 4.53 (m, 2H), 4.39 (q, 2H), 4.02 (s, 3H), 1.82 (m, 2H), 1.39 (t, 3H), 0.96 (t, 3H). |
| 153S | (300 MHz) δ 8.51 (s, 1H), 4.23-4.18 (m, 2H), 3.88 (s, 3H), 1.99-1.95 (m, 1H), 1.85-1.77 (m, 2H), 1.36-1.32 (m, 2H), 1.21-1.17 (m, 2H), 1.03 (t, 3H). |
| 163S | (500 MHz) δ 8.62 (s, 1H), 7.06-6.98 (m, 3H), 4.40 (q, 2H), 3.95 (d, 2H), 1.80-1.70 (m, 1H), 1.66-1.55 (m, 3H), 1.46 (d, 2H), 1.40 (t, 3H), 1.17-0.96 (m, 3H), 0.70 (dd, 2H). |
| 164S | δ 8.59 (s, 1H), 7.55 (m, 3H), 7.42 (m, 2H), 4.40 (q, 2H), 3.92 (m, 1H), 3.10 (d, 2H), 2.64 (d, 2H), 2.41 (m, 2H), 1.98 (m, 2H), 1.40 (t, 3H). |
| 186S | δ 8.57 (s, 1H), 7.71 (m, 1H), 7.52 (m, 1H), 7.24 (m, 1H), 4.39 (m, 3H), 4.04 (d, 2H), 3.17 (m, 4H), 1.58 (m, 3H), 1.39 (t, 3H). |
| 212S | δ 8.80 (s, 1H), 7.14-7.25 (m, 1H), 6.95-7.18 (m, 5H), 6.82-6.92 (m, 2H), 3.94 (s, 3H), 3.78 (s, 3H), 2.26 (s, 3H). |
| 216S | δ 8.57 (s, 1H), 7.64 (m, 2H), 7.43 (m, 2H), 4.40 (q, 2H), 3.89 (m, 1H), 3.24 (s, 1H), 2.75 (dd, 2H), 1.78 (d, 2H), 1.63 (m, 3H), 1.55 (d, 1H), 1.39 (t, 3H), 0.99 (m, 2H). |
| 242S | δ 8.71 (s, 1H), 7.99 (m, 2H), 7.93 (d, 2H), 7.62 (m, 2H), 7.53 (dd, 1H), 4.42 (q, 2H), 4.01 (m, 2H), 1.71 (m, 2H), 1.42 (t, 3H), 0.75 (t, 3H). |
| 247S | δ 8.60 (s, 1H), 7.51 (m, 3H), 7.42 (m, 2H), 4.39 (q, 2H), 4.12 (m, 1H), 2.32 (m, 2H), 1.98 (m, 2H), 1.39 (t, 3H), 1.18 (m, 12H), 1.02 (m, 3H), 0.66 (m, 3H). |
| 257S | δ 8.47 (s, 1H), 4.34 (m, 4H), 3.02 (m, 2H), 1.82 (m, 6H), 1.36 (m, 3H). |

[a]Mass spectra are reported as the molecular weight of the highest isotopic abundance parent ion (M + 1) formed by addition of H⁺ (molecular weight of 1) to the molecule, observed by mass spectrometry using atmospheric pressure chemical ionization (AP⁺) unless otherwise noted.
[b]¹H NMR data are reported in CDCl₃ at 400 MHz unless otherwise noted; s means singlet, br s means broad singlet, d means doublet, dd means doublet of doublet, ddd means doublet of double of doublets, ddt means doublet of doublet of triplets, t means triplet, td means triplet of doublets, q means quartet, quin means quintet and sxt means sextet.

Biological Examples of the Invention

Test A

Seeds of barnyardgrass (*Echinochloa crus-galli*), large crabgrass (*Digitaria sanguinalis*), giant foxtail (*Setaria faberii*), morning glory (*Ipomoea* spp.), pigweed (*Amaranthus retroflexus*), velvetleaf (*Abutilon theophrasti*), wheat (*Triticum aestivum*) and corn (*Zea mays*) were planted into a blend of loam soil and sand and treated preemergence with a directed soil spray using test chemicals formulated in a non-phytotoxic solvent mixture which included a surfactant. At the same time these species were also treated with postemergence applications of test compounds formulated in the same manner.

Plants ranged in height from two to ten cm and were in the one- to two-leaf stage for the postemergence treatment. Treated plants and untreated controls were maintained in a greenhouse for approximately ten days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compound 217 |
|---|---|
| Postemergence | |
| Barnyardgrass | 90 |
| Corn | 40 |
| Crabgrass, Large | 100 |
| Foxtail, Giant | 80 |
| Morningglory | 100 |
| Pigweed | 100 |
| Velvetleaf | 100 |
| Wheat | 40 |

| 500 g ai/ha | \multicolumn{13}{c}{Compounds} |||||||||||||
|---|---|---|---|---|---|---|---|---|---|---|---|---|---|
|  | 1 | 2 | 3 | 4 | 7 | 8 | 9 | 10 | 11 | 12 | 13 | 14 | 15 | 16 |
| Postemergence | | | | | | | | | | | | | | |
| Barnyardgrass | 60 | 100 | 90 | 100 | 70 | 100 | 100 | 90 | 100 | 90 | 90 | 80 | 40 | 60 |
| Corn | 0 | 90 | 10 | 50 | 40 | 50 | 70 | 90 | 20 | 80 | 50 | 20 | 10 | 20 |
| Crabgrass, Large | 80 | 100 | 90 | 90 | 70 | 90 | 90 | 100 | 90 | 100 | 90 | 90 | 70 | 40 |
| Foxtail, Giant | 40 | 100 | 60 | 90 | 60 | 100 | 90 | 100 | 90 | 90 | 80 | 90 | 70 | 70 |
| Morningglory | 90 | 100 | 90 | 100 | 100 | 100 | 90 | 100 | 90 | 100 | 50 | 100 | 50 | 20 |
| Pigweed | 80 | 100 | 100 | 100 | 100 | 100 | 100 | 100 | 100 | 100 | 100 | 100 | 90 | 70 |
| Velvetleaf | 100 | 100 | 100 | 100 | 100 | 100 | 100 | 100 | 100 | 100 | 100 | 100 | 100 | 100 |
| Wheat | 20 | 20 | 10 | 60 | 40 | 50 | 40 | 60 | 0 | 0 | 60 | 0 | 20 | 10 |

| 500 g ai/ha | | | | | | Compounds | | | | | | | | |
|---|---|---|---|---|---|---|---|---|---|---|---|---|---|---|
|  | 17 | 18 | 19 | 20 | 21 | 22 | 23 | 24 | 25 | 26 | 27 | 28 | 29 | 30 |
| Postemergence | | | | | | | | | | | | | | |
| Barnyardgrass | 70 | 90 | 70 | 10 | 10 | 70 | 60 | 70 | 90 | 80 | 90 | 90 | 90 | 30 |
| Corn | 10 | 20 | 10 | 10 | 0 | 40 | 0 | 30 | 20 | 20 | 30 | 0 | 10 | 0 |
| Crabgrass, Large | 70 | 80 | 20 | 10 | 10 | 80 | 60 | 90 | 90 | 90 | 100 | 80 | 90 | 60 |
| Foxtail, Giant | 30 | 90 | 50 | 0 | 0 | 80 | 50 | 90 | 90 | 90 | 90 | 80 | 90 | 40 |
| Morningglory | 70 | 100 | 60 | 10 | 0 | 100 | 100 | 100 | 90 | 80 | 70 | 10 | 90 | 50 |
| Pigweed | 100 | 100 | 100 | 50 | 50 | 100 | 100 | 100 | 100 | 100 | 100 | 100 | 100 | 80 |
| Velvetleaf | 100 | 100 | 100 | 70 | 70 | 100 | 100 | 100 | 100 | 100 | 100 | 100 | 100 | — |
| Wheat | 10 | 50 | 0 | 0 | 0 | 0 | 0 | 30 | 0 | 0 | 0 | 0 | 0 | 0 |

| 500 g ai/ha | | | | | | Compounds | | | | | | | |
|---|---|---|---|---|---|---|---|---|---|---|---|---|---|
|  | 31 | 32 | 33 | 34 | 35 | 36 | 37 | 38 | 39 | 40 | 41 | 42 | 43 | 44 |
| Postemergence | | | | | | | | | | | | | | |
| Barnyardgrass | 80 | 80 | 100 | 100 | 60 | 100 | 90 | 90 | 90 | 90 | 90 | 90 | 90 | 100 |
| Corn | 20 | 10 | 20 | 30 | 10 | 60 | 40 | 60 | 40 | 50 | 10 | 30 | 50 | 40 |
| Crabgrass, Large | 90 | 90 | 100 | 100 | 80 | 100 | 100 | 100 | 90 | 100 | 70 | 80 | 90 | 90 |
| Foxtail, Giant | 90 | 90 | 100 | 100 | 80 | 100 | 90 | 90 | 90 | 100 | 80 | 70 | 80 | 90 |
| Morningglory | 70 | 100 | 90 | 100 | 80 | 100 | 100 | 100 | 90 | 100 | 70 | 80 | 80 | 90 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 0 | 30 | 20 | 30 | 0 | 0 | 0 | 40 | 0 | 0 | 0 | 0 | 0 | 20 |

| 500 g ai/ha | | | | | | Compounds | | | | | | | |
|---|---|---|---|---|---|---|---|---|---|---|---|---|---|
|  | 45 | 46 | 47 | 48 | 49 | 50 | 51 | 52 | 53 | 54 | 55 | 56 | 57 | 58 |
| Postemergence | | | | | | | | | | | | | | |
| Barnyardgrass | 100 | 90 | 100 | 90 | 90 | 100 | 90 | 90 | 100 | 60 | 70 | 90 | 90 | 90 |
| Corn | 20 | 20 | 70 | 30 | 20 | 30 | 80 | 70 | 80 | 10 | 10 | 50 | 40 | 20 |
| Crabgrass, Large | 90 | 90 | 100 | 100 | 90 | 90 | 100 | 100 | 100 | 70 | 90 | 90 | 90 | 90 |
| Foxtail, Giant | 90 | 90 | 100 | 100 | 80 | 90 | 90 | 100 | 90 | 60 | 60 | 90 | 90 | 90 |
| Morningglory | 100 | 70 | 100 | 100 | 100 | 80 | 100 | 100 | 100 | 90 | 100 | 60 | 100 | 100 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 40 | 0 | 0 | 20 | 0 | 0 | 0 | 40 | 50 | 0 | 0 | 0 | 10 | 0 |

TABLE A-continued

| 500 g ai/ha | Compounds | | | | | | | | | | | | | |
|---|---|---|---|---|---|---|---|---|---|---|---|---|---|---|
| | 59 | 60 | 61 | 62 | 63 | 64 | 65 | 66 | 67 | 68 | 69 | 70 | 71 | 72 |
| Postemergence | | | | | | | | | | | | | | |
| Barnyardgrass | 90 | 90 | 90 | 90 | 90 | 90 | 50 | 90 | 90 | 90 | 100 | 80 | 60 | 90 |
| Corn | 30 | 10 | 10 | 70 | 50 | 60 | 0 | 60 | 10 | 10 | 40 | 20 | 20 | 10 |
| Crabgrass, Large | 100 | 100 | 90 | 90 | 90 | 90 | 60 | 90 | 90 | 100 | 100 | 90 | 80 | 90 |
| Foxtail, Giant | 90 | 90 | 80 | 90 | 80 | 80 | 40 | 80 | 60 | 70 | 90 | 90 | 60 | 60 |
| Morningglory | 100 | 90 | 100 | 100 | 100 | 100 | 60 | 90 | 100 | 90 | 100 | 100 | 100 | 90 |
| Pigweed | 100 | 100 | 100 | 100 | 100 | 100 | 60 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 10 | 50 | 0 | 20 | 0 | 30 | 0 | 0 | 30 | 0 | 10 | 0 | 0 | 0 |

| 500 g ai/ha | Compounds | | | | | | | | | | | | | |
|---|---|---|---|---|---|---|---|---|---|---|---|---|---|---|
| | 73 | 74 | 75 | 76 | 77 | 78 | 79 | 80 | 81 | 82 | 83 | 84 | 85 | 86 |
| Postemergence | | | | | | | | | | | | | | |
| Barnyardgrass | 90 | 90 | 90 | 80 | 90 | 70 | 90 | 80 | 100 | 70 | 90 | 10 | 90 | 90 |
| Corn | 60 | 20 | 50 | 20 | 20 | 20 | 60 | 50 | 70 | 20 | 30 | 20 | 80 | 50 |
| Crabgrass, Large | 90 | 90 | 90 | 90 | 80 | 70 | 90 | 90 | 90 | 90 | 90 | 10 | 90 | 90 |
| Foxtail, Giant | 90 | 80 | 90 | 70 | 70 | 50 | 80 | 90 | 90 | 80 | 90 | 0 | 90 | 90 |
| Morningglory | 100 | 100 | 100 | 90 | 100 | 100 | 100 | 100 | 100 | 100 | 100 | 90 | 100 | 90 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 50 | 20 | 50 | 10 | 0 | 0 | 50 | 0 | 30 | 0 | 0 | 0 | 40 | 50 |

| 500 g ai/ha | Compounds | | | | | | | | | | | | | |
|---|---|---|---|---|---|---|---|---|---|---|---|---|---|---|
| | 87 | 88 | 89 | 90 | 91 | 92 | 93 | 94 | 95 | 96 | 97 | 98 | 99 | 100 |
| Postemergence | | | | | | | | | | | | | | |
| Barnyardgrass | 90 | 90 | 90 | 90 | 100 | 90 | 90 | 90 | 90 | 90 | 90 | 90 | 90 | 90 |
| Corn | 50 | 60 | 10 | 20 | 10 | 20 | 30 | 10 | 10 | 20 | 80 | 60 | 20 | 0 |
| Crabgrass, Large | 90 | 90 | 100 | 90 | 100 | 90 | 100 | 90 | 90 | 100 | 100 | 100 | 100 | 90 |
| Foxtail, Giant | 90 | 90 | 90 | 80 | 80 | 90 | 90 | 80 | 90 | 90 | 80 | 90 | 90 | 90 |
| Morningglory | 100 | 100 | 100 | 100 | 100 | 100 | 100 | 100 | 100 | 100 | 100 | 100 | 100 | 100 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 60 | 0 | 20 | 40 | 50 | 0 | 0 | 0 | 0 | 20 | 20 | 20 | 0 | 30 |

| 500 g ai/ha | Compounds | | | | | | | | | | | | | |
|---|---|---|---|---|---|---|---|---|---|---|---|---|---|---|
| | 101 | 102 | 103 | 104 | 105 | 106 | 107 | 108 | 109 | 110 | 111 | 112 | 113 | 114 |
| Postemergence | | | | | | | | | | | | | | |
| Barnyardgrass | 90 | 90 | 60 | 40 | 50 | 50 | 90 | 90 | 90 | 90 | 90 | 90 | 90 | 90 |
| Corn | 10 | 20 | 20 | 0 | 10 | 10 | 50 | 40 | 30 | 10 | 30 | 20 | 60 | 50 |
| Crabgrass, Large | 90 | 100 | 40 | 0 | 70 | 70 | 90 | 90 | 100 | 90 | 90 | 90 | 100 | 90 |
| Foxtail, Giant | 80 | 90 | 20 | 0 | 20 | 60 | 90 | 90 | 90 | 50 | 90 | 80 | 100 | 80 |
| Morningglory | 70 | 100 | 100 | 100 | 80 | 100 | 100 | 100 | 100 | 100 | 100 | 100 | 100 | 100 |
| Pigweed | 100 | 100 | 100 | 100 | 100 | 100 | 100 | 100 | 100 | 100 | 100 | 100 | 100 | 100 |
| Velvetleaf | 100 | 100 | 100 | 80 | 100 | 100 | 100 | 100 | 100 | 100 | 100 | 100 | 100 | 100 |
| Wheat | 0 | 10 | 0 | 0 | 0 | 0 | 10 | 0 | 0 | 0 | 0 | 10 | 60 | 0 |

| 500 g ai/ha | Compounds | | | | | | | | | | | | | |
|---|---|---|---|---|---|---|---|---|---|---|---|---|---|---|
| | 115 | 116 | 117 | 118 | 119 | 120 | 121 | 122 | 123 | 124 | 125 | 126 | 127 | 128 |
| Postemergence | | | | | | | | | | | | | | |
| Barnyardgrass | 90 | 100 | 90 | 90 | 90 | 90 | 100 | 80 | 90 | 90 | 90 | 90 | 90 | 100 |
| Corn | 20 | 10 | 50 | 30 | 70 | 50 | 40 | 30 | 70 | 20 | 20 | 60 | 20 | 60 |
| Crabgrass, Large | 90 | 80 | 100 | 90 | 90 | 100 | 100 | 90 | 90 | 90 | 90 | 90 | 90 | 90 |
| Foxtail, Giant | 80 | 90 | 80 | 90 | 90 | 90 | 90 | 80 | 80 | 70 | 90 | 80 | 80 | 90 |
| Morningglory | 100 | 100 | 100 | 100 | 100 | 100 | 100 | 100 | 100 | 80 | 100 | 100 | 100 | 100 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 0 | 0 | 30 | 10 | 60 | 70 | 60 | 50 | 20 | 0 | 10 | 20 | 0 | 20 |

TABLE A-continued

| 500 g ai/ha | Compounds | | | | | | | | | | | | | |
|---|---|---|---|---|---|---|---|---|---|---|---|---|---|---|
| | 129 | 130 | 131 | 132 | 133 | 134 | 135 | 136 | 138 | 139 | 140 | 141 | 142 | 143 |
| Postemergence | | | | | | | | | | | | | | |
| Barnyardgrass | 100 | 100 | 90 | 90 | 90 | 60 | 30 | 80 | 90 | 80 | 90 | 90 | 90 | 90 |
| Corn | 50 | 50 | 30 | 40 | 40 | 20 | 0 | 0 | 20 | 40 | 20 | 30 | 20 | 20 |
| Crabgrass, Large | 90 | 100 | 90 | 70 | 100 | 80 | 70 | 90 | 90 | 80 | 90 | 90 | 90 | 90 |
| Foxtail, Giant | 90 | 90 | 90 | 70 | 90 | 70 | 0 | 50 | 90 | 80 | 90 | 90 | 80 | 80 |
| Morningglory | 100 | 100 | 100 | 90 | 70 | 60 | 90 | 100 | 100 | 100 | 100 | 100 | 100 | 100 |
| Pigweed | 100 | 100 | 100 | 90 | 100 | 80 | 90 | 100 | 100 | 100 | 100 | 100 | 100 | 90 |
| Velvetleaf | 100 | 100 | 100 | 100 | 100 | 100 | 100 | 100 | 100 | 100 | 100 | 100 | 100 | 100 |
| Wheat | 20 | 30 | 0 | 30 | 40 | 0 | 0 | 0 | 20 | 40 | 0 | 0 | 20 | 10 |

| 500 g ai/ha | Compounds | | | | | | | | | | | | | |
|---|---|---|---|---|---|---|---|---|---|---|---|---|---|---|
| | 144 | 145 | 146 | 147 | 148 | 149 | 150 | 151 | 152 | 153 | 154 | 155 | 156 | 157 |
| Postemergence | | | | | | | | | | | | | | |
| Barnyardgrass | 100 | 100 | 100 | 90 | 100 | 90 | 80 | 90 | 100 | 90 | 90 | 100 | 90 | 100 |
| Corn | 30 | 40 | 30 | 30 | 60 | 30 | 0 | 10 | 50 | 20 | 10 | 40 | 20 | 30 |
| Crabgrass, Large | 90 | 90 | 90 | 90 | 90 | 70 | 50 | 70 | 100 | 90 | 100 | 90 | 80 | 100 |
| Foxtail, Giant | 90 | 80 | 90 | 80 | 90 | 80 | 70 | 70 | 100 | 80 | 90 | 90 | 90 | 100 |
| Morningglory | 70 | 90 | 90 | 100 | 100 | 100 | 100 | 100 | 100 | 60 | 70 | 100 | 100 | 30 |
| Pigweed | 90 | 100 | 100 | 100 | 100 | 100 | 60 | 100 | 100 | 100 | 100 | 100 | 100 | 100 |
| Velvetleaf | 100 | 100 | 100 | 100 | 100 | 100 | 90 | 100 | 100 | 100 | 100 | 100 | 100 | 100 |
| Wheat | 0 | 0 | 50 | 60 | 0 | 50 | 20 | 20 | 70 | 10 | 0 | 30 | 20 | 0 |

| 500 g ai/ha | Compounds | | | | | | | | | | | | | |
|---|---|---|---|---|---|---|---|---|---|---|---|---|---|---|
| | 158 | 159 | 160 | 161 | 162 | 163 | 164 | 165 | 166 | 167 | 168 | 169 | 170 | 171 |
| Postemergence | | | | | | | | | | | | | | |
| Barnyardgrass | 90 | 100 | 100 | 90 | 100 | 100 | 100 | 80 | 100 | 100 | 100 | 100 | 90 | 90 |
| Corn | 50 | 70 | 60 | 10 | 50 | 20 | 50 | 30 | 40 | 30 | 30 | 30 | 30 | 40 |
| Crabgrass, Large | 100 | 90 | 90 | 90 | 100 | 90 | 100 | 50 | 90 | 90 | 90 | 100 | 90 | 90 |
| Foxtail, Giant | 90 | 100 | 80 | 90 | 100 | 50 | 100 | 30 | 90 | 90 | 90 | 100 | 80 | 90 |
| Morningglory | 100 | 100 | 100 | 100 | 100 | 100 | 100 | 100 | — | 100 | 100 | 100 | 100 | 100 |
| Pigweed | 100 | 100 | 100 | 100 | 100 | 100 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 50 | 60 | 50 | 0 | 50 | 0 | 20 | 0 | 0 | 0 | 50 | 20 | 20 | 50 |

| 500 g ai/ha | Compounds | | | | | | | | | | | | | |
|---|---|---|---|---|---|---|---|---|---|---|---|---|---|---|
| | 172 | 173 | 174 | 175 | 176 | 177 | 178 | 179 | 180 | 181 | 182 | 183 | 184 | 185 |
| Postemergence | | | | | | | | | | | | | | |
| Barnyardgrass | 90 | 100 | 100 | 100 | 90 | 100 | 90 | 90 | 100 | 100 | 90 | 90 | 100 | 90 |
| Corn | 30 | 20 | 20 | 20 | 10 | 0 | 70 | 80 | 40 | 50 | 20 | 80 | 80 | 50 |
| Crabgrass, Large | 80 | 90 | 90 | 80 | 60 | 70 | 80 | 100 | 100 | 90 | 90 | 100 | 100 | 70 |
| Foxtail, Giant | 90 | 90 | 60 | 80 | 70 | 40 | 80 | 90 | 100 | 100 | 80 | 100 | 100 | 80 |
| Morningglory | 100 | 100 | 60 | 80 | 50 | 10 | 100 | 100 | 100 | 100 | 100 | 70 | 100 | 100 |
| Pigweed | 100 | 100 | 100 | 100 | 100 | 100 | 80 | 100 | 100 | 100 | 100 | 100 | 100 | 100 |
| Velvetleaf | 100 | 100 | 100 | 100 | 90 | 100 | 100 | 100 | 100 | 100 | 100 | 100 | 100 | 100 |
| Wheat | 20 | 60 | 0 | 0 | 0 | 0 | 30 | 80 | 30 | 60 | 50 | 80 | 50 | 0 |

| 500 g ai/ha | Compounds | | | | | | | | | | | | | |
|---|---|---|---|---|---|---|---|---|---|---|---|---|---|---|
| | 186 | 187 | 188 | 189 | 190 | 191 | 192 | 193 | 194 | 195 | 196 | 197 | 198 | 199 |
| Postemergence | | | | | | | | | | | | | | |
| Barnyardgrass | 90 | 100 | 90 | 90 | 100 | 100 | 90 | 100 | 100 | 90 | 90 | 100 | 100 | 100 |
| Corn | 60 | 50 | 10 | 40 | 0 | 50 | 40 | 40 | 10 | 20 | 40 | 50 | 30 | 50 |
| Crabgrass, Large | 90 | 100 | 90 | 90 | 90 | 100 | 80 | 100 | 90 | 90 | 90 | 100 | 100 | 100 |
| Foxtail, Giant | 90 | 90 | 80 | 90 | 90 | 100 | 70 | 100 | 50 | 70 | 100 | 100 | 90 | 100 |
| Morningglory | 100 | 100 | 100 | 100 | 100 | 100 | 70 | 100 | 100 | — | 100 | 100 | 100 | 100 |
| Pigweed | 100 | 100 | 100 | 100 | 100 | 90 | 80 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 0 | 0 | 0 | 0 | 0 | 50 | 0 | 70 | 0 | 0 | 30 | 0 | 0 | 10 |

TABLE A-continued

| 500 g ai/ha | 200 | 202 | 203 | 204 | 205 | 206 | 207 | 208 | 209 | 210 | 211 | 212 | 213 | 214 |
|---|---|---|---|---|---|---|---|---|---|---|---|---|---|---|
| Postemergence | | | | | | | | | | | | | | |
| Barnyardgrass | 10 | 100 | 100 | 100 | 100 | 100 | 90 | 90 | 100 | 90 | 100 | 100 | 100 | 90 |
| Corn | 0 | 30 | 30 | 10 | 20 | 0 | 30 | 20 | 40 | 0 | 20 | 0 | 20 | 30 |
| Crabgrass, Large | 10 | 100 | 70 | 100 | 90 | 100 | 90 | 80 | 100 | 30 | 80 | 30 | 50 | 90 |
| Foxtail, Giant | 10 | 100 | 80 | 100 | 90 | 90 | 90 | 80 | 100 | 70 | 80 | 40 | 40 | 90 |
| Morningglory | 60 | 100 | 100 | 100 | 100 | 100 | 80 | 100 | 100 | 100 | 100 | 100 | 100 | 100 |
| Pigweed | 80 | 100 | 100 | 100 | 100 | 100 | 100 | 90 | 100 | 100 | 90 | 100 | 100 | 100 |
| Velvetleaf | 100 | 100 | 100 | 100 | 100 | 100 | 100 | 100 | 100 | 70 | 70 | 70 | 60 | 100 |
| Wheat | 0 | 50 | 30 | 40 | 10 | 0 | 0 | 10 | 0 | 10 | 0 | 0 | 0 | 20 |

| 500 g ai/ha | 215 | 216 | 218 | 219 | 220 | 221 | 222 | 223 | 224 | 225 | 226 | 227 | 228 | 229 |
|---|---|---|---|---|---|---|---|---|---|---|---|---|---|---|
| Postemergence | | | | | | | | | | | | | | |
| Barnyardgrass | 100 | 90 | 90 | 90 | 90 | 20 | 80 | 50 | 90 | 100 | 90 | 90 | 90 | 100 |
| Corn | 30 | 0 | 70 | 30 | 30 | 20 | 0 | 20 | 50 | 50 | 60 | 60 | 90 | 40 |
| Crabgrass, Large | 70 | 80 | 70 | 100 | 90 | 20 | 30 | 60 | 100 | 100 | 100 | 100 | 100 | 100 |
| Foxtail, Giant | 80 | 70 | 70 | 90 | 60 | 10 | 40 | 70 | 100 | 90 | 90 | 90 | 90 | 100 |
| Morningglory | 100 | 90 | 100 | 100 | 100 | 20 | 40 | 80 | 100 | 100 | 100 | 100 | 100 | 100 |
| Pigweed | 100 | 90 | 100 | 100 | 100 | 70 | 70 | 70 | 100 | 100 | 100 | 100 | 100 | 100 |
| Velvetleaf | 100 | 100 | 100 | 100 | 100 | 80 | 90 | 80 | 100 | 100 | 100 | 100 | 100 | 100 |
| Wheat | 0 | 30 | 0 | 30 | 20 | 0 | 0 | 0 | 60 | 40 | 50 | 0 | 20 | 20 |

| 500 g ai/ha | 230 | 231 | 232 | 233 | 234 | 235 | 236 | 237 | 238 | 239 | 240 | 241 | 242 | 243 |
|---|---|---|---|---|---|---|---|---|---|---|---|---|---|---|
| Postemergence | | | | | | | | | | | | | | |
| Barnyardgrass | 90 | 90 | 90 | 90 | 100 | 100 | 90 | 100 | 100 | 90 | 100 | 90 | 90 | 100 |
| Corn | 20 | 40 | 60 | 80 | 50 | 90 | 50 | 80 | 80 | 30 | 80 | 50 | 20 | 90 |
| Crabgrass, Large | 90 | 70 | 60 | 90 | 90 | 100 | 90 | 100 | 100 | 90 | 100 | 70 | 60 | 90 |
| Foxtail, Giant | 50 | 80 | 90 | 90 | 90 | 100 | 90 | 100 | 100 | 80 | 100 | 90 | 80 | 100 |
| Morningglory | 90 | 100 | 100 | 100 | 100 | 100 | 100 | 100 | 100 | 100 | 100 | 100 | 100 | 100 |
| Pigweed | 90 | 90 | 90 | 100 | 90 | 100 | 100 | 100 | 100 | 90 | 100 | 80 | 30 | 100 |
| Velvetleaf | 100 | 100 | 80 | 100 | 100 | 100 | 100 | 100 | 100 | 100 | 100 | 100 | 90 | 100 |
| Wheat | 0 | 0 | 50 | 60 | 20 | 80 | 40 | 70 | 80 | 0 | 40 | 60 | 30 | 90 |

| 500 g ai/ha | 244 | 245 | 246 | 247 | 248 | 249 | 250 | 251 | 252 | 253 | 254 | 255 | 256 |
|---|---|---|---|---|---|---|---|---|---|---|---|---|---|
| Postemergence | | | | | | | | | | | | | | |
| Barnyardgrass | 100 | 100 | 100 | 80 | 100 | 100 | 100 | 100 | 90 | 100 | 90 | 100 | 90 |
| Corn | 80 | 90 | 90 | 30 | 30 | 20 | 70 | 20 | 10 | 40 | 10 | 70 | 10 |
| Crabgrass, Large | 90 | 90 | 100 | 70 | 80 | 100 | 100 | 90 | 60 | 100 | 70 | 100 | 80 |
| Foxtail, Giant | 90 | 100 | 100 | 30 | 100 | 90 | 100 | 90 | 60 | 100 | 50 | 90 | 70 |
| Morningglory | 100 | 100 | 100 | 100 | 100 | 100 | 100 | 100 | 100 | 100 | 50 | 100 | 80 |
| Pigweed | 100 | 100 | 100 | 90 | 90 | 100 | 100 | 80 | 90 | 100 | 90 | 100 | 100 |
| Velvetleaf | 100 | 100 | 100 | 100 | 100 | 100 | 100 | 100 | 90 | 100 | 90 | 100 | 100 |
| Wheat | 70 | 80 | 50 | 0 | 0 | 50 | 20 | 10 | 10 | 20 | 0 | 50 | 0 |

| 125 g ai/ha | 1 | 2 | 3 | 4 | 7 | 8 | 9 | 10 | 11 | 12 | 13 | 14 | 15 | 16 |
|---|---|---|---|---|---|---|---|---|---|---|---|---|---|---|
| Postemergence | | | | | | | | | | | | | | |
| Barnyardgrass | 20 | 100 | 50 | 90 | 30 | 90 | 80 | 90 | 40 | 90 | 30 | 30 | 10 | 20 |
| Corn | 0 | 30 | 0 | 10 | 0 | 10 | 10 | 30 | 0 | 40 | 0 | 0 | 0 | 0 |
| Crabgrass, Large | 50 | 90 | 90 | 70 | 50 | 80 | 70 | 90 | 50 | 90 | 30 | 30 | 20 | 10 |
| Foxtail, Giant | 10 | 90 | 30 | 80 | 40 | 90 | 80 | 90 | 70 | 90 | 30 | 30 | 10 | 30 |
| Morningglory | 70 | 90 | 80 | 100 | 100 | 90 | 80 | 100 | 90 | 100 | 0 | 20 | 10 | 10 |
| Pigweed | 70 | 100 | 100 | 100 | 80 | 100 | 100 | 100 | 90 | 100 | 80 | 80 | 60 | 50 |
| Velvetleaf | 100 | 100 | 100 | 100 | 100 | 100 | 100 | 100 | 100 | 100 | 100 | 100 | 100 | 70 |
| Wheat | 10 | 0 | 0 | 0 | 0 | 10 | 0 | 40 | 0 | 0 | 10 | 0 | 0 | 0 |

TABLE A-continued

| 125 g ai/ha | Compounds | | | | | | | | | | | | | |
|---|---|---|---|---|---|---|---|---|---|---|---|---|---|---|
| | 17 | 18 | 19 | 20 | 21 | 22 | 23 | 24 | 25 | 26 | 27 | 28 | 29 | 30 |
| Postemergence | | | | | | | | | | | | | | |
| Barnyardgrass | 10 | 20 | 0 | 0 | 0 | 10 | 10 | 10 | 30 | 30 | 50 | 30 | 20 | 10 |
| Corn | 0 | 0 | 0 | 0 | 0 | 0 | 0 | 0 | 0 | 0 | 0 | 0 | 0 | 0 |
| Crabgrass, Large | 10 | 30 | 0 | 0 | 0 | 40 | 30 | 70 | 40 | 70 | 70 | 40 | 70 | 30 |
| Foxtail, Giant | 0 | 40 | 20 | 0 | 0 | 30 | 10 | 70 | 50 | 50 | 80 | 30 | 70 | 10 |
| Morningglory | 20 | 40 | 0 | 0 | 0 | 30 | 50 | 70 | 50 | 50 | 60 | 0 | 60 | 30 |
| Pigweed | 80 | 100 | 80 | 10 | 0 | 80 | 80 | 90 | 80 | 90 | 100 | 100 | 80 | 70 |
| Velvetleaf | 100 | 100 | 100 | 20 | 30 | 100 | 100 | 100 | 100 | 100 | 100 | 100 | 100 | 100 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 31 | 32 | 33 | 34 | 35 | 36 | 37 | 38 | 39 | 40 | 41 | 42 | 43 | 44 |
| Postemergence | | | | | | | | | | | | | | |
| Barnyardgrass | 10 | 20 | 80 | 90 | 10 | 90 | 50 | 60 | 60 | 90 | 50 | 60 | 70 | 90 |
| Corn | 0 | 0 | 0 | 0 | 0 | 0 | 0 | 0 | 0 | 0 | 0 | 0 | 0 | 0 |
| Crabgrass, Large | 50 | 50 | 70 | 90 | 50 | 80 | 70 | 60 | 80 | 90 | 20 | 60 | 70 | 80 |
| Foxtail, Giant | 70 | 30 | 60 | 90 | 40 | 80 | 70 | 50 | 80 | 90 | 20 | 40 | 60 | 80 |
| Morningglory | 20 | 50 | 80 | 80 | — | 50 | 80 | 100 | 80 | 50 | 10 | 80 | 20 | 80 |
| Pigweed | 70 | 100 | 90 | 100 | 80 | 90 | 100 | 100 | 100 | 100 | 100 | 100 | 100 | 100 |
| Velvetleaf | 100 | 100 | 100 | 100 | 100 | 100 | 100 | 100 | 100 | 100 | 100 | 100 | 100 | 100 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 45 | 46 | 47 | 48 | 49 | 50 | 51 | 52 | 53 | 54 | 55 | 56 | 57 | 58 |
| Postemergence | | | | | | | | | | | | | | |
| Barnyardgrass | 90 | 80 | 90 | 80 | 60 | 90 | 90 | 90 | 90 | 10 | 50 | 90 | 70 | 50 |
| Corn | 0 | 0 | 0 | 0 | 0 | 0 | 0 | 0 | 0 | 0 | 0 | 10 | 0 | 0 |
| Crabgrass, Large | 60 | 70 | 90 | 90 | 90 | 90 | 90 | 90 | 90 | 40 | 70 | 80 | 80 | 80 |
| Foxtail, Giant | 50 | 60 | 90 | 90 | 50 | 90 | 90 | 90 | 90 | 10 | 20 | 80 | 80 | 70 |
| Morningglory | 80 | 60 | 80 | 90 | 100 | 80 | 100 | 100 | 100 | 40 | 90 | 90 | 50 | 80 |
| Pigweed | 90 | 80 | 90 | 100 | 100 | 100 | 100 | 90 | 100 | 100 | 90 | 90 | 90 | 100 |
| Velvetleaf | 100 | 100 | 100 | 100 | 100 | 100 | 100 | 100 | 100 | 100 | 100 | 100 | 100 | 100 |
| Wheat | 0 | 0 | 0 | 0 | 0 | 0 | 0 | 0 | 30 | 0 | 0 | 0 | 0 | 0 |

| 125 g ai/ha | Compounds | | | | | | | | | | | | | |
|---|---|---|---|---|---|---|---|---|---|---|---|---|---|---|
| | 59 | 60 | 61 | 62 | 63 | 64 | 65 | 66 | 67 | 68 | 69 | 70 | 71 | 72 |
| Postemergence | | | | | | | | | | | | | | |
| Barnyardgrass | 90 | 60 | 70 | 80 | 70 | 50 | 10 | 80 | 70 | 80 | 90 | 50 | 0 | 80 |
| Corn | 10 | 0 | 0 | 30 | 10 | 0 | 0 | — | — | 0 | 20 | 0 | 0 | 0 |
| Crabgrass, Large | 90 | 90 | 80 | 70 | 80 | 80 | 30 | 70 | 60 | 80 | 80 | 50 | 30 | 80 |
| Foxtail, Giant | 80 | 80 | 50 | 70 | 60 | 60 | 10 | 70 | 30 | 50 | 80 | 50 | 20 | 40 |
| Morningglory | 100 | 60 | 100 | 100 | 100 | 90 | 50 | 90 | 100 | 90 | 100 | 100 | 80 | 90 |
| Pigweed | 100 | 100 | 100 | 90 | 90 | 90 | 20 | 100 | 100 | 100 | 100 | 100 | 70 | 80 |
| Velvetleaf | 100 | 100 | 100 | 100 | 100 | 100 | 90 | 100 | 100 | 100 | 100 | 100 | 100 | 100 |
| Wheat | 0 | 20 | 0 | 0 | 0 | 0 | 0 | 0 | 20 | 0 | 0 | 0 | 0 | 0 |

| 125 g ai/ha | Compounds | | | | | | | | | | | | | |
|---|---|---|---|---|---|---|---|---|---|---|---|---|---|---|
| | 73 | 74 | 75 | 76 | 77 | 78 | 79 | 80 | 81 | 82 | 83 | 84 | 85 | 86 |
| Postemergence | | | | | | | | | | | | | | |
| Barnyardgrass | 70 | 80 | 80 | 50 | 80 | 50 | 80 | 30 | 100 | 10 | 70 | 0 | 90 | 90 |
| Corn | 30 | 0 | 0 | 0 | 0 | 0 | 10 | 0 | 10 | 0 | 0 | 0 | 10 | 0 |
| Crabgrass, Large | 90 | 90 | 90 | 70 | 60 | 30 | 80 | 70 | 90 | 40 | 80 | 0 | 90 | 90 |
| Foxtail, Giant | 80 | 40 | 80 | 40 | 50 | 20 | 50 | 70 | 80 | 10 | 70 | 0 | 70 | 80 |
| Morningglory | 100 | 90 | 90 | 90 | 90 | 70 | 100 | 100 | 90 | 90 | 100 | 90 | 100 | 90 |
| Pigweed | 100 | 100 | 100 | 90 | 100 | 100 | 100 | 100 | 100 | 90 | 90 | 100 | 100 | 100 |
| Velvetleaf | 100 | 90 | 100 | 100 | 100 | 100 | 100 | 100 | 100 | 100 | 100 | 70 | 100 | 100 |
| Wheat | 10 | 0 | 0 | 0 | 0 | 0 | 0 | 0 | 0 | 0 | 0 | 0 | 0 | 0 |

TABLE A-continued

| | Compounds | | | | | | | | | | | | | |
|---|---|---|---|---|---|---|---|---|---|---|---|---|---|---|
| 125 g ai/ha | 87 | 88 | 89 | 90 | 91 | 92 | 93 | 94 | 95 | 96 | 97 | 98 | 99 | 100 |
| | Postemergence | | | | | | | | | | | | | |
| Barnyardgrass | 80 | 80 | 90 | 80 | 90 | 80 | 90 | 90 | 80 | 90 | 90 | 80 | 90 | 80 |
| Corn | 10 | 0 | 0 | 0 | 0 | 0 | 10 | 0 | 0 | 0 | 50 | 0 | 0 | 0 |
| Crabgrass, Large | 90 | 90 | 90 | 80 | 90 | 90 | 90 | 80 | 90 | 90 | 80 | 90 | 90 | 80 |
| Foxtail, Giant | 70 | 60 | 60 | 70 | 80 | 80 | 80 | 30 | 70 | 70 | 60 | 70 | 80 | 80 |
| Morningglory | 90 | 90 | 100 | 100 | 100 | 100 | 100 | 100 | 100 | 100 | 100 | 100 | 100 | 90 |
| Pigweed | 100 | 100 | 100 | 100 | 100 | 100 | 100 | 100 | 100 | 100 | 100 | 100 | 100 | 90 |
| Velvetleaf | 100 | 100 | 100 | 100 | 100 | 100 | 100 | 100 | 100 | 100 | 100 | 100 | 100 | 100 |
| Wheat | 30 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 101 | 102 | 103 | 104 | 105 | 106 | 107 | 108 | 109 | 110 | 111 | 112 | 113 | 114 |
| | Postemergence | | | | | | | | | | | | | |
| Barnyardgrass | 80 | 80 | 30 | 10 | 20 | 10 | 90 | 90 | 80 | 60 | 90 | 60 | 70 | 70 |
| Corn | 0 | 0 | 0 | 0 | 0 | 0 | 0 | 0 | 0 | 0 | 0 | 0 | 0 | 10 |
| Crabgrass, Large | 90 | 90 | 10 | 0 | 20 | 40 | 80 | 90 | 90 | 80 | 90 | 80 | 100 | 80 |
| Foxtail, Giant | 60 | 80 | 0 | 0 | 0 | 20 | 70 | 60 | 70 | 10 | 60 | 70 | 90 | 60 |
| Morningglory | 60 | 100 | 100 | 70 | 10 | 100 | 100 | 100 | 90 | 90 | 100 | 90 | 100 | 90 |
| Pigweed | 90 | 100 | 100 | 100 | 90 | 80 | 100 | 100 | 100 | 90 | 100 | 90 | 100 | 100 |
| Velvetleaf | 100 | 100 | 100 | 70 | 100 | 100 | 100 | 100 | 100 | 90 | 100 | 100 | 100 | 100 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 115 | 116 | 117 | 118 | 119 | 120 | 121 | 122 | 123 | 124 | 125 | 126 | 127 | 128 |
| | Postemergence | | | | | | | | | | | | | |
| Barnyardgrass | 70 | 80 | 80 | 90 | 80 | 90 | 80 | 60 | 80 | 40 | 70 | 80 | 80 | 100 |
| Corn | 0 | 0 | 20 | 0 | 0 | 10 | 0 | 0 | 20 | 0 | 0 | 10 | 20 | 20 |
| Crabgrass, Large | 60 | 60 | 80 | 90 | 80 | 90 | 80 | 70 | 80 | 70 | 70 | 90 | 80 | 90 |
| Foxtail, Giant | 50 | 60 | 70 | 80 | 70 | 80 | 90 | 70 | 70 | 50 | 70 | 70 | 70 | 90 |
| Morningglory | 90 | 100 | 100 | 100 | 90 | 100 | 100 | 90 | 100 | 100 | 80 | 100 | 90 | 100 |
| Pigweed | 100 | 100 | 100 | 100 | 100 | 90 | 100 | 100 | 100 | 90 | 90 | 90 | 90 | 100 |
| Velvetleaf | 100 | 70 | 100 | 100 | 100 | 100 | 100 | 100 | 100 | 100 | 100 | 100 | 100 | 100 |
| Wheat | 0 | 0 | 0 | 0 | 50 | 20 | 30 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 129 | 130 | 131 | 132 | 133 | 134 | 135 | 136 | 138 | 139 | 140 | 141 | 142 | 143 |
| | Postemergence | | | | | | | | | | | | | |
| Barnyardgrass | 90 | 100 | 90 | 10 | 20 | 10 | 10 | 30 | 90 | 60 | 90 | 90 | 70 | 70 |
| Corn | 20 | 10 | 0 | 0 | 10 | 0 | 0 | 0 | 20 | 20 | 0 | 20 | 0 | 10 |
| Crabgrass, Large | 90 | 70 | 90 | 20 | 40 | 50 | 40 | 80 | 70 | 70 | 90 | 80 | 70 | 70 |
| Foxtail, Giant | 90 | 80 | 80 | 0 | 20 | 40 | 0 | 30 | 60 | 50 | 80 | 80 | 30 | 60 |
| Morningglory | 100 | 100 | 100 | 90 | 40 | 0 | 70 | 100 | 50 | 100 | 100 | 70 | 100 | 90 |
| Pigweed | 100 | 100 | 100 | 60 | 80 | 70 | 80 | 80 | 100 | 90 | 90 | 90 | 90 | 70 |
| Velvetleaf | 100 | 100 | 100 | 100 | 100 | 100 | 100 | 100 | 100 | 100 | 100 | 100 | 100 | 100 |
| Wheat | 0 | 0 | 0 | 0 | 20 | 0 | 0 | 0 | 20 | 0 | 0 | 0 | 0 | 0 |

| | Compounds | | | | | | | | | | | | | |
|---|---|---|---|---|---|---|---|---|---|---|---|---|---|---|
| 125 g ai/ha | 144 | 145 | 146 | 147 | 148 | 149 | 150 | 151 | 152 | 153 | 154 | 155 | 156 | 157 |
| | Postemergence | | | | | | | | | | | | | |
| Barnyardgrass | 70 | 70 | 100 | 80 | 90 | 70 | 40 | 60 | 100 | 80 | 90 | 90 | 90 | 90 |
| Corn | 0 | 30 | 20 | 20 | 0 | 0 | 0 | 0 | 0 | 0 | 0 | 20 | 20 | 0 |
| Crabgrass, Large | 50 | 70 | 80 | 80 | 70 | 40 | 20 | 30 | 90 | 90 | 70 | 70 | 70 | 80 |
| Foxtail, Giant | 40 | 60 | 70 | 70 | 60 | 60 | 40 | 20 | 80 | 70 | 60 | 80 | 80 | 90 |
| Morningglory | 30 | 90 | 90 | 100 | 100 | 100 | 100 | 40 | 100 | 50 | 30 | 100 | 100 | 10 |
| Pigweed | 80 | 100 | 100 | 100 | 90 | 70 | 30 | 100 | 100 | 100 | 60 | 100 | 100 | 90 |
| Velvetleaf | 100 | 100 | 100 | 100 | 100 | 100 | 50 | 100 | 100 | 100 | 100 | 100 | 100 | 100 |
| Wheat | 0 | 0 | 20 | 20 | 0 | 20 | 0 | 0 | 20 | 0 | 0 | 0 | 0 | 0 |

TABLE A-continued

| Compounds | | | | | | | | | | | | | | |
|---|---|---|---|---|---|---|---|---|---|---|---|---|---|---|
| 125 g ai/ha | 158 | 159 | 160 | 161 | 162 | 163 | 164 | 165 | 166 | 167 | 168 | 169 | 170 | 171 |
| Postemergence | | | | | | | | | | | | | | |
| Barnyardgrass | 90 | 90 | 90 | 30 | 100 | 50 | 100 | 0 | 80 | 60 | 30 | 90 | 40 | 50 |
| Corn | 10 | 0 | 20 | 0 | 0 | 0 | 10 | 0 | 30 | 30 | 20 | 0 | 20 | 30 |
| Crabgrass, Large | 70 | 90 | 90 | 60 | 80 | 60 | 90 | 20 | 40 | 60 | 50 | 90 | 60 | 60 |
| Foxtail, Giant | 70 | 90 | 70 | 40 | 70 | 20 | 100 | 20 | 60 | 90 | 50 | 80 | 50 | 60 |
| Morningglory | 70 | 100 | 100 | 60 | 100 | 10 | 100 | 50 | 100 | 60 | 100 | 100 | 100 | 100 |
| Pigweed | 100 | 100 | 100 | 80 | 100 | 80 | 100 | 80 | 70 | 90 | 100 | 100 | 80 | 100 |
| Velvetleaf | 100 | 100 | 100 | 100 | 100 | 100 | 100 | 100 | 100 | 100 | 100 | 100 | 100 | 100 |
| Wheat | 0 | 10 | 0 | 0 | 30 | 0 | 0 | 0 | 0 | 0 | 0 | 20 | 0 | 20 |

| Compounds | | | | | | | | | | | | | | |
|---|---|---|---|---|---|---|---|---|---|---|---|---|---|---|
| 125 g ai/ha | 172 | 173 | 174 | 175 | 176 | 177 | 178 | 179 | 180 | 181 | 182 | 183 | 184 | 185 |
| Postemergence | | | | | | | | | | | | | | |
| Barnyardgrass | 90 | 90 | 90 | 50 | 50 | 80 | 80 | 60 | 90 | 100 | 70 | 60 | 90 | 70 |
| Corn | 20 | 0 | 10 | 0 | 0 | 0 | 0 | 10 | 10 | 10 | 0 | 10 | 10 | 0 |
| Crabgrass, Large | 60 | 70 | 70 | 40 | 10 | 30 | 50 | 60 | 90 | 90 | 80 | 80 | 80 | 50 |
| Foxtail, Giant | 60 | 70 | 20 | 30 | 10 | 0 | 50 | 40 | 70 | 100 | 50 | 80 | 90 | 50 |
| Morningglory | 90 | 100 | 30 | 10 | 0 | 0 | 50 | 60 | 40 | 30 | 100 | 40 | 50 | 100 |
| Pigweed | 100 | 100 | 100 | 100 | 100 | 100 | 60 | 90 | 100 | 100 | 80 | 100 | 100 | 90 |
| Velvetleaf | 100 | 100 | 100 | 100 | 80 | 90 | 90 | 100 | 100 | 100 | 100 | 100 | 100 | 90 |
| Wheat | 0 | 0 | 0 | 0 | 0 | 0 | 0 | 40 | 0 | 30 | 0 | 50 | 0 | 0 |

| Compounds | | | | | | | | | | | | | | |
|---|---|---|---|---|---|---|---|---|---|---|---|---|---|---|
| 125 g ai/ha | 186 | 187 | 188 | 189 | 190 | 191 | 192 | 193 | 194 | 195 | 196 | 197 | 198 | 199 |
| Postemergence | | | | | | | | | | | | | | |
| Barnyardgrass | 80 | 90 | 70 | 90 | 90 | 90 | 60 | 90 | 90 | 70 | 80 | 80 | 70 | 90 |
| Corn | 0 | 0 | 0 | 10 | 0 | 0 | 0 | 10 | 0 | 0 | 10 | 20 | 0 | 0 |
| Crabgrass, Large | 90 | 90 | 80 | 90 | 90 | 70 | 30 | 100 | 60 | 40 | 50 | 70 | 70 | 70 |
| Foxtail, Giant | 80 | 80 | 40 | 80 | 80 | 80 | 50 | 90 | 30 | 30 | 70 | 80 | 60 | 100 |
| Morningglory | 100 | 100 | 90 | 100 | 100 | 90 | — | 100 | 90 | 60 | 100 | 100 | 100 | 100 |
| Pigweed | 100 | 100 | 90 | 100 | 100 | 80 | 60 | 100 | 100 | 90 | 80 | 100 | 90 | 100 |
| Velvetleaf | 100 | 100 | 100 | 100 | 100 | 100 | 70 | 100 | 100 | 100 | 100 | 100 | 100 | 100 |
| Wheat | 0 | 0 | 0 | 0 | 0 | 0 | 0 | 40 | 0 | 0 | 0 | 0 | 0 | 0 |

| Compounds | | | | | | | | | | | | | | |
|---|---|---|---|---|---|---|---|---|---|---|---|---|---|---|
| 125 g ai/ha | 200 | 202 | 203 | 204 | 205 | 206 | 207 | 208 | 209 | 210 | 211 | 212 | 213 | 214 |
| Postemergence | | | | | | | | | | | | | | |
| Barnyardgrass | 0 | 90 | 80 | 100 | 90 | 90 | 60 | 30 | 80 | 40 | 50 | 50 | 20 | 80 |
| Corn | 0 | 10 | 0 | 0 | 0 | 0 | 0 | 0 | 0 | 0 | 0 | 0 | 0 | 0 |
| Crabgrass, Large | 10 | 70 | 30 | 60 | 60 | 60 | 60 | 30 | 50 | 10 | 40 | 10 | 20 | 80 |
| Foxtail, Giant | 0 | 80 | 30 | 30 | 40 | 50 | 60 | 30 | 60 | 10 | 50 | 0 | 10 | 50 |
| Morningglory | 50 | 100 | 100 | 30 | 100 | 100 | 40 | 50 | 30 | 50 | 70 | 50 | 60 | 80 |
| Pigweed | 60 | 100 | 100 | 100 | 90 | 90 | 100 | 80 | 60 | 90 | 70 | 100 | 80 | 90 |
| Velvetleaf | 100 | 100 | 90 | 100 | 100 | 100 | 100 | 100 | 100 | 70 | 60 | 70 | 70 | 100 |
| Wheat | 0 | 20 | 0 | 0 | 0 | 0 | 0 | 0 | 0 | 0 | 0 | 0 | 0 | 0 |

| Compounds | | | | | | | | | | | | | | |
|---|---|---|---|---|---|---|---|---|---|---|---|---|---|---|
| 125 g ai/ha | 215 | 216 | 218 | 219 | 220 | 221 | 222 | 223 | 224 | 225 | 226 | 227 | 228 | 229 |
| Postemergence | | | | | | | | | | | | | | |
| Barnyardgrass | 90 | 10 | 80 | 90 | 90 | 10 | 10 | 0 | 90 | 90 | 90 | 90 | 90 | 90 |
| Corn | 0 | 0 | 0 | 0 | 0 | 0 | 0 | 0 | 10 | 10 | 10 | 10 | 50 | 0 |
| Crabgrass, Large | 40 | 40 | 20 | 80 | 50 | 10 | 0 | 0 | 70 | 90 | 90 | 90 | 90 | 80 |
| Foxtail, Giant | 40 | 30 | 40 | 50 | 20 | 0 | 0 | 0 | 70 | 70 | 90 | 90 | 90 | 90 |
| Morningglory | 100 | 70 | 80 | 100 | 100 | 10 | 30 | 60 | 100 | 100 | 100 | 100 | 100 | 100 |
| Pigweed | 90 | 90 | 100 | 100 | 100 | 40 | 40 | 50 | 100 | 100 | 100 | 100 | 100 | 100 |
| Velvetleaf | 100 | 90 | 100 | 100 | 100 | 80 | 60 | 50 | 100 | 100 | 100 | 100 | 100 | 100 |
| Wheat | 0 | 20 | 0 | 0 | 0 | 0 | 0 | 0 | 0 | 0 | 0 | 0 | 0 | 0 |

TABLE A-continued

| | Compounds | | | | | | | | | | | | | |
|---|---|---|---|---|---|---|---|---|---|---|---|---|---|---|
| 125 g ai/ha | 230 | 231 | 232 | 233 | 234 | 235 | 236 | 237 | 238 | 239 | 240 | 241 | 242 | 243 |
| Postemergence | | | | | | | | | | | | | | |
| Barnyardgrass | 70 | 70 | 60 | 90 | 80 | 90 | 90 | 100 | 100 | 90 | 100 | 90 | 50 | 100 |
| Corn | 0 | 0 | 10 | 60 | 20 | 80 | 20 | 40 | 40 | 30 | 40 | 20 | 0 | 70 |
| Crabgrass, Large | 80 | 50 | 20 | 90 | 40 | 100 | 80 | 80 | 90 | 80 | 90 | 50 | 20 | 90 |
| Foxtail, Giant | 30 | 60 | 60 | 90 | 70 | 90 | 70 | 90 | 90 | 70 | 90 | 80 | 50 | 100 |
| Morningglory | 70 | 90 | 100 | 100 | 100 | 100 | 100 | 100 | 100 | 100 | 100 | 100 | 40 | 100 |
| Pigweed | 80 | 80 | 70 | 100 | 70 | 100 | 80 | 90 | 100 | 80 | 90 | 70 | 20 | 100 |
| Velvetleaf | 100 | 90 | 70 | 100 | 100 | 100 | 100 | 100 | 100 | 100 | 100 | 100 | 50 | 100 |
| Wheat | 0 | 0 | 20 | 20 | 0 | 50 | 0 | 20 | 50 | 0 | 20 | 40 | 0 | 70 |

| | Compounds | | | | | | | | | | | | |
|---|---|---|---|---|---|---|---|---|---|---|---|---|---|
| 125 g ai/ha | 244 | 245 | 246 | 247 | 248 | 249 | 250 | 251 | 252 | 253 | 254 | 255 | 256 |
| Postemergence | | | | | | | | | | | | | |
| Barnyardgrass | 90 | 90 | 70 | 30 | 90 | 90 | 50 | 80 | 80 | 100 | 0 | 90 | 40 |
| Corn | 40 | 40 | 0 | 0 | 0 | 0 | 0 | 0 | 0 | 10 | 0 | 30 | 0 |
| Crabgrass, Large | 90 | 90 | 70 | 40 | 50 | 90 | 60 | 50 | 30 | 80 | 20 | 90 | 30 |
| Foxtail, Giant | 90 | 100 | 80 | 0 | 50 | 80 | 90 | 50 | 40 | 60 | 10 | 90 | 20 |
| Morningglory | 100 | 100 | 90 | 100 | 100 | 100 | 100 | 100 | 80 | 100 | 20 | 100 | 30 |
| Pigweed | 100 | 100 | 90 | 70 | 80 | 90 | 100 | 70 | 70 | 90 | 60 | 90 | 90 |
| Velvetleaf | 100 | 100 | 100 | 100 | 100 | 100 | 100 | 100 | 70 | 100 | 50 | 100 | 100 |
| Wheat | 40 | 40 | 0 | 0 | 0 | 10 | 0 | 0 | 0 | 0 | 0 | 10 | 0 |

| | Compound |
|---|---|
| 1000 g ai/ha | 217 |
| Preemergence | |
| Barnyardgrass | 80 |
| Corn | 0 |
| Crabgrass, Large | 100 |
| Foxtail, Giant | 80 |
| Morningglory | 70 |
| Pigweed | 100 |
| Velvetleaf | 100 |
| Wheat | 30 |

| | Compounds | | | | | | | | | | | | | |
|---|---|---|---|---|---|---|---|---|---|---|---|---|---|---|
| 500 g ai/ha | 1 | 2 | 3 | 4 | 7 | 8 | 9 | 10 | 11 | 12 | 13 | 14 | 15 | 16 |
| Preemergence | | | | | | | | | | | | | | |
| Barnyardgrass | 10 | 70 | 60 | 70 | 10 | 80 | 100 | 90 | 70 | 70 | 90 | 70 | 90 | 70 |
| Corn | 0 | 0 | 0 | 20 | 0 | 20 | 0 | 0 | 0 | 0 | 20 | 0 | 0 | 20 |
| Crabgrass, Large | 70 | 100 | 80 | 90 | 40 | 100 | 100 | 100 | 90 | 90 | 100 | 90 | 90 | 70 |
| Foxtail, Giant | 10 | 90 | 10 | 70 | 20 | 90 | 90 | 100 | 50 | 90 | 90 | 90 | 70 | 70 |
| Morningglory | 50 | 90 | 100 | 70 | 40 | 70 | 90 | 90 | 70 | 90 | 0 | 60 | 60 | 0 |
| Pigweed | 100 | 100 | 100 | 90 | 80 | 90 | 100 | 100 | 100 | 100 | 100 | 100 | 90 | 50 |
| Velvetleaf | 80 | 100 | 90 | 100 | 100 | 90 | 100 | 100 | 100 | 90 | 100 | 100 | 90 | 40 |
| Wheat | 0 | 0 | 0 | 20 | 0 | 20 | 0 | 50 | 0 | 0 | 40 | 0 | 20 | 0 |

| | Compounds | | | | | | | | | | | | | |
|---|---|---|---|---|---|---|---|---|---|---|---|---|---|---|
| 500 g ai/ha | 17 | 18 | 19 | 20 | 21 | 22 | 23 | 24 | 25 | 26 | 27 | 28 | 29 | 30 |
| Preemergence | | | | | | | | | | | | | | |
| Barnyardgrass | 80 | 100 | 90 | 20 | 0 | 100 | 70 | 90 | 80 | 60 | 80 | 70 | 100 | 40 |
| Corn | 0 | 20 | 0 | 0 | 0 | 0 | 0 | 0 | 0 | 0 | 0 | 0 | 0 | 0 |
| Crabgrass, Large | 100 | 100 | 80 | 30 | 20 | 90 | 90 | 100 | 100 | 90 | 90 | 60 | 100 | 60 |
| Foxtail, Giant | 20 | 90 | 30 | 20 | 10 | 80 | 20 | 100 | 90 | 70 | 90 | 30 | 100 | 10 |
| Morningglory | 10 | 70 | 50 | 0 | 0 | 70 | 70 | 80 | 60 | 70 | 80 | 80 | 80 | 60 |
| Pigweed | 90 | 100 | 90 | — | 70 | 90 | 70 | 100 | 80 | 100 | 90 | 100 | 100 | 80 |
| Velvetleaf | 100 | 100 | 100 | 50 | 0 | 100 | 100 | 100 | 100 | 100 | 100 | 80 | 100 | 70 |
| Wheat | 0 | 40 | 0 | 0 | 0 | 0 | 0 | 20 | 20 | 0 | 0 | 0 | 0 | 0 |

TABLE A-continued

| 500 g ai/ha | Compounds | | | | | | | | | | | | | |
|---|---|---|---|---|---|---|---|---|---|---|---|---|---|---|
| | 31 | 32 | 33 | 34 | 35 | 36 | 37 | 38 | 39 | 40 | 41 | 42 | 43 | 44 |
| Preemergence | | | | | | | | | | | | | | |
| Barnyardgrass | 40 | 90 | 90 | 100 | 0 | 50 | 30 | 90 | 90 | 100 | 80 | 60 | 80 | 100 |
| Corn | 0 | 0 | 30 | 0 | 0 | 0 | 0 | 30 | 0 | 0 | 0 | 0 | 0 | 0 |
| Crabgrass, Large | 90 | 90 | 100 | 100 | 60 | 80 | 50 | 100 | 90 | 100 | 80 | 90 | 100 | 90 |
| Foxtail, Giant | 40 | 90 | 90 | 100 | 10 | 60 | 50 | 80 | 90 | 90 | 30 | 40 | 70 | 90 |
| Morningglory | 50 | 80 | 50 | 60 | 20 | 30 | 30 | 70 | 60 | 80 | 20 | 50 | 10 | 70 |
| Pigweed | 80 | 100 | 90 | 100 | 100 | 80 | 100 | 100 | 90 | 90 | 90 | 100 | 100 | 90 |
| Velvetleaf | 70 | 70 | 80 | 100 | 70 | 100 | 90 | 100 | 90 | 100 | 80 | 100 | 100 | 100 |
| Wheat | 0 | 20 | 10 | 0 | 0 | 20 | 0 | 20 | 0 | 0 | 0 | 0 | 0 | 0 |

| 500 g ai/ha | Compounds | | | | | | | | | | | | | |
|---|---|---|---|---|---|---|---|---|---|---|---|---|---|---|
| | 45 | 46 | 47 | 48 | 49 | 50 | 51 | 52 | 53 | 54 | 55 | 56 | 57 | 58 |
| Preemergence | | | | | | | | | | | | | | |
| Barnyardgrass | 80 | 50 | 90 | 100 | 60 | 90 | 90 | 100 | 100 | 10 | 10 | 90 | 90 | 90 |
| Corn | 0 | 0 | 0 | 0 | 0 | 0 | 0 | 10 | 0 | 0 | 0 | 0 | 0 | 0 |
| Crabgrass, Large | 100 | 80 | 100 | 100 | 90 | 100 | 100 | 100 | 100 | 30 | 50 | 90 | 100 | 90 |
| Foxtail, Giant | 80 | 60 | 90 | 90 | 50 | 80 | 100 | 100 | 100 | 0 | 0 | 90 | 90 | 80 |
| Morningglory | 90 | 70 | 90 | 80 | 80 | 80 | 90 | 90 | 90 | 0 | 60 | 90 | 80 | 100 |
| Pigweed | 100 | 90 | 100 | 100 | 90 | 100 | 100 | 100 | 100 | 90 | 100 | 100 | 100 | 100 |
| Velvetleaf | 100 | 70 | 100 | 100 | 90 | 90 | 90 | 100 | 90 | 70 | 60 | 100 | 100 | 100 |
| Wheat | 20 | 20 | 0 | 0 | 0 | 0 | 0 | 0 | 10 | 0 | 0 | 0 | 0 | 0 |

| 500 g ai/ha | Compounds | | | | | | | | | | | | | |
|---|---|---|---|---|---|---|---|---|---|---|---|---|---|---|
| | 59 | 60 | 61 | 62 | 63 | 64 | 65 | 66 | 67 | 68 | 69 | 70 | 71 | 72 |
| Preemergence | | | | | | | | | | | | | | |
| Barnyardgrass | 90 | 90 | 90 | 90 | 90 | 90 | 10 | 70 | 40 | 50 | 60 | 10 | 0 | 60 |
| Corn | 0 | 10 | 0 | 20 | 0 | 0 | 0 | 0 | 0 | 0 | 0 | 0 | 0 | 20 |
| Crabgrass, Large | 100 | 100 | 100 | 90 | 100 | 90 | 80 | 100 | 90 | 100 | 100 | 90 | 50 | 100 |
| Foxtail, Giant | 80 | 90 | 60 | 70 | 80 | 70 | 40 | 80 | 50 | 60 | 70 | 60 | 10 | 30 |
| Morningglory | 90 | 80 | 80 | 100 | 70 | 0 | 0 | 30 | 50 | 50 | 50 | 10 | 0 | 70 |
| Pigweed | 100 | 100 | 90 | 100 | 100 | 100 | 0 | 100 | 90 | 100 | 100 | 100 | 90 | 90 |
| Velvetleaf | 100 | 100 | 100 | 90 | 90 | 90 | 50 | 100 | 80 | 100 | 100 | 80 | 70 | 100 |
| Wheat | 0 | 40 | 0 | 10 | 0 | 0 | 0 | 0 | 0 | 0 | 10 | 0 | 0 | 0 |

| 500 g ai/ha | Compounds | | | | | | | | | | | | | |
|---|---|---|---|---|---|---|---|---|---|---|---|---|---|---|
| | 73 | 74 | 75 | 76 | 77 | 78 | 79 | 80 | 81 | 82 | 83 | 84 | 85 | 86 |
| Preemergence | | | | | | | | | | | | | | |
| Barnyardgrass | 70 | 60 | 80 | 30 | 50 | 30 | 70 | 10 | 90 | 10 | 90 | 0 | 100 | 100 |
| Corn | 0 | 0 | 0 | 0 | 0 | 0 | 0 | 0 | 0 | 0 | 20 | 0 | 10 | — |
| Crabgrass, Large | 100 | 90 | 100 | 100 | 90 | 50 | 100 | 90 | 100 | 100 | 100 | 0 | 100 | — |
| Foxtail, Giant | 70 | 40 | 70 | 30 | 20 | 10 | 50 | 60 | 80 | 40 | 90 | 0 | 90 | 100 |
| Morningglory | 80 | 60 | 90 | 50 | 70 | 0 | 50 | 30 | 70 | 60 | 60 | 10 | 80 | 60 |
| Pigweed | 100 | 100 | 100 | 100 | 90 | 100 | 100 | 90 | 100 | 100 | 100 | 100 | — | — |
| Velvetleaf | 100 | 90 | 100 | 70 | 100 | 50 | 100 | 100 | 100 | 90 | 100 | 40 | — | 100 |
| Wheat | 30 | 0 | 0 | 20 | 0 | 0 | 30 | 0 | 20 | 0 | 30 | 0 | 40 | — |

| 500 g ai/ha | Compounds | | | | | | | | | | | | | |
|---|---|---|---|---|---|---|---|---|---|---|---|---|---|---|
| | 87 | 88 | 89 | 90 | 91 | 92 | 93 | 94 | 95 | 96 | 97 | 98 | 99 | 100 |
| Preemergence | | | | | | | | | | | | | | |
| Barnyardgrass | 90 | 90 | 80 | 70 | 100 | 100 | 100 | 30 | 80 | 100 | 100 | 60 | 90 | 90 |
| Corn | 0 | 0 | 0 | 0 | 0 | 0 | 0 | 0 | 0 | 10 | 0 | 0 | 0 | 0 |
| Crabgrass, Large | 100 | — | 90 | 100 | 100 | 100 | 100 | 90 | 90 | 100 | 100 | 100 | 100 | 90 |
| Foxtail, Giant | 80 | 100 | 70 | 60 | 70 | 80 | 80 | 40 | 60 | 80 | 90 | 80 | 80 | 80 |
| Morningglory | 80 | 70 | 70 | 70 | 80 | 80 | 90 | 40 | 90 | 80 | 80 | 80 | 80 | 80 |
| Pigweed | — | — | 100 | 100 | 90 | 100 | 100 | 100 | 100 | 100 | 100 | 100 | 100 | 100 |
| Velvetleaf | 100 | 100 | 100 | 100 | 100 | 100 | 100 | 70 | 100 | 100 | 100 | 100 | 100 | 80 |
| Wheat | 40 | 10 | 30 | 0 | 20 | 0 | 0 | 0 | 0 | 0 | 0 | 0 | 0 | 0 |

TABLE A-continued

| | Compounds | | | | | | | | | | | | | |
|---|---|---|---|---|---|---|---|---|---|---|---|---|---|---|
| 500 g ai/ha | 101 | 102 | 103 | 104 | 105 | 106 | 107 | 108 | 109 | 110 | 111 | 112 | 113 | 114 |
| | Preemergence | | | | | | | | | | | | | |
| Barnyardgrass | 70 | 90 | 20 | 0 | 0 | 50 | 90 | 90 | 70 | 60 | 90 | 80 | 90 | 90 |
| Corn | 0 | 0 | 0 | 0 | 0 | 0 | — | 0 | 0 | 0 | 0 | 0 | — | 0 |
| Crabgrass, Large | 90 | 100 | 80 | 0 | 50 | 80 | 100 | 90 | 90 | 80 | 100 | 100 | 100 | 100 |
| Foxtail, Giant | 50 | 100 | 60 | 0 | 50 | 70 | 90 | 40 | 30 | 10 | 70 | 60 | 90 | 80 |
| Morningglory | 80 | 80 | 60 | 0 | — | 80 | 90 | 90 | 70 | 70 | 80 | 80 | 80 | 80 |
| Pigweed | 80 | 100 | 100 | 90 | 90 | 90 | 100 | 100 | 100 | 90 | 100 | 100 | 100 | 100 |
| Velvetleaf | 100 | 100 | 90 | 40 | 70 | 60 | 100 | 90 | 100 | 70 | 100 | 70 | 100 | 100 |
| Wheat | 0 | 0 | 0 | 0 | 0 | 0 | 0 | 0 | 0 | 0 | 0 | 0 | 0 | 20 |

| | Compounds | | | | | | | | | | | | | |
|---|---|---|---|---|---|---|---|---|---|---|---|---|---|---|
| 500 g ai/ha | 115 | 116 | 117 | 118 | 119 | 120 | 121 | 122 | 123 | 124 | 125 | 126 | 127 | 128 |
| | Preemergence | | | | | | | | | | | | | |
| Barnyardgrass | 80 | 70 | 90 | 90 | 100 | 100 | 100 | 100 | 100 | 60 | 90 | 100 | 100 | 100 |
| Corn | 0 | 0 | 20 | 0 | 30 | 30 | 30 | 0 | 30 | 0 | 0 | 20 | 0 | 0 |
| Crabgrass, Large | 80 | 70 | 100 | 90 | 100 | 100 | 100 | 100 | 100 | 90 | 100 | 100 | 100 | 100 |
| Foxtail, Giant | 70 | 60 | 70 | 50 | 100 | 100 | 100 | 100 | 100 | 40 | 80 | 90 | 90 | 90 |
| Morningglory | 80 | 40 | 90 | 70 | 90 | 90 | 70 | 80 | — | 80 | 0 | 90 | 80 | — |
| Pigweed | 100 | 100 | 100 | 100 | 100 | 100 | 100 | 100 | 100 | 100 | 90 | 100 | 100 | 100 |
| Velvetleaf | 90 | 60 | 90 | 80 | 100 | 100 | 100 | 100 | 100 | 100 | 100 | 100 | 100 | 100 |
| Wheat | 0 | 0 | 20 | 0 | 60 | 70 | 50 | 40 | 20 | 0 | 0 | 20 | 0 | 30 |

| | Compounds | | | | | | | | | | | | | |
|---|---|---|---|---|---|---|---|---|---|---|---|---|---|---|
| 500 g ai/ha | 129 | 130 | 131 | 132 | 133 | 134 | 135 | 136 | 138 | 139 | 140 | 141 | 142 | 143 |
| | Preemergence | | | | | | | | | | | | | |
| Barnyardgrass | 100 | 90 | 100 | 100 | 100 | 10 | 0 | 60 | 90 | 90 | 100 | 100 | 80 | 90 |
| Corn | 0 | 30 | 0 | 20 | 20 | 0 | 0 | 0 | 20 | 20 | 0 | 0 | 0 | 0 |
| Crabgrass, Large | 90 | 100 | 100 | 100 | 100 | 30 | 40 | 60 | 70 | 100 | 90 | 100 | 80 | 90 |
| Foxtail, Giant | 80 | 90 | 80 | 90 | 80 | 30 | 0 | 0 | 70 | 70 | 90 | 80 | 20 | 70 |
| Morningglory | 90 | 80 | 80 | 30 | 0 | 30 | 50 | 60 | 0 | 80 | 50 | 30 | 50 | 70 |
| Pigweed | 100 | 100 | 100 | 80 | 100 | 60 | 80 | 100 | 90 | 100 | 100 | 100 | 100 | 90 |
| Velvetleaf | 90 | 90 | 100 | 80 | 100 | 70 | 70 | 100 | 80 | 90 | 100 | 100 | 60 | 100 |
| Wheat | 0 | 0 | 0 | 10 | 20 | 0 | 0 | 0 | 20 | 10 | 0 | 0 | 0 | 0 |

| | Compounds | | | | | | | | | | | | | |
|---|---|---|---|---|---|---|---|---|---|---|---|---|---|---|
| 500 g ai/ha | 144 | 145 | 146 | 147 | 148 | 149 | 150 | 151 | 152 | 153 | 154 | 155 | 156 | 157 |
| | Preemergence | | | | | | | | | | | | | |
| Barnyardgrass | 20 | 90 | 100 | 100 | 30 | 50 | 0 | 100 | 100 | 80 | 40 | 90 | 80 | 50 |
| Corn | 0 | 20 | 30 | 0 | 0 | 20 | 0 | 0 | 30 | 20 | 0 | 30 | 20 | 0 |
| Crabgrass, Large | 30 | 100 | 100 | 100 | 50 | 80 | 10 | 50 | 100 | 100 | 50 | 90 | 50 | 70 |
| Foxtail, Giant | 10 | 70 | 90 | 90 | 10 | 60 | 0 | 60 | 90 | 70 | 30 | 60 | 50 | 50 |
| Morningglory | 10 | 80 | — | 90 | 0 | 40 | 0 | 30 | 80 | 70 | 0 | 0 | 0 | 0 |
| Pigweed | 90 | 100 | 100 | 100 | 60 | 100 | 0 | 70 | 100 | 100 | 80 | 90 | 80 | 50 |
| Velvetleaf | 70 | 100 | 100 | 100 | 80 | 70 | 0 | 70 | 100 | 100 | 80 | 100 | 50 | 100 |
| Wheat | 0 | 20 | 40 | 20 | 0 | 20 | 0 | 20 | 50 | 20 | 0 | 0 | 0 | 0 |

| | Compounds | | | | | | | | | | | | | |
|---|---|---|---|---|---|---|---|---|---|---|---|---|---|---|
| 500 g ai/ha | 158 | 159 | 160 | 161 | 162 | 163 | 164 | 165 | 166 | 167 | 168 | 169 | 170 | 171 |
| | Preemergence | | | | | | | | | | | | | |
| Barnyardgrass | 80 | 90 | 80 | 90 | 100 | 20 | 80 | 0 | 20 | 30 | 20 | 50 | 60 | 70 |
| Corn | 20 | 40 | 20 | 0 | 0 | 0 | 0 | 0 | 0 | 0 | 0 | 20 | 0 | 20 |
| Crabgrass, Large | 100 | 100 | 100 | 90 | 100 | 10 | 90 | 0 | 70 | 90 | 80 | 40 | 70 | 100 |
| Foxtail, Giant | 80 | 90 | 70 | 80 | 90 | 10 | 70 | 0 | 20 | 50 | 70 | 50 | 70 | 80 |
| Morningglory | 80 | 50 | — | 40 | 80 | 0 | 50 | 0 | 0 | 0 | 70 | 20 | 70 | 60 |
| Pigweed | 100 | 100 | 100 | 100 | 100 | 60 | 100 | 0 | 40 | 90 | 50 | 50 | 50 | 80 |
| Velvetleaf | 80 | 100 | 30 | 90 | 100 | 50 | 70 | 0 | 100 | 100 | 60 | 50 | 80 | 100 |
| Wheat | 10 | 20 | 20 | 0 | 50 | 0 | 0 | 0 | 0 | 0 | 0 | 0 | 20 | 40 |

TABLE A-continued

| 500 g ai/ha | Compounds | | | | | | | | | | | | | |
|---|---|---|---|---|---|---|---|---|---|---|---|---|---|---|
| | 172 | 173 | 174 | 175 | 176 | 177 | 178 | 179 | 180 | 181 | 182 | 183 | 184 | 185 |
| Preemergence | | | | | | | | | | | | | | |
| Barnyardgrass | 80 | 60 | 40 | 30 | 30 | 10 | 50 | 70 | 80 | 100 | 90 | 100 | 90 | 50 |
| Corn | 0 | 10 | 20 | 0 | 0 | 20 | 0 | 0 | 0 | 0 | 20 | 0 | 20 | 0 |
| Crabgrass, Large | 90 | 100 | 60 | 50 | 20 | 10 | 70 | 100 | 100 | 100 | 100 | 100 | 100 | 30 |
| Foxtail, Giant | 60 | 40 | 40 | 50 | 50 | 20 | 50 | 90 | 70 | 80 | 80 | 90 | 90 | 50 |
| Morningglory | 50 | — | 0 | 10 | 20 | — | 40 | 40 | — | 30 | 80 | 50 | 60 | 30 |
| Pigweed | 100 | 90 | 90 | 100 | 100 | 50 | 40 | 90 | 100 | 100 | 100 | 100 | 90 | 70 |
| Velvetleaf | 80 | 100 | 70 | 50 | 50 | 40 | 60 | 100 | 100 | 100 | 100 | 100 | 100 | 50 |
| Wheat | 0 | 20 | 0 | 0 | 0 | 0 | 0 | 60 | 20 | 20 | 50 | 50 | 0 | 0 |

| 500 g ai/ha | Compounds | | | | | | | | | | | | | |
|---|---|---|---|---|---|---|---|---|---|---|---|---|---|---|
| | 186 | 187 | 188 | 189 | 190 | 191 | 192 | 193 | 194 | 195 | 196 | 197 | 198 | 199 |
| Preemergence | | | | | | | | | | | | | | |
| Barnyardgrass | 60 | 90 | 30 | 90 | 100 | 80 | 30 | 90 | 40 | 10 | 50 | 40 | 50 | 90 |
| Corn | 0 | 0 | 0 | 0 | 0 | 30 | 40 | 0 | 0 | 0 | 20 | 30 | 20 | 30 |
| Crabgrass, Large | 80 | 90 | 70 | 80 | 90 | 100 | 40 | 100 | 40 | 50 | 70 | 60 | 90 | 100 |
| Foxtail, Giant | 60 | 90 | 40 | 60 | 90 | 90 | 40 | 90 | — | 30 | 80 | 50 | 70 | 90 |
| Morningglory | 90 | 90 | 80 | 80 | 70 | 70 | 0 | 90 | 20 | 0 | 40 | 60 | 30 | 80 |
| Pigweed | 100 | 70 | 80 | 100 | 100 | 100 | 50 | 100 | 100 | 10 | 30 | 100 | 100 | 100 |
| Velvetleaf | 100 | 100 | 80 | 100 | 100 | 100 | 60 | 100 | 70 | 50 | 50 | 90 | 80 | 100 |
| Wheat | 0 | 0 | 0 | 0 | 0 | 20 | 20 | 50 | 0 | 20 | 20 | 20 | 20 | 20 |

| 500 g ai/ha | Compounds | | | | | | | | | | | | | |
|---|---|---|---|---|---|---|---|---|---|---|---|---|---|---|
| | 200 | 202 | 203 | 204 | 205 | 206 | 207 | 208 | 209 | 210 | 211 | 212 | 213 | 214 |
| Preemergence | | | | | | | | | | | | | | |
| Barnyardgrass | 0 | 100 | 70 | 80 | 10 | 20 | 50 | 80 | 50 | 70 | 70 | 90 | 30 | 60 |
| Corn | 0 | 40 | 20 | 20 | 0 | 0 | 0 | 20 | 20 | 0 | 0 | 0 | 0 | 0 |
| Crabgrass, Large | 0 | 100 | 70 | 100 | 90 | 60 | 100 | 100 | 70 | 50 | 90 | 40 | 50 | 90 |
| Foxtail, Giant | 0 | 100 | 90 | 90 | 80 | 60 | 80 | 70 | 60 | 90 | 50 | 50 | 30 | 70 |
| Morningglory | — | 100 | 70 | 80 | 60 | 0 | 70 | 70 | 30 | 50 | 10 | 80 | 60 | 80 |
| Pigweed | 20 | 100 | 100 | 100 | 90 | 80 | 100 | 100 | 70 | 100 | 60 | 90 | 90 | 90 |
| Velvetleaf | 60 | 100 | 80 | 90 | 80 | 60 | 100 | 90 | 100 | 60 | 60 | 70 | 60 | 100 |
| Wheat | 0 | 40 | 30 | 40 | 0 | 0 | 0 | 20 | 0 | 0 | 0 | 0 | 0 | 30 |

| 500 g ai/ha | Compounds | | | | | | | | | | | | | |
|---|---|---|---|---|---|---|---|---|---|---|---|---|---|---|
| | 215 | 216 | 218 | 219 | 220 | 221 | 222 | 223 | 224 | 225 | 226 | 227 | 228 | 229 |
| Preemergence | | | | | | | | | | | | | | |
| Barnyardgrass | 20 | 20 | 100 | 100 | 90 | 0 | 60 | 70 | 90 | 90 | 100 | 100 | 100 | 70 |
| Corn | 0 | 20 | 0 | 0 | 10 | 0 | 0 | 0 | 20 | 20 | 0 | 10 | 50 | 0 |
| Crabgrass, Large | 60 | 80 | 80 | 100 | 90 | 10 | 20 | 80 | 100 | 100 | 100 | 100 | 100 | 100 |
| Foxtail, Giant | 30 | 60 | 50 | 80 | 40 | 10 | 60 | 90 | 70 | 80 | 90 | 80 | 90 | 60 |
| Morningglory | 70 | 30 | 80 | 80 | 70 | 0 | 40 | — | 30 | 80 | 80 | 80 | 80 | 80 |
| Pigweed | 90 | 50 | 90 | 100 | 100 | 60 | 0 | 90 | 100 | 100 | 100 | 100 | 100 | 100 |
| Velvetleaf | 70 | 30 | 90 | 90 | 100 | 30 | 60 | 60 | 80 | 100 | 100 | 100 | 100 | 100 |
| Wheat | 0 | 0 | 0 | 20 | 0 | 0 | 0 | 0 | 30 | 30 | 10 | 10 | 0 | 0 |

| 500 g ai/ha | Compounds | | | | | | | | | | | | | |
|---|---|---|---|---|---|---|---|---|---|---|---|---|---|---|
| | 230 | 231 | 232 | 233 | 234 | 235 | 236 | 237 | 238 | 239 | 240 | 241 | 242 | 243 |
| Preemergence | | | | | | | | | | | | | | |
| Barnyardgrass | 80 | 60 | 50 | 100 | 80 | 100 | 90 | 90 | 100 | 80 | — | 90 | 0 | 100 |
| Corn | 0 | 20 | 0 | 0 | 20 | 70 | 10 | 50 | 50 | 0 | 40 | 20 | 0 | 60 |
| Crabgrass, Large | 90 | 90 | 40 | 100 | 90 | 100 | 100 | 100 | 100 | 100 | 100 | 90 | 10 | 100 |
| Foxtail, Giant | 50 | 60 | 70 | 80 | 60 | 90 | 70 | 90 | 90 | 70 | 80 | 70 | 0 | 100 |
| Morningglory | 20 | 80 | 40 | 90 | 10 | 90 | 80 | 80 | 90 | 50 | 0 | 30 | 0 | 90 |
| Pigweed | 80 | 80 | 90 | 100 | 60 | 90 | 90 | 100 | 100 | 100 | 100 | 50 | 0 | 100 |
| Velvetleaf | 80 | 60 | 60 | 80 | 90 | 100 | 100 | 100 | 100 | 100 | 80 | 60 | 0 | 100 |
| Wheat | 0 | 0 | 30 | 40 | 20 | 40 | 30 | 30 | 40 | 30 | 40 | 40 | 0 | 70 |

TABLE A-continued

| | Compounds | | | | | | | | | | | | |
|---|---|---|---|---|---|---|---|---|---|---|---|---|---|
| 500 g ai/ha | 244 | 245 | 246 | 247 | 248 | 249 | 250 | 251 | 252 | 253 | 254 | 255 | 256 |
| | Preemergence | | | | | | | | | | | | |
| Barnyardgrass | 100 | 100 | 100 | 0 | 30 | 40 | 40 | 20 | 0 | 20 | 10 | 100 | 70 |
| Corn | 40 | 20 | 50 | 0 | 20 | 0 | 0 | 0 | 0 | — | 0 | 0 | 0 |
| Crabgrass, Large | 100 | 100 | 100 | 0 | 70 | 80 | 90 | 80 | 20 | 80 | 50 | 90 | 80 |
| Foxtail, Giant | 100 | 90 | 90 | 0 | 20 | 40 | 60 | 40 | 10 | 70 | 30 | 50 | 30 |
| Morningglory | 80 | 60 | 60 | 0 | 40 | 70 | 60 | 40 | 10 | 70 | — | 60 | 50 |
| Pigweed | 100 | 90 | 100 | 0 | 40 | 100 | 100 | 60 | 40 | 80 | 0 | 90 | 90 |
| Velvetleaf | 100 | 100 | 100 | 0 | 60 | 90 | 90 | 70 | 50 | 90 | 20 | 100 | 80 |
| Wheat | 40 | 20 | 50 | 0 | 20 | 0 | 10 | 0 | 0 | 20 | 0 | 0 | 0 |

| | Compounds | | | | | | | | | | | | |
|---|---|---|---|---|---|---|---|---|---|---|---|---|---|
| 125 g ai/ha | 1 | 2 | 3 | 4 | 7 | 8 | 9 | 10 | 11 | 12 | 13 | 14 | 15 | 16 |
| | Preemergence | | | | | | | | | | | | |
| Barnyardgrass | 0 | 10 | 30 | 10 | 0 | 10 | 0 | 30 | 0 | 10 | 10 | 10 | 10 | 0 |
| Corn | 0 | 0 | 0 | 0 | 0 | 0 | 0 | 0 | 0 | 0 | 0 | 0 | 0 | 0 |
| Crabgrass, Large | 10 | 80 | 50 | 20 | 0 | 40 | 90 | 90 | 20 | 50 | 60 | 30 | 40 | 40 |
| Foxtail, Giant | 0 | 50 | 0 | 10 | 0 | 40 | 40 | 70 | 10 | 20 | 50 | 40 | 40 | 30 |
| Morningglory | — | 60 | 0 | 0 | 0 | 0 | 20 | 10 | 0 | 30 | 0 | 10 | 0 | 0 |
| Pigweed | 20 | 100 | 80 | 90 | 10 | 90 | 50 | 100 | 60 | 80 | 40 | 100 | 30 | 30 |
| Velvetleaf | 60 | 60 | 80 | 40 | 60 | 50 | 70 | 90 | 60 | 70 | 80 | 90 | 40 | 0 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 125 g ai/ha | 17 | 18 | 19 | 20 | 21 | 22 | 23 | 24 | 25 | 26 | 27 | 28 | 29 | 30 |
| | Preemergence | | | | | | | | | | | | |
| Barnyardgrass | 0 | 10 | 10 | 0 | 0 | 10 | 0 | 10 | 20 | 0 | 10 | 10 | 0 | 0 |
| Corn | 0 | 0 | 0 | 0 | 0 | 0 | 0 | 0 | 0 | 0 | 0 | 0 | 0 | 0 |
| Crabgrass, Large | 20 | 60 | 20 | 0 | 0 | 40 | 10 | 30 | 60 | 20 | 30 | 20 | 20 | 0 |
| Foxtail, Giant | 0 | 40 | 10 | 0 | 0 | 20 | 0 | 40 | 50 | 30 | 30 | 0 | 30 | 0 |
| Morningglory | 0 | 20 | 0 | 0 | 0 | 20 | 0 | 20 | 0 | 10 | 20 | 20 | 40 | 0 |
| Pigweed | 80 | 70 | 80 | 0 | — | 70 | 50 | 90 | 50 | 60 | 70 | 80 | 50 | 0 |
| Velvetleaf | 40 | 30 | 50 | 0 | 0 | 30 | 40 | 90 | 80 | 20 | 60 | 20 | 20 | 20 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 125 g ai/ha | 31 | 32 | 33 | 34 | 35 | 36 | 37 | 38 | 39 | 40 | 41 | 42 | 43 | 44 |
| | Preemergence | | | | | | | | | | | | |
| Barnyardgrass | 0 | 0 | 10 | 10 | 0 | 10 | 0 | 10 | 10 | 10 | 0 | 0 | 10 | 30 |
| Corn | 0 | 0 | 0 | 0 | 0 | 0 | 0 | 0 | 0 | 0 | 0 | 0 | 0 | 0 |
| Crabgrass, Large | 0 | 20 | 80 | 90 | 10 | 10 | 10 | 30 | 60 | 60 | 20 | 40 | 50 | 80 |
| Foxtail, Giant | 0 | 10 | 30 | 60 | 0 | 10 | 10 | 10 | 50 | 50 | 10 | 10 | 10 | 30 |
| Morningglory | 0 | 0 | 0 | 10 | — | 0 | 0 | 0 | 40 | 10 | 0 | 0 | 0 | 20 |
| Pigweed | 40 | 30 | 80 | 90 | 10 | 0 | 50 | 50 | 60 | 70 | 90 | 90 | 90 | 60 |
| Velvetleaf | 10 | 20 | 50 | 50 | 0 | 60 | 50 | 70 | 70 | 70 | 30 | 70 | 60 | 70 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 125 g ai/ha | 45 | 46 | 47 | 48 | 49 | 50 | 51 | 52 | 53 | 54 | 55 | 56 | 57 | 58 |
| | Preemergence | | | | | | | | | | | | |
| Barnyardgrass | 40 | 0 | 10 | 20 | 20 | 50 | 10 | 40 | 40 | 0 | 0 | 50 | 40 | 30 |
| Corn | 0 | 0 | 0 | 0 | 0 | 0 | 0 | 0 | 0 | 0 | 0 | 0 | 0 | 0 |
| Crabgrass, Large | 50 | 30 | 70 | 90 | 60 | 90 | 30 | 90 | 90 | 0 | 0 | 80 | 90 | 70 |
| Foxtail, Giant | 0 | 0 | 50 | 70 | 20 | 50 | 30 | 80 | 70 | 0 | 0 | 70 | 70 | 50 |
| Morningglory | 20 | 10 | 60 | 40 | 30 | 40 | — | 30 | 80 | 0 | 30 | 50 | 20 | — |
| Pigweed | 80 | 60 | 80 | 90 | 80 | 90 | 90 | 100 | 90 | 80 | 50 | 90 | 90 | 70 |
| Velvetleaf | 60 | 40 | 70 | 80 | 80 | 80 | 70 | 100 | 80 | 60 | 60 | 80 | 80 | 70 |
| Wheat | 0 | 0 | 0 | 0 | 0 | 0 | 0 | 0 | 0 | 0 | 0 | 0 | 0 | 0 |

TABLE A-continued

| | Compounds | | | | | | | | | | | | | |
|---|---|---|---|---|---|---|---|---|---|---|---|---|---|---|
| 125 g ai/ha | 59 | 60 | 61 | 62 | 63 | 64 | 65 | 66 | 67 | 68 | 69 | 70 | 71 | 72 |
| | Preemergence | | | | | | | | | | | | | |
| Barnyardgrass | 40 | 60 | 30 | 10 | 10 | 10 | 0 | 20 | 0 | 0 | 10 | 0 | 0 | 10 |
| Corn | 0 | 0 | 0 | 0 | 0 | 0 | 0 | 0 | 0 | 0 | 0 | 0 | 0 | 0 |
| Crabgrass, Large | 90 | 90 | 60 | 60 | 90 | 80 | 10 | 90 | 30 | 70 | 90 | 40 | 10 | 70 |
| Foxtail, Giant | 50 | 60 | 10 | 60 | 50 | 50 | 0 | — | — | — | 40 | 30 | 0 | 0 |
| Morningglory | — | — | 60 | 90 | 10 | 0 | 0 | 0 | 30 | 20 | 0 | 0 | 0 | — |
| Pigweed | 90 | 90 | 80 | 80 | 100 | 80 | 0 | 90 | 90 | 90 | 100 | 60 | — | 50 |
| Velvetleaf | 100 | 80 | 60 | 70 | 80 | 60 | 30 | 70 | 70 | 70 | 70 | 70 | 50 | 90 |
| Wheat | 0 | 0 | 0 | 0 | — | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 73 | 74 | 75 | 76 | 77 | 78 | 79 | 80 | 81 | 82 | 83 | 84 | 85 | 86 |
| | Preemergence | | | | | | | | | | | | | |
| Barnyardgrass | 0 | 30 | 40 | 0 | 20 | 0 | 0 | 0 | 50 | 0 | 30 | 0 | 50 | 20 |
| Corn | 0 | 0 | 0 | 0 | 0 | 0 | 0 | 0 | 0 | 0 | 0 | 0 | 0 | — |
| Crabgrass, Large | 70 | 70 | 90 | 50 | 50 | 10 | 50 | 50 | 90 | — | 70 | 0 | 100 | — |
| Foxtail, Giant | 50 | 0 | 50 | 0 | 0 | 0 | 0 | 10 | 30 | 10 | 40 | 0 | — | — |
| Morningglory | 10 | 40 | 60 | 0 | — | 0 | 0 | 0 | 0 | 0 | 20 | 0 | 50 | 0 |
| Pigweed | 100 | 90 | 100 | 50 | 80 | 50 | 100 | 60 | 100 | 90 | 80 | 90 | — | — |
| Velvetleaf | 80 | 70 | 90 | 20 | 70 | 20 | 70 | 50 | 100 | 50 | 70 | 0 | 70 | — |
| Wheat | 10 | 0 | 0 | 0 | 0 | 0 | 0 | 0 | 0 | 0 | 0 | 0 | 0 | — |

| | Compounds | | | | | | | | | | | | | |
|---|---|---|---|---|---|---|---|---|---|---|---|---|---|---|
| 125 g ai/ha | 87 | 88 | 89 | 90 | 91 | 92 | 93 | 94 | 95 | 96 | 97 | 98 | 99 | 100 |
| | Preemergence | | | | | | | | | | | | | |
| Barnyardgrass | 20 | 10 | 20 | 40 | 60 | 60 | 80 | 0 | 40 | 90 | 60 | 0 | 10 | 40 |
| Corn | 0 | 0 | 0 | 0 | 0 | 0 | 0 | 0 | 0 | 0 | 0 | 0 | 0 | 0 |
| Crabgrass, Large | — | — | 60 | 60 | 90 | 90 | 90 | 30 | 50 | 100 | 100 | 90 | 60 | 80 |
| Foxtail, Giant | — | — | 20 | 30 | 40 | 70 | 60 | 0 | 30 | 50 | 60 | 40 | 40 | 50 |
| Morningglory | 50 | 50 | 0 | 0 | 20 | 0 | 80 | 10 | 70 | 80 | 70 | 70 | — | 70 |
| Pigweed | — | — | 90 | 80 | 90 | 100 | 100 | 70 | 100 | 100 | 100 | 100 | 80 | 80 |
| Velvetleaf | 100 | 80 | 70 | 70 | 100 | 90 | 90 | 40 | 90 | 100 | 100 | 90 | 80 | 60 |
| Wheat | 10 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 101 | 102 | 103 | 104 | 105 | 106 | 107 | 108 | 109 | 110 | 111 | 112 | 113 | 114 |
| | Preemergence | | | | | | | | | | | | | |
| Barnyardgrass | 20 | 40 | 0 | 0 | 0 | 10 | 40 | 30 | 10 | 20 | 30 | 0 | 10 | 30 |
| Corn | 0 | 0 | 0 | 0 | 0 | 0 | 20 | 0 | 0 | 0 | 0 | 0 | 0 | 0 |
| Crabgrass, Large | 70 | 80 | 40 | 0 | 30 | 70 | 90 | 70 | 40 | 40 | 90 | 60 | 70 | 90 |
| Foxtail, Giant | 30 | 80 | 0 | 0 | 30 | 40 | 60 | 30 | 0 | 0 | — | 20 | 70 | 40 |
| Morningglory | 80 | 80 | 20 | 0 | 0 | 50 | 70 | 80 | 40 | 40 | 50 | 0 | 30 | 0 |
| Pigweed | 70 | 60 | 90 | 80 | 80 | 80 | 100 | 90 | 90 | 80 | 100 | 20 | 100 | 100 |
| Velvetleaf | 80 | 80 | 60 | 0 | 0 | 40 | 100 | 80 | 70 | 60 | 90 | 40 | 100 | 70 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 115 | 116 | 117 | 118 | 119 | 120 | 121 | 122 | 123 | 124 | 125 | 126 | 127 | 128 |
| | Preemergence | | | | | | | | | | | | | |
| Barnyardgrass | 0 | 10 | 50 | 30 | 70 | 70 | 20 | 30 | 50 | 20 | 10 | 70 | 40 | 10 |
| Corn | 0 | 0 | 0 | 0 | 20 | 20 | 0 | 0 | 0 | 0 | 0 | 0 | 0 | 0 |
| Crabgrass, Large | 20 | 30 | 60 | 60 | 100 | 100 | 90 | 90 | 100 | 60 | 80 | 90 | 90 | 80 |
| Foxtail, Giant | 20 | 10 | 20 | 10 | 90 | 90 | 80 | 30 | 50 | 10 | 40 | 60 | 50 | 60 |
| Morningglory | 60 | 0 | 40 | 10 | 60 | 30 | 0 | 40 | 70 | 60 | 0 | 70 | 10 | 80 |
| Pigweed | 70 | 60 | 90 | 90 | 100 | 100 | 80 | 100 | 90 | 100 | 90 | 100 | 100 | 80 |
| Velvetleaf | 60 | 30 | 70 | 70 | 90 | 80 | 80 | 100 | 70 | 70 | 60 | 80 | 70 | 80 |
| Wheat | 0 | 0 | 0 | 0 | 20 | 0 | 0 | 0 | 0 | 0 | 0 | 0 | 0 | 0 |

TABLE A-continued

| | Compounds | | | | | | | | | | | | | |
|---|---|---|---|---|---|---|---|---|---|---|---|---|---|---|
| 125 g ai/ha | 129 | 130 | 131 | 132 | 133 | 134 | 135 | 136 | 138 | 139 | 140 | 141 | 142 | 143 |
| | Preemergence | | | | | | | | | | | | | |
| Barnyardgrass | 30 | 20 | 50 | 10 | 10 | 0 | 0 | 0 | 20 | 40 | 60 | 60 | 10 | 40 |
| Corn | 0 | 20 | 0 | 0 | 0 | 0 | 0 | 0 | 0 | 0 | 0 | 0 | 0 | 0 |
| Crabgrass, Large | 70 | 40 | 80 | 50 | 50 | 0 | 0 | 20 | 40 | 90 | 70 | 80 | 30 | 50 |
| Foxtail, Giant | 40 | 20 | 60 | 20 | 40 | 0 | 0 | 0 | 30 | 20 | 40 | 40 | 0 | 10 |
| Morningglory | — | 10 | — | 0 | 0 | — | 20 | 30 | 0 | 0 | 30 | 0 | 0 | 10 |
| Pigweed | 100 | 90 | 100 | 10 | 40 | 0 | 40 | 80 | 50 | 70 | 80 | 70 | 90 | 70 |
| Velvetleaf | 80 | 80 | 80 | 50 | 50 | 70 | 40 | 70 | 20 | 60 | 80 | 70 | 20 | 70 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 144 | 145 | 146 | 147 | 148 | 149 | 150 | 151 | 152 | 153 | 154 | 155 | 156 | 157 |
| | Preemergence | | | | | | | | | | | | | |
| Barnyardgrass | 0 | 20 | 60 | 70 | 10 | 20 | 0 | 20 | 50 | 40 | 0 | 10 | 0 | 0 |
| Corn | 0 | 0 | 0 | 0 | 0 | 0 | 0 | 0 | 0 | 20 | 0 | 0 | 0 | 0 |
| Crabgrass, Large | 10 | 50 | 60 | 100 | 0 | 30 | 0 | 10 | 90 | 80 | 10 | 60 | 10 | 20 |
| Foxtail, Giant | 0 | 30 | 30 | 70 | 0 | 10 | 0 | 20 | 60 | 20 | 10 | 30 | 10 | 10 |
| Morningglory | 0 | 0 | 10 | 40 | 0 | 0 | 0 | — | 60 | 20 | 0 | 0 | 0 | 0 |
| Pigweed | 0 | 70 | 70 | 90 | 0 | 80 | 0 | 50 | 100 | 100 | 30 | 90 | 70 | 0 |
| Velvetleaf | 20 | 90 | 70 | 80 | 30 | 40 | 0 | 50 | 60 | 100 | 40 | 60 | 0 | 60 |
| Wheat | 0 | 0 | 0 | 0 | 0 | 0 | 0 | 0 | 20 | 0 | 0 | 0 | 0 | 0 |

| | Compounds | | | | | | | | | | | | | |
|---|---|---|---|---|---|---|---|---|---|---|---|---|---|---|
| 125 g ai/ha | 158 | 159 | 160 | 161 | 162 | 163 | 164 | 165 | 166 | 167 | 168 | 169 | 170 | 171 |
| | Preemergence | | | | | | | | | | | | | |
| Barnyardgrass | 20 | 30 | 40 | 10 | 10 | 0 | 10 | 0 | 0 | 0 | 0 | 0 | 0 | 20 |
| Corn | 0 | 0 | 0 | 0 | 0 | 0 | 0 | 0 | 0 | 0 | 0 | 0 | 0 | 0 |
| Crabgrass, Large | 70 | 80 | 80 | 50 | 90 | 0 | 30 | 0 | 10 | 20 | 30 | 40 | 10 | 70 |
| Foxtail, Giant | 10 | 60 | 20 | 50 | 30 | 0 | 40 | 0 | 0 | 10 | 10 | 40 | 10 | 30 |
| Morningglory | 0 | 0 | 70 | 0 | 0 | 0 | 10 | — | 0 | 0 | 0 | 0 | 0 | 0 |
| Pigweed | 100 | 100 | 80 | 90 | 100 | 0 | 60 | 0 | 0 | 10 | 10 | 0 | 30 | 50 |
| Velvetleaf | 50 | 70 | 60 | 70 | 60 | 10 | 40 | 0 | 40 | 70 | 0 | 20 | 10 | 80 |
| Wheat | 0 | 0 | 0 | 0 | 0 | 0 | 0 | 0 | 0 | 0 | 0 | 0 | 0 | 20 |

| | Compounds | | | | | | | | | | | | | |
|---|---|---|---|---|---|---|---|---|---|---|---|---|---|---|
| 125 g ai/ha | 172 | 173 | 174 | 175 | 176 | 177 | 178 | 179 | 180 | 181 | 182 | 183 | 184 | 185 |
| | Preemergence | | | | | | | | | | | | | |
| Barnyardgrass | 10 | 0 | 0 | 0 | 10 | 0 | 0 | 0 | 30 | 20 | 70 | 20 | 20 | 0 |
| Corn | 0 | 0 | 10 | 0 | 0 | 0 | 0 | 0 | 0 | 0 | 0 | 0 | 0 | 0 |
| Crabgrass, Large | 10 | 40 | 20 | 30 | 0 | 0 | 10 | 20 | 80 | 90 | 100 | 90 | 30 | 0 |
| Foxtail, Giant | 10 | 20 | 0 | 0 | 10 | 0 | 10 | 10 | 30 | 30 | 50 | 60 | 30 | 0 |
| Morningglory | 0 | 0 | 0 | 0 | 0 | 0 | 0 | 0 | 0 | 0 | 70 | 20 | 10 | — |
| Pigweed | 10 | 50 | 30 | 60 | 60 | 0 | 0 | 50 | 90 | 100 | 90 | 90 | 70 | 0 |
| Velvetleaf | 50 | 70 | 20 | 40 | 10 | 0 | 10 | 50 | 80 | 70 | 70 | 100 | 80 | 0 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 125 g ai/ha | 186 | 187 | 188 | 189 | 190 | 191 | 192 | 193 | 194 | 195 | 196 | 197 | 198 | 199 |
| | Preemergence | | | | | | | | | | | | | |
| Barnyardgrass | 0 | 20 | 0 | 20 | 10 | 10 | 10 | 80 | 0 | 0 | 0 | 0 | 0 | 20 |
| Corn | 0 | 0 | 0 | 0 | 0 | 0 | 40 | 0 | 0 | 0 | 0 | 0 | 0 | 20 |
| Crabgrass, Large | 30 | 30 | 30 | 30 | 60 | 50 | 10 | 90 | 20 | 0 | 0 | 0 | 10 | 60 |
| Foxtail, Giant | 20 | 30 | 10 | 30 | 60 | 40 | 0 | 90 | — | 0 | 0 | 0 | 70 | 60 |
| Morningglory | 20 | 80 | 70 | — | — | 0 | 0 | 80 | — | 0 | 0 | 0 | 0 | 70 |
| Pigweed | 50 | 60 | 60 | 70 | 70 | 80 | 0 | 100 | 50 | 0 | 0 | 20 | 10 | 80 |
| Velvetleaf | 60 | 70 | 70 | 70 | 70 | 60 | 0 | 100 | 30 | 0 | 0 | 40 | 0 | 90 |
| Wheat | 0 | 0 | 0 | 0 | 0 | 0 | 0 | 0 | 0 | 0 | 0 | 0 | 0 | 0 |

TABLE A-continued

| 125 g ai/ha | Compounds | | | | | | | | | | | | | |
|---|---|---|---|---|---|---|---|---|---|---|---|---|---|---|
| | 200 | 202 | 203 | 204 | 205 | 206 | 207 | 208 | 209 | 210 | 211 | 212 | 213 | 214 |
| Preemergence | | | | | | | | | | | | | | |
| Barnyardgrass | 0 | 20 | 30 | 30 | 0 | 0 | 10 | 10 | 0 | 10 | 10 | 10 | 0 | 10 |
| Corn | 0 | 20 | 0 | 20 | 0 | 0 | 0 | 0 | 0 | 0 | 0 | 0 | 0 | 0 |
| Crabgrass, Large | 0 | 50 | 20 | 40 | 20 | 10 | 60 | 80 | 20 | 10 | 10 | 0 | 0 | 30 |
| Foxtail, Giant | 0 | 50 | 30 | 20 | 10 | 0 | 30 | 40 | 10 | 20 | 20 | 10 | 10 | 30 |
| Morningglory | 0 | 0 | 0 | 0 | 0 | 0 | 0 | 0 | 0 | 0 | 0 | 0 | — | 0 |
| Pigweed | 0 | 90 | 100 | 100 | 10 | 30 | 80 | 60 | 0 | 60 | 40 | 60 | 50 | 70 |
| Velvetleaf | 0 | 70 | 50 | 50 | 10 | 0 | 70 | 0 | 60 | 40 | 30 | 50 | 40 | 90 |
| Wheat | 0 | 0 | 0 | 20 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 215 | 216 | 218 | 219 | 220 | 221 | 222 | 223 | 224 | 225 | 226 | 227 | 228 | 229 |
| Preemergence | | | | | | | | | | | | | | |
| Barnyardgrass | 0 | 0 | 20 | 40 | 10 | 0 | 0 | 0 | 0 | 20 | 30 | 50 | 40 | 0 |
| Corn | 0 | 0 | 0 | 0 | 0 | 0 | 0 | 0 | 20 | 0 | 0 | 0 | 0 | 0 |
| Crabgrass, Large | 0 | 0 | 10 | 50 | 20 | 0 | 20 | 30 | 70 | 60 | 90 | 90 | 100 | 80 |
| Foxtail, Giant | 10 | 0 | 0 | 10 | 0 | 0 | 30 | 30 | 20 | 40 | 70 | 40 | 50 | 50 |
| Morningglory | 0 | 0 | 0 | 20 | 0 | 0 | 0 | 10 | — | 30 | 60 | 50 | 70 | 40 |
| Pigweed | 20 | 0 | 20 | 90 | 80 | 0 | 0 | 60 | 70 | 90 | 100 | 80 | 100 | 90 |
| Velvetleaf | 0 | 0 | 50 | 30 | 40 | 20 | 0 | 0 | 50 | 80 | 80 | 90 | 100 | 100 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 230 | 231 | 232 | 233 | 234 | 235 | 236 | 237 | 238 | 239 | 240 | 241 | 242 | 243 |
| Preemergence | | | | | | | | | | | | | | |
| Barnyardgrass | 10 | 0 | 0 | 30 | 0 | 90 | 50 | 20 | 70 | 20 | 40 | 10 | 0 | 70 |
| Corn | 0 | 0 | 0 | 0 | 0 | 20 | 0 | 0 | 0 | 0 | 0 | 0 | 0 | 30 |
| Crabgrass, Large | 30 | 40 | 10 | 40 | 60 | 100 | 80 | 40 | 90 | 70 | 50 | 20 | 0 | 100 |
| Foxtail, Giant | 40 | 0 | 0 | 20 | 10 | 70 | 40 | 40 | 50 | 20 | 40 | 10 | 0 | 90 |
| Morningglory | 0 | 10 | 0 | 50 | — | 80 | 70 | 10 | 40 | — | 0 | 0 | 0 | 70 |
| Pigweed | — | 50 | 0 | 70 | 50 | 90 | 80 | 30 | 100 | 70 | 20 | 20 | 0 | 100 |
| Velvetleaf | 60 | 50 | 0 | 60 | 30 | 100 | 80 | 80 | 90 | 80 | 60 | 20 | 0 | 90 |
| Wheat | 0 | 0 | 0 | 0 | 0 | 10 | 0 | 0 | 0 | 0 | 0 | 0 | 0 | 30 |

| 125 g ai/ha | Compounds | | | | | | | | | | | | |
|---|---|---|---|---|---|---|---|---|---|---|---|---|---|
| | 244 | 245 | 246 | 247 | 248 | 249 | 250 | 251 | 252 | 253 | 254 | 255 | 256 |
| Preemergence | | | | | | | | | | | | | | |
| Barnyardgrass | 30 | 40 | 10 | 0 | 0 | 0 | 0 | 0 | 0 | 10 | 0 | 10 | 0 |
| Corn | 20 | 0 | 0 | 0 | 0 | 0 | 0 | 0 | 0 | 0 | 0 | 0 | 0 |
| Crabgrass, Large | 90 | 80 | 100 | 0 | 10 | 40 | 30 | 20 | 10 | 30 | 0 | 20 | 10 |
| Foxtail, Giant | 70 | 80 | 90 | 0 | 10 | 20 | 30 | 10 | 0 | 20 | 0 | 0 | 0 |
| Morningglory | 30 | 20 | 20 | 0 | 0 | 30 | 10 | 0 | 0 | 40 | 0 | 40 | 0 |
| Pigweed | 100 | 80 | 100 | 0 | 0 | 80 | 60 | 0 | 0 | 20 | 0 | 70 | 0 |
| Velvetleaf | 50 | 70 | 90 | 0 | 20 | 60 | 50 | 50 | 20 | 50 | 0 | 60 | 20 |
| Wheat | 0 | 0 | 0 | 0 | 0 | 0 | 0 | 0 | 0 | 0 | 0 | 0 | 0 |

Test B

Seeds of plant species selected from blackgrass (*Alopecurus myosuroides*), downy bromegrass (*Bromus tectorum*), green foxtail (*Setaria viridis*), Italian ryegrass (*Lolium multiflorum*), wheat (*Triticum aestivum*), wild oat (*Avena fatua*), deadnettle (henbit deadnettle, *Lamium amplexicaule*), galium (catchweed bedstraw, *Galium aparine*), bermudagrass (*Cynodon dactylon*), Surinam grass (*Brachiaria decumbens*), cocklebur (*Xanthium strumarium*), corn (*Zea mays*), large crabgrass (*Digitaria sanguinalis*), woolly cupgrass (*Eriochloa villosa*), giant foxtail (*Setaria faberii*), goosegrass (*Eleusine indica*), johnsongrass (*Sorghum halepense*), kochia (*Kochia scoparia*), lambsquarters (*Chenopodium album*), morning glory (*Ipomoea coccinea*), nightshade (eastern black nightshade, *Solanum ptycanthum*), yellow nutsedge (*Cyperus esculentus*), pigweed (*Amaranthus retroflexus*), ragweed (common ragweed, *Ambrosia elatior*), Russian thistle (*Salsola kali*), soybean (*Glycine max*), sunflower (common oilseed sunflower, *Helianthus annuus*) and velvetleaf (*Abutilon theophrasti*) were planted into a blend of loam soil and sand and treated preemergence with test compounds formulated in a non-phytotoxic solvent mixture which included a surfactant.

At the same time, plants selected from these crop and weed species and also winter barley (*Hordeum vulgare*), canarygrass (*Phalaris minor*), chickweed (*Stellaria media*) and windgrass (*Apera spica-venti*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of some of the test chemicals formulated in the same manner. Plants ranged in height from 2 to 18 cm (1- to 4-leaf stage) for postemergence treatments.

Plant species in the flooded paddy test consisted of rice (*Oryza sativa*), umbrella sedge (*Cyperus difformis*), ducksalad (*Heteranthera limosa*) and barnyardgrass (*Echinochloa crus-galli*) grown to the 2-leaf stage for testing. At the time of treatment, test pots were flooded with water to 3 cm above the soil surface, treated by application of test compounds directly to the paddy water, and then maintained at that water depth for the duration of the test.

Treated plants and controls were maintained in a greenhouse for 13 to 15 days, after which time all treated plants were visually evaluated and compared to controls. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| | 1 | 2 | 3 | 4 | 7 | 8 | 9 | 10 | 11 | 12 | 13 | 14 | 15 | 16 |
| | Flood | | | | | | | | | | | | | |
| Barnyardgrass | 0 | 0 | 0 | 20 | 0 | 45 | 50 | 0 | 25 | 0 | 35 | 0 | 35 | 10 |
| Ducksalad | 0 | 78 | 70 | 85 | 0 | 90 | 75 | 80 | 80 | 55 | 95 | 40 | 60 | 75 |
| Rice | 0 | 8 | 0 | 0 | 0 | 50 | 0 | 0 | 25 | 0 | 25 | 0 | 0 | 10 |
| Sedge, Umbrella | 0 | 75 | 60 | 90 | 0 | 95 | 75 | 55 | 85 | 65 | 85 | 40 | 30 | 50 |
| 250 g ai/ha | Compounds | | | | | | | | | | | | | |
| | 17 | 18 | 19 | 20 | 21 | 22 | 23 | 24 | 25 | 26 | 27 | 28 | 29 | 30 |
| | Flood | | | | | | | | | | | | | |
| Barnyardgrass | 25 | 50 | 15 | 0 | 0 | 0 | 0 | 20 | 0 | 0 | 40 | 20 | 30 | 0 |
| Ducksalad | 45 | 90 | 90 | 75 | 75 | 60 | 45 | 75 | 0 | 85 | 85 | 85 | 85 | 50 |
| Rice | 15 | 25 | 0 | 15 | 0 | 0 | 15 | 0 | 0 | 0 | 0 | 0 | 0 | 0 |
| Sedge, Umbrella | 80 | 85 | 95 | 60 | 65 | 65 | 45 | 75 | 0 | 85 | 85 | 80 | 80 | 50 |
| 250 g ai/ha | Compounds | | | | | | | | | | | | | |
| | 31 | 32 | 33 | 34 | 35 | 36 | 37 | 38 | 39 | 40 | 41 | 42 | 43 | 44 |
| | Flood | | | | | | | | | | | | | |
| Barnyardgrass | 0 | 40 | 40 | 0 | 0 | 15 | 0 | 0 | 30 | 40 | 30 | 0 | 20 | 30 |
| Ducksalad | 75 | 95 | 95 | 65 | 0 | 40 | 60 | 65 | 90 | 90 | 75 | 50 | 80 | 90 |
| Rice | 0 | 30 | 50 | 0 | — | 35 | 20 | 0 | 15 | 25 | 0 | 20 | 40 | 40 |
| Sedge, Umbrella | 75 | 90 | 85 | 40 | 0 | 20 | 40 | 40 | 90 | 85 | 80 | 30 | 80 | 90 |
| 250 g ai/ha | Compounds | | | | | | | | | | | | | |
| | 45 | 46 | 47 | 48 | 49 | 50 | 51 | 52 | 53 | 54 | 55 | 56 | 57 | 58 |
| | Flood | | | | | | | | | | | | | |
| Barnyardgrass | 30 | 0 | 20 | 35 | 0 | 60 | 55 | 55 | 75 | 0 | 20 | 35 | 25 | 0 |
| Ducksalad | 90 | 20 | 95 | 85 | 70 | 85 | 95 | 70 | 75 | 40 | 50 | 50 | 60 | 0 |
| Rice | 20 | 10 | 25 | 65 | 15 | 20 | 60 | 60 | 85 | 0 | 25 | 20 | 25 | 0 |
| Sedge, Umbrella | 85 | 65 | 85 | 75 | 85 | 95 | 90 | 40 | 90 | 40 | 60 | 75 | 75 | 0 |
| 250 g ai/ha | Compounds | | | | | | | | | | | | | |
| | 59 | 60 | 61 | 62 | 63 | 64 | 65 | 66 | 67 | 68 | 69 | 70 | 71 | 72 |
| | Flood | | | | | | | | | | | | | |
| Barnyardgrass | 45 | 40 | 20 | 0 | 10 | 0 | 0 | 45 | 0 | 20 | 30 | 20 | 0 | 30 |
| Ducksalad | 40 | 60 | 0 | 30 | 40 | 60 | 0 | 20 | 0 | 40 | 20 | 0 | 0 | 0 |
| Rice | 15 | 15 | 0 | 0 | 10 | 0 | 0 | 20 | 0 | 30 | 0 | 20 | 0 | 20 |
| Sedge, Umbrella | 75 | 85 | 0 | 0 | 0 | 40 | 0 | 50 | 0 | 0 | 40 | 20 | 25 | 30 |
| 250 g ai/ha | Compounds | | | | | | | | | | | | | |
| | 73 | 74 | 75 | 76 | 77 | 78 | 79 | 80 | 81 | 82 | 83 | 84 | 85 | 86 |
| | Flood | | | | | | | | | | | | | |
| Barnyardgrass | 0 | 40 | 60 | 0 | 65 | 0 | 30 | 30 | 60 | 20 | 40 | 0 | 65 | 60 |
| Ducksalad | 0 | 0 | 50 | 0 | 40 | 20 | 40 | 30 | 40 | 20 | 50 | 20 | 65 | 65 |
| Rice | 0 | 0 | 45 | 0 | 15 | 20 | 20 | 15 | 15 | 20 | 30 | 0 | 20 | 40 |
| Sedge, Umbrella | 0 | 60 | 50 | 0 | 40 | 40 | 30 | 40 | 40 | 50 | 50 | 50 | 80 | 85 |

TABLE B-continued

| 250 g ai/ha | Compounds | | | | | | | | | | | | | |
|---|---|---|---|---|---|---|---|---|---|---|---|---|---|---|
| | 87 | 88 | 89 | 90 | 91 | 92 | 93 | 94 | 95 | 96 | 97 | 98 | 99 | 100 |
| | Flood | | | | | | | | | | | | | |
| Barnyardgrass | 60 | 60 | 40 | 30 | 65 | 45 | 85 | 60 | 70 | 85 | 75 | 50 | 55 | 75 |
| Ducksalad | 20 | 80 | 100 | 90 | 100 | 85 | 80 | 30 | 20 | 75 | 70 | 0 | 80 | 85 |
| Rice | 70 | 50 | 15 | 0 | 15 | 40 | 45 | 35 | 30 | 15 | 40 | 40 | 60 | — |
| Sedge, Umbrella | 70 | 65 | 85 | 80 | 100 | 85 | 90 | 85 | 75 | 90 | 80 | 75 | 85 | 85 |

| 250 g ai/ha | Compounds | | | | | | | | | | | | | |
|---|---|---|---|---|---|---|---|---|---|---|---|---|---|---|
| | 101 | 102 | 103 | 104 | 105 | 106 | 107 | 108 | 109 | 110 | 111 | 112 | 113 | 114 |
| | Flood | | | | | | | | | | | | | |
| Barnyardgrass | 40 | 70 | 0 | 0 | 0 | 15 | 60 | 30 | 20 | 40 | 60 | 40 | 15 | 40 |
| Ducksalad | 30 | 85 | 0 | 0 | 0 | 0 | 40 | 70 | 100 | 75 | 75 | 95 | 70 | 75 |
| Rice | 20 | 35 | 0 | 0 | 0 | 20 | 45 | 10 | 25 | 30 | 30 | 15 | 0 | 20 |
| Sedge, Umbrella | 65 | 75 | 0 | 0 | 0 | 0 | 85 | 95 | 80 | 75 | 85 | 90 | 70 | 40 |

| 250 g ai/ha | Compounds | | | | | | | | | | | | | |
|---|---|---|---|---|---|---|---|---|---|---|---|---|---|---|
| | 115 | 116 | 117 | 118 | 119 | 120 | 121 | 122 | 123 | 124 | 125 | 126 | 127 | 128 |
| | Flood | | | | | | | | | | | | | |
| Barnyardgrass | 65 | 75 | 75 | 70 | 50 | 65 | 70 | 40 | 70 | 30 | 60 | 75 | 75 | 40 |
| Ducksalad | 85 | 85 | 100 | 100 | 70 | 85 | 80 | 0 | 95 | 0 | 70 | 85 | 80 | 100 |
| Rice | 20 | 0 | 15 | 15 | 35 | 40 | 55 | 15 | 40 | 20 | 0 | 15 | 35 | 35 |
| Sedge, Umbrella | 90 | 90 | 95 | 85 | 75 | 75 | 70 | 45 | 85 | 40 | 90 | 85 | 80 | 75 |

| 250 g ai/ha | Compounds | | | | | | | | | | | | | |
|---|---|---|---|---|---|---|---|---|---|---|---|---|---|---|
| | 129 | 130 | 131 | 132 | 133 | 134 | 135 | 136 | 138 | 139 | 140 | 141 | 142 | 143 |
| | Flood | | | | | | | | | | | | | |
| Barnyardgrass | 60 | 85 | 50 | 30 | 0 | 0 | 0 | 25 | 25 | 35 | 45 | 50 | 10 | 20 |
| Ducksalad | 100 | 100 | 85 | 100 | 100 | 0 | 40 | 75 | 80 | 90 | 85 | 85 | 80 | 90 |
| Rice | 30 | 25 | 55 | 0 | 0 | 0 | 0 | 20 | 15 | 30 | 40 | 35 | 0 | 0 |
| Sedge, Umbrella | 60 | 100 | 85 | 100 | 100 | 0 | 0 | 50 | 80 | 85 | 85 | 85 | 80 | 65 |

| 250 g ai/ha | Compounds | | | | | | | | | | | | | |
|---|---|---|---|---|---|---|---|---|---|---|---|---|---|---|
| | 144 | 145 | 146 | 147 | 148 | 151 | 152 | 153 | 154 | 155 | 156 | 158 | 161 | 162 |
| | Flood | | | | | | | | | | | | | |
| Barnyardgrass | 20 | 25 | 30 | 75 | 50 | 55 | 75 | 45 | 40 | 45 | 60 | 60 | 30 | 55 |
| Ducksalad | 100 | 80 | 100 | 100 | 100 | 100 | 100 | 100 | 100 | 95 | 100 | 100 | 80 | 100 |
| Rice | 25 | 0 | 35 | 15 | 50 | 50 | 60 | 65 | 75 | 45 | 35 | 85 | 50 | 90 |
| Sedge, Umbrella | 100 | 80 | 90 | 80 | 95 | 100 | 100 | 95 | 100 | 100 | 100 | 100 | 60 | 100 |

| 250 g ai/ha | Compounds | | | | | | | | | | | | | |
|---|---|---|---|---|---|---|---|---|---|---|---|---|---|---|
| | 164 | 178 | 179 | 183 | 184 | 185 | 186 | 187 | 188 | 189 | 190 | 191 | 192 | 193 |
| | Flood | | | | | | | | | | | | | |
| Barnyardgrass | 0 | 80 | 30 | 35 | 25 | 0 | 30 | 80 | 0 | 70 | 30 | 25 | 0 | 50 |
| Ducksalad | 85 | 100 | 100 | 95 | 100 | 75 | 100 | 100 | 85 | 100 | 100 | 100 | 75 | 100 |
| Rice | 35 | 70 | 65 | 0 | 15 | 0 | 65 | 70 | 15 | 60 | 15 | 0 | 20 | 65 |
| Sedge, Umbrella | 90 | 95 | 95 | 90 | 95 | 60 | 90 | 100 | 85 | 100 | 95 | 85 | 60 | 90 |

| 250 g ai/ha | Compounds | | | | | | | | | | | | | |
|---|---|---|---|---|---|---|---|---|---|---|---|---|---|---|
| | 194 | 195 | 196 | 197 | 198 | 199 | 200 | 203 | 204 | 206 | 207 | 208 | 209 | 210 |
| | Flood | | | | | | | | | | | | | |
| Barnyardgrass | 15 | 20 | 30 | 30 | 35 | 25 | 38 | 20 | 60 | 0 | 20 | 25 | 20 | 40 |
| Ducksalad | 80 | 85 | 95 | 85 | 95 | 90 | 85 | 95 | 100 | 90 | 50 | 75 | 85 | 90 |
| Rice | 0 | 15 | 65 | 45 | 50 | 0 | 23 | 0 | 60 | 20 | 15 | 0 | 20 | 25 |
| Sedge, Umbrella | 65 | 65 | 80 | 85 | 80 | 85 | 70 | 85 | 95 | 85 | 70 | 70 | 80 | 80 |

TABLE B-continued

| 250 g ai/ha | Compounds | | | | | | | | | | | | | |
|---|---|---|---|---|---|---|---|---|---|---|---|---|---|---|
| | 211 | 212 | 213 | 214 | 215 | 216 | 217 | 218 | 219 | 220 | 221 | 222 | 223 | 224 |
| Flood | | | | | | | | | | | | | | |
| Barnyardgrass | 35 | 50 | 30 | 20 | 40 | 0 | 0 | 40 | 60 | 40 | 20 | 0 | 0 | 30 |
| Ducksalad | 85 | 95 | 100 | 95 | 85 | 95 | 40 | 95 | 90 | 100 | 70 | 65 | 0 | 75 |
| Rice | 15 | 10 | 20 | 15 | 15 | 0 | 20 | 15 | 75 | 70 | 15 | 0 | 0 | 60 |
| Sedge, Umbrella | 80 | 95 | 90 | 85 | 90 | 100 | 40 | 85 | 85 | 85 | 75 | 40 | 0 | 75 |

| 250 g ai/ha | Compounds | | | | | | | | | | | | | |
|---|---|---|---|---|---|---|---|---|---|---|---|---|---|---|
| | 226 | 227 | 228 | 229 | 230 | 231 | 232 | 233 | 234 | 235 | 236 | 237 | 238 | 239 |
| Flood | | | | | | | | | | | | | | |
| Barnyardgrass | 95 | 60 | 80 | 30 | 40 | 40 | 50 | 65 | 0 | 75 | 20 | 30 | 40 | 15 |
| Ducksalad | 40 | 80 | 80 | 40 | 0 | 0 | 85 | 100 | 70 | 100 | 70 | 100 | 100 | 80 |
| Rice | 65 | 55 | 60 | 20 | 45 | 0 | 0 | 50 | 0 | 55 | 0 | 45 | 0 | 0 |
| Sedge, Umbrella | 60 | 85 | 85 | 70 | 75 | 75 | 80 | 85 | 40 | 80 | 40 | 100 | 80 | 75 |

| 250 g ai/ha | Compounds | | | | | | | | | | | | |
|---|---|---|---|---|---|---|---|---|---|---|---|---|---|
| | 243 | 244 | 245 | 246 | 248 | 249 | 250 | 251 | 252 | 253 | 254 | 255 | 256 |
| Flood | | | | | | | | | | | | | | |
| Barnyardgrass | 85 | 75 | 65 | 60 | 40 | 0 | 10 | 20 | 0 | 20 | 15 | 0 | 0 |
| Ducksalad | 100 | 100 | 100 | 100 | 90 | 90 | 75 | 80 | 0 | 90 | 100 | 80 | 85 |
| Rice | 75 | 85 | 90 | 65 | 0 | 15 | 0 | 10 | 0 | 20 | 0 | 0 | 0 |
| Sedge, Umbrella | 100 | 100 | 100 | 100 | 85 | 90 | 70 | 75 | 0 | 85 | 80 | 60 | 75 |

| 125 g ai/ha | Compounds | | | | | | | | | | | | | |
|---|---|---|---|---|---|---|---|---|---|---|---|---|---|---|
| | 1 | 2 | 3 | 4 | 7 | 8 | 9 | 10 | 11 | 12 | 13 | 14 | 16 | 17 |
| Flood | | | | | | | | | | | | | | |
| Barnyardgrass | 0 | 0 | 0 | 0 | 0 | 20 | 0 | 0 | 0 | 0 | 0 | 0 | 0 | 25 |
| Ducksalad | 0 | 58 | 70 | 75 | 0 | 85 | 60 | 75 | 65 | 35 | 0 | 30 | 75 | 30 |
| Rice | 0 | 0 | 0 | 0 | 0 | 15 | 0 | 0 | 20 | 0 | 0 | 0 | 0 | 0 |
| Sedge, Umbrella | 0 | 45 | 60 | 80 | 0 | 85 | 70 | 55 | 40 | 50 | 60 | 0 | 40 | 70 |

| 125 g ai/ha | Compounds | | | | | | | | | | | | | |
|---|---|---|---|---|---|---|---|---|---|---|---|---|---|---|
| | 18 | 19 | 20 | 21 | 22 | 23 | 33 | 34 | 35 | 36 | 37 | 38 | 49 | 50 |
| Flood | | | | | | | | | | | | | | |
| Barnyardgrass | 20 | 0 | 0 | 0 | 0 | 0 | 30 | 0 | 0 | 0 | 0 | 0 | 0 | 35 |
| Ducksalad | 65 | 85 | 65 | 70 | 30 | 45 | 80 | 30 | 0 | 0 | 50 | 60 | 40 | 85 |
| Rice | 25 | 0 | 0 | 0 | 0 | 0 | 20 | 0 | 0 | 20 | 0 | 0 | 10 | 15 |
| Sedge, Umbrella | 50 | 85 | 50 | 60 | 40 | 40 | 50 | 0 | 0 | 0 | 30 | 30 | 0 | 85 |

| 125 g ai/ha | Compounds | | | | | | | | | | | | | |
|---|---|---|---|---|---|---|---|---|---|---|---|---|---|---|
| | 51 | 52 | 53 | 54 | 55 | 56 | 57 | 58 | 59 | 60 | 61 | 62 | 63 | 64 |
| Flood | | | | | | | | | | | | | | |
| Barnyardgrass | 40 | 40 | 55 | 0 | 20 | 20 | 20 | 0 | 20 | 30 | 0 | 0 | 0 | 0 |
| Ducksalad | 85 | 40 | 75 | 30 | 0 | 40 | 40 | 0 | 0 | 40 | 0 | 0 | 40 | 50 |
| Rice | 25 | 50 | 60 | 0 | 15 | 15 | 15 | 0 | 15 | 0 | 0 | 0 | 0 | 0 |
| Sedge, Umbrella | 85 | 30 | 90 | 0 | 40 | 60 | 50 | 0 | 50 | 75 | 0 | 0 | 0 | 0 |

| 125 g ai/ha | Compounds | | | | | | | | | | | | | |
|---|---|---|---|---|---|---|---|---|---|---|---|---|---|---|
| | 65 | 66 | 67 | 68 | 69 | 70 | 71 | 72 | 76 | 79 | 80 | 81 | 82 | 83 |
| Flood | | | | | | | | | | | | | | |
| Barnyardgrass | 0 | 0 | 0 | 0 | 20 | 0 | 0 | 0 | 0 | 20 | 25 | 40 | 15 | 15 |
| Ducksalad | 0 | 0 | 0 | 30 | 0 | 0 | 0 | 0 | 0 | 15 | 30 | 15 | 0 | 40 |
| Rice | 0 | 0 | 0 | 20 | 0 | 0 | 0 | 20 | 0 | 15 | 0 | 15 | 15 | 0 |
| Sedge, Umbrella | 0 | 30 | 0 | 0 | 0 | 0 | 20 | 0 | 0 | 0 | 30 | 30 | 40 | 40 |

TABLE B-continued

| | Compounds | | | | | | | | | | | | | |
|---|---|---|---|---|---|---|---|---|---|---|---|---|---|---|
| 125 g ai/ha | 84 | 85 | 86 | 87 | 88 | 89 | 90 | 91 | 92 | 93 | 94 | 95 | 96 | 97 |
| | Flood | | | | | | | | | | | | | |
| Barnyardgrass | 0 | 55 | 50 | 55 | 40 | 30 | 15 | 60 | 20 | 75 | 40 | 65 | 80 | 60 |
| Ducksalad | 0 | 60 | 55 | 20 | 75 | 100 | 80 | 90 | 70 | 80 | 25 | 0 | 50 | 30 |
| Rice | 0 | 15 | 20 | 60 | 40 | 0 | 0 | 15 | 25 | 20 | 20 | 30 | 15 | 0 |
| Sedge, Umbrella | 30 | 80 | 70 | 50 | 40 | 85 | 75 | 100 | 70 | 80 | 85 | 50 | 85 | 70 |

| | Compounds | | | | | | | | | | | | | |
|---|---|---|---|---|---|---|---|---|---|---|---|---|---|---|
| 125 g ai/ha | 98 | 99 | 100 | 101 | 102 | 103 | 104 | 105 | 106 | 108 | 109 | 110 | 111 | 123 |
| | Flood | | | | | | | | | | | | | |
| Barnyardgrass | 30 | 20 | 60 | 40 | 60 | 0 | 0 | 0 | 0 | 15 | 20 | 20 | 50 | 55 |
| Ducksalad | 0 | 75 | 85 | 30 | 80 | 0 | 0 | 0 | 0 | 60 | 65 | 75 | 75 | 90 |
| Rice | 0 | 0 | 35 | 0 | 20 | 0 | 0 | 0 | 20 | 0 | 20 | 30 | 0 | 30 |
| Sedge, Umbrella | 75 | 65 | 80 | 30 | 65 | 0 | 0 | 0 | 0 | 60 | 75 | 50 | 80 | 75 |

| | Compounds | | | | | | | | | | | | | |
|---|---|---|---|---|---|---|---|---|---|---|---|---|---|---|
| 125 g ai/ha | 124 | 125 | 126 | 127 | 128 | 129 | 130 | 132 | 133 | 142 | 143 | 144 | 145 | 146 |
| | Flood | | | | | | | | | | | | | |
| Barnyardgrass | 0 | 40 | 60 | 65 | 15 | 10 | 0 | 0 | 0 | 0 | 0 | 0 | 0 | 0 |
| Ducksalad | 0 | 60 | 85 | 60 | 95 | 90 | 80 | 80 | 100 | 80 | 80 | 75 | 80 | 80 |
| Rice | 20 | 0 | 0 | 25 | 10 | 0 | 0 | 0 | 0 | 0 | 0 | 20 | 0 | 0 |
| Sedge, Umbrella | 20 | 90 | 80 | 60 | 60 | 60 | 75 | 60 | 95 | 65 | 0 | 95 | 60 | 80 |

| | Compounds | | | | | | | | | | | | | |
|---|---|---|---|---|---|---|---|---|---|---|---|---|---|---|
| 125 g ai/ha | 147 | 148 | 151 | 152 | 153 | 154 | 155 | 156 | 157 | 158 | 161 | 162 | 163 | 164 |
| | Flood | | | | | | | | | | | | | |
| Barnyardgrass | 45 | 15 | 30 | 50 | 35 | 0 | 20 | 40 | 0 | 20 | 0 | 40 | 0 | 0 |
| Ducksalad | 80 | 90 | 100 | 100 | 100 | 70 | 85 | 80 | 70 | 100 | 0 | 100 | 60 | 0 |
| Rice | 10 | 20 | 15 | 30 | 55 | 60 | 25 | 20 | 0 | 40 | 45 | 90 | 20 | 20 |
| Sedge, Umbrella | 40 | 85 | 100 | 85 | 80 | 95 | 85 | 100 | 75 | 100 | 0 | 100 | 70 | 0 |

| | Compounds | | | | | | | | | | | | | |
|---|---|---|---|---|---|---|---|---|---|---|---|---|---|---|
| 125 g ai/ha | 166 | 167 | 168 | 170 | 171 | 172 | 173 | 174 | 175 | 176 | 177 | 178 | 179 | 180 |
| | Flood | | | | | | | | | | | | | |
| Barnyardgrass | 20 | 20 | 0 | 30 | 20 | 20 | 15 | 0 | 20 | 0 | 15 | 60 | 20 | 15 |
| Ducksalad | 60 | 70 | 30 | 45 | 70 | 60 | 75 | 95 | 95 | 75 | 70 | 100 | 95 | 75 |
| Rice | 0 | 0 | 0 | 20 | 0 | 0 | 15 | 0 | 0 | 20 | 20 | 70 | 25 | 30 |
| Sedge, Umbrella | 70 | 60 | 20 | 35 | 80 | 75 | 85 | 95 | 85 | 85 | 75 | 95 | 85 | 65 |

| | Compounds | | | | | | | | | | | | | |
|---|---|---|---|---|---|---|---|---|---|---|---|---|---|---|
| 125 g ai/ha | 181 | 182 | 183 | 184 | 185 | 186 | 190 | 191 | 192 | 193 | 194 | 195 | 196 | 197 |
| | Flood | | | | | | | | | | | | | |
| Barnyardgrass | 70 | 0 | 0 | 20 | 0 | 30 | 20 | 0 | 0 | 45 | 10 | 0 | 20 | 20 |
| Ducksalad | 90 | 85 | 80 | 100 | 75 | 90 | 40 | 75 | 75 | 85 | 50 | 70 | 95 | 80 |
| Rice | 65 | 0 | 0 | 15 | 0 | 45 | 15 | 0 | 0 | 30 | 0 | 0 | 40 | 30 |
| Sedge, Umbrella | 85 | 75 | 65 | 80 | 65 | 80 | 30 | 80 | 50 | 70 | 0 | 50 | 75 | 75 |

| | Compounds | | | | | | | | | | | | | |
|---|---|---|---|---|---|---|---|---|---|---|---|---|---|---|
| 125 g ai/ha | 198 | 199 | 200 | 203 | 204 | 207 | 208 | 209 | 210 | 211 | 212 | 213 | 215 | 216 |
| | Flood | | | | | | | | | | | | | |
| Barnyardgrass | 30 | 15 | 23 | 0 | 25 | 0 | 15 | 0 | 20 | 25 | 0 | 0 | 30 | 0 |
| Ducksalad | 85 | 85 | 85 | 95 | 90 | 0 | 40 | 85 | 90 | 85 | 90 | 90 | 85 | 90 |
| Rice | 20 | 0 | 10 | 0 | 0 | 15 | 0 | 10 | 20 | 0 | 0 | 0 | 0 | 0 |
| Sedge, Umbrella | 80 | 75 | 43 | 75 | 90 | 60 | 40 | 70 | 75 | 70 | 90 | 85 | 75 | 80 |

TABLE B-continued

| 125 g ai/ha | 218 | 219 | 220 | 221 | 223 | 224 | 226 | 227 | 228 | 229 | 230 | 235 | 236 | 237 |
|---|---|---|---|---|---|---|---|---|---|---|---|---|---|---|
| Flood | | | | | | | | | | | | | | |
| Barnyardgrass | 30 | 20 | 30 | 0 | 0 | 0 | 95 | 50 | 75 | 0 | 20 | 50 | 0 | 0 |
| Ducksalad | 85 | 65 | 85 | 70 | 0 | 0 | 30 | 75 | 75 | 0 | 0 | 100 | 60 | 90 |
| Rice | 10 | 70 | 50 | 0 | 0 | 0 | 60 | 45 | 35 | 0 | 30 | 45 | 0 | 0 |
| Sedge, Umbrella | 85 | 60 | 20 | 75 | 0 | 0 | 50 | 85 | 75 | 50 | 40 | 80 | 0 | 55 |

| 125 g ai/ha | 238 | 239 | 243 | 244 | 245 | 246 | 248 | 249 | 250 | 251 | 253 | 254 | 255 | 256 |
|---|---|---|---|---|---|---|---|---|---|---|---|---|---|---|
| Flood | | | | | | | | | | | | | | |
| Barnyardgrass | 30 | 0 | 75 | 40 | 40 | 20 | 0 | 0 | 10 | 0 | 0 | 10 | 0 | 0 |
| Ducksalad | 80 | 70 | 100 | 100 | 100 | 100 | 80 | 80 | 70 | 50 | 85 | 85 | 60 | 80 |
| Rice | 0 | 0 | 95 | 60 | 50 | 65 | 0 | 0 | 0 | 0 | 0 | 0 | 0 | 0 |
| Sedge, Umbrella | 65 | 40 | 100 | 100 | 100 | 100 | 75 | 85 | 65 | 65 | 75 | 75 | 50 | 75 |

| 62 g ai/ha | 1 | 2 | 3 | 4 | 7 | 8 | 9 | 10 | 11 | 12 | 13 | 14 | 15 | 16 |
|---|---|---|---|---|---|---|---|---|---|---|---|---|---|---|
| Flood | | | | | | | | | | | | | | |
| Barnyardgrass | 0 | 0 | 0 | 0 | 0 | 0 | 0 | 0 | 0 | 0 | 0 | 0 | 20 | 0 |
| Ducksalad | 0 | 40 | 0 | 40 | 0 | 85 | 30 | 20 | 0 | 25 | 0 | 20 | 0 | 40 |
| Rice | 0 | 0 | 0 | 0 | 0 | 0 | 0 | 0 | 10 | 0 | 0 | 0 | 0 | 0 |
| Sedge, Umbrella | 0 | 0 | 50 | 65 | 0 | 65 | 30 | 40 | 0 | 40 | 0 | 0 | 0 | 0 |

| 62 g ai/ha | 17 | 18 | 19 | 20 | 21 | 22 | 23 | 24 | 25 | 26 | 27 | 28 | 29 | 30 |
|---|---|---|---|---|---|---|---|---|---|---|---|---|---|---|
| Flood | | | | | | | | | | | | | | |
| Barnyardgrass | 20 | 20 | 0 | 0 | 0 | 0 | 0 | 0 | 0 | 0 | 0 | 10 | 0 | 0 |
| Ducksalad | 30 | 50 | 75 | 60 | 70 | 20 | 35 | 20 | 0 | 75 | 75 | 70 | 70 | 20 |
| Rice | 0 | 15 | 0 | 0 | 0 | 0 | 0 | 0 | 0 | 0 | 0 | 0 | 0 | 0 |
| Sedge, Umbrella | 70 | 30 | 70 | 40 | 50 | 30 | 30 | 0 | 0 | 75 | 75 | 70 | 70 | 20 |

| 62 g ai/ha | 31 | 32 | 33 | 34 | 35 | 36 | 37 | 38 | 39 | 40 | 41 | 42 | 43 | 44 |
|---|---|---|---|---|---|---|---|---|---|---|---|---|---|---|
| Flood | | | | | | | | | | | | | | |
| Barnyardgrass | 0 | 10 | 20 | 0 | 0 | 0 | 0 | 0 | 0 | 0 | 0 | 0 | 20 | 0 |
| Ducksalad | 60 | 75 | 75 | 0 | 0 | 0 | 30 | 20 | 80 | 0 | 70 | 30 | 70 | 80 |
| Rice | 0 | 0 | 0 | 0 | 0 | 0 | 0 | 0 | 0 | 0 | 0 | 0 | 0 | 20 |
| Sedge, Umbrella | 60 | 75 | 30 | 0 | 0 | 0 | 20 | 0 | 90 | 70 | 70 | 30 | 30 | 80 |

| 62 g ai/ha | 45 | 46 | 47 | 48 | 49 | 50 | 51 | 52 | 53 | 54 | 55 | 56 | 57 | 58 |
|---|---|---|---|---|---|---|---|---|---|---|---|---|---|---|
| Flood | | | | | | | | | | | | | | |
| Barnyardgrass | 0 | 0 | 0 | 0 | 0 | 0 | 20 | 0 | 40 | 0 | 20 | 15 | 0 | 0 |
| Ducksalad | 20 | 20 | 65 | 0 | 0 | 75 | 30 | 0 | 65 | 0 | 0 | 20 | 0 | 0 |
| Rice | 15 | 10 | 15 | 0 | 0 | 10 | 15 | 0 | 20 | 0 | 10 | 0 | 0 | 0 |
| Sedge, Umbrella | 70 | 45 | 70 | 40 | 0 | 75 | 40 | 30 | 85 | 0 | 30 | 40 | 0 | 0 |

| 62 g ai/ha | 59 | 60 | 61 | 62 | 63 | 64 | 65 | 66 | 67 | 68 | 69 | 70 | 71 | 72 |
|---|---|---|---|---|---|---|---|---|---|---|---|---|---|---|
| Flood | | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 0 | 20 | 30 | 0 | 0 | 0 | 0 | 0 | 0 | 0 | 0 |
| Rice | 15 | 0 | 0 | 0 | 0 | 0 | 0 | 0 | 0 | 15 | 0 | 0 | 0 | 0 |
| Sedge, Umbrella | 40 | 30 | 0 | 0 | 0 | 0 | 0 | 0 | 0 | 0 | 0 | 0 | 0 | 0 |

TABLE B-continued

| | Compounds | | | | | | | | | | | | | |
|---|---|---|---|---|---|---|---|---|---|---|---|---|---|---|
| 62 g ai/ha | 73 | 74 | 75 | 76 | 77 | 78 | 79 | 80 | 81 | 82 | 83 | 84 | 85 | 86 |
| | Flood | | | | | | | | | | | | | |
| Barnyardgrass | 0 | 0 | 20 | 0 | 30 | 0 | 0 | 20 | 0 | 0 | 0 | 0 | 25 | 40 |
| Ducksalad | 0 | 0 | 30 | 0 | 30 | 0 | 0 | 20 | 0 | 0 | 30 | 0 | 50 | 55 |
| Rice | 0 | 0 | 0 | 0 | 0 | 0 | 0 | 0 | 0 | 0 | 0 | 0 | 0 | 0 |
| Sedge, Umbrella | 0 | 30 | 0 | 0 | 40 | 30 | 0 | 20 | 0 | 0 | 30 | 0 | 75 | 30 |

| | Compounds | | | | | | | | | | | | | |
|---|---|---|---|---|---|---|---|---|---|---|---|---|---|---|
| 62 g ai/ha | 87 | 88 | 89 | 90 | 91 | 92 | 93 | 94 | 95 | 96 | 97 | 98 | 99 | 100 |
| | Flood | | | | | | | | | | | | | |
| Barnyardgrass | 45 | 20 | 20 | 0 | 20 | 0 | 60 | 0 | 35 | 65 | 40 | 30 | 20 | 45 |
| Ducksalad | 30 | 40 | 90 | 65 | 90 | 30 | 55 | 20 | 0 | 0 | 30 | 0 | 40 | 75 |
| Rice | 20 | 0 | 0 | 0 | 15 | 0 | 15 | 0 | 20 | 15 | 0 | 0 | 0 | 30 |
| Sedge, Umbrella | 20 | 30 | 85 | 60 | 95 | 65 | 75 | 70 | 20 | 75 | 40 | 65 | 50 | 75 |

| | Compounds | | | | | | | | | | | | | |
|---|---|---|---|---|---|---|---|---|---|---|---|---|---|---|
| 62 g ai/ha | 101 | 102 | 103 | 104 | 105 | 106 | 107 | 108 | 109 | 110 | 111 | 112 | 113 | 114 |
| | Flood | | | | | | | | | | | | | |
| Barnyardgrass | 40 | 60 | 0 | 0 | 0 | 0 | 40 | 0 | 0 | 0 | 40 | 35 | 10 | 20 |
| Ducksalad | 30 | 40 | 0 | 0 | 0 | 0 | 0 | 50 | 60 | 40 | 30 | 85 | 25 | 65 |
| Rice | 0 | 15 | 0 | 0 | 0 | 0 | 20 | 0 | 0 | 0 | 0 | 0 | 0 | 0 |
| Sedge, Umbrella | 20 | 40 | 0 | 0 | 0 | 0 | 60 | 40 | 60 | 35 | 75 | 85 | 40 | 30 |

| | Compounds | | | | | | | | | | | | | |
|---|---|---|---|---|---|---|---|---|---|---|---|---|---|---|
| 62 g ai/ha | 115 | 116 | 117 | 118 | 119 | 120 | 121 | 122 | 123 | 124 | 125 | 126 | 127 | 128 |
| | Flood | | | | | | | | | | | | | |
| Barnyardgrass | 50 | 65 | 65 | 50 | 30 | 20 | 30 | 20 | 40 | 0 | 25 | 45 | 40 | 10 |
| Ducksalad | 85 | 80 | — | 100 | 30 | 30 | 45 | 0 | 80 | 0 | 40 | 80 | 30 | 95 |
| Rice | 20 | 0 | 0 | 0 | 20 | 0 | 0 | 0 | 20 | 15 | 0 | 0 | 15 | 0 |
| Sedge, Umbrella | 70 | 75 | 95 | 70 | 25 | 40 | 30 | 20 | 70 | 0 | 35 | 70 | 20 | 30 |

| | Compounds | | | | | | | | | | | | | |
|---|---|---|---|---|---|---|---|---|---|---|---|---|---|---|
| 62 g ai/ha | 129 | 130 | 131 | 132 | 133 | 134 | 135 | 136 | 138 | 139 | 140 | 141 | 142 | 143 |
| | Flood | | | | | | | | | | | | | |
| Barnyardgrass | 0 | 0 | 20 | 0 | 0 | 0 | 0 | 20 | 0 | 10 | 20 | 20 | 0 | 0 |
| Ducksalad | 90 | 80 | 40 | 50 | 60 | 0 | 30 | 55 | 70 | 75 | 50 | 75 | 0 | 80 |
| Rice | 0 | 0 | 25 | 0 | 0 | 0 | 0 | 15 | 0 | 10 | 0 | 0 | 0 | 0 |
| Sedge, Umbrella | 0 | 60 | 20 | 0 | 60 | 0 | 0 | 45 | 70 | 70 | 75 | 80 | 0 | 0 |

| | Compounds | | | | | | | | | | | | | |
|---|---|---|---|---|---|---|---|---|---|---|---|---|---|---|
| 62 g ai/ha | 144 | 145 | 146 | 147 | 148 | 151 | 152 | 153 | 154 | 155 | 156 | 158 | 161 | 162 |
| | Flood | | | | | | | | | | | | | |
| Barnyardgrass | 0 | 0 | 0 | 10 | 0 | 15 | 25 | 0 | 0 | 0 | 20 | 20 | 0 | 25 |
| Ducksalad | 60 | 80 | 60 | 60 | 90 | 80 | 90 | 65 | 50 | 60 | 65 | 75 | 0 | 100 |
| Rice | 20 | 0 | 0 | 0 | 10 | 0 | 20 | 35 | 0 | 0 | 30 | 30 | 50 | 25 |
| Sedge, Umbrella | 65 | 0 | 50 | 40 | 80 | 85 | 0 | 0 | 95 | 60 | 95 | 85 | 0 | 100 |

| | Compounds | | | | | | | | | | | | | |
|---|---|---|---|---|---|---|---|---|---|---|---|---|---|---|
| 62 g ai/ha | 164 | 178 | 179 | 183 | 184 | 185 | 186 | 187 | 188 | 189 | 190 | 191 | 192 | 193 |
| | Flood | | | | | | | | | | | | | |
| Barnyardgrass | 0 | 20 | 10 | 0 | 0 | 0 | 20 | 45 | 0 | 30 | 0 | 0 | 0 | 20 |
| Ducksalad | 0 | 75 | 90 | 65 | 100 | 70 | 90 | 95 | 70 | 100 | 20 | 85 | 60 | 50 |
| Rice | 0 | 20 | 0 | 0 | 15 | 0 | 20 | 15 | 0 | 20 | 15 | 0 | 0 | 15 |
| Sedge, Umbrella | 0 | 85 | 80 | 50 | 80 | 75 | 80 | 95 | 80 | 95 | 0 | 75 | 40 | 30 |

TABLE B-continued

| 62 g ai/ha | Compounds | | | | | | | | | | | | | |
|---|---|---|---|---|---|---|---|---|---|---|---|---|---|---|
| | 194 | 195 | 196 | 197 | 198 | 199 | 200 | 203 | 204 | 206 | 207 | 208 | 209 | 210 |
| | Flood | | | | | | | | | | | | | |
| Barnyardgrass | 0 | 0 | 0 | 0 | 0 | 0 | 0 | 0 | 15 | 0 | 0 | 0 | 0 | 0 |
| Ducksalad | 50 | 50 | 60 | 65 | 50 | 85 | 83 | 75 | 70 | 70 | 0 | 30 | 50 | 85 |
| Rice | 0 | 0 | 0 | 0 | 20 | 0 | 0 | 0 | 0 | 0 | 0 | 0 | 0 | 0 |
| Sedge, Umbrella | 0 | 0 | 30 | 70 | 20 | 70 | 33 | 65 | 75 | 60 | 40 | 40 | 50 | 75 |

| 62 g ai/ha | Compounds | | | | | | | | | | | | | |
|---|---|---|---|---|---|---|---|---|---|---|---|---|---|---|
| | 211 | 212 | 213 | 214 | 215 | 216 | 217 | 218 | 219 | 220 | 221 | 222 | 223 | 224 |
| | Flood | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | — | 85 | 85 | 0 | 75 | 90 | 0 | 80 | 20 | 40 | 65 | 50 | 0 | 0 |
| Rice | 0 | 0 | 0 | 0 | 0 | 0 | 0 | 0 | 0 | 15 | 0 | 0 | 0 | 0 |
| Sedge, Umbrella | 0 | 85 | 80 | 0 | 0 | 65 | 40 | 80 | 40 | 0 | 60 | 30 | 0 | 0 |

| 62 g ai/ha | Compounds | | | | | | | | | | | | | |
|---|---|---|---|---|---|---|---|---|---|---|---|---|---|---|
| | 226 | 227 | 228 | 229 | 230 | 231 | 232 | 233 | 234 | 235 | 236 | 237 | 238 | 239 |
| | Flood | | | | | | | | | | | | | |
| Barnyardgrass | 60 | 40 | 40 | 0 | 0 | 40 | 30 | 20 | 0 | 20 | 0 | 0 | 0 | 0 |
| Ducksalad | 0 | — | 50 | 0 | 0 | 0 | 85 | 100 | 20 | 95 | 0 | 65 | 40 | 0 |
| Rice | 40 | 30 | 20 | 0 | 20 | 0 | 0 | 25 | 0 | 0 | 0 | 0 | 0 | 0 |
| Sedge, Umbrella | 40 | 85 | 75 | 0 | 30 | 0 | 80 | 70 | 0 | 70 | 0 | 45 | 0 | 0 |

| 62 g ai/ha | Compounds | | | | | | | | | | | | |
|---|---|---|---|---|---|---|---|---|---|---|---|---|---|
| | 243 | 244 | 245 | 246 | 248 | 249 | 250 | 251 | 252 | 253 | 254 | 255 | 256 |
| | Flood | | | | | | | | | | | | |
| Barnyardgrass | 30 | 20 | 0 | 0 | 0 | 0 | 0 | 0 | 0 | 0 | 0 | 0 | 0 |
| Ducksalad | 85 | 80 | 100 | 100 | 80 | 65 | 30 | 0 | 0 | 75 | 85 | 50 | 40 |
| Rice | 60 | 0 | 50 | 30 | 0 | 0 | 0 | 0 | 0 | 0 | 0 | 0 | 0 |
| Sedge, Umbrella | 90 | 0 | 100 | 85 | 65 | 60 | 65 | 50 | 0 | 65 | 50 | 20 | 40 |

| 31 g ai/ha | Compounds | | | | | | | | | | | | | |
|---|---|---|---|---|---|---|---|---|---|---|---|---|---|---|
| | 1 | 2 | 3 | 4 | 7 | 8 | 9 | 10 | 11 | 12 | 13 | 14 | 16 | 17 |
| | Flood | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 15 | 0 | 20 | 0 | 30 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 40 | 50 | 0 | 30 | 0 | 0 | 0 | 20 | 0 | 0 | 0 | 0 |

| 31 g ai/ha | Compounds | | | | | | | | | | | | | |
|---|---|---|---|---|---|---|---|---|---|---|---|---|---|---|
| | 18 | 19 | 20 | 21 | 22 | 23 | 33 | 34 | 35 | 36 | 37 | 38 | 49 | 50 |
| | Flood | | | | | | | | | | | | | |
| Barnyardgrass | 10 | 0 | 0 | 0 | 0 | 0 | 0 | 0 | 0 | 0 | 0 | 0 | 0 | 0 |
| Ducksalad | 20 | 0 | 60 | 60 | 0 | 20 | 60 | 0 | 0 | 0 | 0 | 0 | 0 | 70 |
| Rice | 10 | 0 | 0 | 0 | 0 | 0 | 0 | 0 | 0 | 0 | 0 | 0 | 0 | 0 |
| Sedge, Umbrella | 0 | 0 | 0 | 40 | 0 | 20 | 20 | 0 | 0 | 0 | 0 | 0 | 0 | 75 |

| 31 g ai/ha | Compounds | | | | | | | | | | | | | |
|---|---|---|---|---|---|---|---|---|---|---|---|---|---|---|
| | 51 | 52 | 53 | 54 | 55 | 56 | 57 | 58 | 59 | 60 | 61 | 62 | 63 | 64 |
| | Flood | | | | | | | | | | | | | |
| Barnyardgrass | 15 | 0 | 20 | 0 | 0 | 10 | 0 | 0 | 0 | 0 | 0 | 0 | 0 | 0 |
| Ducksalad | 0 | 0 | 40 | 0 | 0 | 0 | 0 | 0 | 0 | 0 | 0 | 0 | 0 | 30 |
| Rice | 10 | 0 | 15 | 0 | 0 | 0 | 0 | 0 | 0 | 0 | 0 | 0 | 0 | 0 |
| Sedge, Umbrella | 30 | 20 | 40 | 0 | 0 | 30 | 0 | 0 | 30 | 0 | 0 | 0 | 0 | 0 |

TABLE B-continued

| | Compounds | | | | | | | | | | | | | |
|---|---|---|---|---|---|---|---|---|---|---|---|---|---|---|
| 31 g ai/ha | 65 | 66 | 67 | 68 | 69 | 70 | 71 | 72 | 76 | 79 | 80 | 81 | 82 | 83 |
| | Flood | | | | | | | | | | | | | |
| Barnyardgrass | 0 | 0 | 0 | 0 | 0 | 0 | 0 | 0 | 0 | 0 | 15 | 0 | 0 | 0 |
| Ducksalad | 0 | 0 | 0 | 0 | 0 | 0 | 0 | 0 | 0 | 0 | 0 | 0 | 0 | 20 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 84 | 85 | 86 | 87 | 88 | 89 | 90 | 91 | 92 | 93 | 94 | 95 | 96 | 97 |
| | Flood | | | | | | | | | | | | | |
| Barnyardgrass | 0 | 25 | 30 | 20 | 0 | 20 | 0 | 15 | 0 | 30 | 0 | 20 | 60 | 30 |
| Ducksalad | 0 | 40 | 0 | 20 | 30 | 45 | 50 | 65 | 20 | 40 | 0 | 0 | 0 | 30 |
| Rice | 0 | 0 | 0 | 0 | 0 | 0 | 0 | 0 | 0 | 0 | 0 | 0 | 10 | 0 |
| Sedge, Umbrella | 0 | 50 | 20 | 0 | 0 | 30 | 50 | 75 | 65 | 70 | 20 | 0 | 50 | 30 |

| | Compounds | | | | | | | | | | | | | |
|---|---|---|---|---|---|---|---|---|---|---|---|---|---|---|
| 31 g ai/ha | 98 | 99 | 100 | 101 | 102 | 103 | 104 | 105 | 106 | 108 | 109 | 110 | 111 | 123 |
| | Flood | | | | | | | | | | | | | |
| Barnyardgrass | 0 | 0 | 20 | 20 | 15 | 0 | 0 | 0 | 0 | 0 | 0 | 0 | 0 | 30 |
| Ducksalad | 0 | 30 | 35 | 20 | 30 | 0 | 0 | 0 | 0 | 40 | 50 | 0 | 30 | 30 |
| Rice | 0 | 0 | 0 | 0 | 10 | 0 | 0 | 0 | 0 | 0 | 0 | 0 | 0 | 0 |
| Sedge, Umbrella | 40 | 50 | 40 | 0 | 30 | 0 | 0 | 0 | 0 | 0 | 50 | 30 | 0 | 40 |

| | Compounds | | | | | | | | | | | | |
|---|---|---|---|---|---|---|---|---|---|---|---|---|---|
| 31 g ai/ha | 124 | 125 | 126 | 127 | 128 | 129 | 130 | 132 | 133 | 142 | 143 | 144 | 145 | 146 |
| | Flood | | | | | | | | | | | | | |
| Barnyardgrass | 0 | 0 | 20 | 0 | 0 | 0 | 0 | 0 | 0 | 0 | 0 | 0 | 0 | 0 |
| Ducksalad | 0 | 20 | 75 | 0 | 90 | 0 | 60 | 0 | 60 | 0 | 80 | 50 | 80 | 0 |
| Rice | 0 | 0 | 0 | 0 | 0 | 0 | 0 | 0 | 0 | 0 | 15 | 0 | 0 | 0 |
| Sedge, Umbrella | 0 | 25 | 50 | 0 | 0 | 0 | 40 | 0 | 0 | 0 | 0 | 50 | 0 | 0 |

| | Compounds | | | | | | | | | | | | | |
|---|---|---|---|---|---|---|---|---|---|---|---|---|---|---|
| 31 g ai/ha | 147 | 148 | 151 | 152 | 153 | 154 | 155 | 156 | 157 | 158 | 161 | 162 | 163 | 164 |
| | Flood | | | | | | | | | | | | | |
| Barnyardgrass | 0 | 0 | 0 | 15 | 0 | 0 | 0 | 0 | 0 | 20 | 0 | 20 | 0 | 0 |
| Ducksalad | 60 | 90 | 80 | 0 | 0 | 0 | 0 | 0 | 50 | 50 | 0 | 98 | 30 | 0 |
| Rice | 0 | 20 | 20 | 20 | 35 | 0 | 0 | 30 | 0 | 20 | 25 | 0 | 10 | 0 |
| Sedge, Umbrella | 0 | 80 | 85 | 0 | 0 | 0 | 60 | 0 | 40 | 70 | 0 | 95 | 70 | 0 |

| | Compounds | | | | | | | | | | | | | |
|---|---|---|---|---|---|---|---|---|---|---|---|---|---|---|
| 31 g ai/ha | 166 | 167 | 168 | 170 | 171 | 172 | 173 | 174 | 175 | 176 | 177 | 178 | 179 | 180 |
| | Flood | | | | | | | | | | | | | |
| Barnyardgrass | 0 | 0 | 0 | 0 | 0 | 0 | 0 | 0 | 0 | 0 | 0 | 20 | 0 | 0 |
| Ducksalad | 0 | 0 | 0 | 0 | 40 | 20 | 30 | 80 | 75 | 40 | 30 | 75 | 90 | 60 |
| Rice | 0 | 0 | 0 | 15 | 0 | 0 | 0 | 0 | 0 | 15 | 15 | 0 | 0 | 15 |
| Sedge, Umbrella | 50 | 20 | 0 | 0 | 70 | 0 | 0 | 85 | 75 | 70 | 60 | 55 | 40 | 20 |

| | Compounds | | | | | | | | | | | | | |
|---|---|---|---|---|---|---|---|---|---|---|---|---|---|---|
| 31 g ai/ha | 181 | 182 | 183 | 184 | 185 | 186 | 190 | 191 | 192 | 193 | 194 | 195 | 196 | 197 |
| | Flood | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 85 | 60 | 30 | 95 | 75 | 90 | 20 | 65 | 60 | 40 | 40 | 0 | 40 | 65 |
| Rice | 0 | 0 | 0 | 15 | 0 | 10 | 15 | 0 | 0 | 0 | 0 | 0 | 0 | 0 |
| Sedge, Umbrella | 75 | 50 | 0 | 65 | 65 | 70 | 0 | 60 | 0 | 0 | 0 | 0 | 20 | 65 |

TABLE B-continued

| 31 g ai/ha | Compounds | | | | | | | | | | | | | |
|---|---|---|---|---|---|---|---|---|---|---|---|---|---|---|
| | 198 | 199 | 200 | 203 | 204 | 207 | 208 | 209 | 210 | 211 | 212 | 213 | 215 | 216 |
| | Flood | | | | | | | | | | | | | |
| Barnyardgrass | 0 | 0 | 0 | 0 | 10 | 0 | 0 | 0 | 0 | 0 | 0 | 0 | 0 | 0 |
| Ducksalad | 40 | 85 | 38 | 40 | 50 | 0 | 0 | 0 | 75 | 50 | 85 | 75 | 70 | 50 |
| Rice | 15 | 0 | 0 | 0 | 0 | 0 | 0 | 0 | 0 | 0 | 0 | 0 | 0 | 0 |
| Sedge, Umbrella | 20 | 60 | 30 | 0 | 70 | 0 | 0 | 0 | 50 | 0 | 80 | 65 | 0 | 0 |

| 31 g ai/ha | Compounds | | | | | | | | | | | | | |
|---|---|---|---|---|---|---|---|---|---|---|---|---|---|---|
| | 218 | 219 | 220 | 221 | 223 | 224 | 226 | 227 | 228 | 229 | 230 | 235 | 236 | 237 |
| | Flood | | | | | | | | | | | | | |
| Barnyardgrass | 0 | 0 | 0 | 0 | 0 | 0 | 50 | 20 | 15 | 0 | 0 | 0 | 0 | 0 |
| Ducksalad | 75 | 0 | 30 | 20 | 0 | 0 | 0 | — | 40 | 0 | 0 | 95 | 0 | 0 |
| Rice | 0 | 0 | 0 | 0 | 0 | 0 | 20 | 20 | 0 | 0 | 0 | 0 | 0 | 0 |
| Sedge, Umbrella | 75 | 20 | 0 | 0 | 0 | 0 | 30 | 80 | 65 | 0 | 0 | 0 | 0 | 0 |

| 31 g ai/ha | Compounds | | | | | | | | | | | | |
|---|---|---|---|---|---|---|---|---|---|---|---|---|---|
| | 238 | 239 | 243 | 244 | 245 | 246 | 248 | 249 | 250 | 251 | 253 | 254 | 255 | 256 |
| | Flood | | | | | | | | | | | | | |
| Barnyardgrass | 0 | 0 | 0 | 0 | 0 | 0 | 0 | 0 | 0 | 0 | 0 | 0 | 0 | 0 |
| Ducksalad | 0 | 0 | 0 | 35 | 100 | 85 | 75 | 0 | 30 | 0 | 60 | 45 | 0 | 30 |
| Rice | 0 | 0 | 45 | 0 | 50 | 0 | 0 | 0 | 0 | 0 | 0 | 0 | 0 | 0 |
| Sedge, Umbrella | 0 | 0 | 0 | 0 | 60 | 0 | 50 | 0 | 0 | 0 | 60 | 30 | 0 | 30 |

| 250 g ai/ha | Compounds | | | | | | | | | | | | | |
|---|---|---|---|---|---|---|---|---|---|---|---|---|---|---|
| | 1 | 3 | 4 | 7 | 8 | 9 | 10 | 11 | 12 | 14 | 24 | 26 | 27 | 29 |
| | Postemergence | | | | | | | | | | | | | |
| Barley | 0 | 0 | 10 | 0 | 20 | 35 | 5 | 10 | 0 | 40 | 70 | 0 | 20 | 0 |
| Bermudagrass | 65 | 80 | 100 | 70 | 100 | 98 | 95 | 100 | 100 | 80 | 100 | 75 | 100 | 100 |
| Blackgrass | 5 | 5 | 50 | 5 | 20 | 70 | 50 | 40 | 20 | 5 | 50 | 40 | 50 | 50 |
| Bromegrass, Downy | 10 | 45 | 55 | 5 | 10 | 50 | 20 | 45 | 20 | 70 | 75 | 40 | 30 | 45 |
| Canarygrass | 0 | 5 | 80 | 0 | 85 | 60 | 40 | 90 | 40 | 50 | 60 | 60 | 50 | 40 |
| Chickweed | 90 | 100 | 100 | 100 | 100 | 98 | 98 | 100 | 100 | 80 | 100 | 85 | 80 | 85 |
| Cocklebur | 85 | 100 | 100 | 70 | 100 | 45 | 98 | 100 | 100 | 98 | 100 | 100 | 98 | 98 |
| Corn | 0 | 15 | 85 | 10 | 80 | 80 | 65 | 85 | 75 | 70 | 85 | 50 | 70 | 60 |
| Crabgrass, Large | 65 | 90 | 100 | 60 | 100 | 95 | 80 | 100 | 90 | 85 | 100 | 80 | 60 | 80 |
| Cupgrass, Woolly | 20 | 55 | 100 | 65 | 100 | 85 | 75 | 95 | 80 | 80 | 95 | 85 | 80 | 85 |
| Deadnettle | — | — | — | — | — | — | — | — | — | — | — | — | — | — |
| Foxtail, Giant | 50 | 65 | 100 | 60 | 100 | 100 | 95 | 100 | 98 | 95 | 95 | 95 | 90 | 95 |
| Foxtail, Green | 40 | 50 | 60 | 40 | 95 | 95 | 70 | 98 | 70 | 85 | 95 | 95 | 90 | 90 |
| *Galium* | — | — | — | — | — | — | — | — | — | — | — | — | — | — |
| Goosegrass | 80 | 95 | 98 | 35 | 100 | 100 | 98 | 98 | 100 | 85 | 98 | 95 | 98 | 95 |
| Johnsongrass | 20 | 15 | 98 | 0 | 100 | 95 | 75 | 98 | 75 | 80 | 80 | 70 | 80 | 45 |
| *Kochia* | 45 | 95 | 100 | 50 | 100 | 85 | 20 | 98 | 65 | — | 100 | — | 100 | — |
| Lambsquarters | 90 | 100 | 100 | 75 | 100 | 95 | 95 | 98 | 98 | 85 | 100 | 98 | 98 | 98 |
| Morningglory | 65 | 70 | 95 | 20 | 100 | 75 | 55 | 90 | 95 | 95 | 90 | 75 | 90 | 98 |
| Nutsedge, Yellow | 45 | 80 | 80 | 0 | 85 | 70 | 75 | 60 | 80 | 50 | 70 | 35 | 55 | 70 |
| Oat, Wild | 10 | 50 | 50 | 10 | 35 | 55 | 40 | 70 | 20 | 50 | 80 | 60 | 65 | 80 |
| Pigweed | 90 | 100 | 100 | 98 | 100 | 100 | 100 | 98 | 100 | 98 | 80 | 98 | 100 | 85 |
| Ragweed | 75 | 100 | 100 | 85 | 100 | 100 | 98 | 100 | 100 | 98 | 98 | 100 | 100 | 100 |
| Ryegrass, Italian | 0 | 5 | 20 | 20 | 50 | 45 | 20 | 40 | 5 | 50 | 50 | 45 | 10 | 45 |
| Soybean | 80 | 90 | 100 | 85 | 100 | 98 | 98 | 100 | 100 | 90 | 100 | 98 | 100 | 98 |
| Surinam Grass | 20 | 65 | 90 | 25 | 80 | 85 | 80 | 85 | 85 | 55 | 80 | 60 | 80 | 85 |
| Velvetleaf | 90 | 100 | 100 | 98 | 100 | 98 | 85 | 100 | 100 | 100 | 98 | 98 | 90 | 98 |
| Wheat | 5 | 30 | 70 | 15 | 35 | 30 | 5 | 45 | 0 | 20 | 50 | 30 | 30 | 40 |
| Windgrass | 5 | 5 | 75 | 5 | 40 | 80 | 40 | 98 | 50 | 50 | 80 | 60 | 60 | 50 |

| 250 g ai/ha | Compounds | | | | | | | | | | | | | |
|---|---|---|---|---|---|---|---|---|---|---|---|---|---|---|
| | 33 | 34 | 36 | 37 | 38 | 39 | 40 | 42 | 44 | 45 | 46 | 47 | 48 | 49 |
| | Postemergence | | | | | | | | | | | | | |
| Barley | 0 | 30 | — | 0 | 35 | 10 | 10 | 5 | 15 | 5 | 0 | 35 | 10 | 0 |
| Bermudagrass | 98 | 98 | 100 | 100 | 100 | 100 | 100 | 98 | 98 | 100 | 90 | — | 100 | 98 |
| Blackgrass | 30 | 40 | 15 | 30 | 40 | 20 | 15 | 20 | 30 | 25 | 10 | 30 | 30 | 30 |
| Bromegrass, Downy | 20 | 50 | 65 | 45 | 85 | 0 | 85 | 25 | 85 | 50 | 25 | 55 | 70 | 5 |
| Canarygrass | 5 | 50 | 50 | 30 | 45 | 20 | 35 | 0 | 40 | 30 | 0 | 40 | 45 | 0 |

TABLE B-continued

| | | | | | | | | | | | | | | |
|---|---|---|---|---|---|---|---|---|---|---|---|---|---|---|
| Chickweed | 100 | 100 | 100 | 100 | 100 | 100 | 100 | 95 | 100 | 100 | 98 | 100 | 100 | 90 |
| Cocklebur | 95 | 95 | — | — | — | 98 | — | 95 | 98 | 95 | 90 | 100 | 98 | 85 |
| Corn | 15 | 50 | 85 | 75 | 90 | 65 | 90 | 45 | 85 | 80 | 75 | — | 85 | 15 |
| Crabgrass, Large | 98 | 98 | 98 | 90 | 100 | 90 | 100 | 90 | 98 | 85 | 75 | 100 | 95 | 85 |
| Cupgrass, Woolly | 90 | 95 | 98 | 100 | 100 | 90 | 98 | 55 | 95 | 80 | 45 | 100 | 95 | 55 |
| Deadnettle | — | — | — | — | — | — | — | — | — | — | — | — | — | — |
| Foxtail, Giant | 95 | 95 | 98 | 100 | 100 | 95 | 100 | 85 | 98 | 98 | 85 | 98 | 98 | 75 |
| Foxtail, Green | 90 | 95 | 90 | 95 | 95 | 90 | 95 | 85 | 90 | 95 | 85 | 95 | 95 | 90 |
| *Galium* | — | — | — | — | — | — | — | — | — | — | — | — | — | — |
| Goosegrass | 85 | 95 | 95 | 95 | 95 | 75 | 98 | 95 | 95 | 90 | 80 | 98 | 98 | 70 |
| Johnsongrass | 40 | 100 | 100 | 85 | 100 | 98 | 100 | 65 | 95 | 100 | 75 | — | 95 | 10 |
| *Kochia* | 98 | 100 | 65 | 65 | 100 | 95 | 75 | 100 | 95 | 98 | 30 | 100 | 100 | 90 |
| Lambsquarters | 100 | 100 | 100 | 100 | 100 | 100 | 100 | 100 | 98 | 100 | 95 | 100 | 100 | 98 |
| Morningglory | 85 | 95 | 75 | 95 | 100 | 95 | 85 | 98 | 80 | 90 | 80 | 95 | 80 | 85 |
| Nutsedge, Yellow | 80 | 65 | 60 | 65 | 55 | 45 | — | 70 | 55 | 60 | 75 | 70 | 70 | 70 |
| Oat, Wild | 55 | 70 | 85 | 80 | 85 | 40 | 90 | 25 | 85 | 70 | 30 | 60 | 85 | 40 |
| Pigweed | 100 | 98 | 98 | 100 | 100 | 100 | 100 | 100 | 100 | 100 | 80 | 100 | 100 | 98 |
| Ragweed | 98 | 98 | 95 | 98 | 95 | 98 | 98 | 85 | 98 | 98 | 80 | 95 | 98 | 90 |
| Ryegrass, Italian | 45 | 40 | 15 | 30 | 65 | 20 | 10 | 15 | 35 | 35 | 10 | 50 | 30 | 0 |
| Soybean | 100 | 100 | 100 | 100 | 100 | 100 | 100 | 95 | 95 | 98 | 90 | 98 | 98 | 85 |
| Surinam Grass | 90 | 85 | 95 | 95 | 95 | 70 | 100 | 65 | 95 | 95 | 90 | 100 | 98 | 70 |
| Velvetleaf | 100 | 100 | 100 | 100 | 100 | 95 | 100 | 98 | 100 | 95 | 90 | 100 | 100 | 98 |
| Wheat | 5 | 55 | 5 | 5 | 60 | 20 | 35 | 10 | 30 | 30 | 0 | 15 | 30 | 30 |
| Windgrass | 60 | 80 | 85 | 70 | 90 | — | 90 | — | — | — | 50 | — | — | 30 |

| | Compounds | | | | | | | | | | | | | |
|---|---|---|---|---|---|---|---|---|---|---|---|---|---|---|
| 250 g ai/ha | 50 | 51 | 52 | 53 | 55 | 56 | 58 | 59 | 61 | 62 | 63 | 64 | 66 | 67 |
| | Postemergence | | | | | | | | | | | | | |
| Barley | 5 | 50 | 25 | 70 | 0 | — | 10 | 10 | 0 | 30 | 0 | 35 | 0 | 30 |
| Bermudagrass | 100 | 98 | 100 | 98 | 90 | 100 | 100 | 100 | 90 | 90 | 95 | 98 | 95 | 85 |
| Blackgrass | 15 | 55 | 30 | 50 | 10 | 20 | 40 | 60 | 5 | 50 | 50 | 15 | 15 | 10 |
| Bromegrass, Downy | 20 | 60 | 70 | 60 | 0 | 60 | 50 | 45 | 5 | 50 | 40 | 85 | 25 | 5 |
| Canarygrass | 5 | 98 | 85 | 90 | 0 | 40 | 85 | 70 | 0 | 5 | 0 | 60 | 0 | 5 |
| Chickweed | 98 | 95 | 98 | 100 | 90 | 98 | 90 | 100 | 98 | 80 | 95 | 100 | 98 | 100 |
| Cocklebur | 90 | 90 | 85 | 90 | 75 | 95 | 90 | 100 | 85 | 75 | 95 | 95 | 45 | 90 |
| Corn | 25 | 85 | 80 | 85 | 10 | 70 | 80 | 75 | 15 | 80 | 45 | 90 | 75 | 75 |
| Crabgrass, Large | 98 | 90 | 98 | 100 | 85 | 95 | 90 | 100 | 75 | 85 | 90 | 98 | 70 | 95 |
| Cupgrass, Woolly | 85 | 90 | 95 | 98 | 20 | 85 | 95 | 95 | 60 | 65 | 65 | 98 | 75 | 75 |
| Deadnettle | — | — | — | — | — | — | — | — | — | — | — | — | — | — |
| Foxtail, Giant | 95 | 85 | 90 | 95 | 75 | 95 | 98 | 95 | 75 | 80 | 80 | 100 | 95 | 90 |
| Foxtail, Green | 95 | 100 | 100 | 100 | 80 | 100 | 100 | 70 | 80 | 85 | 90 | 100 | 98 | 95 |
| *Galium* | — | — | — | — | — | — | — | — | — | — | — | — | — | — |
| Goosegrass | 90 | 85 | 85 | 85 | 75 | 90 | 90 | 95 | 80 | 75 | 75 | 90 | 95 | 80 |
| Johnsongrass | 70 | 98 | 95 | 100 | 20 | 100 | 100 | 100 | 10 | 10 | 15 | 100 | 65 | 10 |
| *Kochia* | 100 | 35 | 65 | 80 | 85 | 100 | 25 | 75 | 85 | 80 | 65 | 80 | 98 | 85 |
| Lambsquarters | 100 | 98 | 95 | 98 | 98 | 100 | 100 | 100 | 98 | 100 | 98 | 100 | 100 | 100 |
| Morningglory | 80 | 100 | 85 | 98 | 85 | 100 | 90 | 80 | 80 | 75 | 75 | 90 | 100 | 100 |
| Nutsedge, Yellow | 75 | 80 | 65 | 75 | 65 | 75 | 75 | 75 | 65 | 55 | 60 | 25 | 70 | 70 |
| Oat, Wild | 30 | 90 | 95 | 85 | 5 | 45 | 85 | 80 | 5 | 40 | 20 | 98 | 10 | 10 |
| Pigweed | 100 | 100 | 98 | 100 | 95 | 100 | 100 | 100 | 98 | 100 | 100 | 100 | 100 | 100 |
| Ragweed | 98 | 95 | 85 | 98 | 98 | 75 | 98 | 95 | 90 | 80 | 80 | 90 | 60 | 90 |
| Ryegrass, Italian | 0 | 30 | 60 | 45 | 0 | 50 | 70 | 80 | 0 | 50 | 10 | 30 | 10 | 5 |
| Soybean | 95 | 95 | 98 | 95 | 75 | 98 | 95 | 95 | 50 | 95 | 85 | 98 | 98 | 98 |
| Surinam Grass | 85 | 90 | 98 | 98 | 60 | 100 | 98 | 90 | 75 | 70 | 75 | 98 | 98 | 25 |
| Velvetleaf | 100 | 95 | 100 | 98 | 100 | 98 | 95 | 98 | 98 | 100 | 98 | 100 | 100 | 100 |
| Wheat | 15 | 30 | 35 | 50 | 10 | 0 | 0 | 0 | 60 | 10 | 30 | 10 | 55 | 0 | 25 |
| Windgrass | 80 | 85 | 100 | 95 | 5 | 85 | 70 | 70 | 20 | 50 | 60 | 100 | 80 | 5 |

| | Compounds | | | | | | | | | | | | | |
|---|---|---|---|---|---|---|---|---|---|---|---|---|---|---|
| 250 g ai/ha | 68 | 70 | 71 | 72 | 73 | 74 | 75 | 77 | 79 | 80 | 81 | 82 | 83 | 85 |
| | Postemergence | | | | | | | | | | | | | |
| Barley | 30 | 90 | 5 | 0 | 10 | 0 | 0 | 0 | 55 | 75 | 5 | 5 | 5 | 20 |
| Bermudagrass | 98 | 98 | 98 | 85 | 90 | 98 | 98 | 95 | 85 | 55 | 95 | 95 | 90 | 90 |
| Blackgrass | 20 | 50 | 5 | 0 | 30 | 45 | 20 | 5 | 45 | 10 | 30 | 15 | 0 | 50 |
| Bromegrass, Downy | 40 | 70 | 30 | 20 | 60 | 35 | 50 | 5 | 65 | 80 | 50 | 30 | 60 | 30 |
| Canarygrass | 35 | 98 | 20 | 0 | 40 | 0 | 0 | 0 | 50 | 70 | 20 | 35 | 25 | 60 |
| Chickweed | 100 | 100 | 98 | 90 | 100 | 100 | 100 | 98 | 98 | 100 | 100 | 100 | 100 | 98 |
| Cocklebur | 90 | 40 | 95 | 95 | 80 | 95 | 95 | 85 | 98 | 65 | 90 | 100 | 90 | 98 |
| Corn | 80 | 75 | 15 | 10 | 85 | 60 | 55 | 75 | 75 | 65 | 65 | 15 | 25 | 85 |
| Crabgrass, Large | 98 | 100 | 95 | 90 | 95 | 95 | 100 | 85 | 95 | 95 | 98 | 90 | 98 | 95 |
| Cupgrass, Woolly | 75 | 90 | 100 | 50 | 65 | 75 | 80 | 40 | 75 | 75 | 90 | 75 | 95 | 90 |
| Deadnettle | — | — | — | — | — | — | — | — | — | — | — | — | — | — |
| Foxtail, Giant | 90 | 98 | 95 | 80 | 90 | 85 | 95 | 80 | 95 | 95 | 98 | 95 | 98 | 98 |
| Foxtail, Green | 95 | 98 | 98 | 90 | 95 | 85 | 90 | 80 | 98 | 98 | 95 | 90 | 98 | 98 |

TABLE B-continued

| | | | | | | | | | | | | | | |
|---|---|---|---|---|---|---|---|---|---|---|---|---|---|---|
| *Galium* | — | — | — | — | — | — | — | — | — | — | — | — | — | — |
| Goosegrass | 95 | 95 | 90 | 70 | 80 | 85 | 98 | 85 | 80 | 85 | 80 | 85 | 95 | 85 |
| Johnsongrass | 100 | 98 | 100 | 45 | 75 | 85 | 75 | 10 | 75 | 45 | 100 | 95 | 100 | 98 |
| *Kochia* | 98 | 98 | 65 | 90 | 90 | 98 | 100 | 95 | 80 | 60 | 100 | 75 | 95 | 90 |
| Lambsquarters | 100 | 100 | 98 | 100 | 100 | 98 | 100 | 98 | 100 | 100 | 100 | 100 | 100 | 100 |
| Morningglory | 100 | 100 | 80 | 90 | 95 | 100 | 95 | 90 | 100 | 100 | 100 | 100 | 100 | 100 |
| Nutsedge, Yellow | 80 | 60 | 25 | 75 | 70 | 70 | 75 | 80 | 80 | 75 | 80 | 55 | 85 | 85 |
| Oat, Wild | 70 | 95 | 5 | 40 | 95 | 80 | 60 | 5 | 75 | 50 | 55 | 10 | 10 | 60 |
| Pigweed | 100 | 100 | 100 | 100 | 100 | 100 | 100 | 100 | 100 | 100 | 100 | 100 | 100 | 100 |
| Ragweed | 95 | 80 | 95 | 95 | 85 | 90 | 95 | 85 | 98 | 75 | 100 | 95 | 98 | 98 |
| Ryegrass, Italian | 50 | 70 | 5 | 30 | 70 | 35 | 60 | 10 | 55 | 5 | 55 | 10 | 5 | 45 |
| Soybean | 98 | 98 | 98 | 95 | 95 | 95 | 98 | 70 | 98 | 95 | 98 | 98 | 95 | 95 |
| Surinam Grass | 90 | 100 | 85 | 100 | 85 | 75 | 85 | 80 | 90 | 65 | 100 | 80 | 90 | 85 |
| Velvetleaf | 100 | 100 | 95 | 100 | 100 | 100 | 100 | 100 | 100 | 100 | 100 | 95 | 100 | 98 |
| Wheat | 10 | 35 | 5 | 10 | 50 | 50 | 25 | 10 | 40 | 35 | 25 | 5 | 0 | 35 |
| Windgrass | 85 | 100 | 60 | 65 | 98 | 95 | 90 | 25 | 90 | 80 | 70 | 50 | 30 | 95 |

| | Compounds | | | | | | | | | | | | | |
|---|---|---|---|---|---|---|---|---|---|---|---|---|---|---|
| 250 g ai/ha | 86 | 87 | 88 | 89 | 90 | 91 | 92 | 93 | 94 | 95 | 96 | 97 | 98 | 99 |
| | Postemergence | | | | | | | | | | | | | |
| Barley | 65 | 5 | 80 | 20 | 20 | 40 | 0 | 5 | 5 | 0 | 5 | 5 | 15 | 30 |
| Bermudagrass | 95 | 100 | 85 | 95 | 85 | 95 | 85 | 85 | 98 | 90 | 98 | 98 | 98 | 98 |
| Blackgrass | 55 | 40 | 10 | 30 | 30 | 50 | 5 | 30 | 20 | 5 | 40 | 50 | 50 | 15 |
| Bromegrass, Downy | 50 | 80 | 60 | 5 | 10 | 30 | 20 | 0 | 0 | 0 | 10 | 10 | 40 | 25 |
| Canarygrass | 85 | 35 | 90 | 60 | 30 | 75 | 0 | 10 | 35 | 0 | 45 | 30 | 50 | 70 |
| Chickweed | 98 | 100 | 95 | 98 | 90 | 100 | 100 | 98 | 100 | 100 | 100 | 100 | 100 | 98 |
| Cocklebur | 98 | 100 | 95 | 70 | 100 | 95 | 98 | 98 | 90 | 100 | 100 | 100 | 100 | 100 |
| Corn | 85 | 75 | 80 | 98 | 75 | 60 | 60 | 60 | 80 | 35 | 80 | 75 | 70 | 80 |
| Crabgrass, Large | 98 | 98 | 98 | 98 | 80 | 100 | 100 | 90 | 90 | 80 | 90 | 95 | 95 | 95 |
| Cupgrass, Woolly | 95 | 90 | 95 | 75 | 55 | 98 | 70 | 70 | 70 | 65 | 85 | 75 | 95 | 85 |
| Deadnettle | — | — | — | — | — | — | — | — | — | — | — | — | — | — |
| Foxtail, Giant | 98 | 95 | 95 | 98 | 85 | 98 | 98 | 85 | 98 | 85 | 85 | 90 | 85 | 95 |
| Foxtail, Green | 100 | 95 | 100 | 80 | 90 | 98 | 98 | 90 | 80 | 90 | 85 | 95 | 95 | 98 |
| *Galium* | — | — | — | — | — | — | — | — | — | — | — | — | — | — |
| Goosegrass | 95 | 98 | 70 | 80 | 75 | 85 | 90 | 75 | 85 | 90 | 85 | 98 | 90 | 80 |
| Johnsongrass | 100 | 45 | 100 | 100 | 65 | 100 | 100 | 70 | 45 | 45 | 80 | 85 | 98 | 95 |
| *Kochia* | 98 | 100 | 85 | 100 | 98 | 95 | 100 | 98 | 90 | 100 | 100 | 100 | 98 | 100 |
| Lambsquarters | 100 | 100 | 100 | 100 | 100 | 100 | 100 | 98 | 100 | 100 | 100 | 100 | 100 | 100 |
| Morningglory | 100 | 65 | 95 | 100 | 100 | 98 | 100 | 100 | 100 | 100 | 100 | 100 | 100 | 100 |
| Nutsedge, Yellow | 85 | 75 | 75 | 75 | 75 | 75 | 75 | 70 | 65 | 85 | 85 | 80 | 75 | 75 |
| Oat, Wild | 80 | 90 | 80 | 50 | 20 | 50 | 10 | 5 | 30 | 0 | 30 | 10 | 50 | 80 |
| Pigweed | 100 | 100 | 100 | 100 | 100 | 100 | 100 | 100 | 100 | 100 | 100 | 100 | 100 | 100 |
| Ragweed | 98 | 98 | 98 | 100 | 95 | 98 | 75 | 98 | 80 | 95 | 95 | 100 | 90 | 95 |
| Ryegrass, Italian | 60 | 60 | 80 | 30 | 0 | 20 | 30 | 0 | 10 | 0 | 10 | 5 | 15 | 20 |
| Soybean | 98 | 100 | 98 | 98 | 100 | 98 | 98 | 98 | 95 | 98 | 98 | 100 | 100 | 100 |
| Surinam Grass | 100 | 85 | 98 | 95 | 75 | 98 | 75 | 70 | 80 | 70 | 85 | 85 | 90 | 80 |
| Velvetleaf | 100 | 100 | 98 | 100 | 100 | 100 | 100 | 98 | 80 | 100 | 100 | 100 | 98 | 100 |
| Wheat | 45 | 50 | 5 | 10 | 35 | 50 | 0 | 5 | 5 | 0 | 15 | 5 | 20 | 5 |
| Windgrass | 95 | 95 | 70 | 50 | 50 | 65 | 90 | 55 | 50 | 0 | 45 | 85 | 70 | 60 |

| | Compounds | | | | | | | | | | | | | |
|---|---|---|---|---|---|---|---|---|---|---|---|---|---|---|
| 250 g ai/ha | 100 | 102 | 107 | 108 | 109 | 111 | 113 | 117 | 118 | 119 | 120 | 121 | 123 | 126 |
| | Postemergence | | | | | | | | | | | | | |
| Barley | 50 | 60 | 30 | 0 | 5 | 30 | 20 | 0 | 0 | 5 | 5 | 10 | 50 | 40 |
| Bermudagrass | 85 | 100 | 98 | 100 | 95 | 100 | 95 | 100 | 98 | 98 | 98 | 100 | 98 | 95 |
| Blackgrass | 40 | 45 | 20 | 30 | 50 | 40 | 5 | 40 | 40 | 50 | 60 | 60 | 80 | 45 |
| Bromegrass, Downy | 35 | 30 | 30 | 5 | 5 | 10 | 90 | 45 | 35 | 85 | 80 | 90 | 45 | 40 |
| Canarygrass | 10 | 50 | 80 | 5 | 45 | 15 | 90 | 5 | 15 | 30 | 55 | 30 | 85 | 90 |
| Chickweed | 100 | 100 | 100 | 100 | 100 | 100 | 100 | 100 | 100 | 100 | 100 | 100 | 100 | 98 |
| Cocklebur | 98 | 100 | 100 | 100 | 100 | 100 | 98 | 100 | 98 | 95 | 80 | 100 | 100 | 98 |
| Corn | 45 | 70 | 85 | 65 | 60 | 60 | 85 | 25 | 25 | 70 | 75 | 85 | 80 | 80 |
| Crabgrass, Large | 80 | 90 | 95 | 85 | 85 | 85 | 95 | 95 | 95 | 95 | 98 | 98 | 90 | 90 |
| Cupgrass, Woolly | 75 | 85 | 80 | 75 | 75 | 75 | 95 | 98 | 95 | 100 | 100 | 100 | 90 | 90 |
| Deadnettle | — | — | — | — | — | — | — | — | — | — | — | — | — | — |
| Foxtail, Giant | 85 | 95 | 95 | 80 | 90 | 70 | 95 | 95 | 95 | 95 | 98 | 98 | 85 | 90 |
| Foxtail, Green | 85 | 95 | 98 | 80 | 98 | 70 | 95 | 95 | 95 | 100 | 100 | 100 | 90 | 95 |
| *Galium* | — | — | — | — | — | — | — | — | — | — | — | — | — | — |
| Goosegrass | 75 | 90 | 85 | 85 | 85 | 85 | 90 | 85 | 90 | 95 | 98 | 98 | 85 | 85 |
| Johnsongrass | 25 | 75 | 90 | 60 | 75 | 40 | 95 | 25 | 35 | 80 | 80 | 85 | 90 | 90 |
| *Kochia* | 100 | 100 | 100 | 100 | 98 | 100 | 100 | 85 | 98 | 100 | 98 | 100 | 100 | 85 |
| Lambsquarters | 98 | 100 | 100 | 100 | 100 | 100 | 98 | 100 | 100 | 100 | 100 | 100 | 98 | 98 |
| Morningglory | 100 | 100 | 100 | 100 | 100 | 100 | 100 | 100 | 80 | 95 | 90 | 45 | 100 | 100 |
| Nutsedge, Yellow | 40 | 80 | 85 | 85 | 80 | 85 | 75 | 35 | 65 | 75 | 75 | 50 | 80 | 80 |
| Oat, Wild | 30 | 80 | 40 | 0 | 40 | 10 | 85 | 35 | 40 | 95 | 95 | 98 | 60 | 50 |

TABLE B-continued

| | | | | | | | | | | | | | | |
|---|---|---|---|---|---|---|---|---|---|---|---|---|---|---|
| Pigweed | 98 | 98 | 100 | 100 | 100 | 100 | 100 | 100 | 100 | 100 | 100 | 100 | 100 | 98 |
| Ragweed | 80 | 95 | 98 | 98 | 98 | 98 | 98 | 98 | 98 | 98 | 80 | 95 | 98 | 90 |
| Ryegrass, Italian | 50 | 10 | 5 | 0 | 40 | 5 | 85 | 50 | 60 | 85 | 80 | 75 | 50 | 50 |
| Soybean | 100 | 100 | 100 | 85 | 100 | 98 | 98 | 95 | 100 | 80 | 98 | 100 | 90 | 98 |
| Surinam Grass | 75 | 85 | 85 | 80 | 80 | 80 | 90 | 85 | 90 | 98 | 100 | 100 | 85 | 98 |
| Velvetleaf | 85 | 100 | 100 | 100 | 100 | 100 | 98 | 100 | 100 | 100 | 100 | 100 | 100 | 98 |
| Wheat | 35 | 30 | 15 | 5 | 15 | 30 | 50 | 25 | 10 | 60 | 80 | 80 | 50 | 50 |
| Windgrass | 60 | 70 | 85 | 40 | 80 | 70 | 80 | 65 | 80 | 100 | 90 | 100 | 90 | 60 |

| | Compounds | | | | | | | | | | | | | |
|---|---|---|---|---|---|---|---|---|---|---|---|---|---|---|
| 250 g ai/ha | 127 | 128 | 129 | 130 | 140 | 141 | 146 | 147 | 152 | 155 | 156 | 157 | 160 | 162 |
| | Postemergence | | | | | | | | | | | | | |
| Barley | 60 | 5 | 0 | 0 | 0 | 5 | 30 | 0 | 90 | 85 | 85 | 30 | 50 | 85 |
| Bermudagrass | 98 | 100 | 98 | 95 | 90 | 90 | 100 | 98 | 98 | 100 | 98 | 100 | 95 | 100 |
| Blackgrass | 40 | 15 | 5 | 5 | 5 | 25 | 50 | 55 | 70 | 65 | 50 | 40 | 25 | 65 |
| Bromegrass, Downy | 40 | 50 | 35 | 40 | 20 | 45 | 35 | 10 | 85 | 50 | 40 | 65 | 55 | 50 |
| Canarygrass | 60 | 30 | 0 | 25 | 5 | 5 | 10 | 5 | 85 | 65 | 60 | 90 | 35 | 90 |
| Chickweed | 98 | 100 | 100 | 100 | 75 | 95 | 98 | 98 | 95 | 100 | 100 | 100 | 100 | 100 |
| Cocklebur | 100 | 100 | 100 | 100 | 95 | 100 | — | 100 | 100 | 100 | 98 | 100 | 100 | 100 |
| Corn | 75 | 60 | 60 | 80 | 45 | 45 | 35 | 40 | 80 | 65 | 60 | 100 | 60 | 85 |
| Crabgrass, Large | 95 | 100 | 85 | 100 | 90 | 85 | 98 | 90 | 95 | 90 | 80 | 100 | 95 | 98 |
| Cupgrass, Woolly | 85 | 95 | 85 | 90 | 65 | 70 | 75 | 80 | 100 | 75 | 65 | 98 | 95 | 100 |
| Deadnettle | — | — | — | — | — | — | — | — | — | — | — | — | — | — |
| Foxtail, Giant | 90 | 98 | 98 | 98 | 90 | 85 | 98 | 90 | 98 | 95 | 90 | 100 | 85 | 98 |
| Foxtail, Green | 95 | 98 | 95 | 98 | 95 | 90 | 90 | 90 | 100 | 80 | 85 | 95 | 98 | 100 |
| Galium | — | — | — | — | — | — | — | — | — | — | — | — | — | — |
| Goosegrass | 85 | 98 | 95 | 95 | 85 | 80 | 95 | 95 | 98 | 98 | 80 | 100 | 90 | 98 |
| Johnsongrass | 95 | 85 | 85 | 80 | 45 | 65 | 95 | 60 | 100 | 70 | 65 | 100 | 75 | 100 |
| Kochia | 100 | 98 | 98 | 100 | 35 | 90 | 90 | 100 | 100 | 100 | 25 | 45 | 100 | 80 |
| Lambsquarters | 95 | 100 | 98 | 100 | 80 | 100 | 100 | 100 | 100 | 100 | 100 | 100 | 98 | 100 |
| Morningglory | 98 | 90 | 90 | 100 | 65 | 65 | 95 | 100 | 95 | 100 | 100 | 100 | 100 | 100 |
| Nutsedge, Yellow | 80 | 60 | 85 | 40 | 75 | 60 | 40 | 75 | 80 | 75 | 75 | 45 | 80 | 80 |
| Oat, Wild | 60 | 80 | 30 | 60 | 40 | 40 | 70 | 45 | 85 | 70 | 50 | 70 | 60 | 55 |
| Pigweed | 100 | 100 | 98 | 100 | 98 | 98 | 100 | 100 | 100 | 100 | 100 | 98 | 100 | 100 |
| Ragweed | 98 | 98 | 95 | 98 | 75 | 95 | 98 | 98 | 98 | 95 | 90 | 100 | 98 | 100 |
| Ryegrass, Italian | 30 | 30 | 0 | 5 | 5 | 5 | 15 | 40 | 80 | 60 | 40 | 35 | 35 | 90 |
| Soybean | 98 | 98 | 98 | 100 | 80 | 90 | 100 | 85 | 100 | 100 | 98 | 100 | 98 | 100 |
| Surinam Grass | 90 | 85 | 85 | 90 | 65 | 75 | 75 | 75 | 95 | 75 | 70 | 100 | 75 | 85 |
| Velvetleaf | 100 | 100 | 100 | 100 | 85 | 98 | 100 | 100 | 100 | 100 | 100 | 100 | 100 | 100 |
| Wheat | 40 | 5 | 0 | 10 | 15 | 10 | 45 | 10 | 90 | 70 | 45 | 30 | 45 | 40 |
| Windgrass | 70 | 85 | 85 | 85 | 30 | 50 | 60 | 70 | 98 | 85 | 60 | 80 | 80 | 80 |

| | Compounds | | | | | | | | | | | | | |
|---|---|---|---|---|---|---|---|---|---|---|---|---|---|---|
| 250 g ai/ha | 164 | 173 | 181 | 184 | 186 | 187 | 189 | 190 | 191 | 193 | 197 | 217 | 218 | 219 |
| | Postemergence | | | | | | | | | | | | | |
| Barley | 35 | 50 | 55 | 60 | 5 | 40 | 40 | 70 | 70 | 50 | 40 | 10 | 35 | 30 |
| Bermudagrass | 100 | 100 | 100 | 100 | 98 | 100 | 70 | 100 | 100 | 100 | 100 | 100 | 100 | 100 |
| Blackgrass | 35 | 50 | 15 | 50 | 20 | 5 | 5 | 40 | 60 | 60 | 45 | 30 | 5 | 90 |
| Bromegrass, Downy | 95 | 70 | 85 | 60 | 50 | 40 | 10 | 35 | 75 | 85 | 30 | 65 | 30 | 80 |
| Canarygrass | 98 | 80 | 90 | 95 | 40 | 60 | 10 | 55 | 85 | 25 | 60 | 20 | 5 | 55 |
| Chickweed | 100 | 100 | 100 | 100 | 100 | 100 | 100 | 100 | 100 | 100 | 100 | 100 | 100 | 100 |
| Cocklebur | 100 | 100 | 100 | 100 | 100 | 100 | 100 | 100 | 100 | 100 | 100 | — | — | — |
| Corn | 70 | 85 | 95 | 98 | 65 | 80 | 45 | 65 | 85 | 60 | 65 | 35 | 80 | 80 |
| Crabgrass, Large | 100 | 100 | 100 | 100 | 95 | 100 | 100 | 90 | 100 | 100 | 100 | 98 | 90 | 98 |
| Cupgrass, Woolly | 100 | 100 | 100 | 100 | 85 | 95 | 80 | 85 | 98 | 98 | 98 | 55 | 80 | 98 |
| Deadnettle | — | — | — | 100 | 100 | 100 | 100 | 100 | 100 | 100 | 100 | — | — | — |
| Foxtail, Giant | 100 | 100 | 100 | 100 | 95 | 100 | 98 | 95 | 100 | 100 | 100 | 90 | 85 | 95 |
| Foxtail, Green | 100 | 90 | 98 | 98 | 95 | 98 | 95 | 70 | 98 | 80 | 70 | 90 | 90 | 90 |
| Galium | — | — | — | 60 | 70 | 85 | 85 | 85 | 60 | 90 | 80 | — | — | — |
| Goosegrass | 98 | 100 | 100 | 100 | 100 | 100 | 90 | 98 | 100 | 100 | 100 | 95 | 35 | 95 |
| Johnsongrass | 98 | — | 100 | 100 | 100 | 100 | 70 | 80 | 100 | 80 | 100 | 65 | 80 | 100 |
| Kochia | 100 | 100 | 100 | 10 | 100 | 80 | 100 | 98 | 35 | 100 | 98 | 100 | 100 | 100 |
| Lambsquarters | 100 | 100 | 100 | 100 | 100 | 100 | 100 | 100 | 100 | 100 | 100 | 100 | 100 | 100 |
| Morningglory | 100 | 95 | 100 | 100 | 100 | 100 | 100 | 100 | 90 | 100 | 80 | 98 | 100 | 100 |
| Nutsedge, Yellow | 75 | 75 | 85 | 75 | 80 | 75 | 65 | 75 | 70 | 75 | 75 | 70 | 60 | 85 |
| Oat, Wild | 90 | 85 | 100 | 98 | 45 | 45 | 25 | 50 | 80 | 75 | 85 | 85 | 60 | 85 |
| Pigweed | 100 | 100 | 100 | 100 | 100 | 100 | 100 | 100 | 100 | 100 | 100 | 100 | 100 | 100 |
| Ragweed | 100 | 98 | 100 | — | 100 | 100 | 80 | — | — | — | — | 98 | 100 | 100 |
| Ryegrass, Italian | 40 | 30 | 65 | 60 | 30 | 30 | 5 | 30 | 50 | 45 | 35 | 40 | 70 | 40 |
| Soybean | 100 | 100 | 100 | 100 | 100 | 100 | 100 | 98 | 100 | 100 | 100 | 100 | 98 | 100 |
| Surinam Grass | 98 | — | 100 | 100 | — | — | 85 | 90 | 98 | 95 | 70 | 95 | 90 | 65 |
| Velvetleaf | 95 | 100 | 100 | 100 | 100 | 100 | 100 | 100 | 100 | 100 | 100 | 100 | 100 | 98 |
| Wheat | 50 | 50 | 70 | 60 | 5 | 5 | 0 | 30 | 65 | 60 | 40 | 50 | 0 | 50 |
| Windgrass | 85 | 75 | 65 | 100 | 65 | 80 | 80 | 65 | 100 | 75 | 98 | 85 | 45 | 85 |

TABLE B-continued

| 250 g ai/ha | Compounds | | | | | | | | | | | | | |
|---|---|---|---|---|---|---|---|---|---|---|---|---|---|---|
| | 220 | 226 | 227 | 228 | 229 | 233 | 235 | 236 | 237 | 238 | 239 | 240 | 243 | 244 |
| Postemergence | | | | | | | | | | | | | | |
| Barley | 15 | 60 | 30 | 40 | 25 | 10 | — | 0 | 40 | 40 | 5 | 15 | 95 | 98 |
| Bermudagrass | 100 | 98 | 90 | 95 | 90 | 100 | 100 | — | 100 | 100 | 100 | 100 | 100 | 100 |
| Blackgrass | 40 | 60 | 20 | 55 | 30 | 50 | — | 40 | 80 | 70 | 50 | 65 | 98 | 85 |
| Bromegrass, Downy | 30 | 30 | 25 | 10 | 30 | 60 | 85 | 25 | 95 | 85 | 10 | 50 | 100 | 80 |
| Canarygrass | 30 | 60 | 10 | 10 | 60 | 20 | 30 | 10 | 50 | 30 | 0 | 40 | 100 | 100 |
| Chickweed | 100 | 95 | 90 | 100 | 98 | 100 | 100 | 100 | 100 | 100 | 100 | 100 | 100 | 100 |
| Cocklebur | — | 100 | 95 | 100 | 100 | 100 | — | 100 | — | — | 100 | — | — | — |
| Corn | 75 | 98 | 85 | 90 | 85 | 85 | 100 | — | 100 | 95 | 75 | 100 | 100 | 100 |
| Crabgrass, Large | 90 | 98 | 90 | 98 | 90 | 100 | 100 | 100 | 100 | 98 | 98 | 100 | 100 | 100 |
| Cupgrass, Woolly | 65 | 95 | 95 | 98 | 90 | 100 | 100 | — | 100 | 100 | 95 | 100 | 100 | 100 |
| Deadnettle | — | — | — | — | — | — | — | — | — | — | — | — | — | — |
| Foxtail, Giant | 95 | 95 | 98 | 95 | 95 | 98 | 100 | 98 | 100 | 100 | 98 | 100 | 98 | 100 |
| Foxtail, Green | 90 | 90 | 90 | 100 | 95 | 100 | 98 | 98 | 95 | 98 | 95 | 98 | 100 | 100 |
| *Galium* | — | — | — | — | — | — | — | — | — | — | — | — | — | — |
| Goosegrass | 90 | 85 | 80 | 90 | 80 | 98 | 100 | 100 | 98 | 98 | 100 | 98 | 98 | 98 |
| Johnsongrass | 90 | 100 | 65 | 100 | 100 | 25 | 100 | 55 | 100 | 100 | — | 100 | 100 | 100 |
| *Kochia* | 100 | 100 | 100 | 100 | 100 | — | 100 | 100 | 100 | 100 | 98 | 100 | 100 | 100 |
| Lambsquarters | 100 | 98 | 98 | 100 | 98 | 100 | 100 | 100 | 100 | 100 | 100 | 100 | 100 | 100 |
| Morningglory | 100 | 100 | 100 | 100 | 100 | 100 | 100 | — | 100 | 100 | 100 | — | 100 | 100 |
| Nutsedge, Yellow | 55 | 75 | 65 | 70 | 55 | 25 | 60 | 65 | 45 | 25 | 70 | 45 | 85 | 75 |
| Oat, Wild | 50 | 50 | 30 | 40 | 35 | 60 | 95 | 60 | 90 | 60 | 30 | 60 | 100 | 98 |
| Pigweed | 100 | 98 | 100 | 100 | 100 | — | 100 | — | 100 | 100 | 100 | 100 | 100 | 100 |
| Ragweed | 98 | 90 | 85 | 98 | 95 | 98 | 100 | 98 | 100 | 100 | 100 | 100 | 100 | 100 |
| Ryegrass, Italian | 60 | 20 | 10 | 0 | 10 | 60 | 60 | 5 | 60 | 70 | 0 | 40 | 95 | 95 |
| Soybean | 100 | 100 | 98 | 100 | 98 | 100 | 100 | 100 | 100 | 100 | 98 | 100 | 100 | 100 |
| Surinam Grass | 75 | 85 | 95 | 98 | 90 | 100 | 100 | — | 100 | 100 | 75 | 100 | 100 | 100 |
| Velvetleaf | 100 | 98 | 98 | 100 | 85 | 100 | 100 | 100 | 100 | 100 | 100 | 100 | 100 | 100 |
| Wheat | 15 | 30 | 20 | 35 | 35 | 65 | 80 | 60 | 85 | 80 | 30 | 50 | 100 | 95 |
| Windgrass | 60 | 85 | 50 | 90 | 65 | 60 | 98 | 85 | 100 | 95 | 70 | 98 | 100 | 95 |

| 250 g ai/ha | Compounds | |
|---|---|---|
| | 245 | 255 |
| Postemergence | | |
| Barley | 95 | 50 |
| Bermudagrass | 100 | 100 |
| Blackgrass | 80 | 60 |
| Bromegrass, Downy | 95 | 85 |
| Canarygrass | 100 | 60 |
| Chickweed | 100 | 100 |
| Cocklebur | — | — |
| Corn | 100 | 85 |
| Crabgrass, Large | 100 | 95 |
| Cupgrass, Woolly | 100 | 98 |
| Deadnettle | — | — |
| Foxtail, Giant | 100 | 100 |
| Foxtail, Green | 100 | 90 |
| *Galium* | — | — |
| Goosegrass | 100 | 98 |
| Johnsongrass | 100 | 95 |
| *Kochia* | 100 | 65 |
| Lambsquarters | 100 | 100 |
| Morningglory | 100 | 100 |
| Nutsedge, Yellow | 75 | 60 |
| Oat, Wild | 100 | 90 |
| Pigweed | 100 | 100 |
| Ragweed | 100 | 95 |
| Ryegrass, Italian | 85 | 80 |
| Soybean | 100 | 100 |
| Surinam Grass | 100 | 90 |
| Velvetleaf | 100 | 100 |
| Wheat | 98 | 80 |
| Windgrass | 98 | 95 |

TABLE B-continued

| 125 g ai/ha | Compounds | | | | | | | | | | | | | |
|---|---|---|---|---|---|---|---|---|---|---|---|---|---|---|
| | 1 | 2 | 3 | 4 | 7 | 8 | 9 | 10 | 11 | 12 | 14 | 24 | 26 | 27 |
| | Postemergence | | | | | | | | | | | | | |
| Barley | 0 | 30 | 0 | 0 | 0 | 5 | 20 | 0 | 10 | 0 | 5 | 50 | 0 | 10 |
| Bermudagrass | 60 | 90 | 70 | 85 | 65 | 95 | 98 | 90 | 100 | 98 | 80 | 100 | 60 | 100 |
| Blackgrass | 5 | 45 | 0 | 30 | 0 | 10 | 40 | 50 | 40 | 10 | 5 | 40 | 10 | 45 |
| Bromegrass, Downy | 0 | 80 | 0 | 50 | 5 | 10 | 40 | 10 | 45 | 20 | 50 | 70 | 20 | 20 |
| Canarygrass | 0 | 80 | 0 | 75 | 0 | 70 | 50 | 5 | 90 | 5 | 20 | — | 50 | 30 |
| Chickweed | 65 | 95 | 98 | 100 | 90 | 100 | 95 | 95 | 100 | 100 | 80 | 95 | 85 | 50 |
| Cocklebur | 70 | 95 | 85 | 100 | 65 | 100 | 35 | 95 | 100 | 100 | 90 | 98 | 95 | 95 |
| Corn | 0 | 35 | 10 | 50 | 0 | 75 | 75 | 45 | 80 | 45 | 45 | 85 | 40 | 50 |
| Crabgrass, Large | 55 | 90 | 80 | 100 | 45 | 90 | 85 | 75 | 100 | 80 | 85 | 95 | 50 | 60 |
| Cupgrass, Woolly | 0 | 85 | 20 | 100 | 50 | 90 | 80 | 70 | 90 | 70 | 80 | 95 | 85 | 70 |
| Deadnettle | — | — | — | — | — | — | — | — | — | — | — | — | — | — |
| Foxtail, Giant | 20 | 85 | 60 | 98 | 55 | 100 | 95 | 80 | 98 | 98 | 80 | 90 | 70 | 90 |
| Foxtail, Green | 30 | 100 | 35 | 60 | 30 | 85 | 80 | 70 | 85 | 70 | 50 | 90 | 85 | 80 |
| Galium | — | — | — | — | — | — | — | — | — | — | — | — | — | — |
| Goosegrass | 65 | 95 | 70 | 85 | 35 | 95 | 90 | 95 | 95 | 98 | 80 | 85 | 95 | 98 |
| Johnsongrass | 0 | 98 | — | 95 | 0 | 98 | 85 | 60 | 90 | 60 | 80 | 70 | 50 | 45 |
| Kochia | 25 | 80 | 85 | 100 | 45 | 100 | 25 | 15 | 75 | 60 | — | 80 | — | 100 |
| Lambsquarters | 90 | 95 | 98 | 100 | 65 | 100 | 80 | 90 | 95 | 98 | 85 | 90 | 90 | 95 |
| Morningglory | 45 | 95 | 55 | 90 | 15 | 100 | 70 | 45 | 70 | 70 | 80 | 60 | 75 | 80 |
| Nutsedge, Yellow | 20 | 75 | 65 | 75 | 0 | 80 | 60 | 60 | 50 | 65 | 30 | 30 | 35 | 50 |
| Oat, Wild | 10 | 55 | 5 | 50 | 0 | 35 | 40 | 20 | 70 | 20 | 50 | 60 | 45 | 50 |
| Pigweed | 85 | 95 | 100 | 100 | 90 | 100 | 100 | 95 | 85 | 98 | 80 | 80 | 85 | 100 |
| Ragweed | 70 | 90 | 98 | 100 | 80 | 100 | 75 | 90 | 100 | 100 | 85 | 90 | 98 | 100 |
| Ryegrass, Italian | 0 | 40 | 5 | 15 | 0 | 30 | 30 | 0 | 40 | 5 | 5 | 40 | 10 | 5 |
| Soybean | 70 | 95 | 80 | 100 | 75 | 98 | 85 | 95 | 100 | 100 | 90 | 95 | 95 | 95 |
| Surinam Grass | 10 | 85 | 40 | 75 | 20 | 75 | 75 | 70 | 85 | 65 | 50 | 60 | 60 | 80 |
| Velvetleaf | 85 | 90 | 100 | 90 | 90 | 95 | 90 | 75 | 100 | 98 | 90 | 98 | 95 | 80 |
| Wheat | 0 | 20 | 10 | 50 | 10 | 35 | 30 | 0 | 40 | 0 | 0 | 30 | 5 | 10 |
| Windgrass | 0 | 50 | 0 | 60 | 5 | 30 | 60 | 30 | 85 | 45 | 30 | 60 | 40 | 50 |

| 125 g ai/ha | Compounds | | | | | | | | | | | | | |
|---|---|---|---|---|---|---|---|---|---|---|---|---|---|---|
| | 29 | 33 | 34 | 36 | 37 | 38 | 39 | 40 | 42 | 44 | 45 | 46 | 47 | 48 |
| | Postemergence | | | | | | | | | | | | | |
| Barley | 0 | 0 | 30 | 20 | 0 | 0 | 0 | 10 | 0 | 5 | 5 | 0 | 10 | 10 |
| Bermudagrass | 90 | 98 | 95 | 100 | 98 | 100 | 85 | 100 | 95 | 95 | 95 | 90 | 98 | 98 |
| Blackgrass | 40 | 30 | 10 | 15 | 5 | 15 | 0 | 10 | 15 | 30 | 10 | 10 | 25 | 20 |
| Bromegrass, Downy | 40 | 10 | 50 | 45 | 15 | 85 | 0 | 70 | 15 | 80 | 45 | 10 | 50 | 50 |
| Canarygrass | 40 | 5 | 50 | 50 | 10 | 10 | 0 | 30 | 0 | 30 | 30 | 0 | 40 | 45 |
| Chickweed | 50 | 100 | 98 | 100 | 85 | 100 | 100 | 100 | 80 | 98 | 98 | 95 | 100 | 95 |
| Cocklebur | 95 | 95 | 85 | — | — | — | 95 | — | 85 | 90 | 70 | 80 | 95 | 98 |
| Corn | 50 | 10 | 45 | 65 | 60 | 75 | 45 | 85 | 20 | 80 | 60 | 60 | 80 | 85 |
| Crabgrass, Large | 55 | 90 | 95 | 95 | 85 | 98 | 85 | 100 | 85 | 95 | 75 | 75 | 90 | 95 |
| Cupgrass, Woolly | 85 | 70 | 90 | 95 | 75 | 95 | 85 | 98 | 25 | 85 | 75 | 25 | 90 | 90 |
| Deadnettle | — | — | — | — | — | — | — | — | — | — | — | — | — | — |
| Foxtail, Giant | 90 | 85 | 95 | 98 | 95 | 100 | 95 | 100 | 75 | 95 | 95 | 80 | 98 | 95 |
| Foxtail, Green | 75 | 90 | 90 | 90 | 85 | 95 | 90 | 95 | 60 | 90 | 85 | 85 | 95 | 95 |
| Galium | — | — | — | — | — | — | — | — | — | — | — | — | — | — |
| Goosegrass | 85 | 85 | 90 | 90 | 85 | 90 | 65 | 95 | 90 | 90 | 80 | 80 | 95 | 95 |
| Johnsongrass | 40 | 35 | 95 | 85 | 60 | 95 | 90 | 75 | 40 | 90 | 98 | 70 | 98 | 80 |
| Kochia | — | 95 | 100 | 60 | 15 | 100 | 60 | 10 | 100 | 75 | 15 | 20 | 98 | 100 |
| Lambsquarters | 90 | 98 | 100 | 100 | 98 | 100 | 100 | 100 | 100 | 95 | 100 | 90 | 98 | 100 |
| Morningglory | 80 | 80 | 85 | 75 | 75 | 75 | 75 | 75 | 75 | 75 | 80 | 45 | 90 | 80 |
| Nutsedge, Yellow | 70 | 75 | 55 | 25 | 25 | 15 | 15 | 55 | 70 | 50 | 45 | 70 | 70 | 60 |
| Oat, Wild | 60 | 40 | 60 | 75 | 40 | 80 | 30 | 90 | 10 | 80 | 60 | 20 | 60 | 85 |
| Pigweed | 80 | 98 | 98 | 90 | 98 | 98 | 100 | 100 | 100 | 98 | 100 | 80 | 100 | 100 |
| Ragweed | 100 | 98 | 95 | 95 | 95 | 80 | 95 | 98 | 85 | 95 | 95 | 80 | 95 | 90 |
| Ryegrass, Italian | 40 | 40 | 20 | 10 | 5 | 60 | 5 | 0 | 10 | 10 | 35 | 5 | 30 | 30 |
| Soybean | 98 | 98 | 95 | 100 | 95 | 90 | 98 | 100 | 95 | 95 | 98 | 90 | 98 | 98 |
| Surinam Grass | 70 | 75 | 80 | 85 | 75 | 90 | 65 | 98 | 45 | 95 | 95 | 80 | 98 | 95 |
| Velvetleaf | 80 | 98 | 98 | 100 | 95 | 100 | 80 | 100 | 95 | 100 | 90 | 85 | 98 | 98 |
| Wheat | 10 | 5 | 35 | 5 | 0 | 40 | 5 | 30 | 5 | 30 | 15 | 0 | 5 | 10 |
| Windgrass | 30 | 30 | 50 | 80 | 50 | 85 | 5 | 80 | 70 | 85 | 70 | 15 | 80 | 90 |

| 125 g ai/ha | Compounds | | | | | | | | | | | | |
|---|---|---|---|---|---|---|---|---|---|---|---|---|---|
| | 49 | 50 | 51 | 52 | 53 | 55 | 56 | 58 | 59 | 61 | 62 | 63 | 64 | 66 |
| | Postemergence | | | | | | | | | | | | | |
| Barley | 0 | 5 | 30 | 25 | 70 | 0 | 30 | 5 | 10 | 0 | 5 | 0 | — | 0 |
| Bermudagrass | 95 | 100 | 90 | 95 | 98 | 85 | 100 | 98 | 98 | 90 | 85 | 85 | 98 | 95 |

TABLE B-continued

| | | | | | | | | | | | | | | |
|---|---|---|---|---|---|---|---|---|---|---|---|---|---|---|
| Blackgrass | 0 | 5 | 50 | 25 | 40 | 5 | 20 | 20 | 40 | 0 | 30 | 35 | 5 | 10 |
| Bromegrass, Downy | 0 | 20 | 55 | 60 | 55 | 0 | 50 | 45 | 35 | 0 | 50 | 20 | 60 | 20 |
| Canarygrass | 0 | 5 | 60 | 65 | 90 | 0 | 40 | 80 | 50 | 0 | 0 | 0 | 40 | 0 |
| Chickweed | 80 | 98 | 85 | 95 | 98 | 80 | 98 | 90 | 98 | 95 | 75 | 80 | 98 | 95 |
| Cocklebur | 80 | 90 | 90 | 85 | 85 | 65 | 75 | 85 | 90 | 70 | 55 | 90 | 95 | 25 |
| Corn | 5 | 25 | 80 | 65 | 80 | 5 | 65 | 65 | 75 | 10 | 75 | 25 | 85 | 70 |
| Crabgrass, Large | 80 | 95 | 85 | 90 | 95 | 80 | 90 | 90 | 95 | 75 | 80 | 80 | 98 | 65 |
| Cupgrass, Woolly | 55 | 80 | 80 | 85 | 95 | 15 | 65 | 70 | 90 | 60 | 60 | 65 | 98 | 60 |
| Deadnettle | — | — | — | — | — | — | — | — | — | — | — | — | — | — |
| Foxtail, Giant | 70 | 95 | 85 | 90 | 90 | 55 | 85 | 90 | 95 | 65 | 75 | 65 | 98 | 80 |
| Foxtail, Green | 75 | 95 | 95 | 98 | 100 | 80 | 98 | 98 | 70 | 60 | 80 | 70 | 100 | 90 |
| *Galium* | — | — | — | — | — | — | — | — | — | — | — | — | — | — |
| Goosegrass | 70 | 90 | 85 | 85 | 80 | 65 | 75 | 85 | 95 | 65 | 65 | 70 | 85 | 70 |
| Johnsongrass | 10 | 65 | 85 | 90 | 95 | 10 | 85 | 98 | 100 | 10 | 0 | 10 | 100 | 65 |
| *Kochia* | 80 | 100 | 25 | 55 | 75 | 75 | 100 | 25 | 45 | 70 | 60 | 25 | 80 | 90 |
| Lambsquarters | 90 | 100 | 95 | 90 | 98 | 95 | 100 | 100 | 100 | 95 | 98 | 98 | 100 | 95 |
| Morningglory | 80 | 70 | 90 | 75 | 80 | 75 | 100 | 90 | 80 | 70 | 75 | 75 | 85 | 100 |
| Nutsedge, Yellow | 70 | 70 | 75 | 45 | 75 | 55 | 75 | 55 | 70 | 60 | 35 | 50 | 10 | 65 |
| Oat, Wild | 5 | 10 | 60 | 95 | 85 | 0 | 40 | 60 | 55 | 0 | 25 | 5 | 95 | 5 |
| Pigweed | 95 | 100 | 98 | 95 | 100 | 90 | 100 | 98 | 100 | 90 | 100 | 95 | 100 | 100 |
| Ragweed | 80 | 98 | 90 | 80 | 95 | 95 | 75 | 90 | 90 | 85 | 75 | 80 | 90 | 25 |
| Ryegrass, Italian | 0 | 0 | 10 | 55 | 40 | 0 | 50 | 30 | 70 | 0 | 50 | 0 | 0 | 5 |
| Soybean | 85 | 95 | 95 | 95 | 95 | 60 | 95 | 95 | 95 | 10 | 90 | 85 | 98 | 98 |
| Surinam Grass | 55 | 80 | 90 | 90 | 98 | 45 | 85 | 95 | 90 | 75 | 65 | 35 | 98 | 85 |
| Velvetleaf | 98 | 98 | 90 | 98 | 95 | 98 | 98 | 85 | 95 | 95 | 95 | 98 | 98 | 98 |
| Wheat | 15 | 5 | 10 | 35 | 30 | 5 | 0 | 0 | 10 | 0 | 5 | 0 | 30 | 0 |
| Windgrass | 5 | 60 | 60 | 90 | 85 | 0 | 60 | 60 | 60 | 0 | 35 | 40 | 95 | 70 |

| | Compounds | | | | | | | | | | | | | |
|---|---|---|---|---|---|---|---|---|---|---|---|---|---|---|
| 125 g ai/ha | 67 | 68 | 69 | 70 | 71 | 72 | 73 | 74 | 75 | 77 | 79 | 80 | 81 | 82 |

Postemergence

| | | | | | | | | | | | | | | |
|---|---|---|---|---|---|---|---|---|---|---|---|---|---|---|
| Barley | 20 | 25 | 15 | 90 | 0 | 0 | 0 | 0 | 0 | 0 | 35 | 30 | 0 | 0 |
| Bermudagrass | 70 | 95 | 98 | 95 | 80 | 85 | 90 | 95 | 98 | 95 | 85 | 45 | 95 | 85 |
| Blackgrass | 5 | 0 | 0 | 35 | 0 | 0 | 10 | 25 | 0 | 0 | 30 | 5 | 30 | 5 |
| Bromegrass, Downy | 0 | 25 | 70 | 70 | 10 | 0 | 50 | 0 | 35 | 5 | 30 | 60 | 30 | 5 |
| Canarygrass | 0 | 35 | 25 | 85 | 5 | 0 | 5 | 0 | 0 | 0 | 35 | 50 | 10 | 15 |
| Chickweed | 95 | 98 | 98 | 98 | 95 | 90 | 95 | 95 | 98 | 95 | 95 | 100 | 98 | 98 |
| Cocklebur | 90 | 90 | 20 | 40 | 95 | 90 | 65 | 90 | 95 | 60 | 98 | 45 | 65 | 95 |
| Corn | 65 | 80 | 25 | 60 | 0 | 5 | 80 | 15 | 20 | 60 | 60 | 65 | 15 | 5 |
| Crabgrass, Large | 90 | 90 | 98 | 95 | 80 | 85 | 90 | 95 | 100 | 75 | 90 | 90 | 95 | 80 |
| Cupgrass, Woolly | 70 | 55 | 95 | 90 | 85 | 50 | 65 | 55 | 55 | 35 | 65 | 70 | 90 | 65 |
| Deadnettle | — | — | — | — | — | — | — | — | — | — | — | — | — | — |
| Foxtail, Giant | 85 | 85 | 98 | 95 | 80 | 75 | 80 | 70 | 85 | 75 | 95 | 95 | 95 | 95 |
| Foxtail, Green | 80 | 85 | 100 | 98 | 70 | 90 | 90 | 80 | 90 | 80 | 80 | 95 | 95 | 85 |
| *Galium* | — | — | — | — | — | — | — | — | — | — | — | — | — | — |
| Goosegrass | 65 | 85 | 85 | 85 | 90 | 65 | 75 | 80 | 95 | 75 | 70 | 80 | 70 | 80 |
| Johnsongrass | 5 | 75 | 100 | 80 | 98 | 40 | 70 | 10 | 20 | 10 | 70 | 10 | 75 | 80 |
| *Kochia* | 85 | 95 | 80 | 75 | 25 | 90 | 90 | 95 | 100 | 95 | 75 | 20 | 90 | 65 |
| Lambsquarters | 98 | 100 | 100 | 100 | 90 | 100 | 100 | 95 | 100 | 98 | 100 | 98 | 100 | 100 |
| Morningglory | 95 | 98 | 75 | 100 | 75 | 90 | 75 | 95 | 95 | 80 | 100 | 100 | 100 | 100 |
| Nutsedge, Yellow | 65 | 70 | 40 | 40 | 10 | 65 | 50 | 70 | 70 | 70 | 70 | 55 | 80 | 45 |
| Oat, Wild | 10 | 50 | 85 | 90 | 0 | 30 | 80 | 60 | 50 | 5 | 60 | 40 | 50 | 5 |
| Pigweed | 98 | 100 | 100 | 98 | 98 | 100 | 100 | 100 | 100 | 100 | 100 | 100 | 100 | 100 |
| Ragweed | 85 | 80 | 100 | 75 | 80 | 90 | 85 | 85 | 90 | 80 | 95 | 65 | 98 | 95 |
| Ryegrass, Italian | 5 | 15 | 50 | 50 | 0 | 10 | 60 | 20 | 40 | 5 | 50 | 5 | 45 | 5 |
| Soybean | 98 | 98 | 98 | 95 | 95 | 85 | 90 | 95 | 98 | 70 | 95 | 90 | 95 | 95 |
| Surinam Grass | 20 | 70 | 100 | 95 | 65 | 80 | 85 | 65 | 70 | 75 | 75 | 60 | 98 | 75 |
| Velvetleaf | 98 | 100 | 98 | 100 | 90 | 100 | 100 | 100 | 100 | 98 | 98 | 100 | 100 | 90 |
| Wheat | 25 | 5 | 10 | 35 | 0 | 10 | 40 | 30 | 10 | 10 | 35 | 20 | 25 | 0 |
| Windgrass | 5 | 65 | 80 | 90 | 45 | 60 | 90 | 80 | 70 | 20 | 65 | 70 | 60 | 20 |

| | Compounds | | | | | | | | | | | | | |
|---|---|---|---|---|---|---|---|---|---|---|---|---|---|---|
| 125 g ai/ha | 83 | 85 | 86 | 87 | 88 | 89 | 90 | 91 | 92 | 93 | 94 | 95 | 96 | 97 |

Postemergence

| | | | | | | | | | | | | | | |
|---|---|---|---|---|---|---|---|---|---|---|---|---|---|---|
| Barley | 5 | 20 | 60 | 0 | 40 | 10 | 10 | 30 | 0 | 5 | 5 | 0 | 0 | 0 |
| Bermudagrass | 85 | 90 | 95 | 98 | 80 | 95 | 85 | 95 | 85 | 85 | 98 | 75 | 95 | 95 |
| Blackgrass | 0 | 35 | 45 | 20 | 5 | 20 | 5 | 30 | 5 | 30 | 10 | 0 | 30 | 30 |
| Bromegrass, Downy | 45 | 25 | 35 | 60 | 45 | 5 | 10 | 5 | 20 | 0 | 0 | 0 | 5 | 5 |
| Canarygrass | 25 | 55 | 80 | 35 | 80 | 50 | 30 | 65 | 0 | 5 | 30 | 0 | 30 | 10 |
| Chickweed | 98 | 95 | 95 | 100 | 95 | 98 | 85 | 98 | 98 | 95 | 100 | 98 | 98 | 100 |
| Cocklebur | 80 | 98 | 95 | 100 | 95 | 65 | 100 | 95 | 98 | 95 | 60 | 100 | 98 | 100 |
| Corn | 15 | 85 | 80 | 75 | 65 | 98 | 45 | 45 | 45 | 50 | 70 | 25 | 65 | 60 |
| Crabgrass, Large | 95 | 90 | 98 | 95 | 98 | 95 | 75 | 98 | 98 | 80 | 90 | 75 | 85 | 85 |
| Cupgrass, Woolly | 90 | 90 | 95 | 75 | 90 | 65 | 50 | 98 | 65 | 65 | 65 | 65 | 85 | 70 |

TABLE B-continued

| | | | | | | | | | | | | | | |
|---|---|---|---|---|---|---|---|---|---|---|---|---|---|---|
| Deadnettle | — | — | — | — | — | — | — | — | — | — | — | — | — | — |
| Foxtail, Giant | 95 | 90 | 98 | 85 | 95 | 90 | 75 | 98 | 90 | 80 | 85 | 75 | 80 | 85 |
| Foxtail, Green | 98 | 95 | 100 | 90 | 100 | 70 | 80 | 98 | 98 | 80 | 70 | 65 | 70 | 85 |
| *Galium* | — | — | — | — | — | — | — | — | — | — | — | — | — | — |
| Goosegrass | 80 | 80 | 85 | 95 | 70 | 75 | 75 | 85 | 75 | 65 | 75 | 75 | 85 | 80 |
| Johnsongrass | 100 | 95 | 100 | 35 | 100 | 100 | 30 | 95 | 98 | 50 | 45 | 15 | 70 | 75 |
| *Kochia* | 80 | 85 | 98 | 100 | 80 | 85 | 85 | 85 | 95 | 95 | 80 | 100 | 95 | 98 |
| Lambsquarters | 100 | 98 | 100 | 100 | 100 | 98 | 100 | 100 | 100 | 95 | 100 | 98 | 100 | 100 |
| Morningglory | 85 | 100 | 90 | 65 | 95 | 90 | 100 | 98 | 100 | 95 | 100 | 100 | 100 | 100 |
| Nutsedge, Yellow | 70 | 85 | 75 | 70 | 70 | 70 | 70 | 75 | 70 | 70 | 60 | 85 | 85 | 80 |
| Oat, Wild | 10 | 25 | 60 | 65 | 70 | 20 | 10 | 45 | 5 | 0 | 5 | 0 | 25 | 5 |
| Pigweed | 100 | 100 | 100 | — | 100 | 100 | 100 | 100 | 100 | 98 | 100 | 100 | 98 | 100 |
| Ragweed | 85 | 85 | 95 | 98 | 95 | 95 | 85 | 95 | 75 | 85 | 65 | 95 | 95 | 100 |
| Ryegrass, Italian | 0 | 35 | 50 | 40 | 30 | 20 | 0 | 10 | 5 | 0 | 0 | 0 | 10 | 0 |
| Soybean | 90 | 90 | 98 | 100 | 98 | 98 | 98 | 95 | 98 | 95 | 95 | 98 | 75 | 95 |
| Surinam Grass | 85 | 85 | 98 | — | 95 | 80 | 70 | 98 | 70 | 70 | 65 | 45 | 75 | 80 |
| Velvetleaf | 95 | 98 | 100 | 100 | 95 | 98 | 100 | 100 | 100 | 95 | 75 | 100 | 98 | 100 |
| Wheat | 0 | 20 | 40 | 50 | 5 | 5 | 15 | 35 | 0 | 0 | 0 | 0 | 10 | 0 |
| Windgrass | 15 | 80 | 85 | 85 | 65 | 30 | 5 | 50 | 80 | 50 | 45 | 0 | 45 | 60 |

| | Compounds | | | | | | | | | | | | | |
|---|---|---|---|---|---|---|---|---|---|---|---|---|---|---|
| 125 g ai/ha | 98 | 99 | 100 | 102 | 107 | 108 | 109 | 111 | 113 | 117 | 118 | 119 | 120 | 121 |
| | Postemergence | | | | | | | | | | | | | |
| Barley | 10 | 10 | 30 | 30 | 25 | 0 | 5 | 5 | 5 | 0 | 0 | 5 | 5 | 5 |
| Bermudagrass | 85 | 80 | 75 | 85 | 95 | 100 | 90 | 100 | 95 | 95 | 98 | 98 | 98 | 100 |
| Blackgrass | 20 | 5 | 10 | 30 | 15 | 20 | 40 | 25 | 5 | 40 | 35 | 50 | 60 | 40 |
| Bromegrass, Downy | 5 | 25 | 15 | 10 | 10 | 5 | 5 | 5 | 80 | 15 | 30 | 60 | 60 | 80 |
| Canarygrass | 35 | 60 | 5 | 30 | 60 | 5 | 30 | 0 | — | 5 | 10 | 30 | 55 | 5 |
| Chickweed | 98 | 98 | 95 | 95 | 100 | 100 | 98 | 100 | 100 | 98 | 95 | 100 | 85 | 100 |
| Cocklebur | 100 | 100 | 95 | 100 | 100 | 100 | 100 | 100 | 98 | 98 | 85 | 80 | 25 | 85 |
| Corn | 55 | 65 | 20 | 65 | 75 | 50 | 60 | 55 | 80 | 25 | 20 | 60 | 50 | 55 |
| Crabgrass, Large | 80 | 95 | 75 | 85 | 90 | 75 | 75 | 80 | 95 | 95 | 80 | 95 | 95 | 95 |
| Cupgrass, Woolly | 75 | 80 | 70 | 75 | 75 | 70 | 60 | 75 | 95 | 95 | 75 | 98 | 100 | 100 |
| Deadnettle | — | — | — | — | — | — | — | — | — | — | — | — | — | — |
| Foxtail, Giant | 85 | 95 | 80 | 80 | 85 | 75 | 80 | 65 | 90 | 80 | 85 | 95 | 85 | 98 |
| Foxtail, Green | 85 | 95 | 80 | 90 | 90 | 80 | 85 | 65 | 80 | 80 | 95 | 95 | 95 | 100 |
| *Galium* | — | — | — | — | — | — | — | — | — | — | — | — | — | — |
| Goosegrass | 80 | 75 | 75 | 80 | 75 | 75 | 80 | 85 | 85 | 75 | 80 | 85 | 85 | 98 |
| Johnsongrass | 75 | 80 | 10 | 60 | 70 | 20 | 50 | 20 | 90 | — | 20 | 75 | 75 | — |
| *Kochia* | 80 | 100 | 98 | 100 | 100 | 98 | 85 | 100 | 100 | — | 70 | 95 | 80 | — |
| Lambsquarters | 100 | 100 | 98 | 100 | 100 | 100 | 100 | 100 | 98 | 100 | 100 | 100 | 98 | 100 |
| Morningglory | 100 | 100 | 100 | 100 | 100 | 100 | 100 | 100 | 100 | 80 | 70 | 95 | 80 | 25 |
| Nutsedge, Yellow | 70 | 70 | 15 | 75 | 75 | 80 | 75 | 80 | 75 | 25 | 65 | 65 | 65 | 45 |
| Oat, Wild | 20 | 40 | 30 | 40 | 20 | 0 | 30 | 0 | 45 | 30 | 10 | 95 | 80 | 98 |
| Pigweed | 100 | 100 | 98 | 95 | 100 | 100 | 100 | 100 | 100 | — | 100 | 100 | 100 | 100 |
| Ragweed | 80 | 80 | 75 | 85 | 95 | 95 | 95 | 98 | 98 | 90 | 95 | 95 | 75 | 90 |
| Ryegrass, Italian | 15 | 20 | 10 | 5 | 5 | 0 | 5 | 0 | 50 | 15 | 5 | 60 | 60 | 70 |
| Soybean | 98 | 100 | 100 | 95 | 100 | 65 | 98 | 95 | 98 | 95 | 95 | 60 | 95 | 95 |
| Surinam Grass | 85 | 75 | 65 | 75 | 80 | 65 | 65 | 70 | 90 | — | 75 | 95 | 100 | 100 |
| Velvetleaf | 95 | 100 | 70 | 100 | 100 | 100 | 100 | 100 | 98 | 95 | 98 | 100 | 98 | 100 |
| Wheat | 5 | 5 | 15 | 20 | 5 | 0 | 5 | 5 | 40 | 20 | 5 | 60 | 60 | 45 |
| Windgrass | 50 | 10 | 45 | 60 | 80 | 30 | 60 | 35 | 35 | 65 | 70 | 100 | 90 | 100 |

| | Compounds | | | | | | | | | | | | |
|---|---|---|---|---|---|---|---|---|---|---|---|---|---|
| 125 g ai/ha | 122 | 123 | 126 | 127 | 128 | 129 | 130 | 131 | 140 | 141 | 146 | 147 | 152 | 155 |
| | Postemergence | | | | | | | | | | | | |
| Barley | 50 | 25 | 15 | 35 | 0 | 0 | 0 | 0 | 0 | 5 | 15 | 0 | 85 | 45 |
| Bermudagrass | 85 | 90 | 90 | 98 | 98 | 95 | 90 | 85 | 85 | 85 | 100 | 95 | 98 | 98 |
| Blackgrass | 15 | 40 | 30 | 25 | 10 | 5 | 5 | 0 | 5 | 10 | 35 | 45 | 55 | 60 |
| Bromegrass, Downy | 50 | 10 | 30 | 20 | 40 | 15 | 35 | 0 | 5 | 10 | 10 | 5 | 60 | 35 |
| Canarygrass | 45 | 55 | 60 | 35 | 30 | 0 | 20 | 0 | 5 | 5 | 5 | 5 | 80 | 50 |
| Chickweed | 80 | 95 | 98 | 98 | 95 | 90 | 100 | 90 | 45 | 90 | 98 | 98 | 90 | 100 |
| Cocklebur | 85 | 100 | 80 | 95 | 100 | 98 | 95 | 100 | 65 | 95 | — | 90 | 98 | 98 |
| Corn | 25 | 75 | 55 | 25 | 60 | 60 | 80 | 20 | 25 | 45 | 20 | 25 | 65 | 40 |
| Crabgrass, Large | 85 | 85 | 85 | 90 | 95 | 85 | 95 | 80 | 80 | 80 | 85 | 85 | 95 | 80 |
| Cupgrass, Woolly | 75 | 75 | 85 | 85 | 90 | 85 | 85 | 65 | 65 | 65 | 65 | 80 | 98 | 65 |
| Deadnettle | — | — | — | — | — | — | — | — | — | — | — | — | — | — |
| Foxtail, Giant | 80 | 80 | 85 | 85 | 98 | 90 | 98 | 80 | 80 | 80 | 95 | 85 | 95 | 90 |
| Foxtail, Green | 85 | 85 | 90 | 90 | 95 | 90 | 95 | 95 | 85 | 90 | 80 | 80 | 98 | 80 |
| *Galium* | — | — | — | — | — | — | — | — | — | — | — | — | — | — |
| Goosegrass | 70 | 80 | 75 | 75 | 98 | 90 | 95 | 75 | 70 | 75 | 95 | 80 | 95 | 85 |
| Johnsongrass | 75 | 75 | 85 | 80 | 85 | 70 | 80 | 50 | 35 | 50 | 70 | 60 | 95 | 65 |
| *Kochia* | 45 | 80 | 25 | 100 | 95 | 95 | 100 | 75 | 10 | 85 | 85 | 80 | 95 | 100 |
| Lambsquarters | 90 | 98 | 85 | 90 | 100 | 95 | 100 | 98 | 75 | 98 | 100 | 98 | 98 | 100 |

TABLE B-continued

| | | | | | | | | | | | | | | |
|---|---|---|---|---|---|---|---|---|---|---|---|---|---|---|
| Morningglory | 85 | 100 | 100 | 90 | 90 | 90 | 100 | 75 | 65 | 60 | 85 | 65 | 75 | 100 |
| Nutsedge, Yellow | 75 | 75 | 80 | 75 | 60 | 60 | 35 | 45 | 65 | 60 | 20 | 70 | 80 | 70 |
| Oat, Wild | 35 | 30 | 35 | 25 | 60 | 20 | 40 | 0 | 10 | 15 | 50 | 20 | 80 | 60 |
| Pigweed | 98 | 100 | 98 | 95 | 98 | 98 | 100 | 100 | 75 | 95 | 100 | 100 | 100 | 100 |
| Ragweed | 75 | 95 | 85 | 98 | 95 | 95 | 98 | 95 | 65 | 85 | 98 | 90 | 95 | 90 |
| Ryegrass, Italian | 40 | 5 | 5 | 5 | 5 | 0 | 0 | 0 | 0 | 0 | 10 | 30 | 45 | 40 |
| Soybean | 80 | 85 | 85 | 98 | 98 | 98 | 98 | 98 | 75 | 75 | 98 | 65 | 98 | 100 |
| Surinam Grass | 90 | 85 | 85 | 85 | 85 | 85 | 80 | 65 | 55 | 70 | 75 | 75 | 90 | 65 |
| Velvetleaf | 98 | 95 | 95 | 100 | 95 | 95 | 98 | 98 | 80 | 98 | 98 | 95 | 100 | 100 |
| Wheat | 50 | 15 | 35 | 25 | 0 | 0 | 5 | 0 | 10 | 5 | 15 | 5 | 85 | 40 |
| Windgrass | 50 | 80 | 40 | 55 | 70 | 80 | 75 | 5 | 5 | 40 | 60 | 55 | 85 | 70 |

| | Compounds | | | | | | | | | | | | | |
|---|---|---|---|---|---|---|---|---|---|---|---|---|---|---|
| 125 g ai/ha | 156 | 157 | 160 | 162 | 164 | 169 | 173 | 181 | 184 | 186 | 187 | 189 | 190 | 191 |
| | Postemergence | | | | | | | | | | | | | |
| Barley | 60 | 30 | 35 | 50 | 30 | 0 | 35 | 50 | 60 | 5 | 40 | 15 | 40 | 50 |
| Bermudagrass | 95 | 100 | 90 | 100 | 98 | 100 | 100 | 100 | 100 | 95 | 100 | 65 | 100 | 100 |
| Blackgrass | 35 | 10 | 20 | 55 | 10 | 10 | 30 | 15 | 40 | 5 | 5 | 5 | 35 | 50 |
| Bromegrass, Downy | 35 | 60 | 50 | 45 | 85 | 90 | 40 | 60 | 50 | 30 | 35 | 5 | 35 | 50 |
| Canarygrass | 40 | 80 | 20 | 90 | 90 | 80 | 40 | 85 | 80 | 40 | 55 | 5 | 25 | 60 |
| Chickweed | 100 | 100 | 95 | 100 | 98 | 100 | 100 | 100 | 100 | 100 | 100 | 100 | 100 | 98 |
| Cocklebur | 75 | 100 | 100 | 100 | 100 | 100 | 100 | 100 | 100 | 100 | 100 | 100 | 95 | 98 |
| Corn | 45 | 95 | 50 | 80 | 45 | 55 | 60 | 95 | 85 | 30 | 75 | 35 | 40 | 75 |
| Crabgrass, Large | 65 | 98 | 95 | 98 | 98 | 100 | 95 | 100 | 100 | 85 | 100 | 95 | 80 | 100 |
| Cupgrass, Woolly | 55 | 98 | 85 | 100 | 98 | 100 | 100 | 100 | 100 | 80 | 85 | 75 | 80 | 90 |
| Deadnettle | — | — | — | — | — | — | — | — | 100 | 100 | — | 100 | 100 | 100 |
| Foxtail, Giant | 85 | 100 | 75 | 98 | 98 | 100 | 100 | 100 | 100 | 95 | 100 | 90 | 90 | 100 |
| Foxtail, Green | 85 | 85 | 70 | 98 | 98 | 95 | 90 | 95 | 85 | 85 | 98 | 90 | 45 | 80 |
| *Galium* | — | — | — | — | — | — | — | 60 | 70 | 55 | 85 | 60 | 60 | |
| Goosegrass | 70 | 98 | 90 | 90 | 98 | 100 | 95 | 100 | 100 | 98 | 100 | 90 | 80 | 100 |
| Johnsongrass | 45 | 100 | 65 | 100 | 95 | 65 | 95 | 100 | 100 | 75 | 100 | 65 | 75 | 100 |
| *Kochia* | 20 | 10 | 100 | 75 | 100 | 100 | 98 | 100 | 5 | 100 | 70 | 98 | 98 | 25 |
| Lambsquarters | 95 | 100 | 98 | 98 | 100 | 100 | 100 | 100 | 100 | 100 | 100 | 100 | 100 | 98 |
| Morningglory | 100 | 95 | 100 | 90 | 98 | 100 | 80 | 100 | 100 | 100 | 100 | 100 | 85 | 90 |
| Nutsedge, Yellow | 70 | 40 | 80 | 75 | 70 | 55 | 60 | 80 | 45 | 75 | 65 | 55 | 65 | 55 |
| Oat, Wild | 35 | 60 | 50 | 45 | 85 | 85 | 70 | 90 | 80 | 20 | 45 | 10 | 40 | 70 |
| Pigweed | 98 | 90 | 100 | 100 | 100 | 100 | 100 | 100 | 75 | 100 | 100 | 100 | 100 | 98 |
| Ragweed | 75 | 100 | 98 | 100 | 98 | 100 | 90 | 100 | — | 100 | 100 | 75 | — | — |
| Ryegrass, Italian | 20 | 30 | 35 | 80 | 20 | 10 | 30 | 60 | 45 | 0 | 10 | 5 | 20 | 50 |
| Soybean | 98 | 100 | 98 | 100 | 100 | 95 | 95 | 100 | 100 | 100 | 100 | 98 | 95 | 100 |
| Surinam Grass | 60 | 98 | 60 | 75 | 95 | — | — | 95 | 100 | — | — | 80 | 75 | 90 |
| Velvetleaf | 95 | 100 | 100 | 95 | 80 | 100 | 100 | 100 | 100 | 100 | 100 | 100 | 100 | 90 |
| Wheat | 35 | 20 | 40 | 35 | 35 | 5 | 40 | 50 | 55 | 0 | 5 | 0 | 30 | 55 |
| Windgrass | 55 | 70 | 60 | 60 | 75 | 55 | 70 | 60 | 90 | 50 | 65 | 60 | 65 | 85 |

| | Compounds | | | | | | | | | | | | | |
|---|---|---|---|---|---|---|---|---|---|---|---|---|---|---|
| 125 g ai/ha | 193 | 197 | 217 | 218 | 219 | 220 | 225 | 226 | 227 | 228 | 229 | 233 | 235 | 236 |
| | Postemergence | | | | | | | | | | | | | |
| Barley | 50 | 10 | 10 | 35 | 30 | 10 | 40 | 30 | 5 | 40 | 5 | 10 | 40 | 0 |
| Bermudagrass | 100 | 100 | 98 | 95 | 100 | 98 | 85 | 85 | 85 | 90 | 85 | 100 | 100 | 98 |
| Blackgrass | 40 | 10 | 30 | 5 | 55 | 30 | 15 | 40 | 5 | 50 | 5 | 30 | 70 | 30 |
| Bromegrass, Downy | 40 | 30 | 40 | 20 | 80 | 15 | 85 | 5 | 0 | 10 | 20 | 50 | 50 | 10 |
| Canarygrass | 25 | 40 | 20 | 0 | 55 | 10 | 85 | 50 | 5 | 5 | 50 | 10 | 30 | 0 |
| Chickweed | 100 | 100 | 100 | 100 | 100 | 98 | 95 | 85 | 80 | 100 | 90 | 100 | 100 | 100 |
| Cocklebur | 100 | 100 | 98 | — | — | — | 100 | 100 | 95 | 100 | 100 | 100 | — | 100 |
| Corn | 40 | 45 | 25 | 75 | 75 | 55 | 70 | 98 | 75 | 85 | 85 | 85 | 100 | 70 |
| Crabgrass, Large | 98 | 98 | 90 | 70 | 95 | 85 | 95 | 95 | 85 | 98 | 90 | 98 | 98 | 98 |
| Cupgrass, Woolly | 95 | 90 | 45 | 60 | 95 | 65 | 85 | 85 | 90 | 95 | 80 | 100 | 100 | 95 |
| Deadnettle | 100 | 100 | — | — | — | — | — | — | — | — | — | — | — | — |
| Foxtail, Giant | 95 | 98 | 85 | 65 | 80 | 55 | 85 | 95 | 90 | 95 | 80 | 98 | 100 | 95 |
| Foxtail, Green | 60 | 50 | 85 | 90 | 90 | 80 | 98 | 90 | 90 | 98 | 80 | 95 | 95 | 98 |
| *Galium* | 90 | — | — | — | — | — | — | — | — | — | — | — | — | — |
| Goosegrass | 98 | 100 | 85 | 15 | 95 | 85 | 95 | 85 | 75 | 85 | 70 | 98 | 98 | 95 |
| Johnsongrass | 70 | 95 | 60 | 55 | 98 | 80 | 75 | 100 | 60 | 95 | 100 | 25 | 100 | 20 |
| *Kochia* | 100 | 95 | 100 | 100 | 98 | 75 | 15 | 100 | 85 | 100 | 80 | — | 100 | 100 |
| Lambsquarters | 98 | 100 | 100 | 100 | 100 | 100 | 98 | 95 | 98 | 100 | 95 | 100 | 100 | 100 |
| Morningglory | 65 | 100 | 80 | 80 | 100 | 98 | 95 | 100 | 100 | 100 | 100 | 98 | 100 | 95 |
| Nutsedge, Yellow | 75 | 65 | 70 | 15 | 70 | 25 | 25 | 70 | 65 | 60 | 40 | 25 | 55 | 15 |
| Oat, Wild | 70 | 70 | 50 | 60 | 80 | 30 | 85 | 50 | 10 | 15 | 10 | 45 | 85 | 20 |
| Pigweed | 100 | 98 | 100 | 100 | 100 | 100 | 98 | 98 | 100 | 100 | 95 | — | 100 | 98 |
| Ragweed | — | — | 85 | 98 | 98 | 98 | 90 | 85 | 70 | 95 | 80 | 98 | 100 | 98 |
| Ryegrass, Italian | 40 | 30 | 40 | 60 | 40 | 30 | 40 | 5 | 5 | 0 | 0 | 50 | 55 | 0 |
| Soybean | 98 | 100 | 95 | 100 | 100 | 90 | 98 | 100 | 95 | 100 | 98 | 100 | 100 | 98 |
| Surinam Grass | 80 | 65 | 80 | 85 | 35 | 60 | 85 | 80 | 80 | 95 | 80 | 100 | 100 | 75 |

TABLE B-continued

| | | | | | | | | | | | | | | |
|---|---|---|---|---|---|---|---|---|---|---|---|---|---|---|
| Velvetleaf | 100 | 100 | 100 | 100 | 95 | 95 | 90 | 90 | 98 | 100 | 85 | 95 | 100 | 100 |
| Wheat | 60 | 5 | 50 | 0 | 50 | 0 | 55 | 25 | 10 | 20 | 5 | 60 | 80 | 30 |
| Windgrass | 70 | 50 | 80 | 45 | 60 | 40 | 80 | 70 | 40 | 80 | 50 | 60 | 95 | 70 |

| | Compounds | | | | | | | |
|---|---|---|---|---|---|---|---|---|
| 125 g ai/ha | 237 | 238 | 239 | 240 | 243 | 244 | 245 | 255 |

Postemergence

| | | | | | | | | |
|---|---|---|---|---|---|---|---|---|
| Barley | 40 | 35 | 5 | 15 | 95 | 90 | 85 | 35 |
| Bermudagrass | 100 | 100 | 100 | 100 | 100 | 100 | 100 | 95 |
| Blackgrass | 70 | 60 | 30 | 65 | 85 | 65 | 80 | 10 |
| Bromegrass, Downy | 90 | 50 | 5 | 25 | 95 | 75 | 95 | 80 |
| Canarygrass | 50 | 30 | 0 | 30 | 100 | 98 | 100 | 50 |
| Chickweed | 100 | 100 | 98 | 100 | 100 | 98 | 100 | 100 |
| Cocklebur | — | — | 100 | — | — | — | — | — |
| Corn | 100 | 95 | 45 | 100 | 100 | 95 | 100 | 85 |
| Crabgrass, Large | 100 | 98 | 95 | 100 | 100 | 100 | 100 | 90 |
| Cupgrass, Woolly | 100 | 100 | 95 | 100 | 100 | 100 | 100 | 95 |
| Deadnettle | — | — | — | — | — | — | — | — |
| Foxtail, Giant | 98 | 100 | 90 | 100 | 98 | 95 | 100 | 98 |
| Foxtail, Green | 95 | 98 | 90 | 95 | 100 | 98 | 100 | 90 |
| *Galium* | — | — | — | — | — | — | — | — |
| Goosegrass | 98 | 98 | 98 | 98 | 98 | 98 | 100 | 95 |
| Johnsongrass | 100 | 98 | 60 | 100 | 100 | 100 | 100 | 90 |
| *Kochia* | 100 | 100 | 98 | 100 | 100 | 100 | 100 | 15 |
| Lambsquarters | 100 | 100 | 100 | 100 | 100 | 100 | 100 | 98 |
| Morningglory | 100 | 100 | 100 | — | 100 | 100 | 100 | 85 |
| Nutsedge, Yellow | 45 | 20 | 65 | 20 | 70 | 65 | 70 | 15 |
| Oat, Wild | 60 | 50 | 5 | 45 | 85 | 95 | 85 | 85 |
| Pigweed | 100 | 100 | 98 | 100 | 100 | 100 | 100 | 98 |
| Ragweed | 100 | 100 | 100 | 100 | 98 | 98 | 100 | 95 |
| Ryegrass, Italian | 60 | 25 | 0 | 40 | 85 | 80 | 70 | 30 |
| Soybean | 100 | 100 | 98 | 95 | 100 | 100 | 100 | 100 |
| Surinam Grass | 100 | 100 | 45 | 100 | 100 | 100 | 100 | 90 |
| Velvetleaf | 100 | 100 | 100 | 85 | 100 | 100 | 100 | 98 |
| Wheat | 85 | 80 | 5 | 50 | 95 | 85 | 95 | 50 |
| Windgrass | 98 | 85 | 30 | 98 | 98 | 80 | 95 | 80 |

| | Compounds | | | | | | | | | | | | |
|---|---|---|---|---|---|---|---|---|---|---|---|---|---|
| 62 g ai/ha | 1 | 2 | 3 | 4 | 7 | 8 | 9 | 10 | 11 | 12 | 14 | 24 | 26 | 27 |

Postemergence

| | | | | | | | | | | | | | | |
|---|---|---|---|---|---|---|---|---|---|---|---|---|---|---|
| Barley | 0 | 20 | 0 | 0 | 0 | 0 | 0 | 0 | 10 | 0 | 0 | 5 | 0 | 0 |
| Bermudagrass | 50 | 85 | 25 | 85 | 45 | 85 | 95 | 75 | 100 | 85 | 70 | 95 | 50 | 90 |
| Blackgrass | 0 | 30 | 0 | 20 | 0 | 10 | 0 | 0 | 5 | 10 | 0 | 10 | 0 | 5 |
| Bromegrass, Downy | 0 | 60 | 0 | 15 | 0 | 5 | 30 | 0 | 35 | 10 | 30 | 50 | 15 | 5 |
| Canarygrass | 0 | 50 | 0 | 20 | 0 | 50 | 25 | 0 | 50 | 5 | 20 | 40 | 30 | 10 |
| Chickweed | 60 | 90 | 98 | 100 | 80 | 100 | 85 | 95 | 98 | 100 | — | 90 | 50 | 45 |
| Cocklebur | 65 | 90 | 80 | 100 | 45 | 100 | 0 | 90 | 100 | 98 | 90 | 98 | 80 | 95 |
| Corn | 0 | 25 | 0 | 25 | 0 | 65 | 45 | 15 | 75 | 30 | 40 | 50 | 35 | 40 |
| Crabgrass, Large | 50 | 85 | 70 | 85 | 45 | 85 | 80 | 70 | 85 | 75 | 55 | 75 | 50 | 50 |
| Cupgrass, Woolly | 0 | 80 | 15 | 95 | 50 | 80 | 75 | 70 | 75 | 60 | 80 | 80 | 40 | 60 |
| Deadnettle | — | — | — | — | — | — | — | — | — | — | — | — | — | — |
| Foxtail, Giant | 15 | 85 | 45 | 98 | 55 | 100 | 85 | 75 | 85 | 90 | 70 | 85 | 60 | 85 |
| Foxtail, Green | 10 | 90 | 10 | 40 | 20 | 70 | 40 | 25 | 60 | 60 | 45 | 40 | 40 | 80 |
| *Galium* | — | — | — | — | — | — | — | — | — | — | — | — | — | — |
| Goosegrass | 60 | 90 | 50 | 75 | 25 | 85 | 85 | 75 | 85 | 85 | 80 | 85 | 90 | 90 |
| Johnsongrass | 0 | 90 | 0 | 80 | 0 | 98 | 70 | 55 | 70 | 60 | 80 | 60 | 50 | 45 |
| *Kochia* | 20 | 75 | 80 | 100 | 45 | 100 | 15 | 15 | 25 | 20 | — | 70 | — | — |
| Lambsquarters | 75 | 90 | 95 | 100 | 65 | 100 | 80 | 80 | 70 | 85 | 85 | 90 | 90 | 95 |
| Morningglory | 20 | 80 | 20 | 85 | 15 | 90 | 45 | 45 | 15 | 60 | 70 | 60 | 50 | 80 |
| Nutsedge, Yellow | 20 | 60 | 45 | 65 | 0 | 70 | 25 | 55 | 35 | 55 | 30 | 30 | 30 | 40 |
| Oat, Wild | 5 | 45 | 0 | 50 | 0 | 15 | 5 | 5 | 50 | 5 | 40 | 50 | 40 | 50 |
| Pigweed | 80 | 90 | 90 | 100 | 75 | 100 | 85 | 85 | 80 | 95 | 80 | 80 | 80 | 98 |
| Ragweed | 70 | 80 | 85 | 100 | 65 | 100 | 75 | 80 | 100 | 100 | 80 | 80 | 85 | 98 |
| Ryegrass, Italian | 0 | 40 | 0 | 10 | 0 | 20 | 0 | 0 | 10 | 0 | 5 | 5 | 0 | 5 |
| Soybean | 65 | 90 | 70 | 100 | 65 | 98 | 75 | 95 | 100 | 100 | 85 | 95 | 95 | 95 |
| Surinam Grass | 0 | 75 | 25 | 70 | 10 | 65 | 65 | 70 | 70 | 55 | 50 | 55 | 40 | 70 |
| Velvetleaf | 75 | 85 | 100 | 75 | 80 | 80 | 85 | 70 | 95 | 85 | 90 | 90 | 70 | 60 |
| Wheat | 0 | 10 | 0 | 5 | 0 | 30 | 5 | 0 | 35 | 0 | 0 | 10 | 0 | 5 |
| Windgrass | 0 | 15 | 0 | 55 | 5 | 20 | 55 | 10 | 85 | 40 | 30 | 30 | 30 | 10 |

TABLE B-continued

| 62 g ai/ha | Compounds | | | | | | | | | | | | | |
|---|---|---|---|---|---|---|---|---|---|---|---|---|---|---|
| | 29 | 33 | 34 | 36 | 37 | 38 | 39 | 40 | 42 | 44 | 45 | 46 | 47 | 48 |
| | Postemergence | | | | | | | | | | | | | |
| Barley | 0 | 0 | 30 | 10 | 0 | 0 | 0 | 0 | 0 | 0 | 5 | 0 | 10 | 5 |
| Bermudagrass | 90 | 95 | 95 | 98 | 90 | 100 | 60 | 100 | 75 | 95 | 85 | 85 | — | 95 |
| Blackgrass | 20 | 15 | 5 | 5 | 0 | 15 | 0 | 10 | 10 | 10 | 5 | 5 | 20 | 5 |
| Bromegrass, Downy | 10 | 5 | 50 | 30 | 10 | 70 | 0 | 50 | 5 | 70 | 20 | 5 | 40 | 25 |
| Canarygrass | 20 | 0 | 50 | 45 | 5 | 10 | 0 | 20 | 0 | 20 | 10 | 0 | 30 | 30 |
| Chickweed | 50 | 98 | 75 | 98 | 80 | 90 | 100 | 100 | 70 | 95 | 85 | 95 | 98 | 90 |
| Cocklebur | 95 | 90 | 25 | — | — | — | 75 | — | 45 | 80 | 50 | 80 | — | 95 |
| Corn | 35 | 10 | 0 | 55 | 15 | 70 | 45 | 80 | 10 | 80 | 45 | 35 | — | 70 |
| Crabgrass, Large | 50 | 85 | 85 | 95 | 75 | 90 | 80 | 98 | 75 | 90 | 75 | 65 | 85 | 85 |
| Cupgrass, Woolly | 85 | 65 | 80 | 90 | 65 | 90 | 85 | 95 | 20 | 80 | 75 | 20 | 90 | 80 |
| Deadnettle | — | — | — | — | — | — | — | — | — | — | — | — | — | — |
| Foxtail, Giant | 90 | 80 | 90 | 95 | 85 | 98 | 85 | 100 | 65 | 95 | 90 | 80 | 98 | 85 |
| Foxtail, Green | 75 | 85 | 90 | 90 | 65 | 90 | 80 | 95 | 55 | 90 | 80 | 60 | 90 | 95 |
| *Galium* | — | — | — | — | — | — | — | — | — | — | — | — | — | — |
| Goosegrass | 85 | 75 | 80 | 85 | 85 | 85 | 55 | 90 | 85 | 90 | 75 | 75 | 95 | 85 |
| Johnsongrass | 20 | 35 | 90 | 75 | 40 | 75 | 65 | — | 0 | 70 | 90 | 50 | — | 80 |
| *Kochia* | — | 80 | 95 | 0 | 0 | 80 | 45 | 0 | 100 | 75 | 0 | 0 | 95 | 98 |
| Lambsquarters | 85 | 98 | 98 | 100 | 98 | 95 | 95 | 100 | 95 | 95 | 98 | 85 | 98 | 95 |
| Morningglory | 70 | 60 | 80 | 70 | 70 | 70 | 75 | — | 70 | 70 | 75 | 30 | 80 | 70 |
| Nutsedge, Yellow | 50 | 50 | 25 | 20 | 15 | 0 | 0 | 35 | 60 | 50 | 10 | 70 | 65 | 45 |
| Oat, Wild | 50 | 15 | 50 | 75 | 10 | 75 | 20 | 85 | 10 | 80 | 55 | 5 | 60 | 50 |
| Pigweed | 65 | 95 | 90 | 85 | 85 | 98 | 100 | 98 | 95 | 95 | 98 | 75 | 98 | 85 |
| Ragweed | 85 | 95 | 85 | 90 | 80 | 85 | 85 | 98 | 75 | 95 | 85 | 75 | 90 | 85 |
| Ryegrass, Italian | 20 | 10 | 10 | 5 | 0 | 50 | 5 | 0 | 5 | 5 | 30 | 5 | 30 | 5 |
| Soybean | 95 | 98 | 95 | 98 | 80 | 85 | 95 | 100 | 90 | 95 | 95 | 80 | 95 | 95 |
| Surinam Grass | 50 | 65 | 75 | 85 | 70 | 85 | 65 | 95 | 40 | 95 | 75 | 75 | 95 | 85 |
| Velvetleaf | 55 | 90 | 95 | 100 | 80 | 100 | 80 | 100 | 80 | 98 | 80 | 80 | 85 | 85 |
| Wheat | 0 | 0 | 10 | 5 | 0 | 20 | 5 | 20 | 0 | 10 | 15 | 0 | 0 | 0 |
| Windgrass | 10 | 25 | 40 | 70 | 30 | 80 | 0 | 70 | 60 | 70 | 60 | 10 | — | 80 |

| 62 g ai/ha | Compounds | | | | | | | | | | | | | |
|---|---|---|---|---|---|---|---|---|---|---|---|---|---|---|
| | 49 | 50 | 51 | 52 | 53 | 55 | 56 | 58 | 59 | 61 | 62 | 63 | 64 | 66 |
| | Postemergence | | | | | | | | | | | | | |
| Barley | 0 | 0 | 25 | 0 | 50 | 0 | 10 | 5 | 0 | 0 | 5 | 0 | — | 0 |
| Bermudagrass | 85 | 100 | 90 | 95 | 95 | 80 | 85 | 85 | 90 | 90 | 80 | 85 | 95 | 70 |
| Blackgrass | 0 | 5 | 30 | 5 | 30 | 0 | 10 | 10 | 35 | 0 | 30 | 35 | 0 | 10 |
| Bromegrass, Downy | 0 | 5 | 50 | 55 | 50 | 0 | 45 | 40 | 30 | 0 | 45 | 20 | 45 | 10 |
| Canarygrass | 0 | 0 | 60 | 50 | 80 | 0 | 30 | 60 | 5 | 0 | 0 | 0 | 40 | 0 |
| Chickweed | 75 | 80 | 80 | 95 | 98 | 75 | 95 | 80 | 98 | 80 | 70 | 65 | 98 | 85 |
| Cocklebur | 80 | 85 | 85 | 85 | 85 | 60 | 55 | 85 | 85 | 65 | 55 | 80 | 95 | 10 |
| Corn | 5 | 10 | 80 | 45 | 80 | 5 | 65 | 45 | 0 | 0 | 70 | 20 | 85 | 55 |
| Crabgrass, Large | 75 | 85 | 85 | 90 | 95 | 75 | 85 | 80 | 85 | 65 | 75 | 75 | 90 | 55 |
| Cupgrass, Woolly | 50 | 75 | 75 | 75 | 90 | 10 | 45 | 65 | 75 | 55 | 55 | 60 | 95 | 40 |
| Deadnettle | — | — | — | — | — | — | — | — | — | — | — | — | — | — |
| Foxtail, Giant | 60 | 85 | 80 | 80 | 85 | 30 | 80 | 85 | 90 | 65 | 85 | 85 | 95 | 75 |
| Foxtail, Green | 50 | 80 | 95 | 98 | 100 | 40 | 85 | 90 | 70 | 55 | 70 | 70 | 85 | 85 |
| *Galium* | — | — | — | — | — | — | — | — | — | — | — | — | — | — |
| Goosegrass | 70 | 80 | 80 | 80 | 80 | 60 | 75 | 75 | 80 | 50 | 65 | 70 | 80 | 65 |
| Johnsongrass | 0 | 10 | 75 | 85 | 95 | 0 | 80 | 85 | 75 | 0 | 0 | 10 | 98 | 60 |
| *Kochia* | 65 | 100 | 20 | 25 | 65 | 65 | 95 | 10 | 10 | 25 | 25 | 25 | 55 | 85 |
| Lambsquarters | 80 | 98 | 90 | 85 | 95 | 80 | 98 | 95 | 98 | 95 | 95 | 95 | 100 | 95 |
| Morningglory | 80 | 25 | 80 | 45 | 75 | 60 | — | 80 | 50 | 70 | 15 | 70 | 80 | 100 |
| Nutsedge, Yellow | 65 | 70 | 65 | 25 | 65 | 10 | 70 | 40 | 60 | 60 | 25 | 20 | 10 | 45 |
| Oat, Wild | 5 | 5 | 60 | 90 | 70 | 0 | 20 | 60 | 0 | 0 | 10 | 0 | 90 | 0 |
| Pigweed | 90 | 98 | 95 | 90 | 95 | 85 | 98 | 95 | 100 | 85 | 98 | 95 | 100 | 98 |
| Ragweed | 80 | 90 | 80 | 80 | 85 | 80 | 55 | 85 | 80 | 80 | 75 | 75 | 85 | 10 |
| Ryegrass, Italian | 0 | 0 | 0 | 45 | 5 | 0 | 0 | 0 | 50 | 0 | 5 | 0 | 0 | 0 |
| Soybean | 65 | 85 | 90 | 95 | 95 | 60 | 85 | 85 | 95 | 0 | 80 | 75 | 98 | 95 |
| Surinam Grass | 30 | 75 | 85 | 85 | 95 | 15 | 80 | 80 | 80 | 65 | 45 | 25 | 95 | 70 |
| Velvetleaf | 95 | 98 | 85 | 98 | 85 | 98 | 90 | 75 | 90 | 80 | 95 | 98 | 98 | 90 |
| Wheat | 5 | 5 | 10 | 25 | 25 | 0 | 0 | 0 | 5 | 0 | 0 | 0 | 15 | — |
| Windgrass | 0 | 50 | 60 | 80 | 80 | 0 | 40 | 50 | 60 | 0 | 35 | 30 | 90 | 60 |

| 62 g ai/ha | Compounds | | | | | | | | | | | | |
|---|---|---|---|---|---|---|---|---|---|---|---|---|---|
| | 67 | 68 | 69 | 70 | 71 | 72 | 73 | 74 | 75 | 77 | 79 | 80 | 81 | 82 |
| | Postemergence | | | | | | | | | | | | | |
| Barley | 5 | 0 | 5 | 30 | 0 | 0 | 0 | 0 | 0 | 0 | 30 | 30 | 0 | 0 |
| Bermudagrass | 70 | 75 | 98 | 85 | 75 | 80 | 80 | 80 | 98 | 90 | 80 | 40 | 85 | 85 |

TABLE B-continued

| Compounds 62 g ai/ha | 83 | 85 | 86 | 87 | 88 | 89 | 90 | 91 | 92 | 93 | 94 | 95 | 96 | 97 |
|---|---|---|---|---|---|---|---|---|---|---|---|---|---|---|
| Blackgrass | 0 | 0 | 0 | 35 | 0 | 0 | 10 | 0 | 0 | 0 | 15 | 0 | 10 | 0 |
| Bromegrass, Downy | 0 | 5 | 55 | 50 | 5 | 0 | 45 | 5 | 20 | 5 | 10 | 60 | 5 | 0 |
| Canarygrass | 0 | 0 | 0 | 80 | 5 | 0 | 0 | 0 | 0 | 0 | 30 | 50 | 5 | 0 |
| Chickweed | 95 | 90 | 98 | 90 | 90 | 85 | 80 | 85 | 90 | 85 | 95 | 98 | 98 | 90 |
| Cocklebur | 75 | 75 | 0 | 0 | 65 | 80 | 45 | 85 | 80 | 0 | 98 | 10 | 55 | 90 |
| Corn | 10 | 15 | 10 | 35 | 0 | 0 | 80 | 0 | 0 | 5 | 45 | 35 | 10 | 5 |
| Crabgrass, Large | 80 | 90 | 95 | 90 | 75 | 80 | 85 | 80 | 98 | 60 | 85 | 80 | 95 | 75 |
| Cupgrass, Woolly | 70 | 10 | 95 | 65 | 45 | 45 | 65 | 10 | 55 | 20 | 40 | 70 | 75 | 55 |
| Deadnettle | — | — | — | — | — | — | — | — | — | — | — | — | — | — |
| Foxtail, Giant | 80 | 80 | 98 | 85 | 75 | 70 | 75 | 55 | 80 | 75 | 75 | 90 | 85 | 80 |
| Foxtail, Green | 80 | 85 | 98 | 85 | 60 | 70 | 90 | 20 | 85 | 80 | 60 | 95 | 85 | 60 |
| *Galium* | — | — | — | — | — | — | — | — | — | — | — | — | — | — |
| Goosegrass | 55 | 70 | 80 | 85 | 75 | 65 | 75 | 75 | 80 | 75 | 65 | 75 | 70 | 75 |
| Johnsongrass | 0 | 10 | 100 | 70 | 75 | 10 | 65 | 0 | 10 | 0 | 65 | 0 | 10 | 80 |
| *Kochia* | 80 | 90 | 70 | 65 | 0 | 85 | 80 | 75 | 95 | 80 | 75 | 20 | 80 | 60 |
| Lambsquarters | 95 | 98 | 100 | 98 | 85 | 100 | 98 | 95 | 100 | 98 | 98 | 95 | 98 | 95 |
| Morningglory | 90 | 85 | 70 | 100 | 65 | 85 | 50 | 85 | 90 | 75 | 95 | 100 | 90 | 100 |
| Nutsedge, Yellow | 65 | 10 | 10 | 15 | 10 | 65 | 20 | 20 | 65 | 60 | 60 | 15 | 80 | 15 |
| Oat, Wild | 5 | 20 | 80 | 70 | 0 | — | 80 | 20 | 20 | 5 | 45 | 30 | 35 | 0 |
| Pigweed | 98 | 95 | 100 | 98 | 85 | 100 | 98 | 98 | 100 | 98 | 100 | 100 | 100 | 98 |
| Ragweed | 80 | 80 | 90 | 70 | 80 | 80 | 80 | 75 | 85 | 75 | 85 | 60 | 80 | 80 |
| Ryegrass, Italian | 5 | 5 | 50 | 10 | 0 | 0 | 45 | 20 | 15 | 5 | 20 | 0 | 5 | 0 |
| Soybean | 90 | 95 | 90 | 75 | 70 | 80 | 85 | 75 | 95 | 50 | 90 | 80 | 95 | 90 |
| Surinam Grass | 20 | 55 | 90 | 65 | 55 | 80 | 85 | 45 | 50 | 65 | 45 | 45 | 90 | 65 |
| Velvetleaf | 95 | 100 | 98 | 80 | 85 | 100 | 100 | 100 | 100 | 98 | 98 | 100 | 100 | 90 |
| Wheat | 5 | 5 | 5 | 20 | 0 | 5 | 35 | 5 | 0 | 5 | 25 | 10 | 20 | 0 |
| Windgrass | 0 | 50 | 60 | 85 | 10 | 20 | 80 | 60 | 50 | 10 | 65 | 60 | 50 | 5 |

| Compounds 62 g ai/ha | 83 | 85 | 86 | 87 | 88 | 89 | 90 | 91 | 92 | 93 | 94 | 95 | 96 | 97 |
|---|---|---|---|---|---|---|---|---|---|---|---|---|---|---|
| Postemergence |  |  |  |  |  |  |  |  |  |  |  |  |  |  |
| Barley | 5 | 10 | 40 | 0 | 30 | 5 | 5 | 30 | 0 | 0 | 0 | 0 | 0 | 0 |
| Bermudagrass | 75 | 85 | 90 | 90 | 80 | 85 | 80 | 95 | 80 | 75 | 80 | 75 | 95 | 95 |
| Blackgrass | 0 | 35 | 30 | 5 | 5 | 15 | 5 | 20 | 0 | 5 | 10 | 0 | 20 | 20 |
| Bromegrass, Downy | 45 | 5 | 10 | 50 | 45 | 0 | 5 | 5 | 5 | 0 | 0 | 0 | 0 | 0 |
| Canarygrass | 20 | 40 | 20 | 30 | 70 | 35 | 10 | 55 | 0 | 0 | 5 | 0 | 5 | 10 |
| Chickweed | 90 | 95 | 95 | 100 | 85 | 80 | 80 | 95 | 95 | 80 | 100 | 85 | 95 | 100 |
| Cocklebur | 80 | 95 | 95 | 100 | 90 | 60 | 90 | 65 | 80 | 90 | 45 | 95 | 95 | 100 |
| Corn | 5 | 70 | 60 | 55 | 65 | 95 | 25 | 35 | 35 | 45 | 55 | 0 | 60 | 40 |
| Crabgrass, Large | 85 | 90 | 98 | 85 | 98 | 95 | 75 | 95 | 90 | 80 | 75 | 65 | 80 | 80 |
| Cupgrass, Woolly | 85 | 85 | 85 | 75 | 80 | 50 | 45 | 85 | 25 | 45 | 65 | 55 | 75 | 60 |
| Deadnettle | — | — | — | — | — | — | — | — | — | — | — | — | — | — |
| Foxtail, Giant | 95 | 80 | 95 | 80 | 95 | 85 | 70 | 98 | 75 | 80 | 75 | 65 | 70 | 75 |
| Foxtail, Green | 95 | 95 | 95 | 80 | 98 | 70 | 65 | 85 | 80 | 60 | 60 | 50 | 65 | 85 |
| *Galium* | — | — | — | — | — | — | — | — | — | — | — | — | — | — |
| Goosegrass | 80 | 70 | 75 | 80 | 70 | 65 | 60 | 75 | 70 | 65 | 70 | 75 | 70 | 70 |
| Johnsongrass | 100 | 95 | 98 | 25 | 100 | 90 | 25 | 90 | 85 | 10 | 15 | 10 | 45 | 55 |
| *Kochia* | 75 | 85 | 85 | 100 | 75 | 75 | 85 | 80 | 90 | 85 | 55 | 100 | 85 | 90 |
| Lambsquarters | 98 | 98 | 100 | 98 | 98 | 98 | 95 | 100 | 98 | 95 | 95 | 98 | 98 | 100 |
| Morningglory | 75 | 100 | 80 | 45 | 90 | 85 | 95 | 90 | 95 | 80 | 75 | 100 | 95 | 100 |
| Nutsedge, Yellow | 20 | 85 | 70 | 60 | 65 | 55 | 65 | 65 | 60 | 20 | 75 | 70 | 75 | 75 |
| Oat, Wild | 10 | 25 | 50 | 60 | 55 | 10 | 5 | 30 | 5 | 0 | 5 | 0 | 5 | 5 |
| Pigweed | 90 | 100 | 100 | 98 | 100 | 98 | 98 | 100 | 100 | 95 | 100 | 98 | 95 | 100 |
| Ragweed | 80 | 85 | 90 | 95 | 80 | 85 | 75 | 85 | 60 | 75 | 45 | 80 | 80 | 98 |
| Ryegrass, Italian | 0 | 10 | 30 | 10 | 5 | 5 | 0 | 5 | 0 | 0 | 0 | 0 | 5 | 0 |
| Soybean | 90 | 85 | 95 | 98 | 90 | 90 | 98 | 85 | 98 | 80 | 80 | 98 | 75 | 80 |
| Surinam Grass | 75 | 85 | 95 | 75 | 95 | 75 | 65 | 98 | 65 | 65 | 60 | 45 | 75 | 75 |
| Velvetleaf | 90 | 98 | 100 | 100 | 90 | 95 | 98 | 100 | 100 | 90 | 70 | 95 | 98 | 100 |
| Wheat | 0 | 5 | 35 | 35 | 5 | 5 | 10 | 10 | 0 | 0 | 0 | 0 | 5 | 0 |
| Windgrass | 10 | 70 | 60 | 60 | 60 | 5 | 5 | 40 | 50 | 10 | 40 | 0 | 10 | 50 |

| Compounds 62 g ai/ha | 98 | 99 | 100 | 102 | 107 | 108 | 109 | 111 | 113 | 117 | 118 | 119 | 120 | 121 |
|---|---|---|---|---|---|---|---|---|---|---|---|---|---|---|
| Postemergence |  |  |  |  |  |  |  |  |  |  |  |  |  |  |
| Barley | 5 | 5 | 20 | 10 | 5 | 0 | 0 | 0 | 5 | 0 | 0 | 0 | 5 | 5 |
| Bermudagrass | 80 | 75 | 70 | 85 | 80 | 90 | 85 | 100 | 90 | 90 | 95 | 98 | 95 | 98 |
| Blackgrass | 5 | 0 | 5 | 5 | 5 | 5 | 5 | 5 | 0 | 10 | 10 | 20 | 30 | 40 |
| Bromegrass, Downy | 5 | 5 | 10 | 10 | 5 | 0 | 0 | 0 | 60 | 10 | 5 | 30 | 60 | 50 |
| Canarygrass | 20 | 60 | 5 | 20 | 15 | 5 | 0 | 0 | 90 | 0 | 0 | 5 | 30 | 5 |
| Chickweed | 80 | 98 | 75 | 80 | 100 | 100 | 98 | 100 | 98 | 95 | 95 | 80 | 75 | 100 |
| Cocklebur | 100 | 100 | 85 | 95 | 100 | 95 | 98 | 98 | 95 | 75 | 40 | 10 | 15 | 45 |
| Corn | 35 | 65 | 10 | 15 | 65 | 35 | 15 | 45 | 60 | 15 | 0 | 45 | 20 | 55 |
| Crabgrass, Large | 75 | 85 | 60 | 80 | 85 | 70 | 75 | 75 | 90 | 80 | 75 | 85 | 85 | 90 |
| Cupgrass, Woolly | 70 | 75 | 65 | 75 | 65 | 60 | 60 | 50 | 85 | 85 | 70 | 98 | 75 | 100 |

TABLE B-continued

| | | | | | | | | | | | | | | |
|---|---|---|---|---|---|---|---|---|---|---|---|---|---|---|
| Deadnettle | — | — | — | — | — | — | — | — | — | — | — | — | — | — |
| Foxtail, Giant | 75 | 80 | 75 | 75 | 80 | 60 | 75 | 65 | 85 | 75 | 80 | 85 | 80 | 98 |
| Foxtail, Green | 85 | 90 | 70 | 90 | 75 | 30 | 80 | 60 | 80 | 70 | 85 | 90 | 95 | 90 |
| *Galium* | — | — | — | — | — | — | — | — | — | — | — | — | — | — |
| Goosegrass | 75 | 75 | 70 | 70 | 75 | 70 | 75 | 70 | 75 | 75 | 65 | 75 | 80 | 98 |
| Johnsongrass | 70 | 75 | 5 | 25 | 70 | 20 | 30 | 15 | 85 | 20 | 10 | 40 | 25 | 70 |
| *Kochia* | 70 | 80 | 95 | 70 | 98 | 95 | 75 | 100 | 100 | 50 | 65 | 75 | 40 | 100 |
| Lambsquarters | 98 | 100 | 98 | 98 | 100 | 98 | 98 | 98 | 98 | 98 | 98 | 100 | 85 | 100 |
| Morningglory | 85 | 100 | 100 | 100 | 100 | 90 | 98 | 100 | 100 | 75 | 60 | 60 | 50 | 20 |
| Nutsedge, Yellow | 60 | 70 | 5 | 65 | 75 | 75 | 65 | 75 | 75 | 0 | 45 | 50 | 35 | 45 |
| Oat, Wild | 20 | 20 | 10 | 15 | 5 | 0 | 0 | 0 | 40 | 10 | 5 | 60 | 80 | 90 |
| Pigweed | 100 | 100 | 98 | 70 | 100 | 98 | 100 | 100 | 100 | 98 | 100 | 98 | 98 | 100 |
| Ragweed | 75 | 80 | 70 | 80 | 85 | 85 | 95 | 95 | 95 | 75 | 85 | 75 | 75 | 85 |
| Ryegrass, Italian | 5 | 0 | 5 | 0 | 0 | 0 | 0 | 0 | 45 | 10 | 5 | 30 | 40 | 40 |
| Soybean | 98 | 100 | 98 | 85 | 98 | 55 | 95 | 80 | 98 | 80 | 90 | 50 | 80 | 90 |
| Surinam Grass | 75 | 70 | 65 | 75 | 75 | 60 | 65 | — | 85 | 75 | — | 85 | 85 | 100 |
| Velvetleaf | 95 | 100 | 70 | 100 | 100 | 100 | 98 | 98 | 95 | 85 | 75 | 80 | 95 | 98 |
| Wheat | 5 | 5 | 5 | 10 | 5 | 0 | 5 | 0 | 15 | 5 | 5 | 40 | 40 | 45 |
| Windgrass | 20 | 5 | 40 | 10 | 40 | 10 | 40 | 30 | 30 | 45 | 60 | 85 | 80 | 98 |

| | Compounds | | | | | | | | | | | | | |
|---|---|---|---|---|---|---|---|---|---|---|---|---|---|---|
| 62 g ai/ha | 122 | 123 | 126 | 127 | 128 | 129 | 130 | 131 | 140 | 141 | 146 | 147 | 152 | 155 |
| | Postemergence | | | | | | | | | | | | | |
| Barley | 10 | 10 | 5 | 20 | 0 | 0 | 0 | 0 | 0 | 0 | 0 | 0 | 45 | 30 |
| Bermudagrass | 80 | 85 | 85 | 95 | 85 | 80 | 90 | 75 | 75 | 85 | 90 | 90 | 95 | 98 |
| Blackgrass | 5 | 20 | 25 | 20 | 5 | 5 | 5 | 0 | 0 | 5 | 30 | 40 | 35 | 35 |
| Bromegrass, Downy | 5 | 5 | 15 | 10 | 35 | 10 | 15 | 0 | 5 | 5 | 5 | 5 | 55 | 30 |
| Canarygrass | 35 | 40 | 40 | 10 | 10 | 0 | 20 | 0 | 0 | 0 | 0 | 0 | 45 | 35 |
| Chickweed | 70 | 75 | 80 | 75 | 90 | 85 | 98 | 80 | 10 | 85 | 95 | 90 | 65 | 100 |
| Cocklebur | 45 | 80 | 65 | 95 | 98 | 98 | 95 | 98 | 15 | 65 | 25 | 75 | 80 | 55 |
| Corn | 15 | 70 | 30 | 25 | 50 | 35 | 60 | 10 | 5 | 45 | 5 | 15 | 45 | 25 |
| Crabgrass, Large | 75 | 80 | 80 | 85 | 85 | 80 | 85 | 75 | 65 | 75 | 75 | 75 | 85 | 75 |
| Cupgrass, Woolly | 70 | 45 | 75 | 75 | 90 | 85 | 85 | 60 | 50 | 65 | 65 | 70 | 98 | 45 |
| Deadnettle | — | — | — | — | — | — | — | — | — | — | — | — | — | — |
| Foxtail, Giant | 75 | 75 | 80 | 85 | 95 | 85 | 90 | 75 | 75 | 75 | 85 | 80 | 85 | 80 |
| Foxtail, Green | 85 | 60 | 80 | 85 | 95 | 90 | 90 | 90 | 60 | 75 | 55 | 65 | 75 | 50 |
| *Galium* | — | — | — | — | — | — | — | — | — | — | — | — | — | — |
| Goosegrass | 65 | 65 | 70 | 75 | 95 | 85 | 85 | 65 | 65 | 75 | 90 | 70 | 85 | 80 |
| Johnsongrass | 65 | 65 | 65 | 70 | 70 | 45 | 60 | 25 | 15 | 15 | 45 | 40 | 90 | 40 |
| *Kochia* | 0 | 65 | 25 | 98 | 85 | 95 | 85 | 60 | 10 | 65 | 45 | 75 | 65 | 100 |
| Lambsquarters | 65 | 95 | 85 | 85 | 98 | 95 | 100 | 95 | 60 | 80 | 98 | 95 | 95 | 100 |
| Morningglory | 75 | 98 | 85 | 80 | 80 | 90 | 95 | 70 | 60 | 60 | 15 | 50 | 75 | 85 |
| Nutsedge, Yellow | 70 | 75 | 75 | 70 | 35 | 35 | 20 | 25 | 45 | 10 | 10 | 60 | 75 | 45 |
| Oat, Wild | 30 | 5 | 10 | 10 | 50 | 5 | 30 | 0 | 5 | 10 | 20 | 10 | 45 | 40 |
| Pigweed | 90 | 98 | 95 | 95 | 98 | 95 | 98 | 95 | 70 | 75 | 98 | 95 | 98 | 100 |
| Ragweed | 60 | 85 | 75 | 85 | 85 | 95 | 90 | 85 | 45 | 75 | 80 | 75 | 80 | 70 |
| Ryegrass, Italian | 10 | 5 | 5 | 5 | 0 | 0 | 0 | 0 | 0 | 0 | 5 | 5 | 30 | 30 |
| Soybean | 75 | 75 | 75 | 98 | 98 | 98 | 98 | 95 | 60 | 70 | 85 | 60 | 70 | 95 |
| Surinam Grass | 75 | 75 | 80 | 75 | 80 | 85 | 80 | 60 | 50 | 65 | 65 | 65 | 85 | 55 |
| Velvetleaf | 90 | 90 | 90 | 95 | 95 | 95 | 95 | 85 | 65 | 95 | 85 | 80 | 95 | 100 |
| Wheat | 30 | 15 | 15 | 10 | 0 | 0 | 5 | 0 | 5 | 5 | 0 | 5 | 50 | 30 |
| Windgrass | 30 | 60 | 10 | 50 | 65 | 60 | 65 | 0 | 5 | 35 | 50 | 50 | 70 | 55 |

| | Compounds | | | | | | | | | | | | | |
|---|---|---|---|---|---|---|---|---|---|---|---|---|---|---|
| 62 g ai/ha | 156 | 157 | 159 | 160 | 162 | 164 | 169 | 173 | 181 | 184 | 186 | 187 | 189 | 190 |
| | Postemergence | | | | | | | | | | | | | |
| Barley | 45 | 15 | 50 | 30 | 35 | 5 | 0 | 20 | 40 | 40 | 5 | 5 | 5 | 5 |
| Bermudagrass | 90 | 90 | 100 | 75 | 95 | 98 | 75 | 98 | 100 | 100 | 80 | 85 | 15 | 100 |
| Blackgrass | 5 | 5 | 25 | 10 | 40 | 5 | 5 | 10 | 5 | 35 | 0 | 0 | 0 | 30 |
| Bromegrass, Downy | 10 | 40 | 50 | 5 | 30 | 80 | 40 | 25 | 50 | 50 | 25 | 30 | 5 | 30 |
| Canarygrass | 30 | 70 | 90 | 20 | 50 | 85 | 80 | 35 | 80 | 50 | 25 | 35 | 0 | 5 |
| Chickweed | 98 | 100 | 100 | 95 | 100 | 90 | 100 | 95 | 100 | 100 | 98 | 100 | 100 | 100 |
| Cocklebur | 40 | 100 | 100 | 100 | 100 | 100 | 100 | 65 | 100 | 100 | 100 | 100 | 70 | 90 |
| Corn | 10 | 80 | 75 | 40 | 75 | 25 | 55 | 25 | 85 | 80 | 10 | 65 | 20 | 0 |
| Crabgrass, Large | 55 | 95 | 95 | 90 | 90 | 98 | 95 | 80 | 100 | 100 | 85 | 98 | 75 | 65 |
| Cupgrass, Woolly | 50 | 85 | 85 | 65 | 100 | 85 | 98 | 95 | 85 | 100 | 75 | 85 | 70 | 80 |
| Deadnettle | — | — | — | — | — | — | — | 100 | 98 | 95 | 98 | 98 | | |
| Foxtail, Giant | 80 | 98 | 95 | 75 | 95 | 98 | 98 | 98 | 98 | 100 | 80 | 98 | 75 | 85 |
| Foxtail, Green | 60 | 85 | 98 | 55 | 98 | 98 | 85 | 70 | 85 | 60 | 80 | 95 | 80 | 40 |
| *Galium* | — | — | — | — | — | — | — | 50 | 40 | 50 | 60 | 50 | | |
| Goosegrass | 70 | 95 | 90 | 85 | 70 | 98 | 95 | 90 | 98 | 100 | 95 | 98 | 80 | 75 |
| Johnsongrass | 45 | 100 | 60 | 55 | 98 | 85 | 65 | 80 | 100 | 100 | 70 | 100 | 55 | 65 |
| *Kochia* | 10 | 0 | 45 | 100 | 45 | 100 | 100 | 65 | 95 | 0 | 85 | 50 | 90 | 10 |
| Lambsquarters | 85 | 98 | 100 | 98 | 95 | 98 | 100 | 98 | 100 | 100 | 98 | 100 | 98 | 98 |

TABLE B-continued

| | | | | | | | | | | | | | | |
|---|---|---|---|---|---|---|---|---|---|---|---|---|---|---|
| Morningglory | 80 | 95 | 65 | 98 | 80 | 95 | 95 | 80 | 100 | 95 | 100 | 95 | 100 | 40 |
| Nutsedge, Yellow | 60 | 40 | 60 | 75 | 60 | 45 | 20 | 45 | 65 | 40 | 65 | 55 | 40 | 45 |
| Oat, Wild | 35 | 50 | 80 | 30 | 40 | 40 | 30 | 50 | 75 | 80 | 5 | 30 | 10 | 0 |
| Pigweed | 95 | 75 | 98 | 100 | 100 | 98 | 100 | 90 | 100 | 70 | 100 | 100 | 100 | 75 |
| Ragweed | 65 | 100 | 90 | 95 | 95 | 98 | 100 | 70 | 100 | — | 90 | 98 | 70 | — |
| Ryegrass, Italian | 5 | 20 | 40 | 5 | 45 | 5 | 0 | 10 | 40 | 40 | 0 | 0 | 0 | 0 |
| Soybean | 90 | 98 | 95 | 98 | 100 | 95 | 95 | 95 | 100 | 100 | 95 | 100 | 98 | 80 |
| Surinam Grass | 60 | 90 | 75 | 55 | 70 | 95 | — | — | 80 | 90 | — | 85 | 70 | 60 |
| Velvetleaf | 80 | 100 | 100 | 100 | 85 | 70 | 100 | 100 | 100 | 98 | 70 | 95 | 90 | 100 |
| Wheat | 30 | 10 | 55 | 30 | 30 | 15 | 0 | 35 | 45 | 45 | 0 | 0 | 0 | 5 |
| Windgrass | 50 | 65 | 60 | 30 | 45 | 40 | 30 | 65 | 50 | 80 | 30 | 50 | 40 | 50 |

| | Compounds | | | | | | | | | | | | | |
|---|---|---|---|---|---|---|---|---|---|---|---|---|---|---|
| 62 g ai/ha | 191 | 193 | 197 | 217 | 218 | 219 | 220 | 225 | 226 | 227 | 228 | 229 | 233 | 235 |
| | Postemergence | | | | | | | | | | | | | |
| Barley | 50 | 0 | 5 | 5 | 30 | 25 | 10 | 35 | 30 | 5 | 5 | 0 | 0 | 30 |
| Bermudagrass | 100 | 100 | 100 | 85 | 80 | 98 | 95 | 85 | 80 | 75 | 85 | 80 | 95 | 98 |
| Blackgrass | 45 | 15 | 10 | 5 | 0 | 55 | 20 | 5 | 30 | 0 | 35 | 0 | 30 | 60 |
| Bromegrass, Downy | 40 | 30 | 15 | 15 | 15 | 50 | 10 | 70 | 0 | 0 | 5 | 15 | 40 | 30 |
| Canarygrass | 50 | 5 | 30 | 20 | 0 | 55 | 10 | 85 | 30 | 0 | 0 | 15 | 5 | 30 |
| Chickweed | 98 | 98 | 100 | 95 | 100 | 100 | 95 | 40 | 75 | 75 | 100 | 85 | 95 | 100 |
| Cocklebur | 98 | 95 | 100 | 98 | — | — | — | 100 | 98 | 80 | 98 | 90 | 100 | — |
| Corn | 75 | 15 | 35 | 10 | 10 | 60 | 50 | 50 | 80 | 75 | 85 | 80 | 50 | 100 |
| Crabgrass, Large | 100 | 90 | 85 | 85 | 45 | 95 | 75 | 85 | 85 | 80 | 98 | 90 | 90 | 98 |
| Cupgrass, Woolly | 90 | 85 | 85 | 45 | 45 | 85 | 60 | 75 | 80 | 75 | 95 | 75 | 85 | 100 |
| Deadnettle | 100 | 100 | 100 | — | — | — | — | — | — | — | — | — | — | — |
| Foxtail, Giant | 100 | 85 | 95 | 75 | 55 | 70 | 50 | 80 | 90 | 80 | 85 | 80 | 95 | 100 |
| Foxtail, Green | 55 | 50 | 30 | 60 | 85 | 80 | 65 | 98 | 80 | 90 | 90 | 80 | 90 | 90 |
| *Galium* | 40 | — | 75 | — | — | — | — | — | — | — | — | — | — | — |
| Goosegrass | 98 | 95 | 98 | 80 | 10 | 95 | 85 | 90 | 80 | 75 | 80 | 70 | 95 | 98 |
| Johnsongrass | 100 | 65 | 85 | 60 | — | 60 | 65 | 75 | 85 | 60 | 75 | 100 | 5 | 80 |
| *Kochia* | 10 | 80 | 80 | 98 | 85 | 98 | 65 | 10 | 85 | 75 | 100 | 70 | 85 | 100 |
| Lambsquarters | 80 | 98 | 100 | 100 | 98 | 100 | 100 | 85 | 90 | 98 | 98 | 95 | 98 | 100 |
| Morningglory | 65 | 60 | 100 | 75 | 70 | 85 | 65 | 95 | 98 | 100 | 100 | 100 | 80 | 98 |
| Nutsedge, Yellow | 40 | 65 | 55 | 60 | 15 | 55 | 25 | 25 | 65 | 45 | 45 | 20 | 5 | 45 |
| Oat, Wild | 60 | 50 | 40 | 40 | 45 | 70 | 20 | 50 | 30 | 0 | 5 | 5 | 35 | 50 |
| Pigweed | 85 | 95 | 90 | 100 | 100 | 100 | 100 | 95 | 85 | 90 | 100 | 95 | 98 | 100 |
| Ragweed | — | — | — | 80 | 95 | 98 | 95 | 80 | 85 | 70 | 80 | 80 | 85 | 100 |
| Ryegrass, Italian | 40 | 40 | 0 | 30 | 40 | 25 | 5 | 35 | 0 | 0 | 0 | 0 | 45 | 30 |
| Soybean | 95 | 98 | 100 | 85 | 100 | 98 | 85 | 95 | 98 | 65 | 98 | 98 | 98 | 100 |
| Surinam Grass | 85 | 65 | 55 | 80 | 80 | 25 | 60 | 75 | 75 | 70 | 85 | 70 | 85 | 90 |
| Velvetleaf | 80 | 100 | 80 | 98 | 100 | 90 | 90 | 90 | 85 | 80 | 100 | 75 | 85 | 100 |
| Wheat | 40 | 35 | 0 | 45 | 0 | 50 | 0 | 40 | 15 | 0 | 5 | 0 | 30 | 80 |
| Windgrass | 85 | 70 | 50 | 50 | 20 | 40 | 40 | 55 | 50 | 30 | 50 | 40 | 55 | 95 |

| | Compounds | | | | | | | | |
|---|---|---|---|---|---|---|---|---|---|
| 62 g ai/ha | 236 | 237 | 238 | 239 | 240 | 243 | 244 | 245 | 255 |
| | Postemergence | | | | | | | | |
| Barley | 0 | 15 | 30 | 0 | 5 | 90 | 65 | 85 | 35 |
| Bermudagrass | 98 | 98 | 98 | 100 | 100 | 98 | 100 | 100 | 95 |
| Blackgrass | 5 | 70 | 60 | 5 | 50 | 80 | 60 | 70 | 5 |
| Bromegrass, Downy | 5 | 45 | 40 | 5 | 20 | 70 | 50 | 95 | 60 |
| Canarygrass | 0 | 40 | 25 | 0 | 5 | 98 | 95 | 95 | 50 |
| Chickweed | 100 | 98 | 90 | 98 | 98 | 100 | 95 | 85 | 98 |
| Cocklebur | 100 | — | — | 100 | — | — | — | — | — |
| Corn | 60 | 98 | 80 | 45 | 95 | 95 | 90 | 100 | 75 |
| Crabgrass, Large | 90 | 98 | 98 | 90 | 98 | 100 | 100 | 100 | 85 |
| Cupgrass, Woolly | 85 | 100 | 100 | 95 | 100 | 95 | 100 | 100 | 95 |
| Deadnettle | — | — | — | — | — | — | — | — | — |
| Foxtail, Giant | 80 | 98 | 100 | 85 | 100 | 95 | 95 | 100 | 98 |
| Foxtail, Green | 95 | 90 | 95 | 85 | 90 | 98 | 98 | 98 | 90 |
| *Galium* | — | — | — | — | — | — | — | — | — |
| Goosegrass | 90 | 98 | 98 | 98 | 98 | 95 | 95 | 98 | 90 |
| Johnsongrass | 15 | 100 | — | 20 | 100 | 100 | 95 | 100 | 85 |
| *Kochia* | 98 | 80 | 98 | 98 | 98 | 95 | 90 | 100 | 15 |
| Lambsquarters | 100 | 100 | 100 | 98 | 100 | 100 | 100 | 100 | 95 |
| Morningglory | 95 | 95 | — | — | — | 100 | 95 | 100 | 85 |
| Nutsedge, Yellow | 15 | 35 | 20 | 30 | 15 | 65 | 50 | 45 | 15 |
| Oat, Wild | 0 | 55 | 35 | 5 | 40 | 85 | 70 | 85 | 80 |
| Pigweed | 85 | 98 | 100 | 98 | 100 | 100 | 100 | 98 | 98 |
| Ragweed | 95 | 98 | 100 | 98 | 98 | 95 | 98 | 98 | 90 |
| Ryegrass, Italian | 0 | 50 | 25 | 0 | 15 | 85 | 60 | 50 | 30 |
| Soybean | 98 | 100 | 100 | 95 | 95 | 98 | 100 | 98 | 95 |
| Surinam Grass | 70 | 98 | 100 | 35 | 98 | 95 | 95 | 100 | 80 |

TABLE B-continued

| | | | | | | | | | | | |
|---|---|---|---|---|---|---|---|---|---|---|---|
| Velvetleaf | 100 | 90 | 90 | 100 | 85 | 100 | 100 | 100 | 98 | | |
| Wheat | 10 | 70 | 45 | 0 | 35 | 95 | 80 | 95 | 40 | | |
| Windgrass | 50 | 90 | 70 | 30 | 80 | 90 | 70 | 70 | 80 | | |

| | Compounds | | | | | | | | | | | | |
|---|---|---|---|---|---|---|---|---|---|---|---|---|---|
| 31 g ai/ha | 1 | 2 | 3 | 4 | 7 | 8 | 9 | 10 | 11 | 12 | 14 | 24 | 26 | 27 |

Postemergence

| | | | | | | | | | | | | | |
|---|---|---|---|---|---|---|---|---|---|---|---|---|---|
| Barley | 0 | 10 | 0 | 0 | 0 | 0 | 0 | 0 | 0 | 0 | 0 | 0 | 0 | 0 |
| Bermudagrass | 40 | 80 | 15 | 15 | 35 | 60 | 90 | 70 | 80 | 65 | 70 | 85 | 40 | 70 |
| Blackgrass | 0 | 10 | 0 | 10 | 0 | 5 | 0 | 0 | 5 | 10 | 0 | 5 | 0 | 0 |
| Bromegrass, Downy | 0 | 35 | 0 | 10 | 0 | 5 | 5 | 0 | 20 | 5 | 10 | 25 | 10 | 5 |
| Canarygrass | 0 | 40 | 0 | 10 | 0 | 20 | 5 | 0 | 50 | 0 | 10 | 40 | 20 | 10 |
| Chickweed | 55 | 75 | 90 | 100 | 60 | 98 | 20 | 90 | 80 | 100 | — | 80 | 40 | 40 |
| Cocklebur | 65 | 80 | 65 | 100 | 45 | 100 | 0 | 70 | 90 | 70 | 80 | 90 | 80 | 90 |
| Corn | 0 | 15 | 0 | 10 | 0 | 15 | 15 | 15 | 70 | 25 | 10 | 30 | 35 | 35 |
| Crabgrass, Large | 40 | 80 | 60 | 70 | 30 | 70 | 70 | 65 | 80 | 65 | 50 | 70 | 40 | 50 |
| Cupgrass, Woolly | 0 | 75 | 0 | 75 | 0 | 75 | 70 | 60 | 55 | 55 | 50 | 80 | 40 | 60 |
| Deadnettle | — | — | — | — | — | — | — | — | — | — | — | — | — | — |
| Foxtail, Giant | 0 | 85 | 15 | 80 | 20 | 98 | 75 | 70 | 75 | 75 | 50 | 70 | 60 | 65 |
| Foxtail, Green | 5 | 75 | 5 | 40 | 5 | 40 | 35 | 10 | 60 | 40 | 45 | 40 | 35 | 80 |
| Galium | — | — | — | — | — | — | — | — | — | — | — | — | — | — |
| Goosegrass | 60 | 80 | 15 | 25 | 20 | 80 | 60 | 45 | 65 | 70 | 80 | 85 | 60 | 90 |
| Johnsongrass | 0 | 85 | 0 | 45 | 0 | 80 | 60 | 0 | 65 | 55 | 45 | 60 | 35 | 40 |
| Kochia | 15 | 60 | 65 | 80 | 0 | 85 | 10 | 10 | 25 | 20 | — | 70 | — | — |
| Lambsquarters | 70 | 90 | 85 | 98 | 0 | 95 | 75 | 80 | 50 | 80 | 85 | 90 | 80 | 90 |
| Morningglory | 0 | 70 | 15 | 60 | 15 | 75 | 45 | 0 | 15 | 15 | 70 | 50 | 50 | 50 |
| Nutsedge, Yellow | 15 | 45 | 15 | 55 | 0 | 65 | 20 | 15 | 25 | 15 | 20 | 20 | 30 | 30 |
| Oat, Wild | 5 | 30 | 0 | 30 | 0 | 10 | 0 | 0 | 50 | 0 | 30 | 40 | 40 | 45 |
| Pigweed | 65 | 85 | 75 | 100 | 75 | 98 | 80 | 85 | 65 | 95 | 80 | 70 | 50 | 98 |
| Ragweed | 60 | 70 | 80 | 100 | 50 | 90 | 70 | 75 | 100 | 100 | 80 | 70 | 70 | 85 |
| Ryegrass, Italian | 0 | 0 | 0 | 10 | 0 | 20 | 0 | 0 | 10 | 0 | 0 | 0 | 0 | 0 |
| Soybean | 50 | 80 | 65 | 95 | 60 | 98 | 70 | 95 | 100 | 98 | 80 | 85 | 95 | 95 |
| Surinam Grass | 0 | 70 | 15 | 60 | 0 | 60 | 55 | 60 | 60 | 25 | 40 | 50 | 30 | 50 |
| Velvetleaf | 55 | 85 | 95 | 70 | 70 | 75 | 85 | 70 | 80 | 80 | 85 | 75 | 70 | 50 |
| Wheat | 0 | 5 | 0 | 5 | 0 | 25 | 0 | 0 | 30 | 0 | 0 | 5 | 0 | 0 |
| Windgrass | 0 | 10 | 0 | 50 | 5 | 5 | 50 | 5 | 40 | 10 | 5 | 20 | 10 | 10 |

| | Compounds | | | | | | | | | | | | |
|---|---|---|---|---|---|---|---|---|---|---|---|---|---|
| 31 g ai/ha | 29 | 33 | 34 | 36 | 37 | 38 | 39 | 40 | 42 | 44 | 45 | 46 | 47 | 48 |

Postemergence

| | | | | | | | | | | | | | |
|---|---|---|---|---|---|---|---|---|---|---|---|---|---|
| Barley | 0 | 0 | 0 | 5 | 0 | 0 | 0 | 0 | 0 | 0 | 5 | 0 | 5 | 5 |
| Bermudagrass | 85 | 75 | 75 | 90 | 85 | 98 | 50 | — | 70 | 80 | 80 | 80 | 85 | 85 |
| Blackgrass | 10 | 10 | 0 | 5 | 0 | 5 | 0 | 0 | 5 | 0 | 5 | 0 | 5 | 0 |
| Bromegrass, Downy | 5 | 5 | 40 | 30 | 0 | 50 | 0 | 45 | 0 | 40 | 10 | 0 | 35 | 10 |
| Canarygrass | 10 | 0 | 5 | 40 | 0 | 10 | 0 | 20 | 0 | 20 | 10 | 0 | 20 | 30 |
| Chickweed | 50 | 80 | 50 | 85 | 80 | 85 | 98 | 100 | 60 | 90 | 75 | 80 | 85 | 85 |
| Cocklebur | 85 | 85 | 0 | — | — | — | 75 | — | 0 | 80 | 10 | 75 | 95 | 95 |
| Corn | 20 | 0 | 0 | 50 | 0 | 55 | 25 | 80 | 0 | 75 | 10 | 20 | 65 | 65 |
| Crabgrass, Large | 45 | 75 | 80 | 90 | 70 | 90 | 75 | 85 | 70 | 85 | 65 | 60 | 85 | 85 |
| Cupgrass, Woolly | 80 | 65 | 80 | 85 | 55 | 80 | 65 | 90 | 15 | 80 | 70 | 10 | 85 | 80 |
| Deadnettle | — | — | — | — | — | — | — | — | — | — | — | — | — | — |
| Foxtail, Giant | 80 | 75 | 85 | 95 | 70 | 95 | 75 | 100 | 45 | 95 | 75 | 70 | 90 | 85 |
| Foxtail, Green | 60 | 50 | 70 | 85 | 60 | 85 | 80 | 90 | 50 | 90 | 50 | 45 | 80 | 85 |
| Galium | — | — | — | — | — | — | — | — | — | — | — | — | — | — |
| Goosegrass | 80 | 70 | 75 | 85 | 80 | 80 | 40 | 85 | 70 | 85 | 75 | 75 | 90 | 85 |
| Johnsongrass | 20 | 15 | 75 | 65 | 0 | 70 | 65 | — | 0 | 70 | 60 | 40 | 85 | 45 |
| Kochia | — | 10 | 85 | 0 | 0 | 65 | 20 | 0 | 80 | 75 | 0 | 0 | 95 | 98 |
| Lambsquarters | 85 | 95 | 95 | 98 | 95 | 90 | 95 | 100 | 90 | 90 | 95 | 80 | 98 | 85 |
| Morningglory | 60 | 60 | 60 | 60 | 60 | 65 | 65 | 70 | 45 | 60 | 75 | 30 | 75 | 70 |
| Nutsedge, Yellow | 40 | 40 | 5 | 10 | 10 | 0 | 0 | 20 | 55 | 40 | 10 | 65 | 65 | 40 |
| Oat, Wild | 40 | 10 | 40 | 60 | 0 | 55 | 10 | 85 | 5 | 50 | 35 | 0 | 40 | 40 |
| Pigweed | 60 | 90 | 70 | 85 | 80 | 95 | 98 | 90 | 85 | 75 | 85 | 75 | 98 | 85 |
| Ragweed | 80 | 90 | 75 | 90 | 80 | 75 | 85 | 98 | 70 | 85 | 80 | 70 | 85 | 85 |
| Ryegrass, Italian | 5 | 5 | 10 | 0 | 0 | 35 | 0 | 0 | 0 | 5 | 30 | 0 | 0 | 0 |
| Soybean | 85 | 95 | 85 | 90 | 75 | 85 | 95 | 100 | 70 | 95 | 80 | 75 | 95 | 95 |
| Surinam Grass | 50 | 45 | 70 | 75 | 60 | 70 | 60 | 85 | 40 | 85 | 70 | 45 | 85 | 70 |
| Velvetleaf | 50 | 80 | 80 | 98 | 75 | 95 | 75 | 98 | 80 | 95 | 70 | 75 | 80 | 85 |
| Wheat | 0 | 0 | 0 | 5 | 0 | 0 | 5 | 0 | 5 | 10 | 0 | 0 | 0 | 0 |
| Windgrass | 5 | 10 | 10 | 50 | 5 | 70 | 0 | 70 | 10 | 65 | 30 | 10 | 60 | 70 |

TABLE B-continued

| 31 g ai/ha | Compounds | | | | | | | | | | | | | |
|---|---|---|---|---|---|---|---|---|---|---|---|---|---|---|
| | 49 | 50 | 51 | 52 | 53 | 55 | 56 | 58 | 59 | 61 | 62 | 63 | 64 | 66 |
| | Postemergence | | | | | | | | | | | | | |
| Barley | 0 | 0 | 5 | 0 | 0 | 0 | 0 | 5 | 0 | 0 | 0 | 0 | 15 | 0 |
| Bermudagrass | 75 | 90 | 80 | 85 | 90 | 80 | 75 | 85 | — | 75 | — | — | 95 | 70 |
| Blackgrass | 0 | 5 | 0 | 5 | 20 | 0 | 0 | 5 | 10 | 0 | 15 | 30 | 0 | 5 |
| Bromegrass, Downy | 0 | 0 | 50 | 50 | 35 | 0 | 35 | 40 | 5 | 0 | 30 | 10 | 25 | 5 |
| Canarygrass | 0 | 0 | 60 | 0 | 40 | 0 | 0 | 60 | 5 | 0 | 0 | 0 | 40 | 0 |
| Chickweed | 75 | 80 | 80 | 95 | 85 | 65 | 90 | 70 | 85 | 80 | 70 | 60 | 98 | 80 |
| Cocklebur | 65 | 85 | 85 | 75 | 80 | 45 | 5 | 85 | 85 | 0 | 25 | 65 | 90 | 10 |
| Corn | 5 | 5 | 75 | 30 | 55 | 0 | 45 | 0 | — | 0 | 70 | — | 80 | 25 |
| Crabgrass, Large | 75 | 75 | 80 | 85 | 85 | 60 | 75 | 75 | 80 | 65 | 55 | 70 | 85 | 50 |
| Cupgrass, Woolly | 50 | 70 | 75 | 70 | 65 | 10 | 15 | 65 | 75 | 55 | 55 | 50 | 75 | 40 |
| Deadnettle | — | — | — | — | — | — | — | — | — | — | — | — | — | — |
| Foxtail, Giant | 45 | 75 | 80 | 80 | 80 | 25 | 75 | 75 | 75 | 55 | 55 | 60 | 90 | 65 |
| Foxtail, Green | 50 | 80 | 85 | 95 | 95 | 30 | 80 | 75 | 50 | 50 | 40 | 60 | 70 | 80 |
| *Galium* | — | — | — | — | — | — | — | — | — | — | — | — | — | — |
| Goosegrass | 65 | 75 | 75 | 75 | 75 | 45 | 65 | 70 | 75 | 40 | 65 | 70 | 80 | 65 |
| Johnsongrass | 0 | 0 | 75 | 75 | 55 | 0 | 55 | 50 | — | 0 | 0 | — | 90 | 45 |
| *Kochia* | 55 | 95 | 20 | 20 | 45 | 20 | 90 | 0 | — | 5 | 10 | 10 | 50 | 80 |
| Lambsquarters | 70 | 98 | 75 | 85 | 90 | 80 | 98 | 95 | 95 | 85 | 85 | — | 95 | 95 |
| Morningglory | 65 | 10 | 75 | 10 | 55 | 55 | — | 65 | — | 45 | — | — | 80 | 98 |
| Nutsedge, Yellow | 65 | 70 | 60 | 20 | 20 | 10 | 20 | 25 | 45 | 20 | 15 | 20 | 0 | 25 |
| Oat, Wild | 0 | 5 | 60 | 90 | 50 | 0 | 5 | 45 | 30 | 0 | 5 | 0 | 60 | 0 |
| Pigweed | 80 | 80 | 85 | 85 | 85 | 80 | 98 | 80 | — | 80 | 98 | 85 | 98 | 98 |
| Ragweed | 75 | 80 | 80 | 75 | 80 | 70 | 55 | 80 | 75 | 75 | 70 | 70 | 85 | 0 |
| Ryegrass, Italian | 0 | 0 | 0 | 40 | 0 | 0 | 0 | 0 | 5 | 0 | 0 | 0 | 0 | 0 |
| Soybean | 55 | 85 | 85 | 80 | 90 | 25 | 85 | 85 | 90 | 0 | 75 | 75 | 85 | 95 |
| Surinam Grass | 15 | 65 | 80 | 75 | 85 | 10 | 75 | 70 | 75 | 20 | 20 | 10 | 85 | 65 |
| Velvetleaf | 90 | 90 | 80 | 95 | 85 | 90 | 85 | 75 | 85 | 80 | 85 | 95 | 85 | 85 |
| Wheat | 0 | 0 | 5 | 15 | 20 | 0 | 0 | 0 | 0 | 0 | 0 | 0 | 10 | 0 |
| Windgrass | 0 | 10 | 50 | 60 | 60 | 0 | 30 | 35 | 20 | 0 | 30 | 10 | 70 | 60 |

| 31 g ai/ha | Compounds | | | | | | | | | | | | | |
|---|---|---|---|---|---|---|---|---|---|---|---|---|---|---|
| | 67 | 68 | 69 | 70 | 71 | 72 | 73 | 74 | 75 | 77 | 79 | 80 | 81 | 82 |
| | Postemergence | | | | | | | | | | | | | |
| Barley | 0 | 0 | 5 | 10 | 0 | 0 | 0 | 0 | 0 | 0 | 5 | 15 | 0 | 0 |
| Bermudagrass | 35 | 75 | 98 | 75 | 65 | 75 | 65 | 75 | 90 | 90 | 80 | 20 | 85 | 80 |
| Blackgrass | 0 | 0 | 0 | 30 | 0 | 0 | 0 | 0 | 0 | 0 | 5 | 0 | 5 | 0 |
| Bromegrass, Downy | 0 | 5 | 40 | 10 | 0 | 0 | 20 | 0 | 5 | 0 | 5 | 45 | 5 | 0 |
| Canarygrass | 0 | 0 | 0 | 50 | 0 | 0 | 0 | 0 | 0 | 0 | 15 | 45 | 0 | 0 |
| Chickweed | 90 | 85 | 98 | 80 | 75 | 70 | 80 | 75 | 85 | 80 | 80 | 90 | 95 | 90 |
| Cocklebur | 75 | 25 | 0 | 0 | 65 | 75 | 0 | 20 | 40 | 0 | 95 | 0 | 5 | 85 |
| Corn | 5 | 0 | 5 | 15 | 0 | 0 | 20 | 0 | 0 | 0 | 5 | 5 | 5 | 0 |
| Crabgrass, Large | 75 | 75 | 95 | 80 | 65 | 75 | 80 | 80 | 95 | 55 | 80 | 75 | 85 | 70 |
| Cupgrass, Woolly | 60 | 10 | 90 | 45 | 10 | 45 | 60 | 10 | 10 | 20 | 10 | 65 | 65 | 55 |
| Deadnettle | — | — | — | — | — | — | — | — | — | — | — | — | — | — |
| Foxtail, Giant | 75 | 65 | 95 | 75 | 20 | 65 | 70 | 25 | 75 | 65 | 70 | 75 | 75 | 75 |
| Foxtail, Green | 10 | 40 | 95 | 80 | 60 | 10 | 70 | 20 | 65 | 40 | 60 | 90 | 5 | 60 |
| *Galium* | — | — | — | — | — | — | — | — | — | — | — | — | — | — |
| Goosegrass | 55 | 65 | 75 | 75 | 75 | 60 | 65 | 65 | 75 | 65 | 45 | 70 | 65 | 75 |
| Johnsongrass | 0 | 10 | 98 | 65 | 65 | 0 | 10 | 0 | 0 | 0 | 0 | 0 | 5 | 65 |
| *Kochia* | 75 | 70 | 60 | 65 | 0 | 75 | 75 | 75 | 75 | 75 | 75 | 0 | 75 | 10 |
| Lambsquarters | 80 | 95 | 100 | 85 | 75 | 90 | 85 | 95 | 98 | 95 | 95 | 95 | 95 | 80 |
| Morningglory | 80 | 80 | 70 | 98 | 65 | 20 | 0 | 60 | 20 | 75 | 80 | 85 | 75 | 65 |
| Nutsedge, Yellow | 60 | 0 | 5 | 10 | 10 | 35 | 20 | 20 | 10 | 45 | 25 | 10 | 65 | 10 |
| Oat, Wild | 0 | 5 | 60 | 55 | 0 | 0 | 55 | 20 | 0 | 0 | 40 | 20 | 25 | 0 |
| Pigweed | 98 | 85 | 98 | 85 | 85 | 80 | 80 | 90 | 100 | 98 | 100 | 100 | 98 | 75 |
| Ragweed | 75 | 75 | 90 | 60 | 75 | 75 | 75 | 75 | 80 | 75 | 80 | 50 | 75 | 75 |
| Ryegrass, Italian | 0 | 5 | 30 | 10 | 0 | 0 | 35 | 5 | 0 | 0 | 20 | 0 | 0 | 0 |
| Soybean | 80 | 80 | 80 | 75 | 65 | 80 | 80 | 75 | 80 | 25 | 75 | 75 | 85 | 75 |
| Surinam Grass | 10 | 25 | 85 | 65 | 50 | 75 | 80 | 20 | 50 | 65 | 20 | 45 | 75 | 65 |
| Velvetleaf | 90 | 95 | 95 | 75 | 75 | 98 | 95 | 98 | 100 | 90 | 95 | 85 | 100 | 85 |
| Wheat | 5 | 5 | 5 | 5 | 0 | 0 | 0 | 5 | 0 | 0 | 10 | 5 | 5 | 0 |
| Windgrass | 0 | 40 | 60 | 80 | 5 | 5 | 70 | 5 | 30 | 10 | 50 | 50 | 10 | 5 |

| 31 g ai/ha | Compounds | | | | | | | | | | | | | |
|---|---|---|---|---|---|---|---|---|---|---|---|---|---|---|
| | 83 | 85 | 86 | 87 | 88 | 89 | 90 | 91 | 92 | 93 | 94 | 95 | 96 | 97 |
| | Postemergence | | | | | | | | | | | | | |
| Barley | 0 | 5 | 30 | 0 | 30 | 0 | 0 | 0 | 0 | 0 | 0 | 0 | 0 | 0 |
| Bermudagrass | 75 | 85 | 85 | 90 | 80 | 75 | 70 | 75 | 20 | 60 | 80 | 45 | 80 | 95 |

TABLE B-continued

| | | | | | | | | | | | | | | |
|---|---|---|---|---|---|---|---|---|---|---|---|---|---|---|
| Blackgrass | 0 | 5 | 15 | 5 | 0 | 10 | 5 | 10 | 0 | 0 | 5 | 0 | 5 | 5 |
| Bromegrass, Downy | 40 | 0 | 10 | 20 | 40 | 0 | 5 | 0 | 0 | 0 | 0 | 0 | 0 | 0 |
| Canarygrass | 20 | 35 | 20 | 0 | 60 | 10 | 5 | 25 | 0 | 0 | 0 | 0 | 0 | 0 |
| Chickweed | 90 | 85 | 80 | 100 | 75 | 75 | 70 | 85 | 90 | 80 | 95 | 75 | 75 | 95 |
| Cocklebur | 75 | 95 | 85 | 98 | 90 | 10 | 75 | 20 | 25 | 70 | 45 | 70 | 75 | 95 |
| Corn | 0 | 50 | 10 | 20 | 15 | 80 | 15 | 25 | 20 | 0 | 0 | 0 | 45 | 20 |
| Crabgrass, Large | 85 | 90 | 85 | 85 | 95 | 85 | 65 | 80 | 80 | 70 | 70 | 45 | 75 | 75 |
| Cupgrass, Woolly | 70 | 75 | 75 | 50 | 75 | 35 | 45 | 70 | 10 | 45 | — | 45 | 70 | 55 |
| Deadnettle | — | — | — | — | — | — | — | — | — | — | — | — | — | — |
| Foxtail, Giant | 80 | 75 | 90 | 75 | 95 | 70 | 65 | 85 | 65 | 70 | 65 | 45 | 65 | 60 |
| Foxtail, Green | 90 | 80 | 70 | 75 | 95 | 60 | 65 | 70 | 75 | 50 | 10 | 20 | 50 | 40 |
| *Galium* | — | — | — | — | — | — | — | — | — | — | — | — | — | — |
| Goosegrass | 75 | 70 | 70 | 75 | 65 | 55 | 60 | 30 | 60 | 60 | 45 | 65 | 70 | 60 |
| Johnsongrass | 95 | 80 | 95 | 5 | 95 | 25 | 10 | 65 | 20 | 10 | — | 5 | 20 | 15 |
| *Kochia* | 65 | 75 | 75 | 100 | 75 | 65 | 65 | 20 | 75 | 65 | — | 80 | 65 | 65 |
| Lambsquarters | 95 | 98 | 100 | 98 | 95 | 95 | 85 | 85 | 90 | 85 | 80 | 80 | 90 | 90 |
| Morningglory | 70 | 95 | 70 | 45 | 90 | 70 | 65 | 75 | 80 | 70 | 55 | 100 | 65 | 100 |
| Nutsedge, Yellow | 10 | 75 | 65 | 10 | 25 | 35 | 60 | 50 | 45 | 45 | 20 | 75 | 70 | 75 |
| Oat, Wild | 10 | 5 | 20 | 50 | 50 | 10 | 0 | 30 | 0 | 0 | 0 | 0 | 0 | 0 |
| Pigweed | 80 | 100 | 98 | 98 | 98 | 80 | 85 | 100 | 90 | 90 | 100 | 85 | 90 | 95 |
| Ragweed | 75 | 80 | 80 | 85 | 75 | 70 | 60 | 85 | 40 | 65 | 40 | 75 | 80 | 85 |
| Ryegrass, Italian | 0 | 0 | 25 | 5 | 5 | 0 | 0 | 0 | 0 | 0 | 0 | 0 | 0 | 0 |
| Soybean | 75 | 80 | 80 | 98 | 75 | 90 | 98 | 75 | 90 | 55 | 65 | 95 | 65 | 70 |
| Surinam Grass | 75 | 75 | 80 | 75 | 95 | 55 | 65 | 85 | 25 | 50 | — | 45 | 75 | 65 |
| Velvetleaf | 85 | 90 | 98 | 100 | 80 | 90 | 85 | 98 | 95 | 85 | — | 85 | 95 | 100 |
| Wheat | 0 | 0 | 5 | 35 | 0 | 0 | 5 | 0 | 0 | 0 | 0 | 0 | 0 | 0 |
| Windgrass | 5 | 40 | 30 | 55 | 40 | 0 | 0 | 10 | 0 | 5 | 0 | 0 | 5 | 5 |

| | Compounds | | | | | | | | | | | | | |
|---|---|---|---|---|---|---|---|---|---|---|---|---|---|---|
| 31 g ai/ha | 98 | 99 | 100 | 102 | 107 | 108 | 109 | 111 | 113 | 117 | 118 | 119 | 120 | 121 |
| | Postemergence | | | | | | | | | | | | | |
| Barley | 0 | 5 | 5 | 0 | 0 | 0 | 0 | 0 | 0 | 0 | 0 | 0 | — | 0 |
| Bermudagrass | 75 | 75 | 70 | 80 | 75 | 85 | 70 | 95 | 80 | 75 | 75 | 75 | 80 | 95 |
| Blackgrass | 0 | 0 | 0 | 0 | 0 | 0 | 0 | 5 | 0 | 0 | 5 | 5 | 30 | 5 |
| Bromegrass, Downy | 5 | 5 | 5 | 0 | 0 | 0 | 0 | 0 | 5 | 5 | 0 | 10 | 20 | 25 |
| Canarygrass | 5 | 40 | 0 | 5 | 5 | 0 | 0 | 0 | 65 | 0 | 0 | 5 | 0 | 0 |
| Chickweed | 80 | 80 | 75 | 60 | 98 | 85 | 90 | 95 | 98 | 85 | 90 | 70 | 60 | 100 |
| Cocklebur | 98 | 95 | 40 | 90 | 98 | 75 | 75 | 98 | 95 | 75 | 40 | 0 | 10 | 40 |
| Corn | 35 | 40 | 0 | — | 65 | 15 | 0 | 10 | 25 | 10 | 0 | 20 | 15 | 25 |
| Crabgrass, Large | 75 | 85 | 55 | 70 | 75 | 60 | 65 | 70 | 85 | 75 | 70 | 75 | 80 | 85 |
| Cupgrass, Woolly | 65 | 70 | — | 70 | 65 | 40 | — | 40 | 85 | 65 | 65 | 75 | 70 | 95 |
| Deadnettle | — | — | — | — | — | — | — | — | — | — | — | — | — | — |
| Foxtail, Giant | 65 | 75 | 70 | 70 | 75 | 45 | 70 | 60 | 80 | 65 | 75 | 75 | 75 | 95 |
| Foxtail, Green | 30 | 50 | 20 | 80 | 70 | 5 | 20 | 40 | 80 | 50 | 50 | 85 | 90 | 80 |
| *Galium* | — | — | — | — | — | — | — | — | — | — | — | — | — | — |
| Goosegrass | 60 | 75 | 70 | 55 | 75 | 60 | 65 | 70 | 70 | 45 | 55 | 75 | 75 | 95 |
| Johnsongrass | 55 | 70 | 0 | 20 | 60 | 10 | 5 | 10 | 65 | 5 | 10 | 10 | 15 | 20 |
| *Kochia* | 65 | 80 | — | 65 | 98 | 70 | 70 | 80 | 98 | 45 | 45 | 40 | 10 | 95 |
| Lambsquarters | 95 | 98 | 95 | 95 | 90 | 98 | 98 | 98 | 95 | 95 | 85 | 85 | 80 | 95 |
| Morningglory | 70 | 100 | 60 | 65 | 100 | 75 | 70 | 100 | 98 | 10 | 10 | 10 | 15 | 5 |
| Nutsedge, Yellow | 50 | 45 | — | 45 | 75 | 50 | — | 65 | 65 | 0 | 35 | 10 | 5 | 5 |
| Oat, Wild | 10 | 10 | 0 | 5 | 0 | 0 | 0 | 0 | 20 | 5 | 5 | 50 | 50 | 60 |
| Pigweed | 100 | 100 | 90 | 70 | 95 | 95 | 100 | 95 | 95 | 95 | 85 | 95 | 95 | 100 |
| Ragweed | 70 | 65 | 70 | 70 | 75 | 80 | 75 | 75 | 80 | 70 | 70 | 70 | 50 | 65 |
| Ryegrass, Italian | 0 | 0 | 5 | 0 | 0 | 0 | 0 | 0 | 40 | 0 | 5 | 5 | 10 | 40 |
| Soybean | 90 | 98 | 95 | 75 | 95 | 45 | 95 | 70 | 98 | 65 | 75 | 0 | 40 | 90 |
| Surinam Grass | 65 | 70 | — | 60 | 75 | 55 | 65 | 60 | 85 | 65 | 50 | 75 | 20 | 95 |
| Velvetleaf | 95 | 95 | — | 98 | 90 | 100 | 90 | 80 | 85 | 70 | 75 | 75 | 75 | 98 |
| Wheat | 0 | 0 | 0 | 0 | 0 | 0 | 0 | 0 | 0 | 0 | 0 | 10 | 20 | 5 |
| Windgrass | 0 | 5 | 0 | 5 | 5 | 0 | 30 | 0 | 5 | 40 | 50 | 60 | 60 | 80 |

| | Compounds | | | | | | | | | | | | | |
|---|---|---|---|---|---|---|---|---|---|---|---|---|---|---|
| 31 g ai/ha | 122 | 123 | 126 | 127 | 128 | 129 | 130 | 131 | 140 | 141 | 146 | 147 | 152 | 155 |
| | Postemergence | | | | | | | | | | | | | |
| Barley | 0 | 5 | 5 | 0 | 0 | 0 | 0 | 0 | 0 | 0 | 0 | 0 | 10 | 30 |
| Bermudagrass | 75 | 80 | 75 | 95 | 75 | 80 | 75 | 65 | 60 | 80 | 85 | 75 | 95 | 85 |
| Blackgrass | 5 | 20 | 5 | 5 | 5 | 0 | 0 | 0 | 0 | 5 | 5 | 10 | 20 | 10 |
| Bromegrass, Downy | 5 | 0 | 5 | 5 | 30 | 5 | 10 | 0 | 0 | 0 | 0 | 0 | 30 | 5 |
| Canarygrass | 10 | 25 | 15 | 5 | 10 | 0 | 5 | 0 | 0 | 0 | 0 | 0 | 35 | 10 |
| Chickweed | 70 | 70 | 65 | 65 | 90 | 85 | 98 | 65 | 0 | 60 | 70 | 70 | 10 | 100 |
| Cocklebur | 20 | 65 | 15 | 75 | 98 | 95 | 85 | 95 | 0 | 40 | 10 | 50 | 70 | 15 |
| Corn | 0 | 35 | 10 | 5 | 40 | 20 | 55 | 0 | 0 | 0 | 0 | 0 | 25 | 5 |
| Crabgrass, Large | 75 | 70 | 75 | 80 | 85 | 80 | 85 | 75 | 50 | 70 | 65 | 60 | 75 | 60 |
| Cupgrass, Woolly | 65 | 25 | 65 | 75 | 85 | 80 | 80 | 50 | 50 | 65 | 60 | 65 | 95 | 20 |

TABLE B-continued

| | | | | | | | | | | | | | | |
|---|---|---|---|---|---|---|---|---|---|---|---|---|---|---|
| Deadnettle | — | — | — | — | — | — | — | — | — | — | — | — | — | — |
| Foxtail, Giant | 70 | 65 | 70 | 80 | 95 | 70 | 90 | 75 | 65 | 75 | 75 | 65 | 80 | 65 |
| Foxtail, Green | 80 | 50 | 50 | 75 | 85 | 80 | 90 | 70 | 45 | 50 | 50 | 40 | 75 | 25 |
| *Galium* | — | — | — | — | — | — | — | — | — | — | — | — | — | — |
| Goosegrass | 40 | 65 | 65 | 65 | 90 | 85 | 85 | 65 | 45 | 65 | 75 | 35 | 80 | 65 |
| Johnsongrass | 45 | 35 | 65 | 65 | 70 | 40 | 60 | 5 | 10 | 15 | 45 | 15 | 70 | 10 |
| *Kochia* | 0 | 60 | 10 | 45 | 60 | 80 | 85 | 35 | 0 | 20 | 40 | 40 | 10 | 35 |
| Lambsquarters | 60 | 80 | 70 | 75 | 95 | 90 | 98 | 85 | 45 | 80 | 95 | 85 | 85 | 98 |
| Morningglory | 60 | 70 | 75 | 65 | 80 | 90 | 95 | 70 | 0 | 60 | 0 | 50 | 45 | 55 |
| Nutsedge, Yellow | 55 | 65 | 65 | 65 | 20 | 35 | 10 | 15 | 10 | 0 | 5 | 50 | 65 | 20 |
| Oat, Wild | 5 | 0 | 5 | 5 | 40 | 0 | 20 | 0 | 0 | 10 | 0 | 5 | 30 | 10 |
| Pigweed | 85 | 80 | 75 | 80 | 95 | 85 | 95 | 90 | 55 | 60 | 95 | 85 | 95 | 98 |
| Ragweed | 60 | 70 | 55 | 70 | 85 | 90 | 85 | 80 | 25 | 65 | 65 | 20 | 60 | 45 |
| Ryegrass, Italian | 5 | 0 | 0 | 0 | 0 | 0 | 0 | 0 | 0 | 0 | 5 | 5 | 5 | 5 |
| Soybean | 45 | 60 | 70 | 95 | 98 | 95 | 98 | 75 | 10 | 70 | 70 | 15 | 70 | 95 |
| Surinam Grass | 75 | 25 | 70 | 75 | 50 | 80 | 80 | 20 | 50 | 40 | 65 | 50 | 75 | 40 |
| Velvetleaf | 80 | 80 | 80 | 90 | 90 | 95 | 95 | 80 | 50 | 75 | 80 | 60 | 85 | 100 |
| Wheat | 15 | 10 | 5 | 5 | 0 | 0 | 5 | 0 | 5 | 0 | 0 | 0 | 35 | 15 |
| Windgrass | 5 | 30 | 10 | 25 | 50 | 45 | 60 | 0 | 0 | 25 | 45 | 10 | 50 | 50 |

| | Compounds | | | | | | | | | | | | | |
|---|---|---|---|---|---|---|---|---|---|---|---|---|---|---|
| 31 g ai/ha | 156 | 157 | 159 | 160 | 162 | 164 | 169 | 173 | 181 | 184 | 186 | 187 | 189 | 190 |
| | Postemergence | | | | | | | | | | | | | |
| Barley | 30 | 5 | 20 | 5 | 30 | 5 | 0 | 5 | 5 | 5 | 0 | 0 | 0 | 0 |
| Bermudagrass | 80 | 75 | 95 | 65 | 85 | 70 | 70 | 98 | 100 | 98 | 80 | 75 | 10 | 98 |
| Blackgrass | 5 | 0 | 20 | 5 | 30 | 5 | 5 | 5 | 0 | 30 | 0 | 0 | 0 | 5 |
| Bromegrass, Downy | 10 | 40 | 50 | 0 | 20 | 40 | 10 | 5 | 40 | 40 | 5 | 5 | 0 | 5 |
| Canarygrass | 15 | 40 | 80 | 5 | 40 | 40 | 40 | 10 | 50 | 45 | 5 | 10 | 0 | 0 |
| Chickweed | 80 | 100 | 100 | 85 | 90 | 80 | 100 | 65 | 100 | 100 | 95 | 100 | 98 | — |
| Cocklebur | 20 | 100 | 95 | 98 | 100 | 98 | 100 | 60 | 100 | 100 | 90 | 100 | 60 | 40 |
| Corn | 10 | 70 | 60 | 15 | 50 | 15 | 45 | 5 | 70 | 80 | 10 | 50 | 20 | 0 |
| Crabgrass, Large | 45 | 80 | 80 | 80 | 80 | 95 | 85 | 70 | 98 | 100 | 80 | 85 | 75 | 60 |
| Cupgrass, Woolly | 40 | 85 | 70 | 65 | 90 | 75 | 85 | 85 | 80 | 75 | 70 | 80 | 70 | 75 |
| Deadnettle | — | — | — | — | — | — | — | — | 100 | 90 | 80 | 85 | 65 | 65 |
| Foxtail, Giant | 75 | 98 | 85 | 70 | 85 | 90 | 95 | 95 | 98 | 98 | 75 | 98 | 75 | 70 |
| Foxtail, Green | 45 | 70 | 85 | 55 | 98 | 70 | 60 | 55 | 70 | 30 | 50 | 65 | 65 | 25 |
| *Galium* | — | — | — | — | — | — | — | — | 50 | 40 | 20 | 20 | 50 | |
| Goosegrass | 65 | 85 | 85 | 80 | 60 | 85 | 95 | 80 | 95 | 100 | 85 | 85 | 60 | 70 |
| Johnsongrass | 15 | 70 | 45 | 45 | 98 | 45 | 60 | 65 | 100 | 100 | 65 | 90 | 50 | 60 |
| *Kochia* | 10 | 0 | 40 | 90 | 20 | 98 | 100 | 65 | 65 | 0 | 75 | 40 | 85 | 0 |
| Lambsquarters | 80 | 98 | 100 | 95 | 80 | 98 | 100 | 98 | 100 | 80 | 98 | 98 | 98 | 80 |
| Morningglory | 80 | 20 | 60 | 75 | 75 | 90 | 95 | 75 | 95 | 40 | 95 | 80 | 100 | 40 |
| Nutsedge, Yellow | 45 | 30 | 40 | 65 | 25 | 40 | 0 | 45 | 60 | 35 | 65 | 45 | 20 | 35 |
| Oat, Wild | 5 | 30 | 60 | 10 | 35 | 25 | 0 | 50 | 65 | 40 | 0 | 10 | 5 | 0 |
| Pigweed | 60 | 65 | 95 | 90 | 100 | 98 | 100 | 85 | 100 | 70 | 85 | 100 | 80 | 65 |
| Ragweed | 65 | 90 | 90 | 80 | 90 | 85 | 100 | 55 | 98 | — | 85 | 95 | 10 | — |
| Ryegrass, Italian | 0 | 10 | 30 | 0 | 40 | 5 | 0 | 0 | 10 | 20 | 0 | 0 | 0 | 0 |
| Soybean | 80 | 95 | 95 | 85 | 98 | 80 | 90 | 60 | 100 | 98 | 85 | 98 | 90 | 80 |
| Surinam Grass | 40 | 75 | 75 | 40 | 65 | 60 | — | — | 70 | 80 | — | 65 | 65 | 60 |
| Velvetleaf | 60 | 100 | 100 | 90 | 80 | 70 | 100 | 100 | 100 | 85 | 70 | 90 | 85 | 100 |
| Wheat | 15 | 0 | 40 | 10 | 10 | 0 | 0 | 10 | 40 | 30 | 0 | 0 | 0 | 0 |
| Windgrass | 40 | 60 | 45 | 20 | 40 | 5 | 15 | 30 | 40 | 60 | 10 | 10 | 25 | 15 |

| | Compounds | | | | | | | | | | | | | |
|---|---|---|---|---|---|---|---|---|---|---|---|---|---|---|
| 31 g ai/ha | 191 | 193 | 197 | 217 | 218 | 219 | 220 | 225 | 226 | 227 | 228 | 229 | 233 | 235 |
| | Postemergence | | | | | | | | | | | | | |
| Barley | 5 | 0 | 0 | 0 | 30 | 0 | 10 | 20 | 10 | 0 | 0 | 0 | 0 | 0 |
| Bermudagrass | 100 | 95 | 95 | 70 | 70 | 95 | 80 | 80 | 80 | 75 | 80 | 75 | 95 | 98 |
| Blackgrass | 30 | 10 | 0 | 0 | 0 | 50 | 10 | 0 | 5 | 0 | 5 | 0 | 5 | 45 |
| Bromegrass, Downy | 35 | 10 | 15 | 10 | 5 | 45 | 10 | 35 | 0 | 0 | 5 | 5 | 40 | 10 |
| Canarygrass | 20 | 5 | 5 | 0 | 0 | 35 | 10 | 60 | 5 | 0 | 0 | 5 | 0 | 20 |
| Chickweed | 98 | 95 | 100 | 75 | 100 | 100 | 95 | 25 | 75 | 65 | 98 | 70 | 90 | 98 |
| Cocklebur | 90 | 95 | 80 | 80 | — | — | — | 98 | 98 | 75 | 98 | 85 | 90 | — |
| Corn | 65 | 0 | 15 | 0 | 0 | 10 | 25 | 40 | 75 | 20 | 80 | 70 | 30 | 95 |
| Crabgrass, Large | 85 | 75 | 75 | 80 | 40 | 90 | 70 | 75 | 85 | 80 | 80 | 80 | 80 | 98 |
| Cupgrass, Woolly | 85 | 75 | 70 | 25 | 40 | 85 | 60 | 75 | 80 | 55 | 75 | 70 | 80 | 95 |
| Deadnettle | 90 | 100 | 100 | — | — | — | — | — | — | — | — | — | — | — |
| Foxtail, Giant | 100 | 75 | 85 | 70 | 40 | 70 | 30 | 75 | 85 | 75 | 85 | 75 | 90 | 98 |
| Foxtail, Green | 40 | 40 | 5 | 55 | 60 | 70 | 60 | 85 | 70 | 50 | 85 | 40 | 85 | 90 |
| *Galium* | 20 | 75 | 75 | — | — | — | — | — | — | — | — | — | — | — |
| Goosegrass | 95 | 85 | 85 | 80 | 0 | 90 | 80 | 85 | 80 | 75 | 80 | 70 | 85 | 95 |
| Johnsongrass | 70 | 50 | 70 | 0 | — | — | 60 | 60 | 85 | 45 | 75 | 70 | 0 | 70 |
| *Kochia* | 5 | 20 | 65 | 75 | 35 | 80 | 45 | 5 | 80 | 70 | 90 | 55 | 70 | 98 |
| Lambsquarters | 75 | 98 | 95 | 90 | 98 | 100 | 100 | 85 | 90 | 90 | 98 | 85 | 98 | 98 |

TABLE B-continued

| | | | | | | | | | | | | | | |
|---|---|---|---|---|---|---|---|---|---|---|---|---|---|---|
| Morningglory | 40 | 40 | 98 | 70 | 70 | 60 | 65 | 95 | 98 | 100 | 100 | 98 | 65 | 95 |
| Nutsedge, Yellow | 40 | 60 | 45 | 10 | 10 | 10 | 10 | 10 | 55 | 10 | 40 | 0 | 0 | 45 |
| Oat, Wild | 50 | 0 | 40 | 30 | 40 | 50 | 10 | 45 | 25 | 0 | 0 | 0 | 30 | 35 |
| Pigweed | 80 | 90 | 80 | 85 | 100 | 100 | 95 | 90 | 75 | 80 | 98 | 80 | 85 | 100 |
| Ragweed | — | — | — | 80 | 95 | 80 | 90 | 75 | 80 | 60 | 70 | 80 | 80 | 98 |
| Ryegrass, Italian | 40 | 5 | 0 | 0 | 30 | 20 | 5 | 0 | 0 | 0 | 0 | 0 | 30 | 30 |
| Soybean | 90 | 80 | 98 | 75 | 85 | 95 | 80 | 85 | 95 | 55 | 95 | 95 | 98 | 98 |
| Surinam Grass | 70 | 65 | 50 | 70 | 75 | 10 | 50 | 75 | 75 | 55 | 75 | 65 | 80 | 80 |
| Velvetleaf | 75 | 90 | 80 | 98 | 85 | 85 | 80 | 80 | 85 | 80 | 80 | 75 | 80 | 95 |
| Wheat | 35 | 30 | 0 | 30 | 0 | 40 | 0 | 30 | 10 | 0 | 0 | 0 | 10 | 45 |
| Windgrass | 55 | 50 | 10 | 50 | 10 | 35 | 5 | 50 | 10 | 0 | 5 | 0 | 50 | 85 |

| | Compounds | | | | | | | | |
|---|---|---|---|---|---|---|---|---|---|
| 31 g ai/ha | 236 | 237 | 238 | 239 | 240 | 243 | 244 | 245 | 255 |
| | Postemergence | | | | | | | | |
| Barley | 0 | 5 | 10 | 0 | 5 | 60 | 50 | 45 | 30 |
| Bermudagrass | 95 | 98 | 95 | 95 | 98 | 98 | 80 | 80 | 90 |
| Blackgrass | 0 | 50 | 40 | 5 | 40 | 60 | 50 | 40 | 5 |
| Bromegrass, Downy | 0 | 30 | 10 | 0 | 10 | 50 | 40 | 60 | 50 |
| Canarygrass | 0 | 30 | 20 | 0 | 5 | 90 | 80 | 80 | 50 |
| Chickweed | 75 | 90 | 80 | 90 | 90 | 80 | 80 | 80 | 95 |
| Cocklebur | — | — | — | 90 | — | — | — | — | — |
| Corn | 15 | 85 | 80 | 5 | 90 | 90 | 85 | 100 | 60 |
| Crabgrass, Large | 75 | 95 | 95 | 75 | 80 | 95 | 80 | 80 | 85 |
| Cupgrass, Woolly | 70 | 100 | 95 | 75 | 98 | 95 | 100 | 100 | 85 |
| Deadnettle | — | — | — | — | — | — | — | — | — |
| Foxtail, Giant | 75 | 98 | 100 | 75 | 100 | 95 | 95 | 98 | 95 |
| Foxtail, Green | 80 | 80 | 85 | 80 | 90 | 98 | 85 | 85 | 85 |
| *Galium* | — | — | — | — | — | — | — | — | — |
| Goosegrass | 80 | 95 | 95 | 80 | 95 | 95 | 85 | 98 | 90 |
| Johnsongrass | 0 | 100 | 60 | 0 | — | 100 | 85 | 100 | 80 |
| *Kochia* | 80 | 65 | 90 | 90 | 80 | 85 | 85 | 85 | 10 |
| Lambsquarters | 98 | 95 | 100 | 98 | 98 | 100 | 100 | 98 | 90 |
| Morningglory | 60 | 85 | — | 95 | — | 95 | 90 | 90 | 75 |
| Nutsedge, Yellow | 0 | 20 | 20 | 30 | 10 | 65 | 45 | 40 | 10 |
| Oat, Wild | 0 | 40 | 30 | 0 | 25 | 80 | 50 | 70 | 65 |
| Pigweed | 85 | 80 | 100 | 95 | — | 85 | 95 | 80 | 80 |
| Ragweed | 80 | 95 | 100 | 95 | 98 | 90 | 98 | 95 | 50 |
| Ryegrass, Italian | 0 | 50 | 20 | 0 | 10 | 60 | 35 | 40 | 10 |
| Soybean | 90 | 95 | 98 | 70 | 95 | 95 | 85 | 95 | 95 |
| Surinam Grass | 60 | 85 | 95 | 25 | 95 | 90 | 90 | 100 | 80 |
| Velvetleaf | 98 | 85 | 80 | 100 | 75 | 100 | 100 | 100 | 95 |
| Wheat | 0 | 50 | 40 | 0 | 30 | 85 | 60 | 75 | 35 |
| Windgrass | 30 | 60 | 45 | 20 | 60 | 80 | 50 | 65 | 50 |

| | Compounds | | | | | | |
|---|---|---|---|---|---|---|---|
| 16 g ai/ha | 2 | 69 | 122 | 131 | 159 | 169 | 225 |
| | Postemergence | | | | | | |
| Barley | 0 | 0 | 0 | 0 | 20 | 0 | 5 |
| Bermudagrass | 40 | 85 | 65 | 60 | 80 | 70 | 40 |
| Blackgrass | 0 | 0 | 0 | 0 | 5 | 0 | 0 |
| Bromegrass, Downy | 20 | 30 | 5 | 0 | 15 | 0 | 30 |
| Canarygrass | 20 | 0 | 0 | 0 | 40 | 5 | 55 |
| Chickweed | 70 | 95 | 65 | 45 | 100 | 90 | 15 |
| Cocklebur | 75 | 0 | 0 | 80 | 80 | 100 | 85 |
| Corn | 15 | 0 | 0 | 0 | 25 | 20 | 10 |
| Crabgrass, Large | 70 | 95 | 65 | 65 | 75 | 75 | 70 |
| Cupgrass, Woolly | 75 | 75 | 65 | 10 | 65 | 75 | 70 |
| Foxtail, Giant | 70 | 80 | 65 | 65 | 80 | 75 | 75 |
| Foxtail, Green | 50 | 75 | 40 | 40 | 80 | 45 | 85 |
| Goosegrass | 80 | 75 | 10 | 65 | 80 | 80 | 80 |
| Johnsongrass | 75 | 75 | 20 | 0 | 45 | 40 | 20 |
| *Kochia* | 55 | 60 | 0 | 20 | 20 | 100 | 5 |
| Lambsquarters | 80 | 100 | 55 | 75 | 95 | 95 | 85 |
| Morningglory | 55 | 65 | 55 | 5 | 10 | 95 | 80 |
| Nutsedge, Yellow | 40 | 5 | 35 | 0 | 20 | 0 | 5 |
| Oat, Wild | 5 | 50 | 5 | 0 | 35 | 0 | 25 |
| Pigweed | 70 | 95 | 75 | 60 | 75 | 90 | 80 |
| Ragweed | 65 | 75 | 55 | 65 | 80 | 98 | 70 |
| Ryegrass, Italian | 0 | 0 | 5 | 0 | 0 | 0 | 0 |
| Soybean | 75 | 45 | 20 | 75 | 85 | 55 | 65 |
| Surinam Grass | 70 | 75 | 25 | 15 | 65 | — | 35 |
| Velvetleaf | — | 75 | 75 | 70 | 100 | 75 | 80 |

TABLE B-continued

| | | | | | | | | |
|---|---|---|---|---|---|---|---|---|
| Wheat | 0 | 0 | 5 | 0 | 35 | 0 | 20 | |
| Windgrass | 10 | 40 | 5 | 0 | 40 | 5 | 5 | |

| | Compound |
|---|---|
| 8 g ai/ha | 159 |

Postemergence

| | |
|---|---|
| Barley | 0 |
| Bermudagrass | 70 |
| Blackgrass | 0 |
| Bromegrass, Downy | 15 |
| Canarygrass | 25 |
| Chickweed | 80 |
| Cocklebur | 75 |
| Corn | 15 |
| Crabgrass, Large | 65 |
| Cupgrass, Woolly | 60 |
| Foxtail, Giant | 75 |
| Foxtail, Green | 50 |
| Goosegrass | 70 |
| Johnsongrass | 10 |
| *Kochia* | 20 |
| Lambsquarters | 90 |
| Morningglory | 0 |
| Nutsedge, Yellow | 10 |
| Oat, Wild | 0 |
| Pigweed | 55 |
| Ragweed | 65 |
| Ryegrass, Italian | 0 |
| Soybean | 80 |
| Surinam Grass | 65 |
| Velvetleaf | 98 |
| Wheat | 10 |
| Windgrass | 10 |

| | Compounds | | | | | | | | | | | | |
|---|---|---|---|---|---|---|---|---|---|---|---|---|---|
| 250 g ai/ha | 3 | 7 | 9 | 10 | 11 | 12 | 14 | 24 | 26 | 27 | 29 | 33 | 34 | 36 |

Preemergence

| | | | | | | | | | | | | | | |
|---|---|---|---|---|---|---|---|---|---|---|---|---|---|---|
| Bermudagrass | 90 | 98 | 100 | 100 | 100 | 100 | 100 | 100 | 100 | 100 | 100 | 100 | 100 | 100 |
| Blackgrass | 0 | 0 | 40 | 20 | 60 | 10 | 0 | 10 | 10 | 30 | 50 | 30 | 50 | 25 |
| Bromegrass, Downy | 0 | 0 | 10 | 0 | 5 | 0 | 0 | 20 | 10 | 30 | 5 | 30 | 80 | 10 |
| Cocklebur | 100 | 75 | 100 | 98 | 100 | 100 | 95 | 95 | 98 | 90 | 90 | 90 | 85 | 80 |
| Corn | 5 | 0 | 10 | 0 | 35 | 75 | 10 | 5 | 0 | 0 | 0 | 0 | 0 | 0 |
| Crabgrass, Large | 100 | 95 | 100 | 95 | 100 | 100 | 100 | 100 | 100 | 100 | 100 | 100 | 100 | 100 |
| Cupgrass, Woolly | 10 | 45 | 60 | 40 | 75 | 85 | 70 | 90 | 85 | 80 | 90 | 85 | 100 | 65 |
| Foxtail, Giant | 0 | 25 | 98 | 45 | 100 | 100 | 90 | 100 | 90 | 95 | 100 | 98 | 100 | 80 |
| Foxtail, Green | 0 | 0 | — | 30 | 65 | 80 | 60 | 100 | 70 | 80 | 100 | 100 | 100 | 85 |
| *Galium* | 50 | 0 | 95 | 85 | 75 | 95 | 80 | 80 | 98 | 95 | 100 | 90 | 98 | 95 |
| Goosegrass | 98 | 60 | 100 | 98 | 100 | 100 | 100 | 100 | 100 | 100 | 100 | 98 | 100 | 100 |
| Johnsongrass | 10 | 0 | 98 | 75 | 98 | 98 | 95 | 90 | 90 | 85 | 90 | 20 | 100 | 85 |
| *Kochia* | 100 | 100 | 100 | 100 | 100 | 100 | 100 | 100 | 100 | 100 | — | 100 | — | — |
| Lambsquarters | 100 | 100 | 100 | 100 | 100 | 100 | 100 | 100 | 100 | 100 | 100 | 100 | 100 | 100 |
| Morningglory | 100 | 20 | 98 | 40 | 100 | 100 | 100 | 100 | 100 | 100 | 100 | 90 | 98 | 20 |
| Nightshade | 100 | 100 | 100 | 100 | 100 | 100 | 100 | 100 | 100 | 100 | 100 | 100 | 100 | 98 |
| Nutsedge, Yellow | 50 | 55 | 95 | 75 | 90 | 90 | 85 | 90 | 85 | 90 | 85 | 90 | 90 | 75 |
| Oat, Wild | 0 | 0 | 60 | 10 | 40 | 5 | 0 | 80 | 5 | 50 | 50 | 50 | 60 | 0 |
| Pigweed | 95 | 100 | 100 | 100 | 100 | 100 | 100 | 100 | 100 | 100 | 100 | 100 | 100 | 100 |
| Ragweed | 90 | 90 | 100 | 100 | 100 | 100 | 90 | 100 | 100 | 100 | 100 | 100 | 90 | 90 |
| Russian Thistle | — | — | — | — | — | — | — | — | — | — | — | — | — | — |
| Ryegrass, Italian | 0 | 0 | 40 | 0 | 0 | 0 | 0 | 10 | 0 | 0 | 40 | 5 | 10 | 0 |
| Soybean | 50 | 30 | 80 | 75 | 95 | 95 | 85 | 85 | 90 | 90 | 95 | 75 | 80 | 40 |
| Sunflower | 85 | 25 | 98 | 98 | 98 | 100 | 98 | 98 | 95 | 100 | 100 | 90 | 90 | 85 |
| Surinam Grass | 5 | 10 | 95 | 80 | 75 | 100 | 80 | 100 | 90 | 95 | 95 | 100 | 90 | 100 |
| Velvetleaf | 100 | 100 | 100 | 100 | 100 | 100 | 100 | 100 | 100 | 95 | 100 | 100 | 100 | 100 |
| Wheat | 0 | 0 | 5 | 5 | 5 | 0 | 0 | 0 | 0 | 5 | 0 | 5 | 0 | 0 |

| | Compounds | | | | | | | | | | | | |
|---|---|---|---|---|---|---|---|---|---|---|---|---|---|
| 250 g ai/ha | 37 | 38 | 39 | 40 | 42 | 44 | 45 | 46 | 47 | 48 | 49 | 50 | 51 | 52 |

Preemergence

| | | | | | | | | | | | | | | |
|---|---|---|---|---|---|---|---|---|---|---|---|---|---|---|
| Bermudagrass | 100 | 100 | 100 | 100 | 100 | 100 | 100 | 98 | 100 | 100 | 100 | 100 | 100 | 100 |
| Blackgrass | 10 | 40 | 0 | 5 | 5 | 60 | 5 | 0 | 5 | 5 | 0 | 5 | 20 | 10 |
| Bromegrass, Downy | 0 | 40 | 0 | 10 | 0 | 5 | 5 | 0 | 10 | 45 | — | 0 | 40 | 5 |
| Cocklebur | 45 | 90 | 45 | 100 | — | 45 | — | 15 | — | 85 | 55 | — | 75 | 75 |

TABLE B-continued

| | | | | | | | | | | | | | | |
|---|---|---|---|---|---|---|---|---|---|---|---|---|---|---|
| Corn | 0 | 0 | 0 | 0 | 0 | 0 | 0 | 0 | 0 | 0 | 0 | 0 | 0 | 0 |
| Crabgrass, Large | 100 | 100 | 100 | 100 | 100 | 100 | 100 | 98 | 100 | 100 | 100 | 100 | 100 | 100 |
| Cupgrass, Woolly | 70 | 80 | 10 | 85 | 5 | 85 | 75 | 60 | 90 | 95 | 20 | 70 | 85 | 80 |
| Foxtail, Giant | 75 | 95 | 75 | 98 | 10 | 98 | 75 | 25 | 100 | 98 | 45 | 90 | 75 | 75 |
| Foxtail, Green | 90 | 100 | 100 | 100 | 85 | 100 | 100 | 10 | 98 | 98 | 30 | 100 | 100 | 100 |
| *Galium* | 100 | 85 | 85 | 90 | 50 | 98 | 85 | 70 | 95 | 70 | 95 | 98 | 95 | 95 |
| Goosegrass | 100 | 100 | 100 | 100 | 100 | 100 | 100 | 98 | 100 | 100 | 100 | 100 | 100 | 100 |
| Johnsongrass | 90 | 95 | 75 | 90 | 65 | 95 | 85 | 70 | 100 | 98 | 10 | 95 | 80 | 95 |
| *Kochia* | — | — | — | — | — | — | — | — | — | — | — | — | — | — |
| Lambsquarters | 100 | 100 | 100 | 100 | 100 | 100 | 100 | 100 | 100 | 100 | 98 | 100 | 98 | 100 |
| Morningglory | 0 | 100 | 100 | 65 | 0 | 95 | 0 | 0 | 55 | 100 | 85 | 55 | 70 | 55 |
| Nightshade | 85 | 100 | 100 | 100 | 100 | 100 | 100 | 98 | 100 | 100 | 98 | 100 | 100 | 100 |
| Nutsedge, Yellow | 90 | 80 | 10 | 85 | 85 | 90 | 70 | 90 | 90 | 90 | 90 | 90 | 90 | 90 |
| Oat, Wild | 10 | 20 | 0 | 30 | 0 | 30 | 5 | 0 | 10 | 15 | 0 | 0 | 0 | 60 |
| Pigweed | 100 | 100 | 100 | 100 | 100 | 100 | 100 | 100 | 100 | 100 | 100 | 100 | 100 | 100 |
| Ragweed | 98 | 95 | 95 | 95 | 80 | 95 | 95 | 100 | 95 | 95 | 95 | 100 | 90 | 95 |
| Russian Thistle | — | — | — | — | — | — | — | — | — | — | — | — | — | — |
| Ryegrass, Italian | 0 | 40 | 0 | 5 | 0 | 0 | 0 | 0 | 0 | 0 | 5 | 0 | 5 | 0 |
| Soybean | 35 | 75 | 0 | 70 | 0 | 0 | 0 | 25 | 0 | 20 | 85 | 0 | 85 | 80 |
| Sunflower | 90 | 75 | 65 | 80 | 75 | 80 | 75 | 60 | 85 | 80 | 75 | 85 | 75 | 75 |
| Surinam Grass | 100 | 80 | 15 | 90 | 75 | 100 | 98 | 90 | 100 | 100 | 85 | 100 | 100 | 98 |
| Velvetleaf | 98 | 100 | 98 | 100 | 90 | 100 | 95 | 65 | 100 | 100 | 100 | 100 | 100 | 100 |
| Wheat | 0 | 5 | 0 | — | 0 | 0 | 0 | 0 | 0 | 0 | 0 | 0 | 10 | 0 |

| | Compounds | | | | | | | | | | | | | |
|---|---|---|---|---|---|---|---|---|---|---|---|---|---|---|
| 250 g ai/ha | 53 | 55 | 56 | 58 | 59 | 61 | 62 | 63 | 64 | 66 | 67 | 68 | 72 | 73 |
| | Preemergence | | | | | | | | | | | | | |
| Bermudagrass | 100 | 100 | 100 | 100 | 98 | 98 | 100 | 98 | 98 | 98 | 100 | 100 | 100 | 100 |
| Blackgrass | 60 | 30 | 5 | 30 | 40 | 0 | 0 | 40 | 0 | 5 | 5 | 5 | 5 | 10 |
| Bromegrass, Downy | 30 | 0 | 5 | 0 | 0 | 0 | 0 | 0 | 0 | 0 | 0 | 5 | 0 | 20 |
| Cocklebur | 70 | 15 | 0 | 65 | 75 | 65 | 10 | 10 | 70 | 0 | 20 | 80 | 80 | 65 |
| Corn | 20 | 0 | 0 | 0 | 0 | 0 | — | 0 | 0 | 0 | 0 | 0 | 0 | 10 |
| Crabgrass, Large | 100 | 98 | 98 | 100 | 98 | 98 | 98 | 100 | 98 | 100 | 100 | 100 | 100 | 100 |
| Cupgrass, Woolly | 95 | 55 | 70 | 85 | 85 | 0 | 10 | 10 | 10 | 75 | 10 | 85 | 65 | 80 |
| Foxtail, Giant | 100 | 10 | 80 | 75 | 75 | 45 | 20 | 10 | 65 | 80 | 65 | 75 | 65 | 80 |
| Foxtail, Green | 98 | 0 | 100 | 100 | 98 | 75 | 10 | 30 | 50 | 75 | 40 | 85 | 90 | 80 |
| *Galium* | 90 | 85 | 85 | 80 | 98 | 98 | 0 | 20 | 70 | 0 | 90 | 85 | 85 | 85 |
| Goosegrass | 100 | 98 | 100 | 100 | 100 | 98 | 98 | 100 | 100 | 98 | 98 | 98 | 100 | 100 |
| Johnsongrass | 75 | 0 | 80 | 85 | 90 | 20 | — | 60 | 75 | 98 | 0 | 95 | 10 | 98 |
| *Kochia* | — | — | — | — | 98 | — | 100 | 100 | 95 | 85 | 85 | 95 | 85 | 90 |
| Lambsquarters | 100 | 100 | 98 | 98 | 100 | — | 100 | 100 | 98 | 100 | 98 | 100 | 100 | 100 |
| Morningglory | 65 | 65 | 65 | 75 | 60 | 65 | 20 | 55 | 0 | 80 | 80 | 85 | 75 | 70 |
| Nightshade | 100 | 100 | 100 | 100 | 100 | — | 98 | 98 | 98 | 98 | 98 | 100 | 100 | 100 |
| Nutsedge, Yellow | 90 | 65 | 90 | 90 | 90 | 90 | — | 90 | 10 | 95 | 75 | 90 | 90 | 85 |
| Oat, Wild | 70 | 0 | 0 | 30 | 0 | 0 | 0 | 0 | 5 | 40 | 0 | 5 | 0 | 65 |
| Pigweed | 100 | 100 | 100 | 100 | 100 | — | 100 | 100 | 98 | 98 | 98 | 100 | 100 | 100 |
| Ragweed | 90 | 90 | 80 | 90 | 95 | 90 | 60 | 85 | 85 | 55 | 50 | 90 | 85 | 85 |
| Russian Thistle | — | — | — | — | — | — | — | — | — | — | 90 | 98 | 80 | — |
| Ryegrass, Italian | 50 | 0 | 0 | 0 | 20 | 5 | 20 | 0 | 0 | 5 | 0 | 0 | 0 | 5 |
| Soybean | 85 | 65 | 90 | 95 | 80 | 20 | — | 15 | — | — | — | — | — | — |
| Sunflower | 65 | 70 | 75 | 75 | 80 | 70 | 55 | 70 | 55 | 10 | 55 | 85 | 80 | 75 |
| Surinam Grass | 100 | 45 | 98 | 95 | 95 | 35 | 60 | 85 | 90 | 100 | 75 | 85 | 98 | 100 |
| Velvetleaf | 100 | 100 | 98 | 95 | 100 | 100 | 95 | 100 | 100 | 100 | 100 | 100 | 100 | 100 |
| Wheat | 10 | 0 | 10 | 0 | 0 | 0 | 0 | 0 | 0 | 0 | 0 | 0 | 0 | 30 |

| | Compounds | | | | | | | | | | | | | |
|---|---|---|---|---|---|---|---|---|---|---|---|---|---|---|
| 250 g ai/ha | 74 | 75 | 77 | 81 | 113 | 119 | 120 | 193 | 217 | 218 | 219 | 220 | 243 | 244 |
| | Preemergence | | | | | | | | | | | | | |
| Bermudagrass | 100 | 100 | 100 | 100 | 100 | 100 | 100 | 98 | 100 | 100 | 100 | 100 | 100 | 100 |
| Blackgrass | 10 | 10 | 0 | 35 | 20 | 70 | 50 | 70 | 0 | 20 | 60 | 35 | 95 | 70 |
| Bromegrass, Downy | 0 | 0 | 0 | 0 | 10 | 55 | 85 | 50 | 0 | 0 | 20 | 5 | 70 | 30 |
| Cocklebur | 80 | 90 | 65 | 85 | 100 | 85 | 98 | 95 | 85 | 100 | 85 | 0 | 98 | 100 |
| Corn | 0 | 0 | 0 | 55 | 0 | 50 | 55 | 5 | 0 | 0 | 0 | 0 | 95 | 85 |
| Crabgrass, Large | 100 | 100 | 100 | 100 | 100 | 100 | 100 | 100 | 100 | 98 | 100 | 100 | 100 | 100 |
| Cupgrass, Woolly | 5 | 75 | 0 | 85 | 95 | 100 | 90 | 90 | 80 | 85 | 80 | 25 | 100 | 100 |
| Foxtail, Giant | 45 | 80 | 45 | 98 | 85 | 100 | 100 | 80 | 85 | 85 | 80 | 75 | 95 | 100 |
| Foxtail, Green | 0 | 98 | 15 | 100 | 100 | 100 | 100 | 98 | 90 | 100 | 100 | 100 | 100 | 90 |
| *Galium* | 98 | 98 | 90 | 100 | 95 | 100 | 98 | 100 | 90 | 100 | 100 | 100 | 100 | 98 |
| Goosegrass | 100 | 100 | 98 | 100 | 100 | 100 | 100 | 100 | 98 | 100 | 100 | 100 | 100 | 100 |
| Johnsongrass | 0 | 70 | 0 | 90 | 70 | 95 | 90 | 60 | 55 | 45 | 80 | 80 | 100 | 100 |
| *Kochia* | 85 | 95 | 95 | 70 | 90 | 98 | 75 | 90 | — | — | — | — | 100 | 100 |
| Lambsquarters | 100 | 100 | 100 | 98 | 100 | 100 | 100 | 100 | 100 | 100 | 100 | 100 | 100 | 100 |
| Morningglory | 80 | 90 | 90 | 95 | — | 95 | 100 | 95 | 0 | 65 | 100 | 90 | 100 | 100 |
| Nightshade | 100 | 100 | 100 | 100 | 100 | 100 | 98 | 100 | 100 | 100 | 100 | 100 | 98 | 100 |

TABLE B-continued

| | | | | | | | | | | | | | | |
|---|---|---|---|---|---|---|---|---|---|---|---|---|---|---|
| Nutsedge, Yellow | 90 | 90 | 90 | 95 | 90 | 98 | 98 | 90 | 90 | 90 | 90 | 90 | 95 | 95 |
| Oat, Wild | 5 | 0 | 0 | 0 | 40 | 80 | 65 | 60 | 0 | 0 | 40 | 60 | 90 | 40 |
| Pigweed | 100 | 100 | 100 | 100 | 100 | 100 | 100 | 100 | 100 | 100 | 100 | 100 | 100 | 100 |
| Ragweed | 100 | 95 | 95 | 90 | 98 | 95 | 95 | 100 | 95 | 100 | 98 | 95 | 98 | 100 |
| Russian Thistle | 98 | — | — | 100 | — | 100 | — | 100 | — | — | — | — | 100 | — |
| Ryegrass, Italian | 0 | 0 | 0 | 0 | 40 | 100 | 100 | 45 | 10 | 5 | 10 | 0 | 70 | 45 |
| Soybean | — | — | — | — | 90 | 80 | 80 | 80 | 0 | 90 | 75 | 75 | 95 | 95 |
| Sunflower | 85 | 85 | 85 | 90 | 95 | 85 | 95 | 95 | 85 | 95 | 85 | 90 | 95 | 100 |
| Surinam Grass | 95 | 75 | 100 | 100 | 98 | 100 | 100 | 45 | 90 | 100 | 100 | 65 | 100 | 100 |
| Velvetleaf | 100 | 100 | 100 | 100 | 100 | 100 | 100 | 100 | 100 | 100 | 95 | 100 | 100 | 100 |
| Wheat | 0 | 0 | 0 | 0 | 10 | 50 | 30 | 25 | 0 | 0 | 0 | 5 | 70 | 45 |

| 250 g ai/ha | Compounds | |
|---|---|---|
| | 245 | 255 |
| Preemergence | | |
| Bermudagrass | 100 | 100 |
| Blackgrass | 45 | 60 |
| Bromegrass, Downy | 15 | 40 |
| Cocklebur | 100 | — |
| Corn | 65 | 0 |
| Crabgrass, Large | 100 | 100 |
| Cupgrass, Woolly | 100 | 90 |
| Foxtail, Giant | 100 | 98 |
| Foxtail, Green | 100 | 100 |
| Galium | 95 | 100 |
| Goosegrass | 100 | 100 |
| Johnsongrass | 100 | 98 |
| Kochia | 100 | — |
| Lambsquarters | 100 | 100 |
| Morningglory | 100 | 90 |
| Nightshade | 100 | 100 |
| Nutsedge, Yellow | 80 | 90 |
| Oat, Wild | 30 | 90 |
| Pigweed | 100 | 100 |
| Ragweed | 100 | 100 |
| Russian Thistle | — | — |
| Ryegrass, Italian | 40 | 30 |
| Soybean | 75 | 80 |
| Sunflower | 95 | 90 |
| Surinam Grass | 100 | 100 |
| Velvetleaf | 100 | 100 |
| Wheat | 15 | 5 |

| 125 g ai/ha | Compounds | | | | | | | | | | | | |
|---|---|---|---|---|---|---|---|---|---|---|---|---|---|
| | 2 | 3 | 7 | 9 | 10 | 11 | 12 | 14 | 24 | 26 | 27 | 29 | 33 | 34 |
| Preemergence | | | | | | | | | | | | | | |
| Bermudagrass | 100 | 80 | 85 | 100 | 100 | 100 | 100 | 100 | 100 | 98 | 100 | 100 | 100 | 100 |
| Blackgrass | 50 | 0 | 0 | 20 | 0 | 30 | 5 | 0 | 0 | 0 | 10 | 50 | 10 | 50 |
| Bromegrass, Downy | 5 | 0 | 0 | 5 | 0 | 0 | 0 | 0 | 0 | 0 | 0 | 0 | 5 | 10 |
| Cocklebur | 80 | 70 | 0 | 65 | 65 | 95 | 98 | 85 | 95 | 85 | 85 | 90 | 85 | 75 |
| Corn | 0 | 0 | 0 | 0 | 0 | 0 | 15 | 0 | 0 | 0 | 0 | 0 | 0 | 0 |
| Crabgrass, Large | 100 | 85 | 45 | 100 | 70 | 100 | 100 | 100 | 100 | 100 | 100 | 100 | 100 | 100 |
| Cupgrass, Woolly | 20 | 0 | 0 | 45 | 35 | 15 | 75 | 50 | 85 | 50 | 60 | 55 | 60 | 100 |
| Foxtail, Giant | 70 | 0 | 0 | 60 | 0 | 75 | 70 | 75 | 90 | 45 | 85 | 100 | 95 | 90 |
| Foxtail, Green | 60 | 0 | 0 | 5 | 0 | 65 | 40 | 10 | 100 | 30 | 50 | 100 | 100 | 90 |
| Galium | — | 30 | 0 | 60 | 85 | 50 | 90 | 40 | 10 | 90 | 85 | 98 | 50 | 90 |
| Goosegrass | 100 | 85 | 45 | 100 | 95 | 100 | 100 | 98 | 100 | 95 | 100 | 100 | 90 | 100 |
| Johnsongrass | 80 | 0 | 0 | 90 | 60 | 85 | 75 | 80 | 90 | 60 | 50 | 30 | 0 | 98 |
| Kochia | 100 | 100 | 100 | 100 | 100 | 100 | 100 | 100 | 100 | 100 | 100 | 100 | — | — |
| Lambsquarters | 100 | 100 | 100 | 100 | 100 | 100 | 100 | 100 | 100 | 100 | 100 | 100 | 100 | 100 |
| Morningglory | 75 | 100 | 0 | 70 | 0 | 35 | 85 | 100 | 100 | 100 | 100 | 100 | 70 | 75 |
| Nightshade | 100 | 98 | 95 | 100 | 100 | 100 | 100 | 100 | 100 | 100 | 100 | 100 | 100 | 100 |
| Nutsedge, Yellow | 70 | 40 | 15 | 80 | 55 | 85 | 75 | 40 | 85 | 50 | 30 | 60 | 70 | 75 |
| Oat, Wild | 50 | 0 | 0 | 0 | 0 | 10 | 0 | 0 | 0 | 0 | 30 | 45 | 30 | 30 |
| Pigweed | 100 | 90 | 100 | 100 | 100 | 100 | 100 | 100 | 100 | 100 | 100 | 100 | 100 | 100 |
| Ragweed | 98 | 90 | 15 | 100 | 100 | 100 | 100 | 90 | 98 | 95 | 100 | 100 | 100 | 90 |
| Russian Thistle | — | — | — | — | — | — | — | — | — | — | — | — | — | — |
| Ryegrass, Italian | 5 | 0 | 0 | 0 | 0 | 0 | 0 | 0 | 10 | 0 | 0 | 10 | 5 | 5 |
| Soybean | 70 | 35 | 20 | — | 65 | 65 | 80 | 50 | 80 | 80 | 80 | 90 | 65 | 65 |
| Sunflower | 90 | 70 | 0 | 95 | 95 | 95 | 98 | 85 | 95 | 90 | 90 | 90 | 75 | 80 |
| Surinam Grass | 60 | 0 | 0 | 95 | 15 | 35 | 95 | 60 | 95 | 90 | 60 | 90 | 95 | 65 |
| Velvetleaf | 100 | 90 | 100 | 100 | 100 | 100 | 100 | 100 | 100 | 90 | 100 | 100 | 100 | 95 |
| Wheat | 0 | 0 | 0 | 0 | 0 | 0 | 0 | 0 | 0 | 0 | 0 | 0 | 0 | 0 |

TABLE B-continued

| 125 g ai/ha | Compounds | | | | | | | | | | | | | |
|---|---|---|---|---|---|---|---|---|---|---|---|---|---|---|
| | 36 | 37 | 38 | 39 | 40 | 42 | 44 | 45 | 46 | 47 | 48 | 49 | 50 | 51 |
| Preemergence | | | | | | | | | | | | | | |
| Bermudagrass | 100 | 98 | 100 | 100 | 100 | 100 | 100 | 100 | — | 100 | 100 | 98 | 100 | 100 |
| Blackgrass | 25 | 5 | 30 | 0 | 0 | 0 | 40 | 0 | 0 | 5 | 0 | 0 | 0 | 10 |
| Bromegrass, Downy | 0 | 0 | 5 | 0 | 5 | 0 | 0 | 0 | 0 | 5 | 0 | 0 | 0 | 5 |
| Cocklebur | — | 0 | 25 | — | 85 | — | — | — | 0 | — | 0 | 45 | 75 | 20 |
| Corn | 0 | 0 | 0 | 0 | 0 | 0 | 0 | 0 | 0 | 0 | 0 | 0 | 0 | 0 |
| Crabgrass, Large | 100 | 10 | 100 | 100 | 100 | 95 | 100 | 100 | 85 | 100 | 100 | 98 | 100 | 100 |
| Cupgrass, Woolly | 10 | 10 | 60 | 0 | 70 | 0 | 80 | 60 | 50 | 75 | 75 | 0 | 15 | 75 |
| Foxtail, Giant | 65 | 0 | 80 | 70 | 80 | 10 | 75 | 45 | 15 | 85 | 85 | 20 | 90 | 50 |
| Foxtail, Green | 85 | 0 | 85 | 75 | 85 | 85 | 98 | 80 | 5 | 98 | 98 | 5 | 95 | 98 |
| *Galium* | 80 | 30 | 85 | 85 | 85 | 10 | 65 | 50 | 0 | 50 | 60 | 90 | 95 | 80 |
| Goosegrass | 95 | 80 | 100 | 100 | 100 | 100 | 100 | 100 | 98 | 100 | 100 | 98 | 100 | 100 |
| Johnsongrass | 80 | 45 | 85 | 65 | 85 | 10 | 90 | 75 | 45 | 80 | 90 | 0 | 90 | 75 |
| *Kochia* | — | — | — | — | — | — | — | — | — | — | — | — | — | — |
| Lambsquarters | 100 | 100 | 100 | 100 | 100 | 100 | 100 | 100 | 95 | 100 | 100 | 98 | 100 | 98 |
| Morningglory | 0 | 0 | 0 | 15 | 0 | 0 | 50 | — | 0 | 0 | 100 | 80 | — | 20 |
| Nightshade | 95 | 80 | 98 | 100 | 98 | 100 | 100 | 100 | 98 | 100 | 100 | 98 | 100 | 98 |
| Nutsedge, Yellow | 40 | 20 | 70 | 0 | 65 | 75 | 75 | 20 | 80 | 80 | 85 | 85 | 90 | 85 |
| Oat, Wild | 0 | 0 | 0 | 0 | 0 | 0 | 5 | 0 | 0 | 0 | 0 | 0 | 0 | 0 |
| Pigweed | 100 | 100 | 100 | 100 | 100 | 100 | 100 | 100 | 95 | 100 | 100 | 100 | 100 | 100 |
| Ragweed | 85 | 65 | 80 | 75 | 90 | 25 | 95 | 80 | 100 | 90 | 90 | 80 | 95 | 80 |
| Russian Thistle | — | — | — | — | — | — | — | — | — | — | — | — | — | — |
| Ryegrass, Italian | 0 | 0 | 5 | 0 | 5 | 0 | 0 | 0 | 0 | 0 | 0 | 0 | 0 | 0 |
| Soybean | 0 | 0 | 0 | 0 | 20 | 0 | 0 | 0 | 15 | 0 | 0 | 85 | — | 80 |
| Sunflower | 55 | 45 | 25 | 25 | 75 | 55 | 75 | 10 | 0 | 80 | 80 | 75 | 85 | 75 |
| Surinam Grass | 100 | 55 | 65 | 10 | 85 | 10 | 90 | 98 | 75 | 100 | 100 | 75 | 98 | 98 |
| Velvetleaf | 100 | 20 | 98 | 75 | 100 | 85 | 100 | 85 | 55 | 90 | 100 | 100 | 100 | 98 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 52 | 53 | 55 | 56 | 58 | 59 | 61 | 62 | 63 | 64 | 66 | 67 | 68 | 69 |
| Preemergence | | | | | | | | | | | | | | |
| Bermudagrass | 98 | 100 | 100 | 100 | 100 | 98 | 75 | 95 | 98 | 98 | 98 | 95 | 98 | 100 |
| Blackgrass | 0 | 5 | 0 | 0 | 5 | 30 | 0 | 0 | 5 | 0 | 5 | 0 | 0 | 0 |
| Bromegrass, Downy | 5 | 5 | 0 | 0 | 0 | 0 | 0 | 0 | 0 | 0 | 0 | 0 | 0 | 0 |
| Cocklebur | 10 | 65 | 10 | 0 | 10 | 10 | 20 | 0 | 0 | 10 | 0 | 15 | — | 10 |
| Corn | 0 | 0 | 0 | 0 | 0 | 0 | 0 | 0 | 0 | 0 | 0 | 0 | 0 | 0 |
| Crabgrass, Large | 100 | 100 | 95 | 98 | 98 | 98 | 98 | 80 | 100 | 98 | 95 | 98 | 98 | 100 |
| Cupgrass, Woolly | 65 | 85 | 0 | 50 | 20 | 65 | 0 | 5 | 0 | 0 | 60 | 0 | 55 | 45 |
| Foxtail, Giant | 25 | 100 | 0 | 75 | 75 | 60 | 15 | 20 | 0 | 35 | 75 | 45 | 55 | 90 |
| Foxtail, Green | 45 | 98 | 0 | 20 | 70 | 90 | 40 | 10 | — | 0 | 30 | — | 25 | 85 |
| *Galium* | 70 | 0 | 20 | 60 | 30 | 95 | 98 | 0 | 0 | 30 | 0 | 85 | 70 | 0 |
| Goosegrass | 100 | 100 | 98 | 95 | 100 | 100 | 98 | 98 | 100 | 98 | 90 | 90 | 98 | 100 |
| Johnsongrass | 90 | 60 | 0 | 55 | 80 | 80 | 10 | 0 | 55 | 55 | 85 | 0 | 75 | 85 |
| *Kochia* | — | — | — | — | — | 60 | 85 | 100 | 100 | 45 | 85 | 80 | 95 | 45 |
| Lambsquarters | 100 | 100 | 98 | 98 | 98 | 100 | 98 | 100 | 100 | 98 | 98 | 98 | 98 | 100 |
| Morningglory | 45 | 25 | 45 | 45 | 55 | 55 | 45 | 0 | 0 | 0 | 25 | 15 | 65 | 0 |
| Nightshade | 98 | 100 | 100 | 98 | 98 | 100 | 98 | 98 | 98 | 95 | 98 | 95 | 100 | 98 |
| Nutsedge, Yellow | 80 | 90 | 45 | 85 | 75 | 85 | 90 | 45 | 25 | 0 | 85 | 65 | 85 | 0 |
| Oat, Wild | 5 | 0 | 0 | 0 | 0 | 0 | 0 | 0 | 0 | 0 | 0 | 0 | 0 | 0 |
| Pigweed | 100 | 100 | 98 | 100 | 100 | 100 | 100 | 100 | 100 | 85 | 98 | 98 | 100 | 100 |
| Ragweed | 85 | 85 | 85 | 70 | 85 | 90 | 75 | 45 | 70 | 75 | 45 | 35 | 80 | 65 |
| Russian Thistle | — | — | — | — | — | — | — | — | — | — | — | — | 80 | 100 |
| Ryegrass, Italian | 0 | 0 | 0 | 0 | 0 | 20 | 5 | 0 | 0 | 0 | 0 | 0 | 0 | 0 |
| Soybean | 55 | 80 | 15 | 80 | 85 | 0 | 0 | 80 | 5 | — | — | — | — | — |
| Sunflower | 70 | 65 | 60 | 65 | 65 | 70 | 60 | 10 | 20 | 0 | 0 | 35 | 75 | 5 |
| Surinam Grass | 95 | 100 | 0 | 98 | 85 | 85 | 0 | 25 | 55 | 85 | 90 | 15 | 55 | 100 |
| Velvetleaf | 98 | 98 | 100 | 98 | 95 | 100 | 98 | 95 | 100 | 95 | 95 | 90 | 100 | 85 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| | 72 | 73 | 74 | 75 | 77 | 81 | 113 | 119 | 120 | 193 | 217 | 218 | 219 | 220 |
| Preemergence | | | | | | | | | | | | | | |
| Bermudagrass | 98 | 98 | 100 | 100 | 100 | 100 | 100 | 100 | 100 | 95 | 100 | 100 | 100 | 98 |
| Blackgrass | 0 | 0 | 0 | 5 | 0 | 35 | 0 | 50 | 50 | 30 | 0 | 0 | 40 | 20 |
| Bromegrass, Downy | 0 | 5 | 0 | 0 | 0 | 0 | 10 | 55 | 30 | 5 | 0 | 0 | 10 | 0 |
| Cocklebur | 70 | 60 | 70 | 75 | 10 | 75 | 90 | 70 | 60 | — | 85 | 90 | — | — |
| Corn | 0 | 0 | 0 | 0 | 0 | 50 | 0 | 50 | 25 | 5 | 0 | 0 | 0 | 0 |
| Crabgrass, Large | 100 | 100 | 100 | 100 | 98 | 100 | 100 | 100 | 100 | 100 | 100 | 65 | 100 | 80 |

TABLE B-continued

| | | | | | | | | | | | | | | |
|---|---|---|---|---|---|---|---|---|---|---|---|---|---|---|
| Cupgrass, Woolly | 45 | 55 | 0 | 55 | 0 | 75 | 85 | 95 | 75 | 80 | 65 | 65 | 20 | 10 |
| Foxtail, Giant | 10 | 75 | 5 | 80 | 5 | 85 | 60 | 95 | 98 | 70 | 75 | 20 | 10 | 0 |
| Foxtail, Green | 50 | 30 | 0 | 50 | 0 | 100 | 60 | 100 | 100 | 50 | 0 | 80 | 90 | — |
| *Galium* | 85 | 80 | 40 | 95 | 85 | 100 | 85 | 90 | 95 | 100 | 70 | 95 | 98 | 90 |
| Goosegrass | 100 | 100 | 100 | 100 | 98 | 100 | 100 | 100 | 100 | 100 | 100 | 98 | 100 | 98 |
| Johnsongrass | 0 | 98 | 0 | 65 | 0 | 90 | 60 | 95 | 80 | 15 | 20 | 20 | 65 | 0 |
| *Kochia* | 85 | 80 | 85 | 90 | 90 | 65 | 85 | 55 | 50 | 80 | — | — | — | — |
| Lambsquarters | 98 | 100 | 98 | 100 | 100 | 98 | 100 | 100 | 100 | 100 | 100 | 100 | 100 | 100 |
| Morningglory | 65 | 45 | 75 | 75 | 75 | 80 | — | 95 | 90 | 95 | 0 | 15 | 15 | 0 |
| Nightshade | 98 | 98 | 98 | 98 | 98 | 98 | 100 | 98 | 95 | 100 | 100 | 100 | 100 | 98 |
| Nutsedge, Yellow | 75 | 65 | 65 | 90 | 90 | 95 | 90 | 98 | 98 | 70 | 70 | 90 | 85 | 60 |
| Oat, Wild | 0 | 0 | 5 | 0 | 0 | 0 | 20 | 50 | 65 | 30 | 0 | 0 | 5 | 0 |
| Pigweed | 100 | 100 | 100 | 100 | 100 | 100 | 100 | 100 | 100 | 100 | 100 | 100 | 100 | 100 |
| Ragweed | 80 | 75 | 98 | 95 | 90 | 90 | 95 | 95 | 95 | 100 | 90 | 98 | 85 | 80 |
| Russian Thistle | 80 | — | 90 | — | — | 100 | — | 100 | 80 | 100 | — | — | — | — |
| Ryegrass, Italian | 0 | 0 | 0 | 0 | 0 | 0 | 5 | 100 | 100 | 25 | 5 | 5 | 5 | 0 |
| Soybean | — | — | — | — | — | — | 85 | 80 | 80 | 60 | 0 | 80 | 65 | 0 |
| Sunflower | 65 | 70 | 70 | 75 | 75 | 85 | 90 | 70 | 85 | 80 | 85 | 90 | 80 | 70 |
| Surinam Grass | 75 | 100 | 85 | 60 | 75 | 100 | 95 | 100 | 100 | 30 | 85 | 98 | 45 | 45 |
| Velvetleaf | 100 | 100 | 100 | 100 | 100 | 100 | 100 | 100 | 100 | 100 | 100 | 90 | 90 | 90 |
| Wheat | 0 | 5 | 0 | 0 | 0 | 0 | 10 | 30 | 25 | 10 | 0 | 0 | 0 | 0 |

| | Compounds | | | |
|---|---|---|---|---|
| 125 g ai/ha | 243 | 244 | 245 | 255 |

Preemergence

| | | | | |
|---|---|---|---|---|
| Bermudagrass | 100 | 100 | 100 | 100 |
| Blackgrass | 70 | 60 | 30 | 40 |
| Bromegrass, Downy | 60 | 5 | 0 | 0 |
| Cocklebur | 95 | 100 | 98 | — |
| Corn | 85 | 60 | 25 | 0 |
| Crabgrass, Large | 100 | 100 | 100 | 100 |
| Cupgrass, Woolly | 95 | 95 | 80 | 75 |
| Foxtail, Giant | 95 | 100 | 90 | 55 |
| Foxtail, Green | 100 | 90 | 75 | 80 |
| *Galium* | 98 | 98 | 95 | 60 |
| Goosegrass | 100 | 100 | 100 | 100 |
| Johnsongrass | 95 | 100 | 80 | 75 |
| *Kochia* | 90 | 95 | 98 | — |
| Lambsquarters | 100 | 100 | 100 | 100 |
| Morningglory | 98 | 98 | 65 | 65 |
| Nightshade | 98 | 100 | 100 | 100 |
| Nutsedge, Yellow | 90 | 80 | 65 | 40 |
| Oat, Wild | 85 | 10 | 30 | 60 |
| Pigweed | 100 | 100 | 100 | 100 |
| Ragweed | 98 | 100 | 100 | 85 |
| Russian Thistle | 100 | — | — | — |
| Ryegrass, Italian | 45 | 5 | 0 | 10 |
| Soybean | 85 | 90 | 55 | 15 |
| Sunflower | 95 | 85 | 80 | 75 |
| Surinam Grass | 100 | 100 | 100 | 95 |
| Velvetleaf | 100 | 100 | 100 | 98 |
| Wheat | 70 | 5 | 5 | 0 |

| | Compounds | | | | | | | | | | | | | |
|---|---|---|---|---|---|---|---|---|---|---|---|---|---|---|
| 62 g ai/ha | 2 | 3 | 7 | 9 | 10 | 11 | 12 | 14 | 24 | 26 | 27 | 29 | 33 | 34 |

Preemergence

| | | | | | | | | | | | | | | |
|---|---|---|---|---|---|---|---|---|---|---|---|---|---|---|
| Bermudagrass | 100 | 70 | 0 | 100 | 80 | 100 | 100 | 75 | 100 | 70 | 98 | 100 | 100 | 100 |
| Blackgrass | 0 | 0 | 0 | 0 | 0 | 5 | 0 | 0 | 0 | 0 | 0 | 5 | 0 | 5 |
| Bromegrass, Downy | 0 | 0 | 0 | 0 | 0 | 0 | 0 | 0 | 0 | 0 | 0 | 0 | 0 | 0 |
| Cocklebur | 65 | 10 | 0 | 25 | 15 | 75 | 80 | 85 | — | 40 | 85 | 80 | 80 | 55 |
| Corn | 0 | 0 | 0 | 0 | 0 | 0 | 0 | 0 | 0 | 0 | 0 | 0 | 0 | 0 |
| Crabgrass, Large | 100 | 70 | 0 | 90 | 0 | 100 | 90 | 50 | 98 | 40 | 80 | 100 | 98 | 100 |
| Cupgrass, Woolly | 15 | 0 | 0 | 15 | 10 | 0 | 10 | 5 | 70 | 5 | 0 | 10 | 50 | 100 |
| Foxtail, Giant | 20 | 0 | 0 | 15 | 0 | 35 | 20 | 10 | 85 | 10 | 5 | 50 | 45 | 55 |
| Foxtail, Green | 5 | 0 | 0 | 0 | 0 | 25 | 0 | 0 | 40 | 0 | 30 | 40 | 45 | 70 |
| *Galium* | — | 5 | 0 | 40 | 10 | 50 | 50 | 0 | 0 | 50 | 50 | 80 | 10 | 50 |
| Goosegrass | 100 | 70 | 25 | 98 | 75 | 95 | 95 | 85 | 98 | 80 | 98 | 100 | 85 | 100 |
| Johnsongrass | 65 | 0 | 0 | 85 | 10 | 55 | 0 | 30 | 85 | 10 | 5 | 5 | 0 | 75 |
| *Kochia* | 100 | — | 100 | 100 | 50 | 100 | 100 | 100 | 100 | 100 | 100 | 100 | — | — |
| Lambsquarters | 100 | — | 100 | 100 | 100 | 100 | 100 | 100 | 100 | 100 | 100 | 100 | 100 | 100 |
| Morningglory | 20 | 100 | 0 | 40 | 0 | 0 | 55 | 100 | 100 | 100 | 100 | 100 | 15 | 0 |
| Nightshade | 100 | — | 90 | 100 | 100 | 100 | 100 | 98 | 98 | 100 | 98 | 90 | 100 | 95 |
| Nutsedge, Yellow | 40 | 10 | 10 | 45 | 0 | 55 | 60 | 30 | 50 | 50 | 20 | 30 | 45 | 45 |
| Oat, Wild | 5 | 0 | 0 | 0 | 0 | 0 | 0 | 0 | 0 | 0 | 0 | 0 | 0 | 10 |

TABLE B-continued

| | | | | | | | | | | | | | | |
|---|---|---|---|---|---|---|---|---|---|---|---|---|---|---|
| Pigweed | 100 | — | 100 | 100 | 100 | 100 | 100 | 98 | 100 | 100 | 100 | 100 | 100 | 100 |
| Ragweed | 85 | 65 | 0 | 90 | 100 | 100 | 98 | 90 | 90 | 85 | 85 | 90 | 85 | 80 |
| Russian Thistle | — | — | — | — | — | — | — | — | — | — | — | — | — | — |
| Ryegrass, Italian | 0 | 0 | 0 | 0 | 0 | 0 | 0 | 0 | 0 | 0 | 0 | 0 | 0 | 0 |
| Soybean | 60 | 30 | 0 | 10 | 60 | 45 | 65 | — | 60 | 60 | 70 | 85 | 60 | 45 |
| Sunflower | 70 | 70 | 0 | 85 | 80 | 85 | 98 | 85 | 90 | 90 | 75 | 85 | 75 | 70 |
| Surinam Grass | 20 | 0 | 0 | 45 | 10 | 25 | 60 | 5 | 75 | 5 | 20 | 20 | 65 | 60 |
| Velvetleaf | 90 | 90 | 85 | 100 | 100 | 100 | 100 | 98 | 100 | 90 | 85 | 90 | 90 | 85 |
| Wheat | 0 | 0 | 0 | 0 | — | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 62 g ai/ha | 36 | 37 | 38 | 39 | 40 | 42 | 44 | 45 | 46 | 47 | 48 | 49 | 50 | 51 |
| | Preemergence | | | | | | | | | | | | | |
| Bermudagrass | 100 | 80 | 100 | 100 | 100 | 100 | 100 | 100 | — | 100 | 100 | — | 100 | 98 |
| Blackgrass | 25 | 0 | 5 | 0 | 0 | 0 | 30 | 0 | 0 | 5 | 0 | 0 | 0 | 0 |
| Bromegrass, Downy | 0 | 0 | 0 | 0 | 0 | 0 | 0 | 0 | 0 | 5 | 0 | 0 | 0 | 0 |
| Cocklebur | — | — | 10 | — | — | 0 | — | — | 0 | 0 | 0 | 20 | 75 | 0 |
| Corn | 0 | 0 | 0 | 0 | 0 | 0 | 0 | 0 | 0 | 0 | 0 | 0 | 0 | 0 |
| Crabgrass, Large | 90 | 0 | 90 | 95 | 98 | 85 | 75 | 95 | 75 | 95 | 90 | 95 | 100 | 98 |
| Cupgrass, Woolly | 0 | 0 | 10 | 0 | 50 | 0 | 45 | 45 | 45 | 45 | 10 | 0 | 5 | 35 |
| Foxtail, Giant | 20 | 0 | 40 | 45 | 65 | 0 | 45 | 0 | 0 | 70 | 75 | 0 | 75 | 45 |
| Foxtail, Green | 80 | 0 | 30 | — | 85 | 65 | 98 | 80 | 0 | 80 | 60 | 0 | 50 | 50 |
| Galium | 80 | 10 | 40 | 80 | 70 | 0 | 65 | 40 | 0 | 50 | 60 | 80 | 95 | 75 |
| Goosegrass | 90 | 0 | 100 | 100 | 98 | 95 | 98 | 100 | 95 | 100 | 100 | 95 | 98 | 100 |
| Johnsongrass | 65 | 0 | 80 | 60 | 80 | 0 | 75 | 45 | 10 | 75 | 45 | 0 | 20 | 5 |
| Kochia | — | — | — | — | — | — | — | — | — | — | — | — | — | — |
| Lambsquarters | 100 | 98 | 98 | 100 | 100 | 100 | 100 | 100 | 90 | 100 | 100 | 95 | 100 | 98 |
| Morningglory | 0 | 0 | 0 | 0 | 0 | 0 | 0 | — | 0 | — | 100 | 80 | 0 | 20 |
| Nightshade | 95 | 40 | 95 | 100 | 98 | 100 | 98 | 100 | 95 | 100 | 100 | 98 | 100 | 98 |
| Nutsedge, Yellow | 0 | 0 | 60 | 0 | 45 | 35 | 60 | 10 | 55 | 45 | 20 | 60 | 85 | 70 |
| Oat, Wild | 0 | 0 | 0 | 0 | 0 | 0 | 0 | 0 | 0 | 0 | 0 | 0 | 0 | 0 |
| Pigweed | 100 | 100 | 100 | 100 | 100 | 100 | 98 | 95 | 85 | 100 | 100 | 100 | 100 | 100 |
| Ragweed | 75 | 10 | 70 | 45 | 75 | 20 | 90 | 80 | 100 | 80 | 85 | 75 | 95 | 70 |
| Russian Thistle | — | — | — | — | — | — | — | — | — | — | — | — | — | — |
| Ryegrass, Italian | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 80 | 0 | 0 | 0 |
| Sunflower | 0 | 0 | 0 | 5 | 55 | 0 | 70 | 0 | 0 | 65 | 75 | 75 | 75 | 70 |
| Surinam Grass | 95 | 45 | 60 | 10 | 75 | 5 | 85 | 60 | 5 | 98 | 90 | — | 95 | 98 |
| Velvetleaf | 85 | 0 | 60 | 45 | 85 | 80 | 90 | 65 | 45 | 90 | 95 | 100 | 85 | 85 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 62 g ai/ha | 52 | 53 | 55 | 56 | 58 | 59 | 61 | 62 | 63 | 64 | 66 | 67 | 68 | 69 |
| | Preemergence | | | | | | | | | | | | | |
| Bermudagrass | 98 | 100 | 98 | 100 | 98 | 98 | 75 | 75 | 98 | 85 | 80 | 90 | 98 | 100 |
| Blackgrass | 0 | 5 | 0 | 0 | 0 | 0 | 0 | 0 | 0 | 0 | 0 | 0 | 0 | 0 |
| Bromegrass, Downy | 5 | 0 | 0 | 0 | 0 | 0 | 0 | 0 | 0 | 0 | 0 | 0 | 0 | 0 |
| Cocklebur | 0 | 20 | 10 | 0 | 0 | 0 | 10 | 0 | 0 | 0 | 0 | 0 | 10 | 0 |
| Corn | 0 | 0 | 0 | 0 | 0 | 0 | 0 | — | 0 | 0 | 0 | 0 | 0 | 0 |
| Crabgrass, Large | 98 | 100 | 60 | 85 | 98 | 95 | 85 | 50 | 85 | 75 | 85 | 65 | 95 | 100 |
| Cupgrass, Woolly | 10 | 55 | 0 | 20 | 10 | 65 | 0 | 0 | 0 | 0 | 40 | 0 | 20 | 0 |
| Foxtail, Giant | 15 | 85 | 0 | 40 | 20 | 0 | 0 | 0 | 0 | 25 | 20 | 0 | 20 | 75 |
| Foxtail, Green | 30 | 60 | 0 | 20 | 5 | 70 | 0 | 0 | — | 0 | 5 | 30 | 5 | 70 |
| Galium | 0 | 0 | 0 | 0 | 0 | 90 | 70 | 0 | 0 | 0 | 0 | 35 | 70 | — |
| Goosegrass | 100 | 100 | 95 | 95 | 98 | 98 | 98 | 95 | 98 | 40 | 75 | 85 | 95 | 100 |
| Johnsongrass | 75 | 55 | 0 | 45 | 20 | — | 0 | 0 | 0 | 0 | 55 | 0 | 5 | 45 |
| Kochia | — | — | — | — | — | 45 | 70 | 100 | 100 | 0 | 80 | 70 | 80 | 20 |
| Lambsquarters | 100 | 100 | 98 | 98 | 98 | 100 | 98 | 98 | 98 | 98 | 98 | 98 | 98 | 100 |
| Morningglory | 0 | 20 | 0 | 0 | 0 | 0 | 0 | 0 | 0 | 0 | 20 | 15 | 55 | 0 |
| Nightshade | 95 | 98 | 98 | 98 | 98 | 98 | 95 | 95 | 95 | 85 | 95 | 95 | 98 | 98 |
| Nutsedge, Yellow | 25 | 80 | 45 | 80 | 75 | 65 | 70 | 25 | 15 | 0 | 30 | 65 | 70 | 0 |
| Oat, Wild | 5 | 0 | 0 | 0 | 0 | 0 | 0 | 0 | 0 | 0 | 0 | 0 | 0 | 0 |
| Pigweed | 100 | 98 | 95 | 100 | 98 | 100 | 100 | 98 | 98 | 75 | 98 | 98 | 98 | 100 |
| Ragweed | 80 | 75 | 65 | 65 | 75 | 90 | 75 | 20 | 65 | 50 | 0 | 25 | 75 | 65 |
| Russian Thistle | — | — | — | — | — | — | — | — | 0 | 0 | — | — | 100 |
| Ryegrass, Italian | 0 | 0 | 0 | 0 | 0 | 0 | 0 | 0 | 0 | 0 | 0 | 0 | 0 | 0 |
| Soybean | 0 | 70 | 0 | — | 0 | 0 | 0 | 80 | 0 | — | — | — | — | 0 |
| Sunflower | 10 | 55 | 60 | 60 | 55 | 65 | 45 | 10 | 15 | 0 | 0 | 20 | 60 | 0 |
| Surinam Grass | 25 | 85 | 0 | 95 | 65 | 75 | 0 | 20 | 0 | 85 | 80 | 10 | 50 | 100 |
| Velvetleaf | 98 | 98 | 98 | 90 | 80 | 90 | 85 | 75 | 90 | 75 | 80 | 85 | 100 | 70 |
| Wheat | 0 | 0 | 0 | 0 | 0 | 0 | 0 | 0 | 0 | 0 | 0 | 0 | 0 | 0 |

TABLE B-continued

| 62 g ai/ha | Compounds | | | | | | | | | | | | | |
|---|---|---|---|---|---|---|---|---|---|---|---|---|---|---|
| | 72 | 73 | 74 | 75 | 77 | 81 | 113 | 119 | 120 | 193 | 217 | 218 | 219 | 220 |
| Preemergence | | | | | | | | | | | | | | |
| Bermudagrass | 98 | 98 | 98 | 100 | 100 | 100 | 95 | 100 | 100 | 95 | 100 | 100 | 100 | 98 |
| Blackgrass | 0 | 0 | 0 | 0 | 0 | 0 | 0 | 30 | 50 | 0 | 0 | 0 | 35 | 20 |
| Bromegrass, Downy | 0 | 5 | 0 | 0 | 0 | 0 | 10 | 50 | 30 | 5 | 0 | 0 | 0 | 0 |
| Cocklebur | 50 | 0 | 45 | 20 | 0 | 10 | 75 | — | 35 | 75 | — | 0 | 75 | 0 |
| Corn | 0 | 0 | 0 | 0 | 0 | 40 | 0 | 40 | — | 0 | 0 | 0 | 0 | 0 |
| Crabgrass, Large | 100 | 98 | 98 | 100 | 98 | 100 | 98 | 100 | 100 | 100 | 100 | 20 | 98 | 75 |
| Cupgrass, Woolly | 0 | 20 | 0 | — | 0 | 55 | 50 | 75 | 70 | 70 | 5 | 0 | 10 | 0 |
| Foxtail, Giant | 5 | 70 | 0 | 25 | 0 | 75 | 40 | 85 | 98 | 65 | 40 | 0 | 0 | 0 |
| Foxtail, Green | 0 | 30 | 0 | 50 | 0 | 90 | 40 | 100 | 98 | 50 | 0 | 30 | 70 | 90 |
| *Galium* | 85 | 30 | 30 | 85 | 20 | 100 | 70 | 85 | 90 | 100 | 10 | 80 | 85 | 50 |
| Goosegrass | 98 | 98 | 98 | 100 | 95 | 98 | 90 | 100 | 100 | 100 | 98 | 60 | 100 | 95 |
| Johnsongrass | 0 | 0 | 0 | 10 | 0 | 80 | 5 | 85 | 70 | 0 | 5 | 0 | 15 | 0 |
| *Kochia* | 75 | — | — | 90 | 90 | 55 | 80 | 0 | 20 | 70 | — | — | — | — |
| Lambsquarters | 98 | 98 | 98 | 100 | 98 | 98 | 100 | 98 | 100 | 100 | 100 | 100 | 100 | 100 |
| Morningglory | 55 | 0 | 60 | 60 | 65 | 65 | — | 95 | 90 | 90 | 0 | 0 | 0 | 0 |
| Nightshade | 95 | 95 | 98 | 98 | 98 | 98 | 98 | 98 | 95 | 100 | 100 | 98 | 98 | 90 |
| Nutsedge, Yellow | 70 | 65 | 55 | 80 | 80 | 75 | 80 | 95 | 90 | 65 | 65 | 75 | 45 | 0 |
| Oat, Wild | 0 | 0 | 0 | 0 | 0 | 0 | 5 | 45 | 10 | 5 | 0 | 0 | 0 | 0 |
| Pigweed | 98 | 100 | 98 | 100 | 100 | 100 | 98 | 90 | 100 | 100 | 100 | 100 | 100 | 100 |
| Ragweed | 70 | 60 | 98 | 75 | 75 | 85 | 90 | 80 | 80 | 100 | 60 | 95 | 75 | 60 |
| Russian Thistle | 30 | — | 80 | — | — | 100 | — | 100 | 80 | 98 | — | — | — | — |
| Ryegrass, Italian | 0 | 0 | 0 | 0 | 0 | 0 | 5 | 100 | 100 | 0 | 0 | 0 | 0 | 0 |
| Soybean | — | — | — | — | — | — | 65 | 55 | 70 | 60 | 0 | 65 | 0 | 0 |
| Sunflower | 25 | 20 | 55 | 55 | 75 | 75 | 80 | 60 | — | 80 | 75 | 80 | 45 | 45 |
| Surinam Grass | 75 | 100 | 80 | 60 | 20 | 100 | 80 | 98 | 100 | 15 | 75 | 65 | 10 | 20 |
| Velvetleaf | 100 | 100 | 100 | 100 | 100 | 100 | 100 | 80 | 100 | 100 | 100 | 85 | 75 | 70 |
| Wheat | 0 | 0 | 0 | 0 | 0 | 0 | 0 | 0 | 0 | 0 | 0 | 0 | 0 | 0 |

| 62 g ai/ha | Compounds | | | |
|---|---|---|---|---|
| | 243 | 244 | 245 | 255 |
| Preemergence | | | | |
| Bermudagrass | 100 | 100 | 100 | 100 |
| Blackgrass | 10 | 35 | 5 | 20 |
| Bromegrass, Downy | 40 | 0 | 0 | 0 |
| Cocklebur | 75 | 90 | 0 | — |
| Corn | 75 | 25 | 5 | 0 |
| Crabgrass, Large | 100 | 100 | 100 | 95 |
| Cupgrass, Woolly | 95 | 55 | 70 | 10 |
| Foxtail, Giant | 85 | 80 | 10 | 45 |
| Foxtail, Green | 100 | 45 | 0 | 80 |
| *Galium* | 90 | 65 | 60 | 50 |
| Goosegrass | 100 | 100 | 100 | 98 |
| Johnsongrass | 95 | 85 | 75 | 60 |
| *Kochia* | 20 | 90 | 45 | — |
| Lambsquarters | 100 | 100 | 100 | 100 |
| Morningglory | — | 90 | 0 | 55 |
| Nightshade | 98 | 100 | 100 | 90 |
| Nutsedge, Yellow | 80 | 60 | 0 | 25 |
| Oat, Wild | 85 | 5 | 0 | 0 |
| Pigweed | 98 | 100 | 95 | 100 |
| Ragweed | 95 | 95 | 85 | 75 |
| Russian Thistle | 100 | — | — | — |
| Ryegrass, Italian | 10 | 0 | 0 | 0 |
| Soybean | 75 | 80 | 10 | 0 |
| Sunflower | 85 | 80 | 70 | 60 |
| Surinam Grass | 98 | 100 | 100 | 85 |
| Velvetleaf | 100 | 100 | 100 | 95 |
| Wheat | 40 | 0 | 0 | 0 |

| 31 g ai/ha | Compounds | | | | | | | | | | | | |
|---|---|---|---|---|---|---|---|---|---|---|---|---|---|
| | 2 | 3 | 7 | 9 | 10 | 11 | 12 | 14 | 24 | 26 | 27 | 29 | 33 | 34 |
| Preemergence | | | | | | | | | | | | | | |
| Bermudagrass | 98 | 10 | 0 | 98 | 45 | 98 | 100 | 70 | 95 | 5 | 70 | 98 | 98 | 100 |
| Blackgrass | 0 | 0 | 0 | 0 | 0 | 0 | 0 | 0 | 0 | 0 | 0 | 5 | 0 | 0 |
| Bromegrass, Downy | 0 | 0 | 0 | 0 | 0 | 0 | 0 | 0 | 0 | 0 | 0 | 0 | 0 | — |
| Cocklebur | 0 | 10 | 0 | 0 | 0 | 35 | 25 | 0 | 10 | 10 | 0 | 5 | 25 | 0 |
| Corn | 0 | 0 | 0 | 0 | 0 | 0 | 0 | 0 | 0 | 0 | 0 | 0 | 0 | 0 |
| Crabgrass, Large | 15 | 0 | 0 | 0 | 0 | 60 | 0 | 5 | 90 | 0 | 5 | 98 | 85 | 55 |

TABLE B-continued

| | | | | | | | | | | | | | | |
|---|---|---|---|---|---|---|---|---|---|---|---|---|---|---|
| Cupgrass, Woolly | 0 | 0 | 0 | 0 | 0 | 0 | 0 | 0 | 5 | 0 | 0 | 5 | 10 | 100 |
| Foxtail, Giant | 15 | 0 | 0 | 0 | 0 | 0 | 0 | 0 | 30 | 5 | 0 | 10 | 10 | 15 |
| Foxtail, Green | 0 | 0 | 0 | 0 | 0 | 0 | 0 | 0 | 0 | 0 | 0 | 0 | 0 | 50 |
| *Galium* | — | 0 | 0 | 0 | 0 | 5 | 0 | 0 | 0 | 0 | 0 | 50 | 0 | 10 |
| Goosegrass | 85 | 30 | 10 | 75 | 0 | 70 | 85 | 70 | 85 | 5 | 80 | 95 | 80 | 95 |
| Johnsongrass | 60 | 0 | 0 | 0 | 0 | 0 | 0 | 5 | 20 | 0 | 0 | 0 | 0 | 20 |
| *Kochia* | 100 | 98 | 15 | 15 | 0 | 15 | 15 | 85 | 100 | 80 | 100 | 98 | — | — |
| Lambsquarters | 100 | 100 | 100 | 100 | 100 | 100 | 100 | 100 | 98 | 98 | 100 | 100 | 98 | 100 |
| Morningglory | 0 | 100 | — | 0 | 0 | 0 | 40 | 100 | 100 | 100 | 100 | 100 | 0 | 0 |
| Nightshade | 98 | 50 | 80 | 100 | 100 | 85 | 100 | 85 | 90 | 85 | 80 | 90 | 80 | 55 |
| Nutsedge, Yellow | 15 | 5 | 0 | 0 | 0 | 0 | 25 | 0 | 30 | 10 | 0 | 0 | 0 | 10 |
| Oat, Wild | — | 0 | 0 | 0 | 0 | 0 | 0 | 0 | 0 | 0 | 0 | 0 | 0 | 10 |
| Pigweed | 100 | 85 | 100 | 50 | 100 | 100 | 100 | 90 | 98 | 98 | 100 | 100 | 100 | 100 |
| Ragweed | 60 | 65 | 0 | 55 | 98 | 65 | 90 | 70 | 85 | 65 | 85 | 80 | 80 | 75 |
| Russian Thistle | — | — | — | — | — | — | — | — | — | — | — | — | — | — |
| Ryegrass, Italian | 0 | 0 | 0 | 0 | 0 | 0 | 0 | 0 | 0 | 0 | 0 | 0 | 0 | 0 |
| Soybean | 15 | 0 | 0 | 0 | 10 | 25 | 60 | 25 | 45 | 50 | 70 | 20 | 60 | 0 |
| Sunflower | 50 | 50 | 0 | 45 | 0 | 75 | 95 | 50 | 85 | 60 | 75 | 75 | 65 | 55 |
| Surinam Grass | 15 | 0 | 0 | 0 | 0 | 0 | 35 | 0 | 65 | 0 | 0 | 0 | 0 | 5 |
| Velvetleaf | 75 | 50 | 40 | 98 | 55 | 100 | 90 | 70 | 98 | 50 | 55 | 10 | 80 | 75 |
| Wheat | 0 | 0 | 0 | 0 | 0 | 0 | 0 | 0 | 0 | 0 | 0 | 0 | 0 | — |

| | Compounds | | | | | | | | | | | | | |
|---|---|---|---|---|---|---|---|---|---|---|---|---|---|---|
| 31 g ai/ha | 36 | 37 | 38 | 39 | 40 | 42 | 44 | 45 | 46 | 47 | 48 | 49 | 50 | 51 |

Preemergence

| | | | | | | | | | | | | | | |
|---|---|---|---|---|---|---|---|---|---|---|---|---|---|---|
| Bermudagrass | 95 | 10 | 98 | 85 | 98 | 90 | 100 | 98 | 0 | 100 | 100 | — | 100 | 95 |
| Blackgrass | 20 | 0 | 0 | 0 | 0 | 0 | 5 | 0 | 0 | 0 | 0 | 0 | 0 | 0 |
| Bromegrass, Downy | 0 | 0 | 0 | 0 | 0 | 0 | 0 | 0 | 0 | 0 | 0 | 0 | 0 | 0 |
| Cocklebur | — | 0 | 0 | 0 | 65 | 0 | — | — | 0 | — | — | 0 | — | 0 |
| Corn | 0 | 0 | 0 | 0 | 0 | 0 | 0 | 0 | 0 | 0 | 0 | 0 | 0 | 0 |
| Crabgrass, Large | 20 | 0 | 60 | 55 | 70 | 45 | 65 | 45 | 45 | 75 | 75 | 75 | 98 | 75 |
| Cupgrass, Woolly | 0 | 0 | 0 | 0 | 0 | 0 | 0 | 45 | 10 | 0 | 10 | 0 | 0 | 10 |
| Foxtail, Giant | 10 | 0 | 0 | 0 | 10 | 0 | 20 | 0 | 0 | 45 | 20 | 0 | 45 | 0 |
| Foxtail, Green | 35 | 0 | 20 | — | 0 | 65 | 0 | 0 | 0 | 65 | 60 | 0 | 50 | 50 |
| *Galium* | 10 | 0 | 0 | 70 | 50 | 0 | 0 | 40 | 0 | 50 | 0 | 0 | 70 | 0 |
| Goosegrass | 0 | 0 | 95 | 85 | 80 | 50 | 90 | 80 | 85 | 95 | 98 | 20 | 95 | 98 |
| Johnsongrass | 0 | 0 | 10 | 0 | 10 | 0 | 10 | 0 | 0 | 65 | 20 | 0 | 0 | 0 |
| *Kochia* | — | — | — | — | — | — | — | — | — | — | — | — | — | — |
| Lambsquarters | 98 | 95 | 98 | 100 | 100 | 100 | 100 | 100 | 90 | 100 | 100 | 95 | 100 | 95 |
| Morningglory | 0 | 0 | 0 | 0 | 0 | 0 | 0 | 0 | 0 | 0 | 0 | 45 | 0 | 0 |
| Nightshade | 80 | 0 | 90 | 50 | 65 | 100 | 95 | 98 | 95 | 100 | 100 | 98 | 100 | 98 |
| Nutsedge, Yellow | 0 | 0 | 10 | 0 | 10 | 10 | 45 | 0 | 25 | 45 | 20 | 60 | 80 | 55 |
| Oat, Wild | 0 | 0 | 0 | 0 | 0 | 0 | 0 | 0 | 0 | 0 | 0 | 0 | 0 | 0 |
| Pigweed | 100 | 100 | 100 | 90 | 98 | 100 | 98 | 85 | 85 | 98 | 100 | 100 | 90 | 100 |
| Ragweed | 35 | 0 | 40 | 0 | 75 | 0 | 20 | 45 | 100 | 45 | 65 | 70 | 75 | 65 |
| Russian Thistle | — | — | — | — | — | — | — | — | — | — | — | — | — | — |
| Ryegrass, Italian | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 |
| Sunflower | 0 | 0 | 0 | 0 | 20 | 0 | 10 | 0 | 0 | 65 | 0 | 60 | 55 | 20 |
| Surinam Grass | 70 | 0 | 40 | 0 | 40 | 0 | 65 | 45 | 0 | 85 | 80 | 0 | 75 | 95 |
| Velvetleaf | 65 | 0 | 55 | 15 | 80 | 75 | 75 | 0 | 0 | 80 | 75 | 95 | 85 | 75 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 52 | 53 | 55 | 56 | 58 | 59 | 61 | 62 | 63 | 64 | 66 | 67 | 68 | 69 |

Preemergence

| | | | | | | | | | | | | | | |
|---|---|---|---|---|---|---|---|---|---|---|---|---|---|---|
| Bermudagrass | 98 | — | 95 | 98 | 98 | 10 | 20 | 20 | 75 | 50 | 20 | 45 | 95 | 98 |
| Blackgrass | 0 | 0 | 0 | 0 | 0 | 0 | 0 | 0 | 0 | 0 | 0 | 0 | 0 | 0 |
| Bromegrass, Downy | 0 | 0 | 0 | 0 | 0 | 0 | 0 | 0 | 0 | 0 | 0 | 0 | 0 | 0 |
| Cocklebur | 0 | 10 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 |
| Crabgrass, Large | 60 | 75 | 10 | 80 | 95 | 55 | 70 | 0 | 50 | 50 | 70 | 40 | 65 | 98 |
| Cupgrass, Woolly | 0 | 0 | 0 | 0 | 10 | 10 | 0 | 0 | 0 | 0 | 25 | 0 | 5 | 0 |
| Foxtail, Giant | 0 | 5 | 0 | 0 | 10 | 0 | 0 | 0 | 0 | 20 | 15 | 0 | 0 | 5 |
| Foxtail, Green | 0 | 60 | 0 | 0 | 0 | — | 0 | 0 | 0 | 0 | 0 | 0 | 0 | — |
| *Galium* | 0 | 0 | 0 | 0 | 0 | 0 | 70 | 0 | 0 | 0 | 0 | 0 | 0 | — |
| Goosegrass | 98 | 98 | 45 | 90 | 95 | 98 | 80 | 15 | 90 | 30 | 35 | 85 | 80 | 95 |
| Johnsongrass | 10 | 10 | 0 | 10 | 10 | — | 0 | 0 | 0 | 0 | 0 | 0 | 0 | 5 |
| *Kochia* | — | — | — | — | — | 0 | 0 | 98 | 0 | 0 | 80 | 70 | 80 | 0 |
| Lambsquarters | 98 | 98 | 95 | 95 | 85 | 98 | 90 | 98 | 98 | 95 | 98 | 98 | 98 | 98 |
| Morningglory | 0 | 0 | 0 | 0 | 0 | — | 0 | 0 | 0 | 0 | 0 | 0 | 0 | 0 |
| Nightshade | 90 | 98 | 60 | 85 | 90 | 95 | 90 | 10 | 80 | 55 | 80 | 70 | 98 | 95 |
| Nutsedge, Yellow | 0 | 65 | 0 | 20 | 20 | 55 | 25 | 15 | 10 | 0 | 10 | 0 | 0 | 0 |
| Oat, Wild | 0 | 0 | 0 | 0 | 0 | 0 | 0 | 0 | 0 | 0 | 0 | 0 | 0 | 0 |

TABLE B-continued

| | | | | | | | | | | | | | | |
|---|---|---|---|---|---|---|---|---|---|---|---|---|---|---|
| Pigweed | 90 | 95 | 45 | 98 | 85 | 90 | 0 | 45 | 95 | 55 | 98 | 98 | 95 | 98 |
| Ragweed | 80 | 65 | 55 | 20 | 20 | 75 | 50 | 0 | 65 | 0 | 0 | 25 | 10 | 65 |
| Russian Thistle | — | — | — | — | — | — | — | — | — | — | 85 | — | 100 | |
| Ryegrass, Italian | 0 | 0 | 0 | 0 | 0 | 0 | — | 0 | 0 | 0 | 0 | 0 | 0 | 0 |
| Soybean | 0 | 0 | 0 | 20 | 10 | — | — | 0 | 0 | — | — | — | — | — |
| Sunflower | 10 | 15 | 10 | 0 | 0 | 55 | 0 | 0 | 5 | 0 | 0 | 0 | 0 | 0 |
| Surinam Grass | 10 | 75 | 0 | 55 | 40 | 5 | 0 | 5 | 0 | 0 | 35 | 0 | 45 | 80 |
| Velvetleaf | 80 | 80 | 75 | 85 | 75 | 75 | 80 | 75 | 75 | 65 | 80 | 75 | 95 | 70 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 72 | 73 | 74 | 75 | 77 | 81 | 113 | 119 | 120 | 193 | 217 | 218 | 219 | 220 |
| Preemergence | | | | | | | | | | | | | | |
| Bermudagrass | 95 | 50 | — | 98 | 55 | 100 | 95 | 100 | 100 | 75 | 98 | 98 | 98 | 80 |
| Blackgrass | 0 | 0 | 0 | 0 | 0 | 0 | 0 | 30 | 5 | 0 | 0 | 0 | 30 | 10 |
| Bromegrass, Downy | 0 | 0 | 0 | 0 | 0 | 0 | 0 | 0 | 10 | 0 | 0 | 0 | 0 | 0 |
| Cocklebur | 10 | 0 | 10 | 10 | 0 | 0 | 45 | 0 | 0 | — | — | — | — | 0 |
| Corn | 0 | 0 | 0 | 0 | 0 | 40 | 0 | 0 | 0 | 0 | 0 | 0 | 0 | 0 |
| Crabgrass, Large | 95 | 85 | 98 | 98 | 70 | 100 | 70 | 100 | 98 | 100 | 95 | 0 | 10 | 0 |
| Cupgrass, Woolly | 0 | 10 | 0 | 5 | 0 | 40 | 5 | 65 | 50 | 10 | 0 | 0 | 0 | 0 |
| Foxtail, Giant | 0 | 0 | 0 | 0 | 0 | 60 | 5 | 55 | 75 | 0 | 5 | 0 | 0 | 0 |
| Foxtail, Green | 0 | 0 | 0 | 5 | 0 | 80 | 10 | 95 | 95 | 5 | 0 | 0 | 20 | 80 |
| Galium | 0 | — | 20 | 60 | 0 | 85 | 50 | 65 | 80 | 75 | 0 | 60 | 75 | 0 |
| Goosegrass | 60 | 85 | 98 | 95 | 55 | 98 | 75 | 100 | 100 | 98 | 95 | 10 | 98 | 65 |
| Johnsongrass | 0 | 0 | 0 | 0 | 0 | 10 | 0 | 50 | 35 | 0 | 0 | 0 | 0 | 0 |
| Kochia | 45 | 0 | 80 | 80 | 85 | 45 | 80 | 0 | 0 | 20 | — | — | — | — |
| Lambsquarters | 98 | 95 | 98 | 98 | 98 | 98 | 98 | 95 | 100 | 100 | 95 | 100 | 100 | 100 |
| Morningglory | 0 | 0 | 10 | 0 | 0 | — | — | 60 | 0 | 75 | 0 | 0 | 0 | 0 |
| Nightshade | 95 | 75 | 85 | 95 | 98 | 98 | 98 | 90 | 90 | 100 | 95 | 98 | 90 | 65 |
| Nutsedge, Yellow | 40 | 20 | 20 | 60 | 75 | 10 | 65 | 75 | 70 | 10 | 60 | 45 | 0 | 0 |
| Oat, Wild | 0 | 0 | 0 | 0 | 0 | 0 | 0 | 0 | 0 | 5 | 0 | 0 | 0 | — |
| Pigweed | 98 | 95 | 98 | 98 | 100 | 100 | 98 | 80 | 95 | 98 | 95 | 100 | 100 | 100 |
| Ragweed | 55 | 45 | 10 | 75 | 50 | 60 | 55 | 80 | 80 | 100 | 60 | 85 | 45 | 15 |
| Russian Thistle | 0 | 0 | 0 | — | — | 100 | — | 100 | — | 90 | — | — | — | — |
| Ryegrass, Italian | 0 | 0 | 0 | 0 | 0 | 0 | 0 | 100 | 100 | 0 | 0 | 0 | 0 | 0 |
| Soybean | — | — | — | — | — | — | 0 | 10 | 15 | 40 | 0 | 0 | 0 | — |
| Sunflower | 25 | 0 | 0 | 30 | 60 | 60 | 75 | 40 | 45 | 70 | 70 | 75 | 0 | 0 |
| Surinam Grass | 45 | 85 | 0 | 40 | 0 | 98 | 0 | 90 | 100 | 0 | 45 | 10 | 10 | 10 |
| Velvetleaf | 98 | 100 | 98 | 100 | 95 | 100 | 80 | 75 | 80 | 85 | 95 | 80 | 0 | 45 |
| Wheat | 0 | 0 | 0 | 0 | 0 | 0 | 0 | 0 | 0 | 0 | 0 | 0 | 0 | 0 |

| | Compounds | | | |
|---|---|---|---|---|
| 31 g ai/ha | 243 | 244 | 245 | 255 |
| Preemergence | | | | |
| Bermudagrass | 100 | 100 | 98 | 100 |
| Blackgrass | 0 | 35 | 0 | 0 |
| Bromegrass, Downy | 0 | 0 | 0 | 0 |
| Cocklebur | — | — | 0 | — |
| Corn | 65 | 5 | 0 | 0 |
| Crabgrass, Large | 100 | 98 | 60 | 80 |
| Cupgrass, Woolly | 75 | 45 | 50 | 0 |
| Foxtail, Giant | 55 | 60 | 0 | 15 |
| Foxtail, Green | 35 | 0 | 0 | 0 |
| Galium | 85 | 55 | 20 | 0 |
| Goosegrass | 98 | 98 | 95 | 80 |
| Johnsongrass | 70 | 70 | 65 | 0 |
| Kochia | 15 | 85 | 0 | — |
| Lambsquarters | 100 | 100 | 100 | 98 |
| Morningglory | — | 85 | 0 | 40 |
| Nightshade | 90 | 98 | 98 | 75 |
| Nutsedge, Yellow | 65 | 20 | 0 | 10 |
| Oat, Wild | 30 | 0 | 0 | 0 |
| Pigweed | 75 | 100 | 80 | 100 |
| Ragweed | 85 | 70 | 75 | 65 |
| Russian Thistle | 100 | — | — | — |
| Ryegrass, Italian | 0 | 0 | 0 | 0 |
| Soybean | 65 | 70 | 0 | 0 |
| Sunflower | 80 | 80 | 45 | 45 |
| Surinam Grass | 80 | 75 | 95 | 65 |
| Velvetleaf | 100 | 100 | 95 | 80 |
| Wheat | 0 | 0 | 0 | 0 |

TABLE B-continued

| 16 g ai/ha | Compounds | |
|---|---|---|
| | 2 | 69 |
| Preemergence | | |
| Bermudagrass | 25 | 90 |
| Blackgrass | 0 | 0 |
| Bromegrass, Downy | 0 | 0 |
| Cocklebur | 0 | 0 |
| Corn | 0 | 0 |
| Crabgrass, Large | 0 | 75 |
| Cupgrass, Woolly | 0 | 0 |
| Foxtail, Giant | 0 | 0 |
| Foxtail, Green | 0 | — |
| Goosegrass | 0 | 55 |
| Johnsongrass | 0 | 0 |
| *Kochia* | 0 | — |
| Lambsquarters | 100 | 95 |
| Morningglory | 0 | 0 |
| Nightshade | 55 | 80 |
| Nutsedge, Yellow | 0 | 0 |
| Oat, Wild | 0 | 0 |
| Pigweed | 98 | 95 |
| Ragweed | 25 | 40 |
| Russian Thistle | — | 100 |
| Ryegrass, Italian | 0 | — |
| Soybean | 0 | — |
| Sunflower | 0 | 0 |
| Surinam Grass | 0 | 75 |
| Velvetleaf | 0 | 0 |
| Wheat | 0 | 0 |

Test C

Seeds of plant species selected from bluegrass (annual bluegrass, *Poa annua*), blackgrass (*Alopecurus myosuroides*), canarygrass (*Phalaris minor*), chickweed (common chickweed, *Stellaria media*), galium (catchweed bedstraw, *Galium aparine*), bromegrass (downy bromegrass, *Bromus tectorum*), field poppy (*Papaver rhoeas*), field violet (*Viola arvensis*), green foxtail (*Setaria viridis*), deadnettle (henbit deadnettle, *Lamium amplexicaule*), Italian ryegrass (*Lolium multiflorum*), kochia (*Kochia scoparia*), lambsquarters (*Chenopodium album*), oilseed rape (*Brassica napus*), pigweed (*Amaranthus retroflexus*), Russian thistle (*Salsola iberica*), spring barley (*Hordeum vulgare*), spring wheat (*Triticum aestivum*), buckwheat (wild buckwheat, *Polygonum convolvulus*), wild mustard (*Sinapis arvensis*), wild oat (*Avena fatua*), wild radish (*Raphanus raphanistrum*), windgrass (*Apera spica-venti*), winter barley (*Hordeum vulgare*), and winter wheat (*Triticum aestivum*) were planted and treated postemergence with test chemicals formulated in a non-phytotoxic solvent mixture which included a surfactant. Plants ranged in height from 2 to 18 cm (1- to 4-leaf stage).

Treated plants and controls were maintained in a controlled growth environment for 14 days after which time all test plants were visually evaluated and compared to controls. Plant response ratings, summarized in Table C, are based on a scale of 0 to 100 where 0 is no effect and 100 is complete control. A dash (-) response means no test result.

TABLE C

| 125 g ai/ha | Compounds | | | | | |
|---|---|---|---|---|---|---|
| | 2 | 4 | 8 | 11 | 12 | 33 |
| Postemergence | | | | | | |
| Barley, Spring | 0 | 15 | 30 | 30 | 0 | 0 |
| Barley, Winter | 30 | 35 | 40 | 60 | 0 | 5 |
| Blackgrass | 30 | 40 | 35 | 35 | 40 | 35 |
| Bluegrass | 65 | 50 | 75 | 80 | 40 | 40 |
| Bromegrass, Downy | 50 | 40 | 40 | 65 | 20 | 20 |
| Buckwheat, Wild | 70 | 100 | 65 | 80 | 50 | 75 |
| Canarygrass | — | 90 | 10 | 10 | — | 5 |
| Chickweed | — | 100 | 98 | 100 | — | 100 |
| Deadnettle | 100 | 100 | 100 | 100 | 100 | 100 |
| Field Poppy | — | 50 | 60 | 70 | — | 98 |
| Field Violet | 50 | 60 | 65 | 35 | 40 | 95 |
| Foxtail, Green | 95 | 95 | 98 | 95 | 90 | 95 |
| *Galium* | 70 | 90 | 90 | 65 | 80 | 60 |
| *Kochia* | 98 | 95 | 90 | 98 | 75 | 70 |
| Lambsquarters | 98 | 100 | 100 | 100 | 95 | 100 |
| Mustard, Wild | — | 100 | 98 | 100 | 95 | 100 |
| Oat, Wild | 25 | 50 | 30 | 70 | 15 | 10 |
| Oilseed Rape | 90 | 100 | 100 | 100 | 95 | 100 |
| Pigweed | 90 | 100 | 98 | 98 | 75 | 98 |
| Radish, Wild | 95 | 95 | 100 | 95 | 90 | 98 |
| Russian Thistle | 95 | 95 | 95 | 95 | 70 | 90 |
| Ryegrass, Italian | 30 | 15 | 35 | 30 | 0 | 10 |
| Wheat, Spring | 0 | 20 | 20 | 40 | 0 | 10 |
| Wheat, Winter | 30 | 20 | 30 | 35 | 10 | 5 |
| Windgrass | 40 | 95 | 60 | 95 | 50 | 40 |

| 62 g ai/ha | Compounds | | | | |
|---|---|---|---|---|---|
| | 2 | 8 | 11 | 12 | 33 |
| Postemergence | | | | | |
| Barley, Spring | 0 | 20 | 20 | 0 | 0 |
| Barley, Winter | 10 | 20 | 40 | 0 | 0 |
| Blackgrass | 20 | 35 | 35 | 30 | 35 |
| Bluegrass | 25 | 50 | 65 | 30 | 15 |
| Bromegrass, Downy | 30 | 35 | 65 | 15 | 15 |
| Buckwheat, Wild | 40 | 65 | 80 | 50 | 75 |
| Canarygrass | — | 10 | 10 | — | 5 |
| Chickweed | — | 95 | 98 | — | 98 |
| Deadnettle | 100 | 98 | 100 | 100 | 98 |
| Field Poppy | — | 40 | 40 | — | 90 |
| Field Violet | 40 | 65 | 35 | 40 | 95 |
| Foxtail, Green | 95 | 95 | 95 | 80 | 95 |

TABLE C-continued

| 31 g ai/ha | Compounds | | | | | |
|---|---|---|---|---|---|---|
| | 2 | 4 | 8 | 11 | 12 | 33 |
| Galium | 50 | 90 | 65 | 60 | 50 | |
| Kochia | 75 | 85 | 95 | 35 | 60 | |
| Lambsquarters | 80 | 98 | 98 | 80 | 100 | |
| Mustard, Wild | 98 | 98 | 98 | 95 | 98 | |
| Oat, Wild | 25 | 30 | 50 | 15 | 5 | |
| Oilseed Rape | 70 | 98 | 98 | 80 | 100 | |
| Pigweed | 75 | 98 | 95 | 75 | 95 | |
| Radish, Wild | 95 | 98 | 95 | 90 | 95 | |
| Russian Thistle | 70 | 95 | 95 | 60 | 90 | |
| Ryegrass, Italian | 15 | 20 | 30 | 0 | 10 | |
| Wheat, Spring | 0 | 5 | 35 | 0 | 10 | |
| Wheat, Winter | 0 | 25 | 30 | 0 | 5 | |
| Windgrass | 25 | 20 | 85 | — | 25 | |

| 31 g ai/ha | Compounds | | | | | |
|---|---|---|---|---|---|---|
| | 2 | 4 | 8 | 11 | 12 | 33 |
| Postemergence | | | | | | |
| Barley, Spring | 0 | 10 | 10 | 15 | 0 | 0 |
| Barley, Winter | 0 | 5 | 20 | 20 | 0 | 0 |
| Blackgrass | 0 | 20 | 30 | 20 | 20 | 5 |
| Bluegrass | 25 | 35 | 25 | 35 | 20 | 0 |
| Bromegrass, Downy | 20 | 35 | 25 | 50 | 10 | 10 |
| Buckwheat, Wild | 20 | 95 | 65 | 70 | 15 | 65 |
| Canarygrass | — | 0 | 5 | 5 | — | 0 |
| Chickweed | — | 98 | 95 | 95 | — | 90 |
| Deadnettle | 95 | 98 | 95 | 98 | 100 | 98 |
| Field Poppy | — | 30 | 20 | 30 | — | 80 |
| Field Violet | 40 | 40 | 65 | 0 | 35 | 90 |
| Foxtail, Green | 75 | 70 | 95 | 95 | 60 | 95 |
| Galium | 30 | 65 | 75 | 30 | 50 | 40 |
| Kochia | 70 | 90 | 70 | 90 | 10 | 50 |
| Lambsquarters | 75 | 100 | 98 | 98 | 80 | 98 |
| Mustard, Wild | 98 | 98 | 95 | 98 | 95 | 98 |
| Oat, Wild | 15 | 20 | 20 | 25 | 15 | 0 |
| Oilseed Rape | 60 | 90 | 90 | 95 | 70 | 98 |
| Pigweed | 40 | 95 | 95 | 95 | 65 | 95 |
| Radish, Wild | 80 | 80 | 95 | 95 | 80 | 95 |
| Russian Thistle | 60 | 70 | 90 | 80 | 60 | 80 |
| Ryegrass, Italian | 0 | 10 | 0 | 5 | 0 | 0 |
| Wheat, Spring | 0 | 15 | 5 | 20 | 0 | 10 |
| Wheat, Winter | 0 | 0 | 10 | 30 | 0 | 0 |
| Windgrass | 20 | 35 | 10 | 70 | 20 | 20 |

| 16 g ai/ha | Compounds | | | | |
|---|---|---|---|---|---|
| | 2 | 8 | 11 | 12 | 33 |
| Postemergence | | | | | |
| Barley, Spring | 0 | 0 | 0 | 0 | 0 |
| Barley, Winter | 0 | 0 | 0 | 0 | 0 |
| Blackgrass | 0 | 20 | 20 | 0 | 0 |
| Bluegrass | 0 | 5 | — | 10 | 0 |
| Bromegrass, Downy | 10 | 10 | 30 | 0 | 0 |
| Buckwheat, Wild | 15 | 65 | 65 | 10 | 60 |
| Canarygrass | — | 0 | 5 | — | 0 |
| Chickweed | — | 95 | 95 | — | 90 |
| Deadnettle | 95 | 85 | 95 | 100 | 95 |
| Field Poppy | — | 0 | 20 | — | 80 |
| Field Violet | 0 | 10 | 0 | 35 | 65 |
| Foxtail, Green | 65 | 95 | 95 | 50 | 80 |
| Galium | 5 | 50 | 20 | 5 | 35 |
| Kochia | 65 | 65 | 70 | 0 | 35 |
| Lambsquarters | 70 | 98 | 98 | 70 | 98 |
| Mustard, Wild | 98 | — | 98 | 80 | 98 |
| Oat, Wild | 0 | 20 | 25 | 0 | 0 |
| Oilseed Rape | 60 | 80 | 90 | 50 | 90 |
| Pigweed | 35 | 95 | 75 | 65 | 75 |
| Radish, Wild | 65 | 85 | 95 | 60 | 90 |
| Russian Thistle | 35 | 90 | 80 | 60 | 80 |
| Ryegrass, Italian | 0 | 0 | 0 | 0 | 0 |
| Wheat, Spring | 0 | 5 | 5 | 0 | 10 |
| Wheat, Winter | 0 | 10 | 0 | 0 | 0 |
| Windgrass | 5 | 0 | 60 | 5 | 0 |

TABLE C-continued

| | Compounds | |
|---|---|---|
| | 2 | 12 |
| Preemergence | | |
| 125 g ai/ha | | |
| Barley, Spring | 0 | 0 |
| Barley, Winter | 0 | 0 |
| Blackgrass | 0 | 0 |
| Bluegrass | 0 | 35 |
| Bromegrass, Downy | 0 | 0 |
| Buckwheat, Wild | 0 | 40 |
| Canarygrass | 10 | 20 |
| Chickweed | 98 | 50 |
| Deadnettle | 98 | 100 |
| Field Poppy | 100 | 98 |
| Field Violet | 0 | 0 |
| Foxtail, Green | 0 | 0 |
| Galium | 50 | 35 |
| Kochia | 90 | 25 |
| Lambsquarters | 100 | 100 |
| Mustard, Wild | 35 | — |
| Oat, Wild | 0 | 0 |
| Oilseed Rape | 65 | 40 |
| Pigweed | 85 | 65 |
| Radish, Wild | 0 | 0 |
| Ryegrass, Italian | 0 | 0 |
| Wheat, Spring | 0 | 0 |
| Wheat, Winter | 0 | 0 |
| Windgrass | 25 | 40 |
| 62 g ai/ha | | |
| Barley, Spring | 0 | 0 |
| Barley, Winter | 0 | 0 |
| Blackgrass | 0 | 0 |
| Bluegrass | 0 | 20 |
| Bromegrass, Downy | 0 | 0 |
| Buckwheat, Wild | 0 | 0 |
| Canarygrass | 0 | — |
| Chickweed | 98 | — |
| Deadnettle | 95 | 90 |
| Field Poppy | 95 | 98 |
| Field Violet | 0 | 0 |
| Foxtail, Green | 0 | 0 |
| Galium | 0 | 35 |
| Kochia | 30 | 5 |
| Lambsquarters | 0 | 70 |
| Mustard, Wild | 5 | 5 |
| Oat, Wild | 0 | 0 |
| Oilseed Rape | 35 | 30 |
| Pigweed | 65 | 50 |
| Radish, Wild | 0 | 0 |
| Russian Thistle | 0 | 0 |
| Ryegrass, Italian | 0 | 0 |
| Wheat, Spring | 0 | 0 |
| Wheat, Winter | 0 | 0 |
| Windgrass | 25 | 40 |
| 31 g ai/ha | | |
| Barley, Spring | 0 | 0 |
| Barley, Winter | 0 | 0 |
| Blackgrass | 0 | 0 |
| Bluegrass | 0 | 0 |
| Bromegrass, Downy | 0 | 0 |
| Buckwheat, Wild | 0 | 0 |
| Canarygrass | 0 | — |
| Chickweed | 98 | — |
| Deadnettle | 75 | 50 |
| Field Poppy | 75 | 80 |
| Field Violet | 0 | 0 |
| Foxtail, Green | 0 | 0 |
| Galium | — | 0 |
| Kochia | 5 | 5 |
| Lambsquarters | 0 | 20 |
| Mustard, Wild | 0 | — |
| Oat, Wild | 0 | 0 |
| Oilseed Rape | 20 | 20 |
| Pigweed | 20 | 0 |

TABLE C-continued

| | | |
|---|---|---|
| Radish, Wild | 0 | 0 |
| Russian Thistle | 0 | 0 |
| Ryegrass, Italian | 0 | 0 |
| Wheat, Spring | 0 | 0 |
| Wheat, Winter | 0 | 0 |
| Windgrass | 15 | 20 |
| 16 g ai/ha | | |
| Barley, Spring | 0 | 0 |
| Barley, Winter | 0 | 0 |
| Blackgrass | 0 | 0 |
| Bluegrass | 0 | 0 |
| Bromegrass, Downy | 0 | 0 |
| Buckwheat, Wild | 0 | 0 |
| Canarygrass | 0 | — |
| Chickweed | 75 | — |
| Deadnettle | 0 | 35 |
| Field Poppy | — | 50 |
| Field Violet | 0 | 0 |
| Foxtail, Green | 0 | 0 |
| *Galium* | — | 0 |
| *Kochia* | 5 | 5 |
| Lambsquarters | 0 | 0 |
| Mustard, Wild | 0 | 0 |
| Oat, Wild | 0 | 0 |
| Oilseed Rape | 0 | 0 |
| Pigweed | 0 | 0 |
| Radish, Wild | 0 | 0 |
| Russian Thistle | 0 | 0 |
| Ryegrass, Italian | 0 | 0 |
| Wheat, Spring | 0 | 0 |
| Wheat, Winter | 0 | 0 |
| Windgrass | 0 | 20 |

Test D

Seeds of plant species selected from bermudagrass (*Cynodon dactylon*), Surinam grass (*Brachiaria decumbens*), large crabgrass (*Digitaria sanguinalis*), green foxtail (*Setaria viridis*), goosegrass (*Eleusine indica*), johnsongrass (*Sorghum halepense*), kochia (*Kochia scoparia*), morning glory (pitted morning glory, *Ipomoea lacunosa*), nutsedge (purple nutsedge, *Cyperus rotundus*), ragweed (common ragweed, *Ambrosia elatior*), black mustard (*Brassica nigra*), guineagrass (*Panicum maximum*), dallisgrass (*Paspalum dilatatum*), barnyardgrass (*Echinochloa crus-galli*), sandbur (southern sandbur, *Cenchrus echinatus*), sowthistle (common sowthistle, *Sonchus oleraceous*), prickly *sida* (*Sida spinosa*), Italian ryegrass (*Lolium multiflorum*), purslane (common purslane, *Portulaca oleracea*), signalgrass (broadleaf signalgrass, *Brachiaria platyphylla*), groundsel (common groundsel, *Senecio vulgaris*), chickweed (common chickweed, *Stellaria media*), dayflower (Virginia (VA) dayflower, *Commelina virginica*), bluegrass (annual bluegrass, *Poa annua*), naked crabgrass (*Digitaria nuda*), itchgrass (*Rottboellia cochinchinensis*), quackgrass (*Elytrigia repens*), field bindweed (*Convolvulus arvensis*), spanishneedles (*Bidens bipinnata*), mallow (common mallow, *Malva sylvestris*) and Russian thistle (*Salsola kali*), were planted into a blend of loam soil and sand and treated preemergence with test chemicals formulated in a non-phytotoxic solvent mixture which included a surfactant. At the same time, plants from these weed species were treated with postemergence applications of the test chemicals formulated in the same manner. Plants ranged in height from 2 to 18 cm (1- to 4-leaf stage) for postemergence treatments.

Treated plants and controls were maintained in a greenhouse for 14 to 21 days, after which time all species were visually evaluated and compared to controls. Plant response ratings, summarized in Table D, are based on a scale of 0 to 100 where 0 is no effect and 100 is complete control. A dash (-) response means no test result.

TABLE D

| 250 g ai/ha | Compounds | | | | | | |
|---|---|---|---|---|---|---|---|
| | 226 | 235 | 238 | 240 | 243 | 244 | 245 |
| Postemergence | | | | | | | |
| Barnyardgrass | 95 | 95 | 95 | 95 | 90 | 90 | 90 |
| Bermudagrass | 98 | 95 | 95 | 95 | 95 | 95 | 80 |
| Black Mustard | 85 | 98 | 98 | 98 | 98 | 98 | 98 |
| Bluegrass | 30 | 50 | 40 | 35 | 35 | 20 | 35 |
| Chickweed | 85 | 70 | 50 | 70 | 70 | 60 | 50 |
| Crabgrass, Large | 85 | 80 | 80 | 70 | 85 | 75 | 75 |
| Crabgrass, Naked | 75 | — | — | — | — | — | — |
| Dallisgrass | 35 | 80 | 75 | 75 | 90 | 80 | 85 |
| Dayflower, VA | 65 | 75 | 75 | 75 | 75 | 70 | 75 |
| Field Bindweed | 80 | 70 | 50 | 70 | 70 | 70 | 70 |
| Foxtail, Green | 98 | 98 | 95 | 98 | 98 | 100 | 95 |
| Goosegrass | 75 | 75 | 75 | 80 | 75 | 70 | 75 |
| Groundsel | 100 | 100 | 100 | 100 | 100 | 100 | 100 |
| Guineagrass | 80 | 75 | 75 | 80 | 85 | 75 | 85 |
| Itchgrass | 90 | 90 | 80 | 80 | 85 | 75 | 75 |
| Johnsongrass | 90 | 85 | 80 | 95 | 75 | 75 | 75 |
| *Kochia* | 70 | 85 | 75 | 70 | 75 | 65 | 75 |
| Mallow | 65 | 70 | 60 | 60 | 70 | 70 | 70 |
| Morningglory | 80 | 95 | 90 | 95 | 85 | 75 | 80 |
| Nutsedge, Purple | 5 | 40 | 20 | 20 | 50 | 35 | 20 |
| Prickly Sida | 75 | 75 | 65 | 75 | 80 | 60 | 70 |
| Purslane | 70 | 70 | 60 | 50 | 50 | 50 | 30 |
| Quackgrass | 35 | 70 | 40 | 50 | 75 | 65 | 65 |
| Ragweed | 98 | 80 | 75 | 90 | 75 | 85 | 75 |
| Russian Thistle | 70 | 60 | 50 | 35 | 60 | 65 | 70 |
| Ryegrass, Italian | 15 | 35 | 5 | 35 | 65 | 60 | 50 |
| Sandbur | 75 | 75 | 85 | 90 | 80 | 75 | 75 |
| Signalgrass | 65 | 95 | 65 | 85 | 95 | 35 | 75 |
| Sowthistle | 98 | 98 | 95 | 98 | 98 | 100 | 95 |

TABLE D-continued

| | | | | | | | |
|---|---|---|---|---|---|---|---|
| Spanishneedles | 80 | 85 | 75 | 75 | 70 | 75 | 75 |
| Surinam Grass | 90 | 85 | 85 | 95 | 85 | 80 | 75 |

| | Compounds | | | | | | | | | | | | |
|---|---|---|---|---|---|---|---|---|---|---|---|---|---|
| 125 g ai/ha | 47 | 51 | 52 | 59 | 66 | 85 | 87 | 113 | 128 | 226 | 228 | 233 | 235 | 238 |
| Postemergence | | | | | | | | | | | | | |
| Barnyardgrass | 70 | 70 | 80 | 75 | 75 | 70 | 70 | 80 | 90 | 95 | 80 | 85 | 95 | 85 |
| Bermudagrass | 90 | 85 | 80 | 80 | 65 | 90 | 85 | 80 | 90 | 95 | 70 | 70 | 95 | 95 |
| Black Mustard | 100 | 100 | 98 | 98 | 98 | 85 | 100 | 100 | 95 | 80 | 50 | 100 | 98 | 98 |
| Bluegrass | 0 | 0 | 35 | 5 | 0 | 5 | 0 | 0 | 0 | 10 | 5 | 0 | 35 | 20 |
| Chickweed | 65 | 70 | 100 | — | 95 | 100 | 100 | — | 70 | 35 | 75 | 60 | 60 | 40 |
| Crabgrass, Large | 65 | 35 | 70 | 70 | 35 | 75 | 75 | 70 | 70 | 75 | 75 | 60 | 75 | 75 |
| Crabgrass, Naked | 65 | 65 | 95 | 70 | 70 | 80 | 75 | 75 | 75 | 70 | — | 70 | — | — |
| Dallisgrass | 15 | 70 | 75 | 50 | 60 | 80 | 75 | 70 | 60 | 30 | 5 | 35 | 80 | 70 |
| Dayflower, VA | 30 | 20 | 60 | — | 30 | 80 | 70 | 60 | 70 | — | 85 | 60 | 75 | 70 |
| Field Bindweed | 65 | 60 | 70 | 60 | 0 | 75 | 40 | — | 65 | 70 | 70 | 70 | 65 | — |
| Foxtail, Green | 95 | 65 | 95 | 35 | 80 | 65 | 60 | 90 | 70 | 80 | 80 | 35 | 98 | 80 |
| Goosegrass | 65 | 65 | 80 | 65 | 75 | 75 | 65 | 65 | 70 | 70 | 70 | 65 | 75 | 75 |
| Groundsel | 100 | 100 | 100 | 100 | 80 | 100 | 100 | 100 | 100 | 95 | 100 | 100 | 100 | 100 |
| Guineagrass | 30 | 50 | 75 | 20 | 30 | 60 | 30 | 70 | 35 | 80 | 15 | 50 | 75 | 65 |
| Itchgrass | 10 | 80 | 65 | 75 | 40 | 70 | 30 | 70 | 65 | 70 | 65 | 80 | 80 | 75 |
| Johnsongrass | 65 | 70 | — | 60 | 60 | 80 | 60 | 75 | 65 | 80 | 70 | 50 | 85 | 75 |
| Kochia | 30 | 20 | 40 | 50 | 40 | 60 | 60 | 50 | 40 | 70 | 75 | 35 | 70 | 65 |
| Mallow | 65 | 20 | 75 | 40 | 60 | 75 | 70 | 20 | 40 | 50 | 65 | 0 | 70 | 50 |
| Morningglory | 50 | 65 | 70 | 50 | 90 | 90 | 50 | 90 | 70 | 70 | 50 | 70 | 95 | 80 |
| Nutsedge, Purple | 20 | 20 | 40 | 25 | 30 | 65 | 50 | 50 | 50 | 0 | 15 | 0 | 30 | 20 |
| Prickly Sida | 90 | 75 | 90 | 70 | 98 | 98 | 95 | 70 | 80 | 70 | 65 | 60 | 70 | 50 |
| Purslane | 30 | 35 | 75 | 50 | 75 | 90 | 35 | 75 | 50 | 65 | 35 | 40 | 60 | 60 |
| Quackgrass | 5 | 0 | 20 | 0 | 5 | 20 | 5 | 30 | 5 | 20 | 5 | 25 | 40 | 30 |
| Ragweed | 95 | 85 | 95 | 80 | 5 | 100 | 98 | 80 | 90 | 90 | 75 | 98 | 80 | 75 |
| Russian Thistle | — | — | — | 65 | — | — | 35 | 20 | — | 40 | 65 | 10 | 50 | 50 |
| Ryegrass, Italian | 30 | 0 | 35 | 5 | 15 | 20 | 5 | 50 | 5 | 0 | 5 | 5 | 5 | 5 |
| Sandbur | 35 | 60 | 80 | 25 | 90 | 95 | 35 | 60 | 35 | 75 | 5 | 75 | 75 | 75 |
| Signalgrass | 20 | 50 | 90 | 20 | 30 | 75 | 60 | 75 | 35 | 65 | 20 | 35 | 90 | 60 |
| Sowthistle | 100 | 100 | 100 | 100 | 90 | 100 | 100 | 100 | 100 | 100 | 98 | 100 | 98 | 95 |
| Spanishneedles | 70 | 70 | 80 | 70 | 80 | 95 | 70 | 60 | 65 | 75 | 70 | 60 | 80 | 70 |
| Surinam Grass | 70 | 80 | 90 | 60 | 90 | 85 | 40 | — | 50 | 90 | 70 | 60 | 75 | 75 |

| | Compounds | | | |
|---|---|---|---|---|
| 125 g ai/ha | 240 | 243 | 244 | 245 |
| Postemergence | | | | |
| Barnyardgrass | 95 | 80 | 85 | 85 |
| Bermudagrass | 95 | 95 | 95 | 80 |
| Black Mustard | 98 | 98 | 95 | 98 |
| Bluegrass | 35 | 35 | 10 | 35 |
| Chickweed | 60 | 60 | 40 | 50 |
| Crabgrass, Large | 65 | 85 | 75 | 75 |
| Crabgrass, Naked | — | — | — | — |
| Dallisgrass | 75 | 90 | 75 | 80 |
| Dayflower, VA | 70 | 70 | 65 | 65 |
| Field Bindweed | 70 | 70 | 65 | 60 |
| Foxtail, Green | 98 | 90 | 95 | 95 |
| Goosegrass | 80 | 70 | 70 | 70 |
| Groundsel | 100 | 100 | 100 | 100 |
| Guineagrass | 80 | 75 | 75 | 75 |
| Itchgrass | 80 | 75 | 75 | 75 |
| Johnsongrass | 95 | 70 | 75 | 75 |
| Kochia | 65 | 70 | 50 | 70 |
| Mallow | 60 | 70 | 60 | 50 |
| Morningglory | 90 | 85 | 75 | 80 |
| Nutsedge, Purple | 5 | 25 | 10 | 5 |
| Prickly Sida | 75 | 70 | 40 | 50 |
| Purslane | — | 50 | 50 | 30 |
| Quackgrass | 35 | 70 | 50 | 40 |
| Ragweed | 80 | 75 | 80 | 75 |
| Russian Thistle | — | 30 | 60 | 60 |
| Ryegrass, Italian | 35 | 30 | 35 | 20 |
| Sandbur | 90 | 75 | 75 | 75 |
| Signalgrass | 75 | 75 | 25 | 50 |
| Sowthistle | 98 | 95 | 100 | 95 |
| Spanishneedles | 75 | 70 | 75 | 70 |
| Surinam Grass | 95 | 75 | 80 | 75 |

TABLE D-continued

| 62 g ai/ha | Compounds | | | | | | | | | | | | | |
|---|---|---|---|---|---|---|---|---|---|---|---|---|---|---|
| | 47 | 51 | 52 | 59 | 66 | 85 | 87 | 113 | 128 | 226 | 233 | 235 | 238 | 240 |
| | Postemergence | | | | | | | | | | | | | |
| Barnyardgrass | 70 | 70 | 75 | 60 | 70 | 65 | 60 | 80 | 70 | 85 | 85 | 80 | 80 | 95 |
| Bermudagrass | 70 | 80 | 75 | 70 | 65 | 80 | 70 | 80 | 80 | 95 | 70 | 95 | 90 | 95 |
| Black Mustard | 100 | — | 98 | 65 | 50 | 75 | 100 | 100 | 95 | 80 | 50 | 80 | 95 | 80 |
| Bluegrass | 0 | 0 | 35 | 0 | 0 | 5 | 0 | 0 | 0 | 10 | 0 | 20 | 5 | 35 |
| Chickweed | — | — | 98 | 70 | 35 | 100 | 75 | — | 65 | 35 | — | 30 | 35 | 50 |
| Crabgrass, Large | 60 | 35 | 70 | 50 | 25 | 75 | 70 | 70 | 60 | 75 | 50 | 75 | 70 | 65 |
| Crabgrass, Naked | 35 | — | 95 | 50 | 65 | 75 | 70 | 70 | 70 | 65 | 60 | — | — | — |
| Dallisgrass | 15 | 30 | 70 | 20 | 35 | 65 | 50 | 60 | 30 | 20 | 10 | 75 | 65 | 70 |
| Dayflower, VA | 20 | 10 | 30 | 60 | 0 | 60 | 60 | 60 | 60 | 50 | 35 | 70 | 65 | 60 |
| Field Bindweed | 50 | 20 | 70 | 30 | 0 | 75 | 25 | 65 | 65 | 70 | 50 | 65 | 50 | 70 |
| Foxtail, Green | 50 | 40 | 85 | 20 | 65 | 35 | 35 | 70 | 65 | 70 | 30 | 95 | 80 | 98 |
| Goosegrass | 65 | 65 | 75 | 50 | 65 | 75 | 65 | 65 | 65 | 70 | 60 | 75 | 70 | 70 |
| Groundsel | 100 | 100 | 100 | 100 | 80 | 100 | 100 | 100 | 100 | 90 | 90 | 100 | 100 | 100 |
| Guineagrass | 20 | 30 | 75 | 20 | 10 | 35 | 20 | 50 | 30 | 80 | 40 | 75 | 50 | 65 |
| Itchgrass | 5 | 40 | 65 | 15 | 35 | 65 | 30 | 65 | 40 | 70 | 70 | 75 | 70 | 75 |
| Johnsongrass | 35 | 60 | 85 | 40 | 50 | 80 | 40 | 65 | 50 | 80 | 50 | 70 | 70 | 90 |
| *Kochia* | 20 | 5 | 0 | 20 | 25 | 20 | 35 | 50 | 30 | 60 | 30 | 60 | 50 | 65 |
| Mallow | 65 | 0 | 65 | 5 | 60 | 70 | 70 | 0 | 40 | 50 | 0 | 50 | 35 | 40 |
| Morningglory | — | 20 | 70 | 50 | 90 | 75 | 40 | 90 | 70 | 70 | 70 | 75 | 80 | 80 |
| Nutsedge, Purple | 10 | 15 | 35 | 20 | 20 | 50 | 20 | 35 | 35 | 0 | 0 | 5 | 10 | 5 |
| Prickly Sida | 80 | 65 | 80 | 70 | 98 | 95 | 80 | 70 | 65 | 65 | 50 | 65 | 30 | 65 |
| Purslane | 30 | 35 | 65 | 35 | 75 | 90 | 35 | 50 | 30 | 50 | 30 | 60 | 60 | 35 |
| Quackgrass | 0 | 0 | 15 | 0 | 5 | 15 | 0 | 20 | 0 | 0 | 10 | 30 | 5 | 30 |
| Ragweed | 80 | 80 | 95 | — | 0 | 80 | 95 | 75 | 90 | 90 | 75 | 70 | 75 | 75 |
| Russian Thistle | 20 | — | — | — | — | — | — | 20 | 20 | — | — | 30 | 40 | 35 |
| Ryegrass, Italian | 20 | 0 | 15 | 5 | 0 | 15 | 0 | 35 | 0 | 0 | 5 | 5 | 5 | 35 |
| Sandbur | 20 | 25 | 75 | 5 | 35 | 65 | 20 | 60 | 5 | 75 | 70 | 75 | 75 | 70 |
| Signalgrass | 15 | 50 | 80 | 10 | 30 | 60 | 60 | 60 | 35 | 40 | 25 | 90 | 35 | 75 |
| Sowthistle | 100 | 100 | 98 | 100 | 70 | 100 | 98 | 100 | 100 | 98 | — | 98 | 95 | 98 |
| Spanishneedles | 65 | 60 | 80 | 70 | 80 | 90 | 60 | 50 | 50 | 75 | 50 | 70 | 70 | 65 |
| Surinam Grass | 60 | 70 | 80 | 50 | 90 | 75 | 40 | 80 | 30 | 70 | 50 | 75 | 75 | 70 |

| 62 g ai/ha | Compounds | | |
|---|---|---|---|
| | 243 | 244 | 245 |
| | Postemergence | | |
| Barnyardgrass | 80 | 80 | 85 |
| Bermudagrass | 85 | 80 | 80 |
| Black Mustard | 75 | 75 | 95 |
| Bluegrass | 5 | 10 | 20 |
| Chickweed | 50 | 20 | 25 |
| Crabgrass, Large | 80 | 75 | 70 |
| Crabgrass, Naked | — | — | — |
| Dallisgrass | 80 | 75 | 75 |
| Dayflower, VA | 65 | 50 | 35 |
| Field Bindweed | 70 | 35 | 50 |
| Foxtail, Green | 85 | 90 | 90 |
| Goosegrass | 70 | 60 | 70 |
| Groundsel | 100 | 100 | 100 |
| Guineagrass | 75 | 75 | 75 |
| Itchgrass | 75 | 70 | 70 |
| Johnsongrass | 70 | 70 | 75 |
| *Kochia* | 60 | 50 | 65 |
| Mallow | 60 | 50 | 50 |
| Morningglory | 85 | 70 | 75 |
| Nutsedge, Purple | 25 | 0 | 5 |
| Prickly Sida | 65 | 35 | 50 |
| Purslane | 50 | 50 | 5 |
| Quackgrass | 40 | 40 | 35 |
| Ragweed | 70 | 70 | 75 |
| Russian Thistle | 30 | 40 | 60 |
| Ryegrass, Italian | 20 | 15 | 5 |
| Sandbur | 75 | 70 | 70 |
| Signalgrass | 75 | 20 | 40 |
| Sowthistle | 90 | 95 | 95 |
| Spanishneedles | 65 | 65 | 70 |
| Surinam Grass | 75 | 75 | 75 |

TABLE D-continued

| 31 g ai/ha | Compounds | | | | | | | | | | | | | |
|---|---|---|---|---|---|---|---|---|---|---|---|---|---|---|
| | 47 | 51 | 52 | 59 | 66 | 85 | 87 | 113 | 128 | 226 | 228 | 233 | 235 | 238 |
| | Postemergence | | | | | | | | | | | | | |
| Barnyardgrass | 70 | 70 | 75 | 60 | 65 | 50 | 50 | 75 | 70 | 85 | 20 | 75 | 80 | 75 |
| Bermudagrass | 50 | 75 | 75 | 40 | 50 | 75 | 65 | 70 | 70 | 90 | 70 | 70 | 80 | 80 |
| Black Mustard | 100 | 95 | 90 | 40 | 20 | 60 | 65 | — | 95 | 65 | 20 | 50 | 80 | 80 |
| Bluegrass | 0 | 0 | 25 | 0 | 0 | 0 | 0 | 0 | 0 | 0 | 0 | 0 | 5 | 0 |
| Chickweed | 65 | — | 90 | 70 | — | 80 | 75 | 70 | — | 20 | 35 | 50 | 5 | 30 |
| Crabgrass, Large | 50 | 35 | 70 | 35 | 25 | 60 | 65 | 60 | 50 | 65 | 65 | 40 | 70 | 50 |
| Crabgrass, Naked | 35 | 50 | 75 | 30 | 50 | 50 | 60 | 65 | 65 | 60 | — | 50 | — | — |
| Dallisgrass | 10 | 20 | 65 | 10 | 35 | 25 | 25 | 10 | 20 | 15 | 0 | 10 | 70 | 10 |
| Dayflower, VA | 15 | 10 | 5 | — | 0 | 30 | 35 | 40 | 50 | 50 | 35 | 35 | 60 | 35 |
| Field Bindweed | 40 | 5 | 70 | 5 | 0 | 75 | 15 | 65 | 50 | 70 | 65 | 50 | 60 | 35 |
| Foxtail, Green | 35 | 20 | 70 | 5 | 35 | 25 | 30 | 60 | 40 | 65 | 70 | 10 | 70 | 75 |
| Goosegrass | 65 | 65 | 75 | 20 | 50 | 65 | 35 | 50 | 40 | 70 | 50 | 50 | 75 | 50 |
| Groundsel | 100 | 98 | 100 | 90 | 60 | 100 | 98 | 90 | 100 | 80 | 100 | 50 | 100 | 100 |
| Guineagrass | 20 | 30 | 70 | 10 | 5 | 20 | 20 | 25 | 30 | 80 | 0 | 30 | 75 | 25 |
| Itchgrass | 5 | 20 | 50 | 15 | 15 | 35 | 0 | 10 | 40 | 50 | 40 | 65 | 70 | 70 |
| Johnsongrass | 15 | 35 | 75 | 35 | 20 | 50 | 30 | 40 | 40 | 50 | 65 | 35 | 70 | 60 |
| *Kochia* | 10 | 5 | 0 | 5 | 25 | 10 | 35 | 40 | 30 | 60 | 65 | 20 | 20 | 20 |
| Mallow | 50 | 0 | 65 | 5 | 30 | 65 | 60 | 0 | 5 | 35 | 40 | 0 | 10 | 25 |
| Morningglory | 5 | 20 | 65 | 40 | 70 | 70 | 40 | 60 | 65 | 50 | 50 | 60 | 75 | 70 |
| Nutsedge, Purple | 0 | 0 | 20 | 0 | 5 | 30 | 10 | 10 | 10 | 0 | 5 | 0 | 5 | 5 |
| Prickly Sida | 70 | 50 | 65 | 40 | 98 | 95 | 80 | 60 | 60 | 40 | 40 | 50 | 65 | 30 |
| Purslane | 20 | 20 | 65 | 35 | 50 | 80 | 25 | 30 | 30 | 50 | — | 30 | 60 | 60 |
| Quackgrass | 0 | 0 | 10 | 0 | 5 | 0 | 0 | 0 | 0 | 0 | 0 | 0 | 5 | 5 |
| Ragweed | 75 | 75 | 95 | 70 | 0 | 80 | 80 | 70 | 75 | 80 | 75 | 75 | 70 | 70 |
| Russian Thistle | — | — | — | — | — | — | — | 0 | 0 | — | 20 | — | 30 | 30 |
| Ryegrass, Italian | 10 | 0 | 0 | 0 | 0 | 0 | 0 | 20 | 0 | 0 | 0 | 0 | 5 | 5 |
| Sandbur | 5 | 25 | 65 | 5 | 35 | 50 | 5 | 10 | 5 | 60 | 5 | 65 | 75 | 50 |
| Signalgrass | 5 | 35 | 60 | 5 | 10 | 35 | 30 | 40 | 30 | 35 | 15 | 5 | 65 | 20 |
| Sowthistle | 100 | 98 | 95 | 100 | 65 | 100 | 98 | 95 | 100 | 90 | 95 | 100 | 98 | 95 |
| Spanishneedles | 40 | 50 | 75 | 50 | 70 | 75 | 60 | 35 | 50 | 70 | 65 | 35 | 65 | 65 |
| Surinam Grass | 50 | 60 | 65 | 35 | 60 | 75 | 40 | 75 | 25 | 65 | 5 | — | 75 | 75 |

| 31 g ai/ha | Compounds | | | |
|---|---|---|---|---|
| | 240 | 243 | 244 | 245 |
| | Postemergence | | | |
| Barnyardgrass | 80 | 75 | 80 | 80 |
| Bermudagrass | 85 | 75 | 80 | 80 |
| Black Mustard | 70 | 50 | 50 | 75 |
| Bluegrass | 5 | 5 | 0 | 5 |
| Chickweed | 25 | 35 | 15 | 5 |
| Crabgrass, Large | 40 | 75 | 70 | 70 |
| Crabgrass, Naked | — | — | — | — |
| Dallisgrass | 5 | 75 | 40 | 65 |
| Dayflower, VA | 35 | 35 | 30 | 20 |
| Field Bindweed | 60 | 65 | 20 | 50 |
| Foxtail, Green | 95 | 80 | 75 | 85 |
| Goosegrass | 70 | 65 | 50 | 70 |
| Groundsel | 100 | 98 | 100 | 95 |
| Guineagrass | 40 | 70 | 70 | 75 |
| Itchgrass | 75 | 75 | 60 | 70 |
| Johnsongrass | 70 | 70 | 70 | 70 |
| *Kochia* | 20 | 50 | 25 | 50 |
| Mallow | 10 | 50 | 50 | 35 |
| Morningglory | 65 | 75 | 65 | 70 |
| Nutsedge, Purple | 0 | 20 | 0 | 5 |
| Prickly Sida | 35 | 60 | 25 | 30 |
| Purslane | 0 | 35 | 25 | 0 |
| Quackgrass | 25 | 35 | 20 | 20 |
| Ragweed | 70 | 65 | 65 | 70 |
| Russian Thistle | 35 | 20 | 20 | 25 |
| Ryegrass, Italian | 0 | 0 | 5 | 5 |
| Sandbur | 70 | 75 | 70 | 65 |
| Signalgrass | 20 | 50 | 20 | 10 |
| Sowthistle | 98 | 90 | 75 | 95 |
| Spanishneedles | 65 | 60 | 65 | 65 |
| Surinam Grass | 70 | 75 | 75 | 75 |

TABLE D-continued

| 16 g ai/ha | Compounds | | | | | | | | | |
|---|---|---|---|---|---|---|---|---|---|---|
| | 47 | 51 | 52 | 59 | 66 | 85 | 87 | 113 | 128 | 233 |
| Postemergence | | | | | | | | | | |
| Barnyardgrass | 70 | 65 | 75 | 40 | 35 | 30 | 35 | 65 | 35 | 65 |
| Bermudagrass | 50 | 65 | 75 | 35 | 5 | 65 | 65 | 65 | 70 | 70 |
| Black Mustard | 95 | 70 | 65 | 10 | 0 | 35 | 40 | 100 | 95 | 20 |
| Bluegrass | 0 | 0 | 15 | 0 | 0 | 0 | 0 | 0 | 0 | 0 |
| Chickweed | 50 | — | 75 | — | — | — | 75 | — | 60 | — |
| Crabgrass, Large | 20 | 25 | 65 | 35 | 20 | 60 | 40 | 60 | 40 | 20 |
| Crabgrass, Naked | 20 | 35 | 70 | 20 | — | — | 50 | 50 | 35 | 30 |
| Dallisgrass | 5 | 20 | 60 | 10 | 35 | 15 | 25 | 10 | 10 | 0 |
| Dayflower, VA | 10 | 10 | 5 | 25 | 0 | 20 | 10 | 20 | 50 | 15 |
| Field Bindweed | 35 | 5 | 50 | 5 | 0 | 65 | 0 | 50 | 50 | 10 |
| Foxtail, Green | 5 | 10 | 70 | 0 | 20 | 20 | 5 | 25 | 25 | 5 |
| Goosegrass | 40 | 35 | 65 | 20 | 50 | 40 | 30 | 40 | 35 | 40 |
| Groundsel | 100 | 85 | 100 | 70 | — | 100 | 98 | 90 | 100 | 30 |
| Guineagrass | 10 | 20 | 50 | 10 | 5 | 10 | 10 | 25 | 20 | 20 |
| Itchgrass | 0 | 0 | 25 | 0 | 10 | 30 | 0 | 0 | 0 | 50 |
| Johnsongrass | 5 | 20 | 65 | 30 | 0 | 35 | 20 | 40 | 35 | 20 |
| *Kochia* | 0 | 5 | 0 | 5 | — | 0 | 25 | 25 | 20 | 10 |
| Mallow | 35 | 0 | 50 | 0 | 25 | 60 | 40 | 0 | 5 | 0 |
| Morningglory | 5 | 0 | 50 | 0 | 65 | 70 | 40 | 50 | 65 | 50 |
| Nutsedge, Purple | 0 | 0 | 0 | 0 | 0 | 5 | 0 | 0 | 0 | 0 |
| Prickly Sida | 60 | 50 | 65 | 40 | — | — | 70 | 50 | 50 | 30 |
| Purslane | 20 | 10 | 65 | 35 | — | 75 | 10 | 30 | 30 | 30 |
| Quackgrass | 0 | 0 | 5 | 0 | 0 | 0 | 0 | 0 | 0 | 0 |
| Ragweed | 75 | 60 | 90 | 70 | 0 | 80 | 70 | 70 | — | 65 |
| Russian Thistle | 20 | 0 | — | — | — | — | — | 0 | 0 | 0 |
| Ryegrass, Italian | 0 | 0 | 0 | 0 | 0 | 0 | 0 | 0 | 0 | 0 |
| Sandbur | 5 | 5 | 65 | 5 | — | 10 | 5 | 5 | 5 | 30 |
| Signalgrass | 0 | 5 | 50 | 5 | 0 | 20 | 20 | 5 | 0 | 0 |
| Sowthistle | 90 | 95 | 80 | 70 | 35 | 100 | 90 | 90 | 100 | 90 |
| Spanishneedles | 35 | 35 | 75 | 30 | 65 | 75 | 60 | 35 | 35 | 35 |
| Surinam Grass | 35 | 50 | — | 30 | — | — | 30 | 60 | — | 30 |

| 250 g ai/ha | Compound 243 |
|---|---|
| Preemergence | |
| Barnyardgrass | 100 |
| Bermudagrass | 100 |
| Black Mustard | 100 |
| Bluegrass | 100 |
| Crabgrass, Large | 100 |
| Crabgrass, Naked | 100 |
| Dallisgrass | 100 |
| Dayflower, VA | 100 |
| Field Bindweed | 100 |
| Foxtail, Green | 100 |
| Goosegrass | 100 |
| Guineagrass | 100 |
| Itchgrass | 100 |
| Johnsongrass | 100 |
| *Kochia* | 100 |
| Mallow | 98 |
| Morningglory | 100 |
| Nutsedge, Purple | 100 |
| Prickly Sida | 100 |
| Purslane | 100 |
| Quackgrass | 98 |
| Ragweed | 100 |
| Russian Thistle | 100 |
| Ryegrass, Italian | 100 |
| Sandbur | 100 |
| Signalgrass | 100 |
| Spanishneedles | 100 |
| Surinam Grass | 100 |

TABLE D-continued

| | Compounds | | | | | | | | | | |
|---|---|---|---|---|---|---|---|---|---|---|---|
| | 47 | 51 | 52 | 59 | 66 | 85 | 87 | 113 | 128 | 233 | 243 |
| | Preemergence | | | | | | | | | | |
| 125 g ai/ha | | | | | | | | | | | |
| Barnyardgrass | 5 | 10 | 10 | 10 | 75 | 98 | 95 | 35 | 15 | 40 | 100 |
| Bermudagrass | 100 | 30 | 100 | 90 | 5 | 100 | 98 | 85 | 75 | 85 | 100 |
| Black Mustard | 100 | 100 | 100 | 100 | 80 | 100 | 100 | 100 | 95 | 65 | 100 |
| Bluegrass | 35 | 0 | 20 | 30 | 0 | 15 | 35 | 0 | 25 | 40 | 95 |
| Chickweed | — | — | 95 | — | 98 | 100 | — | — | — | — | — |
| Crabgrass, Large | 95 | 5 | 98 | 65 | 98 | 100 | 100 | 95 | — | 90 | 100 |
| Crabgrass, Naked | 98 | 0 | 80 | 95 | 25 | 98 | 100 | 100 | 75 | 65 | 100 |
| Dallisgrass | 75 | 90 | 95 | 75 | 95 | 98 | 98 | 100 | 98 | 35 | 100 |
| Dayflower, VA | 50 | 0 | 40 | 35 | 5 | 95 | 65 | 65 | 25 | 100 | 100 |
| Field Bindweed | 35 | 0 | 50 | 60 | 20 | 98 | 70 | 90 | 98 | 85 | 100 |
| Foxtail, Green | 0 | 0 | 15 | 0 | 5 | 70 | 10 | 20 | 0 | 0 | 100 |
| Goosegrass | 75 | 40 | 98 | 80 | 50 | 98 | 100 | 95 | 90 | 100 | 100 |
| Guineagrass | 0 | 75 | — | 0 | 65 | 75 | 75 | 100 | 0 | 0 | 100 |
| Itchgrass | 0 | 0 | 5 | 20 | 0 | 50 | 20 | 0 | 20 | 20 | 50 |
| Johnsongrass | 75 | 70 | 95 | 35 | 30 | 95 | 70 | 10 | 65 | 65 | 100 |
| Kochia | 100 | 50 | 35 | 0 | 90 | 95 | 100 | 100 | 50 | 80 | 100 |
| Mallow | 98 | 65 | — | 65 | 75 | 98 | 100 | 90 | 100 | 60 | 80 |
| Morningglory | 65 | 100 | 100 | 80 | 95 | 100 | 95 | 90 | 90 | 95 | 98 |
| Nutsedge, Purple | 35 | 5 | 40 | 80 | 70 | 95 | 75 | 80 | 70 | 5 | 100 |
| Prickly Sida | 100 | 35 | 100 | 65 | 90 | 100 | 100 | 90 | 30 | 70 | 100 |
| Purslane | 100 | 100 | 100 | 100 | 100 | 100 | 100 | 100 | 100 | 100 | 100 |
| Quackgrass | 0 | 0 | 20 | 0 | 0 | 20 | 0 | 0 | 0 | 0 | 85 |
| Ragweed | 100 | 95 | 98 | 100 | 0 | 100 | 98 | 98 | 100 | 98 | 100 |
| Russian Thistle | 100 | 75 | — | 100 | — | — | 100 | 100 | 100 | 100 | 100 |
| Ryegrass, Italian | 0 | 0 | 15 | 20 | 0 | 20 | 30 | 20 | 0 | 20 | 98 |
| Sandbur | 90 | 75 | 98 | 0 | 80 | 98 | 95 | 90 | 20 | 85 | 100 |
| Signalgrass | 90 | 10 | 90 | 5 | 5 | 95 | 75 | 90 | 5 | 35 | 95 |
| Sowthistle | 100 | 100 | 100 | 100 | 0 | 100 | 100 | 100 | 100 | 100 | — |
| Spanishneedles | 95 | 98 | 98 | 90 | 95 | 100 | 98 | 95 | 100 | 95 | 100 |
| Surinam Grass | — | — | 98 | 100 | 98 | 100 | 100 | 95 | 90 | 100 | 100 |
| 62 g ai/ha | | | | | | | | | | | |
| Barnyardgrass | 5 | 0 | 0 | 0 | 5 | 95 | 50 | 0 | 5 | 5 | 100 |
| Bermudagrass | 50 | 0 | 90 | 40 | 5 | 100 | 98 | 70 | 65 | 85 | 100 |
| Black Mustard | 80 | 75 | 80 | 60 | 35 | 98 | 100 | 80 | 85 | 20 | 100 |
| Bluegrass | 0 | 0 | 0 | 15 | 0 | 0 | 25 | 0 | 25 | 25 | 40 |
| Chickweed | — | — | — | — | 90 | 100 | — | — | — | — | — |
| Crabgrass, Large | 5 | 5 | 75 | 35 | 50 | 100 | 95 | 95 | 60 | 25 | 100 |
| Crabgrass, Naked | 60 | 0 | 20 | 65 | 10 | 95 | 100 | 90 | 0 | 65 | 100 |
| Dallisgrass | 65 | 10 | 50 | 65 | 5 | 95 | 80 | 50 | 65 | 0 | 100 |
| Dayflower, VA | 50 | — | 0 | 35 | 0 | 90 | 65 | 50 | 10 | 100 | 100 |
| Field Bindweed | 0 | 0 | 20 | 20 | 0 | 70 | 40 | 65 | 35 | 85 | 100 |
| Foxtail, Green | 0 | 0 | 0 | 0 | 0 | 40 | 0 | 0 | 0 | 0 | 35 |
| Goosegrass | 5 | 40 | 80 | 20 | 30 | 75 | 95 | 75 | 65 | 98 | 100 |
| Guineagrass | 0 | 0 | 50 | 0 | 0 | 70 | 50 | 100 | 0 | 0 | 100 |
| Itchgrass | 0 | 0 | 0 | 0 | 0 | 35 | 20 | 0 | 0 | 0 | 25 |
| Johnsongrass | 0 | 20 | 75 | 10 | 0 | 80 | 20 | 10 | 15 | 20 | 100 |
| Kochia | 100 | 0 | 25 | 0 | 65 | 75 | 100 | 100 | 50 | 20 | 80 |
| Mallow | 65 | 0 | — | 65 | 5 | 95 | 80 | 5 | 70 | 0 | 50 |
| Morningglory | 20 | 30 | 0 | 0 | 90 | 90 | 80 | 60 | 0 | 95 | — |
| Nutsedge, Purple | 10 | 5 | 30 | 20 | 35 | 95 | 50 | 20 | 0 | 0 | 20 |
| Prickly Sida | 65 | 20 | 50 | 5 | 5 | 100 | 100 | 70 | 25 | 0 | 100 |
| Purslane | 95 | 65 | 90 | 100 | 60 | 100 | 100 | 100 | 100 | 100 | 95 |
| Quackgrass | 0 | 0 | 0 | 0 | 0 | 15 | 0 | 0 | 0 | 0 | 35 |
| Ragweed | 100 | 65 | 70 | 90 | 0 | 100 | 98 | 80 | 90 | 95 | 100 |
| Russian Thistle | 50 | 75 | — | 90 | — | — | 90 | 100 | 95 | 75 | 100 |
| Ryegrass, Italian | 0 | 0 | 0 | 0 | 0 | 10 | 0 | 0 | 0 | 0 | 60 |
| Sandbur | 5 | 5 | 5 | 0 | 10 | 60 | 50 | 65 | 20 | 50 | 100 |
| Signalgrass | 10 | 0 | 50 | 0 | 5 | 75 | 75 | 0 | 0 | 10 | 75 |
| Sowthistle | 100 | 98 | 80 | 100 | 0 | 100 | 100 | 100 | 100 | 100 | — |
| Spanishneedles | 95 | 90 | 95 | 0 | 85 | 98 | 85 | — | 90 | 85 | 100 |
| Surinam Grass | 0 | 100 | 98 | 100 | 95 | 100 | 95 | — | 80 | 65 | 100 |
| 31 g ai/ha | | | | | | | | | | | |
| Barnyardgrass | 0 | 0 | 0 | 0 | 0 | 75 | 5 | 0 | 0 | 0 | 60 |
| Bermudagrass | 25 | 0 | 70 | 0 | 0 | 100 | 65 | 50 | 0 | 5 | 75 |
| Black Mustard | 65 | 50 | 20 | 40 | 5 | 60 | 75 | 0 | 60 | 0 | 80 |
| Bluegrass | 0 | 0 | 0 | 0 | 0 | 0 | 20 | 0 | 0 | 0 | 10 |
| Chickweed | — | — | — | — | 20 | 100 | — | — | — | — | — |
| Crabgrass, Large | 0 | 5 | 20 | 35 | 30 | 98 | 75 | 30 | 25 | 5 | 100 |
| Crabgrass, Naked | 0 | 0 | 0 | 0 | 0 | 95 | 80 | 0 | 0 | 0 | 100 |
| Dallisgrass | 25 | 10 | 10 | 0 | 5 | 80 | 50 | 50 | 20 | 0 | 75 |

TABLE D-continued

| | | | | | | | | | | |
|---|---|---|---|---|---|---|---|---|---|---|
| Dayflower, VA | 35 | 0 | 0 | 0 | 0 | 10 | 0 | 50 | 0 | 80 | 90 |
| Field Bindweed | 0 | 0 | — | 0 | 0 | 70 | 0 | 20 | 0 | 0 | 100 |
| Foxtail, Green | 0 | 0 | 0 | 0 | 0 | 5 | 0 | 0 | 0 | 0 | 20 |
| Goosegrass | 0 | 20 | 60 | 5 | 0 | 75 | 35 | 25 | 5 | 95 | 100 |
| Guineagrass | 0 | 0 | — | 0 | 0 | 10 | 0 | 65 | 0 | 0 | 100 |
| Itchgrass | 0 | 0 | 0 | 0 | 0 | 15 | 20 | 0 | 0 | 0 | 10 |
| Johnsongrass | 0 | 0 | 0 | 0 | 0 | 65 | 5 | 0 | 0 | 0 | 95 |
| *Kochia* | 50 | — | 25 | 0 | 65 | 20 | 98 | 70 | 0 | 0 | — |
| Mallow | 0 | 0 | — | 65 | 0 | — | — | 5 | 70 | 0 | 0 |
| Morningglory | 0 | 0 | 0 | 0 | 0 | 70 | — | 60 | 0 | 80 | 90 |
| Nutsedge, Purple | 0 | 0 | 5 | 20 | 0 | 75 | 5 | 10 | 0 | 0 | 5 |
| Prickly Sida | 50 | 20 | 0 | 0 | 0 | 100 | 60 | 35 | 0 | 0 | 85 |
| Purslane | 0 | 50 | 60 | 100 | 0 | 100 | 100 | 100 | 0 | 0 | 75 |
| Quackgrass | 0 | 0 | 0 | 0 | 0 | 0 | 0 | 0 | 0 | 0 | 0 |
| Ragweed | 50 | 50 | 50 | 50 | 0 | 95 | 98 | 50 | 75 | 70 | 100 |
| Russian Thistle | — | — | — | 90 | — | — | 75 | 65 | 0 | 65 | 100 |
| Ryegrass, Italian | 0 | 0 | 0 | 0 | 0 | 0 | 0 | 0 | 0 | 0 | 50 |
| Sandbur | 0 | 0 | 0 | 0 | 5 | 5 | 25 | 0 | 0 | 0 | 75 |
| Signalgrass | 0 | 0 | 0 | 0 | 5 | 60 | 0 | 0 | 0 | 0 | — |
| Sowthistle | 65 | 75 | 80 | 95 | 0 | 100 | 100 | 75 | 80 | 50 | — |
| Spanishneedles | 95 | 0 | 70 | 0 | 60 | 98 | 65 | 0 | 0 | 50 | 100 |
| Surinam Grass | — | 98 | 98 | 90 | 80 | 100 | 50 | 40 | 35 | 5 | 100 |

| | Compounds | | | | | | | | | |
|---|---|---|---|---|---|---|---|---|---|---|
| 16 g ai/ha | 47 | 51 | 52 | 59 | 66 | 85 | 87 | 113 | 128 | 233 |
| | Preemergence | | | | | | | | | |
| Barnyardgrass | 0 | 0 | 0 | 0 | 0 | 60 | 0 | 0 | 0 | 0 |
| Bermudagrass | 10 | 0 | 30 | 0 | 0 | 80 | 65 | 50 | 0 | 5 |
| Black Mustard | 0 | 0 | 0 | 20 | 0 | 50 | 75 | 0 | 60 | 0 |
| Bluegrass | 0 | 0 | 0 | 0 | 0 | 0 | 20 | 0 | 0 | 0 |
| Chickweed | — | — | — | — | 0 | 90 | — | — | — | — |
| Crabgrass, Large | 0 | 0 | 0 | 0 | 15 | 95 | 50 | 20 | 0 | 0 |
| Crabgrass, Naked | 0 | 0 | 0 | 0 | 0 | 0 | — | 0 | 0 | 0 |
| Dallisgrass | 0 | 0 | 5 | 0 | 0 | 50 | 50 | 5 | 0 | 0 |
| Dayflower, VA | 35 | 0 | 0 | — | 0 | 5 | 0 | 50 | — | 0 |
| Field Bindweed | 0 | 0 | 20 | 0 | 0 | 50 | 0 | 0 | 0 | 0 |
| Foxtail, Green | 0 | 0 | 0 | 0 | 0 | 0 | 0 | 0 | 0 | 0 |
| Goosegrass | 0 | 20 | 5 | 0 | 0 | 65 | 35 | 25 | 0 | 70 |
| Guineagrass | 0 | 0 | 0 | 0 | 0 | 0 | 0 | 0 | 0 | 0 |
| Itchgrass | 0 | 0 | 0 | 0 | 0 | 10 | 0 | 0 | 0 | 0 |
| Johnsongrass | 0 | 0 | 0 | 0 | 0 | 50 | 0 | 0 | 0 | 0 |
| *Kochia* | 0 | 0 | — | 0 | 0 | 5 | 65 | — | 0 | 0 |
| Mallow | 0 | 0 | — | 0 | 0 | 80 | — | 0 | — | 0 |
| Morningglory | 0 | 0 | 0 | 0 | 0 | — | 10 | 60 | — | 0 |
| Nutsedge, Purple | 0 | 0 | 0 | 0 | 0 | 70 | 0 | 0 | 0 | 0 |
| Prickly Sida | 0 | 0 | 0 | 0 | 0 | 90 | 50 | 0 | 0 | 0 |
| Purslane | 0 | 0 | 0 | 65 | 0 | 80 | 70 | 90 | 0 | 0 |
| Quackgrass | 0 | 0 | 0 | 0 | 0 | 0 | 0 | 0 | 0 | 0 |
| Ragweed | 0 | 35 | 30 | 0 | 0 | 90 | 30 | 0 | 0 | 50 |
| Russian Thistle | 0 | — | 0 | — | — | — | 50 | 0 | — | 50 |
| Ryegrass, Italian | 0 | 0 | 0 | 0 | 0 | 0 | 0 | 0 | 0 | 0 |
| Sandbur | 0 | 0 | 0 | 0 | 0 | 5 | 0 | 0 | 0 | 0 |
| Signalgrass | 0 | 0 | 0 | 0 | 0 | 5 | 0 | 0 | 0 | 0 |
| Sowthistle | 65 | 40 | 0 | 0 | 0 | 100 | 98 | 50 | 80 | 0 |
| Spanishneedles | 0 | 0 | 35 | 0 | 0 | 90 | 0 | 0 | 0 | 0 |
| Surinam Grass | 0 | 90 | 0 | 5 | 0 | 98 | 0 | — | 0 | 0 |

Test E

Three plastic pots (ca. 16-cm diameter) for each application were partially filled with sterilized Tama silt loam soil comprising a 35:50:15 ratio of sand, silt and clay and 2.6% organic matter. Separate plantings for each of the three pots were as follows. Seeds from the U.S. of ducksalad (*Heteranthera limosa*), sedge (smallflower umbrella sedge, *Cyperus difformis*), ricefield bulrush (*Scirpus mucronatus*) and redstem (purple redstem, *Ammannia coccinea*), were planted into one 16-cm pot for each rate. Seeds from the U.S. of flatsedge (rice flatsedge, *Cyperus iria*), sprangletop (bearded (i.e. Brdd.) sprangletop, *Leptochloa fascicularis*), one stand of 9 or 10 water seeded rice seedlings (*Oryza sativa* cv. 'Japonica—M202'), and two stands of 3 or 4 transplanted rice seedlings (*Oryza sativa* cv. 'Japonica—M202') were planted into one 16-cm pot for each rate. Seeds from the U.S. of barnyardgrass (*Echinochloa crus-galli*), late watergrass (*Echinochloa oryzicola*), early watergrass (*Echinochloa oryzoides*) and junglerice (*Echinochloa colona*) were planted into one 16-cm pot for each rate. Plantings were sequential so that crop and weed species were at the 2.0 to 2.5-leaf stage at time of treatment.

Potted plants were grown in a greenhouse with day/night temperature settings of 30/27° C., and supplemental balanced lighting was provided to maintain a 16-hour photoperiod. Test pots were maintained in the greenhouse until test completion.

At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 days. Plant response ratings, summarized in Table E, are based on a scale of 0 to 100 where 0 is no effect and 100 is complete control. A dash (-) response means no test result.

TABLE E

|  | Compounds | |
|---|---|---|
| 500 g ai/ha | 4 | 19 |
| Flood | | |
| Barnyardgrass | 60 | 85 |
| Bulrush, Ricefield | 80 | 75 |
| Ducksalad | 100 | 100 |
| Flatsedge, Rice | 90 | 100 |
| Junglerice | 50 | 80 |
| Redstem | 85 | 85 |
| Rice, Transplanted | 15 | 65 |
| Rice, Water Seeded | 50 | 95 |
| Sedge, Umbrella | 100 | 100 |
| Sprangletop, Brdd. | — | 100 |
| Watergrass, Early | 65 | 85 |
| Watergrass, Late | 60 | 55 |

|  | Compounds | | | |
|---|---|---|---|---|
|  | 4 | 19 | 28 | 218 |
| Flood | | | | |
| 250 g ai/ha | | | | |
| Barnyardgrass | 60 | 70 | 0 | 95 |
| Bulrush, Ricefield | 80 | 70 | 65 | 100 |
| Ducksalad | 100 | 100 | 100 | 100 |
| Flatsedge, Rice | 40 | 95 | 45 | 75 |
| Junglerice | 25 | 65 | 0 | 100 |
| Redstem | 80 | 90 | 90 | 80 |
| Rice, Transplanted | 0 | 40 | 15 | 10 |
| Rice, Water Seeded | 20 | 70 | 85 | 35 |
| Sedge, Umbrella | 95 | 100 | 100 | 100 |
| Sprangletop, Brdd. | — | 100 | — | 95 |
| Watergrass, Early | 60 | 65 | 20 | 60 |
| Watergrass, Late | 15 | 60 | 0 | 70 |
| 125 g ai/ha | | | | |
| Barnyardgrass | 0 | 60 | 0 | 30 |
| Bulrush, Ricefield | 40 | 70 | 35 | 90 |
| Ducksalad | 90 | 95 | 80 | 95 |
| Flatsedge, Rice | 0 | 40 | 0 | 70 |
| Junglerice | 0 | 50 | 0 | 65 |
| Redstem | 80 | 90 | 50 | 75 |
| Rice, Transplanted | 0 | 35 | 15 | 0 |
| Rice, Water Seeded | 10 | 40 | 65 | 20 |
| Sedge, Umbrella | 90 | 100 | 90 | 100 |
| Sprangletop, Brdd. | — | 95 | — | 70 |
| Watergrass, Early | 0 | 45 | 0 | 20 |
| Watergrass, Late | 0 | 45 | 0 | 40 |

|  | Compounds | | |
|---|---|---|---|
| 64 g ai/ha | 19 | 28 | 218 |
| Flood | | | |
| Barnyardgrass | 60 | 0 | 0 |
| Bulrush, Ricefield | 50 | 30 | 80 |
| Ducksalad | 85 | 0 | 85 |
| Flatsedge, Rice | 40 | 0 | 70 |
| Junglerice | 0 | 0 | 0 |
| Redstem | 0 | 40 | 65 |
| Rice, Transplanted | 0 | 15 | 0 |
| Rice, Water Seeded | 0 | 60 | 0 |
| Sedge, Umbrella | 90 | 85 | 95 |
| Sprangletop, Brdd. | 75 | — | 70 |

TABLE E-continued

| Watergrass, Early | 20 | 0 | 20 |
|---|---|---|---|
| Watergrass, Late | 0 | 0 | 40 |

|  | Compounds | |
|---|---|---|
| 32 g ai/ha | 28 | 218 |
| Flood | | |
| Barnyardgrass | 0 | 0 |
| Bulrush, Ricefield | 20 | 80 |
| Ducksalad | 0 | 80 |
| Flatsedge, Rice | 0 | 75 |
| Junglerice | 0 | 0 |
| Redstem | 0 | 65 |
| Rice, Transplanted | 0 | 0 |
| Rice, Water Seeded | 45 | 15 |
| Sedge, Umbrella | 0 | 85 |
| Sprangletop, Brdd. | — | 65 |
| Watergrass, Early | 0 | 0 |
| Watergrass, Late | 0 | 20 |

Test F

Test F evaluated the effect of combining compound 2 with bromoxynil. The test species for this experiment was Russian thistle (*Salsola iberica*), which was prepared by sowing seeds into a blend of loam soil and sand. Test chemicals were formulated in a non-phytotoxic solvent mixture that included a surfactant and applied postemergence to plants ranging in height from 12 to 20 cm.

Plants were grown in a greenhouse using supplemental lighting to maintain a photoperiod of 16 hours; day and night temperatures ranged between 24-30° C. and 19-21° C., respectively. Treatments consisted of Compound 2, bromoxynil, or their combination, using a spray volume of 457 L/ha. Each treatment was replicated three times. Treated plants and untreated controls were maintained in a greenhouse for 15 days, after which time all plants were visually evaluated and compared to the untreated controls. Plant responses were calculated as the mean of the three replicates and summarized in Table F. Visual evaluations were based on a scale of 0 to 100 where 0 is no effect and 100 is complete control. Colby's Equation was used to determine the herbicidal effects expected from the mixtures. Colby's Equation (Colby, S. R. "Calculating Synergistic and Antagonistic Responses of Herbicide Combinations," *Weeds*, 15(1), pp 20-22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components:

$P_a$ is the observed percentage effect of the first active ingredient at the same use rate as in the mixture, and $P_b$ is the observed percentage effect of the second active ingredient at the same use rate as in the mixture.

The results and additive effects expected from Colby's Equation are listed in Table F1.

TABLE F1

Observed and Expected Results from
Compound 2, Bromoxynil, or their combination.

| Postemergence Application Rate (g a.i./ha)* | | Russian Thistle | |
|---|---|---|---|
| Cmpd 2 | Bromoxynil | Obsd. | Exp. |
| 62 | — | 42 | — |
| 125 | — | 52 | — |
| — | 70 | 8 | — |
| — | 140 | 13 | — |
| 62 | 70 | 93 | 47 |
| 125 | 140 | 95 | 58 |

*Application rates are grams of active ingredient per hectare (g a.i./ha).
"Obsd." is observed effect. "Exp." is expected effect calculated from Colby's Equation.

The results in Table D1 suggest the combination of Compound 2 and bromoxynil have a synergistic action based on the observed injury being greater than the expected values as calculated by the Colby Equation for an additive effect.

What is claimed is:

1. A compound of Formula 1Q including all stereoisomers, N-oxides, and salts thereof:

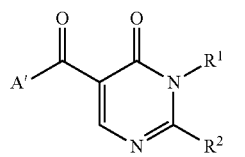

1Q wherein A' is a radical selected from the group consisting of

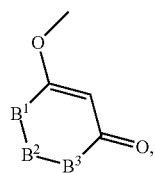

A'-1

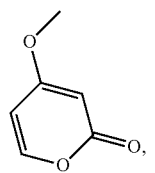

A'-2

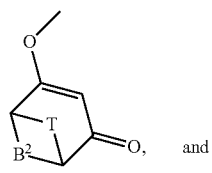

A'-3 and

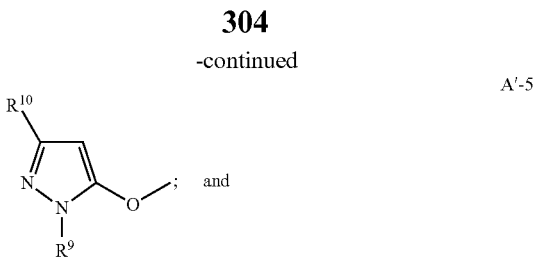

A'-5

$B^1$ and $B^3$ are each independently a radical selected from the group consisting of

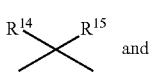

C-1 and

C-2

$B^2$ is a radical selected from the group consisting of

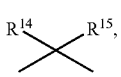

C-3

C-4

C-5

—O— and

C-6

C-7

$R^1$ is phenyl, phenylsulfonyl, —$W^1$(phenyl), —$W^1$(S-phenyl), —$W^1$($SO_2$-phenyl), —$W^2$($SO_2CH_2$-phenyl) or —$W^2$($SCH_2$-phenyl), each optionally substituted on ring members with up to five substituents selected from $R^{21}$; or -G or —$W^2$G; or cyano, hydroxy, amino, —C(=O)OH, —C(=O)NHCN, —C(=O)NHOH, —$SO_2NH_2$, —$SO_2$NHCN, —$SO_2$NHOH, —NHCHO, $C_1$-$C_{10}$ alkyl, $C_2$-$C_{10}$ alkenyl, $C_2$-$C_{10}$ alkynyl, $C_1$-$C_{10}$ haloalkyl, $C_2$-$C_{10}$ haloalkenyl, $C_2$-$C_{12}$ haloalkynyl, $C_3$-$C_{12}$ cycloalkyl, $C_3$-$C_{12}$ halocycloalkyl, $C_4$-$C_{14}$ alkylcycloalkyl, $C_4$-$C_{14}$ cycloalkylalkyl, $C_6$-$C_{18}$ cycloalkylcycloalkyl, $C_4$-$C_{14}$ halocycloalkylalkyl, $C_5$-$C_{16}$ alkylcycloalkylalkyl, $C_3$-$C_{12}$ cycloalkenyl, $C_3$-$C_{12}$ halocycloalkenyl, $C_2$-$C_{12}$ alkoxyalkyl, $C_3$-$C_{12}$ alkoxyalkenyl, $C_4$-$C_{14}$ alkylcycloalkyl, $C_4$-$C_{14}$ alkoxycycloalkyl, $C_4$-$C_{14}$ cycloalkoxyalkyl, $C_5$-$C_{14}$ cycloalkoxyalkoxyalkyl, $C_3$-$C_{14}$ alkoxyalkoxyalkyl, $C_2$-$C_{12}$ alkylthioalkyl, $C_2$-$C_{12}$ alkylsulfinylalkyl, $C_2$-$C_{12}$ alkylsulfonylalkyl, $C_2$-$C_{12}$ alkylaminoalkyl, $C_3$-$C_{14}$ dialkylaminoalkyl, $C_2$-$C_{12}$ haloalkylaminoalkyl, $C_4$-$C_{14}$ cycloalkylaminoalkyl, $C_2$-$C_{12}$ alkylcarbonyl, $C_2$-$C_{12}$ haloalkylcarbonyl, $C_4$-$C_{14}$ cycloalkylcarbonyl, $C_2$-$C_{12}$ alkoxycarbonyl, $C_4$-$C_{16}$ cycloalkoxycarbonyl, $C_5$-$C_{14}$ cycloalkylalkoxycarbonyl, $C_2$-$C_{12}$ alkylaminocarbonyl, $C_3$-$C_{14}$ dialkylaminocarbonyl, $C_4$-$C_{14}$ cycloalkylaminocarbonyl, $C_2$-$C_9$ cyanoalkyl, $C_1$-$C_{10}$ hydroxyalkyl, $C_4$-$C_{14}$ cycloalkenylalkyl, $C_2$-$C_{12}$ haloalkoxyalkyl, $C_2$-$C_{12}$ alkoxyhaloalkyl, $C_2$-$C_{12}$ haloalkoxyhaloalkyl, $C_4$-$C_{14}$ halocycloalkoxyalkyl, $C_4$-$C_{14}$ cycloalkenyloxyalkyl, $C_4$-$C_{14}$ halocycloalkenyloxyalkyl, $C_3$-$C_{14}$ dialkoxyalkyl, $C_3$-$C_{14}$ alkoxyalkylcarbonyl, $C_3$-$C_{14}$ alkoxycarbonylalkyl, $C_2$-$C_{12}$ haloalkoxycarbonyl, $C_1$-$C_{10}$ alkoxy, $C_1$-$C_{10}$ haloalkoxy, $C_3$-$C_{12}$ cycloalkoxy, $C_3$-$C_{12}$ halocycloalkoxy, $C_4$-$C_{14}$ cycloalkylalkoxy, $C_2$-$C_{10}$ alkenyloxy, $C_2$-$C_{10}$ haloalkenyloxy, $C_2$-$C_{10}$ alkynyloxy, $C_3$-$C_{10}$ haloalkynyloxy, $C_2$-$C_{12}$ alkoxyalkoxy, $C_2$-$C_{12}$ alkylcarbonyloxy, $C_2$-$C_{12}$ haloalkylcarbonyloxy, $C_4$-$C_{14}$ cycloalkylcarbonyloxy, $C_3$-$C_{14}$ alkylcarbonylalkoxy, $C_1$-$C_{10}$ alkylthio, $C_1$-$C_{10}$ haloalkylthio, $C_3$-$C_{12}$ cycloalkylthio, $C_1$-$C_{10}$ alkylsulfinyl, $C_1$-$C_{10}$ haloalkylsulfinyl, $C_1$-$C_{10}$ alkylsulfonyl, $C_1$-$C_{10}$ haloalkylsulfonyl, $C_3$-$C_{12}$ cycloalkylsulfonyl, $C_2$-$C_{12}$ alkylcarbonylthio, $C_2$-$C_{12}$ alkyl(thiocarbonyl)thio, $C_3$-$C_{12}$ cycloalkylsulfinyl, $C_1$-$C_{10}$ alkylaminosulfonyl, $C_2$-$C_{12}$ dialkylaminosulfonyl, $C_1$-$C_{10}$ alkylamino, $C_2$-$C_{12}$ dialkylamino, $C_1$-$C_{10}$ haloalkylamino, $C_2$-$C_{12}$ halodialkylamino, $C_3$-$C_{12}$ cycloalkylamino, $C_2$-$C_{12}$ alkylcarbonylamino, $C_2$-$C_{12}$ haloalkylcarbonylamino, $C_1$-$C_{10}$ alkylsulfonylamino, $C_1$-$C_{10}$ haloalkylsulfonylamino or $C_4$-$C_{14}$ cycloalkyl(alkyl)amino;

$W^1$ is $C_1$-$C_6$ alkylene, $C_2$-$C_6$ alkenylene or $C_2$-$C_6$ alkynylene;

$W^2$ is $C_1$-$C_6$ alkylene;

$R^2$ is phenyl or —$W^3$(phenyl), each optionally substituted on ring members with up to five substituents selected from $R^{21}$; or -G or —$W^4$G; or H, cyano, hydroxy, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —SF$_5$, —NHCHO, —NHNH$_2$, —NHOH, —NHCN, —NHC(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_2$-$C_5$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_3$-$C_{10}$ alkoxyalkylcarbonyl, $C_3$-$C_{10}$ alkoxycarbonylalkyl, $C_2$-$C_8$ haloalkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_3$-$C_{10}$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_8$ trialkylsilyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_2$-$C_8$ alkylcarbonylthio, $C_2$-$C_8$ alkyl(thiocarbonyl)thio, $C_3$-$C_8$ cycloalkylsulfinyl, $C_1$-$C_6$ alkylaminosulfonyl, $C_2$-$C_8$ dialkylaminosulfonyl, $C_3$-$C_{10}$ halotrialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino or $C_4$-$C_{10}$ cycloalkyl(alkyl)amino; or $R^1$ and $R^2$ are taken together along with the atoms to which they are attached to make a 5-, 6- or 7-membered unsaturated, partially unsaturated or fully unsaturated ring along with members consisting of up to 2 oxygen atoms, 2 nitrogen atoms or 2 sulfur atoms or up to two —S(O)—, —S(O)$_2$—, —C(O)— groups optionally substituted with halogen, cyano, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl on carbon atom ring members and H or $C_1$-$C_6$ alkyl on nitrogen ring members;

$W^3$ is $C_1$-$C_6$ alkylene, $C_2$-$C_6$ alkenylene or $C_2$-$C_6$ alkynylene;

$W^4$ is $C_1$-$C_6$ alkylene;

$R^9$ is H, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

$R^{10}$ is H, halogen, cyano, hydroxy, amino, nitro, SH, —SO$_2$NH$_2$, —SO$_2$NHCN, —SO$_2$NHOH, —OCN, —SCN, —SF$_5$, —NHCHO, —NHNH$_2$, —N$_3$, —NHOH, —NHCN, —NHC(=O)NH$_2$, —N=C=O, —N=C=S, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl or $C_2$-$C_8$ alkylthioalkyl;

n is 0, 1, or 2;

each $R^{14}$, $R^{15}$, $R^{18}$ and $R^{19}$ is independently H, halogen, cyano, hydroxy or $C_1$-$C_6$ alkyl; or a pair of $R^{14}$ and $R^{18}$ is taken together as $C_2$-$C_6$ alkylene or $C_2$-$C_6$ alkenylene;

$R^{20}$ is H, $C_1$-$C_6$ haloalkyl, $C_2$-$C_6$ haloalkenyl, $C_1$-$C_6$ alkoxy, $C_1$-$C_6$ haloalkoxy, $C_3$-$C_8$ cycloalkoxy, $C_1$-$C_6$ alkyl, $C_2$-$C_6$ alkenyl, $C_2$-$C_6$ alkynyl or $C_3$-$C_8$ cycloalkyl;

T is $C_1$-$C_6$ alkylene or $C_2$-$C_6$ alkenylene;

each G is independently a 5- or 6-membered heterocyclic ring or an 8-, 9- or 10-membered fused bicyclic ring system, each ring or ring system optionally substituted with up to five substituents selected from $R^{21}$ on carbon ring members and $R^{22}$ on nitrogen ring members;

each $R^{21}$ is independently halogen, cyano, hydroxy, amino, nitro, —CHO, —C(=O)OH, —C(=O)NH$_2$, —C(=S)NH$_2$, —C(=O)NHCN, —C(=O)NHOH, —SH, —SO$_2$NH$_2$, —SO$_2$NHCN, —SO$_2$NHOH, —OCN, —SCN, —SF$_5$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkoxyhaloalkyl, $C_2$-$C_5$ cyanoalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_8$ alkoxyalkoxy, $C_2$-$C_8$ alkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylamino, $C_2$-$C_8$ dialkylamino, $C_1$-$C_6$ haloalkylamino, $C_2$-$C_8$ halodialkylamino or $C_3$-$C_8$ cycloalkylamino; and each $R^{22}$ is independently $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl or $C_2$-$C_8$ alkoxyalkyl.

2. A compound of claim 1 wherein

A' is A'-1, A'-3 or A'-5;

$B^1$ is C-1;

$B^2$ is C-3;

$B^3$ is C-1;

$R^1$ is phenyl, —$W^1$(phenyl), —$W^1$(S-phenyl), —$W^1$(SO$_2$-phenyl), —$W^2$(SO$_2$CH$_2$-phenyl) or —$W^2$(SCH$_2$-phenyl), each optionally substituted on ring members with up to five substituents selected from $R^{21}$; or —G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_3$-$C_{10}$ alkoxyalkenyl, $C_4$-$C_{10}$ alkylcycloalkyl, $C_4$-$C_{10}$ alkoxycycloalkyl, $C_3$-$C_{10}$ alkoxyalkoxyalkyl, $C_2$-$C_8$ alkylthioalkyl, $C_2$-$C_{12}$ alkylsulfinylalkyl or $C_2$-$C_8$ alkylsulfonylalkyl;

$W^1$ is $C_1$-$C_6$ alkylene;

$W^2$ is —CH$_2$—;

$R^2$ is phenyl or —$W^3$(phenyl), each optionally substituted on ring members with up to two substituents selected from $R^{21}$; or —G or; or $C_1$-$C_6$ alkyl or $C_3$-$C_8$ cycloalkyl;

$W^3$ is —CH$_2$—;

$R^{14}$ and $R^{18}$ are H or $C_1$-$C_6$ alkyl;

each $R^{15}$ and $R^{19}$ is H or CH$_3$;

T is —CH$_2$CH$_2$— or —CH=CH—;

G is

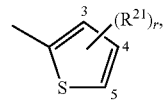

G-2

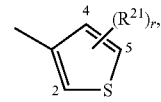

G-3

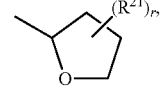

G-9

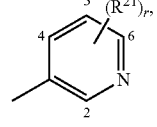

G-15

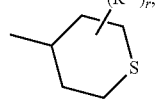

G-18

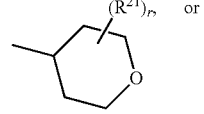

G-19 or

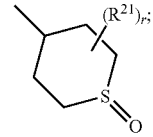

G-20 r is 0, 1, 2 or 3; and each $R^{21}$ is independently halogen, nitro, $C_1$-$C_6$ alkyl, $C_1$-$C_6$ haloalkyl, $C_1$-$C_6$ alkoxy, $C_1$-$C_6$ haloalkoxy or $C_1$-$C_6$ alkylthio.

3. A compound of claim 2 wherein

A' is A'-1 or A'-3;

$R^1$ is phenyl or —$W^1$(phenyl), each optionally substituted on ring members with up to two substituents selected from $R^{21}$; or —G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl $C_3$-$C_{10}$ alkoxyalkenyl, $C_4$-$C_{10}$ alkylcycloalkyl or $C_4$-$C_{10}$ alkoxycycloalkyl;

$W^1$ is —CH$_2$—;

$R^2$ is phenyl optionally substituted on ring members with up to two substituents selected from $R^{21}$; or —G; or $C_1$-$C_6$ alkyl or $C_3$-$C_8$ cycloalkyl;

$R^{14}$ and $R^{18}$ are H or CH$_3$;

each $R^{15}$ and $R^{19}$ is H;

G is G-19 or G-20;

each $R^{21}$ is independently fluorine, chlorine, bromine, CH$_3$, CF$_3$, OCH$_3$, OCF$_3$ or SCH$_3$.

4. A compound of claim 2 wherein

A' is A'-1 or A'-3;

$R^1$ is phenyl or —$W^1$(phenyl), each optionally substituted on ring members with up to two substituents selected from $R^{21}$; or —G or —$W^2$G; or $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_3$-$C_8$ cycloalkyl, $C_4$-$C_{10}$ cycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl $C_3$-$C_{10}$ alkoxyalkenyl, $C_4$-$C_{10}$ alkylcycloalkyl or $C_4$-$C_{10}$ alkoxycycloalkyl;

$W^1$ is —$CH_2$—;

$R^2$ is phenyl optionally substituted on ring members with up to two substituents selected from $R^{21}$; or —G; or $C_1$-$C_6$ alkyl or $C_3$-$C_8$ cycloalkyl;

$R^{14}$ and $R^{18}$ are H or $CH_3$;

each $R^{15}$ and $R^{19}$ is H;

G is G-2, G-3 or G-15; and each $R^{21}$ is independently fluorine, chlorine, bromine, $CH_3$, $CF_3$, $OCH_3$, $OCF_3$ or $SCH_3$.

5. A compound of claim 2 wherein

A' is A'-3;

$R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl;

$R^2$ is phenyl, 2-methylphenyl, 3-methylphenyl, 3-bromophenyl, 3-chlorophenyl, 4-chlorophenyl, 3-fluorophenyl or 3,5-difluorophenyl;

T is —$CH_2CH_2$—;

$R^{18}$ is H; and $R^{19}$ is H.

6. A compound of claim 2 wherein

A' is A'-3;

$R^1$ is n-Pr, i-Pr, n-Bu, c-hexyl, —$CH_2CH_2OCH_3$, —$CH_2CH_2CH_2OCH_3$ or —$CH_2CH_2OCH_2CH_3$;

$R^2$ is phenyl, 2-methylphenyl, 3-methylphenyl, 3-bromophenyl, 3-chlorophenyl, 4-chlorophenyl, 3-fluorophenyl or 3,5-difluorophenyl; and T is —$CH_2CH_2$—;

$R^{18}$ is H; and $R^{19}$ is H.

7. A compound of claim 2 wherein

A is A'-3;

$R^1$ is —$CH_2CH_2CH_2OCH_3$;

$R^2$ is 3-methoxyphenyl;

T is —$CH_2CH_2$—;

$R^{18}$ is H; and $R^{19}$ is H.

8. A compound of claim 2 wherein

A' is A'-1;

$R^1$ is phenyl, 2-fluorophenyl, 3-fluorophenyl, 4-fluorophenyl, 2-chlorophenyl, 3-chlorophenyl, 4-chlorophenyl, 4-methylphenyl, 4-ethylphenyl, 2-methylphenyl, 3-methoxyphenyl, 4-methoxyphenyl, 3,5-dimethylphenyl, 3,4-dimethoxyphenyl, 2,3-dimethylphenyl, 3-fluoro-2-methylphenyl, 4-fluoro-3-methylphenyl or 5-chloro-2-methylphenyl;

$R^2$ is phenyl, 2-methylphenyl, 3-methylphenyl, 3-bromophenyl, 3-chlorophenyl, 4-chlorophenyl, 3-fluorophenyl or 3,5-difluorophenyl;

$R^{14}$ and $R^{18}$ are H; and $R^{15}$ and $R^{19}$ are H.

9. A compound of claim 2 wherein

A' is A'-1;

$R^1$ is n-Pr, i-Pr, n-Bu, c-hexyl, —$CH_2CH_2OCH_3$, —$CH_2CH_2CH_2OCH_3$ or —$CH_2CH_2OCH_2CH_3$;

$R^2$ is phenyl, 2-methylphenyl, 3-methylphenyl, 3-bromophenyl, 3-chlorophenyl, 4-chlorophenyl, 3-fluorophenyl or 3,5-difluorophenyl;

$R^{14}$ and $R^{18}$ are H; and $R^{15}$ and $R^{19}$ are H.

10. A compound of claim 2 wherein

A is A'-1;

$R^1$ is —$CH_2CH_2CH_2OCH_3$;

$R^2$ is 3-methoxyphenyl;

$R^{14}$ and $R^{18}$ are H; and $R^{15}$ and $R^{19}$ are H.

\* \* \* \* \*